US012522661B2

(12) United States Patent
Timmer et al.

(10) Patent No.: US 12,522,661 B2
(45) Date of Patent: Jan. 13, 2026

(54) CD28 SINGLE DOMAIN ANTIBODIES AND MULTIVALENT AND MULTISPECIFIC CONSTRUCTS THEREOF

(71) Applicant: Inhibrx Biosciences, Inc., La Jolla, CA (US)

(72) Inventors: John C. Timmer, La Jolla, CA (US); Rutger H. Jackson, La Jolla, CA (US); Katelyn M. Willis, La Jolla, CA (US); William S. Crago, La Jolla, CA (US); Michael D. Kaplan, La Jolla, CA (US); Brendan P. Eckelman, La Jolla, CA (US)

(73) Assignee: Inhibrx Biosciences, Inc., La Jolla, CA (US)

( * ) Notice: Subject to any disclaimer, the term of this patent is extended or adjusted under 35 U.S.C. 154(b) by 747 days.

(21) Appl. No.: 17/795,500

(22) PCT Filed: Jan. 28, 2021

(86) PCT No.: PCT/US2021/015590

§ 371 (c)(1),
(2) Date: Jul. 26, 2022

(87) PCT Pub. No.: WO2021/155071

PCT Pub. Date: Aug. 5, 2021

(65) Prior Publication Data

US 2023/0348600 A1 Nov. 2, 2023

Related U.S. Application Data

(60) Provisional application No. 62/967,533, filed on Jan. 29, 2020.

(51) Int. Cl.
*C07K 16/28* (2006.01)
*A61P 37/04* (2006.01)

(52) U.S. Cl.
CPC .......... *C07K 16/2818* (2013.01); *A61P 37/04* (2018.01); *C07K 2317/24* (2013.01); *C07K 2317/31* (2013.01); *C07K 2317/35* (2013.01); *C07K 2317/52* (2013.01); *C07K 2317/569* (2013.01)

(58) Field of Classification Search
None
See application file for complete search history.

(56) References Cited

U.S. PATENT DOCUMENTS

| | | | |
|---|---|---|---|
| 4,522,811 | A | 6/1985 | Eppstein et al. |
| 4,816,567 | A | 3/1989 | Cabilly et al. |
| 5,258,498 | A | 11/1993 | Huston et al. |
| 5,525,491 | A | 6/1996 | Huston et al. |
| 5,731,168 | A | 3/1998 | Carter et al. |
| 5,821,337 | A | 10/1998 | Carter et al. |
| 6,132,992 | A | 10/2000 | Ledbetter et al. |
| 6,982,321 | B2 | 1/2006 | Winter |
| 7,087,409 | B2 | 8/2006 | Barbas et al. |
| 7,183,076 | B2 | 2/2007 | Arathoon et al. |
| 7,527,791 | B2 | 5/2009 | Adams et al. |
| 8,044,178 | B2 | 10/2011 | Boghaert et al. |
| 9,346,884 | B2 | 5/2016 | Beste et al. |
| 9,605,084 | B2 | 3/2017 | Moore et al. |
| 9,644,016 | B2 | 5/2017 | Stagliano et al. |
| 9,650,446 | B2 | 5/2017 | Moore et al. |
| 9,701,759 | B2 | 7/2017 | Desjarlais et al. |
| 10,010,626 | B2 | 7/2018 | Chang et al. |
| 10,066,015 | B2 | 9/2018 | Zhukovsky et al. |
| 10,858,417 | B2 | 12/2020 | Moore et al. |
| 2005/0123546 | A1 | 6/2005 | Umana et al. |
| 2006/0270045 | A1 | 11/2006 | Cregg et al. |
| 2011/0097339 | A1 | 4/2011 | Holmes et al. |
| 2012/0149876 | A1 | 6/2012 | Von Kreudenstein et al. |
| 2013/0273054 | A1 | 10/2013 | Bossenmaier et al. |
| 2014/0072581 | A1 | 3/2014 | Dixit et al. |
| 2014/0154253 | A1 | 6/2014 | Ng et al. |
| 2014/0288275 | A1 | 9/2014 | Moore et al. |
| 2014/0294823 | A1 | 10/2014 | Moore et al. |
| 2014/0322129 | A1 | 10/2014 | Leong et al. |
| 2014/0363426 | A1 | 12/2014 | Moore et al. |
| 2015/0079088 | A1 | 3/2015 | Lowman et al. |
| 2015/0087810 | A1 | 3/2015 | Moore et al. |
| 2015/0239991 | A1 | 8/2015 | Blein et al. |
| 2015/0307628 | A1 | 10/2015 | Kim et al. |

(Continued)

FOREIGN PATENT DOCUMENTS

| | | |
|---|---|---|
| CN | 108084265 | 5/2018 |
| EP | 3502140 | 11/1998 |

(Continued)

OTHER PUBLICATIONS

Muyldermans et al (ARB:82:775-97, 2013).*
Farzaneh et al (Can Immunol Immunother, 56: 129-134, 2007).*
Al-Lazikani et al., "Standard Conformations for the Canonical Structures of Immunoglobulins," J. Mol. Biol. (1997) 273: 927-948.
Alegre et al., "Effect of a single amino acid mutation on the activating and immunosuppressive properties of a "humanized" OKT3 monoclonal antibody," J Immunol (1992) 148(11):3461-3468.
Almagro et al., "Humanization of Antibodies," Frontiers in Bioscience. (2008) 13:1619-1633.

(Continued)

*Primary Examiner* — Brad Duffy
(74) *Attorney, Agent, or Firm* — McNeill PLLC

(57) ABSTRACT

Provided herein are binding polypeptides that specifically bind CD28. More specifically, provided herein are fusion proteins, including multivalent and/or multispecific constructs that bind at least CD28. Also provided are pharmaceutical compositions containing the polypeptides, nucleic acid molecules encoding the polypeptides and vectors thereof, and methods of use and uses of the provided CD28 binding polypeptides for treating diseases and conditions, such as cancer.

32 Claims, 18 Drawing Sheets

Specification includes a Sequence Listing.

(56) References Cited

U.S. PATENT DOCUMENTS

| | | | |
|---|---|---|---|
| 2016/0039942 | A1 | 2/2016 | Cobbold et al. |
| 2016/0122425 | A1 | 5/2016 | Daugherty et al. |
| 2016/0194399 | A1 | 7/2016 | Irving et al. |
| 2016/0207981 | A1 | 7/2016 | Eckelman et al. |
| 2016/0289324 | A1 | 10/2016 | Moore et al. |
| 2017/0037130 | A1 | 2/2017 | Raum et al. |
| 2017/0081397 | A1 | 3/2017 | Stagliano et al. |
| 2017/0204139 | A1 | 7/2017 | Moore et al. |
| 2018/0011883 | A1 | 1/2018 | Goldbrenner et al. |
| 2018/0016354 | A1 | 1/2018 | Wozniak-Knopp et al. |
| 2018/0230225 | A1 | 8/2018 | Fan et al. |
| 2019/0010242 | A1 | 1/2019 | Eckelman et al. |
| 2019/0218515 | A1 | 7/2019 | Ballesteros Nobell et al. |
| 2019/0330366 | A1 | 10/2019 | Eckelman et al. |
| 2020/0048350 | A1 | 2/2020 | Eckelman et al. |
| 2020/0190193 | A1 | 6/2020 | Pandit et al. |
| 2021/0340273 | A1 | 11/2021 | Timmer et al. |
| 2021/0380679 | A1 | 12/2021 | Eckelman et al. |
| 2023/0124851 | A1 | 4/2023 | Eckelman et al. |
| 2023/0295336 | A1 | 9/2023 | Eckelman et al. |

FOREIGN PATENT DOCUMENTS

| | | |
|---|---|---|
| EP | 1 391 213 | 2/2004 |
| WO | WO-1998/050431 | 11/1998 |
| WO | WO-2000/024884 | 5/2000 |
| WO | WO-2004/092219 | 10/2004 |
| WO | WO-2005/063816 | 7/2005 |
| WO | WO-2005/100402 | 10/2005 |
| WO | WO-2006/029879 | 3/2006 |
| WO | WO 2009/018386 | 2/2009 |
| WO | WO-2009/067800 | 6/2009 |
| WO | WO-2009/089004 | 7/2009 |
| WO | WO-2009/124931 | 10/2009 |
| WO | WO-2010/151792 | 12/2010 |
| WO | WO-2011/056983 | 5/2011 |
| WO | WO-2011/133886 | 10/2011 |
| WO | WO-2011/143545 | 11/2011 |
| WO | WO 2012/025525 | 3/2012 |
| WO | WO-2012/058768 | 5/2012 |
| WO | WO-2012/162067 | 11/2012 |
| WO | WO 2013/041687 | 3/2013 |
| WO | WO-2013/101909 | 7/2013 |
| WO | WO 2013/128194 | 9/2013 |
| WO | WO-2014/067011 | 5/2014 |
| WO | WO-2014/099997 | 6/2014 |
| WO | WO-2014/125273 | 8/2014 |
| WO | WO-2014/145806 | 9/2014 |
| WO | WO-2015/001085 | 1/2015 |
| WO | WO-2016/020309 | 2/2016 |
| WO | WO-2016/033225 | 3/2016 |
| WO | WO-2016/034666 | 3/2016 |
| WO | WO 2016/046778 | 3/2016 |
| WO | WO-2016/055593 | 4/2016 |
| WO | WO-2016/086189 | 6/2016 |
| WO | WO-2016/087416 | 6/2016 |
| WO | WO-2016/097408 | 6/2016 |
| WO | WO-2016/105450 | 6/2016 |
| WO | WO-2016/138038 | 9/2016 |
| WO | WO-2016/180982 | 11/2016 |
| WO | WO-2016/192613 | 12/2016 |
| WO | WO-2017/021349 | 2/2017 |
| WO | WO-2017/030926 | 2/2017 |
| WO | WO-2017/055398 | 4/2017 |
| WO | WO-2017/060144 | 4/2017 |
| WO | WO-2017/134140 | 8/2017 |
| WO | WO-2017/134440 | 8/2017 |
| WO | WO-2017/172981 | 10/2017 |
| WO | WO-2017/182672 | 10/2017 |
| WO | WO-2018/014260 | 1/2018 |
| WO | WO-2018/027025 | 2/2018 |
| WO | WO-2018/127473 | 7/2018 |
| WO | WO-2018/167486 | 9/2018 |
| WO | WO-2018/185045 | 10/2018 |
| WO | WO-2018/191438 | 10/2018 |
| WO | WO-2020/023553 | 1/2020 |
| WO | WO-2020/076970 | 4/2020 |
| WO | WO-2020/076977 | 4/2020 |
| WO | WO-2020/076992 | 4/2020 |

OTHER PUBLICATIONS

Asano et al. "Domain order of a bispecific diabody dramatically enhances its antitumor activity beyond structural format conversion: the case of the hEx3 diabody." *Protein Engineering, Design & Selection* 26.5 (2013): 359-367.

Attarwala, "TGN1412: From Discovery to Disaster," J Young Pharm, (2010) 2(3): 332-336.

Baca et al., "Antibody Humanization Using Monovalent Phage Display," J. Biol. Chem. (1997) 272(16): 10678-10684.

Bacac et al., "CD20 Tcb (RG6026), a Novel "2:1" T Cell Bispecific Antibody for the Treatment of B Cell Malignancies," Blood (2016) 128:1836.

Barthelemy et al. "Comprehensive analysis of the factors contributing to the stability and solubility of autonomous human VH domains." *Journal of Biological Chemistry* 283.6 (2008): 3639-3654.

Beiboer et al. "Guided selection of a pan carcinoma specific antibody reveals similar binding characteristics yet structural divergence between the original murine antibody and its human equivalent." *Journal of Molecular Biology* 296.3 (2000): 833-849.

Beliveau et al., "Probing the substrate specificities of matriptase, matriptase-2, hepsin and DESC1 with internally quenched fluorescent peptides," FEBS J. (2009) 276(8):2213-2226.

Brinkmann et al., "The making of bispecific antibodies," MABS (2017) 9(2):182-212.

Bruggemann et al., "Comparison of the effector functions of human immunoglobulins using a matched set of chimeric antibodies," J Exp Med (1987) 166(5):1351-1361.

Capel et al., "Heterogeneity of Human IgG Fc Receptors," Immunomethods (1994) 4(1):25-34.

Carter et al., "Bispecific human lgG by design," J Immunol Methods (2001) 248(1-2):7-15.

Carter et al., "Humanization of an Anti-p185HER2 Antibody For Human Cancer Therapy," Proc. Natl. Acad. Sci. USA (1992) 89: 4285-4289.

Chen et al., "Fusion protein linkers: property, design and functionality," Adv Drug Deliv Rev (2013) 65(10):1357-1369.

Choi et al. "Predicting antibody complementarity determining region structures without classification." *Molecular BioSystems* 7.12 (2011): 3327-3334.

Clackson et al., "Making Antibody Fragments Using Phage Display Libraries," Nature (1991) 352: 624-628.

Clynes et al., "Fc receptors are required in passive and active immunity to melanoma," Proc Natl Acad Sci USA (1998) 95(2):652-656.

Cragg et al., "Antibody specificity controls in vivo effector mechanisms of anti-CD20 reagents," Blood (2004) 103:2738-2743.

Cragg et al., "Complement-mediated lysis by anti-CD20 mAb correlates with segregation into lipid rafts," Blood (2003) 101(3):1045-1052.

Daeron, "Fc receptor biology," Annu Rev Immunol. (1997) 15: 203-34.

Dall'Acqua et al., "Properties of Human IgG1s Engineered for Enhanced Binding to the Neonatal Fc Receptor (FcRn)*," J Biol Chem (2006) 281(33):23514-23524.

Dall'Acqua et al., "Antibody Humanization by Framework Shuffling," Methods (2005) 36:43-60.

Davis et al., "SEEDbodies: fusion proteins based on strand-exchange engineered domain (SEED) CH3 heterodimers in an Fc analogue platform for asymmetric binders or immunofusions and bispecific antibodies," Protein Eng. Des Sel (2010) 23(4):195-202.

De Haas, M. et al. "Fc Gamma receptors of Phagocytes," J. Lab. Clin. Med. (1995) 126:330-341.

Deer et al., "High-Level Expression of Proteins in Mammalian Cells Using Transcription Regulatory Sequences From the Chinese Hamster EF-1Alpha Gene," Biotechnol. Prog. (2004) 20(3): 880-889.

(56) References Cited

OTHER PUBLICATIONS

Deisenhofer, "Crystallographic refinement and atomic models of a human Fc fragment and its complex with fragment B of protein A from *Staphylococcusaureus* at 2.9- and 2.8-.ANG. resolution," Biochemistry (1981) 20(9):2361-2370.
De Genst et al. "Antibody repertoire development in camelids." *Developmental & Comparative Immunology* 30.1-2 (2006): 187-198.
Driessens et al. "Costimulatory and coinhibitory receptors in anti-tumor immunity." *Immunological reviews* (2009) 229.1: 126-144.
Endo et al., "High-Throughput, Genome-Scale Protein Production Method Based on the Wheat Germ Cell-Free Expression System," Biotechnol. Adv. (2003) 21; 695-713.
Esensten et al., "CD28 Costimulation: From Mechanism to Therapy," Immunity (2016) 44(5):973-988.
Gazzano-Santoro et al., "A non-radioactive complement-dependent cytotoxicity assay for anti-CD20 monoclonal antibody," J Immunol Methods. (1997) 202(2):163-171.
Ghetie et al,. "FcRn: the MHC Class I-related Receptor That Is More Than an IgG Transporter," Immunol. Today (1997) 18(12): 592-598.
Ghetie et al., "Increasing the Serum Persistence of an IgG Fragment by Random Mutagenesis," Nat Biotech (1997) 15:637-640.
Griffiths et al. "Human anti-self antibodies with high specificity from phage display libraries." *The EMBO journal* 12.2 (1993): 725-734.
Gunasekaran et al., "Enhancing antibody Fc heterodimer formation through electrostatic steering effects: applications to bispecific molecules and monovalent IgG," J Biol Chem (2010) 285(25):19637-19646.
Guyer et al., "Immunoglobulin binding by mouse intestinal epithelial cell receptors," J Immunol. (1976) 117(2): 587-593.
Ha et al., "Immunoglobulin Fc Heterodimer Platform Technology: From Design to Applications in Therapeutic Antibodies and Proteins," Front Immunol (2016) 7:394.
Harwood et al., "ATTACK, a novel bispecific T cell-recruiting antibody with trivalent EGFR binding and monovalent CD3 binding for cancer immunotherapy," Oncoimmunology (2018) 7(1):e1377874.
Hellstrom et al., "Antitumor effects of L6, an IgG2a antibody that reacts with most human carcinomas," Proc Natl Acad Sci USA (1986) 83(18):7059-7063.
Hellstrom et al., "Strong antitumor activities of lgG3 antibodies to a human melanoma-associated ganglioside," Proc Natl Acad Sci USA (1985) 82(5):1499-1502.
Henry et al., "Stability-Diversity tradeoffs impose fundamental constraints on selection of synthetic human VH/VL single-domain antibodies from in vitro display libraries," Frontiers in Immunology (2017) 8:1-15.
Hermanson et al., "Heterobifunctional Cross-linkers," Bioconjugate Techniques (1996) 234-242.
Hernandez-Hoyos et al., "MOR209/ES414, a Novel Bispecific Antibody Targeting PSMA for the Treatment of Metastatic Castration-Resistant Prostate Cancer," Mol Cancer Ther (2016) 15(9):2155-2165.
Hinman et al. "Preparation and characterization of monoclonal antibody conjugates of the calicheamicins: a novel and potent family of antitumor antibiotics," Cancer Res. (1993) 53(14): 3336-3342.
Hinton et al., "Engineered Human IgG Antibodies with Longer Serum Half-lives in Primates," J. Biol. Chem. (2004) 279(8): 6213-6216.
Honegger et al., "Yet Another Numbering Scheme for Immunoglobulin Variable Domains: An Automatic Modeling and Analysis Tool," J Mol Biol. (2001) 309(3): 657-670.
Huet et al., "Multivalent nanobodies targeting death receptor 5 elicit superior tumor killing through efficient caspase induction," MABS (2014) 6(6):1560-70.
Huff et al., "The Evolving Role of CD8+CD28-Immunosenescent T cells in Cancer Immunology," Int J Mol Sci. (2019) 20(11):2810; 1-22.
Husain et al., "Expanding the boundaries of biotherapeutics with bispecific antibodies," Biodrugs (2018) 32(5):441-64.
Idusogie et al., "Engineered antibodies with increased activity to recruit complement," J Immunol (2001) 166(4):2571-2575.
IMGT Scientific Chart (IMGT®, the international ImMunoGeneTics information system®, http://www.imgt.org/IMGTScientificChart/Numbering/Hu_IGHGnber.html (created: May 17, 2001, last updated: Jan. 10, 2013).
Jendeberg et al., "Engineering of Fc(1) and Fc(3) from human immunoglobulin G to analyse subclass specificity for staphylococcal protein A," J Immnuol Methods (1997) 201(1):25-34.
Kabat et al., Sequences of Proteins of Immunological Interest, 5th Edition, U.S. Department of Health and Human Services, (1991) NIH Publication No. 91-3242, p. 689.
Kaneko et al., "Optimizing Therapeutic Antibody Function," Biodrugs (2011) 25(1):1-11.
Kashmiri et al., "SDR grafting—A New Approach to Antibody Humanization," Methods. (2005) 36: 25-34.
Kim et al., "Mutational approaches to improve the biophysical properties of human single-domain antibodies," Biochimica et Biophysica Acta (2014) 1844:1983-2001.
Kim et al., "Localization of the Site of the Murine IgGI Molecule That is Involved in Binding to the Murine Intestinal Fc Receptor," Eur. J. Immunol. (1994) 24:2429-2434.
Kindt, T.J. et al. (2007). "Antigens and Antibodies," Chapter 4 In Kuby Immunology 6th Ed., W.H. Freeman and Co., p. 91, 14 pages.
Klimka et al., "Human Anti-CD30 Recombinant Antibodies by Guided Phage Antibody Selection Using Cell Panning," Br. J. Cancer (2000) 83(2):252-260.
Kohler et al., "Continuous Culture of Fused Cells Secreting Antibody of Predefined Specificity," Nature (1975) 256:495-497.
Kumar et al., "Molecular cloning and expression of the Fabs of human autoantibodies in *Escherichia coli*," J. Biol. Chem. (2000) 275:35129-36.
Kuo et al., "Engineering a CD123xCD3 bispecific scFv immunofusion for the treatment of leukemia and elimination of leukemia stem cells," Protein Eng Des Sel. (2012) 25(10): 561-9.
La Rocca et al., "Zymographic detection and clinical correlations of MMP-2 and MMP-9 in breast cancer sera," British Journal of Cancer (2004) 90:1414-1421.
Lazar et al., "Engineered antibody Fc variants with enhanced effector function," Proc Natl Acad Sci USA (2006) 103(11):4005-4010.
Leaver-Fay et al., "Computationally Designed Bispecific Antibodies using Negative State Repertoires," Structure (2016) 24(4):641-651.
Lefranc et al., "IMGT unique numbering for immunoglobulin and T cell receptor variable domains and Ig superfamily V-like domains," Dev Comp Immunol (2003) 27(1):55-77.
Liu et al., "Eradication of Large Colon Tumor Xenografts by Targeted Delivery of Maytansinoids," Proc. Natl. Acad. Sci. USA (1996) 93: 8618-8623.
Lode et al., "Targeted therapy with a novel enediyene antibiotic calicheamicin theta(I)1 effectively suppresses growth and dissemination of liver metastases in a syngeneic model of murine neuroblastoma," Cancer Res. (1998) 58:2925-2928.
Ma et al., "Targeting immunotherapy for bladder cancer using anti-CD3x B7-H3 bispecific antibody," Cancer Med (2018) 7(10):5167-5177.
Maccallum et al., "Antibody-antigen interactions: Contact analysis and binding site topography," J. Mol. Biol. (1996) 262, 732-745.
Maeda et al., "Engineering of functional chimeric protein G-Vargula luciferase," Anal Biochem. (1997) 249(2):147-52.
Malia et al. "Epitope mapping and structural basis for the recognition of phosphorylated tau by the anti-tau antibody AT8." *Proteins: Structure, Function, and Bioinformatics* 84.4 (2016): 427-434.
Mandler et al., "Synthesis and evaluation of antiproliferative activity of a geldanamycin-Herceptin immunoconjugate," Bioorg Med Chem Lett. (2000) 10(10): 1025-1028.
Mandler et al., "Modifications in Synthesis Strategy Improve the Yield and Efficacy of Geldanamycin-Herceptin Immunoconjugates," Bioconjugate Chem. (2002) 13:786-791.

(56) References Cited

OTHER PUBLICATIONS

Mandler et al., "Immunoconjugates of Geldananlycin and Anti-HER2 Monoclonal Antibodies: Antiproliferative Activity on Human Breast Carcinoma Cell Lines," J. Nat. Cancer Inst. (2000) 92(19): 1573-1581.
Martin et al., "Modeling antibody hypervariable loops: a combined algorithm," Proc Natl Acad Sci U S A. (1989) 86(23): 9268-9272.
Mccafferty et al., "Phage antibodies: filamentous phage displaying antibody variable domains," Nature (1990) 348:552-554.
Merchant et al., "An efficient route to human bispecific IgG," Nat Biotechnol. (1998) 16(7):677-681.
Miller, "Protein-protein recognition and the association of immunoglobulin constant domains," JMB (1990) 216(4):965-973.
Moore et al., "A novel bispecific antibody format enables simultaneous bivalent and monovalent co-engagement of distinct target antigens," MAbs (2011) 3(6):546-557.
Moore et al., "Engineered Fc variant antibodies with enhanced ability to recruit complement and mediate effector functions," MAbs (2010) 2(2):181-189.
Natsume et al., "Engineered Antibodies of IgG1/IgG3 Mixed Isotype with Enhanced Cytotoxic Activities," Cancer Res (2008) 68(10):3863-3872.
Ohannesian et al., "Carcinoembryonic antigen and other glycoconjugates act as ligands for galectin-3 in human colon carcinoma cells," Cancer Res. (1995) 55(10): 2191-2199.
Osbourn, et al., "From Rodent Regents to Human Therapeutics Using Antibody Guided Selection," Methods. (2005) 36:61-68.
Padlan, "A possible procedure for reducing the immunogenicity of antibody variable domains while preserving their ligand-binding properties," Mol Immunol (1991) 28(4- 5):489-498.
Pessano, S et al., "The T3/T Cell Receptor Complex: Antigenic Distinction Between the Two 20-kd T3 (T3-δ and T3-ϵ) Subunits," The EMBO Journal (1985) 4(2):337-344.
Petkova et al., "Enhanced half-life of genetically engineered human IgG1 antibodies in a humanized FcRn mouse model: potential application in humorally mediated autoimmune disease," Int Immunol (2006) 18(12):1759-1769.
Portolano et al., "Lack of promiscuity in autoantigen-specific H and L chain combinations as revealed by human H and L chain "roulette"," J. Immunol. (1993) 150:880-887.
Presta et al., "Humanization of an Antibody Directed Against IgE," J. Immunol. (1993) 151(2): 2623-2632.
Queen et al., "A humanized antibody that binds to the interleukin 2 receptor," Proc Natl Acad Sci USA (1989) 86:10029-10033.
Ravetch et al., "Fc receptors," Annu Rev Immunol. (1991) 9:457-92.
Ridgway et al., "'Knobs-into-holes' engineering of antibody CH3 domains for heavy chain heterodimerization," Protein engineering (1996) 9(7):617-621.
Riechmann et al., "Reshaping Human Antibodies for Therapy," Nature (1988) 332: 323-327.
Rosenberg et al., "Use of Tumor-Infiltrating Lymphocytes and Interleukin-2 in the Immunotherapy of Patients With Metastatic Melanoma. A Preliminary Report," N Engl J Med. (1988) 319(25): 1676-1680.
Rosok et al., "A Combinatorial Library Strategy for the Rapid Humanization of Anticarcinoma BR96 Fab," J. Biol. Chem. (1996) 271(37): 22611-22618.
Rowland et al., "Drug Localisation and Growth Inhibition Studies of Vindesine-Monoclonal Anti-CEA Conjugates in a Human Tumour Xenograft," Cancer Immunol. Immunother. (1986) 21:183-187.
Schmiedel e tal. "Expression of a bispecific dsFv-dsFv' antibody fragment in *Escherichia coli*." Protein Engineering 13.10 (2000): 725-734.
Shields et al., "High Resolution Mapping of the Binding Site on Human IgG1 for FcyRI, FcyRII, FcyRIII, and FcRn and Design of IgG1 Variants with Improved Binding to the FcyR*," JBC (2001) 276(9):6591-6604.
Sims et al., "A Humanized CD18 Antibody Can Block Function Without Cell Destruction," J. Immunol. (1993) 151(4): 2296-2308.
Sitaraman et al., "High-throughput protein expression using cell-free system," Methods Mol. Biol. (2009) 498: 229-44.
Smith-Gill et al., "Contributions of immunoglobulin heavy and light chains to antibody specificity for lysozyme and two haptens," J. Immunol. (1987) 139:4135-44.
Song et al., "Light chain of natural antibody plays a dominant role in protein antigen binding," Biochem. Biophys. Res. Comm. (2000) 268:390-94.
Spirin, "High-Throughput Cell-Free Systems for Synthesis of Functionally Active Proteins," Trends Biotechnol. (2004) 22(10): 538-545.
Stavenhagen et al., "Enhancing the potency of therapeutic monoclonal antibodies via Fc optimization," Adv Enzyme Regul (2008) 48:152-164.
Stavenhagen et al., "Fc Optimization of Therapeutic Antibodies Enhances Their Ability to Kill Tumor Cells In vitro and Controls Tumor Expansion In vivo via Low-Affinity Activating Fcγ Receptors," Cancer Res (2007) 67(18):8882-8890.
Suntharalingam et al., "Cytokine Storm in a Phase 1 Trial of the Anti-CD28 Monoclonal Antibody TGN1412" N Engl J Med (2006) 355(10):1018-1028.
Taylor et al., "Nanocell targeting using engineered bispecific antibodies," Mabs (2015) 7(1):53-65.
Von Kreudenstein et al., "Improving biophysical properties of a bispecific antibody scaffold to aid developability: quality by molecular design," Mabs. (2013) 5(5):646-654.
Ward et al., "Binding activities of a repertoire of single immunoglobulin variable domains secreted from *Escherichia coli*," Nature (1989) 341:544-56. (This is not in any of the ISR nor specifications. Not sure where this came from?).
Weidle et al. "The intriguing options of multispecific antibody formats for treatment of cancer." *Cancer genomics & proteomics* 10.1 (2013): 1-18.
Xing et al., "BiHC, a T-Cell-Engaging Bispecific Recombinant Antibody, Has Potent Cytotoxic Activity Against Her2 Tumor Cells," Transl Oncol (2017) 10(5):780-785.
Zalevsky et al., "Enhanced antibody half-life improves in vivo activity," Nat Biotechnol (2010) 28(2):157-159.

* cited by examiner

SEQUENCE LISTING

<160> NUMBER OF SEQ ID NOS: 398

<210> SEQ ID NO 1
<211> LENGTH: 6
<212> TYPE: PRT
<213> ORGANISM: Artificial Sequence
<220> FEATURE:
<223> OTHER INFORMATION: linker

<400> SEQUENCE: 1

```
Gly Gly Ser Gly Gly Ser
1               5
```

<210> SEQ ID NO 2
<211> LENGTH: 9
<212> TYPE: PRT
<213> ORGANISM: Artificial Sequence
<220> FEATURE:
<223> OTHER INFORMATION: linker

<400> SEQUENCE: 2

```
Gly Gly Ser Gly Gly Ser Gly Gly Ser
1               5
```

<210> SEQ ID NO 3
<211> LENGTH: 12
<212> TYPE: PRT
<213> ORGANISM: Artificial Sequence
<220> FEATURE:
<223> OTHER INFORMATION: linker

<400> SEQUENCE: 3

```
Gly Gly Ser Gly Gly Ser Gly Gly Ser Gly Gly Ser
1               5                   10
```

<210> SEQ ID NO 4
<211> LENGTH: 15
<212> TYPE: PRT
<213> ORGANISM: Artificial Sequence
<220> FEATURE:
<223> OTHER INFORMATION: linker

<400> SEQUENCE: 4

```
Gly Gly Ser Gly Gly Ser Gly Gly Ser Gly Gly Ser Gly Gly Ser
1               5                   10                  15
```

<210> SEQ ID NO 5
<211> LENGTH: 4
<212> TYPE: PRT
<213> ORGANISM: Artificial Sequence
<220> FEATURE:
<223> OTHER INFORMATION: glycine linker

<400> SEQUENCE: 5

Gly Gly Gly Gly
1

<210> SEQ ID NO 6
<211> LENGTH: 5
<212> TYPE: PRT
<213> ORGANISM: Artificial Sequence
<220> FEATURE:
<223> OTHER INFORMATION: glycine linker

<400> SEQUENCE: 6

Gly Gly Gly Gly Gly
1 5

<210> SEQ ID NO 7
<211> LENGTH: 6
<212> TYPE: PRT
<213> ORGANISM: Artificial Sequence
<220> FEATURE:
<223> OTHER INFORMATION: glycine linker

<400> SEQUENCE: 7

Gly Gly Gly Gly Gly Gly
1 5

<210> SEQ ID NO 8
<211> LENGTH: 218
<212> TYPE: PRT
<213> ORGANISM: Artificial Sequence
<220> FEATURE:
<223> OTHER INFORMATION: human IgG1 Fc

<400> SEQUENCE: 8

Pro Ala Pro Glu Leu Leu Gly Gly Pro Ser Val Phe Leu Phe Pro Pro
1 5 10 15

Lys Pro Lys Asp Thr Leu Met Ile Ser Arg Thr Pro Glu Val Thr Cys
20 25 30

Val Val Val Asp Val Ser His Glu Asp Pro Glu Val Lys Phe Asn Trp
35 40 45

Tyr Val Asp Gly Val Glu Val His Asn Ala Lys Thr Lys Pro Arg Glu
50 55 60

Glu Gln Tyr Asn Ser Thr Tyr Arg Val Val Ser Val Leu Thr Val Leu
65 70 75 80

His Gln Asp Trp Leu Asn Gly Lys Glu Tyr Lys Cys Lys Val Ser Asn
85 90 95

Lys Ala Leu Pro Ala Pro Ile Glu Lys Thr Ile Ser Lys Ala Lys Gly
100 105 110

Gln Pro Arg Glu Pro Gln Val Tyr Thr Leu Pro Pro Ser Arg Asp Glu
115 120 125

Leu Thr Lys Asn Gln Val Ser Leu Thr Cys Leu Val Lys Gly Phe Tyr
130 135 140

Pro Ser Asp Ile Ala Val Glu Trp Glu Ser Asn Gly Gln Pro Glu Asn
145 150 155 160

Asn Tyr Lys Thr Thr Pro Pro Val Leu Asp Ser Asp Gly Ser Phe Phe
165 170 175

Leu Tyr Ser Lys Leu Thr Val Asp Lys Ser Arg Trp Gln Gln Gly Asn
180 185 190

Val Phe Ser Cys Ser Val Met His Glu Ala Leu His Asn His Tyr Thr
195 200 205

```
Gln Lys Ser Leu Ser Leu Ser Pro Gly Lys
    210                 215


<210> SEQ ID NO 9
<211> LENGTH: 215
<212> TYPE: PRT
<213> ORGANISM: Artificial Sequence
<220> FEATURE:
<223> OTHER INFORMATION: Fc xELL

<400> SEQUENCE: 9

Pro Ala Pro Gly Gly Pro Ser Val Phe Leu Phe Pro Pro Lys Pro Lys
1               5                   10                  15

Asp Thr Leu Met Ile Ser Arg Thr Pro Glu Val Thr Cys Val Val Val
            20                  25                  30

Asp Val Ser His Glu Asp Pro Glu Val Lys Phe Asn Trp Tyr Val Asp
        35                  40                  45

Gly Val Glu Val His Asn Ala Lys Thr Lys Pro Arg Glu Glu Gln Tyr
    50                  55                  60

Asn Ser Thr Tyr Arg Val Val Ser Val Leu Thr Val Leu His Gln Asp
65                  70                  75                  80

Trp Leu Asn Gly Lys Glu Tyr Lys Cys Lys Val Ser Asn Lys Ala Leu
                85                  90                  95

Pro Ala Pro Ile Glu Lys Thr Ile Ser Lys Ala Lys Gly Gln Pro Arg
            100                 105                 110

Glu Pro Gln Val Tyr Thr Leu Pro Pro Ser Arg Asp Glu Leu Thr Lys
        115                 120                 125

Asn Gln Val Ser Leu Thr Cys Leu Val Lys Gly Phe Tyr Pro Ser Asp
    130                 135                 140

Ile Ala Val Glu Trp Glu Ser Asn Gly Gln Pro Glu Asn Asn Tyr Lys
145                 150                 155                 160

Thr Thr Pro Pro Val Leu Asp Ser Asp Gly Ser Phe Phe Leu Tyr Ser
                165                 170                 175

Lys Leu Thr Val Asp Lys Ser Arg Trp Gln Gln Gly Asn Val Phe Ser
            180                 185                 190

Cys Ser Val Met His Glu Ala Leu His Asn His Tyr Thr Gln Lys Ser
        195                 200                 205

Leu Ser Leu Ser Pro Gly Lys
    210                 215


<210> SEQ ID NO 10
<211> LENGTH: 217
<212> TYPE: PRT
<213> ORGANISM: Artificial Sequence
<220> FEATURE:
<223> OTHER INFORMATION: human IgG2 Fc

<400> SEQUENCE: 10

Pro Ala Pro Pro Val Ala Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Gln Phe Asn Trp Tyr
        35                  40                  45

Val Asp Gly Val Glu Val His Asn Ala Lys Thr Lys Pro Arg Glu Glu
    50                  55                  60

Gln Phe Asn Ser Thr Phe Arg Val Val Ser Val Leu Thr Val Val His
65                  70                  75                  80
```

```
Gln Asp Trp Leu Asn Gly Lys Glu Tyr Lys Cys Lys Val Ser Asn Lys
                85                  90                  95

Gly Leu Pro Ala Pro Ile Glu Lys Thr Ile Ser Lys Thr Lys Gly Gln
            100                 105                 110

Pro Arg Glu Pro Gln Val Tyr Thr Leu Pro Pro Ser Arg Glu Glu Met
        115                 120                 125

Thr Lys Asn Gln Val Ser Leu Thr Cys Leu Val Lys Gly Phe Tyr Pro
    130                 135                 140

Ser Asp Ile Ser Val Glu Trp Glu Ser Asn Gly Gln Pro Glu Asn Asn
145                 150                 155                 160

Tyr Lys Thr Thr Pro Pro Met Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly Lys
    210                 215


<210> SEQ ID NO 11
<211> LENGTH: 218
<212> TYPE: PRT
<213> ORGANISM: Artificial Sequence
<220> FEATURE:
<223> OTHER INFORMATION: human IgG3 Fc

<400> SEQUENCE: 11

Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser His Glu Asp Pro Glu Val Gln Phe Lys Trp
        35                  40                  45

Tyr Val Asp Gly Val Glu Val His Asn Ala Lys Thr Lys Pro Arg Glu
    50                  55                  60

Glu Gln Tyr Asn Ser Thr Phe Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Ala Leu Pro Ala Pro Ile Glu Lys Thr Ile Ser Lys Thr Lys Gly
            100                 105                 110

Gln Pro Arg Glu Pro Gln Val Tyr Thr Leu Pro Pro Ser Arg Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Ser Gly Gln Pro Glu Asn
145                 150                 155                 160

Asn Tyr Asn Thr Thr Pro Pro Met Leu Asp Ser Asp Gly Ser Phe Phe
                165                 170                 175

Leu Tyr Ser Lys Leu Thr Val Asp Lys Ser Arg Trp Gln Gln Gly Asn
            180                 185                 190

Ile Phe Ser Cys Ser Val Met His Glu Ala Leu His Asn Arg Phe Thr
        195                 200                 205

Gln Lys Ser Leu Ser Leu Ser Pro Gly Lys
    210                 215
```

<210> SEQ ID NO 12
<211> LENGTH: 218
<212> TYPE: PRT
<213> ORGANISM: Artificial Sequence
<220> FEATURE:
<223> OTHER INFORMATION: human IgG4 Fc

<400> SEQUENCE: 12

```
Pro Ala Pro Glu Phe Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
                85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Lys Ser Leu Ser Leu Ser Leu Gly Lys
    210                 215
```

<210> SEQ ID NO 13
<211> LENGTH: 218
<212> TYPE: PRT
<213> ORGANISM: Artificial Sequence
<220> FEATURE:
<223> OTHER INFORMATION: human IgG4 Fc

<400> SEQUENCE: 13

```
Pro Ala Pro Glu Leu Leu Gly Gly Pro Ser Val Phe Leu Phe Pro Pro
1               5                   10                  15

Lys Pro Lys Asp Thr Leu Met Ile Ser Arg Thr Pro Glu Val Thr Cys
            20                  25                  30

Val Val Val Asp Val Ser Gln Glu Asp Pro Glu Val Gln Phe Asn Trp
        35                  40                  45

Tyr Val Asp Gly Val Glu Val His Asn Ala Lys Thr Lys Pro Arg Glu
    50                  55                  60

Glu Gln Phe Asn Ser Thr Tyr Arg Val Val Ser Val Leu Thr Val Leu
65                  70                  75                  80

His Gln Asp Trp Leu Asn Gly Lys Glu Tyr Lys Cys Lys Val Ser Asn
```

```
                85                  90                  95

Lys Gly Leu Pro Ser Ser Ile Glu Lys Thr Ile Ser Lys Ala Lys Gly
            100                 105                 110

Gln Pro Arg Glu Pro Gln Val Tyr Thr Leu Pro Pro Ser Gln Glu Glu
        115                 120                 125

Met Thr Lys Asn Gln Val Ser Leu Thr Cys Leu Val Lys Gly Phe Tyr
    130                 135                 140

Pro Ser Asp Ile Ala Val Glu Trp Glu Ser Asn Gly Gln Pro Glu Asn
145                 150                 155                 160

Asn Tyr Lys Thr Thr Pro Pro Val Leu Asp Ser Asp Gly Ser Phe Phe
                165                 170                 175

Leu Tyr Ser Arg Leu Thr Val Asp Lys Ser Arg Trp Gln Glu Gly Asn
            180                 185                 190

Val Phe Ser Cys Ser Val Met His Glu Ala Leu His Asn His Tyr Thr
        195                 200                 205

Gln Lys Ser Leu Ser Leu Ser Leu Gly Lys
    210                 215


<210> SEQ ID NO 14
<211> LENGTH: 14
<212> TYPE: PRT
<213> ORGANISM: Artificial Sequence
<220> FEATURE:
<223> OTHER INFORMATION: modified IgG1 hinge

<400> SEQUENCE: 14

Glu Pro Lys Ser Ser Asp Lys Thr His Thr Cys Pro Pro Cys
1               5                   10


<210> SEQ ID NO 15
<211> LENGTH: 9
<212> TYPE: PRT
<213> ORGANISM: Artificial Sequence
<220> FEATURE:
<223> OTHER INFORMATION: truncated IgG1 hinge

<400> SEQUENCE: 15

Asp Lys Thr His Thr Cys Pro Pro Cys
1               5


<210> SEQ ID NO 16
<211> LENGTH: 11
<212> TYPE: PRT
<213> ORGANISM: Artificial Sequence
<220> FEATURE:
<223> OTHER INFORMATION: modified IgG4 hinge

<400> SEQUENCE: 16

Glu Ser Lys Tyr Gly Pro Pro Cys Pro Pro Cys
1               5                   10


<210> SEQ ID NO 17
<211> LENGTH: 12
<212> TYPE: PRT
<213> ORGANISM: Artificial Sequence
<220> FEATURE:
<223> OTHER INFORMATION: carboxy-terminal sequence

<400> SEQUENCE: 17

Gly Gln Gly Thr Leu Val Thr Val Lys Pro Gly Gly
1               5                   10
```

<210> SEQ ID NO 18
<211> LENGTH: 12
<212> TYPE: PRT
<213> ORGANISM: Artificial Sequence
<220> FEATURE:
<223> OTHER INFORMATION: carboxy-terminal sequence

<400> SEQUENCE: 18

Gly Gln Gly Thr Leu Val Thr Val Glu Pro Gly Gly
1               5                   10

<210> SEQ ID NO 19
<211> LENGTH: 119
<212> TYPE: PRT
<213> ORGANISM: Artificial Sequence
<220> FEATURE:
<223> OTHER INFORMATION: OKT3 VH

<400> SEQUENCE: 19

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Cys Leu Asp Tyr Trp Gly Gln Gly
            100                 105                 110

Thr Pro Val Thr Val Ser Ser
        115

<210> SEQ ID NO 20
<211> LENGTH: 106
<212> TYPE: PRT
<213> ORGANISM: Artificial Sequence
<220> FEATURE:
<223> OTHER INFORMATION: OKT3 VL

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Ser Ala Ser Ser Ser Val Ser Tyr Met
            20                  25                  30

Asn Trp Tyr Gln Gln Thr Pro Gly Lys Ala Pro Lys Arg Trp Ile Tyr
        35                  40                  45

Asp Thr Ser Lys Leu Ala Ser Gly Val Pro Ser Arg Phe Ser Gly Ser
    50                  55                  60

Gly Ser Gly Thr Asp Tyr Thr Phe Thr Ile Ser Ser Leu Gln Pro Glu
65                  70                  75                  80

Asp Ile Ala Thr Tyr Tyr Cys Gln Gln Trp Ser Ser Asn Pro Phe Thr
                85                  90                  95

Phe Gly Gln Gly Thr Lys Leu Gln Ile Thr
            100                 105

<210> SEQ ID NO 21

```
<211> LENGTH: 119
<212> TYPE: PRT
<213> ORGANISM: Artificial Sequence
<220> FEATURE:
<223> OTHER INFORMATION: OKT3 humanized VH

<400> SEQUENCE: 21

Gln Val Gln Leu Val Gln Ser Gly Gly Gly Val Val Gln Pro Gly Arg
1               5                   10                  15

Ser Leu Arg Leu Ser Cys Lys Ala Ser Gly Tyr Thr Phe Thr Arg Tyr
            20                  25                  30

Thr Met His Trp Val Arg Gln Ala Pro Gly Lys Gly Leu Glu Trp Ile
        35                  40                  45

Gly Tyr Ile Asn Pro Ser Arg Gly Tyr Thr Asn Tyr Asn Gln Lys Val
    50                  55                  60

Lys Asp Arg Phe Thr Ile Ser Arg Asp Asn Ser Lys Asn Thr Ala Phe
65                  70                  75                  80

Leu Gln Met Asp Ser Leu Arg Pro Glu Asp Thr Gly Val Tyr Phe Cys
                85                  90                  95

Ala Arg Tyr Tyr Asp Asp His Tyr Ser Leu Asp Tyr Trp Gly Gln Gly
            100                 105                 110

Thr Pro Val Thr Val Ser Ser
        115


<210> SEQ ID NO 22
<211> LENGTH: 119
<212> TYPE: PRT
<213> ORGANISM: Artificial Sequence
<220> FEATURE:
<223> OTHER INFORMATION: OKT3 humanized VH

<400> SEQUENCE: 22

Asp Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Arg Tyr
            20                  25                  30

Thr Met His Trp Val Arg Gln Ala Pro Gly Gln Gly Leu Glu Trp Ile
        35                  40                  45

Gly Tyr Ile Asn Pro Ser Arg Gly Tyr Thr Asn Tyr Ala Asp Ser Val
    50                  55                  60

Lys Gly Arg Phe Thr Ile Thr Thr Asp Lys Ser Thr Ser Thr Ala Tyr
65                  70                  75                  80

Met Glu Leu Ser Ser Leu Arg Ser Glu Asp Thr Ala Thr Tyr Tyr Cys
                85                  90                  95

Ala Arg Tyr Tyr Asp Asp His Tyr Cys Leu Asp Tyr Trp Gly Gln Gly
            100                 105                 110

Thr Thr Val Thr Val Ser Ser
        115


<210> SEQ ID NO 23
<211> LENGTH: 119
<212> TYPE: PRT
<213> ORGANISM: Artificial Sequence
<220> FEATURE:
<223> OTHER INFORMATION: OKT3 humanized VH

<400> SEQUENCE: 23

Gln Val Gln Leu Val Gln Ser Gly Ala Glu Leu Lys Lys Pro Gly Ala
1               5                   10                  15
```

```
Ser Val Lys Val Ser Cys Lys Ala Ser Gly Tyr Thr Phe Thr Arg Tyr
            20                  25                  30

Thr Met His Trp Val Arg Gln Ala Pro Gly Gln Cys Leu Glu Trp Met
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Ala Asp Lys Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Leu Val Thr Val Ser Ser
        115


<210> SEQ ID NO 24
<211> LENGTH: 106
<212> TYPE: PRT
<213> ORGANISM: Artificial Sequence
<220> FEATURE:
<223> OTHER INFORMATION: OKT3 humanized VL

<400> SEQUENCE: 24

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn
            100                 105


<210> SEQ ID NO 25
<211> LENGTH: 106
<212> TYPE: PRT
<213> ORGANISM: Artificial Sequence
<220> FEATURE:
<223> OTHER INFORMATION: OKT3 humanized VL

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Val Ala Ser Gly Val Pro Ala Arg Phe Ser Gly Ser
    50                  55                  60

Gly Ser Gly Thr Asp Tyr Ser Leu Thr Ile Asn Ser Leu Glu Ala Glu
65                  70                  75                  80

Asp Ala Ala Thr Tyr Tyr Cys Gln Gln Trp Ser Ser Asn Pro Leu Thr
                85                  90                  95
```

```
Phe Gly Gly Gly Thr Lys Val Glu Ile Lys
            100                 105


<210> SEQ ID NO 26
<211> LENGTH: 108
<212> TYPE: PRT
<213> ORGANISM: Artificial Sequence
<220> FEATURE:
<223> OTHER INFORMATION: OKT3 humanized VL

<400> SEQUENCE: 26

Asp Ile Gln Leu Thr Gln Ser Pro Ser Ile Leu Ser Ala Ser Val Gly
1               5                   10                  15

Asp Arg Val Thr Ile Thr Cys Arg Ala Ser Ser Ser Val Ser Tyr Met
            20                  25                  30

Asn Trp Tyr Gln Gln Lys Pro Gly Lys Ala Pro Lys Arg Trp Ile Tyr
        35                  40                  45

Asp Thr Ser Lys Val Ala Ser Gly Val Pro Tyr Arg Phe Ser Gly Ser
    50                  55                  60

Gly Ser Gly Thr Glu Tyr Thr Leu Thr Ile Ser Ser Met Gln Pro Glu
65                  70                  75                  80

Asp Phe Ala Thr Tyr Tyr Cys Gln Gln Trp Ser Ser Asn Pro Leu Thr
                85                  90                  95

Phe Gly Cys Gly Thr Lys Val Glu Ile Lys Arg Thr
            100                 105


<210> SEQ ID NO 27
<211> LENGTH: 125
<212> TYPE: PRT
<213> ORGANISM: Artificial Sequence
<220> FEATURE:
<223> OTHER INFORMATION: anti-CD3 Hv

<400> SEQUENCE: 27

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ala
        115                 120                 125


<210> SEQ ID NO 28
<211> LENGTH: 109
<212> TYPE: PRT
<213> ORGANISM: Artificial Sequence
<220> FEATURE:
<223> OTHER INFORMATION: anti-CD3 Lv

<400> SEQUENCE: 28
```

```
Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105


<210> SEQ ID NO 29
<211> LENGTH: 5
<212> TYPE: PRT
<213> ORGANISM: Artificial Sequence
<220> FEATURE:
<223> OTHER INFORMATION: anti-CD3 VH CDR1

<400> SEQUENCE: 29

Thr Tyr Ala Met Asn
1               5


<210> SEQ ID NO 30
<211> LENGTH: 19
<212> TYPE: PRT
<213> ORGANISM: Artificial Sequence
<220> FEATURE:
<223> OTHER INFORMATION: anti-CD3 VH CDR2

<400> SEQUENCE: 30

Arg Ile Arg Ser Lys Tyr Asn Asn Tyr Ala Thr Tyr Tyr Ala Asp Ser
1               5                   10                  15

Val Lys Asp


<210> SEQ ID NO 31
<211> LENGTH: 14
<212> TYPE: PRT
<213> ORGANISM: Artificial Sequence
<220> FEATURE:
<223> OTHER INFORMATION: anti-CD3 VH CDR3

<400> SEQUENCE: 31

His Gly Asn Phe Gly Asn Ser Tyr Val Ser Trp Phe Ala Tyr
1               5                   10


<210> SEQ ID NO 32
<211> LENGTH: 14
<212> TYPE: PRT
<213> ORGANISM: Artificial Sequence
<220> FEATURE:
<223> OTHER INFORMATION: anti-CD3 VL CDR1

<400> SEQUENCE: 32

Arg Ser Ser Thr Gly Ala Val Thr Thr Ser Asn Tyr Ala Asn
1               5                   10


<210> SEQ ID NO 33
<211> LENGTH: 7
<212> TYPE: PRT
```

<213> ORGANISM: Artificial Sequence
<220> FEATURE:
<223> OTHER INFORMATION: anti-CD3 VL CDR2

<400> SEQUENCE: 33

Gly Thr Asn Lys Arg Ala Pro
1 5

<210> SEQ ID NO 34
<211> LENGTH: 9
<212> TYPE: PRT
<213> ORGANISM: Artificial Sequence
<220> FEATURE:
<223> OTHER INFORMATION: anti-CD3 VL CDR3

<400> SEQUENCE: 34

Ala Leu Trp Tyr Ser Asn Leu Trp Val
1 5

<210> SEQ ID NO 35
<211> LENGTH: 125
<212> TYPE: PRT
<213> ORGANISM: Artificial Sequence
<220> FEATURE:
<223> OTHER INFORMATION: anti-CD3 VH1

<400> SEQUENCE: 35

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Gly Leu Glu Trp Val
35 40 45

Gly Arg Ile Arg Ser Lys Tyr Asn Asn Tyr Ala Thr Tyr Tyr Ala Asp
50 55 60

Ser Val Lys Asp Arg Phe Thr Ile Ser Arg Asp Asp Ser Lys Asn Ser
65 70 75 80

Leu Tyr Leu Gln Met Asn Ser Leu Lys Thr Glu Asp Thr Ala Val Tyr
85 90 95

Tyr Cys Val Arg His Gly Asn Phe Gly Asn Ser Tyr Val Ser Trp Phe
100 105 110

Ala Tyr Trp Gly Gln Gly Thr Leu Val Thr Val Ser Ser
115 120 125

<210> SEQ ID NO 36
<211> LENGTH: 125
<212> TYPE: PRT
<213> ORGANISM: Artificial Sequence
<220> FEATURE:
<223> OTHER INFORMATION: anti-CD3 VH2

<400> SEQUENCE: 36

Glu Val Lys Leu Val Glu Ser Gly Gly Gly Leu Val Gln Pro Gly Gly
1 5 10 15

Ser Leu Arg Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Asp Arg Phe Thr Ile Ser Arg Asp Asp Ser Lys Ser Ser

```
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125


<210> SEQ ID NO 37
<211> LENGTH: 125
<212> TYPE: PRT
<213> ORGANISM: Artificial Sequence
<220> FEATURE:
<223> OTHER INFORMATION: anti-CD3 VH3

<400> SEQUENCE: 37

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125


<210> SEQ ID NO 38
<211> LENGTH: 125
<212> TYPE: PRT
<213> ORGANISM: Artificial Sequence
<220> FEATURE:
<223> OTHER INFORMATION: anti-CD3 VH4

<400> SEQUENCE: 38

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 39
<211> LENGTH: 125
<212> TYPE: PRT
<213> ORGANISM: Artificial Sequence
<220> FEATURE:
<223> OTHER INFORMATION: anti-CD3 VH5

<400> SEQUENCE: 39

```
Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 40
<211> LENGTH: 125
<212> TYPE: PRT
<213> ORGANISM: Artificial Sequence
<220> FEATURE:
<223> OTHER INFORMATION: anti-CD3 VH6

<400> SEQUENCE: 40

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 41
<211> LENGTH: 125
<212> TYPE: PRT
<213> ORGANISM: Artificial Sequence
<220> FEATURE:
<223> OTHER INFORMATION: anti-CD3 VH7

<400> SEQUENCE: 41

```
Glu Val Gln Leu Val Glu Ser Gly Gly Gly Leu Val Gln Pro Gly Gly
```

1 5 10 15

Ser Leu Arg Leu Ser Cys Ala Ala Ser Gly Phe Thr Phe Ser Thr Tyr
20 25 30

Ala Met Ser Trp Val Arg Gln Ala Pro Gly Lys Gly Leu Glu Trp Val
35 40 45

Gly Arg Ile Arg Ser Lys Tyr Asn Asn Tyr Ala Thr Tyr Tyr Ala Asp
50 55 60

Ser Val Lys Gly Arg Phe Thr Ile Ser Arg Asp Asp Ser Lys Asn Thr
65 70 75 80

Leu Tyr Leu Gln Met Asn Ser Leu Arg Ala Glu Asp Thr Ala Val Tyr
85 90 95

Tyr Cys Val Arg His Gly Asn Phe Gly Asp Ser Tyr Val Ser Trp Phe
100 105 110

Ala Tyr Trp Gly Gln Gly Thr Leu Val Thr Val Ser Ser
115 120 125

<210> SEQ ID NO 42
<211> LENGTH: 124
<212> TYPE: PRT
<213> ORGANISM: Artificial Sequence
<220> FEATURE:
<223> OTHER INFORMATION: anti-CD3 VH8

<400> SEQUENCE: 42

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Asn Lys Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

Ser Val Lys Asp Arg Phe Thr Ile Ser Arg Asp Asp Ser Lys Asn Thr
65 70 75 80

Ala Tyr Leu Gln Met Asn Asn Leu Lys Thr Glu Asp Thr Ala Val Tyr
85 90 95

Tyr Cys Val Arg His Gly Asn Phe Gly Asn Ser Tyr Ile Ser Tyr Trp
100 105 110

Ala Tyr Trp Gly Gln Gly Thr Leu Val Thr Val Ser
115 120

<210> SEQ ID NO 43
<211> LENGTH: 125
<212> TYPE: PRT
<213> ORGANISM: Artificial Sequence
<220> FEATURE:
<223> OTHER INFORMATION: anti-CD3 VH9

<400> SEQUENCE: 43

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Thr Tyr
20 25 30

Ala Met Asn Trp Val Arg Gln Ala Pro Gly Lys Gly Leu Glu Trp Val
35 40 45

Ala Arg Ile Arg Ser Lys Tyr Asn Asn Tyr Ala Thr Tyr Tyr Ala Asp
50 55 60

```
Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Thr Val Thr Val Ser Ser
        115                 120                 125


<210> SEQ ID NO 44
<211> LENGTH: 125
<212> TYPE: PRT
<213> ORGANISM: Artificial Sequence
<220> FEATURE:
<223> OTHER INFORMATION: anti-CD3 VH10

<400> SEQUENCE: 44

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser
        115                 120                 125


<210> SEQ ID NO 45
<211> LENGTH: 125
<212> TYPE: PRT
<213> ORGANISM: Artificial Sequence
<220> FEATURE:
<223> OTHER INFORMATION: anti-CD3 VH11

<400> SEQUENCE: 45

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 46
<211> LENGTH: 125
<212> TYPE: PRT
<213> ORGANISM: Artificial Sequence
<220> FEATURE:
<223> OTHER INFORMATION: anti-CD3 VH12

<400> SEQUENCE: 46

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Lys Pro
        115                 120                 125
```

<210> SEQ ID NO 47
<211> LENGTH: 125
<212> TYPE: PRT
<213> ORGANISM: Artificial Sequence
<220> FEATURE:
<223> OTHER INFORMATION: anti-CD3 VH13

<400> SEQUENCE: 47

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Lys Pro
        115                 120                 125
```

<210> SEQ ID NO 48
<211> LENGTH: 125
<212> TYPE: PRT
<213> ORGANISM: Artificial Sequence
<220> FEATURE:
<223> OTHER INFORMATION: anti-CD3 VH14

<400> SEQUENCE: 48

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Cys Gly Thr Leu Val Thr Val Lys Pro
        115                 120                 125


<210> SEQ ID NO 49
<211> LENGTH: 125
<212> TYPE: PRT
<213> ORGANISM: Artificial Sequence
<220> FEATURE:
<223> OTHER INFORMATION: anti-CD3 VH15

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125


<210> SEQ ID NO 50
<211> LENGTH: 125
<212> TYPE: PRT
<213> ORGANISM: Artificial Sequence
<220> FEATURE:
<223> OTHER INFORMATION: anti-CD3 VH16

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60
```

```
Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 51
<211> LENGTH: 125
<212> TYPE: PRT
<213> ORGANISM: Artificial Sequence
<220> FEATURE:
<223> OTHER INFORMATION: anti-CD3 VH17

<400> SEQUENCE: 51

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 52
<211> LENGTH: 125
<212> TYPE: PRT
<213> ORGANISM: Artificial Sequence
<220> FEATURE:
<223> OTHER INFORMATION: anti-CD3 VH18

<400> SEQUENCE: 52

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
```

115 120 125

<210> SEQ ID NO 53
<211> LENGTH: 125
<212> TYPE: PRT
<213> ORGANISM: Artificial Sequence
<220> FEATURE:
<223> OTHER INFORMATION: anti-CD3 VH19

<400> SEQUENCE: 53

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Thr Tyr
20 25 30

Ala Met Asn Trp Val Arg Gln Ala Pro Gly Lys Cys Leu Glu Trp Val
35 40 45

Ser Arg Ile Arg Ser Lys Tyr Asn Asn Tyr Ala Thr Tyr Tyr Ala Asp
50 55 60

Ser Val Lys Gly Arg Phe Thr Ile Ser Arg Asp Asp Ala Lys Asn Thr
65 70 75 80

Leu Tyr Leu Gln Met Ser Ser Leu Arg Ala Glu Asp Thr Ala Val Tyr
85 90 95

Tyr Cys Val Arg His Gly Asn Phe Gly Asn Ser Tyr Val Ser Trp Phe
100 105 110

Ala Tyr Trp Gly Gln Gly Thr Leu Val Thr Val Ser Ser
115 120 125

<210> SEQ ID NO 54
<211> LENGTH: 125
<212> TYPE: PRT
<213> ORGANISM: Artificial Sequence
<220> FEATURE:
<223> OTHER INFORMATION: anti-CD3 VH20

<400> SEQUENCE: 54

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Thr Tyr
20 25 30

Ala Met Asn Trp Val Arg Gln Ala Pro Gly Lys Cys Leu Glu Trp Val
35 40 45

Ser Arg Ile Arg Ser Lys Tyr Asn Asn Tyr Ala Thr Tyr Tyr Ala Asp
50 55 60

Ser Val Lys Gly Arg Phe Thr Ile Ser Arg Asp Asp Ala Lys Asn Thr
65 70 75 80

Leu Tyr Leu Gln Met Ser Ser Leu Arg Ala Glu Asp Thr Ala Val Tyr
85 90 95

Tyr Cys Val Arg His Gly Asn Phe Gly Asn Ser Tyr Val Ser Trp Phe
100 105 110

Ala Tyr Trp Gly Gln Gly Thr Leu Val Thr Val Ser Ser
115 120 125

<210> SEQ ID NO 55
<211> LENGTH: 125
<212> TYPE: PRT
<213> ORGANISM: Artificial Sequence
<220> FEATURE:
<223> OTHER INFORMATION: anti-CD3 VH21

<400> SEQUENCE: 55

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Asn Ser
65                  70                  75                  80

Leu Tyr Leu Gln Met Asn Ser Leu Lys Thr Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 56
<211> LENGTH: 125
<212> TYPE: PRT
<213> ORGANISM: Artificial Sequence
<220> FEATURE:
<223> OTHER INFORMATION: anti-CD3 VH22

<400> SEQUENCE: 56

```
Glu Val Lys Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ser
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 57
<211> LENGTH: 125
<212> TYPE: PRT
<213> ORGANISM: Artificial Sequence
<220> FEATURE:
<223> OTHER INFORMATION: anti-CD3 VH23

<400> SEQUENCE: 57

```
Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
```

```
    50                  55                  60

Ser Val Lys Asp Arg Phe Thr Ile Ser Arg Asp Asp Ser Lys Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125


<210> SEQ ID NO 58
<211> LENGTH: 125
<212> TYPE: PRT
<213> ORGANISM: Artificial Sequence
<220> FEATURE:
<223> OTHER INFORMATION: anti-CD3 VH24

<400> SEQUENCE: 58

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125


<210> SEQ ID NO 59
<211> LENGTH: 125
<212> TYPE: PRT
<213> ORGANISM: Artificial Sequence
<220> FEATURE:
<223> OTHER INFORMATION: anti-CD3 VH25

<400> SEQUENCE: 59

Glu Val Lys Leu Val Glu Ser Gly Gly Gly Leu Val Lys Pro Gly Arg
1               5                   10                  15

Ser Leu Arg Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Lys Ser Ile
65                  70                  75                  80

Leu Tyr Leu Gln Met Asn Ser Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110
```

```
Ala Tyr Trp Gly Gln Gly Thr Leu Val Thr Val Ser Ser
        115                 120                 125


<210> SEQ ID NO 60
<211> LENGTH: 125
<212> TYPE: PRT
<213> ORGANISM: Artificial Sequence
<220> FEATURE:
<223> OTHER INFORMATION: anti-CD3 VH26

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Ser Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125


<210> SEQ ID NO 61
<211> LENGTH: 125
<212> TYPE: PRT
<213> ORGANISM: Artificial Sequence
<220> FEATURE:
<223> OTHER INFORMATION: anti-CD3 VH27

<400> SEQUENCE: 61

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Ser Trp Val Arg Gln Ala Pro Gly Lys Cys Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125


<210> SEQ ID NO 62
<211> LENGTH: 124
<212> TYPE: PRT
<213> ORGANISM: Artificial Sequence
<220> FEATURE:
<223> OTHER INFORMATION: anti-CD3 VH28
```

<400> SEQUENCE: 62

Glu Val Gln Leu Val Glu Ser Gly Gly Gly Leu Val Gln Pro Gly Gly
1 5 10 15

Ser Leu Lys Leu Ser Cys Ala Ala Ser Gly Phe Thr Phe Asn Lys Tyr
20 25 30

Ala Met Asn Trp Val Arg Gln Ala Pro Gly Lys Cys Leu Glu Trp Val
35 40 45

Ala Arg Ile Arg Ser Lys Tyr Asn Asn Tyr Ala Thr Tyr Tyr Ala Asp
50 55 60

Ser Val Lys Asp Arg Phe Thr Ile Ser Arg Asp Asp Ser Lys Asn Thr
65 70 75 80

Ala Tyr Leu Gln Met Asn Asn Leu Lys Thr Glu Asp Thr Ala Val Tyr
85 90 95

Tyr Cys Val Arg His Gly Asn Phe Gly Asn Ser Tyr Ile Ser Tyr Trp
100 105 110

Ala Tyr Trp Gly Gln Gly Thr Leu Val Thr Val Ser
115 120

<210> SEQ ID NO 63
<211> LENGTH: 125
<212> TYPE: PRT
<213> ORGANISM: Artificial Sequence
<220> FEATURE:
<223> OTHER INFORMATION: anti-CD3 VH29

<400> SEQUENCE: 63

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Thr Tyr
20 25 30

Ala Met Asn Trp Val Arg Gln Ala Pro Gly Lys Cys Leu Glu Trp Val
35 40 45

Ala Arg Ile Arg Ser Lys Tyr Asn Asn Tyr Ala Thr Tyr Tyr Ala Asp
50 55 60

Ser Val Lys Gly Arg Phe Thr Ile Ser Arg Asp Asp Ser Lys Asn Thr
65 70 75 80

Leu Tyr Leu Gln Met Asn Ser Leu Arg Ala Glu Asp Thr Ala Val Tyr
85 90 95

Tyr Cys Val Arg His Gly Asn Phe Gly Asn Ser Tyr Val Ser Trp Phe
100 105 110

Ala Tyr Trp Gly Gln Gly Thr Thr Val Thr Val Ser Ser
115 120 125

<210> SEQ ID NO 64
<211> LENGTH: 125
<212> TYPE: PRT
<213> ORGANISM: Artificial Sequence
<220> FEATURE:
<223> OTHER INFORMATION: anti-CD3 VH30

<400> SEQUENCE: 64

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Asn Thr Tyr
20 25 30

Ala Met Asn Trp Val Arg Gln Ala Pro Gly Lys Cys Leu Glu Trp Val
35 40 45

```
Ala Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asn Ser Tyr Val Ser Tyr Phe
            100                 105                 110

Ala Tyr Trp Gly Gln Gly Thr Thr Val Thr Val Ser Ser
        115                 120                 125
```

```
<210> SEQ ID NO 65
<211> LENGTH: 125
<212> TYPE: PRT
<213> ORGANISM: Artificial Sequence
<220> FEATURE:
<223> OTHER INFORMATION: anti-CD3 VH31

<400> SEQUENCE: 65

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Ser Val Lys Asp Arg Phe Thr Ile Ser Arg Asp Asp Ser Gln Ser Ile
65                  70                  75                  80

Leu Tyr Leu Gln Met Asn Asn Leu Lys Thr Glu Asp Thr Ala Met Tyr
                85                  90                  95

Tyr Cys Val Arg His Gly Asn Phe Gly Asn Ser Tyr Val Ser Trp Phe
            100                 105                 110

Ala Tyr Trp Gly Gln Gly Thr Leu Val Thr Val Ser Ser
        115                 120                 125
```

```
<210> SEQ ID NO 66
<211> LENGTH: 109
<212> TYPE: PRT
<213> ORGANISM: Artificial Sequence
<220> FEATURE:
<223> OTHER INFORMATION: anti-CD3 VL1

<400> SEQUENCE: 66

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 67
<211> LENGTH: 109
<212> TYPE: PRT
<213> ORGANISM: Artificial Sequence
<220> FEATURE:
<223> OTHER INFORMATION: anti-CD3 VL2

<400> SEQUENCE: 67

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Cys Gly Thr Lys Leu Glu Ile Lys
            100                 105
```

<210> SEQ ID NO 68
<211> LENGTH: 109
<212> TYPE: PRT
<213> ORGANISM: Artificial Sequence
<220> FEATURE:
<223> OTHER INFORMATION: anti-CD3 VL3

<400> SEQUENCE: 68

```
Gln Ala Val Val Thr Gln Glu Pro Ser Leu Thr Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Lys Pro Gly Gln Ala Pro Arg Gly
        35                  40                  45

Leu Ile Gly Gly Thr Asn Lys Arg Ala Pro Trp Thr Pro Ala Arg Phe
    50                  55                  60

Ser Gly Ser Leu Leu Gly Gly Lys Ala Ala Leu Thr Ile Thr Gly Ala
65                  70                  75                  80

Gln Ala Glu Asp Glu Ala Asp Tyr Tyr Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 69
<211> LENGTH: 109
<212> TYPE: PRT
<213> ORGANISM: Artificial Sequence
<220> FEATURE:
<223> OTHER INFORMATION: anti-CD3 VL4

<400> SEQUENCE: 69

```
Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30
```

```
Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105


<210> SEQ ID NO 70
<211> LENGTH: 109
<212> TYPE: PRT
<213> ORGANISM: Artificial Sequence
<220> FEATURE:
<223> OTHER INFORMATION: anti-CD3 VL5

<400> SEQUENCE: 70

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Ile Tyr Phe Cys Ala Leu Trp Tyr Ser Asn
                85                  90                  95

Leu Trp Val Phe Gly Gly Gly Thr Lys Leu Thr Val Leu
            100                 105


<210> SEQ ID NO 71
<211> LENGTH: 109
<212> TYPE: PRT
<213> ORGANISM: Artificial Sequence
<220> FEATURE:
<223> OTHER INFORMATION: anti-CD3 VL6

<400> SEQUENCE: 71

Gln Ala Val Val Thr Gln Glu Pro Ser Phe Ser Val Ser Pro Gly Gly
1               5                   10                  15

Thr Val Thr Leu Thr Cys Arg Ser Ser Thr Gly Ala Val Thr Thr Ser
            20                  25                  30

Asn Tyr Ala Asn Trp Val Gln Gln Thr Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Ile Leu Gly Asn Lys Ala Ala Leu Thr Ile Thr Gly Ala
65                  70                  75                  80

Gln Ala Asp Asp Glu Ser Asp Tyr Tyr Cys Ala Leu Trp Tyr Ser Asn
                85                  90                  95

Leu Trp Val Phe Gly Gly Gly Thr Lys Leu Thr Val Leu
            100                 105


<210> SEQ ID NO 72
```

<211> LENGTH: 109
<212> TYPE: PRT
<213> ORGANISM: Artificial Sequence
<220> FEATURE:
<223> OTHER INFORMATION: anti-CD3 VL7

<400> SEQUENCE: 72

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Glu Lys Pro Gly Gln Ala Phe Arg Gly
        35                  40                  45

Leu Ile Gly Gly Thr Asn Lys Arg Ala Pro Gly Thr Pro Ala Arg Phe
    50                  55                  60

Ser Gly Ser Leu Leu Gly Gly Lys Ala Ala Leu Thr Leu Ser Gly Ala
65                  70                  75                  80

Gln Pro Glu Asp Glu Ala Glu Tyr Tyr Cys Ala Leu Trp Tyr Ser Asn
                85                  90                  95

Leu Trp Val Phe Gly Gly Gly Thr Lys Leu Thr Val Leu
            100                 105
```

<210> SEQ ID NO 73
<211> LENGTH: 109
<212> TYPE: PRT
<213> ORGANISM: Artificial Sequence
<220> FEATURE:
<223> OTHER INFORMATION: anti-CD3 VL8

<400> SEQUENCE: 73

```
Gln Thr Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Ser Gly
            20                  25                  30

Asn Tyr Pro Asn Trp Val Gln Gln Lys Pro Gly Gln Ala Pro Arg Gly
        35                  40                  45

Leu Ile Gly Gly Thr Lys Phe Leu Ala Pro Gly Thr Pro Ala Arg Phe
    50                  55                  60

Ser Gly Ser Leu Leu Gly Gly Lys Ala Ala Leu Thr Leu Ser Gly Val
65                  70                  75                  80

Gln Pro Glu Asp Glu Ala Glu Tyr Tyr Cys Val Leu Trp Tyr Ser Asn
                85                  90                  95

Arg Trp Val Phe Gly Gly Gly Thr Lys Leu Thr Val Leu
            100                 105
```

<210> SEQ ID NO 74
<211> LENGTH: 109
<212> TYPE: PRT
<213> ORGANISM: Artificial Sequence
<220> FEATURE:
<223> OTHER INFORMATION: anti-CD3 VL9

<400> SEQUENCE: 74

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45
```

```
Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Glu Ile Lys
            100                 105


<210> SEQ ID NO 75
<211> LENGTH: 109
<212> TYPE: PRT
<213> ORGANISM: Artificial Sequence
<220> FEATURE:
<223> OTHER INFORMATION: anti-CD3 VL10

<400> SEQUENCE: 75

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Cys Gly Thr Lys Leu Glu Ile Lys
            100                 105


<210> SEQ ID NO 76
<211> LENGTH: 109
<212> TYPE: PRT
<213> ORGANISM: Artificial Sequence
<220> FEATURE:
<223> OTHER INFORMATION: anti-CD3 VL11

<400> SEQUENCE: 76

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Cys Phe Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Glu Gly Thr Lys Leu Glu Ile Lys
            100                 105


<210> SEQ ID NO 77
<211> LENGTH: 109
<212> TYPE: PRT
<213> ORGANISM: Artificial Sequence
```

<220> FEATURE:
<223> OTHER INFORMATION: anti-CD3 VL12

<400> SEQUENCE: 77

Gln Ala Val Val Thr Gln Glu Ser Ala Leu Thr Thr Ser Pro Gly Glu
1 5 10 15

Thr Val Thr Leu Thr Cys Arg Ser Ser Thr Gly Ala Val Thr Thr Ser
20 25 30

Asn Tyr Ala Asn Trp Val Gln Glu Lys Pro Asp His Leu Phe Thr Gly
35 40 45

Leu Ile Gly Gly Thr Asn Lys Arg Ala Pro Gly Val Pro Ala Arg Phe
50 55 60

Ser Gly Ser Leu Ile Gly Asp Lys Ala Ala Leu Thr Ile Thr Gly Ala
65 70 75 80

Gln Thr Glu Asp Glu Ala Ile Tyr Phe Cys Ala Leu Trp Tyr Ser Asn
85 90 95

Leu Trp Val Phe Gly Cys Gly Thr Lys Leu Thr Val Leu
100 105

<210> SEQ ID NO 78
<211> LENGTH: 109
<212> TYPE: PRT
<213> ORGANISM: Artificial Sequence
<220> FEATURE:
<223> OTHER INFORMATION: anti-CD3 VL13

<400> SEQUENCE: 78

Gln Ala Val Val Thr Gln Glu Pro Ser Leu Thr Val Ser Pro Gly Gly
1 5 10 15

Thr Val Thr Leu Thr Cys Gly Ser Ser Thr Gly Ala Val Thr Thr Ser
20 25 30

Asn Tyr Ala Asn Trp Val Gln Gln Lys Pro Gly Lys Ser Pro Arg Gly
35 40 45

Leu Ile Gly Gly Thr Asn Lys Arg Ala Pro Gly Val Pro Ala Arg Phe
50 55 60

Ser Gly Ser Leu Leu Gly Gly Lys Ala Ala Leu Thr Ile Ser Gly Ala
65 70 75 80

Gln Pro Glu Asp Glu Ala Asp Tyr Tyr Cys Ala Leu Trp Tyr Ser Asn
85 90 95

His Trp Val Phe Gly Gly Gly Thr Lys Leu Glu Ile Lys
100 105

<210> SEQ ID NO 79
<211> LENGTH: 109
<212> TYPE: PRT
<213> ORGANISM: Artificial Sequence
<220> FEATURE:
<223> OTHER INFORMATION: anti-CD3 VL14

<400> SEQUENCE: 79

Gln Ala Val Val Thr Gln Glu Pro Ser Leu Thr Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Gln Lys Pro Gly Gln Ala Pro Arg Gly
35 40 45

Leu Ile Gly Gly Thr Asn Lys Arg Ala Pro Trp Thr Pro Ala Arg Phe
50 55 60

Ser Gly Ser Leu Leu Gly Gly Lys Ala Ala Leu Thr Ile Thr Gly Ala
65 70 75 80

Gln Ala Glu Asp Glu Ala Asp Tyr Tyr Cys Ala Leu Trp Tyr Ser Asn
85 90 95

Leu Trp Val Phe Gly Cys Gly Thr Lys Leu Thr Val Leu
100 105

<210> SEQ ID NO 80
<211> LENGTH: 109
<212> TYPE: PRT
<213> ORGANISM: Artificial Sequence
<220> FEATURE:
<223> OTHER INFORMATION: anti-CD3 VL15

<400> SEQUENCE: 80

Gln Ala Val Val Thr Gln Glu Pro Ser Phe Ser Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Gln Thr Pro Gly Gln Ala Phe Arg Gly
35 40 45

Leu Ile Gly Gly Thr Asn Lys Arg Ala Pro Gly Val Pro Ala Arg Phe
50 55 60

Ser Gly Ser Leu Ile Gly Asp Lys Ala Ala Leu Thr Ile Thr Gly Ala
65 70 75 80

Gln Ala Asp Asp Glu Ser Ile Tyr Phe Cys Ala Leu Trp Tyr Ser Asn
85 90 95

Leu Trp Val Phe Gly Gly Gly Thr Lys Leu Thr Val Leu
100 105

<210> SEQ ID NO 81
<211> LENGTH: 109
<212> TYPE: PRT
<213> ORGANISM: Artificial Sequence
<220> FEATURE:
<223> OTHER INFORMATION: anti-CD3 VL16

<400> SEQUENCE: 81

Gln Ala Val Val Thr Gln Glu Pro Ser Phe Ser Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Gln Thr Pro Gly Gln Ala Phe Arg Gly
35 40 45

Leu Ile Gly Gly Thr Asn Lys Arg Ala Pro Gly Val Pro Ala Arg Phe
50 55 60

Ser Gly Ser Ile Leu Gly Asn Lys Ala Ala Leu Thr Ile Thr Gly Ala
65 70 75 80

Gln Ala Asp Asp Glu Ser Ile Tyr Phe Cys Ala Leu Trp Tyr Ser Asn
85 90 95

Leu Trp Val Phe Gly Cys Gly Thr Lys Leu Thr Val Leu
100 105

<210> SEQ ID NO 82
<211> LENGTH: 109
<212> TYPE: PRT
<213> ORGANISM: Artificial Sequence
<220> FEATURE:
<223> OTHER INFORMATION: anti-CD3 VL17

<400> SEQUENCE: 82

Gln Ala Val Val Thr Gln Glu Pro Ser Phe Ser Val Ser Pro Gly Gly
1 5 10 15

Thr Val Thr Leu Thr Cys Arg Ser Ser Thr Gly Ala Val Thr Thr Ser
20 25 30

Asn Tyr Ala Asn Trp Val Gln Gln Thr Pro Gly Gln Ala Phe Arg Gly
35 40 45

Leu Ile Gly Gly Thr Asn Lys Arg Ala Pro Gly Val Pro Ala Arg Phe
50 55 60

Ser Gly Ser Ile Leu Gly Asn Lys Ala Ala Leu Thr Ile Thr Gly Ala
65 70 75 80

Gln Ala Asp Asp Glu Ser Asp Tyr Tyr Cys Ala Leu Trp Tyr Ser Asn
85 90 95

Leu Trp Val Phe Gly Cys Gly Thr Lys Leu Thr Val Leu
100 105

<210> SEQ ID NO 83
<211> LENGTH: 109
<212> TYPE: PRT
<213> ORGANISM: Artificial Sequence
<220> FEATURE:
<223> OTHER INFORMATION: anti-CD3 VL18

<400> SEQUENCE: 83

Gln Ala Val Val Thr Gln Glu Pro Ser Leu Thr Val Ser Pro Gly Gly
1 5 10 15

Thr Val Thr Leu Thr Cys Gly Ser Ser Thr Gly Ala Val Thr Thr Ser
20 25 30

Asn Tyr Ala Asn Trp Val Gln Glu Lys Pro Gly Gln Ala Phe Arg Gly
35 40 45

Leu Ile Gly Gly Thr Asn Lys Arg Ala Pro Gly Thr Pro Ala Arg Phe
50 55 60

Ser Gly Ser Leu Leu Gly Gly Lys Ala Ala Leu Thr Leu Ser Gly Ala
65 70 75 80

Gln Pro Glu Asp Glu Ala Glu Tyr Tyr Cys Ala Leu Trp Tyr Ser Asn
85 90 95

Leu Trp Val Phe Gly Cys Gly Thr Lys Leu Thr Val Leu
100 105

<210> SEQ ID NO 84
<211> LENGTH: 109
<212> TYPE: PRT
<213> ORGANISM: Artificial Sequence
<220> FEATURE:
<223> OTHER INFORMATION: anti-CD3 VL19

<400> SEQUENCE: 84

Gln Thr Val Val Thr Gln Glu Pro Ser Leu Thr Val Ser Pro Gly Gly
1 5 10 15

Thr Val Thr Leu Thr Cys Gly Ser Ser Thr Gly Ala Val Thr Ser Gly
20 25 30

Asn Tyr Pro Asn Trp Val Gln Gln Lys Pro Gly Gln Ala Pro Arg Gly
35 40 45

Leu Ile Gly Gly Thr Lys Phe Leu Ala Pro Gly Thr Pro Ala Arg Phe
50 55 60

Ser Gly Ser Leu Leu Gly Gly Lys Ala Ala Leu Thr Leu Ser Gly Val
65 70 75 80

Gln Pro Glu Asp Glu Ala Glu Tyr Tyr Cys Val Leu Trp Tyr Ser Asn
85 90 95

Arg Trp Val Phe Gly Cys Gly Thr Lys Leu Thr Val Leu
100 105

<210> SEQ ID NO 85
<211> LENGTH: 129
<212> TYPE: PRT
<213> ORGANISM: Artificial Sequence
<220> FEATURE:
<223> OTHER INFORMATION: anti-CD3 VHH

<400> SEQUENCE: 85

Gln Val Gln Leu Gln Glu Ser Gly Gly Gly Leu Val Gln Ala Gly Gly
1 5 10 15

Ser Leu Arg Leu Ser Cys Ala Ala Ser Gly Arg Thr Phe Ser Asn Tyr
20 25 30

His Met Gly Trp Phe Arg Gln Ala Pro Gly Lys Glu Arg Glu Leu Val
35 40 45

Ala Ala Ile Ser Gly Ser Gly Gly Ser Thr Tyr Tyr Thr Asp Ser Val
50 55 60

Lys Gly Arg Phe Thr Ile Ser Arg Asn Asn Ala Lys Asn Thr Met Ser
65 70 75 80

Leu Gln Met Ser Asn Leu Lys Pro Glu Asp Thr Gly Val Tyr Tyr Cys
85 90 95

Thr Thr Pro Thr Glu Lys Gly Ser Ser Ile Asp Tyr Trp Gly Gln Gly
100 105 110

Thr Gln Val Thr Val Ser Ser Gly Arg Tyr Pro Tyr Asp Val Pro Asp
115 120 125

Tyr

<210> SEQ ID NO 86
<211> LENGTH: 220
<212> TYPE: PRT
<213> ORGANISM: homo sapiens
<220> FEATURE:
<223> OTHER INFORMATION: Canonical CD28 sequence (e.g., UniProt No.
P10747)

<400> SEQUENCE: 86

Met Leu Arg Leu Leu Leu Ala Leu Asn Leu Phe Pro Ser Ile Gln Val
1 5 10 15

Thr Gly Asn Lys Ile Leu Val Lys Gln Ser Pro Met Leu Val Ala Tyr
20 25 30

Asp Asn Ala Val Asn Leu Ser Cys Lys Tyr Ser Tyr Asn Leu Phe Ser
35 40 45

Arg Glu Phe Arg Ala Ser Leu His Lys Gly Leu Asp Ser Ala Val Glu
50 55 60

Val Cys Val Val Tyr Gly Asn Tyr Ser Gln Gln Leu Gln Val Tyr Ser
65 70 75 80

Lys Thr Gly Phe Asn Cys Asp Gly Lys Leu Gly Asn Glu Ser Val Thr
85 90 95

Phe Tyr Leu Gln Asn Leu Tyr Val Asn Gln Thr Asp Ile Tyr Phe Cys
100 105 110

Lys Ile Glu Val Met Tyr Pro Pro Pro Tyr Leu Asp Asn Glu Lys Ser
115 120 125

Asn Gly Thr Ile Ile His Val Lys Gly Lys His Leu Cys Pro Ser Pro
130 135 140

Leu Phe Pro Gly Pro Ser Lys Pro Phe Trp Val Leu Val Val Val Gly
145 150 155 160

Gly Val Leu Ala Cys Tyr Ser Leu Leu Val Thr Val Ala Phe Ile Ile
165 170 175

Phe Trp Val Arg Ser Lys Arg Ser Arg Leu Leu His Ser Asp Tyr Met
180 185 190

Asn Met Thr Pro Arg Arg Pro Gly Pro Thr Arg Lys His Tyr Gln Pro
195 200 205

Tyr Ala Pro Pro Arg Asp Phe Ala Ala Tyr Arg Ser
210 215 220

<210> SEQ ID NO 87
<211> LENGTH: 3
<212> TYPE: PRT
<213> ORGANISM: Artificial Sequence
<220> FEATURE:
<223> OTHER INFORMATION: linker

<400> SEQUENCE: 87

Gly Gly Gly
1

<210> SEQ ID NO 88
<211> LENGTH: 134
<212> TYPE: PRT
<213> ORGANISM: homo sapiens
<220> FEATURE:
<223> OTHER INFORMATION: CD28 ECD (aa 19-152 of human CD28, e.g., UniProt No. P10747)

<400> SEQUENCE: 88

Asn Lys Ile Leu Val Lys Gln Ser Pro Met Leu Val Ala Tyr Asp Asn
1 5 10 15

Ala Val Asn Leu Ser Cys Lys Tyr Ser Tyr Asn Leu Phe Ser Arg Glu
20 25 30

Phe Arg Ala Ser Leu His Lys Gly Leu Asp Ser Ala Val Glu Val Cys
35 40 45

Val Val Tyr Gly Asn Tyr Ser Gln Gln Leu Gln Val Tyr Ser Lys Thr
50 55 60

Gly Phe Asn Cys Asp Gly Lys Leu Gly Asn Glu Ser Val Thr Phe Tyr
65 70 75 80

Leu Gln Asn Leu Tyr Val Asn Gln Thr Asp Ile Tyr Phe Cys Lys Ile
85 90 95

Glu Val Met Tyr Pro Pro Pro Tyr Leu Asp Asn Glu Lys Ser Asn Gly
100 105 110

Thr Ile Ile His Val Lys Gly Lys His Leu Cys Pro Ser Pro Leu Phe
115 120 125

Pro Gly Pro Ser Lys Pro
130

<210> SEQ ID NO 89
<211> LENGTH: 8
<212> TYPE: PRT
<213> ORGANISM: Artificial Sequence
<220> FEATURE:
<223> OTHER INFORMATION: linker

<400> SEQUENCE: 89

Gly Gly Ser Gly Gly Gly Gly Ser
1 5

<210> SEQ ID NO 90
<211> LENGTH: 6
<212> TYPE: PRT
<213> ORGANISM: Artificial Sequence
<220> FEATURE:
<223> OTHER INFORMATION: linker

<400> SEQUENCE: 90

```
Gly Gly Gly Ser Gly Ser
1               5
```

<210> SEQ ID NO 91
<211> LENGTH: 112
<212> TYPE: PRT
<213> ORGANISM: Artificial Sequence
<220> FEATURE:
<223> OTHER INFORMATION: CD3zeta signaling domain

<400> SEQUENCE: 91

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 92
<211> LENGTH: 42
<212> TYPE: PRT
<213> ORGANISM: Artificial Sequence
<220> FEATURE:
<223> OTHER INFORMATION: 4-1BB-derived costimulatory domain

<400> SEQUENCE: 92

```
Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

<210> SEQ ID NO 93
<211> LENGTH: 40
<212> TYPE: PRT
<213> ORGANISM: Artificial Sequence
<220> FEATURE:
<223> OTHER INFORMATION: CD28-derived costimulatory domain

<400> SEQUENCE: 93

```
Ser Lys Arg Ser Arg Leu Leu His Ser Asp Tyr Met Asn Met Thr Pro
1               5                   10                  15

Arg Arg Pro Gly Pro Thr Arg Lys His Tyr Gln Pro Tyr Ala Pro Pro
            20                  25                  30
```

```
Arg Asp Phe Ala Ala Tyr Arg Ser
        35                  40


<210> SEQ ID NO 94
<211> LENGTH: 41
<212> TYPE: PRT
<213> ORGANISM: Artificial Sequence
<220> FEATURE:
<223> OTHER INFORMATION: CD28-derived costimulatory domain 2

<400> SEQUENCE: 94

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40


<210> SEQ ID NO 95
<211> LENGTH: 44
<212> TYPE: PRT
<213> ORGANISM: Artificial Sequence
<220> FEATURE:
<223> OTHER INFORMATION: CD28-derived costimulatory domain 3

<400> SEQUENCE: 95

Phe Trp Val Arg Ser Lys Arg Ser Arg Leu Leu His Ser Asp Tyr Met
1               5                   10                  15

Asn Met Thr Pro Arg Arg Pro Gly Pro Thr Arg Lys His Tyr Gln Pro
            20                  25                  30

Tyr Ala Pro Pro Arg Asp Phe Ala Ala Tyr Arg Ser
        35                  40


<210> SEQ ID NO 96
<211> LENGTH: 71
<212> TYPE: PRT
<213> ORGANISM: Artificial Sequence
<220> FEATURE:
<223> OTHER INFORMATION: CD8-derived hinge and transmembrane domain

<400> SEQUENCE: 96

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Ser Arg Pro Ala
            20                  25                  30

Ala Gly Gly Ala Val His Thr Arg Gly Leu Asp Phe Ala Ser Asp Ile
        35                  40                  45

Tyr Ile Trp Ala Pro Leu Ala Gly Thr Cys Gly Val Leu Leu Leu Ser
    50                  55                  60

Leu Val Ile Thr Leu Tyr Cys
65                  70


<210> SEQ ID NO 97
<211> LENGTH: 69
<212> TYPE: PRT
<213> ORGANISM: Artificial Sequence
<220> FEATURE:
<223> OTHER INFORMATION: CD8-derived hinge and transmembrane domain

<400> SEQUENCE: 97

Ala Lys Pro Thr Thr Thr Pro Ala Pro Arg Pro Pro Thr Pro Ala Pro
1               5                   10                  15
```

```
Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

Ile Tyr Ile Trp Ala Pro Leu Ala Gly Thr Cys Gly Val Leu Leu Leu
    50                  55                  60

Ser Leu Val Ile Thr
65


<210> SEQ ID NO 98
<211> LENGTH: 68
<212> TYPE: PRT
<213> ORGANISM: Artificial Sequence
<220> FEATURE:
<223> OTHER INFORMATION: CD8 hinge and transmembrane domain

<400> SEQUENCE: 98

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr Ile Trp Ala Pro Leu Ala Gly Thr Cys Gly Val Leu Leu Leu Ser
    50                  55                  60

Leu Val Ile Thr
65


<210> SEQ ID NO 99
<211> LENGTH: 111
<212> TYPE: PRT
<213> ORGANISM: Artificial Sequence
<220> FEATURE:
<223> OTHER INFORMATION: PDL1 sdAb

<400> SEQUENCE: 99

Glu Val Gln Leu Leu Glu Ser Gly Gly Gly Glu Val Gln Pro Gly Gly
1               5                   10                  15

Ser Leu Arg Leu Ser Cys Ala Ala Ser Gly Gly Ile Phe Ala Ile Lys
            20                  25                  30

Pro Ile Ser Trp Tyr Arg Gln Ala Pro Gly Lys Gln Arg Glu Trp Val
        35                  40                  45

Ser Thr Thr Thr Ser Ser Gly Ala Thr Asn Tyr Ala Glu Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ala Glu Asp Thr Ala Val Tyr Tyr Cys Asn
                85                  90                  95

Val Phe Glu Tyr Trp Gly Gln Gly Thr Leu Val Thr Val Lys Pro
            100                 105                 110


<210> SEQ ID NO 100
<211> LENGTH: 10
<212> TYPE: PRT
<213> ORGANISM: Artificial Sequence
<220> FEATURE:
<223> OTHER INFORMATION: CDR1 PDL1

<400> SEQUENCE: 100
```

Gly Gly Ile Phe Ala Ile Lys Pro Ile Ser
1 5 10

<210> SEQ ID NO 101
<211> LENGTH: 9
<212> TYPE: PRT
<213> ORGANISM: Artificial Sequence
<220> FEATURE:
<223> OTHER INFORMATION: CDR2 PDL1

<400> SEQUENCE: 101

Thr Thr Thr Ser Ser Gly Ala Thr Asn
1 5

<210> SEQ ID NO 102
<211> LENGTH: 3
<212> TYPE: PRT
<213> ORGANISM: Artificial Sequence
<220> FEATURE:
<223> OTHER INFORMATION: CDR3 PDL1

<400> SEQUENCE: 102

Phe Glu Tyr
1

<210> SEQ ID NO 103
<211> LENGTH: 226
<212> TYPE: PRT
<213> ORGANISM: Artificial Sequence
<220> FEATURE:
<223> OTHER INFORMATION: Knob Fc

<400> SEQUENCE: 103

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Cys Arg Asp Glu Leu Thr Lys Asn Gln Val Ser
130 135 140

Leu Trp Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser

```
    210                 215                 220

Pro Thr
225


<210> SEQ ID NO 104
<211> LENGTH: 226
<212> TYPE: PRT
<213> ORGANISM: Artificial Sequence
<220> FEATURE:
<223> OTHER INFORMATION: Hole Fc

<400> SEQUENCE: 104

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Arg Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Thr
225


<210> SEQ ID NO 105
<211> LENGTH: 223
<212> TYPE: PRT
<213> ORGANISM: Artificial Sequence
<220> FEATURE:
<223> OTHER INFORMATION: Knob Fc

<400> SEQUENCE: 105

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45
```

```
Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Thr
    210                 215                 220


<210> SEQ ID NO 106
<211> LENGTH: 223
<212> TYPE: PRT
<213> ORGANISM: Artificial Sequence
<220> FEATURE:
<223> OTHER INFORMATION: Hole Fc

<400> SEQUENCE: 106

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Arg Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190
```

```
Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Thr
    210                 215                 220


<210> SEQ ID NO 107
<211> LENGTH: 226
<212> TYPE: PRT
<213> ORGANISM: Artificial Sequence
<220> FEATURE:
<223> OTHER INFORMATION: Knob Fc

<400> SEQUENCE: 107

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225


<210> SEQ ID NO 108
<211> LENGTH: 226
<212> TYPE: PRT
<213> ORGANISM: Artificial Sequence
<220> FEATURE:
<223> OTHER INFORMATION: Hole Fc

<400> SEQUENCE: 108

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Arg Ser Arg Thr Pro Glu Val Thr Cys Val Val Val Asp Val Ser His
        35                  40                  45
```

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly
225

<210> SEQ ID NO 109
<211> LENGTH: 223
<212> TYPE: PRT
<213> ORGANISM: Artificial Sequence
<220> FEATURE:
<223> OTHER INFORMATION: Knob Fc

<400> SEQUENCE: 109

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

```
Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly
    210                 215                 220


<210> SEQ ID NO 110
<211> LENGTH: 223
<212> TYPE: PRT
<213> ORGANISM: Artificial Sequence
<220> FEATURE:
<223> OTHER INFORMATION: Hole Fc

<400> SEQUENCE: 110

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Arg Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly
    210                 215                 220


<210> SEQ ID NO 111
<211> LENGTH: 226
<212> TYPE: PRT
<213> ORGANISM: Artificial Sequence
<220> FEATURE:
<223> OTHER INFORMATION: Hole Fc

<400> SEQUENCE: 111

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
```

```
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Thr
225
```

<210> SEQ ID NO 112
<211> LENGTH: 223
<212> TYPE: PRT
<213> ORGANISM: Artificial Sequence
<220> FEATURE:
<223> OTHER INFORMATION: Hole Fc

<400> SEQUENCE: 112

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
```

```
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn Arg Tyr Thr Gln Lys Ser Leu Ser Leu Ser Pro Thr
    210                 215                 220


<210> SEQ ID NO 113
<211> LENGTH: 226
<212> TYPE: PRT
<213> ORGANISM: Artificial Sequence
<220> FEATURE:
<223> OTHER INFORMATION: Hole Fc

<400> SEQUENCE: 113

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn Arg Tyr Thr Gln Lys Ser Leu Ser Leu Ser
    210                 215                 220

Pro Gly
225


<210> SEQ ID NO 114
<211> LENGTH: 223
<212> TYPE: PRT
<213> ORGANISM: Artificial Sequence
<220> FEATURE:
<223> OTHER INFORMATION: Hole Fc

<400> SEQUENCE: 114

Asp Lys Thr His Thr Cys Pro Pro Cys Pro Ala Pro Gly Gly Pro Ser
1               5                   10                  15
```

```
Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn Arg Tyr Thr Gln Lys Ser Leu Ser Leu Ser Pro Gly
    210                 215                 220


<210> SEQ ID NO 115
<211> LENGTH: 226
<212> TYPE: PRT
<213> ORGANISM: Artificial Sequence
<220> FEATURE:
<223> OTHER INFORMATION: Knob Fc

<400> SEQUENCE: 115

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160
```

```
Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn His Tyr Thr Gln Lys Ser Leu Ser Leu Ser
    210                 215                 220

Pro Thr
225


<210> SEQ ID NO 116
<211> LENGTH: 223
<212> TYPE: PRT
<213> ORGANISM: Artificial Sequence
<220> FEATURE:
<223> OTHER INFORMATION: Knob Fc

<400> SEQUENCE: 116

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125

Pro Pro Cys Arg Asp Glu Leu Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn His Tyr Thr Gln Lys Ser Leu Ser Leu Ser Pro Thr
    210                 215                 220


<210> SEQ ID NO 117
<211> LENGTH: 226
<212> TYPE: PRT
<213> ORGANISM: Artificial Sequence
<220> FEATURE:
<223> OTHER INFORMATION: Knob Fc

<400> SEQUENCE: 117

Asp Lys Thr His Thr Cys Pro Pro Cys Pro Ala Pro Glu Leu Leu Gly
1               5                   10                  15
```

Gly Pro Ser Val Phe Leu Phe Pro Pro Lys Pro Lys Asp Thr Leu Tyr
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Cys Arg Asp Glu Leu Thr Lys Asn Gln Val Ser
130 135 140

Leu Trp Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Val
195 200 205

His Glu Ala Leu His Asn His Tyr Thr Gln Lys Ser Leu Ser Leu Ser
210 215 220

Pro Gly
225

<210> SEQ ID NO 118
<211> LENGTH: 223
<212> TYPE: PRT
<213> ORGANISM: Artificial Sequence
<220> FEATURE:
<223> OTHER INFORMATION: Knob Fc

<400> SEQUENCE: 118

Asp Lys Thr His Thr Cys Pro Pro Cys Pro Ala Pro Gly Gly Pro Ser
1 5 10 15

Val Phe Leu Phe Pro Pro Lys Pro Lys Asp Thr Leu Tyr Ile Ser Arg
20 25 30

Thr Pro Glu Val Thr Cys Val Val Val Asp Val Ser His Glu Asp Pro
35 40 45

Glu Val Lys Phe Asn Trp Tyr Val Asp Gly Val Glu Val His Asn Ala
50 55 60

Lys Thr Lys Pro Arg Glu Glu Gln Tyr Asn Ser Thr Tyr Arg Val Val
65 70 75 80

Ser Val Leu Thr Val Leu His Gln Asp Trp Leu Asn Gly Lys Glu Tyr
85 90 95

Lys Cys Lys Val Ser Asn Lys Ala Leu Pro Ala Pro Ile Glu Lys Thr
100 105 110

Ile Ser Lys Ala Lys Gly Gln Pro Arg Glu Pro Gln Val Tyr Thr Leu
115 120 125

Pro Pro Cys Arg Asp Glu Leu Thr Lys Asn Gln Val Ser Leu Trp Cys
130 135 140

```
Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn His Tyr Thr Gln Lys Ser Leu Ser Leu Ser Pro Gly
    210                 215                 220


<210> SEQ ID NO 119
<211> LENGTH: 226
<212> TYPE: PRT
<213> ORGANISM: Artificial Sequence
<220> FEATURE:
<223> OTHER INFORMATION: Hole Fc

<400> SEQUENCE: 119

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn Arg Tyr Thr Gln Lys Ser Leu Ser Leu Ser
    210                 215                 220

Pro Thr
225


<210> SEQ ID NO 120
<211> LENGTH: 223
<212> TYPE: PRT
<213> ORGANISM: Artificial Sequence
<220> FEATURE:
<223> OTHER INFORMATION: Hole Fc
```

<400> SEQUENCE: 120

Asp Lys Thr His Thr Cys Pro Pro Cys Pro Ala Pro Gly Gly Pro Ser
1 5 10 15

Val Phe Leu Phe Pro Pro Lys Pro Lys Asp Thr Leu Tyr Ile Ser Arg
20 25 30

Thr Pro Glu Val Thr Cys Val Val Val Asp Val Ser His Glu Asp Pro
35 40 45

Glu Val Lys Phe Asn Trp Tyr Val Asp Gly Val Glu Val His Asn Ala
50 55 60

Lys Thr Lys Pro Arg Glu Glu Gln Tyr Asn Ser Thr Tyr Arg Val Val
65 70 75 80

Ser Val Leu Thr Val Leu His Gln Asp Trp Leu Asn Gly Lys Glu Tyr
85 90 95

Lys Cys Lys Val Ser Asn Lys Ala Leu Pro Ala Pro Ile Glu Lys Thr
100 105 110

Ile Ser Lys Ala Lys Gly Gln Pro Arg Glu Pro Gln Val Cys Thr Leu
115 120 125

Pro Pro Ser Arg Asp Glu Leu Thr Lys Asn Gln Val Ser Leu Ser Cys
130 135 140

Ala Val Lys Gly Phe Tyr Pro Ser Asp Ile Ala Val Glu Trp Glu Ser
145 150 155 160

Asn Gly Gln Pro Glu Asn Asn Tyr Lys Thr Thr Pro Pro Val Leu Asp
165 170 175

Ser Asp Gly Ser Phe Phe Leu Val Ser Lys Leu Thr Val Asp Lys Ser
180 185 190

Arg Trp Gln Gln Gly Asn Val Phe Ser Cys Ser Val Val His Glu Ala
195 200 205

Leu His Asn Arg Tyr Thr Gln Lys Ser Leu Ser Leu Ser Pro Thr
210 215 220

<210> SEQ ID NO 121
<211> LENGTH: 226
<212> TYPE: PRT
<213> ORGANISM: Artificial Sequence
<220> FEATURE:
<223> OTHER INFORMATION: Hole Fc

<400> SEQUENCE: 121

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Tyr
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Cys Thr Leu Pro Pro Ser Arg Asp Glu Leu Thr Lys Asn Gln Val Ser

```
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn Arg Tyr Thr Gln Lys Ser Leu Ser Leu Ser
    210                 215                 220

Pro Gly
225


<210> SEQ ID NO 122
<211> LENGTH: 223
<212> TYPE: PRT
<213> ORGANISM: Artificial Sequence
<220> FEATURE:
<223> OTHER INFORMATION: Hole Fc

<400> SEQUENCE: 122

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn Arg Tyr Thr Gln Lys Ser Leu Ser Leu Ser Pro Gly
    210                 215                 220


<210> SEQ ID NO 123
<211> LENGTH: 5
<212> TYPE: PRT
<213> ORGANISM: Artificial Sequence
<220> FEATURE:
<223> OTHER INFORMATION: linker
```

<220> FEATURE:
<221> NAME/KEY: REPEAT
<222> LOCATION: (1)...(5)
<223> OTHER INFORMATION: repeated 1 to 5 times

<400> SEQUENCE: 123

Gly Gly Gly Gly Ser
1               5

<210> SEQ ID NO 124
<211> LENGTH: 6
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)...(6)
<223> OTHER INFORMATION: repeated 1 to 4 times

<400> SEQUENCE: 124

Gly Gly Gly Gly Gly Ser
1               5

<210> SEQ ID NO 125
<211> LENGTH: 5
<212> TYPE: PRT
<213> ORGANISM: Artificial Sequence
<220> FEATURE:
<223> OTHER INFORMATION: linker

<400> SEQUENCE: 125

Gly Gly Gly Gly Ser
1               5

<210> SEQ ID NO 126
<211> LENGTH: 6
<212> TYPE: PRT
<213> ORGANISM: Artificial Sequence
<220> FEATURE:
<223> OTHER INFORMATION: linker

<400> SEQUENCE: 126

Gly Gly Gly Gly Gly Ser
1               5

<210> SEQ ID NO 127
<211> LENGTH: 18
<212> TYPE: PRT
<213> ORGANISM: Artificial Sequence
<220> FEATURE:
<223> OTHER INFORMATION: linker

<400> SEQUENCE: 127

Gly Gly Gly Gly Gly Ser Gly Gly Gly Gly Gly Ser Gly Gly Gly Gly
1               5                   10                  15

Gly Ser

<210> SEQ ID NO 128
<211> LENGTH: 15
<212> TYPE: PRT
<213> ORGANISM: Artificial Sequence
<220> FEATURE:
<223> OTHER INFORMATION: linker

<400> SEQUENCE: 128

Gly Gly Gly Gly Ser Gly Gly Gly Gly Ser Gly Gly Gly Gly Ser 1 5 10 15

<210> SEQ ID NO 129
<211> LENGTH: 18
<212> TYPE: PRT
<213> ORGANISM: Artificial Sequence
<220> FEATURE:
<223> OTHER INFORMATION: linker

<400> SEQUENCE: 129

Gly Gly Ser Gly Gly Gly Gly Ser Gly Gly Gly Gly Ser Gly Gly Gly
1 5 10 15

Gly Ser

<210> SEQ ID NO 130
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: VARIANT
<222> LOCATION: (2)...(2)
<223> OTHER INFORMATION: Xaa is A, V, L, I, M,F, W, P, G, S, T, C, Y, N, Q, K, R, H, D, or E
<220> FEATURE:
<221> NAME/KEY: VARIANT
<222> LOCATION: (4)...(4)
<223> OTHER INFORMATION: Xaa is A, V, L, I, M,F, W, P, G, S, T, C, Y, N, Q, K, R, H, D, or E
<220> FEATURE:
<221> NAME/KEY: REPEAT
<222> LOCATION: (1)...(1)
<223> OTHER INFORMATION: repeated 1-5 times
<220> FEATURE:
<221> NAME/KEY: REPEAT
<222> LOCATION: (3)...(3)
<223> OTHER INFORMATION: repeated 1-5 times
<220> FEATURE:
<221> NAME/KEY: REPEAT
<222> LOCATION: (5)...(5)
<223> OTHER INFORMATION: repeated 1-5 times

<400> SEQUENCE: 130

Gly Xaa Gly Xaa Gly
1 5

<210> SEQ ID NO 131
<211> LENGTH: 11
<212> TYPE: PRT
<213> ORGANISM: Artificial Sequence
<220> FEATURE:
<223> OTHER INFORMATION: linker
<220> FEATURE:
<221> NAME/KEY: VARIANT
<222> LOCATION: (4)...(4)
<223> OTHER INFORMATION: Xaa is A, V, L, I, M,F, W, P, G, S, T, C, Y, N, Q, K, R, H, D, or E
<220> FEATURE:
<221> NAME/KEY: VARIANT
<222> LOCATION: (8)...(8)
<223> OTHER INFORMATION: Xaa is A, V, L, I, M,F, W, P, G, S, T, C, Y, N, Q, K, R, H, D, or E

<400> SEQUENCE: 131

Gly Gly Gly Xaa Gly Gly Gly Xaa Gly Gly Gly
1 5 10

<210> SEQ ID NO 132
<211> LENGTH: 5
<212> TYPE: PRT

<213> ORGANISM: Artificial Sequence
<220> FEATURE:
<223> OTHER INFORMATION: linker
<220> FEATURE:
<221> NAME/KEY: REPEAT
<222> LOCATION: (1)...(5)
<223> OTHER INFORMATION: repeated 1 to 9 times

<400> SEQUENCE: 132

Ser Ser Ser Ser Gly
1               5

<210> SEQ ID NO 133
<211> LENGTH: 11
<212> TYPE: PRT
<213> ORGANISM: Artificial Sequence
<220> FEATURE:
<223> OTHER INFORMATION: linker

<400> SEQUENCE: 133

Gly Gly Gly Gly Gly Cys Gly Gly Gly Gly Gly
1               5                   10

<210> SEQ ID NO 134
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)...(5)
<223> OTHER INFORMATION: repeated 2 to 20 times

<400> SEQUENCE: 134

Glu Ala Ala Ala Lys
1               5

<210> SEQ ID NO 135
<211> LENGTH: 6
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (3)...(4)
<223> OTHER INFORMATION: repeated 2 to 20 times

<400> SEQUENCE: 135

Ala Ser Ala Pro Gly Thr
1               5

<210> SEQ ID NO 136
<211> LENGTH: 9
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (3)...(7)
<223> OTHER INFORMATION: repeated 2 to 20 times

<400> SEQUENCE: 136

Ala Ser Glu Ala Ala Ala Lys Gly Thr
1               5

<210> SEQ ID NO 137

<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)...(5)
<223> OTHER INFORMATION: repeated 2 to 20 times

<400> SEQUENCE: 137

Gly Gly Gly Gly Ala
1               5

<210> SEQ ID NO 138
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)...(5)
<223> OTHER INFORMATION: repeated 2 to 20 times

<400> SEQUENCE: 138

Pro Gly Gly Gly Ser
1               5

<210> SEQ ID NO 139
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)...(5)
<223> OTHER INFORMATION: repeated 2 to 20 times

<400> SEQUENCE: 139

Ala Gly Gly Gly Ser
1               5

<210> SEQ ID NO 140
<211> LENGTH: 20
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (4)...(17)
<223> OTHER INFORMATION: repeated 2 to 20 times

<400> SEQUENCE: 140

Gly Gly Ser Glu Gly Lys Ser Ser Gly Ser Gly Ser Glu Ser Lys Ser
1               5                   10                  15

Thr Gly Gly Ser
            20

<210> SEQ ID NO 141
<211> LENGTH: 9
<212> TYPE: PRT
<213> ORGANISM: Artificial Sequence
<220> FEATURE:
<223> OTHER INFORMATION: linker

<400> SEQUENCE: 141

```
Ser Ser Ser Ala Ser Ala Ser Ser Ala
1               5


<210> SEQ ID NO 142
<211> LENGTH: 7
<212> TYPE: PRT
<213> ORGANISM: Artificial Sequence
<220> FEATURE:
<223> OTHER INFORMATION: linker

<400> SEQUENCE: 142

Gly Ser Pro Gly Ser Pro Gly
1               5


<210> SEQ ID NO 143
<211> LENGTH: 11
<212> TYPE: PRT
<213> ORGANISM: Artificial Sequence
<220> FEATURE:
<223> OTHER INFORMATION: linker

<400> SEQUENCE: 143

Ala Thr Thr Thr Gly Ser Ser Pro Gly Pro Thr
1               5                   10


<210> SEQ ID NO 144
<211> LENGTH: 5
<212> TYPE: PRT
<213> ORGANISM: Artificial Sequence
<220> FEATURE:
<223> OTHER INFORMATION: linker consensus
<220> FEATURE:
<221> NAME/KEY: VARIANT
<222> LOCATION: (1)...(1)
<223> OTHER INFORMATION: Xaa is I, L, Y, M, F, V, or A
<220> FEATURE:
<221> NAME/KEY: VARIANT
<222> LOCATION: (2)...(2)
<223> OTHER INFORMATION: Xaa is A, G, S, V, E, D, Q, N, or Y
<220> FEATURE:
<221> NAME/KEY: VARIANT
<222> LOCATION: (3)...(3)
<223> OTHER INFORMATION: Xaa is H, P, A, V, G, S, or T
<220> FEATURE:
<221> NAME/KEY: VARIANT
<222> LOCATION: (4)...(4)
<223> OTHER INFORMATION: Xaa is D or E
<220> FEATURE:
<221> NAME/KEY: VARIANT
<222> LOCATION: (5)...(5)
<223> OTHER INFORMATION: Xaa is I, L, Y, M, F, V, T, S, G or A

<400> SEQUENCE: 144

Xaa Xaa Xaa Xaa Xaa
1               5


<210> SEQ ID NO 145
<211> LENGTH: 5
<212> TYPE: PRT
<213> ORGANISM: Artificial Sequence
<220> FEATURE:
<223> OTHER INFORMATION: linker consensus
<220> FEATURE:
<221> NAME/KEY: VARIANT
<222> LOCATION: (1)...(1)
<223> OTHER INFORMATION: Xaa is I or L
<220> FEATURE:
<221> NAME/KEY: VARIANT
<222> LOCATION: (3)...(3)
<223> OTHER INFORMATION: Xaa is P or A
<220> FEATURE:
<221> NAME/KEY: VARIANT
```

<222> LOCATION: (5)...(5)
<223> OTHER INFORMATION: Xaa is I, V, T, S, or G

<400> SEQUENCE: 145

Xaa Glu Xaa Asp Xaa
1               5

<210> SEQ ID NO 146
<211> LENGTH: 4
<212> TYPE: PRT
<213> ORGANISM: Artificial Sequence
<220> FEATURE:
<223> OTHER INFORMATION: granzyme B substrate

<400> SEQUENCE: 146

Leu Glu Ala Asp
1

<210> SEQ ID NO 147
<211> LENGTH: 4
<212> TYPE: PRT
<213> ORGANISM: Artificial Sequence
<220> FEATURE:
<223> OTHER INFORMATION: linker

<400> SEQUENCE: 147

Leu Glu Pro Asp
1

<210> SEQ ID NO 148
<211> LENGTH: 4
<212> TYPE: PRT
<213> ORGANISM: Artificial Sequence
<220> FEATURE:
<223> OTHER INFORMATION: linker

<400> SEQUENCE: 148

Leu Glu Ala Glu
1

<210> SEQ ID NO 149
<211> LENGTH: 5
<212> TYPE: PRT
<213> ORGANISM: Artificial Sequence
<220> FEATURE:
<223> OTHER INFORMATION: linker

<400> SEQUENCE: 149

Ile Glu Pro Asp Ile
1               5

<210> SEQ ID NO 150
<211> LENGTH: 5
<212> TYPE: PRT
<213> ORGANISM: Artificial Sequence
<220> FEATURE:
<223> OTHER INFORMATION: linker

<400> SEQUENCE: 150

Leu Glu Pro Asp Gly
1               5

<210> SEQ ID NO 151
<211> LENGTH: 5
<212> TYPE: PRT
<213> ORGANISM: Artificial Sequence
<220> FEATURE:

<223> OTHER INFORMATION: linker

<400> SEQUENCE: 151

Leu Glu Ala Asp Thr
1 5

<210> SEQ ID NO 152
<211> LENGTH: 5
<212> TYPE: PRT
<213> ORGANISM: Artificial Sequence
<220> FEATURE:
<223> OTHER INFORMATION: linker

<400> SEQUENCE: 152

Ile Glu Pro Asp Gly
1 5

<210> SEQ ID NO 153
<211> LENGTH: 5
<212> TYPE: PRT
<213> ORGANISM: Artificial Sequence
<220> FEATURE:
<223> OTHER INFORMATION: linker

<400> SEQUENCE: 153

Ile Glu Pro Asp Val
1 5

<210> SEQ ID NO 154
<211> LENGTH: 5
<212> TYPE: PRT
<213> ORGANISM: Artificial Sequence
<220> FEATURE:
<223> OTHER INFORMATION: linker

<400> SEQUENCE: 154

Ile Glu Pro Asp Ser
1 5

<210> SEQ ID NO 155
<211> LENGTH: 5
<212> TYPE: PRT
<213> ORGANISM: Artificial Sequence
<220> FEATURE:
<223> OTHER INFORMATION: linker

<400> SEQUENCE: 155

Ile Glu Pro Asp Thr
1 5

<210> SEQ ID NO 156
<211> LENGTH: 5
<212> TYPE: PRT
<213> ORGANISM: Artificial Sequence
<220> FEATURE:
<223> OTHER INFORMATION: linker consensus
<220> FEATURE:
<221> NAME/KEY: VARIANT
<222> LOCATION: (1)...(1)
<223> OTHER INFORMATION: Xaa is any amino acid
<220> FEATURE:
<221> NAME/KEY: VARIANT
<222> LOCATION: (5)...(5)
<223> OTHER INFORMATION: Xaa is A or V

<400> SEQUENCE: 156

Xaa Gln Ala Arg Xaa
1 5

<210> SEQ ID NO 157
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: VARIANT
<222> LOCATION: (5)...(5)
<223> OTHER INFORMATION: Xaa is A or V

<400> SEQUENCE: 157

Arg Gln Ala Arg Xaa
1               5

<210> SEQ ID NO 158
<211> LENGTH: 4
<212> TYPE: PRT
<213> ORGANISM: Artificial Sequence
<220> FEATURE:
<223> OTHER INFORMATION: matriptase substrate

<400> SEQUENCE: 158

Arg Gln Ala Arg
1

<210> SEQ ID NO 159
<211> LENGTH: 5
<212> TYPE: PRT
<213> ORGANISM: Artificial Sequence
<220> FEATURE:
<223> OTHER INFORMATION: linker

<400> SEQUENCE: 159

Arg Gln Ala Arg Val
1               5

<210> SEQ ID NO 160
<211> LENGTH: 4
<212> TYPE: PRT
<213> ORGANISM: Artificial Sequence
<220> FEATURE:
<223> OTHER INFORMATION: Linker consensus
<220> FEATURE:
<221> NAME/KEY: VARIANT
<222> LOCATION: (1)...(1)
<223> OTHER INFORMATION: Xaa is P, V or A
<220> FEATURE:
<221> NAME/KEY: VARIANT
<222> LOCATION: (2)...(2)
<223> OTHER INFORMATION: Xaa is Q or D
<220> FEATURE:
<221> NAME/KEY: VARIANT
<222> LOCATION: (3)...(3)
<223> OTHER INFORMATION: Xaa is A or N
<220> FEATURE:
<221> NAME/KEY: VARIANT
<222> LOCATION: (4)...(4)
<223> OTHER INFORMATION: Xaa is L, I or M

<400> SEQUENCE: 160

Xaa Xaa Xaa Xaa
1

<210> SEQ ID NO 161
<211> LENGTH: 4
<212> TYPE: PRT
<213> ORGANISM: Artificial Sequence
<220> FEATURE:

```
<223> OTHER INFORMATION: Linker consensus
<220> FEATURE:
<221> NAME/KEY: VARIANT
<222> LOCATION: (2)...(2)
<223> OTHER INFORMATION: Xaa is Q or D
<220> FEATURE:
<221> NAME/KEY: VARIANT
<222> LOCATION: (3)...(3)
<223> OTHER INFORMATION: Xaa is A or N
<220> FEATURE:
<221> NAME/KEY: VARIANT
<222> LOCATION: (4)...(4)
<223> OTHER INFORMATION: Xaa is  L or I

<400> SEQUENCE: 161

Pro Xaa Xaa Xaa
1


<210> SEQ ID NO 162
<211> LENGTH: 4
<212> TYPE: PRT
<213> ORGANISM: Artificial Sequence
<220> FEATURE:
<223> OTHER INFORMATION: MMP substrate

<400> SEQUENCE: 162

Pro Ala Gly Leu
1


<210> SEQ ID NO 163
<211> LENGTH: 19
<212> TYPE: PRT
<213> ORGANISM: Artificial Sequence
<220> FEATURE:
<223> OTHER INFORMATION: linker

<400> SEQUENCE: 163

Thr Gly Leu Glu Ala Asp Gly Ser Pro Ala Gly Leu Gly Arg Gln Ala
1               5                   10                  15

Arg Val Gly


<210> SEQ ID NO 164
<211> LENGTH: 19
<212> TYPE: PRT
<213> ORGANISM: Artificial Sequence
<220> FEATURE:
<223> OTHER INFORMATION: linker

<400> SEQUENCE: 164

Thr Gly Leu Glu Ala Asp Gly Ser Arg Gln Ala Arg Val Gly Pro Ala
1               5                   10                  15

Gly Leu Gly


<210> SEQ ID NO 165
<211> LENGTH: 19
<212> TYPE: PRT
<213> ORGANISM: Artificial Sequence
<220> FEATURE:
<223> OTHER INFORMATION: linker

<400> SEQUENCE: 165

Thr Gly Ser Pro Ala Gly Leu Glu Ala Asp Gly Ser Arg Gln Ala Arg
1               5                   10                  15

Val Gly Ser


<210> SEQ ID NO 166
```

<211> LENGTH: 19
<212> TYPE: PRT
<213> ORGANISM: Artificial Sequence
<220> FEATURE:
<223> OTHER INFORMATION: linker

<400> SEQUENCE: 166

```
Thr Gly Pro Ala Gly Leu Gly Leu Glu Ala Asp Gly Ser Arg Gln Ala
1               5                   10                  15

Arg Val Gly
```

<210> SEQ ID NO 167
<211> LENGTH: 19
<212> TYPE: PRT
<213> ORGANISM: Artificial Sequence
<220> FEATURE:
<223> OTHER INFORMATION: linker

<400> SEQUENCE: 167

```
Thr Gly Arg Gln Ala Arg Val Gly Leu Glu Ala Asp Gly Ser Pro Ala
1               5                   10                  15

Gly Leu Gly
```

<210> SEQ ID NO 168
<211> LENGTH: 18
<212> TYPE: PRT
<213> ORGANISM: Artificial Sequence
<220> FEATURE:
<223> OTHER INFORMATION: linker

<400> SEQUENCE: 168

```
Thr Gly Ser Arg Gln Ala Arg Val Gly Pro Ala Gly Leu Glu Ala Asp
1               5                   10                  15

Gly Ser
```

<210> SEQ ID NO 169
<211> LENGTH: 20
<212> TYPE: PRT
<213> ORGANISM: Artificial Sequence
<220> FEATURE:
<223> OTHER INFORMATION: linker

<400> SEQUENCE: 169

```
Thr Gly Pro Ala Gly Leu Gly Ser Arg Gln Ala Arg Val Gly Leu Glu
1               5                   10                  15

Ala Asp Gly Ser
            20
```

<210> SEQ ID NO 170
<211> LENGTH: 18
<212> TYPE: PRT
<213> ORGANISM: Artificial Sequence
<220> FEATURE:
<223> OTHER INFORMATION: linker

<400> SEQUENCE: 170

```
Gly Pro Ala Gly Leu Gly Leu Glu Pro Asp Gly Ser Arg Gln Ala Arg
1               5                   10                  15

Val Gly
```

<210> SEQ ID NO 171
<211> LENGTH: 18
<212> TYPE: PRT
<213> ORGANISM: Artificial Sequence
<220> FEATURE:
<223> OTHER INFORMATION: linker

<400> SEQUENCE: 171

Gly Gly Ser Gly Gly Gly Gly Ile Glu Pro Asp Ile Gly Gly Ser Gly
1 5 10 15

Gly Ser

<210> SEQ ID NO 172
<211> LENGTH: 18
<212> TYPE: PRT
<213> ORGANISM: Artificial Sequence
<220> FEATURE:
<223> OTHER INFORMATION: linker

<400> SEQUENCE: 172

Gly Gly Ser Gly Gly Gly Gly Leu Glu Ala Asp Thr Gly Gly Ser Gly
1 5 10 15

Gly Ser

<210> SEQ ID NO 173
<211> LENGTH: 9
<212> TYPE: PRT
<213> ORGANISM: Artificial Sequence
<220> FEATURE:
<223> OTHER INFORMATION: linker

<400> SEQUENCE: 173

Gly Ser Ile Glu Pro Asp Ile Gly Ser
1 5

<210> SEQ ID NO 174
<211> LENGTH: 9
<212> TYPE: PRT
<213> ORGANISM: Artificial Sequence
<220> FEATURE:
<223> OTHER INFORMATION: linker

<400> SEQUENCE: 174

Gly Ser Leu Glu Ala Asp Thr Gly Ser
1 5

<210> SEQ ID NO 175
<211> LENGTH: 18
<212> TYPE: PRT
<213> ORGANISM: Artificial Sequence
<220> FEATURE:
<223> OTHER INFORMATION: linker

<400> SEQUENCE: 175

Gly Gly Ser Gly Gly Gly Gly Ile Glu Pro Asp Gly Gly Gly Ser Gly
1 5 10 15

Gly Ser

<210> SEQ ID NO 176
<211> LENGTH: 18
<212> TYPE: PRT
<213> ORGANISM: Artificial Sequence
<220> FEATURE:
<223> OTHER INFORMATION: linker

<400> SEQUENCE: 176

Gly Gly Ser Gly Gly Gly Gly Ile Glu Pro Asp Val Gly Gly Ser Gly
1 5 10 15

Gly Ser

<210> SEQ ID NO 177
<211> LENGTH: 18
<212> TYPE: PRT
<213> ORGANISM: Artificial Sequence
<220> FEATURE:
<223> OTHER INFORMATION: linker

<400> SEQUENCE: 177

Gly Gly Ser Gly Gly Gly Gly Ile Glu Pro Asp Ser Gly Gly Ser Gly
1 5 10 15

Gly Ser

<210> SEQ ID NO 178
<211> LENGTH: 18
<212> TYPE: PRT
<213> ORGANISM: Artificial Sequence
<220> FEATURE:
<223> OTHER INFORMATION: linker

<400> SEQUENCE: 178

Gly Gly Ser Gly Gly Gly Gly Ile Glu Pro Asp Thr Gly Gly Ser Gly
1 5 10 15

Gly Ser

<210> SEQ ID NO 179
<211> LENGTH: 12
<212> TYPE: PRT
<213> ORGANISM: Artificial Sequence
<220> FEATURE:
<223> OTHER INFORMATION: linker

<400> SEQUENCE: 179

Gly Gly Gly Ser Leu Glu Pro Asp Gly Ser Gly Ser
1 5 10

<210> SEQ ID NO 180
<211> LENGTH: 18
<212> TYPE: PRT
<213> ORGANISM: Artificial Sequence
<220> FEATURE:
<223> OTHER INFORMATION: linker

<400> SEQUENCE: 180

Gly Pro Ala Gly Leu Gly Leu Glu Ala Asp Gly Ser Arg Gln Ala Arg
1 5 10 15

Val Gly

<210> SEQ ID NO 181
<211> LENGTH: 15
<212> TYPE: PRT
<213> ORGANISM: Artificial Sequence
<220> FEATURE:
<223> OTHER INFORMATION: linker

<400> SEQUENCE: 181

Gly Gly Glu Gly Gly Gly Gly Ser Gly Gly Ser Gly Gly Gly Ser
1 5 10 15

<210> SEQ ID NO 182
<211> LENGTH: 18
<212> TYPE: PRT
<213> ORGANISM: Artificial Sequence
<220> FEATURE:

<223> OTHER INFORMATION: linker

<400> SEQUENCE: 182

Gly Ser Ser Ala Gly Ser Glu Ala Gly Gly Ser Gly Gln Ala Gly Val
1 5 10 15

Gly Ser

<210> SEQ ID NO 183
<211> LENGTH: 18
<212> TYPE: PRT
<213> ORGANISM: Artificial Sequence
<220> FEATURE:
<223> OTHER INFORMATION: linker

<400> SEQUENCE: 183

Gly Gly Ser Gly Gly Gly Gly Leu Glu Ala Glu Gly Ser Gly Gly Gly
1 5 10 15

Gly Ser

<210> SEQ ID NO 184
<211> LENGTH: 18
<212> TYPE: PRT
<213> ORGANISM: aritifcial sequence

<400> SEQUENCE: 184

Gly Gly Ser Gly Gly Gly Gly Ile Glu Pro Asp Pro Gly Gly Ser Gly
1 5 10 15

Gly Ser

<210> SEQ ID NO 185
<211> LENGTH: 19
<212> TYPE: PRT
<213> ORGANISM: Artificial Sequence
<220> FEATURE:
<223> OTHER INFORMATION: linker

<400> SEQUENCE: 185

Thr Gly Gly Ser Gly Gly Gly Gly Ile Glu Pro Asp Ile Gly Gly Ser
1 5 10 15

Gly Gly Ser

<210> SEQ ID NO 186
<211> LENGTH: 120
<212> TYPE: PRT
<213> ORGANISM: Artificial Sequence
<220> FEATURE:
<223> OTHER INFORMATION: 1G7 CD28 sdAb

<400> SEQUENCE: 186

Glu Val Gln Leu Val Gln Ser Gly Gly Ala Leu Val Gln Ala Gly Gly
1 5 10 15

Ser Leu Arg Leu Ser Cys Val Ala Pro Arg Thr Ile Gly Leu Ile Ser
20 25 30

Leu Met Gly Trp Tyr Arg Gln Ala Pro Gly Lys Gln Arg Glu Leu Val
35 40 45

Ala Thr Ile Ile Ala Ser Gly Arg Thr Asn Tyr Ala Glu Ser Val Lys
50 55 60

Asp Arg Phe Thr Ile Ser Arg Asp Asn Ala Glu Asn Lys Val Tyr Leu
65 70 75 80

Gln Val Asn Ser Leu Lys Pro Glu Asp Thr Ala Val Tyr Tyr Cys Arg
85 90 95

Val Asn Ala Glu Thr Ala Pro Trp Ser Arg Arg Gly Phe Trp Gly Gln
100 105 110

Gly Thr Gln Val Thr Val Lys Pro
115 120

<210> SEQ ID NO 187
<211> LENGTH: 117
<212> TYPE: PRT
<213> ORGANISM: Artificial Sequence
<220> FEATURE:
<223> OTHER INFORMATION: 2F11 CD28 sdAb

<400> SEQUENCE: 187

Gln Val Gln Leu Gln Gln Ser Gly Gly Gly Leu Val Gln Ala Gly Gly
1 5 10 15

Ser Leu Arg Leu Ser Cys Val Ala Ser Gly Ile Ser Phe Asn Val Val
20 25 30

Asp Met Asp Trp His Arg Gln Ala Pro Gly Lys Glu Arg Glu Leu Val
35 40 45

Ala Gly Ile Thr Arg Gly Gly Ala Thr Tyr Tyr Ala Asp Ser Val Lys
50 55 60

Gly Arg Phe Thr Ile Ser Arg Asp Asn Ala Lys Asn Ser Ala Tyr Leu
65 70 75 80

Gln Leu Ala Asn Leu Lys Pro Glu Asp Thr Ala Val Tyr Tyr Cys Asn
85 90 95

Ala Arg Trp Pro Ser Arg Tyr Gln Asn Tyr Trp Gly Gln Gly Thr Gln
100 105 110

Val Thr Val Lys Pro
115

<210> SEQ ID NO 188
<211> LENGTH: 124
<212> TYPE: PRT
<213> ORGANISM: Artificial Sequence
<220> FEATURE:
<223> OTHER INFORMATION: 1C9 CD28 sdAb

<400> SEQUENCE: 188

Glu Val Gln Leu Val Gln Ser Gly Gly Gly Leu Val Gln Thr Gly Gly
1 5 10 15

Ser Leu Arg Leu Ser Cys Ala Ala Ser Gly Arg Met Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Arg Asp Ser Ala Asp Tyr Ala Asp Ser Val
50 55 60

Lys Gly Arg Phe Thr Ile Ser Arg Asp Asn Ala Lys Asn Thr Val Tyr
65 70 75 80

Leu Glu Met Asn Ser Leu Lys Pro Glu Asp Thr Ala Ile Tyr Tyr Cys
85 90 95

Gly Phe Thr Tyr Ala Gly Trp Ala Ser Ser Arg Arg Asp Asp Tyr Asn
100 105 110

Tyr Trp Gly Gln Gly Thr Gln Val Thr Val Lys Pro
115 120

<210> SEQ ID NO 189
<211> LENGTH: 10
<212> TYPE: PRT

<213> ORGANISM: Artificial Sequence
<220> FEATURE:
<223> OTHER INFORMATION: CDR1 (1G7)

<400> SEQUENCE: 189

Arg Thr Ile Gly Leu Ile Ser Leu Met Gly
1 5 10

<210> SEQ ID NO 190
<211> LENGTH: 9
<212> TYPE: PRT
<213> ORGANISM: Artificial Sequence
<220> FEATURE:
<223> OTHER INFORMATION: CDR2 (1G7)

<400> SEQUENCE: 190

Thr Ile Ile Ala Ser Gly Arg Thr Asn
1 5

<210> SEQ ID NO 191
<211> LENGTH: 12
<212> TYPE: PRT
<213> ORGANISM: Artificial Sequence
<220> FEATURE:
<223> OTHER INFORMATION: CDR3 (1G7)

<400> SEQUENCE: 191

Asn Ala Glu Thr Ala Pro Trp Ser Arg Arg Gly Phe
1 5 10

<210> SEQ ID NO 192
<211> LENGTH: 10
<212> TYPE: PRT
<213> ORGANISM: Artificial Sequence
<220> FEATURE:
<223> OTHER INFORMATION: CDR1 (2F11)

<400> SEQUENCE: 192

Gly Ile Ser Phe Asn Val Val Asp Met Asp
1 5 10

<210> SEQ ID NO 193
<211> LENGTH: 9
<212> TYPE: PRT
<213> ORGANISM: Artificial Sequence
<220> FEATURE:
<223> OTHER INFORMATION: CDR2 (2F11)

<400> SEQUENCE: 193

Gly Ile Thr Arg Gly Gly Ala Thr Tyr
1 5

<210> SEQ ID NO 194
<211> LENGTH: 9
<212> TYPE: PRT
<213> ORGANISM: Artificial Sequence
<220> FEATURE:
<223> OTHER INFORMATION: CDR3 (2F11)

<400> SEQUENCE: 194

Arg Trp Pro Ser Arg Tyr Gln Asn Tyr
1 5

<210> SEQ ID NO 195
<211> LENGTH: 10
<212> TYPE: PRT
<213> ORGANISM: Artificial Sequence
<220> FEATURE:
<223> OTHER INFORMATION: CDR1 (1C9, v1-v4, v7-v9, v12-v27)

<400> SEQUENCE: 195

Gly Arg Met Phe Ser Asn Tyr Ala Met Gly
1 5 10

<210> SEQ ID NO 196
<211> LENGTH: 10
<212> TYPE: PRT
<213> ORGANISM: Artificial Sequence
<220> FEATURE:
<223> OTHER INFORMATION: CDR2 (1C9, v1-v6, v10, v11)

<400> SEQUENCE: 196

Ala Ile Asn Tyr Arg Arg Asp Ser Ala Asp
1 5 10

<210> SEQ ID NO 197
<211> LENGTH: 15
<212> TYPE: PRT
<213> ORGANISM: Artificial Sequence
<220> FEATURE:
<223> OTHER INFORMATION: CDR3 (1C9, v1-v27)

<400> SEQUENCE: 197

Thr Tyr Ala Gly Trp Ala Ser Ser Arg Arg Asp Asp Tyr Asn Tyr
1 5 10 15

<210> SEQ ID NO 198
<211> LENGTH: 10
<212> TYPE: PRT
<213> ORGANISM: Artificial Sequence
<220> FEATURE:
<223> OTHER INFORMATION: CDR1 (1C9v5)

<400> SEQUENCE: 198

Gly Arg Ile Phe Ser Asn Tyr Ala Met Gly
1 5 10

<210> SEQ ID NO 199
<211> LENGTH: 10
<212> TYPE: PRT
<213> ORGANISM: Artificial Sequence
<220> FEATURE:
<223> OTHER INFORMATION: CDR1 (1C9v6)

<400> SEQUENCE: 199

Gly Arg Leu Phe Ser Asn Tyr Ala Met Gly
1 5 10

<210> SEQ ID NO 200
<211> LENGTH: 10
<212> TYPE: PRT
<213> ORGANISM: Artificial Sequence
<220> FEATURE:
<223> OTHER INFORMATION: CDR1 (1C9v10)

<400> SEQUENCE: 200

Gly Arg Thr Phe Ser Asn Tyr Ala Met Gly
1 5 10

<210> SEQ ID NO 201
<211> LENGTH: 10
<212> TYPE: PRT
<213> ORGANISM: Artificial Sequence
<220> FEATURE:

<223> OTHER INFORMATION: CDR1 (1C9v11)

<400> SEQUENCE: 201

Gly Phe Thr Phe Ser Asn Tyr Ala Met Gly
1 5 10

<210> SEQ ID NO 202
<211> LENGTH: 10
<212> TYPE: PRT
<213> ORGANISM: Artificial Sequence
<220> FEATURE:
<223> OTHER INFORMATION: CDR2 (1C9v7)

<400> SEQUENCE: 202

Ala Ile Asn Tyr Arg Arg Glu Ser Ala Asp
1 5 10

<210> SEQ ID NO 203
<211> LENGTH: 10
<212> TYPE: PRT
<213> ORGANISM: Artificial Sequence
<220> FEATURE:
<223> OTHER INFORMATION: CDR2 (1C9v8)

<400> SEQUENCE: 203

Ala Ile Asn Tyr Arg Arg Asp Ala Ala Asp
1 5 10

<210> SEQ ID NO 204
<211> LENGTH: 10
<212> TYPE: PRT
<213> ORGANISM: Artificial Sequence
<220> FEATURE:
<223> OTHER INFORMATION: CDR2 (1C9v9)

<400> SEQUENCE: 204

Ala Ile Asn Tyr Arg Arg Asp Thr Ala Asp
1 5 10

<210> SEQ ID NO 205
<211> LENGTH: 10
<212> TYPE: PRT
<213> ORGANISM: Artificial Sequence
<220> FEATURE:
<223> OTHER INFORMATION: CDR2 (1C9v12)

<400> SEQUENCE: 205

Ala Ile Asn Tyr Arg Arg Asp Val Ala Asp
1 5 10

<210> SEQ ID NO 206
<211> LENGTH: 10
<212> TYPE: PRT
<213> ORGANISM: Artificial Sequence
<220> FEATURE:
<223> OTHER INFORMATION: CDR2 (1C9v13, 16, 17, 22-27)

<400> SEQUENCE: 206

Ala Ile Asn Tyr Arg Arg Asp Asp Ala Asp
1 5 10

<210> SEQ ID NO 207
<211> LENGTH: 10
<212> TYPE: PRT
<213> ORGANISM: Artificial Sequence
<220> FEATURE:
<223> OTHER INFORMATION: CDR2 (1C9v14)

<400> SEQUENCE: 207

Ala Ile Asn Tyr Arg Arg Ser Asp Ala Asp
1 5 10

<210> SEQ ID NO 208
<211> LENGTH: 10
<212> TYPE: PRT
<213> ORGANISM: Artificial Sequence
<220> FEATURE:
<223> OTHER INFORMATION: CDR2 (1C9v15)

<400> SEQUENCE: 208

Ala Ile Asn Tyr Arg Arg Thr Cys Ala Asp
1 5 10

<210> SEQ ID NO 209
<211> LENGTH: 10
<212> TYPE: PRT
<213> ORGANISM: Artificial Sequence
<220> FEATURE:
<223> OTHER INFORMATION: CDR2 (1C9v18)

<400> SEQUENCE: 209

Ala Ile Asn Tyr Arg Arg Asp Asp Ala Ala
1 5 10

<210> SEQ ID NO 210
<211> LENGTH: 10
<212> TYPE: PRT
<213> ORGANISM: Artificial Sequence
<220> FEATURE:
<223> OTHER INFORMATION: CDR2 (1C9v19)

<400> SEQUENCE: 210

Ala Ile Asn Tyr Arg Arg Ser Ser Ala Asp
1 5 10

<210> SEQ ID NO 211
<211> LENGTH: 10
<212> TYPE: PRT
<213> ORGANISM: Artificial Sequence
<220> FEATURE:
<223> OTHER INFORMATION: CDR2 (1C9v20)

<400> SEQUENCE: 211

Ala Ile Asn Tyr Arg Arg Asp Asp Thr Asp
1 5 10

<210> SEQ ID NO 212
<211> LENGTH: 10
<212> TYPE: PRT
<213> ORGANISM: Artificial Sequence
<220> FEATURE:
<223> OTHER INFORMATION: CDR2 (1C9v21)

<400> SEQUENCE: 212

Ala Ile Asn Tyr Arg Arg Asp Glu Ala Asp
1 5 10

<210> SEQ ID NO 213
<211> LENGTH: 124
<212> TYPE: PRT
<213> ORGANISM: Artificial Sequence
<220> FEATURE:
<223> OTHER INFORMATION: 1C9v1 CD28 sdAb

<400> SEQUENCE: 213

Glu Val Gln Leu Val Glu Ser Gly Gly Gly Glu Val Gln Pro Gly Gly
1 5 10 15

Ser Leu Arg Leu Ser Cys Ala Ala Ser Gly Arg Met Phe Ser Asn Tyr
20 25 30

Ala Met Gly Trp Phe Arg Gln Ala Pro Gly Lys Gly Arg Glu Phe Val
35 40 45

Ser Ala Ile Asn Tyr Arg Arg Asp Ser Ala Asp Tyr Ala Glu Ser Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Val Tyr Tyr Cys
85 90 95

Gly Phe Thr Tyr Ala Gly Trp Ala Ser Ser Arg Arg Asp Asp Tyr Asn
100 105 110

Tyr Trp Gly Gln Gly Thr Leu Val Thr Val Lys Pro
115 120

<210> SEQ ID NO 214
<211> LENGTH: 124
<212> TYPE: PRT
<213> ORGANISM: Artificial Sequence
<220> FEATURE:
<223> OTHER INFORMATION: 1C9v2 CD28 sdAb

<400> SEQUENCE: 214

Glu Val Gln Leu Val Glu Ser Gly Gly Gly Glu Val Gln Pro Gly Gly
1 5 10 15

Ser Leu Arg Leu Ser Cys Ala Ala Ser Gly Arg Met Phe Ser Asn Tyr
20 25 30

Ala Met Gly Trp Phe Arg Gln Ala Pro Gly Lys Glu Arg Glu Phe Val
35 40 45

Ser Ala Ile Asn Tyr Arg Arg Asp Ser Ala Asp Tyr Ala Glu Ser Val
50 55 60

Lys Gly Arg Phe Thr Ile Ser Arg Asp Asn Ala Lys Asn Thr Leu Tyr
65 70 75 80

Leu Gln Met Asn Ser Leu Arg Ala Glu Asp Thr Ala Val Tyr Tyr Cys
85 90 95

Gly Phe Thr Tyr Ala Gly Trp Ala Ser Ser Arg Arg Asp Asp Tyr Asn
100 105 110

Tyr Trp Gly Gln Gly Thr Leu Val Thr Val Lys Pro
115 120

<210> SEQ ID NO 215
<211> LENGTH: 124
<212> TYPE: PRT
<213> ORGANISM: Artificial Sequence
<220> FEATURE:
<223> OTHER INFORMATION: 1C9v3 CD28 sdAb

<400> SEQUENCE: 215

Glu Val Gln Leu Val Glu Ser Gly Gly Gly Glu Val Gln Pro Gly Gly
1 5 10 15

Ser Leu Arg Leu Ser Cys Ala Ala Ser Gly Arg Met Phe Ser Asn Tyr
20 25 30

Ala Met Gly Trp Phe Arg Gln Ala Pro Gly Lys Glu Arg Glu Phe Val
35 40 45

```
Ser Ala Ile Asn Tyr Arg Arg Asp Ser Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120
```

<210> SEQ ID NO 216
<211> LENGTH: 124
<212> TYPE: PRT
<213> ORGANISM: Artificial Sequence
<220> FEATURE:
<223> OTHER INFORMATION: 1C9v4 CD28 sdAb

<400> SEQUENCE: 216

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Ser Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120
```

<210> SEQ ID NO 217
<211> LENGTH: 124
<212> TYPE: PRT
<213> ORGANISM: Artificial Sequence
<220> FEATURE:
<223> OTHER INFORMATION: 1C9v5 CD28 sdAb

<400> SEQUENCE: 217

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Ile Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Ser Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110
```

```
Tyr Trp Gly Gln Gly Thr Leu Val Thr Val Lys Pro
        115                 120


<210> SEQ ID NO 218
<211> LENGTH: 124
<212> TYPE: PRT
<213> ORGANISM: Artificial Sequence
<220> FEATURE:
<223> OTHER INFORMATION: 1C9v6 CD28 sdAb

<400> SEQUENCE: 218

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Leu Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Ser Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 219
<211> LENGTH: 124
<212> TYPE: PRT
<213> ORGANISM: Artificial Sequence
<220> FEATURE:
<223> OTHER INFORMATION: 1C9v7 CD28 sdAb

<400> SEQUENCE: 219

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Glu Ser Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 220
<211> LENGTH: 124
<212> TYPE: PRT
<213> ORGANISM: Artificial Sequence
<220> FEATURE:
<223> OTHER INFORMATION: 1C9v8 CD28 sdAb
```

<400> SEQUENCE: 220

Glu Val Gln Leu Val Glu Ser Gly Gly Gly Glu Val Gln Pro Gly Gly
1 5 10 15

Ser Leu Arg Leu Ser Cys Ala Ala Ser Gly Arg Met Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Arg Asp Ala Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Asn Ser Leu Arg Ala Glu Asp Thr Ala Val Tyr Tyr Cys
85 90 95

Gly Phe Thr Tyr Ala Gly Trp Ala Ser Ser Arg Arg Asp Asp Tyr Asn
100 105 110

Tyr Trp Gly Gln Gly Thr Leu Val Thr Val Lys Pro
115 120

<210> SEQ ID NO 221
<211> LENGTH: 124
<212> TYPE: PRT
<213> ORGANISM: Artificial Sequence
<220> FEATURE:
<223> OTHER INFORMATION: 1C9v9 CD28 sdAb

<400> SEQUENCE: 221

Glu Val Gln Leu Val Glu Ser Gly Gly Gly Glu Val Gln Pro Gly Gly
1 5 10 15

Ser Leu Arg Leu Ser Cys Ala Ala Ser Gly Arg Met Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Arg Asp Thr Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Asn Ser Leu Arg Ala Glu Asp Thr Ala Val Tyr Tyr Cys
85 90 95

Gly Phe Thr Tyr Ala Gly Trp Ala Ser Ser Arg Arg Asp Asp Tyr Asn
100 105 110

Tyr Trp Gly Gln Gly Thr Leu Val Thr Val Lys Pro
115 120

<210> SEQ ID NO 222
<211> LENGTH: 124
<212> TYPE: PRT
<213> ORGANISM: Artificial Sequence
<220> FEATURE:
<223> OTHER INFORMATION: 1C9v10 CD28 sdAb

<400> SEQUENCE: 222

Glu Val Gln Leu Val Glu Ser Gly Gly Gly Glu Val Gln Pro Gly Gly
1 5 10 15

Ser Leu Arg Leu Ser Cys Ala Ala Ser Gly Arg Thr Phe Ser Asn Tyr
20 25 30

Ala Met Gly Trp Phe Arg Gln Ala Pro Gly Lys Glu Arg Glu Phe Val
35 40 45

```
Ala Ala Ile Asn Tyr Arg Arg Asp Ser Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 223
<211> LENGTH: 124
<212> TYPE: PRT
<213> ORGANISM: Artificial Sequence
<220> FEATURE:
<223> OTHER INFORMATION: 1C9v11 CD28 sdAb

<400> SEQUENCE: 223

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Ser Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 224
<211> LENGTH: 124
<212> TYPE: PRT
<213> ORGANISM: Artificial Sequence
<220> FEATURE:
<223> OTHER INFORMATION: 1C9v12 CD28 sdAb

<400> SEQUENCE: 224

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Val Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
```

100 105 110

Tyr Trp Gly Gln Gly Thr Leu Val Thr Val Lys Pro
115 120

<210> SEQ ID NO 225
<211> LENGTH: 124
<212> TYPE: PRT
<213> ORGANISM: Artificial Sequence
<220> FEATURE:
<223> OTHER INFORMATION: 1C9v13 CD28 sdAb

<400> SEQUENCE: 225

Glu Val Gln Leu Val Glu Ser Gly Gly Gly Glu Val Gln Pro Gly Gly
1 5 10 15

Ser Leu Arg Leu Ser Cys Ala Ala Ser Gly Arg Met Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Arg Asp Asp Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Asn Ser Leu Arg Ala Glu Asp Thr Ala Val Tyr Tyr Cys
85 90 95

Gly Phe Thr Tyr Ala Gly Trp Ala Ser Ser Arg Arg Asp Asp Tyr Asn
100 105 110

Tyr Trp Gly Gln Gly Thr Leu Val Thr Val Lys Pro
115 120

<210> SEQ ID NO 226
<211> LENGTH: 124
<212> TYPE: PRT
<213> ORGANISM: Artificial Sequence
<220> FEATURE:
<223> OTHER INFORMATION: 1C9v14 CD28 sdAb

<400> SEQUENCE: 226

Glu Val Gln Leu Val Glu Ser Gly Gly Gly Glu Val Gln Pro Gly Gly
1 5 10 15

Ser Leu Arg Leu Ser Cys Ala Ala Ser Gly Arg Met Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Arg Ser Asp Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Asn Ser Leu Arg Ala Glu Asp Thr Ala Val Tyr Tyr Cys
85 90 95

Gly Phe Thr Tyr Ala Gly Trp Ala Ser Ser Arg Arg Asp Asp Tyr Asn
100 105 110

Tyr Trp Gly Gln Gly Thr Leu Val Thr Val Lys Pro
115 120

<210> SEQ ID NO 227
<211> LENGTH: 124
<212> TYPE: PRT
<213> ORGANISM: Artificial Sequence
<220> FEATURE:

```
<223> OTHER INFORMATION: 1C9v15 CD28 sdAb

<400> SEQUENCE: 227

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Thr Cys Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 228
<211> LENGTH: 124
<212> TYPE: PRT
<213> ORGANISM: Artificial Sequence
<220> FEATURE:
<223> OTHER INFORMATION: 1C9v16 CD28 sdAb

<400> SEQUENCE: 228

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Gly Arg Glu Phe Val
        35                  40                  45

Ala Ala Ile Asn Tyr Arg Arg Asp Asp Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 229
<211> LENGTH: 124
<212> TYPE: PRT
<213> ORGANISM: Artificial Sequence
<220> FEATURE:
<223> OTHER INFORMATION: 1C9v17 CD28 sdAb

<400> SEQUENCE: 229

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Gly Arg Glu Phe Val
```

```
        35                  40                  45

Ala Ala Ile Asn Tyr Arg Arg Asp Asp Ala Asp Tyr Ala Glu Ser Val
    50                  55                  60

Lys Asp Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 230
<211> LENGTH: 124
<212> TYPE: PRT
<213> ORGANISM: Artificial Sequence
<220> FEATURE:
<223> OTHER INFORMATION: 1C9v18 CD28 sdAb

<400> SEQUENCE: 230

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Asp Ala Ala Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 231
<211> LENGTH: 124
<212> TYPE: PRT
<213> ORGANISM: Artificial Sequence
<220> FEATURE:
<223> OTHER INFORMATION: 1C9v19 CD28 sdAb

<400> SEQUENCE: 231

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Ser Ser Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95
```

```
Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 232
<211> LENGTH: 124
<212> TYPE: PRT
<213> ORGANISM: Artificial Sequence
<220> FEATURE:
<223> OTHER INFORMATION: 1C9v20 CD28 sdAb

<400> SEQUENCE: 232

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Asp Thr Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 233
<211> LENGTH: 124
<212> TYPE: PRT
<213> ORGANISM: Artificial Sequence
<220> FEATURE:
<223> OTHER INFORMATION: 1C9v21 CD28 sdAb

<400> SEQUENCE: 233

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Glu Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 234
<211> LENGTH: 124
<212> TYPE: PRT
<213> ORGANISM: Artificial Sequence
```

```
<220> FEATURE:
<223> OTHER INFORMATION: 1C9v22 CD28 sdAb

<400> SEQUENCE: 234

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Trp Val
        35                  40                  45

Ala Ala Ile Asn Tyr Arg Arg Asp Asp Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 235
<211> LENGTH: 124
<212> TYPE: PRT
<213> ORGANISM: Artificial Sequence
<220> FEATURE:
<223> OTHER INFORMATION: 1C9v23 CD28 sdAb

<400> SEQUENCE: 235

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Val Arg Gln Ala Pro Gly Lys Glu Arg Glu Phe Val
        35                  40                  45

Ala Ala Ile Asn Tyr Arg Arg Asp Asp Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 236
<211> LENGTH: 124
<212> TYPE: PRT
<213> ORGANISM: Artificial Sequence
<220> FEATURE:
<223> OTHER INFORMATION: 1C9v24 CD28 sdAb

<400> SEQUENCE: 236

Glu Val Gln Leu Val Glu Ser Gly Gly Gly Glu Val Gln Thr Gly Gly
1               5                   10                  15

Ser Leu Arg Leu Ser Cys Ala Ala Ser Gly Arg Met Phe Ser Asn Tyr
            20                  25                  30
```

```
Ala Met Gly Trp Phe Arg Gln Ala Pro Gly Lys Glu Arg Glu Phe Val
        35                  40                  45

Ala Ala Ile Asn Tyr Arg Arg Asp Asp Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 237
<211> LENGTH: 124
<212> TYPE: PRT
<213> ORGANISM: Artificial Sequence
<220> FEATURE:
<223> OTHER INFORMATION: 1C9v25 CD28 sdAb

<400> SEQUENCE: 237

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Asp Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Glu Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 238
<211> LENGTH: 124
<212> TYPE: PRT
<213> ORGANISM: Artificial Sequence
<220> FEATURE:
<223> OTHER INFORMATION: 1C9v26 CD28 sdAb

<400> SEQUENCE: 238

Glu Val Gln Leu Val Glu Ser Gly Gly Gly Glu Val Gln Thr Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Asp Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Glu Met Asn Ser Leu Arg Ala Glu Asp Thr Ala Val Tyr Tyr Cys
                85                  90                  95
```

Gly Phe Thr Tyr Ala Gly Trp Ala Ser Ser Arg Arg Asp Asp Tyr Asn
100 105 110

Tyr Trp Gly Gln Gly Thr Leu Val Thr Val Lys Pro
115 120

<210> SEQ ID NO 239
<211> LENGTH: 124
<212> TYPE: PRT
<213> ORGANISM: Artificial Sequence
<220> FEATURE:
<223> OTHER INFORMATION: 1C9v27 CD28 sdAb

<400> SEQUENCE: 239

Glu Val Gln Leu Val Glu Ser Gly Gly Gly Glu Val Gln Pro Gly Gly
1 5 10 15

Ser Leu Arg Leu Ser Cys Ala Ala Ser Gly Arg Met Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Arg Asp Asp Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Asn Ser Leu Arg Ala Glu Asp Thr Ala Ile Tyr Tyr Cys
85 90 95

Gly Phe Thr Tyr Ala Gly Trp Ala Ser Ser Arg Arg Asp Asp Tyr Asn
100 105 110

Tyr Trp Gly Gln Gly Thr Leu Val Thr Val Lys Pro
115 120

<210> SEQ ID NO 240
<211> LENGTH: 122
<212> TYPE: PRT
<213> ORGANISM: Artificial Sequence
<220> FEATURE:
<223> OTHER INFORMATION: 5T4 sdAb

<400> SEQUENCE: 240

Glu Val Gln Leu Val Glu Ser Gly Gly Gly Glu Val Gln Pro Gly Gly
1 5 10 15

Ser Leu Arg Leu Ser Cys Ala Ala Ser Gly Arg Pro Phe Ser Ser Lys
20 25 30

Thr Met Ala Trp Phe Arg Gln Ala Pro Gly Lys Glu Arg Glu Phe Val
35 40 45

Ala Ala Val Arg Trp Ile Gly Gly Ala Thr Arg Tyr Thr Glu Ser Val
50 55 60

Lys Gly Arg Phe Thr Ile Ser Arg Asp Asn Ala Lys Asn Thr Val Tyr
65 70 75 80

Leu Gln Met Ser Ser Leu Arg Ala Glu Asp Thr Ala Val Tyr Tyr Cys
85 90 95

Ala Ala Gly Gln Ala Trp Gly Thr Lys Phe Thr Asp Tyr Ser Asp Trp
100 105 110

Gly Gln Gly Thr Leu Val Thr Val Lys Pro
115 120

<210> SEQ ID NO 241
<211> LENGTH: 10
<212> TYPE: PRT

<213> ORGANISM: Artificial Sequence
<220> FEATURE:
<223> OTHER INFORMATION: CDR1 5T4 sdAb

<400> SEQUENCE: 241

Gly Arg Pro Phe Ser Ser Lys Thr Met Ala
1 5 10

<210> SEQ ID NO 242
<211> LENGTH: 10
<212> TYPE: PRT
<213> ORGANISM: Artificial Sequence
<220> FEATURE:
<223> OTHER INFORMATION: CDR2 5T4 sdAb

<400> SEQUENCE: 242

Ala Val Arg Trp Ile Gly Gly Ala Thr Arg
1 5 10

<210> SEQ ID NO 243
<211> LENGTH: 13
<212> TYPE: PRT
<213> ORGANISM: Artificial Sequence
<220> FEATURE:
<223> OTHER INFORMATION: CDR3 5T4 sdAb

<400> SEQUENCE: 243

Gly Gln Ala Trp Gly Thr Lys Phe Thr Asp Tyr Ser Asp
1 5 10

<210> SEQ ID NO 244
<211> LENGTH: 6
<212> TYPE: PRT
<213> ORGANISM: Artificial Sequence
<220> FEATURE:
<223> OTHER INFORMATION: Linker
<220> FEATURE:
<221> NAME/KEY: REPEAT
<222> LOCATION: (4)...(6)
<223> OTHER INFORMATION: Repeated 0 to 10 times

<400> SEQUENCE: 244

Gly Gly Ser Gly Gly Ser
1 5

<210> SEQ ID NO 245
<211> LENGTH: 129
<212> TYPE: PRT
<213> ORGANISM: Artificial Sequence
<220> FEATURE:
<223> OTHER INFORMATION: 5T4 sdAb

<400> SEQUENCE: 245

Glu Val Gln Leu Val Glu Ser Gly Gly Gly Glu Val Gln Pro Gly Gly
1 5 10 15

Ser Leu Arg Leu Ser Cys Ala Ala Ser Gly Arg Pro Phe Ser Ser Tyr
20 25 30

Ala Met Gly Trp Phe Arg Gln Ala Pro Gly Lys Glu Arg Glu Thr Val
35 40 45

Ala Ala Val Ser Arg Asn Ala Gly Ser Ser Tyr Tyr Ala Glu Ser Val
50 55 60

Lys Gly Arg Phe Thr Ile Ser Arg Asp Asn Ala Lys Asn Thr Val Tyr
65 70 75 80

Leu Gln Met Ser Ser Leu Arg Ala Glu Asp Thr Ala Val Tyr Tyr Cys
85 90 95

```
Ala Ala Arg Ser Ala Ala Tyr Ser Arg Ser Ser Glu Thr Tyr Thr Glu
            100                 105                 110

Lys His Asp Tyr Thr Tyr Trp Gly Gln Gly Thr Leu Val Thr Val Lys
        115                 120                 125

Pro


<210> SEQ ID NO 246
<211> LENGTH: 10
<212> TYPE: PRT
<213> ORGANISM: Artificial Sequence
<220> FEATURE:
<223> OTHER INFORMATION: CDR1 5T4 sdAb

<400> SEQUENCE: 246

Gly Arg Pro Phe Ser Ser Tyr Ala Met Gly
1               5                   10


<210> SEQ ID NO 247
<211> LENGTH: 10
<212> TYPE: PRT
<213> ORGANISM: Artificial Sequence
<220> FEATURE:
<223> OTHER INFORMATION: CDR2 5T4 sdAb

<400> SEQUENCE: 247

Ala Val Ser Arg Asn Ala Gly Ser Ser Tyr
1               5                   10


<210> SEQ ID NO 248
<211> LENGTH: 11
<212> TYPE: PRT
<213> ORGANISM: Artificial Sequence
<220> FEATURE:
<223> OTHER INFORMATION: CDR3 5T4 sdAb

<400> SEQUENCE: 248

Trp Gly Gln Gly Thr Leu Val Thr Val Lys Pro
1               5                   10


<210> SEQ ID NO 249
<211> LENGTH: 2
<212> TYPE: PRT
<213> ORGANISM: Artificial Sequence
<220> FEATURE:
<223> OTHER INFORMATION: linker

<400> SEQUENCE: 249

Gly Gly
1


<210> SEQ ID NO 250
<211> LENGTH: 5
<212> TYPE: PRT
<213> ORGANISM: Artificial Sequence
<220> FEATURE:
<223> OTHER INFORMATION: linker

<400> SEQUENCE: 250

Pro Gly Gly Gly Gly
1               5


<210> SEQ ID NO 251
<211> LENGTH: 5
<212> TYPE: PRT
<213> ORGANISM: Artificial Sequence
```

<220> FEATURE:
<223> OTHER INFORMATION: linker

<400> SEQUENCE: 251

Ile Glu Pro Asp Pro
1 5

<210> SEQ ID NO 252
<211> LENGTH: 10
<212> TYPE: PRT
<213> ORGANISM: Artificial Sequence
<220> FEATURE:
<223> OTHER INFORMATION: anti-CD3 VH CDR1

<400> SEQUENCE: 252

Gly Phe Thr Phe Asn Thr Tyr Ala Met Asn
1 5 10

<210> SEQ ID NO 253
<211> LENGTH: 129
<212> TYPE: PRT
<213> ORGANISM: Artificial Sequence
<220> FEATURE:
<223> OTHER INFORMATION: FRalpha sdAb

<400> SEQUENCE: 253

Gln Leu Gln Leu Gln Glu Ser Gly Gly Gly Leu Val Gln Pro Gly Gly
1 5 10 15

Ser Leu Arg Leu Ser Cys Ala Ala Ser Gly Phe Thr Leu Asp Asn Tyr
20 25 30

Ala Ile Gly Trp Phe Arg Gln Ala Pro Gly Lys Glu Arg Glu Gly Val
35 40 45

Ser Cys Ile Ser Ser Ser Asp Gly Ser Thr Tyr Tyr Ala Asp Ser Val
50 55 60

Lys Gly Arg Phe Thr Ile Ser Arg Asn Asn Ala Lys Gly Thr Val Tyr
65 70 75 80

Leu Leu Met Asn Ser Leu Lys Pro Glu Asp Thr Ala Val Tyr Tyr Cys
85 90 95

Ala Thr Glu Leu Val Pro Ala Cys Thr Tyr Ser Asn Gly Arg Gly Pro
100 105 110

Leu Asp Gly Met Asp Tyr Trp Gly Lys Gly Thr Gln Val Thr Val Lys
115 120 125

Pro

<210> SEQ ID NO 254
<211> LENGTH: 119
<212> TYPE: PRT
<213> ORGANISM: Artificial Sequence
<220> FEATURE:
<223> OTHER INFORMATION: FRalpha sdAb

<400> SEQUENCE: 254

Glu Val Gln Leu Leu Glu Ser Gly Gly Gly Glu Val Gln Pro Gly Gly
1 5 10 15

Ser Leu Arg Leu Ser Cys Ala Ala Ser Gly Ser Ile Phe Ser Ile Asp
20 25 30

Ala Thr Ala Trp Tyr Arg Gln Ala Pro Gly Lys Gln Arg Glu Leu Val
35 40 45

Ala Ile Ile Thr Ser Ser Gly Ser Thr Asn Tyr Pro Glu Ser Val Lys
50 55 60

```
Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Asn
                85                  90                  95

Ala Ile Thr Arg Tyr Gly Gly Ser Thr Tyr Asp Phe Trp Gly Gln Gly
            100                 105                 110

Thr Leu Val Thr Val Lys Pro
        115
```

<210> SEQ ID NO 255
<211> LENGTH: 101
<212> TYPE: PRT
<213> ORGANISM: Artificial Sequence
<220> FEATURE:
<223> OTHER INFORMATION: FRalpha sdAb

<400> SEQUENCE: 255

```
Glu Val Gln Pro Gly Gly Ser Leu Arg Leu Ser Cys Ala Ala Ser Glu
1               5                   10                  15

Thr Phe Gly Val Val Phe Thr Leu Gly Trp Tyr Arg Gln Ala Pro Gly
            20                  25                  30

Lys Gly Arg Glu Phe Val Ala Arg Val Thr Gly Thr Asp Thr Val Asp
        35                  40                  45

Tyr Ala Glu Ser Val Lys Gly Arg Phe Thr Ile Ser Ser Asp Phe Ala
    50                  55                  60

Arg Asn Thr Val Tyr Leu Gln Met Asn Ser Leu Arg Ala Glu Asp Thr
65                  70                  75                  80

Ala Val Tyr Tyr Cys Asn Thr Gly Ala Tyr Trp Gly Gln Gly Thr Leu
                85                  90                  95

Val Thr Val Lys Pro
            100
```

<210> SEQ ID NO 256
<211> LENGTH: 225
<212> TYPE: PRT
<213> ORGANISM: Artificial Sequence
<220> FEATURE:
<223> OTHER INFORMATION: 5T4 Fd

<400> SEQUENCE: 256

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Tyr Cys Val Arg Gln Trp Asp Tyr Asp Val Arg Ala Met Asn Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140
```

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

Val Pro Ser Ser Ser Leu Gly Thr Gln Thr Tyr Ile Cys Asn Val Asn
195 200 205

His Lys Pro Ser Asn Thr Lys Val Asp Lys Lys Val Glu Pro Lys Ser
210 215 220

Cys
225

<210> SEQ ID NO 257
<211> LENGTH: 214
<212> TYPE: PRT
<213> ORGANISM: Artificial Sequence
<220> FEATURE:
<223> OTHER INFORMATION: 5T4 LC

<400> SEQUENCE: 257

Asp Ile Val Met Thr Gln Ser His Ile Phe Met Ser Thr Ser Val Gly
1 5 10 15

Asp Arg Val Ser Ile Thr Cys Lys Ala Ser Gln Asp Val Asp Thr Ala
20 25 30

Val Ala Trp Tyr Gln Gln Lys Pro Gly Gln Ser Pro Lys Leu Leu Ile
35 40 45

Tyr Trp Ala Ser Thr Arg Leu Thr Gly Val Pro Asp Arg Phe Thr Gly
50 55 60

Ser Gly Ser Gly Thr Asp Phe Thr Leu Thr Ile Ser Asn Val Gln Ser
65 70 75 80

Glu Asp Leu Ala Asp Tyr Phe Cys Gln Gln Tyr Ser Ser Tyr Pro Tyr
85 90 95

Thr Phe Gly Gly Gly Thr Lys Leu Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 258
<211> LENGTH: 122
<212> TYPE: PRT
<213> ORGANISM: Artificial Sequence
<220> FEATURE:
<223> OTHER INFORMATION: anti-5T4 VH
<220> FEATURE:

<221> NAME/KEY: VARIANT
<222> LOCATION: (97)...(97)
<223> OTHER INFORMATION: Xaa is cysteine or tyrosine

<400> SEQUENCE: 258

```
Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn Thr Tyr
            20                  25                  30

Ala Met Asn Trp Val Arg Gln Ala Pro Gly Lys Gly Leu Glu Trp Val
        35                  40                  45

Ala Arg Ile Arg Ser Lys Ser Asn Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Leu Tyr Leu Gln Met Asn Asn Leu Lys Thr Glu Asp Thr Ala Met Tyr
                85                  90                  95

Xaa Cys Val Arg Gln Trp Asp Tyr Asp Val Arg Ala Met Asn Tyr Trp
            100                 105                 110

Gly Gln Gly Thr Ser Val Thr Val Ser Ser
        115                 120
```

<210> SEQ ID NO 259
<211> LENGTH: 107
<212> TYPE: PRT
<213> ORGANISM: Artificial Sequence
<220> FEATURE:
<223> OTHER INFORMATION: anti-5T4 VL

<400> SEQUENCE: 259

```
Asp Ile Val Met Thr Gln Ser His Ile Phe Met Ser Thr Ser Val Gly
1               5                   10                  15

Asp Arg Val Ser Ile Thr Cys Lys Ala Ser Gln Asp Val Asp Thr Ala
            20                  25                  30

Val Ala Trp Tyr Gln Gln Lys Pro Gly Gln Ser Pro Lys Leu Leu Ile
        35                  40                  45

Tyr Trp Ala Ser Thr Arg Leu Thr Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Asp Tyr Phe Cys Gln Gln Tyr Ser Ser Tyr Pro Tyr
                85                  90                  95

Thr Phe Gly Gly Gly Thr Lys Leu Glu Ile Lys
            100                 105
```

<210> SEQ ID NO 260
<211> LENGTH: 125
<212> TYPE: PRT
<213> ORGANISM: Artificial Sequence
<220> FEATURE:
<223> OTHER INFORMATION: cMET sdAb

<400> SEQUENCE: 260

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ile Leu Asp Tyr Tyr
            20                  25                  30

Ala Ile Gly Trp Phe Arg Gln Ala Pro Gly Lys Glu Arg Glu Gly Val
        35                  40                  45
```

```
Leu Cys Ile Asp Ala Ser Asp Asp Ile Thr Tyr Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Ser Leu Lys Pro Glu Asp Thr Gly Val Tyr Tyr Cys
                85                  90                  95

Ala Thr Pro Ile Gly Leu Ser Ser Ser Cys Leu Leu Glu Tyr Asp Tyr
            100                 105                 110

Asp Tyr Trp Gly Gln Gly Thr Leu Val Thr Val Lys Pro
        115                 120                 125


<210> SEQ ID NO 261
<211> LENGTH: 245
<212> TYPE: PRT
<213> ORGANISM: Artificial Sequence
<220> FEATURE:
<223> OTHER INFORMATION: B7H3 scFv

<400> SEQUENCE: 261

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val Ser Ser Ser Gly Gly Gly Gly Ser
        115                 120                 125

Gly Gly Gly Gly Ser Gly Gly Gly Gly Ser Asp Ile Gln Leu Thr Gln
    130                 135                 140

Ser Pro Ser Phe Leu Ser Ala Ser Val Gly Asp Arg Val Thr Ile Thr
145                 150                 155                 160

Cys Lys Ala Ser Gln Asn Val Asp Thr Asn Val Ala Trp Tyr Gln Gln
                165                 170                 175

Lys Pro Gly Lys Ala Pro Lys Ala Leu Ile Tyr Ser Ala Ser Tyr Arg
            180                 185                 190

Tyr Ser Gly Val Pro Ser Arg Phe Ser Gly Ser Gly Ser Gly Thr Asp
        195                 200                 205

Phe Thr Leu Thr Ile Ser Ser Leu Gln Pro Glu Asp Phe Ala Thr Tyr
    210                 215                 220

Tyr Cys Gln Gln Tyr Asn Asn Tyr Pro Phe Thr Phe Gly Gln Gly Thr
225                 230                 235                 240

Lys Leu Glu Ile Lys
                245


<210> SEQ ID NO 262
<211> LENGTH: 118
<212> TYPE: PRT
<213> ORGANISM: Artificial Sequence
```

```
<220> FEATURE:
<223> OTHER INFORMATION: B7H3 sdAb

<400> SEQUENCE: 262

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Ser Phe Ser Ser Asn
            20                  25                  30

Val Met Met Trp Val Arg Gln Ala Pro Gly Lys Gly Leu Glu Trp Val
        35                  40                  45

Ser Thr Ile Tyr Ser Ser Gly Thr Gly Thr Phe Tyr Ala Glu Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Pro Glu Asp Thr Ala Val Tyr Tyr Cys
                85                  90                  95

Ala Thr Ser Gly Pro Val Arg Gly Trp Gly Pro Arg Ser Gln Gly Thr
            100                 105                 110

Leu Val Thr Val Lys Pro
        115


<210> SEQ ID NO 263
<211> LENGTH: 117
<212> TYPE: PRT
<213> ORGANISM: Artificial Sequence
<220> FEATURE:
<223> OTHER INFORMATION: B7H3 sdAb

<400> SEQUENCE: 263

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Thr Phe Ser Ser Tyr
            20                  25                  30

His Met Ser Trp Phe Arg Gln Ala Pro Gly Lys Gln Arg Glu Pro Val
        35                  40                  45

Ala Thr Ser His His Gly Gly Thr Thr Asn Tyr Ala Gly Ser Val Lys
    50                  55                  60

Gly Arg Phe Thr Ile Ser Arg Asp Asn Ala Lys Asn Thr Val Tyr Leu
65                  70                  75                  80

Gln Met Asn Thr Leu Arg Ala Glu Asp Thr Ala Val Tyr Tyr Cys Lys
                85                  90                  95

Ala Asp His Gly Tyr Gln Gly Arg Gly Tyr Trp Gly Gln Gly Thr Leu
            100                 105                 110

Val Thr Val Lys Pro
        115


<210> SEQ ID NO 264
<211> LENGTH: 117
<212> TYPE: PRT
<213> ORGANISM: Artificial Sequence
<220> FEATURE:
<223> OTHER INFORMATION: B7H3 sdAb

<400> SEQUENCE: 264

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Ser Tyr
            20                  25                  30
```

```
His Met Ser Trp Phe Arg Gln Ala Pro Gly Lys Gln Arg Glu Leu Val
        35                  40                  45

Ala Thr Ser His His Gly Gly Thr Thr Asn Tyr Ala Gly Ser Val Lys
    50                  55                  60

Gly Arg Phe Thr Ile Ser Arg Asp Asn Ala Lys Asn Thr Val Tyr Leu
65                  70                  75                  80

Gln Met Asn Thr Leu Arg Ala Glu Asp Thr Ala Val Tyr Tyr Cys Lys
                85                  90                  95

Ala Asp His Gly Tyr Gln Gly Arg Gly Tyr Trp Gly Gln Gly Thr Leu
            100                 105                 110

Val Thr Val Lys Pro
        115


<210> SEQ ID NO 265
<211> LENGTH: 117
<212> TYPE: PRT
<213> ORGANISM: Artificial Sequence
<220> FEATURE:
<223> OTHER INFORMATION: B7H3sdAb

<400> SEQUENCE: 265

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Ser Tyr
            20                  25                  30

His Met Ser Trp Phe Arg Gln Ala Pro Gly Lys Gln Arg Glu Pro Val
        35                  40                  45

Ala Thr Ser His His Gly Gly Thr Thr Asn Tyr Ala Gly Ser Val Lys
    50                  55                  60

Gly Arg Phe Thr Ile Ser Arg Asp Asn Ala Lys Asn Thr Val Tyr Leu
65                  70                  75                  80

Gln Met Asn Thr Leu Arg Ala Glu Asp Thr Ala Val Tyr Tyr Cys Lys
                85                  90                  95

Ala Asp His Gly Tyr Gln Gly Arg Gly Tyr Trp Gly Gln Gly Thr Leu
            100                 105                 110

Val Thr Val Lys Pro
        115


<210> SEQ ID NO 266
<211> LENGTH: 125
<212> TYPE: PRT
<213> ORGANISM: Artificial Sequence
<220> FEATURE:
<223> OTHER INFORMATION: B7H3 sdAb

<400> SEQUENCE: 266

Glu Val Gln Leu Val Glu Ser Gly Gly Gly Glu Val Gln Pro Gly Gly
1               5                   10                  15

Ser Leu Arg Leu Ser Cys Ala Pro Ser Glu Arg Thr Phe Ser Thr Tyr
            20                  25                  30

Thr Met Gly Trp Phe Arg Gln Ala Pro Gly Lys Glu Arg Glu Phe Val
        35                  40                  45

Ala Val Val Asn Trp Gly Gly Gly Ser Lys Tyr Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95
```

```
Ala Ala Gly Gly Ala Tyr Ser Gly Pro Tyr Tyr Asp Thr Arg Gln Tyr
            100                 105                 110

Thr Tyr Trp Gly Gln Gly Thr Leu Val Thr Val Lys Pro
        115                 120                 125


<210> SEQ ID NO 267
<211> LENGTH: 225
<212> TYPE: PRT
<213> ORGANISM: Artificial Sequence
<220> FEATURE:
<223> OTHER INFORMATION: B7H3 Fd

<400> SEQUENCE: 267

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Gly Met His Trp Val Arg Gln Ala Pro Gly Lys Gly Leu Glu Trp Val
        35                  40                  45

Ala Tyr Ile Ser Ser Asp Ser Ser Ala Ile Tyr Tyr Ala Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Gly Arg Gly Arg Glu Asn Ile Tyr Tyr Gly Ser Arg Leu Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys
225


<210> SEQ ID NO 268
<211> LENGTH: 214
<212> TYPE: PRT
<213> ORGANISM: Artificial Sequence
<220> FEATURE:
<223> OTHER INFORMATION: B7H3 LC

<400> SEQUENCE: 268

Asp Ile Gln Leu Thr Gln Ser Pro Ser Phe Leu Ser Ala Ser Val Gly
1               5                   10                  15

Asp Arg Val Thr Ile Thr Cys Lys Ala Ser Gln Asn Val Asp Thr Asn
            20                  25                  30

Val Ala Trp Tyr Gln Gln Lys Pro Gly Lys Ala Pro Lys Ala Leu Ile
```

```
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Phe
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 269
<211> LENGTH: 119
<212> TYPE: PRT
<213> ORGANISM: Artificial Sequence
<220> FEATURE:
<223> OTHER INFORMATION: CD20 VH

<400> SEQUENCE: 269

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Ser
        115


<210> SEQ ID NO 270
<211> LENGTH: 115
<212> TYPE: PRT
<213> ORGANISM: Artificial Sequence
<220> FEATURE:
<223> OTHER INFORMATION: CD20 VL

<400> SEQUENCE: 270
```

```
Asp Ile Val Met Thr Gln Thr Pro Leu Ser Leu Pro Val Thr Pro Gly
1               5                   10                  15

Glu Pro Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Val Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Tyr Thr Phe Gly Gly Gly Thr Lys Val Glu Ile Lys
            100                 105                 110

Arg Thr Val
        115


<210> SEQ ID NO 271
<211> LENGTH: 247
<212> TYPE: PRT
<213> ORGANISM: Artificial Sequence
<220> FEATURE:
<223> OTHER INFORMATION: CD20 scFv

<400> SEQUENCE: 271

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Ala Phe Ser Tyr Ser
            20                  25                  30

Trp Ile Asn Trp Val Arg Gln Ala Pro Gly Gln Gly Leu Glu Trp Met
        35                  40                  45

Gly Arg Ile Phe Pro Gly Asp Gly Asp Thr Asp Tyr Asn Gly Lys Phe
    50                  55                  60

Lys Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Val Phe Asp Gly Tyr Trp Leu Val Tyr Trp Gly Gln Gly
            100                 105                 110

Thr Leu Val Thr Val Ser Gly Ser Gly Gly Gly Gly Ser Gly Gly Gly
        115                 120                 125

Gly Thr Gly Gly Gly Gly Ser Asp Ile Val Met Thr Gln Thr Pro Leu
    130                 135                 140

Ser Leu Pro Val Thr Pro Gly Glu Pro Ala Ser Ile Ser Cys Arg Ser
145                 150                 155                 160

Ser Lys Ser Leu Leu His Ser Asn Gly Ile Thr Tyr Leu Tyr Trp Tyr
                165                 170                 175

Leu Gln Lys Pro Gly Gln Ser Pro Gln Leu Leu Ile Tyr Gln Met Ser
            180                 185                 190

Asn Leu Val Ser Gly Val Pro Asp Arg Phe Ser Gly Ser Gly Ser Gly
        195                 200                 205

Thr Asp Phe Thr Leu Lys Ile Ser Arg Val Glu Ala Glu Asp Val Gly
    210                 215                 220

Val Tyr Tyr Cys Ala Gln Asn Leu Glu Leu Pro Tyr Thr Phe Gly Gly
225                 230                 235                 240
```

Gly Thr Lys Val Glu Ile Lys
245

<210> SEQ ID NO 272
<211> LENGTH: 241
<212> TYPE: PRT
<213> ORGANISM: Artificial Sequence
<220> FEATURE:
<223> OTHER INFORMATION: DLL3 scFv

<400> SEQUENCE: 272

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Pro Pro Gly Lys Gly Leu Glu Trp Ile
35 40 45

Gly Tyr Val Tyr Tyr Ser Gly Thr Thr Asn Tyr Asn Pro Ser Leu Lys
50 55 60

Ser Arg Val Thr Ile Ser Val Asp Thr Ser Lys Asn Gln Phe Ser Leu
65 70 75 80

Lys Leu Ser Ser Val Thr Ala Ala Asp Thr Ala Val Tyr Tyr Cys Ala
85 90 95

Ser Ile Ala Val Thr Gly Phe Tyr Phe Asp Tyr Trp Gly Gln Gly Thr
100 105 110

Leu Val Thr Val Ser Ser Gly Gly Gly Gly Ser Gly Gly Gly Gly Ser
115 120 125

Gly Gly Gly Gly Ser Glu Ile Val Leu Thr Gln Ser Pro Gly Thr Leu
130 135 140

Ser Leu Ser Pro Gly Glu Arg Val Thr Leu Ser Cys Arg Ala Ser Gln
145 150 155 160

Arg Val Asn Asn Asn Tyr Leu Ala Trp Tyr Gln Gln Arg Pro Gly Gln
165 170 175

Ala Pro Arg Leu Leu Ile Tyr Gly Ala Ser Ser Arg Ala Thr Gly Ile
180 185 190

Pro Asp Arg Phe Ser Gly Ser Gly Ser Gly Thr Asp Phe Thr Leu Thr
195 200 205

Ile Ser Arg Leu Glu Pro Glu Asp Phe Ala Val Tyr Tyr Cys Gln Gln
210 215 220

Tyr Asp Arg Ser Pro Leu Thr Phe Gly Gly Gly Thr Lys Leu Glu Ile
225 230 235 240

Lys

<210> SEQ ID NO 273
<211> LENGTH: 241
<212> TYPE: PRT
<213> ORGANISM: Artificial Sequence
<220> FEATURE:
<223> OTHER INFORMATION: DLL3 scFv

<400> SEQUENCE: 273

Gln Val Gln Leu Gln Glu Ser Gly Pro Gly Leu Val Lys Pro Ser Glu
1 5 10 15

Thr Leu Ser Leu Thr Cys Thr Val Ser Gly Gly Ser Ile Ser Ser Tyr
20 25 30

Tyr Trp Ser Trp Ile Arg Gln Pro Pro Gly Lys Gly Leu Glu Trp Ile
35 40 45

```
Gly Tyr Val Tyr Tyr Ser Gly Thr Thr Asn Tyr Asn Pro Ser Leu Lys
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Ser Ile Ala Val Thr Gly Phe Tyr Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Val Leu Thr Gln Ser Pro Gly Thr Leu
    130                 135                 140

Ser Leu Ser Pro Gly Glu Arg Val Thr Leu Ser Cys Arg Ala Ser Gln
145                 150                 155                 160

Arg Val Asn Asn Asn Tyr Leu Ala Trp Tyr Gln Gln Arg Pro Gly Gln
                165                 170                 175

Ala Pro Arg Leu Leu Ile Tyr Gly Ala Ser Ser Arg Ala Thr Gly Ile
            180                 185                 190

Pro Asp Arg Phe Ser Gly Ser Gly Ser Gly Thr Asp Phe Thr Leu Thr
        195                 200                 205

Ile Ser Arg Leu Glu Pro Glu Asp Phe Ala Val Tyr Tyr Cys Gln Gln
    210                 215                 220

Tyr Asp Arg Ser Pro Leu Thr Phe Gly Gly Gly Thr Lys Leu Glu Ile
225                 230                 235                 240

Lys


<210> SEQ ID NO 274
<211> LENGTH: 120
<212> TYPE: PRT
<213> ORGANISM: Artificial Sequence
<220> FEATURE:
<223> OTHER INFORMATION: DLL3 sdAb

<400> SEQUENCE: 274

Glu Val Gln Leu Val Glu Ser Gly Gly Gly Glu Val Gln Pro Gly Gly
1               5                   10                  15

Ser Leu Arg Leu Ser Cys Ala Ala Ser Gly Ser Ile Phe Ser Ile Asn
            20                  25                  30

Ala Met Gly Trp Tyr Arg Gln Ala Pro Gly Lys Gln Arg Glu Leu Val
        35                  40                  45

Ala Gly Phe Thr Gly Asp Thr Asn Thr Ile Tyr Ala Glu Ser Val Lys
    50                  55                  60

Gly Arg Phe Thr Ile Ser Arg Asp Asn Ala Lys Asn Thr Val Tyr Leu
65                  70                  75                  80

Gln Met Ser Ser Leu Arg Ala Glu Asp Thr Ala Val Tyr Tyr Cys Ala
                85                  90                  95

Ala Asp Val Gln Leu Phe Ser Arg Asp Tyr Glu Phe Tyr Trp Gly Gln
            100                 105                 110

Gly Thr Leu Val Thr Val Lys Pro
        115                 120


<210> SEQ ID NO 275
<211> LENGTH: 115
<212> TYPE: PRT
<213> ORGANISM: Artificial Sequence
<220> FEATURE:
<223> OTHER INFORMATION: DLL3 sdAb
```

<400> SEQUENCE: 275

Glu Val Gln Leu Val Glu Ser Gly Gly Gly Glu Val Gln Pro Gly Gly
1 5 10 15

Ser Leu Arg Leu Ser Cys Gly Pro Ser Glu Ile Ile Thr Ser Asp Lys
20 25 30

Ser Met Gly Trp Val Arg Gln Ala Pro Gly Lys Gln Arg Asn Leu Val
35 40 45

Ala Gly Ile Ser Asn Val Gly Ser Thr Asn Tyr Ala Gln Ser Val Lys
50 55 60

Gly Arg Phe Thr Ile Ser Arg Asp Asn Ala Lys Asn Thr Val Tyr Leu
65 70 75 80

Gln Met Ser Ser Leu Arg Ala Glu Asp Thr Ala Val Tyr Tyr Cys Tyr
85 90 95

Ala Arg Asp Phe Glu Asn Glu Tyr Trp Gly Gln Gly Thr Leu Val Thr
100 105 110

Val Lys Pro
115

<210> SEQ ID NO 276
<211> LENGTH: 223
<212> TYPE: PRT
<213> ORGANISM: Artificial Sequence
<220> FEATURE:
<223> OTHER INFORMATION: DLL3 Fd

<400> SEQUENCE: 276

Gln Ile Gln Leu Val Gln Ser Gly Pro Glu Leu Lys Lys Pro Gly Glu
1 5 10 15

Thr Val Lys Ile Ser Cys Lys Ala Ser Gly Tyr Thr Phe Thr Asn Tyr
20 25 30

Gly Met Asn Trp Val Lys Gln Ala Pro Gly Lys Gly Leu Lys Trp Met
35 40 45

Ala Trp Ile Asn Thr Tyr Thr Gly Glu Pro Thr Tyr Ala Asp Asp Phe
50 55 60

Lys Gly Arg Phe Ala Phe Ser Leu Glu Thr Ser Ala Ser Thr Ala Ser
65 70 75 80

Leu Gln Ile Ile Asn Leu Lys Asn Glu Asp Thr Ala Thr Tyr Phe Cys
85 90 95

Ala Arg Ile Gly Asp Ser Ser Pro Ser Asp Tyr Trp Gly Gln Gly Thr
100 105 110

Thr Leu Thr Val Ser Ser Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys
210 215 220

<210> SEQ ID NO 277
<211> LENGTH: 214
<212> TYPE: PRT
<213> ORGANISM: Artificial Sequence
<220> FEATURE:
<223> OTHER INFORMATION: DLL3 LC

<400> SEQUENCE: 277

Ser Ile Val Met Thr Gln Thr Pro Lys Phe Leu Leu Val Ser Ala Gly
1               5                   10                  15

Asp Arg Val Thr Ile Thr Cys Lys Ala Ser Gln Ser Val Ser Asn Asp
            20                  25                  30

Val Val Trp Tyr Gln Gln Lys Pro Gly Gln Ser Pro Lys Leu Leu Ile
        35                  40                  45

Tyr Tyr Ala Ser Asn Arg Tyr Thr Gly Val Pro Asp Arg Phe Ala Gly
    50                  55                  60

Ser Gly Tyr Gly Thr Asp Phe Ser Phe Thr Ile Ser Thr Val Gln Ala
65                  70                  75                  80

Glu Asp Leu Ala Val Tyr Phe Cys Gln Gln Asp Tyr Thr Ser Pro Trp
                85                  90                  95

Thr Phe Gly Gly Gly Thr Lys Leu Glu Ile Arg Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 278
<211> LENGTH: 222
<212> TYPE: PRT
<213> ORGANISM: Artificial Sequence
<220> FEATURE:
<223> OTHER INFORMATION: gpNMB Fd

<400> SEQUENCE: 278

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Phe
            20                  25                  30

Asn Tyr Tyr Trp Ser Trp Ile Arg His His Pro Gly Lys Gly Leu Glu
        35                  40                  45

Trp Ile Gly Tyr Ile Tyr Tyr Ser Gly Ser Thr Tyr Ser Asn Pro Ser
    50                  55                  60

Leu Lys Ser Arg Val Thr Ile Ser Val Asp Thr Ser Lys Asn Gln Phe
65                  70                  75                  80

Ser Leu Thr Leu Ser Ser Val Thr Ala Ala Asp Thr Ala Val Tyr Tyr
                85                  90                  95

```
Cys Ala Arg Gly Tyr Asn Trp Asn Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys
    210                 215                 220


<210> SEQ ID NO 279
<211> LENGTH: 215
<212> TYPE: PRT
<213> ORGANISM: Artificial Sequence
<220> FEATURE:
<223> OTHER INFORMATION: gpNMB LC

<400> SEQUENCE: 279

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Asp Asn Asn
            20                  25                  30

Leu Val Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Pro
                85                  90                  95

Trp Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215


<210> SEQ ID NO 280
```

<211> LENGTH: 124
<212> TYPE: PRT
<213> ORGANISM: Artificial Sequence
<220> FEATURE:
<223> OTHER INFORMATION: 1C9v8D CD28 sdAb

<400> SEQUENCE: 280

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Ala Ala Asp Tyr Ala Glu Ser Val
    50                  55                  60

Lys Asp Arg Phe Thr Ile Ser Arg Asp Asn Ala Lys Asn Thr Val Tyr
65                  70                  75                  80

Leu Gln Met Asn Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120
```

<210> SEQ ID NO 281
<211> LENGTH: 109
<212> TYPE: PRT
<213> ORGANISM: Artificial Sequence
<220> FEATURE:
<223> OTHER INFORMATION: anti-CD3 VL (CON)

<400> SEQUENCE: 281

```
Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Gln Ala Phe Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Cys Gly Thr Lys Leu Thr Val Leu
            100                 105
```

<210> SEQ ID NO 282
<211> LENGTH: 10
<212> TYPE: PRT
<213> ORGANISM: Artificial Sequence
<220> FEATURE:
<223> OTHER INFORMATION: CDR1

<400> SEQUENCE: 282

```
Glu Ile Ile Thr Ser Asp Lys Ser Met Gly
1               5                   10
```

<210> SEQ ID NO 283
<211> LENGTH: 125

<212> TYPE: PRT
<213> ORGANISM: Artificial Sequence
<220> FEATURE:
<223> OTHER INFORMATION: CD3-VH33

<400> SEQUENCE: 283

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Gly Arg Ile Arg Ser Lys Tyr Asn Asn Tyr Ala Thr Tyr Tyr Ala Asp
    50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 284
<211> LENGTH: 226
<212> TYPE: PRT
<213> ORGANISM: Artificial Sequence
<220> FEATURE:
<223> OTHER INFORMATION: Fc-Het-1

<400> SEQUENCE: 284

```
Asp Lys Thr His Thr Cys Pro Pro Cys Pro Ala Pro Pro Val Ala Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Lys His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Glu Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Glu Glu Met Thr Lys Asn Gln Val Ser Leu
    130                 135                 140

Thr Cys Asp Val Ser Gly Phe Tyr Pro Ser Asp Ile Ala Val Glu Trp
145                 150                 155                 160

Glu Ser Asp Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Glu Gln Gly Asp Val Phe Ser Cys Ser Val Met His
        195                 200                 205
```

Glu Ala Leu His Asn His Tyr Thr Gln Lys Ser Leu Ser Leu Ser Pro
    210                 215                 220

Gly Lys
225

<210> SEQ ID NO 285
<211> LENGTH: 226
<212> TYPE: PRT
<213> ORGANISM: Artificial Sequence
<220> FEATURE:
<223> OTHER INFORMATION: Fc-Het-2

<400> SEQUENCE: 285

Asp Lys Thr His Thr Cys Pro Pro Cys Pro Ala Pro Pro Val Ala Gly
1               5                   10                  15

Pro Ser Val Phe Leu Phe Pro Pro Lys Pro Lys Asp Thr Leu Met Ile
            20                  25                  30

Ser Arg Thr Pro Glu Val Thr Cys Val Val Val Asp Val Lys His Glu
        35                  40                  45

Asp Pro Glu Val Lys Phe Asn Trp Tyr Val Asp Gly Val Glu Val His
    50                  55                  60

Asn Ala Lys Thr Lys Pro Arg Glu Glu Gln Tyr Asn Ser Thr Tyr Arg
65                  70                  75                  80

Val Val Ser Val Leu Thr Val Leu His Gln Asp Trp Leu Asn Gly Lys
                85                  90                  95

Glu Tyr Lys Cys Lys Val Ser Asn Lys Ala Leu Pro Ala Pro Ile Glu
            100                 105                 110

Lys Thr Ile Ser Lys Ala Lys Gly Gln Pro Arg Glu Pro Gln Val Tyr
        115                 120                 125

Thr Leu Pro Pro Ser Arg Glu Gln Met Thr Lys Asn Gln Val Lys Leu
    130                 135                 140

Thr Cys Leu Val Lys Gly Phe Tyr Pro Ser Asp Ile Ala Val Glu Trp
145                 150                 155                 160

Glu Ser Asn Gly Gln Pro Glu Asn Asn Tyr Lys Thr Thr Pro Pro Val
                165                 170                 175

Leu Asp Ser Asp Gly Ser Phe Phe Leu Tyr Ser Lys Leu Thr Val Asp
            180                 185                 190

Lys Ser Arg Trp Gln Gln Gly Asn Val Phe Ser Cys Ser Val Met His
        195                 200                 205

Glu Ala Leu His Asn His Tyr Thr Gln Lys Ser Leu Ser Leu Ser Pro
    210                 215                 220

Gly Lys
225

<210> SEQ ID NO 286
<211> LENGTH: 12
<212> TYPE: PRT
<213> ORGANISM: Artificial Sequence
<220> FEATURE:
<223> OTHER INFORMATION: anti-CD3 VH CDR2

<400> SEQUENCE: 286

Arg Ile Arg Ser Lys Tyr Asn Asn Tyr Ala Thr Tyr
1               5                   10

<210> SEQ ID NO 287
<211> LENGTH: 14
<212> TYPE: PRT

<213> ORGANISM: Artificial Sequence
<220> FEATURE:
<223> OTHER INFORMATION: CD3-VH7, VH33 CDR3

<400> SEQUENCE: 287

His Gly Asn Phe Gly Asp Ser Tyr Val Ser Trp Phe Ala Tyr
1 5 10

<210> SEQ ID NO 288
<211> LENGTH: 9
<212> TYPE: PRT
<213> ORGANISM: Artificial Sequence
<220> FEATURE:
<223> OTHER INFORMATION: CD3-VL2, VL21 CDR3

<400> SEQUENCE: 288

Ala Leu Trp Tyr Ser Asn His Trp Val
1 5

<210> SEQ ID NO 289
<211> LENGTH: 9
<212> TYPE: PRT
<213> ORGANISM: Artificial Sequence
<220> FEATURE:
<223> OTHER INFORMATION: CD3-VL8 CDR3

<400> SEQUENCE: 289

Val Leu Trp Tyr Ser Asn Arg Trp Val
1 5

<210> SEQ ID NO 290
<211> LENGTH: 10
<212> TYPE: PRT
<213> ORGANISM: Artificial Sequence
<220> FEATURE:
<223> OTHER INFORMATION: CDRH1 (C05)

<400> SEQUENCE: 290

Gly Ser Ile Phe Arg Ile Asn Val Met Gly
1 5 10

<210> SEQ ID NO 291
<211> LENGTH: 9
<212> TYPE: PRT
<213> ORGANISM: Artificial Sequence
<220> FEATURE:
<223> OTHER INFORMATION: CDRH2 (C05)

<400> SEQUENCE: 291

Arg Ile Phe Ser Gly Gly Ser Pro Asn
1 5

<210> SEQ ID NO 292
<211> LENGTH: 14
<212> TYPE: PRT
<213> ORGANISM: Artificial Sequence
<220> FEATURE:
<223> OTHER INFORMATION: CDRH3 (C05)

<400> SEQUENCE: 292

Leu Ile Ala Ser Arg Ala Ala Pro Gly Leu Lys Tyr Asp Tyr
1 5 10

<210> SEQ ID NO 293
<211> LENGTH: 10
<212> TYPE: PRT
<213> ORGANISM: Artificial Sequence

<220> FEATURE:
<223> OTHER INFORMATION: CDRH1 (E08)

<400> SEQUENCE: 293

Ile Ser Ile Phe Ser Ile Asn Arg Met Gly
1 5 10

<210> SEQ ID NO 294
<211> LENGTH: 9
<212> TYPE: PRT
<213> ORGANISM: Artificial Sequence
<220> FEATURE:
<223> OTHER INFORMATION: CDRH2 (E08)

<400> SEQUENCE: 294

Ala Met Thr Ser Gly Gly Ser Thr Asn
1 5

<210> SEQ ID NO 295
<211> LENGTH: 7
<212> TYPE: PRT
<213> ORGANISM: Artificial Sequence
<220> FEATURE:
<223> OTHER INFORMATION: CDRH3 (E08)

<400> SEQUENCE: 295

Ala Ser Arg Arg Glu Leu Tyr
1 5

<210> SEQ ID NO 296
<211> LENGTH: 10
<212> TYPE: PRT
<213> ORGANISM: Artificial Sequence
<220> FEATURE:
<223> OTHER INFORMATION: CDRH1 (B11)

<400> SEQUENCE: 296

Gly Ala Ile Phe Ser Lys Thr Glu Val Gly
1 5 10

<210> SEQ ID NO 297
<211> LENGTH: 9
<212> TYPE: PRT
<213> ORGANISM: Artificial Sequence
<220> FEATURE:
<223> OTHER INFORMATION: CDRH2 (B11)

<400> SEQUENCE: 297

Thr Ile Ser Ala Gly Asp Arg Thr Asn
1 5

<210> SEQ ID NO 298
<211> LENGTH: 7
<212> TYPE: PRT
<213> ORGANISM: Artificial Sequence
<220> FEATURE:
<223> OTHER INFORMATION: CDRH3 (B11)

<400> SEQUENCE: 298

Arg Arg Gly Asp Thr Ile Leu
1 5

<210> SEQ ID NO 299
<211> LENGTH: 10
<212> TYPE: PRT
<213> ORGANISM: Artificial Sequence
<220> FEATURE:

<223> OTHER INFORMATION: CDRH1 (B10)

<400> SEQUENCE: 299

Gly Ile Ile Phe Arg Glu Tyr Ala Met Gly
1 5 10

<210> SEQ ID NO 300
<211> LENGTH: 9
<212> TYPE: PRT
<213> ORGANISM: Artificial Sequence
<220> FEATURE:
<223> OTHER INFORMATION: CDRH2 (B10)

<400> SEQUENCE: 300

Val Ile Ser Lys Thr Gly Thr Thr Ile
1 5

<210> SEQ ID NO 301
<211> LENGTH: 7
<212> TYPE: PRT
<213> ORGANISM: Artificial Sequence
<220> FEATURE:
<223> OTHER INFORMATION: CDRH3 (B10)

<400> SEQUENCE: 301

Thr Arg Gly Gln Leu Asp Tyr
1 5

<210> SEQ ID NO 302
<211> LENGTH: 10
<212> TYPE: PRT
<213> ORGANISM: Artificial Sequence
<220> FEATURE:
<223> OTHER INFORMATION: CD3 VH33 CDR1

<400> SEQUENCE: 302

Gly Phe Thr Phe Ser Thr Tyr Ala Met Asn
1 5 10

<210> SEQ ID NO 303
<211> LENGTH: 12
<212> TYPE: PRT
<213> ORGANISM: Artificial Sequence
<220> FEATURE:
<223> OTHER INFORMATION: CD3 VH33 CDR2

<400> SEQUENCE: 303

Arg Ile Arg Ser Lys Tyr Asn Asn Tyr Ala Thr Tyr
1 5 10

<210> SEQ ID NO 304
<211> LENGTH: 14
<212> TYPE: PRT
<213> ORGANISM: Artificial Sequence
<220> FEATURE:
<223> OTHER INFORMATION: CD3 VL21 CDR1

<400> SEQUENCE: 304

Gly Ser Ser Thr Gly Ala Val Thr Thr Ser Asn Tyr Ala Asn
1 5 10

<210> SEQ ID NO 305
<211> LENGTH: 122
<212> TYPE: PRT
<213> ORGANISM: Artificial Sequence
<220> FEATURE:
<223> OTHER INFORMATION: Anti-CD3 VH 312557

<400> SEQUENCE: 305

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Gly Leu Glu Trp Val
35 40 45

Ser Gly Ile Ser Trp Asn Ser Gly Ser Ile Gly Tyr Ala Asp Ser Val
50 55 60

Lys Gly Phe Thr Ile Ser Arg Asp Asn Ala Lys Asn Ser Leu Tyr Leu
65 70 75 80

Gln Met Asn Ser Leu Arg Ala Glu Asp Thr Ala Leu Tyr Tyr Cys Ala
85 90 95

Lys Asp Ser Arg Gly Tyr Gly Asp Tyr Arg Leu Gly Gly Ala Tyr Trp
100 105 110

Gly Gln Gly Thr Leu Val Thr Val Ser Ser
115 120

<210> SEQ ID NO 306
<211> LENGTH: 122
<212> TYPE: PRT
<213> ORGANISM: Artificial Sequence
<220> FEATURE:
<223> OTHER INFORMATION: Anti-CD3 VH 312557 G44C

<400> SEQUENCE: 306

Glu Val Gln Leu Val Glu Ser Gly Gly Gly Leu Val Gln Pro Gly Arg
1 5 10 15

Ser Leu Arg Leu Ser Cys Ala Ala Ser Gly Phe Thr Phe Asp Asp Tyr
20 25 30

Ala Met His Trp Val Arg Gln Ala Pro Gly Lys Cys Leu Glu Trp Val
35 40 45

Ser Gly Ile Ser Trp Asn Ser Gly Ser Ile Gly Tyr Ala Asp Ser Val
50 55 60

Lys Gly Phe Thr Ile Ser Arg Asp Asn Ala Lys Asn Ser Leu Tyr Leu
65 70 75 80

Gln Met Asn Ser Leu Arg Ala Glu Asp Thr Ala Leu Tyr Tyr Cys Ala
85 90 95

Lys Asp Ser Arg Gly Tyr Gly Asp Tyr Arg Leu Gly Gly Ala Tyr Trp
100 105 110

Gly Gln Gly Thr Leu Val Thr Val Ser Ser
115 120

<210> SEQ ID NO 307
<211> LENGTH: 107
<212> TYPE: PRT
<213> ORGANISM: Artificial Sequence
<220> FEATURE:
<223> OTHER INFORMATION: Anti-CD3 VL 312557

<400> SEQUENCE: 307

Glu Ile Val Met Thr Gln Ser Pro Ala Thr Leu Ser Val Ser Pro Gly
1 5 10 15

Glu Arg Ala Thr Leu Ser Cys Arg Ala Ser Gln Ser Val Ser Ser Asn
20 25 30

Leu Ala Trp Tyr Gln Gln Lys Pro Gly Gln Ala Pro Arg Leu Leu Ile
35 40 45

```
Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Gln Gly Thr Lys Val Glu Ile Lys
            100                 105


<210> SEQ ID NO 308
<211> LENGTH: 107
<212> TYPE: PRT
<213> ORGANISM: Artificial Sequence
<220> FEATURE:
<223> OTHER INFORMATION: Anti-CD3 VL 312557Q100C

<400> SEQUENCE: 308

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Trp
                85                  90                  95

Thr Phe Gly Cys Gly Thr Lys Val Glu Ile Lys
            100                 105


<210> SEQ ID NO 309
<211> LENGTH: 124
<212> TYPE: PRT
<213> ORGANISM: Artificial Sequence
<220> FEATURE:
<223> OTHER INFORMATION: CD3-VH-G

<400> SEQUENCE: 309

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asp Asp Tyr
            20                  25                  30

Ser Met His Trp Val Arg Gln Ala Pro Gly Lys Gly Leu Glu Trp Val
        35                  40                  45

Ser Gly Ile Ser Trp Asn Ser Gly Ser Lys Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
        115                 120
```

```
<210> SEQ ID NO 310
<211> LENGTH: 124
<212> TYPE: PRT
<213> ORGANISM: Artificial Sequence
<220> FEATURE:
<223> OTHER INFORMATION: CD3-VH-G

<400> SEQUENCE: 310

Glu Val Gln Leu Val Glu Ser Gly Gly Gly Leu Val Gln Pro Gly Arg
1               5                   10                  15

Ser Leu Arg Leu Ser Cys Val Ala Ser Gly Phe Thr Phe Asp Asp Tyr
            20                  25                  30

Ser Met His Trp Val Arg Gln Ala Pro Gly Lys Cys Leu Glu Trp Val
        35                  40                  45

Ser Gly Ile Ser Trp Asn Ser Gly Ser Lys Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Leu Tyr Tyr Cys
                85                  90                  95

Ala Lys Tyr Gly Ser Gly Tyr Gly Lys Phe Tyr His Tyr Gly Leu Asp
            100                 105                 110

Val Trp Gly Gln Gly Thr Thr Val Thr Val Ser Ser
        115                 120


<210> SEQ ID NO 311
<211> LENGTH: 108
<212> TYPE: PRT
<213> ORGANISM: Artificial Sequence
<220> FEATURE:
<223> OTHER INFORMATION: VK1-39Jk5

<400> SEQUENCE: 311

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105


<210> SEQ ID NO 312
<211> LENGTH: 108
<212> TYPE: PRT
<213> ORGANISM: Artificial Sequence
<220> FEATURE:
<223> OTHER INFORMATION: VK1-39Jk5Q100C

<400> SEQUENCE: 312

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30
```

```
Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Cys Gly Thr Arg Leu Glu Ile Lys
            100                 105


<210> SEQ ID NO 313
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)...(5)
<223> OTHER INFORMATION: repeated 2 to 20 times

<400> SEQUENCE: 313

Ala Asp Ala Ala Pro
1               5


<210> SEQ ID NO 314
<211> LENGTH: 6
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)...(5)
<223> OTHER INFORMATION: repeated 2 to 20 times

<400> SEQUENCE: 314

Ala Asp Ala Ala Pro Gly
1               5


<210> SEQ ID NO 315
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)...(5)
<223> OTHER INFORMATION: repeated 2 to 20 times

<400> SEQUENCE: 315

Gly Glu Pro Gln Gly
1               5


<210> SEQ ID NO 316
<211> LENGTH: 6
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)...(5)
<223> OTHER INFORMATION: repeated 2 to 20 times
```

<400> SEQUENCE: 316

Gly Glu Pro Gln Gly Gly
1 5

<210> SEQ ID NO 317
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)...(5)
<223> OTHER INFORMATION: repeated 2 to 20 times

<400> SEQUENCE: 317

Ala Gly Gly Glu Pro
1 5

<210> SEQ ID NO 318
<211> LENGTH: 6
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)...(5)
<223> OTHER INFORMATION: repeated 2 to 20 times

<400> SEQUENCE: 318

Ala Gly Gly Glu Pro Gly
1 5

<210> SEQ ID NO 319
<211> LENGTH: 5
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)...(5)
<223> OTHER INFORMATION: repeated 2 to 20 times

<400> SEQUENCE: 319

Ala Gly Ser Glu Pro
1 5

<210> SEQ ID NO 320
<211> LENGTH: 6
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)...(5)
<223> OTHER INFORMATION: repeated 2 to 20 times

<400> SEQUENCE: 320

Ala Gly Ser Glu Pro Gly
1 5

<210> SEQ ID NO 321
<211> LENGTH: 5
<212> TYPE: PRT
<213> ORGANISM: Artificial Sequence
<220> FEATURE:

<223> OTHER INFORMATION: linker
<220> FEATURE:
<221> NAME/KEY: REPEAT
<222> LOCATION: (1)...(5)
<223> OTHER INFORMATION: repeated 2 to 20 times

<400> SEQUENCE: 321

Gly Gly Gly Glu Gln
1 5

<210> SEQ ID NO 322
<211> LENGTH: 6
<212> TYPE: PRT
<213> ORGANISM: Artificial Sequence
<220> FEATURE:
<223> OTHER INFORMATION: linker
<220> FEATURE:
<221> NAME/KEY: REPEAT
<222> LOCATION: (1)...(5)
<223> OTHER INFORMATION: repeated 2 to 20 times

<400> SEQUENCE: 322

Gly Gly Gly Glu Gln Gly
1 5

<210> SEQ ID NO 323
<211> LENGTH: 11
<212> TYPE: PRT
<213> ORGANISM: Artificial Sequence
<220> FEATURE:
<223> OTHER INFORMATION: linker

<400> SEQUENCE: 323

Ala Asp Ala Ala Pro Ala Asp Ala Ala Pro Gly
1 5 10

<210> SEQ ID NO 324
<211> LENGTH: 11
<212> TYPE: PRT
<213> ORGANISM: Artificial Sequence
<220> FEATURE:
<223> OTHER INFORMATION: linker

<400> SEQUENCE: 324

Gly Glu Pro Gln Gly Gly Glu Pro Gln Gly Gly
1 5 10

<210> SEQ ID NO 325
<211> LENGTH: 11
<212> TYPE: PRT
<213> ORGANISM: Artificial Sequence
<220> FEATURE:
<223> OTHER INFORMATION: linker

<400> SEQUENCE: 325

Ala Gly Gly Glu Pro Ala Gly Gly Glu Pro Gly
1 5 10

<210> SEQ ID NO 326
<211> LENGTH: 11
<212> TYPE: PRT
<213> ORGANISM: Artificial Sequence
<220> FEATURE:
<223> OTHER INFORMATION: linker

<400> SEQUENCE: 326

Ala Gly Ser Glu Pro Ala Gly Ser Glu Pro Gly
1 5 10

<210> SEQ ID NO 327
<211> LENGTH: 11
<212> TYPE: PRT
<213> ORGANISM: Artificial Sequence
<220> FEATURE:
<223> OTHER INFORMATION: linker

<400> SEQUENCE: 327

Gly Gly Gly Glu Gln Gly Gly Gly Glu Gln Gly
1 5 10

<210> SEQ ID NO 328
<211> LENGTH: 225
<212> TYPE: PRT
<213> ORGANISM: Artificial Sequence
<220> FEATURE:
<223> OTHER INFORMATION: Knob Fc

<400> SEQUENCE: 328

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Tyr Thr Leu Pro Pro Cys Arg Asp Glu Leu Thr Lys Asn Gln Val Ser
130 135 140

Leu Trp Cys Leu Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Tyr Ser Lys Leu Thr Val
180 185 190

Asp Lys Ser Arg Trp Gln Gln Gly Asn Val Phe Ser Cys Ser Val Met
195 200 205

His Glu Ala Leu His Asn His Tyr Thr Gln Lys Ser Leu Ser Leu Ser
210 215 220

Pro
225

<210> SEQ ID NO 329
<211> LENGTH: 225
<212> TYPE: PRT
<213> ORGANISM: Artificial Sequence
<220> FEATURE:
<223> OTHER INFORMATION: Hole Fc

<400> SEQUENCE: 329

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Arg Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro
225
```

<210> SEQ ID NO 330
<211> LENGTH: 222
<212> TYPE: PRT
<213> ORGANISM: Artificial Sequence
<220> FEATURE:
<223> OTHER INFORMATION: Knob Fc

<400> SEQUENCE: 330

```
Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Tyr Thr Leu
        115                 120                 125
```

```
Pro Pro Cys Arg Asp Glu Leu Thr Lys Asn Gln Val Ser Leu Trp Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro
    210                 215                 220


<210> SEQ ID NO 331
<211> LENGTH: 222
<212> TYPE: PRT
<213> ORGANISM: Artificial Sequence
<220> FEATURE:
<223> OTHER INFORMATION: Hole Fc

<400> SEQUENCE: 331

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Met Arg Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro
    210                 215                 220


<210> SEQ ID NO 332
<211> LENGTH: 225
<212> TYPE: PRT
<213> ORGANISM: Artificial Sequence
<220> FEATURE:
<223> OTHER INFORMATION: Hole Fc

<400> SEQUENCE: 332
```

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val
115 120 125

Cys Thr Leu Pro Pro Ser Arg Asp Glu Leu Thr Lys Asn Gln Val Ser
130 135 140

Leu Ser Cys Ala Val Lys Gly Phe Tyr Pro Ser Asp Ile Ala Val Glu
145 150 155 160

Trp Glu Ser Asn Gly Gln Pro Glu Asn Asn Tyr Lys Thr Thr Pro Pro
165 170 175

Val Leu Asp Ser Asp Gly Ser Phe Phe Leu Val Ser Lys Leu Thr Val
180 185 190

Asp Lys Ser Arg Trp Gln Gln Gly Asn Val Phe Ser Cys Ser Val Met
195 200 205

His Glu Ala Leu His Asn Arg Tyr Thr Gln Lys Ser Leu Ser Leu Ser
210 215 220

Pro
225

<210> SEQ ID NO 333
<211> LENGTH: 222
<212> TYPE: PRT
<213> ORGANISM: Artificial Sequence
<220> FEATURE:
<223> OTHER INFORMATION: Hole Fc

<400> SEQUENCE: 333

Asp Lys Thr His Thr Cys Pro Pro Cys Pro Ala Pro Gly Gly Pro Ser
1 5 10 15

Val Phe Leu Phe Pro Pro Lys Pro Lys Asp Thr Leu Met Ile Ser Arg
20 25 30

Thr Pro Glu Val Thr Cys Val Val Val Asp Val Ser His Glu Asp Pro
35 40 45

Glu Val Lys Phe Asn Trp Tyr Val Asp Gly Val Glu Val His Asn Ala
50 55 60

Lys Thr Lys Pro Arg Glu Glu Gln Tyr Asn Ser Thr Tyr Arg Val Val
65 70 75 80

Ser Val Leu Thr Val Leu His Gln Asp Trp Leu Asn Gly Lys Glu Tyr
85 90 95

Lys Cys Lys Val Ser Asn Lys Ala Leu Pro Ala Pro Ile Glu Lys Thr
100 105 110

Ile Ser Lys Ala Lys Gly Gln Pro Arg Glu Pro Gln Val Cys Thr Leu
115 120 125

```
Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn Arg Tyr Thr Gln Lys Ser Leu Ser Leu Ser Pro
    210                 215                 220


<210> SEQ ID NO 334
<211> LENGTH: 225
<212> TYPE: PRT
<213> ORGANISM: Artificial Sequence
<220> FEATURE:
<223> OTHER INFORMATION: Knob Fc

<400> SEQUENCE: 334

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Tyr
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Cys Arg Asp Glu Leu Thr Lys Asn Gln Val Ser
    130                 135                 140

Leu Trp Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn His Tyr Thr Gln Lys Ser Leu Ser Leu Ser
    210                 215                 220

Pro
225


<210> SEQ ID NO 335
<211> LENGTH: 222
<212> TYPE: PRT
<213> ORGANISM: Artificial Sequence
```

<220> FEATURE:
<223> OTHER INFORMATION: Knob Fc

<400> SEQUENCE: 335

Asp Lys Thr His Thr Cys Pro Pro Cys Pro Ala Pro Gly Gly Pro Ser
1 5 10 15

Val Phe Leu Phe Pro Pro Lys Pro Lys Asp Thr Leu Tyr Ile Ser Arg
20 25 30

Thr Pro Glu Val Thr Cys Val Val Val Asp Val Ser His Glu Asp Pro
35 40 45

Glu Val Lys Phe Asn Trp Tyr Val Asp Gly Val Glu Val His Asn Ala
50 55 60

Lys Thr Lys Pro Arg Glu Glu Gln Tyr Asn Ser Thr Tyr Arg Val Val
65 70 75 80

Ser Val Leu Thr Val Leu His Gln Asp Trp Leu Asn Gly Lys Glu Tyr
85 90 95

Lys Cys Lys Val Ser Asn Lys Ala Leu Pro Ala Pro Ile Glu Lys Thr
100 105 110

Ile Ser Lys Ala Lys Gly Gln Pro Arg Glu Pro Gln Val Tyr Thr Leu
115 120 125

Pro Pro Cys Arg Asp Glu Leu Thr Lys Asn Gln Val Ser Leu Trp Cys
130 135 140

Leu Val Lys Gly Phe Tyr Pro Ser Asp Ile Ala Val Glu Trp Glu Ser
145 150 155 160

Asn Gly Gln Pro Glu Asn Asn Tyr Lys Thr Thr Pro Pro Val Leu Asp
165 170 175

Ser Asp Gly Ser Phe Phe Leu Tyr Ser Lys Leu Thr Val Asp Lys Ser
180 185 190

Arg Trp Gln Gln Gly Asn Val Phe Ser Cys Ser Val Val His Glu Ala
195 200 205

Leu His Asn His Tyr Thr Gln Lys Ser Leu Ser Leu Ser Pro
210 215 220

<210> SEQ ID NO 336
<211> LENGTH: 225
<212> TYPE: PRT
<213> ORGANISM: Artificial Sequence
<220> FEATURE:
<223> OTHER INFORMATION: Hole Fc

<400> SEQUENCE: 336

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Tyr
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

His Asn Ala Lys Thr Lys Pro Arg Glu Glu Gln Tyr Asn Ser Thr Tyr
65 70 75 80

Arg Val Val Ser Val Leu Thr Val Leu His Gln Asp Trp Leu Asn Gly
85 90 95

Lys Glu Tyr Lys Cys Lys Val Ser Asn Lys Ala Leu Pro Ala Pro Ile
100 105 110

Glu Lys Thr Ile Ser Lys Ala Lys Gly Gln Pro Arg Glu Pro Gln Val

```
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Val
        195                 200                 205

His Glu Ala Leu His Asn Arg Tyr Thr Gln Lys Ser Leu Ser Leu Ser
    210                 215                 220

Pro
225


<210> SEQ ID NO 337
<211> LENGTH: 222
<212> TYPE: PRT
<213> ORGANISM: Artificial Sequence
<220> FEATURE:
<223> OTHER INFORMATION: Hole Fc

<400> SEQUENCE: 337

Asp Lys Thr His Thr Cys Pro Pro Cys Pro Ala Pro Gly Gly Pro Ser
1               5                   10                  15

Val Phe Leu Phe Pro Pro Lys Pro Lys Asp Thr Leu Tyr Ile Ser Arg
            20                  25                  30

Thr Pro Glu Val Thr Cys Val Val Val Asp Val Ser His Glu Asp Pro
        35                  40                  45

Glu Val Lys Phe Asn Trp Tyr Val Asp Gly Val Glu Val His Asn Ala
    50                  55                  60

Lys Thr Lys Pro Arg Glu Glu Gln Tyr Asn Ser Thr Tyr Arg Val Val
65                  70                  75                  80

Ser Val Leu Thr Val Leu His Gln Asp Trp Leu Asn Gly Lys Glu Tyr
                85                  90                  95

Lys Cys Lys Val Ser Asn Lys Ala Leu Pro Ala Pro Ile Glu Lys Thr
            100                 105                 110

Ile Ser Lys Ala Lys Gly Gln Pro Arg Glu Pro Gln Val Cys Thr Leu
        115                 120                 125

Pro Pro Ser Arg Asp Glu Leu Thr Lys Asn Gln Val Ser Leu Ser Cys
    130                 135                 140

Ala Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Val Leu Asp
                165                 170                 175

Ser Asp Gly Ser Phe Phe Leu Val Ser Lys Leu Thr Val Asp Lys Ser
            180                 185                 190

Arg Trp Gln Gln Gly Asn Val Phe Ser Cys Ser Val Val His Glu Ala
        195                 200                 205

Leu His Asn Arg Tyr Thr Gln Lys Ser Leu Ser Leu Ser Pro
    210                 215                 220


<210> SEQ ID NO 338
<211> LENGTH: 109
<212> TYPE: PRT
```

<213> ORGANISM: Artificial Sequence
<220> FEATURE:
<223> OTHER INFORMATION: CD3-VL20

<400> SEQUENCE: 338

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Gly Gly Thr Lys Leu Thr Val Leu
            100                 105

<210> SEQ ID NO 339
<211> LENGTH: 109
<212> TYPE: PRT
<213> ORGANISM: Artificial Sequence
<220> FEATURE:
<223> OTHER INFORMATION: CD3-VL21

<400> SEQUENCE: 339

Gln Ala Val Val Thr Gln Glu Pro Ser Leu Thr Val Ser Pro Gly Gly
1               5                   10                  15

Thr Val Thr Leu Thr Cys Gly Ser Ser Thr Gly Ala Val Thr Thr Ser
            20                  25                  30

Asn Tyr Ala Asn Trp Val Gln Gln Lys Pro Gly Lys Ser Pro Arg Gly
        35                  40                  45

Leu Ile Gly Gly Thr Asn Lys Arg Ala Pro Gly Val Pro Ala Arg Phe
    50                  55                  60

Ser Gly Ser Leu Leu Gly Gly Lys Ala Ala Leu Thr Ile Ser Gly Ala
65                  70                  75                  80

Gln Pro Glu Asp Glu Ala Asp Tyr Tyr Cys Ala Leu Trp Tyr Ser Asn
                85                  90                  95

His Trp Val Phe Gly Cys Gly Thr Lys Leu Thr Val Leu
            100                 105

<210> SEQ ID NO 340
<211> LENGTH: 125
<212> TYPE: PRT
<213> ORGANISM: Artificial Sequence
<220> FEATURE:
<223> OTHER INFORMATION: CD3-VH32

<400> SEQUENCE: 340

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Gly Leu Glu Trp Val
        35                  40                  45

Gly Arg Ile Arg Ser Lys Tyr Asn Asn Tyr Ala Thr Tyr Tyr Ala Asp
    50                  55                  60

```
Ser Val Lys Gly Arg Phe Thr Ile Ser Arg Asp Asp Ser Lys Asn Thr
65                  70                  75                  80

Leu Tyr Leu Gln Met Asn Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val Ser Ser
        115                 120                 125
```

<210> SEQ ID NO 341
<211> LENGTH: 123
<212> TYPE: PRT
<213> ORGANISM: Artificial Sequence
<220> FEATURE:
<223> OTHER INFORMATION: CD3-VH34

<400> SEQUENCE: 341

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Thr Tyr
            20                  25                  30

Ala Met Asn Trp Val Arg Gln Ala Pro Gly Lys Cys Leu Glu Trp Val
        35                  40                  45

Ala Arg Ile Arg Ser Lys Tyr Asn Asn Tyr Ala Thr Tyr Tyr Ala Asp
    50                  55                  60

Thr Val Lys Gly Arg Phe Thr Ile Ser Arg Asp Asp Ala Lys Asn Thr
65                  70                  75                  80

Leu Tyr Leu Gln Met Ser Ser Leu Arg Ala Glu Asp Thr Ala Val Tyr
                85                  90                  95

Tyr Cys Val Arg His Gly Asn Phe Gly Asp Ser Tyr Val Ser Trp Phe
            100                 105                 110

Ala Tyr Trp Gly Gln Gly Thr Leu Val Thr Val
        115                 120
```

<210> SEQ ID NO 342
<211> LENGTH: 124
<212> TYPE: PRT
<213> ORGANISM: Artificial Sequence
<220> FEATURE:
<223> OTHER INFORMATION: 1C9v13.1 CD28 sdAb

<400> SEQUENCE: 342

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Asp Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
```

115 120

<210> SEQ ID NO 343
<211> LENGTH: 124
<212> TYPE: PRT
<213> ORGANISM: Artificial Sequence
<220> FEATURE:
<223> OTHER INFORMATION: 1C9v13.2 CD28 sdAb

<400> SEQUENCE: 343

Glu Val Gln Leu Val Glu Ser Gly Gly Gly Glu Val Gln Pro Gly Gly
1 5 10 15

Ser Leu Arg Leu Ser Cys Ala Ala Ser Gly Arg Met Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Arg Asp Asp Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Ser Ser Leu Arg Ala Glu Asp Thr Ala Val Tyr Tyr Cys
85 90 95

Gly Phe Thr Tyr Ala Gly Trp Ala Ser Ser Arg Arg Asp Asp Tyr Asp
100 105 110

Tyr Trp Gly Gln Gly Thr Leu Val Thr Val Lys Pro
115 120

<210> SEQ ID NO 344
<211> LENGTH: 124
<212> TYPE: PRT
<213> ORGANISM: Artificial Sequence
<220> FEATURE:
<223> OTHER INFORMATION: 1C9v13.3 CD28 sdAb

<400> SEQUENCE: 344

Glu Val Gln Leu Val Glu Ser Gly Gly Gly Glu Val Gln Pro Gly Gly
1 5 10 15

Ser Leu Arg Leu Ser Cys Ala Ala Ser Gly Arg Met Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Arg Asp Asp Ala Asp Tyr Ala Glu Ser Val
50 55 60

Lys Asp Arg Phe Thr Ile Ser Arg Asp Asn Ala Lys Asn Thr Val Tyr
65 70 75 80

Leu Gln Met Ser Ser Leu Arg Ala Glu Asp Thr Ala Val Tyr Tyr Cys
85 90 95

Gly Phe Thr Tyr Ala Gly Trp Ala Ser Ser Arg Arg Asp Asp Tyr Asn
100 105 110

Tyr Trp Gly Gln Gly Thr Leu Val Thr Val Lys Pro
115 120

<210> SEQ ID NO 345
<211> LENGTH: 124
<212> TYPE: PRT
<213> ORGANISM: Artificial Sequence
<220> FEATURE:
<223> OTHER INFORMATION: 1C9v13.4 CD28 sdAb

<400> SEQUENCE: 345

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Asp Ala Asp Tyr Ala Glu Ser Val
    50                  55                  60

Lys Asp Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Ile Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120
```

<210> SEQ ID NO 346
<211> LENGTH: 124
<212> TYPE: PRT
<213> ORGANISM: Artificial Sequence
<220> FEATURE:
<223> OTHER INFORMATION: 1C9v13.5 CD28 sdAb

<400> SEQUENCE: 346

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Asp Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Ile Tyr Tyr Cys
                85                  90                  95

Gly Phe Thr Tyr Ala Gly Trp Ala Ser Ser Arg Arg Asp Asp Tyr Asp
            100                 105                 110

Tyr Trp Gly Gln Gly Thr Leu Val Thr Val Lys Pro
        115                 120
```

<210> SEQ ID NO 347
<211> LENGTH: 124
<212> TYPE: PRT
<213> ORGANISM: Artificial Sequence
<220> FEATURE:
<223> OTHER INFORMATION: 1C9v13.6 CD28 sdAb

<400> SEQUENCE: 347

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Gly Arg Asp Asp Ala Asp Tyr Ala Glu Ser Val
```

```
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 348
<211> LENGTH: 124
<212> TYPE: PRT
<213> ORGANISM: Artificial Sequence
<220> FEATURE:
<223> OTHER INFORMATION: 1C9v13.7 CD28 sdAb

<400> SEQUENCE: 348

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Gly Asp Asp Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 349
<211> LENGTH: 124
<212> TYPE: PRT
<213> ORGANISM: Artificial Sequence
<220> FEATURE:
<223> OTHER INFORMATION: 1C9v13.8 CD28 sdAb

<400> SEQUENCE: 349

Glu Val Gln Leu Val Glu Ser Gly Gly Gly Glu Val Gln Pro Gly Gly
1               5                   10                  15

Ser Leu Arg Leu Ser Cys Ala Ala Ser Gly Arg Met Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Asp Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Gly Arg Asp Asp Tyr Asn
            100                 105                 110
```

Tyr Trp Gly Gln Gly Thr Leu Val Thr Val Lys Pro
115 120

<210> SEQ ID NO 350
<211> LENGTH: 124
<212> TYPE: PRT
<213> ORGANISM: Artificial Sequence
<220> FEATURE:
<223> OTHER INFORMATION: 1C9v13.9 CD28 sdAb

<400> SEQUENCE: 350

Glu Val Gln Leu Val Glu Ser Gly Gly Gly Glu Val Gln Pro Gly Gly
1 5 10 15

Ser Leu Arg Leu Ser Cys Ala Ala Ser Gly Arg Met Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Arg Asp Asp Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Ser Ser Leu Arg Ala Glu Asp Thr Ala Val Tyr Tyr Cys
85 90 95

Gly Phe Thr Tyr Ala Gly Trp Ala Ser Ser Arg Gly Asp Asp Tyr Asn
100 105 110

Tyr Trp Gly Gln Gly Thr Leu Val Thr Val Lys Pro
115 120

<210> SEQ ID NO 351
<211> LENGTH: 124
<212> TYPE: PRT
<213> ORGANISM: Artificial Sequence
<220> FEATURE:
<223> OTHER INFORMATION: 1C9v11.1 CD28 sdAb

<400> SEQUENCE: 351

Glu Val Gln Leu Val Glu Ser Gly Gly Gly Glu Val Gln Pro Gly Gly
1 5 10 15

Ser Leu Arg Leu Ser Cys Ala Ala Ser Gly Phe Thr Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Arg Asp Ser Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Ser Ser Leu Arg Ala Glu Asp Thr Ala Val Tyr Tyr Cys
85 90 95

Gly Phe Thr Tyr Ala Gly Trp Ala Ser Ser Arg Arg Asp Asp Tyr Asn
100 105 110

Tyr Trp Gly Gln Gly Thr Leu Val Thr Val Lys Pro
115 120

<210> SEQ ID NO 352
<211> LENGTH: 124
<212> TYPE: PRT
<213> ORGANISM: Artificial Sequence
<220> FEATURE:
<223> OTHER INFORMATION: 1C9v11.2 CD28 sdAb

<400> SEQUENCE: 352

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Ser Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asp
            100                 105                 110

Tyr Trp Gly Gln Gly Thr Leu Val Thr Val Lys Pro
        115                 120

<210> SEQ ID NO 353
<211> LENGTH: 124
<212> TYPE: PRT
<213> ORGANISM: Artificial Sequence
<220> FEATURE:
<223> OTHER INFORMATION: 1C9v11.3 CD28 sdAb

<400> SEQUENCE: 353

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Ser Ala Asp Tyr Ala Glu Ser Val
    50                  55                  60

Lys Asp Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120

<210> SEQ ID NO 354
<211> LENGTH: 124
<212> TYPE: PRT
<213> ORGANISM: Artificial Sequence
<220> FEATURE:
<223> OTHER INFORMATION: 1C9v11.4 CD28 sdAb

<400> SEQUENCE: 354

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Gly Arg Asp Ser Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Ser Ser Leu Arg Ala Glu Asp Thr Ala Val Tyr Tyr Cys
85 90 95

Gly Phe Thr Tyr Ala Gly Trp Ala Ser Ser Arg Arg Asp Asp Tyr Asn
100 105 110

Tyr Trp Gly Gln Gly Thr Leu Val Thr Val Lys Pro
115 120

<210> SEQ ID NO 355
<211> LENGTH: 124
<212> TYPE: PRT
<213> ORGANISM: Artificial Sequence
<220> FEATURE:
<223> OTHER INFORMATION: 1C9v11.5 CD28 sdAb

<400> SEQUENCE: 355

Glu Val Gln Leu Val Glu Ser Gly Gly Gly Glu Val Gln Pro Gly Gly
1 5 10 15

Ser Leu Arg Leu Ser Cys Ala Ala Ser Gly Phe Thr Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Gly Asp Ser Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Ser Ser Leu Arg Ala Glu Asp Thr Ala Val Tyr Tyr Cys
85 90 95

Gly Phe Thr Tyr Ala Gly Trp Ala Ser Ser Arg Arg Asp Asp Tyr Asn
100 105 110

Tyr Trp Gly Gln Gly Thr Leu Val Thr Val Lys Pro
115 120

<210> SEQ ID NO 356
<211> LENGTH: 124
<212> TYPE: PRT
<213> ORGANISM: Artificial Sequence
<220> FEATURE:
<223> OTHER INFORMATION: 1C9v11.6 CD28 sdAb

<400> SEQUENCE: 356

Glu Val Gln Leu Val Glu Ser Gly Gly Gly Glu Val Gln Pro Gly Gly
1 5 10 15

Ser Leu Arg Leu Ser Cys Ala Ala Ser Gly Phe Thr Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Arg Asp Ser Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Ser Ser Leu Arg Ala Glu Asp Thr Ala Val Tyr Tyr Cys
85 90 95

Gly Phe Thr Tyr Ala Gly Trp Ala Ser Ser Gly Arg Asp Asp Tyr Asn
100 105 110

```
Tyr Trp Gly Gln Gly Thr Leu Val Thr Val Lys Pro
        115                 120


<210> SEQ ID NO 357
<211> LENGTH: 124
<212> TYPE: PRT
<213> ORGANISM: Artificial Sequence
<220> FEATURE:
<223> OTHER INFORMATION: 1C9v11.7 CD28 sdAb

<400> SEQUENCE: 357

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Ser Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Gly Asp Asp Tyr Asn
            100                 105                 110

Tyr Trp Gly Gln Gly Thr Leu Val Thr Val Lys Pro
        115                 120


<210> SEQ ID NO 358
<211> LENGTH: 124
<212> TYPE: PRT
<213> ORGANISM: Artificial Sequence
<220> FEATURE:
<223> OTHER INFORMATION: 1C9v7.1  CD28 sdAb

<400> SEQUENCE: 358

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Glu Ser Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 359
<211> LENGTH: 124
<212> TYPE: PRT
<213> ORGANISM: Artificial Sequence
<220> FEATURE:
<223> OTHER INFORMATION: 1C9v7.2 CD28 sdAb
```

<400> SEQUENCE: 359

Glu Val Gln Leu Val Glu Ser Gly Gly Gly Glu Val Gln Pro Gly Gly
1 5 10 15

Ser Leu Arg Leu Ser Cys Ala Ala Ser Gly Phe Thr Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Arg Glu Ser Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Ser Ser Leu Arg Ala Glu Asp Thr Ala Val Tyr Tyr Cys
85 90 95

Gly Phe Thr Tyr Ala Gly Trp Ala Ser Ser Arg Arg Asp Asp Tyr Asp
100 105 110

Tyr Trp Gly Gln Gly Thr Leu Val Thr Val Lys Pro
115 120

<210> SEQ ID NO 360
<211> LENGTH: 124
<212> TYPE: PRT
<213> ORGANISM: Artificial Sequence
<220> FEATURE:
<223> OTHER INFORMATION: 1C9v7.3 CD28 sdAb

<400> SEQUENCE: 360

Glu Val Gln Leu Val Glu Ser Gly Gly Gly Glu Val Gln Pro Gly Gly
1 5 10 15

Ser Leu Arg Leu Ser Cys Ala Ala Ser Gly Phe Thr Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Arg Glu Ser Ala Asp Tyr Ala Glu Ser Val
50 55 60

Lys Asp Arg Phe Thr Ile Ser Arg Asp Asn Ala Lys Asn Thr Val Tyr
65 70 75 80

Leu Gln Met Ser Ser Leu Arg Ala Glu Asp Thr Ala Val Tyr Tyr Cys
85 90 95

Gly Phe Thr Tyr Ala Gly Trp Ala Ser Ser Arg Arg Asp Asp Tyr Asn
100 105 110

Tyr Trp Gly Gln Gly Thr Leu Val Thr Val Lys Pro
115 120

<210> SEQ ID NO 361
<211> LENGTH: 124
<212> TYPE: PRT
<213> ORGANISM: Artificial Sequence
<220> FEATURE:
<223> OTHER INFORMATION: 1C9v7.5 CD28 sdAb

<400> SEQUENCE: 361

Glu Val Gln Leu Val Glu Ser Gly Gly Gly Glu Val Gln Pro Gly Gly
1 5 10 15

Ser Leu Arg Leu Ser Cys Ala Ala Ser Gly Phe Thr Phe Ser Asn Tyr
20 25 30

Ala Met Gly Trp Phe Arg Gln Ala Pro Gly Lys Glu Arg Glu Phe Val
35 40 45

```
Ala Ala Ile Asn Tyr Gly Arg Glu Ser Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120
```

<210> SEQ ID NO 362
<211> LENGTH: 124
<212> TYPE: PRT
<213> ORGANISM: Artificial Sequence
<220> FEATURE:
<223> OTHER INFORMATION: 1C9v7.6 CD28 sdAb

<400> SEQUENCE: 362

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Gly Glu Ser Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120
```

<210> SEQ ID NO 363
<211> LENGTH: 124
<212> TYPE: PRT
<213> ORGANISM: Artificial Sequence
<220> FEATURE:
<223> OTHER INFORMATION: 1C9v7.7 CD28 sdAb

<400> SEQUENCE: 363

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Glu Ser Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Gly Arg Asp Asp Tyr Asn
```

100 105 110

Tyr Trp Gly Gln Gly Thr Leu Val Thr Val Lys Pro
115 120

<210> SEQ ID NO 364
<211> LENGTH: 124
<212> TYPE: PRT
<213> ORGANISM: Artificial Sequence
<220> FEATURE:
<223> OTHER INFORMATION: 1C9v7.8 CD28 sdAb

<400> SEQUENCE: 364

Glu Val Gln Leu Val Glu Ser Gly Gly Gly Glu Val Gln Pro Gly Gly
1 5 10 15

Ser Leu Arg Leu Ser Cys Ala Ala Ser Gly Phe Thr Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Arg Glu Ser Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Ser Ser Leu Arg Ala Glu Asp Thr Ala Val Tyr Tyr Cys
85 90 95

Gly Phe Thr Tyr Ala Gly Trp Ala Ser Ser Arg Gly Asp Asp Tyr Asn
100 105 110

Tyr Trp Gly Gln Gly Thr Leu Val Thr Val Lys Pro
115 120

<210> SEQ ID NO 365
<211> LENGTH: 124
<212> TYPE: PRT
<213> ORGANISM: Artificial Sequence
<220> FEATURE:
<223> OTHER INFORMATION: 1C9v7.9 CD28 sdAb

<400> SEQUENCE: 365

Glu Val Gln Leu Val Glu Ser Gly Gly Gly Glu Val Gln Pro Gly Gly
1 5 10 15

Ser Leu Arg Leu Ser Cys Ala Ala Ser Gly Phe Thr Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Arg Asp Asp Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Ser Ser Leu Arg Ala Glu Asp Thr Ala Val Tyr Tyr Cys
85 90 95

Gly Phe Thr Tyr Ala Gly Trp Ala Ser Ser Arg Arg Asp Asp Tyr Asn
100 105 110

Tyr Trp Gly Gln Gly Thr Leu Val Thr Val Lys Pro
115 120

<210> SEQ ID NO 366
<211> LENGTH: 124
<212> TYPE: PRT
<213> ORGANISM: Artificial Sequence
<220> FEATURE:

<223> OTHER INFORMATION: 1C9v7.10 CD28 sdAb

<400> SEQUENCE: 366

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Asp Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asp
            100                 105                 110

Tyr Trp Gly Gln Gly Thr Leu Val Thr Val Lys Pro
        115                 120

<210> SEQ ID NO 367
<211> LENGTH: 124
<212> TYPE: PRT
<213> ORGANISM: Artificial Sequence
<220> FEATURE:
<223> OTHER INFORMATION: 1C9v7.11 CD28 sdAb

<400> SEQUENCE: 367

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Asp Ala Asp Tyr Ala Glu Ser Val
    50                  55                  60

Lys Asp Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120

<210> SEQ ID NO 368
<211> LENGTH: 124
<212> TYPE: PRT
<213> ORGANISM: Artificial Sequence
<220> FEATURE:
<223> OTHER INFORMATION: 1C9v7.12 CD28 sdAb

<400> SEQUENCE: 368

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val

```
        35                  40                  45

Ala Ala Ile Asn Tyr Gly Arg Asp Asp Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 369
<211> LENGTH: 124
<212> TYPE: PRT
<213> ORGANISM: Artificial Sequence
<220> FEATURE:
<223> OTHER INFORMATION: 1C9v7.13 CD28 sdAb

<400> SEQUENCE: 369

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Gly Asp Asp Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 370
<211> LENGTH: 124
<212> TYPE: PRT
<213> ORGANISM: Artificial Sequence
<220> FEATURE:
<223> OTHER INFORMATION: 1C9v7.14 CD28 sdAb

<400> SEQUENCE: 370

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Asp Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95
```

```
Gly Phe Thr Tyr Ala Gly Trp Ala Ser Ser Gly Arg Asp Asp Tyr Asn
            100                 105                 110

Tyr Trp Gly Gln Gly Thr Leu Val Thr Val Lys Pro
        115                 120


<210> SEQ ID NO 371
<211> LENGTH: 124
<212> TYPE: PRT
<213> ORGANISM: Artificial Sequence
<220> FEATURE:
<223> OTHER INFORMATION: 1C9v7.15 CD28 sdAb

<400> SEQUENCE: 371

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Asp Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Gly Asp Asp Tyr Asn
            100                 105                 110

Tyr Trp Gly Gln Gly Thr Leu Val Thr Val Lys Pro
        115                 120


<210> SEQ ID NO 372
<211> LENGTH: 124
<212> TYPE: PRT
<213> ORGANISM: Artificial Sequence
<220> FEATURE:
<223> OTHER INFORMATION: 1C9v7.16 CD28 sdAb

<400> SEQUENCE: 372

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Ala Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 373
<211> LENGTH: 124
<212> TYPE: PRT
<213> ORGANISM: Artificial Sequence
```

<220> FEATURE:
<223> OTHER INFORMATION: 1C9v7.17 CD28 sdAb

<400> SEQUENCE: 373

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Ala Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asp
            100                 105                 110

Tyr Trp Gly Gln Gly Thr Leu Val Thr Val Lys Pro
        115                 120
```

<210> SEQ ID NO 374
<211> LENGTH: 124
<212> TYPE: PRT
<213> ORGANISM: Artificial Sequence
<220> FEATURE:
<223> OTHER INFORMATION: 1C9v7.18 CD28 sdAb

<400> SEQUENCE: 374

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Ala Ala Asp Tyr Ala Glu Ser Val
    50                  55                  60

Lys Asp Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120
```

<210> SEQ ID NO 375
<211> LENGTH: 124
<212> TYPE: PRT
<213> ORGANISM: Artificial Sequence
<220> FEATURE:
<223> OTHER INFORMATION: 1C9v7.19 CD28 sdAb

<400> SEQUENCE: 375

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30
```

```
Ala Met Gly Trp Phe Arg Gln Ala Pro Gly Lys Glu Arg Glu Phe Val
        35                  40                  45

Ala Ala Ile Asn Tyr Gly Arg Asp Ala Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 376
<211> LENGTH: 124
<212> TYPE: PRT
<213> ORGANISM: Artificial Sequence
<220> FEATURE:
<223> OTHER INFORMATION: 1C9v7.20 CD28 sdAb

<400> SEQUENCE: 376

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Gly Asp Ala Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 377
<211> LENGTH: 124
<212> TYPE: PRT
<213> ORGANISM: Artificial Sequence
<220> FEATURE:
<223> OTHER INFORMATION: 1C9v7.21 CD28 sdAb

<400> SEQUENCE: 377

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Ala Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95
```

```
Gly Phe Thr Tyr Ala Gly Trp Ala Ser Ser Gly Arg Asp Asp Tyr Asn
            100                 105                 110

Tyr Trp Gly Gln Gly Thr Leu Val Thr Val Lys Pro
        115                 120


<210> SEQ ID NO 378
<211> LENGTH: 124
<212> TYPE: PRT
<213> ORGANISM: Artificial Sequence
<220> FEATURE:
<223> OTHER INFORMATION: 1C9v7.22 CD28 sdAb

<400> SEQUENCE: 378

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Ala Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Gly Asp Asp Tyr Asn
            100                 105                 110

Tyr Trp Gly Gln Gly Thr Leu Val Thr Val Lys Pro
        115                 120


<210> SEQ ID NO 379
<211> LENGTH: 124
<212> TYPE: PRT
<213> ORGANISM: Artificial Sequence
<220> FEATURE:
<223> OTHER INFORMATION: 1C9v7.23 CD28 sdAb

<400> SEQUENCE: 379

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Thr Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120


<210> SEQ ID NO 380
<211> LENGTH: 124
<212> TYPE: PRT
```

<213> ORGANISM: Artificial Sequence
<220> FEATURE:
<223> OTHER INFORMATION: 1C9v7.24 CD28 sdAb

<400> SEQUENCE: 380

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Thr Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asp
            100                 105                 110

Tyr Trp Gly Gln Gly Thr Leu Val Thr Val Lys Pro
        115                 120
```

<210> SEQ ID NO 381
<211> LENGTH: 124
<212> TYPE: PRT
<213> ORGANISM: Artificial Sequence
<220> FEATURE:
<223> OTHER INFORMATION: 1C9v7.25 CD28 sdAb

<400> SEQUENCE: 381

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Thr Ala Asp Tyr Ala Glu Ser Val
    50                  55                  60

Lys Asp Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Arg Asp Asp Tyr Asn
            100                 105                 110

Tyr Trp Gly Gln Gly Thr Leu Val Thr Val Lys Pro
        115                 120
```

<210> SEQ ID NO 382
<211> LENGTH: 124
<212> TYPE: PRT
<213> ORGANISM: Artificial Sequence
<220> FEATURE:
<223> OTHER INFORMATION: 1C9v7.26 CD28 sdAb

<400> SEQUENCE: 382

```
Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30
```

Ala Met Gly Trp Phe Arg Gln Ala Pro Gly Lys Glu Arg Glu Phe Val
35 40 45

Ala Ala Ile Asn Tyr Gly Arg Asp Thr Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Ser Ser Leu Arg Ala Glu Asp Thr Ala Val Tyr Tyr Cys
85 90 95

Gly Phe Thr Tyr Ala Gly Trp Ala Ser Ser Arg Arg Asp Asp Tyr Asn
100 105 110

Tyr Trp Gly Gln Gly Thr Leu Val Thr Val Lys Pro
115 120

<210> SEQ ID NO 383
<211> LENGTH: 124
<212> TYPE: PRT
<213> ORGANISM: Artificial Sequence
<220> FEATURE:
<223> OTHER INFORMATION: 1C9v7.27 CD28 sdAb

<400> SEQUENCE: 383

Glu Val Gln Leu Val Glu Ser Gly Gly Gly Glu Val Gln Pro Gly Gly
1 5 10 15

Ser Leu Arg Leu Ser Cys Ala Ala Ser Gly Phe Thr Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Gly Asp Thr Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Ser Ser Leu Arg Ala Glu Asp Thr Ala Val Tyr Tyr Cys
85 90 95

Gly Phe Thr Tyr Ala Gly Trp Ala Ser Ser Arg Arg Asp Asp Tyr Asn
100 105 110

Tyr Trp Gly Gln Gly Thr Leu Val Thr Val Lys Pro
115 120

<210> SEQ ID NO 384
<211> LENGTH: 124
<212> TYPE: PRT
<213> ORGANISM: Artificial Sequence
<220> FEATURE:
<223> OTHER INFORMATION: 1C9v7.28 CD28 sdAb

<400> SEQUENCE: 384

Glu Val Gln Leu Val Glu Ser Gly Gly Gly Glu Val Gln Pro Gly Gly
1 5 10 15

Ser Leu Arg Leu Ser Cys Ala Ala Ser Gly Phe Thr Phe Ser Asn Tyr
20 25 30

Ala Met Gly Trp Phe Arg Gln Ala Pro Gly Lys Glu Arg Glu Phe Val
35 40 45

Ala Ala Ile Asn Tyr Arg Arg Asp Thr Ala Asp Tyr Ala Glu Ser Val
50 55 60

Lys Gly Arg Phe Thr Ile Ser Arg Asp Asn Ala Lys Asn Thr Val Tyr
65 70 75 80

Leu Gln Met Ser Ser Leu Arg Ala Glu Asp Thr Ala Val Tyr Tyr Cys

```
                85                  90                  95

Gly Phe Thr Tyr Ala Gly Trp Ala Ser Ser Gly Arg Asp Asp Tyr Asn
            100                 105                 110

Tyr Trp Gly Gln Gly Thr Leu Val Thr Val Lys Pro
        115                 120


<210> SEQ ID NO 385
<211> LENGTH: 124
<212> TYPE: PRT
<213> ORGANISM: Artificial Sequence
<220> FEATURE:
<223> OTHER INFORMATION: 1C9v7.29 CD28 sdAb

<400> SEQUENCE: 385

Glu Val Gln Leu Val Glu Ser Gly Gly Gly Glu Val Gln Pro Gly Gly
1               5                   10                  15

Ser Leu Arg Leu Ser Cys Ala Ala Ser Gly Phe Thr Phe Ser Asn Tyr
            20                  25                  30

Ala Met Gly Trp Phe Arg Gln Ala Pro Gly Lys Glu Arg Glu Phe Val
        35                  40                  45

Ala Ala Ile Asn Tyr Arg Arg Asp Thr Ala Asp Tyr Ala Glu Ser Val
    50                  55                  60

Lys Gly Arg Phe Thr Ile Ser Arg Asp Asn Ala Lys Asn Thr Val Tyr
65                  70                  75                  80

Leu Gln Met Ser Ser Leu Arg Ala Glu Asp Thr Ala Val Tyr Tyr Cys
                85                  90                  95

Gly Phe Thr Tyr Ala Gly Trp Ala Ser Ser Arg Gly Asp Asp Tyr Asn
            100                 105                 110

Tyr Trp Gly Gln Gly Thr Leu Val Thr Val Lys Pro
        115                 120


<210> SEQ ID NO 386
<211> LENGTH: 10
<212> TYPE: PRT
<213> ORGANISM: Artificial Sequence
<220> FEATURE:
<223> OTHER INFORMATION: CDR2 (1C9v7.5)

<400> SEQUENCE: 386

Ala Ile Asn Tyr Gly Arg Glu Ser Ala Asp
1               5                   10


<210> SEQ ID NO 387
<211> LENGTH: 10
<212> TYPE: PRT
<213> ORGANISM: Artificial Sequence
<220> FEATURE:
<223> OTHER INFORMATION: CDR2 (1C9v7.6)

<400> SEQUENCE: 387

Ala Ile Asn Tyr Arg Gly Glu Ser Ala Asp
1               5                   10


<210> SEQ ID NO 388
<211> LENGTH: 10
<212> TYPE: PRT
<213> ORGANISM: Artificial Sequence
<220> FEATURE:
<223> OTHER INFORMATION: CDR2 (1C9v7.12; 1C9v13.6)

<400> SEQUENCE: 388

Ala Ile Asn Tyr Gly Arg Asp Asp Ala Asp
```

1 5 10

<210> SEQ ID NO 389
<211> LENGTH: 10
<212> TYPE: PRT
<213> ORGANISM: Artificial Sequence
<220> FEATURE:
<223> OTHER INFORMATION: CDR2 (1C9v7.13; 1C9v13.7)

<400> SEQUENCE: 389

Ala Ile Asn Tyr Arg Gly Asp Asp Ala Asp
1 5 10

<210> SEQ ID NO 390
<211> LENGTH: 10
<212> TYPE: PRT
<213> ORGANISM: Artificial Sequence
<220> FEATURE:
<223> OTHER INFORMATION: CDR2 (1C9v7.19)

<400> SEQUENCE: 390

Ala Ile Asn Tyr Gly Arg Asp Ala Ala Asp
1 5 10

<210> SEQ ID NO 391
<211> LENGTH: 10
<212> TYPE: PRT
<213> ORGANISM: Artificial Sequence
<220> FEATURE:
<223> OTHER INFORMATION: CDR2 (1C9v7.20)

<400> SEQUENCE: 391

Ala Ile Asn Tyr Arg Gly Asp Ala Ala Asp
1 5 10

<210> SEQ ID NO 392
<211> LENGTH: 10
<212> TYPE: PRT
<213> ORGANISM: Artificial Sequence
<220> FEATURE:
<223> OTHER INFORMATION: CDR2 (1C9v7.26)

<400> SEQUENCE: 392

Ala Ile Asn Tyr Gly Arg Asp Thr Ala Asp
1 5 10

<210> SEQ ID NO 393
<211> LENGTH: 10
<212> TYPE: PRT
<213> ORGANISM: Artificial Sequence
<220> FEATURE:
<223> OTHER INFORMATION: CDR2 (C9v7.27)

<400> SEQUENCE: 393

Ala Ile Asn Tyr Arg Gly Asp Thr Ala Asp
1 5 10

<210> SEQ ID NO 394
<211> LENGTH: 10
<212> TYPE: PRT
<213> ORGANISM: Artificial Sequence
<220> FEATURE:
<223> OTHER INFORMATION: CDR2 (1C9v11.4)

<400> SEQUENCE: 394

Ala Ile Asn Tyr Gly Arg Asp Ser Ala Asp
1 5 10

```
<210> SEQ ID NO 395
<211> LENGTH: 10
<212> TYPE: PRT
<213> ORGANISM: Artificial Sequence
<220> FEATURE:
<223> OTHER INFORMATION: CDR2 (1C9v11.5)

<400> SEQUENCE: 395

Ala Ile Asn Tyr Arg Gly Asp Ser Ala Asp
1               5                   10


<210> SEQ ID NO 396
<211> LENGTH: 15
<212> TYPE: PRT
<213> ORGANISM: Artificial Sequence
<220> FEATURE:
<223> OTHER INFORMATION: CDR3 (1C9v7.2, 10, 17, 24; 1C9v11.2; 1C9v13.2,
      5)

<400> SEQUENCE: 396

Thr Tyr Ala Gly Trp Ala Ser Ser Arg Arg Asp Asp Tyr Asp Tyr
1               5                   10                  15


<210> SEQ ID NO 397
<211> LENGTH: 15
<212> TYPE: PRT
<213> ORGANISM: Artificial Sequence
<220> FEATURE:
<223> OTHER INFORMATION: CDR3 (1C9v7.7, 14, 21, 28; 1C9v11.6; 1C9v13.8)

<400> SEQUENCE: 397

Thr Tyr Ala Gly Trp Ala Ser Ser Gly Arg Asp Asp Tyr Asn Tyr
1               5                   10                  15


<210> SEQ ID NO 398
<211> LENGTH: 15
<212> TYPE: PRT
<213> ORGANISM: Artificial Sequence
<220> FEATURE:
<223> OTHER INFORMATION: CDR3 (1C9v7.8, 15, 22, 29; 1C9v11.7; 1C9v13.9)

<400> SEQUENCE: 398

Thr Tyr Ala Gly Trp Ala Ser Ser Arg Gly Asp Asp Tyr Asn Tyr
1               5                   10                  15
```

CD28 SINGLE DOMAIN ANTIBODIES AND MULTIVALENT AND MULTISPECIFIC CONSTRUCTS THEREOF

This application is a national stage application under 35 U.S.C. § 371 of international application No. PCT/US2021/015590, filed internationally on Jan. 28, 2021, which claims priority to U.S. provisional application No. 62/967,533, filed Jan. 29, 2020, entitled "CD28 SINGLE DOMAIN ANTIBODIES AND MULTIVALENT AND MULTISPECIFIC CONSTRUCTS THEREOF," the contents of which are incorporated by reference in their entirety for all purposes.

The present application is being filed with a Sequence Listing in electronic format. The Sequence Listing is provided as a file entitled 744952001500SeqList.txt, created Jul. 24, 2022, which is 325,388 bytes in size. The information in the electronic format of the Sequence Listing is incorporated by reference in its entirety.

FIELD

This disclosure generally provides binding polypeptides that specifically bind cluster of differentiation 28 (CD28). More specifically, the disclosure relates to fusion proteins, including multivalent and/or multispecific constructs that bind at least CD28. The disclosure also provides nucleic acid molecules encoding the polypeptides and vectors thereof, and methods of use and uses of the provided CD28 binding polypeptides for treating diseases and conditions, such as cancer.

BACKGROUND

Cluster of differentiation 28 (CD28) is a homodimeric transmembrane glycoprotein of the immunoglobulin (Ig) superfamily, expressed primarily by T lineage cells. CD28 provides a co-stimulatory signal that is involved in the activation and survival of T cells. The role of T cells against a variety of cancers in humans makes CD28 a desirable therapeutic target. However, some CD28 agonists have resulted in substantial toxicity in vivo. Improved therapeutic molecules targeting CD28 are therefore needed. Provided herein are embodiments that meet such needs.

SUMMARY

Provided herein are CD28-binding polypeptides having at least one single domain antibody (sdAb) that binds CD28, wherein the at least one CD28 sdAb contains a complementarity determining region 1 (CDR1) having an amino acid sequence selected from the group consisting of SEQ ID NO:189, 192, 195, 198, 199, 200, and 201; a complementarity determining region 2 (CDR2) having an amino acid sequence selected from the group consisting of SEQ ID NO:190, 193, 196, 202, 203, 204, 205, 206, 207, 208, 209, 210, 211, and 212; and a complementarity determining region 3 (CDR3) having an amino acid sequence selected from the group consisting of SEQ ID NO: 191, 194, and 197.

In some embodiments, the at least one CD28 sdAb contains: a CDR1 comprising an amino acid sequence set forth in SEQ ID NO:189, a CDR2 comprising the amino acid sequence set forth in SEQ ID NO:190, and a CDR3 comprising the amino acid sequence set forth in SEQ ID NO:191; a CDR1 comprising an amino acid sequence set forth in SEQ ID NO:192, a CDR2 comprising the amino acid sequence set forth in SEQ ID NO:193, and a CDR3 comprising the amino acid sequence set forth in SEQ ID NO:194; a CDR1 comprising an amino acid sequence set forth in SEQ ID NO:195, a CDR2 comprising the amino acid sequence set forth in SEQ ID NO:196, and a CDR3 comprising the amino acid sequence set forth in SEQ ID NO:197; a CDR1 comprising an amino acid sequence set forth in SEQ ID NO:198, a CDR2 comprising the amino acid sequence set forth in SEQ ID NO:196, and a CDR3 comprising the amino acid sequence set forth in SEQ ID NO:197; a CDR1 comprising an amino acid sequence set forth in SEQ ID NO:199, a CDR2 comprising the amino acid sequence set forth in SEQ ID NO:196, and a CDR3 comprising the amino acid sequence set forth in SEQ ID NO:197; a CDR1 comprising an amino acid sequence set forth in SEQ ID NO:200, a CDR2 comprising the amino acid sequence set forth in SEQ ID NO:196, and a CDR3 comprising the amino acid sequence set forth in SEQ ID NO:197; a CDR1 comprising an amino acid sequence set forth in SEQ ID NO:201, a CDR2 comprising the amino acid sequence set forth in SEQ ID NO:196, and a CDR3 comprising the amino acid sequence set forth in SEQ ID NO:197; a CDR1 comprising an amino acid sequence set forth in SEQ ID NO:195, a CDR2 comprising the amino acid sequence set forth in SEQ ID NO:202, and a CDR3 comprising the amino acid sequence set forth in SEQ ID NO:197; a CDR1 comprising an amino acid sequence set forth in SEQ ID NO:195, a CDR2 comprising the amino acid sequence set forth in SEQ ID NO:203, and a CDR3 comprising the amino acid sequence set forth in SEQ ID NO:197; a CDR1 comprising an amino acid sequence set forth in SEQ ID NO:195, a CDR2 comprising the amino acid sequence set forth in SEQ ID NO:204, and a CDR3 comprising the amino acid sequence set forth in SEQ ID NO:197; a CDR1 comprising an amino acid sequence set forth in SEQ ID NO:195, a CDR2 comprising the amino acid sequence set forth in SEQ ID NO:205, and a CDR3 comprising the amino acid sequence set forth in SEQ ID NO:197; a CDR1 comprising an amino acid sequence set forth in SEQ ID NO:195, a CDR2 comprising the amino acid sequence set forth in SEQ ID NO:206, and a CDR3 comprising the amino acid sequence set forth in SEQ ID NO:197; a CDR1 comprising an amino acid sequence set forth in SEQ ID NO:195, a CDR2 comprising the amino acid sequence set forth in SEQ ID NO:207, and a CDR3 comprising the amino acid sequence set forth in SEQ ID NO:197; a CDR1 comprising an amino acid sequence set forth in SEQ ID NO:195, a CDR2 comprising the amino acid sequence set forth in SEQ ID NO:208, and a CDR3 comprising the amino acid sequence set forth in SEQ ID NO:197; a CDR1 comprising an amino acid sequence set forth in SEQ ID NO:195, a CDR2 comprising the amino acid sequence set forth in SEQ ID NO:209, and a CDR3 comprising the amino acid sequence set forth in SEQ ID NO:197; a CDR1 comprising an amino acid sequence set forth in SEQ ID NO:195, a CDR2 comprising the amino acid sequence set forth in SEQ ID NO:210, and a CDR3 comprising the amino acid sequence set forth in SEQ ID NO:197; a CDR1 comprising an amino acid sequence set forth in SEQ ID NO:195, a CDR2 comprising the amino acid sequence set forth in SEQ ID NO:211, and a CDR3 comprising the amino acid sequence set forth in SEQ ID NO:197; or a CDR1 comprising an amino acid sequence set forth in SEQ ID NO:195, a CDR2 comprising the amino acid sequence set forth in SEQ ID NO:212, and a CDR3 comprising the amino acid sequence set forth in SEQ ID NO:197.

Also provided herein are CD28-binding polypeptides having at least one single domain antibody (sdAb) that binds CD28, wherein the at least one CD28 sdAb comprises a complementarity determining region 1 (CDR1) comprising an amino acid sequence selected from the group consisting of SEQ ID NOS:189, 192, 195, 198, 199, 200, and 201; a complementarity determining region 2 (CDR2) comprising an amino acid sequence selected from the group consisting of SEQ ID NOS:190, 193, 196, 202, 203, 204, 205, 206, 207, 208, 209, 210, 211, and 212, 386, 387, 388, 389, 390, 391, 392, 393, 394, and 395; and a complementarity determining region 3 (CDR3) comprising an amino acid sequence selected from the group consisting of SEQ ID NOS: 191, 194, and 197, 396, 397, and 398.

In some embodiments, the at least one CD28 sdAb contains: a CDR1 comprising an the amino acid sequence set forth in SEQ ID NO:189, a CDR2 comprising the amino acid sequence set forth in SEQ ID NO:190, and a CDR3 comprising the amino acid sequence set forth in SEQ ID NO:191; a CDR1 comprising an the amino acid sequence set forth in SEQ ID NO:192, a CDR2 comprising the amino acid sequence set forth in SEQ ID NO:193, and a CDR3 comprising the amino acid sequence set forth in SEQ ID NO:194; a CDR1 comprising an the amino acid sequence set forth in SEQ ID NO:195, a CDR2 comprising the amino acid sequence set forth in SEQ ID NO:196, and a CDR3 comprising the amino acid sequence set forth in SEQ ID NO:197; a CDR1 comprising an the amino acid sequence set forth in SEQ ID NO:198, a CDR2 comprising the amino acid sequence set forth in SEQ ID NO:196, and a CDR3 comprising the amino acid sequence set forth in SEQ ID NO:197; a CDR1 comprising an the amino acid sequence set forth in SEQ ID NO:199, a CDR2 comprising the amino acid sequence set forth in SEQ ID NO:196, and a CDR3 comprising the amino acid sequence set forth in SEQ ID NO:197; a CDR1 comprising an the amino acid sequence set forth in SEQ ID NO:200, a CDR2 comprising the amino acid sequence set forth in SEQ ID NO:196, and a CDR3 comprising the amino acid sequence set forth in SEQ ID NO:197; a CDR1 comprising an the amino acid sequence set forth in SEQ ID NO:201, a CDR2 comprising the amino acid sequence set forth in SEQ ID NO:196, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:202, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:203, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:204, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:205, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:206, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:207, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:208, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:209, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:210, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:211, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:212, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:396; a CDR1 comprising the amino acid sequence set forth in SEQ ID NO:201, a CDR2 comprising the amino acid sequence set forth in SEQ ID NO:386, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:387, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:397; a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:398; a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:396; a CDR1 comprising the amino acid sequence set forth in SEQ ID NO:201, a CDR2 comprising the amino acid sequence set forth in SEQ ID NO:388, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:389, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:397; a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:398; a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:396; a CDR1 comprising the amino acid sequence set forth in SEQ ID NO:201, a CDR2 comprising the amino acid sequence set forth in SEQ ID NO:390, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:391, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:397; a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:398; a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:396; a CDR1 comprising the amino acid sequence set forth in SEQ ID NO:201, a CDR2 comprising the amino acid sequence set forth in SEQ ID NO:392, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:393, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:397; a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:398; a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:396; a CDR1 comprising the amino acid sequence set forth in SEQ ID NO:201, a CDR2 comprising the amino acid sequence set forth in SEQ ID NO:394, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:395, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:397; a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:398; a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:396; a CDR1 comprising the amino acid sequence set forth in SEQ ID NO:195, a CDR2 comprising the amino acid sequence set forth in SEQ ID NO:388, and a CDR3 comprising the amino acid sequence set forth in SEQ ID NO:197; a CDR1 comprising the amino acid sequence set forth in SEQ ID NO:195, a CDR2 comprising the amino acid sequence set forth in SEQ ID NO:389, and a CDR3 comprising the amino acid sequence set forth in SEQ ID NO:197; a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:397; or a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:398.

In some embodiments, the at least one CD28 sdAb contains a CDR1 comprising an the amino acid sequence set forth in SEQ ID NO:189, a CDR2 comprising the amino acid sequence set forth in SEQ ID NO:190, and a CDR3 comprising the amino acid sequence set forth in SEQ ID NO:191. In some embodiments, the at least one CD28 sdAb contains a CDR1 comprising an the amino acid sequence set forth in SEQ ID NO:192, a CDR2 comprising the amino acid sequence set forth in SEQ ID NO:193, and a CDR3 comprising the amino acid sequence set forth in SEQ ID NO:194. In some embodiments, the at least one CD28 sdAb contains a CDR1 comprising an the amino acid sequence set forth in SEQ ID NO:195, a CDR2 comprising the amino acid sequence set forth in SEQ ID NO:196, and a CDR3 comprising the amino acid sequence set forth in SEQ ID NO:197. In some embodiments, the at least one CD28 sdAb contains a CDR1 comprising an the amino acid sequence set forth in SEQ ID NO:198, a CDR2 comprising the amino acid sequence set forth in SEQ ID NO:196, and a CDR3 comprising the amino acid sequence set forth in SEQ ID NO:197. In some embodiments, the at least one CD28 sdAb contains a CDR1 comprising an the amino acid sequence set forth in SEQ ID NO:199, a CDR2 comprising the amino acid sequence set forth in SEQ ID NO:196, and a CDR3 comprising the amino acid sequence set forth in SEQ ID NO:197. In some embodiments, the at least one CD28 sdAb contains a CDR1 comprising an the amino acid sequence set forth in SEQ ID NO:200, a CDR2 comprising the amino acid sequence set forth in SEQ ID NO:196, and a CDR3 comprising the amino acid sequence set forth in SEQ ID NO:197. In some embodiments, the at least one CD28 sdAb contains CDR1 comprising an the amino acid sequence set forth in SEQ ID NO:201, a CDR2 comprising the amino acid sequence set forth in SEQ ID NO:196, and a CDR3 comprising the amino acid sequence set forth in SEQ ID NO:197. In some embodiments, the at least one CD28 sdAb contains a CDR1 comprising an the amino acid sequence set forth in SEQ ID NO:195, a CDR2 comprising the amino acid sequence set forth in SEQ ID NO:202, and a CDR3 comprising the amino acid sequence set forth in SEQ ID NO:197. In some embodiments, the at least one CD28 sdAb contains a CDR1 comprising an the amino acid sequence set forth in SEQ ID NO:195, a CDR2 comprising the amino acid sequence set forth in SEQ ID NO:203, and a CDR3 comprising the amino acid sequence set forth in SEQ ID NO:197. In some embodiments, the at least one CD28 sdAb contains CDR1 comprising an the amino acid sequence set forth in SEQ ID NO:195, a CDR2 comprising the amino acid sequence set forth in SEQ ID NO:204, and a CDR3 comprising the amino acid sequence set forth in SEQ ID NO:197. In some embodiments, the at least one CD28 sdAb contains CDR1 comprising an the amino acid sequence set forth in SEQ ID NO:195, a CDR2 comprising the amino acid sequence set forth in SEQ ID NO:205, and a CDR3 comprising the amino acid sequence set forth in SEQ ID NO:197. In some embodiments, the at least one CD28 sdAb contains CDR1 comprising an the amino acid sequence set forth in SEQ ID NO:195, a CDR2 comprising the amino acid sequence set forth in SEQ ID NO:206, and a CDR3 comprising the amino acid sequence set forth in SEQ ID NO:197. In some embodiments, the at least one CD28 sdAb contains a CDR1 comprising an the amino acid sequence set forth in SEQ ID NO:195, a CDR2 comprising the amino acid sequence set forth in SEQ ID NO:207, and a CDR3 comprising the amino acid sequence set forth in SEQ ID NO:197. In some embodiments, the at least one CD28 sdAb contains CDR1 comprising an the amino acid sequence set forth in SEQ ID NO:195, a CDR2 comprising the amino acid sequence set forth in SEQ ID NO:208, and a CDR3 comprising the amino acid sequence set forth in SEQ ID NO:197. In some embodiments, the at least one CD28 sdAb contains CDR1 comprising an the amino acid sequence set forth in SEQ ID NO:195, a CDR2 comprising the amino acid sequence set forth in SEQ ID NO:209, and a CDR3 comprising the amino acid sequence set forth in SEQ ID NO:197. In some embodiments, the at least one CD28 sdAb contains CDR1 comprising an the amino acid sequence set forth in SEQ ID NO:195, a CDR2 comprising the amino acid sequence set forth in SEQ ID NO:210, and a CDR3 comprising the amino acid sequence set forth in SEQ ID NO:197. In some embodiments, the at least one CD28 sdAb contains a CDR1 comprising an the amino acid sequence set forth in SEQ ID NO:195, a CDR2 comprising the amino acid sequence set forth in SEQ ID NO:211, and a CDR3 comprising the amino acid sequence set forth in SEQ ID NO:197. In some embodiments, the at least one CD28 sdAb contains a CDR1 comprising an the amino acid sequence set forth in SEQ ID NO:195, a CDR2 comprising the amino acid sequence set forth in SEQ ID NO:212, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:396. In some embodiments, the at least one CD28 sdAb contains a CDR1 comprising the amino acid sequence set forth in SEQ ID NO:201, a CDR2 comprising the amino acid sequence set forth in SEQ ID NO:386, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:387, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:397. In some embodiments, the at least one CD28 sdAb contains a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:398. In some embodiments, the at least one CD28 sdAb contains a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:396. In some embodiments, the at least one CD28 sdAb contains a CDR1 comprising the amino acid sequence set forth in SEQ ID NO:201, a CDR2 comprising the amino acid sequence set forth in SEQ ID NO:388, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:389, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:397. In some embodiments, the at least one CD28 sdAb contains a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:398. In some embodiments, the at least one CD28 sdAb contains a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:396. In some embodiments, the at least one CD28 sdAb contains a CDR1 comprising the amino acid sequence set forth in SEQ ID NO:201, a CDR2 comprising the amino acid sequence set forth in SEQ ID NO:390, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:391, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:397. In some embodiments, the at least one CD28 sdAb contains a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:398. In some embodiments, the at least one CD28 sdAb contains a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:396. In some embodiments, the at least one CD28 sdAb contains a CDR1 comprising the amino acid sequence set forth in SEQ ID NO:201, a CDR2 comprising the amino acid sequence set forth in SEQ ID NO:392, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:393, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:397. In some embodiments, the at least one CD28 sdAb contains a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:398. In some embodiments, the at least one CD28 sdAb contains a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:396. In some embodiments, the at least one CD28 sdAb contains a CDR1 comprising the amino acid sequence set forth in SEQ ID NO:201, a CDR2 comprising the amino acid sequence set forth in SEQ ID NO:394, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:395, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:397. In some embodiments, the at least one CD28 sdAb contains a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:398. In some embodiments, the at least one CD28 sdAb contains a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:396. In some embodiments, the at least one CD28 sdAb contains a CDR1 comprising the amino acid sequence set forth in SEQ ID NO:195, a CDR2 comprising the amino acid sequence set forth in SEQ ID NO:388, and a CDR3 comprising the amino acid sequence set forth in SEQ ID NO:197. In some embodiments, the at least one CD28 sdAb contains a CDR1 comprising the amino acid sequence set forth in SEQ ID NO:195, a CDR2 comprising the amino acid sequence set forth in SEQ ID NO:389, and a CDR3 comprising the amino acid sequence set forth in SEQ ID NO:197. In some embodiments, the at least one CD28 sdAb contains a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:397; or a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:398.

Also provided herein are CD28-binding polypeptides having at least one single domain antibody (sdAb) that binds CD28, wherein the at least one CD28 sdAb contains a complementarity determining region 1 (CDR1) having an amino acid sequence selected from the group consisting of SEQ ID NO:189, 192, 195, 198, 199, 200, and 201; a complementarity determining region 2 (CDR2) having an amino acid sequence selected from the group consisting of SEQ ID NO:190, 193, 196, 202, 204, 205, 206, 207, 208, 209, 210, 211, and 212; and a complementarity determining region 3 (CDR3) having an amino acid sequence selected from the group consisting of SEQ ID NO: 191, 194, and 197.

In some embodiments, the at least one CD28 sdAb contains: a CDR1 having an amino acid sequence set forth in SEQ ID NO:189, a CDR2 having the amino acid sequence set forth in SEQ ID NO:190, and a CDR3 having the amino acid sequence set forth in SEQ ID NO:191; a CDR1 having an amino acid sequence set forth in SEQ ID NO:192, a CDR2 having the amino acid sequence set forth in SEQ ID NO:193, and a CDR3 having the amino acid sequence set forth in SEQ ID NO:194; a CDR1 having an amino acid sequence set forth in SEQ ID NO:195, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:198, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:199, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:200, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:201, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:202, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:204, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:205, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:206, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:207, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:208, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:209, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:210, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:211, and a CDR3 having the amino acid sequence set forth in SEQ ID NO:197; or a CDR1 having an amino acid sequence set forth in SEQ ID NO:195, a CDR2 having the amino acid sequence set forth in SEQ ID NO:212, and a CDR3 having the amino acid sequence set forth in SEQ ID NO:197.

Also provided herein are CD28-binding polypeptides containing at least one single domain antibody (sdAb) that binds CD28, wherein the at least one CD28 sdAb comprises a complementarity determining region 1 (CDR1) comprising an amino acid sequence selected from the group consisting of SEQ ID NOS:189, 192, 195, 198, 199, 200, and 201; a complementarity determining region 2 (CDR2) comprising an amino acid sequence selected from the group consisting of SEQ ID NOS:190, 193, 196, 202, 204, 205, 206, 207, 208, 209, 210, 211, and 212, 386, 387, 388, 389, 390, 391, 392, 393, 394, and 395; and a complementarity determining region 3 (CDR3) comprising an amino acid sequence selected from the group consisting of SEQ ID NOS: 191, 194, and 197, 396, 397, and 398.

In some embodiments, the at least one CD28 sdAb contains: a CDR1 comprising an the amino acid sequence set forth in SEQ ID NO:189, a CDR2 comprising the amino acid sequence set forth in SEQ ID NO:190, and a CDR3 comprising the amino acid sequence set forth in SEQ ID NO:191; a CDR1 comprising an the amino acid sequence set forth in SEQ ID NO:192, a CDR2 comprising the amino acid sequence set forth in SEQ ID NO:193, and a CDR3 comprising the amino acid sequence set forth in SEQ ID NO:194; a CDR1 comprising an the amino acid sequence set forth in SEQ ID NO:195, a CDR2 comprising the amino acid sequence set forth in SEQ ID NO:196, and a CDR3 comprising the amino acid sequence set forth in SEQ ID NO:197; a CDR1 comprising an the amino acid sequence set forth in SEQ ID NO:198, a CDR2 comprising the amino acid sequence set forth in SEQ ID NO:196, and a CDR3 comprising the amino acid sequence set forth in SEQ ID NO:197; a CDR1 comprising an the amino acid sequence set forth in SEQ ID NO:199, a CDR2 comprising the amino acid sequence set forth in SEQ ID NO:196, and a CDR3 comprising the amino acid sequence set forth in SEQ ID NO:197; a CDR1 comprising an the amino acid sequence set forth in SEQ ID NO:200, a CDR2 comprising the amino acid sequence set forth in SEQ ID NO:196, and a CDR3 comprising the amino acid sequence set forth in SEQ ID NO:197; a CDR1 comprising an the amino acid sequence set forth in SEQ ID NO:201, a CDR2 comprising the amino acid sequence set forth in SEQ ID NO:196, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:202, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:204, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:205, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:206, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:207, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:208, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:209, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:210, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:211, and a CDR3 comprising the amino acid sequence set forth in SEQ ID NO:197; a CDR1 comprising an the amino acid sequence set forth in SEQ ID NO:195, a CDR2 comprising the amino acid sequence set forth in SEQ ID NO:212, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:396; a CDR1 comprising the amino acid sequence set forth in SEQ ID NO:201, a CDR2 comprising the amino acid sequence set forth in SEQ ID NO:386, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:387, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:397; a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:398; a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:396; a CDR1 comprising the amino acid sequence set forth in SEQ ID NO:201, a CDR2 comprising the amino acid sequence set forth in SEQ ID NO:388, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:389, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:397; a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:398; a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:396; a CDR1 comprising the amino acid sequence set forth in SEQ ID NO:201, a CDR2 comprising the amino acid sequence set forth in SEQ ID NO:390, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:391, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:397; a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:398; a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:396; a CDR1 comprising the amino acid sequence set forth in SEQ ID NO:201, a CDR2 comprising the amino acid sequence set forth in SEQ ID NO:392, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:393, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:397; a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:398; a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:396; a CDR1 comprising the amino acid sequence set forth in SEQ ID NO:201, a CDR2 comprising the amino acid sequence set forth in SEQ ID NO:394, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:395, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:397; a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:398; a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:396; a CDR1 comprising the amino acid sequence set forth in SEQ ID NO:195, a CDR2 comprising the amino acid sequence set forth in SEQ ID NO:388, and a CDR3 comprising the amino acid sequence set forth in SEQ ID NO:197; a CDR1 comprising the amino acid sequence set forth in SEQ ID NO:195, a CDR2 comprising the amino acid sequence set forth in SEQ ID NO:389, and a CDR3 comprising the amino acid sequence set forth in SEQ ID NO:197; a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:397; or a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:398.

Also provided herein are CD28-binding polypeptides containing at least one single domain antibody (sdAb) that binds CD28, wherein the CD28 VHH domain contains: a CDR1, a CDR2, and a CDR3 as contained in the VHH set forth in SEQ ID NO:186; a CDR1, a CDR2, and a CDR3 as contained in the VHH set forth in SEQ ID NO:187; a CDR1, a CDR2, and a CDR3 as contained in the VHH set forth in SEQ ID NO:188; a CDR1, a CDR2, and a CDR3 as contained in the VHH set forth in SEQ ID NO:213; a CDR1, a CDR2, and a CDR3 as contained in the VHH set forth in SEQ ID NO:214; a CDR1, a CDR2, and a CDR3 as contained in the VHH set forth in SEQ ID NO:215; a CDR1, a CDR2, and a CDR3 as contained in the VHH set forth in SEQ ID NO:216; a CDR1, a CDR2, and a CDR3 as contained in the VHH set forth in SEQ ID NO:217; a CDR1, a CDR2, and a CDR3 as contained in the VHH set forth in SEQ ID NO:218; a CDR1, a CDR2, and a CDR3 as contained in the VHH set forth in SEQ ID NO:219; a CDR1, a CDR2, and a CDR3 as contained in the VHH set forth in SEQ ID NO:220; a CDR1, a CDR2, and a CDR3 as contained in the VHH set forth in SEQ ID NO:221; a CDR1, a CDR2, and a CDR3 as contained in the VHH set forth in SEQ ID NO:222; a CDR1, a CDR2, and a CDR3 as contained in the VHH set forth in SEQ ID NO:223; a CDR1, a CDR2, and a CDR3 as contained in the VHH set forth in SEQ ID NO:224; a CDR1, a CDR2, and a CDR3 as contained in the VHH set forth in SEQ ID NO:225; a CDR1, a CDR2, and a CDR3 as contained in the VHH set forth in SEQ ID NO:226; a CDR1, a CDR2, and a CDR3 as contained in the VHH set forth in SEQ ID NO:227; a CDR1, a CDR2, and a CDR3 as contained in the VHH set forth in SEQ ID NO:228; a CDR1, a CDR2, and a CDR3 as contained in the VHH set forth in SEQ ID NO:229; a CDR1, a CDR2, and a CDR3 as contained in the VHH set forth in SEQ ID NO:230; a CDR1, a CDR2, and a CDR3 as contained in the VHH set forth in SEQ ID NO:231; a CDR1, a CDR2, and a CDR3 as contained in the VHH set forth in SEQ ID NO:232; a CDR1, a CDR2, and a CDR3 as contained in the VHH set forth in SEQ ID NO:233; a CDR1, a CDR2, and a CDR3 as contained in the VHH set forth in SEQ ID NO:234; a CDR1, a CDR2, and a CDR3 as contained in the VHH set forth in SEQ ID NO:235; a CDR1, a CDR2, and a CDR3 as contained in the VHH set forth in SEQ ID NO:236; a CDR1, a CDR2, and a CDR3 as contained in the VHH set forth in SEQ ID NO:237; a CDR1, a CDR2, and a CDR3 as contained in the VHH set forth in SEQ ID NO:238; a CDR1, a CDR2, and a CDR3 as contained in the VHH set forth in SEQ ID NO:239; or a CDR1, a CDR2, and a CDR3 as contained in the VHH set forth in SEQ ID NO:280.

Also provided herein are CD28-binding polypeptides containing at least one single domain antibody (sdAb) that binds CD28, wherein the at least one CD28 sdAb (CD28 VHH) domain comprises: a CDR1, a CDR2, and a CDR3 as contained in the amino acid sequence set forth in SEQ ID NO:186; a CDR1, a CDR2, and a CDR3 as contained in the amino acid sequence set forth in SEQ ID NO:187; a CDR1, a CDR2, and a CDR3 as contained in the amino acid sequence set forth in SEQ ID NO:188; a CDR1, a CDR2, and a CDR3 as contained in the amino acid sequence set forth in SEQ ID NO:213; a CDR1, a CDR2, and a CDR3 as contained in the amino acid sequence set forth in SEQ ID NO:214; a CDR1, a CDR2, and a CDR3 as contained in the amino acid sequence set forth in SEQ ID NO:215; a CDR1, a CDR2, and a CDR3 as contained in the amino acid sequence set forth in SEQ ID NO:216; a CDR1, a CDR2, and a CDR3 as contained in the amino acid sequence set forth in SEQ ID NO:217; a CDR1, a CDR2, and a CDR3 as contained in the amino acid sequence set forth in SEQ ID NO:218; a CDR1, a CDR2, and a CDR3 as contained in the amino acid sequence set forth in SEQ ID NO:219; a CDR1, a CDR2, and a CDR3 as contained in the amino acid sequence set forth in SEQ ID NO:220; a CDR1, a CDR2, and a CDR3 as contained in the amino acid sequence set forth in SEQ ID NO:221; a CDR1, a CDR2, and a CDR3 as contained in the amino acid sequence set forth in SEQ ID NO:222; a CDR1, a CDR2, and a CDR3 as contained in the amino acid sequence set forth in SEQ ID NO:223; a CDR1, a CDR2, and a CDR3 as contained in the amino acid sequence set forth in SEQ ID NO:224; a CDR1, a CDR2, and a CDR3 as contained in the amino acid sequence set forth in SEQ ID NO:225; a CDR1, a CDR2, and a CDR3 as contained in the amino acid sequence set forth in SEQ ID NO:226; a CDR1, a CDR2, and a CDR3 as contained in the amino acid sequence set forth in SEQ ID NO:227; a CDR1, a CDR2, and a CDR3 as contained in the amino acid sequence set forth in SEQ ID NO:228; a CDR1, a CDR2, and a CDR3 as contained in the amino acid sequence set forth in SEQ ID NO:229; a CDR1, a CDR2, and a CDR3 as contained in the amino acid sequence set forth in SEQ ID NO:230; a CDR1, a CDR2, and a CDR3 as contained in the amino acid sequence set forth in SEQ ID NO:231; a CDR1, a CDR2, and a CDR3 as contained in the amino acid sequence set forth in SEQ ID NO:232; a CDR1, a CDR2, and a CDR3 as contained in the amino acid sequence set forth in SEQ ID NO:233; a CDR1, a CDR2, and a CDR3 as contained in the amino acid sequence set forth in SEQ ID NO:234; a CDR1, a CDR2, and a CDR3 as contained in the amino acid sequence set forth in SEQ ID NO:235; a CDR1, a CDR2, and a CDR3 as contained in the amino acid sequence set forth in SEQ ID NO:236; a CDR1, a CDR2, and a CDR3 as contained in the amino acid sequence set forth in SEQ ID NO:237; a CDR1, a CDR2, and a CDR3 as contained in the amino acid sequence set forth in SEQ ID NO:238; a CDR1, a CDR2, and a CDR3 as contained in the amino acid sequence set forth in SEQ ID NO:239; a CDR1, a CDR2, and a CDR3 as contained in the amino acid sequence set forth in SEQ ID NO:280; a CDR1, a CDR2, and a CDR3 as contained in the amino acid sequence set forth in SEQ ID NO:342; a CDR1, a CDR2, and a CDR3 as contained in the amino acid sequence set forth in SEQ ID NO:343; a CDR1, a CDR2, and a CDR3 as contained in the amino acid sequence set forth in SEQ ID NO:344; a CDR1, a CDR2, and a CDR3 as contained in the amino acid sequence set forth in SEQ ID NO:345; a CDR1, a CDR2, and a CDR3 as contained in the amino acid sequence set forth in SEQ ID NO:346; a CDR1, a CDR2, and a CDR3 as contained in the amino acid sequence set forth in SEQ ID NO:347; a CDR1, a CDR2, and a CDR3 as contained in the amino acid sequence set forth in SEQ ID NO:348; a CDR1, a CDR2, and a CDR3 as contained in the amino acid sequence set forth in SEQ ID NO:349; a CDR1, a CDR2, and a CDR3 as contained in the amino acid sequence set forth in SEQ ID NO:350; a CDR1, a CDR2, and a CDR3 as contained in the amino acid sequence set forth in SEQ ID NO:351; a CDR1, a CDR2, and a CDR3 as contained in the amino acid sequence set forth in SEQ ID NO:352; a CDR1, a CDR2, and a CDR3 as contained in the amino acid sequence set forth in SEQ ID NO:353; a CDR1, a CDR2, and a CDR3 as contained in the amino acid sequence set forth in SEQ ID NO:354; a CDR1, a CDR2, and a CDR3 as contained in the amino acid sequence set forth in SEQ ID NO:355; a CDR1, a CDR2, and a CDR3 as contained in the amino acid sequence set forth in SEQ ID NO:356; a CDR1, a CDR2, and a CDR3 as contained in the amino acid sequence set forth in SEQ ID NO:357; a CDR1, a CDR2, and a CDR3 as contained in the amino acid sequence set forth in SEQ ID NO:358; a CDR1, a CDR2, and a CDR3 as contained in the amino acid sequence set forth in SEQ ID NO:359; a CDR1, a CDR2, and a CDR3 as contained in the amino acid sequence set forth in SEQ ID NO:360; a CDR1, a CDR2, and a CDR3 as contained in the amino acid sequence set forth in SEQ ID NO:361; a CDR1, a CDR2, and a CDR3 as contained in the amino acid sequence set forth in SEQ ID NO:362; a CDR1, a CDR2, and a CDR3 as contained in the amino acid sequence set forth in SEQ ID NO:363; a CDR1, a CDR2, and a CDR3 as contained in the amino acid sequence set forth in SEQ ID NO:364; a CDR1, a CDR2, and a CDR3 as contained in the amino acid sequence set forth in SEQ ID NO:365; a CDR1, a CDR2, and a CDR3 as contained in the amino acid sequence set forth in SEQ ID NO:366; a CDR1, a CDR2, and a CDR3 as contained in the amino acid sequence set forth in SEQ ID NO:367; a CDR1, a CDR2, and a CDR3 as contained in the amino acid sequence set forth in SEQ ID NO:368; a CDR1, a CDR2, and a CDR3 as contained in the amino acid sequence set forth in SEQ ID NO:369; a CDR1, a CDR2, and a CDR3 as contained in the amino acid sequence set forth in SEQ ID NO:370; a CDR1, a CDR2, and a CDR3 as contained in the amino acid sequence set forth in SEQ ID NO:371; a CDR1, a CDR2, and a CDR3 as contained in the amino acid sequence set forth in SEQ ID NO:372; a CDR1, a CDR2, and a CDR3 as contained in the amino acid sequence set forth in SEQ ID NO:373; a CDR1, a CDR2, and a CDR3 as contained in the amino acid sequence set forth in SEQ ID NO:374; a CDR1, a CDR2, and a CDR3 as contained in the amino acid sequence set forth in SEQ ID NO:375; a CDR1, a CDR2, and a CDR3 as contained in the amino acid sequence set forth in SEQ ID NO:376; a CDR1, a CDR2, and a CDR3 as contained in the amino acid sequence set forth in SEQ ID NO:377; a CDR1, a CDR2, and a CDR3 as contained in the amino acid sequence set forth in SEQ ID NO:378; a CDR1, a CDR2, and a CDR3 as contained in the amino acid sequence set forth in SEQ ID NO:379; a CDR1, a CDR2, and a CDR3 as contained in the amino acid sequence set forth in SEQ ID NO:380; a CDR1, a CDR2, and a CDR3 as contained in the amino acid sequence set forth in SEQ ID NO:381; a CDR1, a CDR2, and a CDR3 as contained in the amino acid sequence set forth in SEQ ID NO:382; a CDR1, a CDR2, and a CDR3 as contained in the amino acid sequence set forth in SEQ ID NO:383; a CDR1, a CDR2, and a CDR3 as contained in the amino acid sequence set forth in SEQ ID NO:384; or a CDR1, a CDR2, and a CDR3 as contained in the amino acid sequence set forth in SEQ ID NO:385.

In some embodiments, the at least one CD28 sdAb domain comprises a CDR1, a CDR2, and a CDR3 as contained in the amino acid sequence set forth in SEQ ID NO:186. In some embodiments, the at least one CD28 sdAb domain comprises a CDR1, a CDR2, and a CDR3 as contained in the amino acid sequence set forth in SEQ ID NO:187. In some embodiments, the at least one CD28 sdAb domain comprises a CDR1, a CDR2, and a CDR3 as contained in the amino acid sequence set forth in SEQ ID NO:188. In some embodiments, the at least one CD28 sdAb domain comprises a CDR1, a CDR2, and a CDR3 as contained in the amino acid sequence set forth in SEQ ID NO:213. In some embodiments, the at least one CD28 sdAb domain comprises a CDR1, a CDR2, and a CDR3 as contained in the amino acid sequence set forth in SEQ ID NO:214. In some embodiments, the at least one CD28 sdAb domain comprises a CDR1, a CDR2, and a CDR3 as contained in the amino acid sequence set forth in SEQ ID NO:215. In some embodiments, the at least one CD28 sdAb domain comprises a CDR1, a CDR2, and a CDR3 as contained in the amino acid sequence set forth in SEQ ID NO:216. In some embodiments, the at least one CD28 sdAb domain comprises a CDR1, a CDR2, and a CDR3 as contained in the amino acid sequence set forth in SEQ ID NO:217. In some embodiments, the at least one CD28 sdAb domain comprises a CDR1, a CDR2, and a CDR3 as contained in the amino acid sequence set forth in SEQ ID NO:218. In some embodiments, the at least one CD28 sdAb domain comprises a CDR1, a CDR2, and a CDR3 as contained in the amino acid sequence set forth in SEQ ID NO:219. In some embodiments, the at least one CD28 sdAb domain comprises a CDR1, a CDR2, and a CDR3 as contained in the amino acid sequence set forth in SEQ ID NO:220. In some embodiments, the at least one CD28 sdAb domain comprises a CDR1, a CDR2, and a CDR3 as contained in the amino acid sequence set forth in SEQ ID NO:221. In some embodiments, the at least one CD28 sdAb domain comprises a CDR1, a CDR2, and a CDR3 as contained in the amino acid sequence set forth in SEQ ID NO:222. In some embodiments, the at least one CD28 sdAb domain comprises a CDR1, a CDR2, and a CDR3 as contained in the amino acid sequence set forth in SEQ ID NO:223. In some embodiments, the at least one CD28 sdAb domain comprises a CDR1, a CDR2, and a CDR3 as contained in the amino acid sequence set forth in SEQ ID NO:224. In some embodiments, the at least one CD28 sdAb domain comprises a CDR1, a CDR2, and a CDR3 as contained in the amino acid sequence set forth in SEQ ID NO:225. In some embodiments, the at least one CD28 sdAb domain comprises a CDR1, a CDR2, and a CDR3 as contained in the amino acid sequence set forth in SEQ ID NO:226. In some embodiments, the at least one CD28 sdAb domain comprises a CDR1, a CDR2, and a CDR3 as contained in the amino acid sequence set forth in SEQ ID NO:227. In some embodiments, the at least one CD28 sdAb domain comprises a CDR1, a CDR2, and a CDR3 as contained in the amino acid sequence set forth in SEQ ID NO:228. In some embodiments, the at least one CD28 sdAb domain comprises a CDR1, a CDR2, and a CDR3 as contained in the amino acid sequence set forth in SEQ ID NO:229. In some embodiments, the at least one CD28 sdAb domain comprises a CDR1, a CDR2, and a CDR3 as contained in the amino acid sequence set forth in SEQ ID NO:230. In some embodiments, the at least one CD28 sdAb domain comprises a CDR1, a CDR2, and a CDR3 as contained in the amino acid sequence set forth in SEQ ID NO:231. In some embodiments, the at least one CD28 sdAb domain comprises a CDR1, a CDR2, and a CDR3 as contained in the amino acid sequence set forth in SEQ ID NO:232. In some embodiments, the at least one CD28 sdAb domain comprises a CDR1, a CDR2, and a CDR3 as contained in the amino acid sequence set forth in SEQ ID NO:233. In some embodiments, the at least one CD28 sdAb domain comprises a CDR1, a CDR2, and a CDR3 as contained in the amino acid sequence set forth in SEQ ID NO:234. In some embodiments, the at least one CD28 sdAb domain comprises a CDR1, a CDR2, and a CDR3 as contained in the amino acid sequence set forth in SEQ ID NO:235. In some embodiments, the at least one CD28 sdAb domain comprises a CDR1, a CDR2, and a CDR3 as contained in the amino acid sequence set forth in SEQ ID NO:236. In some embodiments, the at least one CD28 sdAb domain comprises a CDR1, a CDR2, and a CDR3 as contained in the amino acid sequence set forth in SEQ ID NO:237. In some embodiments, the at least one CD28 sdAb domain comprises a CDR1, a CDR2, and a CDR3 as contained in the amino acid sequence set forth in SEQ ID NO:238. In some embodiments, the at least one CD28 sdAb domain comprises a CDR1, a CDR2, and a CDR3 as contained in the amino acid sequence set forth in SEQ ID NO:239. In some embodiments, the at least one CD28 sdAb domain comprises a CDR1, a CDR2, and a CDR3 as contained in the amino acid sequence set forth in SEQ ID NO:280. In some embodiments, the at least one CD28 sdAb domain comprises a CDR1, a CDR2, and a CDR3 as contained in the amino acid sequence set forth in SEQ ID NO:342. In some embodiments, the at least one CD28 sdAb domain comprises a CDR1, a CDR2, and a CDR3 as contained in the amino acid sequence set forth in SEQ ID NO:343. In some embodiments, the at least one CD28 sdAb domain comprises a CDR1, a CDR2, and a CDR3 as contained in the amino acid sequence set forth in SEQ ID NO:344. In some embodiments, the at least one CD28 sdAb domain comprises a CDR1, a CDR2, and a CDR3 as contained in the amino acid sequence set forth in SEQ ID NO:345. In some embodiments, the at least one CD28 sdAb domain comprises a CDR1, a CDR2, and a CDR3 as contained in the amino acid sequence set forth in SEQ ID NO:346. In some embodiments, the at least one CD28 sdAb domain comprises a CDR1, a CDR2, and a CDR3 as contained in the amino acid sequence set forth in SEQ ID NO:347. In some embodiments, the at least one CD28 sdAb domain comprises a CDR1, a CDR2, and a CDR3 as contained in the amino acid sequence set forth in SEQ ID NO:348. In some embodiments, the at least one CD28 sdAb domain comprises a CDR1, a CDR2, and a CDR3 as contained in the amino acid sequence set forth in SEQ ID NO:349. In some embodiments, the at least one CD28 sdAb domain comprises a CDR1, a CDR2, and a CDR3 as contained in the amino acid sequence set forth in SEQ ID NO:350. In some embodiments, the at least one CD28 sdAb domain comprises a CDR1, a CDR2, and a CDR3 as contained in the amino acid sequence set forth in SEQ ID NO:351. In some embodiments, the at least one CD28 sdAb domain comprises a CDR1, a CDR2, and a CDR3 as contained in the amino acid sequence set forth in SEQ ID NO:352. In some embodiments, the at least one CD28 sdAb domain comprises a CDR1, a CDR2, and a CDR3 as contained in the amino acid sequence set forth in SEQ ID NO:353. In some embodiments, the at least one CD28 sdAb domain comprises a CDR1, a CDR2, and a CDR3 as contained in the amino acid sequence set forth in SEQ ID NO:354. In some embodiments, the at least one CD28 sdAb domain comprises a CDR1, a CDR2, and a CDR3 as contained in the amino acid sequence set forth in SEQ ID NO:355. In some embodiments, the at least one CD28 sdAb domain comprises a CDR1, a CDR2, and a CDR3 as contained in the amino acid sequence set forth in SEQ ID NO:356. In some embodiments, the at least one CD28 sdAb domain comprises a CDR1, a CDR2, and a CDR3 as contained in the amino acid sequence set forth in SEQ ID NO:357. In some embodiments, the at least one CD28 sdAb domain comprises a CDR1, a CDR2, and a CDR3 as contained in the amino acid sequence set forth in SEQ ID NO:358. In some embodiments, the at least one CD28 sdAb domain comprises a CDR1, a CDR2, and a CDR3 as contained in the amino acid sequence set forth in SEQ ID NO:359. In some embodiments, the at least one CD28 sdAb domain comprises a CDR1, a CDR2, and a CDR3 as contained in the amino acid sequence set forth in SEQ ID NO:360. In some embodiments, the at least one CD28 sdAb domain comprises a CDR1, a CDR2, and a CDR3 as contained in the amino acid sequence set forth in SEQ ID NO:361. In some embodiments, the at least one CD28 sdAb domain comprises a CDR1, a CDR2, and a CDR3 as contained in the amino acid sequence set forth in SEQ ID NO:362. In some embodiments, the at least one CD28 sdAb domain comprises a CDR1, a CDR2, and a CDR3 as contained in the amino acid sequence set forth in SEQ ID NO:363. In some embodiments, the at least one CD28 sdAb domain comprises a CDR1, a CDR2, and a CDR3 as contained in the amino acid sequence set forth in SEQ ID NO:364. In some embodiments, the at least one CD28 sdAb domain comprises a CDR1, a CDR2, and a CDR3 as contained in the amino acid sequence set forth in SEQ ID NO:365. In some embodiments, the at least one CD28 sdAb domain comprises a CDR1, a CDR2, and a CDR3 as contained in the amino acid sequence set forth in SEQ ID NO:366. In some embodiments, the at least one CD28 sdAb domain comprises a CDR1, a CDR2, and a CDR3 as contained in the amino acid sequence set forth in SEQ ID NO:367. In some embodiments, the at least one CD28 sdAb domain comprises a CDR1, a CDR2, and a CDR3 as contained in the amino acid sequence set forth in SEQ ID NO:368. In some embodiments, the at least one CD28 sdAb domain comprises a CDR1, a CDR2, and a CDR3 as contained in the amino acid sequence set forth in SEQ ID NO:369. In some embodiments, the at least one CD28 sdAb domain comprises a CDR1, a CDR2, and a CDR3 as contained in the amino acid sequence set forth in SEQ ID NO:370. In some embodiments, the at least one CD28 sdAb domain comprises a CDR1, a CDR2, and a CDR3 as contained in the amino acid sequence set forth in SEQ ID NO:371. In some embodiments, the at least one CD28 sdAb domain comprises a CDR1, a CDR2, and a CDR3 as contained in the amino acid sequence set forth in SEQ ID NO:372. In some embodiments, the at least one CD28 sdAb domain comprises a CDR1, a CDR2, and a CDR3 as contained in the amino acid sequence set forth in SEQ ID NO:373. In some embodiments, the at least one CD28 sdAb domain comprises a CDR1, a CDR2, and a CDR3 as contained in the amino acid sequence set forth in SEQ ID NO:374. In some embodiments, the at least one CD28 sdAb domain comprises a CDR1, a CDR2, and a CDR3 as contained in the amino acid sequence set forth in SEQ ID NO:375. In some embodiments, the at least one CD28 sdAb domain comprises a CDR1, a CDR2, and a CDR3 as contained in the amino acid sequence set forth in SEQ ID NO:376. In some embodiments, the at least one CD28 sdAb domain comprises a CDR1, a CDR2, and a CDR3 as contained in the amino acid sequence set forth in SEQ ID NO:377. In some embodiments, the at least one CD28 sdAb domain comprises a CDR1, a CDR2, and a CDR3 as contained in the amino acid sequence set forth in SEQ ID NO:378. In some embodiments, the at least one CD28 sdAb domain comprises a CDR1, a CDR2, and a CDR3 as contained in the amino acid sequence set forth in SEQ ID NO:379. In some embodiments, the at least one CD28 sdAb domain comprises a CDR1, a CDR2, and a CDR3 as contained in the amino acid sequence set forth in SEQ ID NO:380. In some embodiments, the at least one CD28 sdAb domain comprises a CDR1, a CDR2, and a CDR3 as contained in the amino acid sequence set forth in SEQ ID NO:381. In some embodiments, the at least one CD28 sdAb domain comprises a CDR1, a CDR2, and a CDR3 as contained in the amino acid sequence set forth in SEQ ID NO:382. In some embodiments, the at least one CD28 sdAb domain comprises a CDR1, a CDR2, and a CDR3 as contained in the amino acid sequence set forth in SEQ ID NO:383. In some embodiments, the at least one CD28 sdAb domain comprises a CDR1, a CDR2, and a CDR3 as contained in the amino acid sequence set forth in SEQ ID NO:384; or a CDR1, a CDR2, and a CDR3 as contained in the amino acid sequence set forth in SEQ ID NO:385.

Also provided herein are CD28-binding polypeptides containing at least one single domain antibody (sdAb) that binds CD28 (CD28 VHH), wherein the CD28 VHH domain contains: a CDR1, a CDR2, and a CDR3 as contained in the VHH set forth in SEQ ID NO:186; a CDR1, a CDR2, and a CDR3 as contained in the VHH set forth in SEQ ID NO:187; a CDR1, a CDR2, and a CDR3 as contained in the VHH set forth in SEQ ID NO:188; a CDR1, a CDR2, and a CDR3 as contained in the VHH set forth in SEQ ID NO:213; a CDR1, a CDR2, and a CDR3 as contained in the VHH set forth in SEQ ID NO:214; a CDR1, a CDR2, and a CDR3 as contained in the VHH set forth in SEQ ID NO:215; a CDR1, a CDR2, and a CDR3 as contained in the VHH set forth in SEQ ID NO:216; a CDR1, a CDR2, and a CDR3 as contained in the VHH set forth in SEQ ID NO:217; a CDR1, a CDR2, and a CDR3 as contained in the VHH set forth in SEQ ID NO:218; a CDR1, a CDR2, and a CDR3 as contained in the VHH set forth in SEQ ID NO:219; a CDR1, a CDR2, and a CDR3 as contained in the VHH set forth in SEQ ID NO:221; a CDR1, a CDR2, and a CDR3 as contained in the VHH set forth in SEQ ID NO:222; a CDR1, a CDR2, and a CDR3 as contained in the VHH set forth in SEQ ID NO:223; a CDR1, a CDR2, and a CDR3 as contained in the VHH set forth in SEQ ID NO:224; a CDR1, a CDR2, and a CDR3 as contained in the VHH set forth in SEQ ID NO:225; a CDR1, a CDR2, and a CDR3 as contained in the VHH set forth in SEQ ID NO:226; a CDR1, a CDR2, and a CDR3 as contained in the VHH set forth in SEQ ID NO:227; a CDR1, a CDR2, and a CDR3 as contained in the VHH set forth in SEQ ID NO:228; a CDR1, a CDR2, and a CDR3 as contained in the VHH set forth in SEQ ID NO:229; a CDR1, a CDR2, and a CDR3 as contained in the VHH set forth in SEQ ID NO:230; a CDR1, a CDR2, and a CDR3 as contained in the VHH set forth in SEQ ID NO:231; a CDR1, a CDR2, and a CDR3 as contained in the VHH set forth in SEQ ID NO:232; a CDR1, a CDR2, and a CDR3 as contained in the VHH set forth in SEQ ID NO:233; a CDR1, a CDR2, and a CDR3 as contained in the VHH set forth in SEQ ID NO:234; a CDR1, a CDR2, and a CDR3 as contained in the VHH set forth in SEQ ID NO:235; a CDR1, a CDR2, and a CDR3 as contained in the VHH set forth in SEQ ID NO:236; a CDR1, a CDR2, and a CDR3 as contained in the VHH set forth in SEQ ID NO:237; a CDR1, a CDR2, and a CDR3 as contained in the VHH set forth in SEQ ID NO:238; a CDR1, a CDR2, and a CDR3 as contained in the VHH set forth in SEQ ID NO:239; or a CDR1, a CDR2, and a CDR3 as contained in the VHH set forth in SEQ ID NO:280.

Also provided herein are CD28-binding polypeptides containing at least one single domain antibody (sdAb) that binds CD28, wherein the at least one CD28 sdAb (CD28 VHH) domain comprises: a CDR1, a CDR2, and a CDR3 as contained in the amino acid sequence set forth in SEQ ID NO:186; a CDR1, a CDR2, and a CDR3 as contained in the amino acid sequence set forth in SEQ ID NO:187; a CDR1, a CDR2, and a CDR3 as contained in the amino acid sequence set forth in SEQ ID NO:188; a CDR1, a CDR2, and a CDR3 as contained in the amino acid sequence set forth in SEQ ID NO:213; a CDR1, a CDR2, and a CDR3 as contained in the amino acid sequence set forth in SEQ ID NO:214; a CDR1, a CDR2, and a CDR3 as contained in the amino acid sequence set forth in SEQ ID NO:215; a CDR1, a CDR2, and a CDR3 as contained in the amino acid sequence set forth in SEQ ID NO:216; a CDR1, a CDR2, and a CDR3 as contained in the amino acid sequence set forth in SEQ ID NO:217; a CDR1, a CDR2, and a CDR3 as contained in the amino acid sequence set forth in SEQ ID NO:218; a CDR1, a CDR2, and a CDR3 as contained in the amino acid sequence set forth in SEQ ID NO:219; a CDR1, a CDR2, and a CDR3 as contained in the amino acid sequence set forth in SEQ ID NO:221; a CDR1, a CDR2, and a CDR3 as contained in the amino acid sequence set forth in SEQ ID NO:222; a CDR1, a CDR2, and a CDR3 as contained in the amino acid sequence set forth in SEQ ID NO:223; a CDR1, a CDR2, and a CDR3 as contained in the amino acid sequence set forth in SEQ ID NO:224; a CDR1, a CDR2, and a CDR3 as contained in the amino acid sequence set forth in SEQ ID NO:225; a CDR1, a CDR2, and a CDR3 as contained in the amino acid sequence set forth in SEQ ID NO:226; a CDR1, a CDR2, and a CDR3 as contained in the amino acid sequence set forth in SEQ ID NO:227; a CDR1, a CDR2, and a CDR3 as contained in the amino acid sequence set forth in SEQ ID NO:228; a CDR1, a CDR2, and a CDR3 as contained in the amino acid sequence set forth in SEQ ID NO:229; a CDR1, a CDR2, and a CDR3 as contained in the amino acid sequence set forth in SEQ ID NO:230; a CDR1, a CDR2, and a CDR3 as contained in the amino acid sequence set forth in SEQ ID NO:231; a CDR1, a CDR2, and a CDR3 as contained in the amino acid sequence set forth in SEQ ID NO:232; a CDR1, a CDR2, and a CDR3 as contained in the amino acid sequence set forth in SEQ ID NO:233; a CDR1, a CDR2, and a CDR3 as contained in the amino acid sequence set forth in SEQ ID NO:234; a CDR1, a CDR2, and a CDR3 as contained in the amino acid sequence set forth in SEQ ID NO:235; a CDR1, a CDR2, and a CDR3 as contained in the amino acid sequence set forth in SEQ ID NO:236; a CDR1, a CDR2, and a CDR3 as contained in the amino acid sequence set forth in SEQ ID NO:237; a CDR1, a CDR2, and a CDR3 as contained in the amino acid sequence set forth in SEQ ID NO:238; a CDR1, a CDR2, and a CDR3 as contained in the amino acid sequence set forth in SEQ ID NO:239; a CDR1, a CDR2, and a CDR3 as contained in the amino acid sequence set forth in SEQ ID NO:280; a CDR1, a CDR2, and a CDR3 as contained in the amino acid sequence set forth in SEQ ID NO:342; a CDR1, a CDR2, and a CDR3 as contained in the amino acid sequence set forth in SEQ ID NO:343; a CDR1, a CDR2, and a CDR3 as contained in the amino acid sequence set forth in SEQ ID NO:344; a CDR1, a CDR2, and a CDR3 as contained in the amino acid sequence set forth in SEQ ID NO:345; a CDR1, a CDR2, and a CDR3 as contained in the amino acid sequence set forth in SEQ ID NO:346; a CDR1, a CDR2, and a CDR3 as contained in the amino acid sequence set forth in SEQ ID NO:347; a CDR1, a CDR2, and a CDR3 as contained in the amino acid sequence set forth in SEQ ID NO:348; a CDR1, a CDR2, and a CDR3 as contained in the amino acid sequence set forth in SEQ ID NO:349; a CDR1, a CDR2, and a CDR3 as contained in the amino acid sequence set forth in SEQ ID NO:350; a CDR1, a CDR2, and a CDR3 as contained in the amino acid sequence set forth in SEQ ID NO:351; a CDR1, a CDR2, and a CDR3 as contained in the amino acid sequence set forth in SEQ ID NO:352; a CDR1, a CDR2, and a CDR3 as contained in the amino acid sequence set forth in SEQ ID NO:353; a CDR1, a CDR2, and a CDR3 as contained in the amino acid sequence set forth in SEQ ID NO:354; a CDR1, a CDR2, and a CDR3 as contained in the amino acid sequence set forth in SEQ ID NO:355; a CDR1, a CDR2, and a CDR3 as contained in the amino acid sequence set forth in SEQ ID NO:356; a CDR1, a CDR2, and a CDR3 as contained in the amino acid sequence set forth in SEQ ID NO:357; a CDR1, a CDR2, and a CDR3 as contained in the amino acid sequence set forth in SEQ ID NO:358; a CDR1, a CDR2, and a CDR3 as contained in the amino acid sequence set forth in SEQ ID NO:359; a CDR1, a CDR2, and a CDR3 as contained in the amino acid sequence set forth in SEQ ID NO:360; a CDR1, a CDR2, and a CDR3 as contained in the amino acid sequence set forth in SEQ ID NO:361; a CDR1, a CDR2, and a CDR3 as contained in the amino acid sequence set forth in SEQ ID NO:362; a CDR1, a CDR2, and a CDR3 as contained in the amino acid sequence set forth in SEQ ID NO:363; a CDR1, a CDR2, and a CDR3 as contained in the amino acid sequence set forth in SEQ ID NO:364; a CDR1, a CDR2, and a CDR3 as contained in the amino acid sequence set forth in SEQ ID NO:365; a CDR1, a CDR2, and a CDR3 as contained in the amino acid sequence set forth in SEQ ID NO:366; a CDR1, a CDR2, and a CDR3 as contained in the amino acid sequence set forth in SEQ ID NO:367; a CDR1, a CDR2, and a CDR3 as contained in the amino acid sequence set forth in SEQ ID NO:368; a CDR1, a CDR2, and a CDR3 as contained in the amino acid sequence set forth in SEQ ID NO:369; a CDR1, a CDR2, and a CDR3 as contained in the amino acid sequence set forth in SEQ ID NO:370; a CDR1, a CDR2, and a CDR3 as contained in the amino acid sequence set forth in SEQ ID NO:371; a CDR1, a CDR2, and a CDR3 as contained in the amino acid sequence set forth in SEQ ID NO:372; a CDR1, a CDR2, and a CDR3 as contained in the amino acid sequence set forth in SEQ ID NO:373; a CDR1, a CDR2, and a CDR3 as contained in the amino acid sequence set forth in SEQ ID NO:374; a CDR1, a CDR2, and a CDR3 as contained in the amino acid sequence set forth in SEQ ID NO:375; a CDR1, a CDR2, and a CDR3 as contained in the amino acid sequence set forth in SEQ ID NO:376; a CDR1, a CDR2, and a CDR3 as contained in the amino acid sequence set forth in SEQ ID NO:377; a CDR1, a CDR2, and a CDR3 as contained in the amino acid sequence set forth in SEQ ID NO:378; a CDR1, a CDR2, and a CDR3 as contained in the amino acid sequence set forth in SEQ ID NO:379; a CDR1, a CDR2, and a CDR3 as contained in the amino acid sequence set forth in SEQ ID NO:380; a CDR1, a CDR2, and a CDR3 as contained in the amino acid sequence set forth in SEQ ID NO:381; a CDR1, a CDR2, and a CDR3 as contained in the amino acid sequence set forth in SEQ ID NO:382; a CDR1, a CDR2, and a CDR3 as contained in the amino acid sequence set forth in SEQ ID NO:383; a CDR1, a CDR2, and a CDR3 as contained in the amino acid sequence set forth in SEQ ID NO:384; or a CDR1, a CDR2, and a CDR3 as contained in the amino acid sequence set forth in SEQ ID NO:385.

In some embodiments, the at least one CD28 sdAb contains the amino acid sequence set forth in any of SEQ ID NOS:186, 187, 188, 213, 214, 215, 216, 217, 218, 219, 220, 221, 222, 223, 224, 225, 226, 227, 228, 229, 230, 231, 232, 233, 234, 235, 236, 237, 238, 239, and 280, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS:186, 187, 188, 213, 214, 215, 216, 217, 218, 219, 220, 221, 222, 223, 224, 225, 226, 227, 228, 229, 230, 231, 232, 233, 234, 235, 236, 237, 238, 239, and 280.

In some embodiments, the at least one CD28 sdAb comprises the amino acid sequence set forth in any of SEQ ID NOS:186, 187, 188, 213, 214, 215, 216, 217, 218, 219, 220, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS:186, 187, 188, 213, 214, 215, 216, 217, 218, 219, 220, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385.

In some embodiments, the at least one CD28 sdAb comprises the amino acid sequence set forth in SEQ ID NO:186. In some embodiments, the at least one CD28 sdAb comprises the amino acid sequence set forth in SEQ ID NO:187. In some embodiments, the at least one CD28 sdAb comprises the amino acid sequence set forth in SEQ ID NO:188. In some embodiments, the at least one CD28 sdAb comprises the amino acid sequence set forth in SEQ ID NO:213. In some embodiments, the at least one CD28 sdAb comprises the amino acid sequence set forth in SEQ ID NO:214. In some embodiments, the at least one CD28 sdAb comprises the amino acid sequence set forth in SEQ ID NO:215. In some embodiments, the at least one CD28 sdAb comprises the amino acid sequence set forth in SEQ ID NO:216. In some embodiments, the at least one CD28 sdAb comprises the amino acid sequence set forth in SEQ ID NO:217. In some embodiments, the at least one CD28 sdAb comprises the amino acid sequence set forth in SEQ ID NO:218. In some embodiments, the at least one CD28 sdAb comprises the amino acid sequence set forth in SEQ ID NO:219. In some embodiments, the at least one CD28 sdAb comprises the amino acid sequence set forth in SEQ ID NO:220. In some embodiments, the at least one CD28 sdAb comprises the amino acid sequence set forth in SEQ ID NO:221. In some embodiments, the at least one CD28 sdAb comprises the amino acid sequence set forth in SEQ ID NO:222. In some embodiments, the at least one CD28 sdAb comprises the amino acid sequence set forth in SEQ ID NO:223. In some embodiments, the at least one CD28 sdAb comprises the amino acid sequence set forth in SEQ ID NO:224. In some embodiments, the at least one CD28 sdAb comprises the amino acid sequence set forth in SEQ ID NO:225. In some embodiments, the at least one CD28 sdAb comprises the amino acid sequence set forth in SEQ ID NO:226. In some embodiments, the at least one CD28 sdAb comprises the amino acid sequence set forth in SEQ ID NO:227. In some embodiments, the at least one CD28 sdAb comprises the amino acid sequence set forth in SEQ ID NO:228. In some embodiments, the at least one CD28 sdAb comprises the amino acid sequence set forth in SEQ ID NO:229. In some embodiments, the at least one CD28 sdAb comprises the amino acid sequence set forth in SEQ ID NO:230. In some embodiments, the at least one CD28 sdAb comprises the amino acid sequence set forth in SEQ ID NO:231. In some embodiments, the at least one CD28 sdAb comprises the amino acid sequence set forth in SEQ ID NO:232. In some embodiments, the at least one CD28 sdAb comprises the amino acid sequence set forth in SEQ ID NO:233. In some embodiments, the at least one CD28 sdAb comprises the amino acid sequence set forth in SEQ ID NO:234. In some embodiments, the at least one CD28 sdAb comprises the amino acid sequence set forth in SEQ ID NO:235. In some embodiments, the at least one CD28 sdAb comprises the amino acid sequence set forth in SEQ ID NO:236. In some embodiments, the at least one CD28 sdAb comprises the amino acid sequence set forth in SEQ ID NO:237. In some embodiments, the at least one CD28 sdAb comprises the amino acid sequence set forth in SEQ ID NO:238. In some embodiments, the at least one CD28 sdAb comprises the amino acid sequence set forth in SEQ ID NO:239. In some embodiments, the at least one CD28 sdAb comprises the amino acid sequence set forth in SEQ ID NO:280. In some embodiments, the at least one CD28 sdAb comprises the amino acid sequence set forth in SEQ ID NO:342. In some embodiments, the at least one CD28 sdAb comprises the amino acid sequence set forth in SEQ ID NO:343. In some embodiments, the at least one CD28 sdAb comprises the amino acid sequence set forth in SEQ ID NO:344. In some embodiments, the at least one CD28 sdAb comprises the amino acid sequence set forth in SEQ ID NO:345. In some embodiments, the at least one CD28 sdAb comprises the amino acid sequence set forth in SEQ ID NO:346. In some embodiments, the at least one CD28 sdAb comprises the amino acid sequence set forth in SEQ ID NO:347. In some embodiments, the at least one CD28 sdAb comprises the amino acid sequence set forth in SEQ ID NO:348. In some embodiments, the at least one CD28 sdAb comprises the amino acid sequence set forth in SEQ ID NO:349. In some embodiments, the at least one CD28 sdAb comprises the amino acid sequence set forth in SEQ ID NO:350. In some embodiments, the at least one CD28 sdAb comprises the amino acid sequence set forth in SEQ ID NO:351. In some embodiments, the at least one CD28 sdAb comprises the amino acid sequence set forth in SEQ ID NO:352. In some embodiments, the at least one CD28 sdAb comprises the amino acid sequence set forth in SEQ ID NO:353. In some embodiments, the at least one CD28 sdAb comprises the amino acid sequence set forth in SEQ ID NO:354. In some embodiments, the at least one CD28 sdAb comprises the amino acid sequence set forth in SEQ ID NO:355. In some embodiments, the at least one CD28 sdAb comprises the amino acid sequence set forth in SEQ ID NO:356. In some embodiments, the at least one CD28 sdAb comprises the amino acid sequence set forth in SEQ ID NO:357. In some embodiments, the at least one CD28 sdAb comprises the amino acid sequence set forth in SEQ ID NO:358. In some embodiments, the at least one CD28 sdAb comprises the amino acid sequence set forth in SEQ ID NO:359. In some embodiments, the at least one CD28 sdAb comprises the amino acid sequence set forth in SEQ ID NO:360. In some embodiments, the at least one CD28 sdAb comprises the amino acid sequence set forth in SEQ ID NO:361. In some embodiments, the at least one CD28 sdAb comprises the amino acid sequence set forth in SEQ ID NO:362. In some embodiments, the at least one CD28 sdAb comprises the amino acid sequence set forth in SEQ ID NO:363. In some embodiments, the at least one CD28 sdAb comprises the amino acid sequence set forth in SEQ ID NO:364. In some embodiments, the at least one CD28 sdAb comprises the amino acid sequence set forth in SEQ ID NO:365. In some embodiments, the at least one CD28 sdAb comprises the amino acid sequence set forth in SEQ ID NO:366. In some embodiments, the at least one CD28 sdAb comprises the amino acid sequence set forth in SEQ ID NO:367. In some embodiments, the at least one CD28 sdAb comprises the amino acid sequence set forth in SEQ ID NO:368. In some embodiments, the at least one CD28 sdAb comprises the amino acid sequence set forth in SEQ ID NO:369. In some embodiments, the at least one CD28 sdAb comprises the amino acid sequence set forth in SEQ ID NO:370. In some embodiments, the at least one CD28 sdAb comprises the amino acid sequence set forth in SEQ ID NO:371. In some embodiments, the at least one CD28 sdAb comprises the amino acid sequence set forth in SEQ ID NO:372. In some embodiments, the at least one CD28 sdAb comprises the amino acid sequence set forth in SEQ ID NO:373. In some embodiments, the at least one CD28 sdAb comprises the amino acid sequence set forth in SEQ ID NO:374. In some embodiments, the at least one CD28 sdAb comprises the amino acid sequence set forth in SEQ ID NO:375. In some embodiments, the at least one CD28 sdAb comprises the amino acid sequence set forth in SEQ ID NO:376. In some embodiments, the at least one CD28 sdAb comprises the amino acid sequence set forth in SEQ ID NO:377. In some embodiments, the at least one CD28 sdAb comprises the amino acid sequence set forth in SEQ ID NO:378. In some embodiments, the at least one CD28 sdAb comprises the amino acid sequence set forth in SEQ ID NO:379. In some embodiments, the at least one CD28 sdAb comprises the amino acid sequence set forth in SEQ ID NO:380. In some embodiments, the at least one CD28 sdAb comprises the amino acid sequence set forth in SEQ ID NO:381. In some embodiments, the at least one CD28 sdAb comprises the amino acid sequence set forth in SEQ ID NO:382. In some embodiments, the at least one CD28 sdAb comprises the amino acid sequence set forth in SEQ ID NO:383. In some embodiments, the at least one CD28 sdAb comprises the amino acid sequence set forth in SEQ ID NO:384. In some embodiments, the at least one CD28 sdAb comprises the amino acid sequence set forth in SEQ ID NO: 385.

In some embodiments, the at least one CD28 sdAb contains the amino acid sequence set forth in any of SEQ ID NOS:186, 187, 188, 213, 214, 215, 216, 217, 218, 219, 221, 222, 223, 224, 225, 226, 227, 228, 229, 230, 231, 232, 233, 234, 235, 236, 237, 238, 239, and 280, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS:186, 187, 188, 213, 214, 215, 216, 217, 218, 219, 221, 222, 223, 224, 225, 226, 227, 228, 229, 230, 231, 232, 233, 234, 235, 236, 237, 238, 239, and 280.

In some embodiments, the at least one CD28 sdAb contains the amino acid sequence set forth in any of SEQ ID NOS:186, 187, 188, 213, 214, 215, 216, 217, 218, 219, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS:186, 187, 188, 213, 214, 215, 216, 217, 218, 219, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385.

In some embodiments, the at least one CD28 sdAb contains the sequence set forth in (i) SEQ ID NO: 186, (ii) a humanized variant of SEQ ID NO:186, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 186. In some embodiments, the at least one CD28 sdAb contains the sequence set forth in SEQ ID NO: 186. In some embodiments, the at least one CD28 sdAb contains a humanized variant of SEQ ID NO:186. In some embodiments, the at least one CD28 sdAb contains a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 186. In some embodiments, the at least one CD28 sdAb contains a CDR1 having an amino acid sequence set forth in SEQ ID NO:189; a CDR2 having an amino acid sequence set forth in SEQ ID NO:190; and a CDR3 having an amino acid sequence set forth in SEQ ID NO:191.

In some embodiments, the at least one CD28 sdAb contains the sequence set forth in (i) SEQ ID NO: 187, (ii) a humanized variant of SEQ ID NO:187, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 187. In some embodiments, the at least one CD28 sdAb contains the sequence set forth in SEQ ID NO: 187. In some embodiments, the at least one CD28 sdAb contains a humanized variant of SEQ ID NO:187. In some embodiments, the at least one CD28 sdAb contains a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 187. In some embodiments, the at least one CD28 sdAb contains a CDR1 having an amino acid sequence set forth in SEQ ID NO:192; a CDR2 having an amino acid sequence set forth in SEQ ID NO:193; and a CDR3 having an amino acid sequence set forth in SEQ ID NO:194.

In some embodiments, the at least one CD28 sdAb contains the sequence set forth in (i) SEQ ID NO: 188, (ii) a humanized variant of SEQ ID NO:188, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 188. In some embodiments, the at least one CD28 sdAb contains the sequence set forth in SEQ ID NO: 188. In some embodiments, the at least one CD28 sdAb contains a humanized variant of SEQ ID NO:188. In some embodiments, the at least one CD28 sdAb contains a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 188.

In some embodiments, the at least one CD28 sdAb contains a CDR1 having an amino acid sequence set forth in any of SEQ ID NO:195, 198, 199, 200, and 201; a CDR2 having an amino acid sequence set forth in any of SEQ ID NO:196, 202, 203, 204, 205, 206, 207, 208, 209, 210, 211, and 212; and a CDR3 having an amino acid sequence set forth in SEQ ID NO:197. In some embodiments, the at least one CD28 sdAb contains a CDR1 containing the amino acid sequence set forth in any of SEQ ID NOS:195, 198, 199, 200, and 201; a CDR2 containing the amino acid sequence set forth in any of SEQ ID NOS:196, 202, 203, 204, 205, 206, 207, 208, 209, 210, 211, 212, 386, 387, 388, 389, 390, 391, 392, 393, 394, and 395; and a CDR3 containing the amino acid sequence set forth in any of SEQ ID NOS:197, 396, 397, and 398.

In some embodiments, the at least one CD28 sdAb contains a CDR1, CDR2 and CDR3 set forth in SEQ ID NOS: 195, 196, and 197, respectively; SEQ ID NOS: 198, 196, and 197, respectively; SEQ ID NOS: 199, 196, and 197, respectively; SEQ ID NOS: 200, 196, and 197, respectively; SEQ ID NOS: 201, 196, and 197, respectively; SEQ ID NOS: 195, 202, and 197, respectively; SEQ ID NOS: 195, 203, and 197, respectively; SEQ ID NOS: 195, 204, and 197, respectively; SEQ ID NOS: 195, 205, and 197, respectively; SEQ ID NOS: 195, 206, and 197, respectively; SEQ ID NOS: 195, 207, and 197, respectively; SEQ ID NOS: 195, 208, and 197, respectively; SEQ ID NOS: 195, 209, and 197, respectively; SEQ ID NOS: 195, 210, and 197, respectively; SEQ ID NOS: 195, 211, and 197, respectively; or SEQ ID NOS: 195, 212, and 197, respectively. In some embodiments, the at least one CD28 sdAb contains a CDR1, CDR2 and CDR3 set forth in: SEQ ID NOS: 195, 196, and 197, respectively; SEQ ID NOS: 198, 196, and 197, respectively; SEQ ID NOS: 199, 196, and 197, respectively; SEQ ID NOS: 200, 196, and 197, respectively; SEQ ID NOS: 201, 196, and 197, respectively; SEQ ID NOS: 195, 202, and 197, respectively; SEQ ID NOS: 195, 203, and 197, respectively; SEQ ID NOS: 195, 204, and 197, respectively; SEQ ID NOS: 195, 205, and 197, respectively; SEQ ID NOS: 195, 206, and 197, respectively; SEQ ID NOS: 195, 207, and 197, respectively; SEQ ID NOS: 195, 208, and 197, respectively; SEQ ID NOS: 195, 209, and 197, respectively; SEQ ID NOS: 195, 210, and 197, respectively; SEQ ID NOS: 195, 211, and 197, respectively; SEQ ID NOS: 195, 212, and 197, respectively; SEQ ID NOS: 201, 202, and 197, respectively; SEQ ID NOS: 201, 202, and 396, respectively; SEQ ID NOS: 201, 386, and 197, respectively; SEQ ID NOS: 201, 387, and 197, respectively; SEQ ID NOS: 201, 202, and 397, respectively; SEQ ID NOS: 201, 202, and 398, respectively; SEQ ID NOS: 201, 206, and 197, respectively; SEQ ID NOS: 201, 206, and 398, respectively; SEQ ID NOS: 201, 388, and 197, respectively; SEQ ID NOS: 201, 389, and 197, respectively; SEQ ID NOS: 201, 206, and 397, respectively; SEQ ID NOS: 201, 206, and 398, respectively; SEQ ID NOS: 201, 203, and 197, respectively; SEQ ID NOS: 201, 203, and 396, respectively; SEQ ID NOS: 201, 390, and 197, respectively; SEQ ID NOS: 201, 391, and 197, respectively; SEQ ID NOS: 201, 203, and 397, respectively; SEQ ID NOS: 201, 203, and 398, respectively; SEQ ID NOS: 201, 204, and 197, respectively; SEQ ID NOS: 201, 204, and 396, respectively; SEQ ID NOS: 201, 392, and 197, respectively; SEQ ID NOS: 201, 393, and 197, respectively; SEQ ID NOS: 201, 204, and 397, respectively; SEQ ID NOS: 201, 204, and 398, respectively; SEQ ID NOS: 201, 196, and 396, respectively; SEQ ID NOS: 201, 394, and 197, respectively; SEQ ID NOS: 201, 395, and 197, respectively; SEQ ID NOS: 201, 196, and 397, respectively; SEQ ID NOS: 201, 196, and 398, respectively; SEQ ID NOS: 195, 206, and 396, respectively; SEQ ID NOS: 195, 388, and 197, respectively; SEQ ID NOS: 195, 389, and 197, respectively; SEQ ID NOS: 195, 206, and 397, respectively; or SEQ ID NOS: 195, 206, and 398, respectively.

In some embodiments, the at least one CD28 sdAb contains the sequence of amino acids set forth in any one of SEQ ID NOs:213-239 and 280, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO:213-239 and 280. In some embodiments, the at least one CD28 sdAb contains the sequence of amino acids set forth in any one of SEQ ID NOS:213-239 and 280. In some embodiments, the at least one CD28 sdAb contains the amino acid sequence set forth in any of SEQ ID NOS:213-239, 280, and 342-385, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS:213-239, 280, and 342-385. In some embodiments, the at least one CD28 sdAb contains the amino acid sequence set forth in any of SEQ ID NOS:213-239, 280, and 342-385.

In some embodiments, the at least one CD28 sdAb contains a CDR1 having an amino acid sequence set forth in any of SEQ ID NO:195, 198, 199, 200, and 201; a CDR2 having an amino acid sequence set forth in any of SEQ ID NO:196, 202, 204, 205, 206, 207, 208, 209, 210, 211, and 212; and a CDR3 having an amino acid sequence set forth in SEQ ID NO:197. In some embodiments, at least one CD28 sdAb contains a CDR1 comprising the amino acid sequence set forth in any of SEQ ID NOS:195, 198, 199, 200, and 201; a CDR2 comprising the amino acid sequence set forth in any of SEQ ID NOS:196, 202, 204, 205, 206, 207, 208, 209, 210, 211, 212, 386, 387, 388, 389, 390, 391, 392, 393, 394, and 395; and a CDR3 comprising the amino acid sequence set forth in any of SEQ ID NOS:197, 396, 397, and 398.

In some embodiments, the at least one CD28 sdAb contains a CDR1, CDR2 and CDR3 set forth in SEQ ID NOS: 195, 196, and 197, respectively; SEQ ID NOS: 198, 196, and 197, respectively; SEQ ID NOS: 199, 196, and 197, respectively; SEQ ID NOS: 200, 196, and 197, respectively; SEQ ID NOS: 201, 196, and 197, respectively; SEQ ID NOS: 195, 202, and 197, respectively; SEQ ID NOS: 195, 204, and 197, respectively; SEQ ID NOS: 195, 205, and 197, respectively; SEQ ID NOS: 195, 206, and 197, respectively; SEQ ID NOS: 195, 207, and 197, respectively; SEQ ID NOS: 195, 208, and 197, respectively; SEQ ID NOS: 195, 209, and 197, respectively; SEQ ID NOS: 195, 210, and 197, respectively; SEQ ID NOS: 195, 211, and 197, respectively; or SEQ ID NOS: 195, 212, and 197, respectively. In some embodiments, the at least one CD28 sdAb contains a CDR1, CDR2 and CDR3 set forth in SEQ ID NOS: 195, 196, and 197, respectively; SEQ ID NOS: 198, 196, and 197, respectively; SEQ ID NOS: 199, 196, and 197, respectively; SEQ ID NOS: 200, 196, and 197, respectively; SEQ ID NOS: 201, 196, and 197, respectively; SEQ ID NOS: 195, 202, and 197, respectively; SEQ ID NOS: 195, 204, and 197, respectively; SEQ ID NOS: 195, 205, and 197, respectively; SEQ ID NOS: 195, 206, and 197, respectively; SEQ ID NOS: 195, 207, and 197, respectively; SEQ ID NOS: 195, 208, and 197, respectively; SEQ ID NOS: 195, 209, and 197, respectively; SEQ ID NOS: 195, 210, and 197, respectively; SEQ ID NOS: 195, 211, and 197, respectively; SEQ ID NOS: 195, 212, and 197, respectively; SEQ ID NOS: 201, 202, and 197, respectively; SEQ ID NOS: 201, 202, and 396, respectively; SEQ ID NOS: 201, 386, and 197, respectively; SEQ ID NOS: 201, 387, and 197, respectively; SEQ ID NOS: 201, 202, and 397, respectively; SEQ ID NOS: 201, 202, and 398, respectively; SEQ ID NOS: 201, 206, and 197, respectively; SEQ ID NOS: 201, 206, and 398, respectively; SEQ ID NOS: 201, 388, and 197, respectively; SEQ ID NOS: 201, 389, and 197, respectively; SEQ ID NOS: 201, 206, and 397, respectively; SEQ ID NOS: 201, 206, and 398, respectively; SEQ ID NOS: 201, 203, and 197, respectively; SEQ ID NOS: 201, 203, and 396, respectively; SEQ ID NOS: 201, 390, and 197, respectively; SEQ ID NOS: 201, 391, and 197, respectively; SEQ ID NOS: 201, 203, and 397, respectively; SEQ ID NOS: 201, 203, and 398, respectively; SEQ ID NOS: 201, 204, and 197, respectively; SEQ ID NOS: 201, 204, and 396, respectively; SEQ ID NOS: 201, 392, and 197, respectively; SEQ ID NOS: 201, 393, and 197, respectively; SEQ ID NOS: 201, 204, and 397, respectively; SEQ ID NOS: 201, 204, and 398, respectively; SEQ ID NOS: 201, 196, and 396, respectively; SEQ ID NOS: 201, 394, and 197, respectively; SEQ ID NOS: 201, 395, and 197, respectively; SEQ ID NOS: 201, 196, and 397, respectively; SEQ ID NOS: 201, 196, and 398, respectively; SEQ ID NOS: 195, 206, and 396, respectively; SEQ ID NOS: 195, 388, and 197, respectively; SEQ ID NOS: 195, 389, and 197, respectively; SEQ ID NOS: 195, 206, and 397, respectively; or SEQ ID NOS: 195, 206, and 398, respectively.

In some embodiments, the at least one CD28 sdAb contains the sequence of amino acids set forth in any one of SEQ ID NOs:213-219, 221-239, and 280, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO:213-219, 221-239, and 280. In some embodiments, the at least one CD28 sdAb contains the sequence of amino acids set forth in any one of SEQ ID NOS:213-219, 221-239, and 280.

In some embodiments, the at least one CD28 sdAb contains the amino acid sequence set forth in any of SEQ ID NOS:213-219, 221-239, 280, and 342-385, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS:213-219, 221-239, 280, and 342-385. In some embodiments, the at least one CD28 sdAb contains the amino acid sequence set forth in any of SEQ ID NOS:213-239, 280, and 342-385.

In some embodiments, the at least one sdAb is one CD28 sdAb and/or the CD28-binding polypeptide is monovalent for CD28. In some embodiments, the at least one sdAb is one CD28 sdAb. In some embodiments, the CD28-binding polypeptide is monovalent for CD28. In some embodiments, the at least one sdAb is one CD28 sdAb and the CD28-binding polypeptide is monovalent for CD28.

In some embodiments, the at least one sdAb is two, three, or four CD28 sdAbs and/or the CD28-binding polypeptide is multivalent for CD28. In some embodiments, the at least one sdAb is two CD28 sdAbs and/or the CD28-binding polypeptide is bivalent for CD28. In some embodiments, the at least one sdAb is two CD28 sdAbs. In some embodiments, the CD28-binding polypeptide is bivalent for CD28. In some embodiments, the at least one sdAb is two CD28 sdAbs and the CD28-binding polypeptide is bivalent for CD28. In some embodiments, the two CD28 sdAbs are the same CD28 sdAb. In some embodiments, both of the CD28 sdAbs contain the amino acid sequence set forth in SEQ ID NO:188. In some embodiments, each of the two CD28 sdAbs contain the amino acid sequence set forth in SEQ ID NO:188. In some embodiments, both of the CD28 sdAbs contain the amino acid sequence set forth in SEQ ID NO:220. In some embodiments, each of the two CD28 sdAbs contain the amino acid sequence set forth in SEQ ID NO:220. In some embodiments, both of the CD28 sdAbs contain the amino acid sequence set forth in SEQ ID NO:280. In some embodiments, each of the two CD28 sdAbs contain the amino acid sequence set forth in SEQ ID NO:280. In some embodiments, the two CD28 sdAbs are different CD28 sdAbs. In some embodiments, one of the two CD28 sdAbs contains the amino acid sequence set forth in SEQ ID NO:188 and the other of the two CD28 sdAbs contains the amino acid sequence set forth in SEQ ID NOS:220. In some embodiments, one of the two CD28 sdAbs contains the amino acid sequence set forth in SEQ ID NO:188 and the other of the two CD28 sdAbs contains the amino acid sequence set forth in SEQ ID NOS:280. In some embodiments, one of the two CD28 sdAbs contains the amino acid sequence set forth in SEQ ID NO:220 and the other of the two CD28 sdAbs contains the amino acid sequence set forth in SEQ ID NOS:280.

In some embodiments, the CD28-binding polypeptide includes a moiety that binds protein A. In some embodiments, the at least one CD28 sdAb contains an amino acid modification that reduces binding to protein A. In some embodiments, the amino acid modification of G65D by Kabat in framework region 3 (FR3).

In some embodiments, the CD28-binding polypeptide contains an immunoglobulin Fc region.

Also provide herein are anti-CD28 sdAb-Fc fusion proteins containing any of the CD28-binding polypeptide described herein and an immunoglobulin Fc region.

In some embodiments, the Fc region is linked by a linking peptide (LP) to at least one of the at least one CD28 sdAb. In some embodiments, the at least one CD28 sdAb is linked by a linking peptide (LP) to the Fc region at the N-terminal of the Fc region. In some embodiments, the LP is a non-cleavable linker. In some embodiments, the LP is a peptide of about 1 to 20 amino acids in length. In some embodiments, wherein the CD28-binding polypeptide contains from N-terminal to C-terminal: (CD28 sdAb)-LP-Fc. In some embodiments, the CD28-binding polypeptide contains from N-terminal to C-terminal: (CD28 sdAb)-LP-(CD28 sdAb)-LP-Fc.

In some embodiments, the C28-binding polypeptide is a dimer.

In some embodiments, the Fc region is a homodimeric Fc region. In some embodiments, the Fc region contains a sequence of amino acids selected from the group consisting of SEQ ID NOS: 8, 10, 11, 12 and 13, or a sequence of amino acids that exhibits at least 85%, 86%, 87%, 88%, 89%, 90%, 91%, 92%, 93%, 94%, 95%, 96%, 97%, 98%, or 99% sequence identity to any one of SEQ ID NOS: 8, 10, 11, 12 and 13. In some embodiments, the Fc region consists of a sequence of amino acids selected from the group consisting of SEQ ID NOS: 8, 10, 11, 12 and 13. In some embodiments, the Fc region is a human IgG1. In some embodiments, the Fc region is a human IgG1. In some embodiments, the Fc region contains the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 8. In some embodiments, the Fc region consists of the sequence of amino acids set forth in SEQ ID NO: 8.

In some embodiments, the Fc region is a heterodimeric Fc region.

In some embodiments, the Fc region exhibits effector function.

In some embodiments, the Fc region contains a polypeptide having one or more amino acid modification that reduces effector function. In some embodiments, the Fc region contains a polypeptide having one or more amino acid modification that reduces binding to an effector molecule. In some embodiments, the Fc region contains a polypeptide having one or more amino acid modification that reduces binding to an effector molecule selected from an Fc gamma receptor and C1q. In some embodiments, the Fc region contains a polypeptide having one or more amino acid modification that reduces binding to Fc gamma receptor. In some embodiments, the Fc region contains a polypeptide having one or more amino acid modification that reduces binding to C1q. In some embodiments, the one or more amino acid modification is deletion of one or more of Glu233, Leu234 or Leu235. In some embodiments, the one or more amino acid modification is deletion of one or more of Glu233, Leu234 or Leu235. In some embodiments, the one or more amino acid modification is deletion of Glu233. In some embodiments, the one or more amino acid modification is deletion of Leu234. In some embodiments, the one or more amino acid modification is deletion of Leu235. In some embodiments, the Fc region contains the sequence of amino acids set forth in SEQ ID NO: 9 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 9. In some embodiments, the Fc region consists of the sequence of amino acids set forth in SEQ ID NO: 9.

Provided herein are homodimeric Fc fusion proteins, containing two identical copies of any of the anti-CD28 sdAb-Fc fusion proteins described herein.

Also provide herein are heterodimeric Fc fusion proteins, containing any two of the anti-CD28 sdAb-Fc fusion proteins described herein.

In some embodiments, the CD28-binding polypeptide contains one or more binding domain that binds to a target antigen other than CD28. In some embodiments, the one or more binding domain is one or more single domain antibody (sdAb) that binds a tumor associated antigen (TAA).

In some embodiments, the CD28-binding polypeptide includes a moiety that binds protein A.

Also provided herein are multi-specific binding polypeptides comprising any of the provided anti-CD28 sdAb-Fc fusion proteins and one or more binding domain (BD) that binds to a target antigen other than CD28.

In some embodiments, the one or more BD is one BD. In some embodiments, the one or more BD is two, three, four, or more BDs. In some embodiments, the one or more BDs is two BDs. In some embodiments, the one or more BDs is three BDs. In some embodiments, the one or more BDs is four BDs.

In some embodiments, the one or more binding domain (BD) binds a tumor associated antigen (TAA). In some embodiments, the one or more binding domain (BD) binds a T cell activation marker. In some embodiments, the one or more binding domain (BD) binds a T cell exhaustion marker. In some embodiments, the one or more binding domain (BD) binds a tumor microenvironment (TME) marker. In some embodiments, the one or more binding domain (BD) is a single domain antibody. In some embodiments, the one or more binding domain (BD) is a single domain antibody that binds to a TAA.

In some embodiments, the multi-specific binding polypeptide is an Fc fusion protein, wherein at least one of the one or more BD and/or the at least one CD28 sdAb is linked to an immunoglobulin Fc region.

Provided herein is a multi-specific Fc fusion protein comprising any of the provided multi-specific binding polypeptide and an immunoglobulin Fc region. In some embodiments, the multi-specific binding polypeptide is an Fc fusion protein, wherein at least one of the one or more BD and/or the at least one CD28 sdAb is linked to an immunoglobulin Fc region.

In some embodiments, the Fc fusion protein contains from N-terminus to C-terminus: the one or more BD that binds a target antigen other than CD28; the at least one CD28-binding domain comprising a sdAb that binds CD28; and the Fc region. In some embodiments, at least one of the one or more BD is joined by a linking peptide (LP) to at least one of the at least one CD28 sdAb. In some embodiments, the CD28-binding polypeptide contains from N-terminus to C-terminus: (BD)-LP-(CD28 sdAb)-LP-Fc.

In some embodiments, the multi-specific binding polypeptide is a dimer.

In some embodiments, the Fc region is a homodimeric Fc region. In some embodiments, the Fc region contains an amino acid sequence selected from the group consisting of SEQ ID NOS: 8, 10, 11, 12 and 13, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 8, 10, 11, 12 and 13. In some embodiments, the Fc region is a human IgG1. In some embodiments, the Fc region is a human IgG1. In some embodiments, the Fc region contains the amino acid sequence set forth in SEQ ID NO: 8. In some embodiments, the Fc region contains a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 8.

In some embodiments, the Fc region is a heterodimeric Fc region.

In some embodiments, the Fc region exhibits effector function.

In some embodiments, the Fc region contains a polypeptide having one or more amino acid modification that reduces effector function. In some embodiments, the Fc region contains a polypeptide having one or more amino acid modification that reduces binding to an effector molecule selected from an Fc gamma receptor or C1q. In some embodiments, the Fc region contains a polypeptide having one or more amino acid modification that reduces binding to Fc gamma receptor. In some embodiments, the Fc region contains a polypeptide having one or more amino acid modification that reduces binding to C1q. In some embodiments, the one or more amino acid modification is deletion of one or more of Glu233, Leu234 or Leu235. In some embodiments, the one or more amino acid modification is deletion of one or more of Glu233, Leu234 or Leu235. In some embodiments, the one or more amino acid modification is deletion of Glu233. In some embodiments, the one or more amino acid modification is deletion of Leu234. In some embodiments, the one or more amino acid modification is deletion of Leu235. In some embodiments, the Fc region contains the sequence of amino acids set forth in SEQ ID NO: 9 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 9. In some embodiments, the Fc region consists of the sequence of amino acids set forth in SEQ ID NO: 9.

In any of the provided embodiments, the binding domain (BD) binds to an antigen selected from the group consisting of: 1-92-LFA-3, 2B4, 5T4, Alpha-4 integrin, Alpha-V integrin, alpha4beta1 integrin, alpha4beta7 integrin, alpha-SMA, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD69, CD70, CD71, CD74, CD80, CD81, CD86, CD95, CD107a, CD117, CD123, CD125, CD132, (IL-2RG), CD133, CD137, CD138, CD160, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRalpha), FSP-1, GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HLA-DR, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL13Ra2, IL15, IL17, IL18, IL21, IL23, IL23R, IL27/IL27R (wsx1), IL29, IL-31R, IL31/IL31R, IL2R, IL4, IL4R, IL6, IL6R, IL1 receptor accessory protein (IL1RAP), Insulin Receptor, Jagged Ligands, Jagged 1, Jagged 2, KISS1-R, KLRG1, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidyl-serine, P1GF, PSCA, PSMA, PSGR, RAAG12, RAGE, SLC44A4, Siglec15, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

In some embodiments, the T cell activation marker is selected from CD25, CD44, CD69, CD71, CD107a, CD137, HLA-DR, and/or KLRG1. In some embodiments, the T cell exhaustion marker is selected from 2B4, CD160, LAGS, PD-1, and/or TIGIT. In some embodiments, the tumor microenvironment marker is selected from alpha-SMA, EDB, FAP, FSP-1, PDGFRalpha, and/or PDGFRbeta.

In some embodiments, the one or more TAA BD is one TAA BD and/or the multi-specific binding polypeptide is monovalent for the TAA. In some embodiments, the one or more TAA BD is two, three, or four TAA BDs and/or the multi-specific binding polypeptide is multivalent for one or more TAA. In some embodiments, the one or more TAA BD is two TAA BDs and/or the multi-specific binding polypeptide is bivalent for one or more TAA. In some embodiments, the two TAA BDs are single domain antibodies (sdAbs), and the two sdAbs are the same TAA sdAbs. In some embodiments, the two TAA BDs are single domain antibodies (sdAbs), and the two sdAbs are different TAA sdAbs that bind the same TAA. In some embodiments, the different TAA sdAbs bind different epitopes of the same TAA. In some embodiments, the two TAA BDs are single domain antibodies (sdAbs) and the two sdAbs are different TAA sdAbs that bind different TAAs.

Also provided herein are homodimeric multi-specific Fc fusion proteins containing two identical copies of any of the provided multi-specific polypeptides.

Also provided herein are heterodimeric multi-specific Fc fusion proteins containing any two of the provided multi-specific polypeptides.

In any of the provided embodiments, the Fc fusion protein contains a linking peptide between at least one of the at least one CD28 sdAb and the Fc region. In some embodiments, the Fc fusion protein contains a linking peptide (LP) between at least one of the one or more BD and the Fc region. In some embodiments, the linker is non-cleavable. In some embodiments, the linker is a peptide of about 1 to 20 amino acids in length. In some embodiments, contains the amino acid sequence set forth in any of SEQ ID NOS: 1-7, 89, 90, 123-129, 244, and 249. In some embodiments, consists of the amino acid sequence set forth in any of SEQ ID NOS: 1-7, 89, 90, 123-129, 244, and 249.

In some embodiments, the at least one CD28 sdAb is not able to, or is not substantially able to, bind or engage CD28 unless at least one of the one or more BD is bound to its antigen. In some embodiments, the at least one CD28 sdAb not able to, or is not substantially able to, bind or engage CD28 unless each of the one or more BD is bound to its antigen.

Also provided herein are CD28-binding polypeptides containing from N-terminal to C-terminal: one or more antigen binding domain containing a single domain antibody (sdAb) that binds a tumor associated antigen (TAA); at least one CD28-binding domain containing a sdAb that binds CD28; and an Fc region.

In any of the provided embodiments, at least one of the one or more TAA sdAb is joined by a linking peptide (LP) to at least one of the at least one CD28 sdAb. In some embodiments, the CD28-binding polypeptide contains from N-terminal to C-terminal: (TAA sdAb)-LP-(CD28 sdAb)-LP-Fc.

In some embodiments, the CD28-binding polypeptide is a dimer. In some embodiments, the Fc region is a homodimeric Fc region.

Also provided herein are CD28-binding polypeptides containing, from the N-terminal to the C-terminal: one or more antigen binding domain having a single domain antibody (sdAb) that binds a tumor associated antigen (TAA); at least one CD28-binding domain having a sdAb that binds CD28; and an Fc region, wherein the CD28-binding polypeptide is a dimer containing a homodimeric Fc region.

In some embodiments, the Fc region contains a sequence of amino acids selected from the group consisting of SEQ ID NOS: 8, 10, 11, 12 and 13, or a sequence of amino acids that exhibits at least 85%, 86%, 87%, 88%, 89%, 90%, 91%, 92%, 93%, 94%, 95%, 96%, 97%, 98%, or 99% sequence identity to any one of SEQ ID NOS: 8, 10, 11, 12 and 13. In some embodiments, the Fc region consists of a sequence of amino acids selected from the group consisting of SEQ ID NOS: 8, 10, 11, 12 and 13. In some embodiments, the Fc region is a human IgG1. In some embodiments, the Fc region is a human IgG1. In some embodiments, the Fc region contains the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 8. In some embodiments, the Fc region consists of the sequence of amino acids set forth in SEQ ID NO: 8.

In some embodiments, the Fc region is a heterodimeric Fc region.

In some embodiments, the Fc region exhibits effector function.

In some embodiments, the Fc region contains a polypeptide having one or more amino acid modification that reduces effector function. In some embodiments, the Fc region contains a polypeptide having one or more amino acid modification that reduces binding to an effector molecule selected from an Fc gamma receptor or C1q. In some embodiments, the Fc region contains a polypeptide having one or more amino acid modification that reduces binding to Fc gamma receptor. In some embodiments, the Fc region contains a polypeptide having one or more amino acid modification that reduces binding to C1q. In some embodiments, the one or more amino acid modification is deletion of one or more of Glu233, Leu234 or Leu235. In some embodiments, the one or more amino acid modification is deletion of one or more of Glu233, Leu234 or Leu235. In some embodiments, the one or more amino acid modification is deletion of Glu233. In some embodiments, the one or more amino acid modification is deletion of Leu234. In some embodiments, the one or more amino acid modification is deletion of Leu235. In some embodiments, the Fc region contains the sequence of amino acids set forth in SEQ ID NO: 9 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 9. In some embodiments, the Fc region consists of the sequence of amino acids set forth in SEQ ID NO: 9.

In any of the provided embodiments, the TAA is selected from the group consisting of: 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRalpha), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL13Ra2, IL15, IL17, IL18, IL21, IL23, IL23R, IL27/IL27R (wsx1), IL29, IL-31R, IL31/IL31R, IL2R, IL4, IL4R, IL6, IL6R, IL1 receptor accessory protein (IL1RAP), Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidylserine, P1GF, PSCA, PSMA, PSGR, RAAG12, RAGE, SLC44A4, Siglec15, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

In some embodiments, the one or more TAA sdAb is one TAA sdAb. In some embodiments, the CD28-binding polypeptide is monovalent for the TAA. In some embodiments, the one or more TAA sdAb is two, three, or four TAA sdAbs. In some embodiments, the one or more TAA sdAb is two TAA sdAb. In some embodiments, the one or more TAA sdAb is three TAA sdAb. In some embodiments, the one or more TAA sdAb is four TAA sdAb. In some embodiments, the CD28-binding polypeptide is multivalent for one or more TAA. In some embodiments, the one or more TAA sdAb is two TAA sdAbs. In some embodiments, the CD28-binding polypeptide is bivalent for a TAA. In some embodiments, the CD28-binding polypeptide is bivalent for one or more TAA. In some embodiments, the two TAA sdAbs are the same TAA sdAbs. In some embodiments, the two TAA sdAbs are different TAA sdAbs that bind the same TAA. In some embodiments, the TAA sdAbs bind different epitopes of the same TAA. In some embodiments, the two TAA sdAbs are different TAA sdAbs that bind different TAAs.

In some embodiments, the CD28-binding polypeptide contains a linking peptide (LP) between at least one of the at least one CD28 sdAb and the Fc region. In some embodiments, the CD28-binding polypeptide contains a linking peptide (LP) between at least one of the one or more TAA sdAb and the Fc region. In some embodiments, the LP is a non-cleavable linker. In some embodiments, the LP is a peptide of about 1 to 20 amino acids in length. In some embodiments, the LP is or contains a sequence set forth in any of SEQ ID NOS:1-7, 89, 90, 123-129, 244, and 249.

In any of the provided embodiments, the at least one CD28 sdAb is not able to, or is not substantially able to, bind or engage CD28 unless at least one of the one or more TAA sdAb is bound to its TAA. In any of the provided embodiments, the at least one CD28 sdAb is not able to bind or engage CD28 unless at least one of the one or more TAA sdAb is bound to its TAA. In any of the provided embodiments, the at least one CD28 sdAb is not able to substantially bind or engage CD28 unless at least one of the one or more TAA sdAb is bound to its TAA. In some embodiments, the at least one CD28 sdAb is not able to, or is not substantially able to, bind or engage CD28 unless each of the one or more TAA sdAb is bound to its TAA. In some embodiments, the at least one CD28 sdAb is not able to bind or engage CD28 unless each of the one or more TAA sdAb is bound to its TAA. In some embodiments, the at least one CD28 sdAb is not substantially able to bind or engage CD28 unless each of the one or more TAA sdAb is bound to its TAA.

In any of the provided embodiments, the CD-28 binding polypeptide does not contain a CD3 binding region. In some embodiments, the anti-CD28 sdAb-Fc fusion protein does not contain a CD3 binding region. In some embodiments, the homodimeric Fc fusion protein does not contain a CD3 binding region. In some embodiments, the heterodimeric Fc fusion protein does not contain a CD3 binding region. In some embodiments, the multi-specific binding polypeptide does not contain a CD3 binding region. In some embodiments, the homodimeric multi-specific binding polypeptide does not contain a CD3 binding region. In some embodiments, the heterodimeric multi-specific binding polypeptide does not contain a CD3 binding region. In some embodiments, the fusion protein does not contain a CD3 binding region.

In some embodiments, the CD28-binding polypeptide includes a CD3 binding region.

Provided herein are CD28-binding polypeptides containing at least one CD28 sdAb and a CD3 binding region.

In some embodiments, the at least one CD28 sdAb contains a complementarity determining region 1 (CDR1) having an amino acid sequence selected from the group consisting of SEQ ID NO:189, 192, 195, 198, 199, 200, and 201; a complementarity determining region 2 (CDR2) having an amino acid sequence selected from the group consisting of SEQ ID NO:190, 193, 196, 202, 203, 204, 205, 206, 207, 208, 209, 210, 211, and 212; and a complementarity determining region 3 (CDR3) having an amino acid sequence selected from the group consisting of SEQ ID NO: 191, 194, and 197. In some embodiments, the at least one CD28 sdAb contains a complementarity determining region 1 (CDR1) comprising an amino acid sequence selected from the group consisting of SEQ ID NOS:189, 192, 195, 198, 199, 200, and 201; a complementarity determining region 2 (CDR2) comprising an amino acid sequence selected from the group consisting of SEQ ID NOS:190, 193, 196, 202, 203, 204, 205, 206, 207, 208, 209, 210, 211, 212, 386, 387, 388, 389, 390, 391, 392, 393, 394, and 395; and a complementarity determining region 3 (CDR3) comprising an amino acid sequence selected from the group consisting of SEQ ID NOS: 191, 194, 197, 396, 397, and 398.

In some embodiments, the at least one CD28 sdAb contains: a CDR1 having an amino acid sequence set forth in SEQ ID NO:189, a CDR2 having the amino acid sequence set forth in SEQ ID NO:190, and a CDR3 having the amino acid sequence set forth in SEQ ID NO:191; a CDR1 having an amino acid sequence set forth in SEQ ID NO:192, a CDR2 having the amino acid sequence set forth in SEQ ID NO:193, and a CDR3 having the amino acid sequence set forth in SEQ ID NO:194; a CDR1 having an amino acid sequence set forth in SEQ ID NO:195, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:198, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:199, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:200, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:201, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:202, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:203, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:204, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:205, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:206, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:207, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:208, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:209, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:210, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:211, and a CDR3 having the amino acid sequence set forth in SEQ ID NO:197; or a CDR1 having an amino acid sequence set forth in SEQ ID NO:195, a CDR2 having the amino acid sequence set forth in SEQ ID NO:212, and a CDR3 having the amino acid sequence set forth in SEQ ID NO:197.

In some embodiments, the at least one CD28 sdAb contains: a CDR1 containing an amino acid sequence set forth in SEQ ID NO:189, a CDR2 containing the amino acid sequence set forth in SEQ ID NO:190, and a CDR3 containing the amino acid sequence set forth in SEQ ID NO:191; a CDR1 having an amino acid sequence set forth in SEQ ID NO:192, a CDR2 containing the amino acid sequence set forth in SEQ ID NO:193, and a CDR3 containing the amino acid sequence set forth in SEQ ID NO:194; a CDR1 containing an amino acid sequence set forth in SEQ ID NO:195, a CDR2 containing the amino acid sequence set forth in SEQ ID NO:196, and a CDR3 containing the amino acid sequence set forth in SEQ ID NO:197; a CDR1 containing an amino acid sequence set forth in SEQ ID NO:198, a CDR2 containing the amino acid sequence set forth in SEQ ID NO:196, and a CDR3 containing the amino acid sequence set forth in SEQ ID NO:197; a CDR1 containing an amino acid sequence set forth in SEQ ID NO:199, a CDR2 containing the amino acid sequence set forth in SEQ ID NO:196, and a CDR3 containing the amino acid sequence set forth in SEQ ID NO:197; a CDR1 containing an amino acid sequence set forth in SEQ ID NO:200, a CDR2 containing the amino acid sequence set forth in SEQ ID NO:196, and a CDR3 containing the amino acid sequence set forth in SEQ ID NO:197; a CDR1 containing an amino acid sequence set forth in SEQ ID NO:201, a CDR2 containing the amino acid sequence set forth in SEQ ID NO:196, and a CDR3 containing the amino acid sequence set forth in SEQ ID NO:197; a CDR1 containing an amino acid sequence set forth in SEQ ID NO:195, a CDR2 containing the amino acid sequence set forth in SEQ ID NO:202, and a CDR3 containing the amino acid sequence set forth in SEQ ID NO:197; a CDR1 containing an amino acid sequence set forth in SEQ ID NO:195, a CDR2 containing the amino acid sequence set forth in SEQ ID NO:203, and a CDR3 containing the amino acid sequence set forth in SEQ ID NO:197; a CDR1 containing an amino acid sequence set forth in SEQ ID NO:195, a CDR2 containing the amino acid sequence set forth in SEQ ID NO:204, and a CDR3 containing the amino acid sequence set forth in SEQ ID NO:197; a CDR1 containing an amino acid sequence set forth in SEQ ID NO:195, a CDR2 containing the amino acid sequence set forth in SEQ ID NO:205, and a CDR3 containing the amino acid sequence set forth in SEQ ID NO:197; a CDR1 containing an amino acid sequence set forth in SEQ ID NO:195, a CDR2 containing the amino acid sequence set forth in SEQ ID NO:206, and a CDR3 containing the amino acid sequence set forth in SEQ ID NO:197; a CDR1 containing an amino acid sequence set forth in SEQ ID NO:195, a CDR2 containing the amino acid sequence set forth in SEQ ID NO:207, and a CDR3 containing the amino acid sequence set forth in SEQ ID NO:197; a CDR1 containing an amino acid sequence set forth in SEQ ID NO:195, a CDR2 containing the amino acid sequence set forth in SEQ ID NO:208, and a CDR3 containing the amino acid sequence set forth in SEQ ID NO:197; a CDR1 containing an amino acid sequence set forth in SEQ ID NO:195, a CDR2 containing the amino acid sequence set forth in SEQ ID NO:209, and a CDR3 containing the amino acid sequence set forth in SEQ ID NO:197; a CDR1 containing an amino acid sequence set forth in SEQ ID NO:195, a CDR2 containing the amino acid sequence set forth in SEQ ID NO:210, and a CDR3 containing the amino acid sequence set forth in SEQ ID NO:197; a CDR1 containing an amino acid sequence set forth in SEQ ID NO:195, a CDR2 containing the amino acid sequence set forth in SEQ ID NO:211, and a CDR3 containing the amino acid sequence set forth in SEQ ID NO:197; a CDR1 containing an amino acid sequence set forth in SEQ ID NO:195, a CDR2 containing the amino acid sequence set forth in SEQ ID NO:212, and a CDR3 containing the amino acid sequence set forth in SEQ ID NO:197; a CDR1 containing the amino acid sequence set forth in SEQ ID NO:201, a CDR2 containing the amino acid sequence set forth in SEQ ID NO:202, and a CDR3 containing the amino acid sequence set forth in SEQ ID NO:197; a CDR1 containing the amino acid sequence set forth in SEQ ID NO:201, a CDR2 containing the amino acid sequence set forth in SEQ ID NO:202, and a CDR3 containing the amino acid sequence set forth in SEQ ID NO:396; a CDR1 containing the amino acid sequence set forth in SEQ ID NO:201, a CDR2 containing the amino acid sequence set forth in SEQ ID NO:386, and a CDR3 containing the amino acid sequence set forth in SEQ ID NO:197; a CDR1 containing the amino acid sequence set forth in SEQ ID NO:201, a CDR2 containing the amino acid sequence set forth in SEQ ID NO:387, and a CDR3 containing the amino acid sequence set forth in SEQ ID NO:197; a CDR1 containing the amino acid sequence set forth in SEQ ID NO:201, a CDR2 containing the amino acid sequence set forth in SEQ ID NO:202, and a CDR3 containing the amino acid sequence set forth in SEQ ID NO:397; a CDR1 containing the amino acid sequence set forth in SEQ ID NO:201, a CDR2 containing the amino acid sequence set forth in SEQ ID NO:202, and a CDR3 containing the amino acid sequence set forth in SEQ ID NO:398; a CDR1 containing the amino acid sequence set forth in SEQ ID NO:201, a CDR2 containing the amino acid sequence set forth in SEQ ID NO:206, and a CDR3 containing the amino acid sequence set forth in SEQ ID NO:197; a CDR1 containing the amino acid sequence set forth in SEQ ID NO:201, a CDR2 containing the amino acid sequence set forth in SEQ ID NO:206, and a CDR3 containing the amino acid sequence set forth in SEQ ID NO:396; a CDR1 containing the amino acid sequence set forth in SEQ ID NO:201, a CDR2 containing the amino acid sequence set forth in SEQ ID NO:388, and a CDR3 containing the amino acid sequence set forth in SEQ ID NO:197; a CDR1 containing the amino acid sequence set forth in SEQ ID NO:201, a CDR2 containing the amino acid sequence set forth in SEQ ID NO:389, and a CDR3 containing the amino acid sequence set forth in SEQ ID NO:197; a CDR1 containing the amino acid sequence set forth in SEQ ID NO:201, a CDR2 containing the amino acid sequence set forth in SEQ ID NO:206, and a CDR3 containing the amino acid sequence set forth in SEQ ID NO:397; a CDR1 containing the amino acid sequence set forth in SEQ ID NO:201, a CDR2 containing the amino acid sequence set forth in SEQ ID NO:206, and a CDR3 containing the amino acid sequence set forth in SEQ ID NO:398; a CDR1 containing the amino acid sequence set forth in SEQ ID NO:201, a CDR2 containing the amino acid sequence set forth in SEQ ID NO:203, and a CDR3 containing the amino acid sequence set forth in SEQ ID NO:197; a CDR1 containing the amino acid sequence set forth in SEQ ID NO:201, a CDR2 containing the amino acid sequence set forth in SEQ ID NO:203, and a CDR3 containing the amino acid sequence set forth in SEQ ID NO:396; a CDR1 containing the amino acid sequence set forth in SEQ ID NO:201, a CDR2 containing the amino acid sequence set forth in SEQ ID NO:390, and a CDR3 containing the amino acid sequence set forth in SEQ ID NO:197; a CDR1 containing the amino acid sequence set forth in SEQ ID NO:201, a CDR2 containing the amino acid sequence set forth in SEQ ID NO:391, and a CDR3 containing the amino acid sequence set forth in SEQ ID NO:197; a CDR1 containing the amino acid sequence set forth in SEQ ID NO:201, a CDR2 containing the amino acid sequence set forth in SEQ ID NO:203, and a CDR3 containing the amino acid sequence set forth in SEQ ID NO:397; a CDR1 containing the amino acid sequence set forth in SEQ ID NO:201, a CDR2 containing the amino acid sequence set forth in SEQ ID NO:203, and a CDR3 containing the amino acid sequence set forth in SEQ ID NO:398; a CDR1 containing the amino acid sequence set forth in SEQ ID NO:201, a CDR2 containing the amino acid sequence set forth in SEQ ID NO:204, and a CDR3 containing the amino acid sequence set forth in SEQ ID NO:197; a CDR1 containing the amino acid sequence set forth in SEQ ID NO:201, a CDR2 containing the amino acid sequence set forth in SEQ ID NO:204, and a CDR3 containing the amino acid sequence set forth in SEQ ID NO:396; a CDR1 containing the amino acid sequence set forth in SEQ ID NO:201, a CDR2 containing the amino acid sequence set forth in SEQ ID NO:392, and a CDR3 containing the amino acid sequence set forth in SEQ ID NO:197; a CDR1 containing the amino acid sequence set forth in SEQ ID NO:201, a CDR2 containing the amino acid sequence set forth in SEQ ID NO:393, and a CDR3 containing the amino acid sequence set forth in SEQ ID NO:197; a CDR1 containing the amino acid sequence set forth in SEQ ID NO:201, a CDR2 containing the amino acid sequence set forth in SEQ ID NO:204, and a CDR3 containing the amino acid sequence set forth in SEQ ID NO:397; a CDR1 containing the amino acid sequence set forth in SEQ ID NO:201, a CDR2 containing the amino acid sequence set forth in SEQ ID NO:204, and a CDR3 containing the amino acid sequence set forth in SEQ ID NO:398; a CDR1 containing the amino acid sequence set forth in SEQ ID NO:201, a CDR2 containing the amino acid sequence set forth in SEQ ID NO:196, and a CDR3 containing the amino acid sequence set forth in SEQ ID NO:396; a CDR1 containing the amino acid sequence set forth in SEQ ID NO:201, a CDR2 containing the amino acid sequence set forth in SEQ ID NO:394, and a CDR3 containing the amino acid sequence set forth in SEQ ID NO:197; a CDR1 containing the amino acid sequence set forth in SEQ ID NO:201, a CDR2 containing the amino acid sequence set forth in SEQ ID NO:395, and a CDR3 containing the amino acid sequence set forth in SEQ ID NO:197; a CDR1 containing the amino acid sequence set forth in SEQ ID NO:201, a CDR2 containing the amino acid sequence set forth in SEQ ID NO:196, and a CDR3 containing the amino acid sequence set forth in SEQ ID NO:397; a CDR1 containing the amino acid sequence set forth in SEQ ID NO:201, a CDR2 containing the amino acid sequence set forth in SEQ ID NO:196, and a CDR3 containing the amino acid sequence set forth in SEQ ID NO:398; a CDR1 containing the amino acid sequence set forth in SEQ ID NO:195, a CDR2 containing the amino acid sequence set forth in SEQ ID NO:206, and a CDR3 containing the amino acid sequence set forth in SEQ ID NO:396; a CDR1 containing the amino acid sequence set forth in SEQ ID NO:195, a CDR2 containing the amino acid sequence set forth in SEQ ID NO:388, and a CDR3 containing the amino acid sequence set forth in SEQ ID NO:197; a CDR1 containing the amino acid sequence set forth in SEQ ID NO:195, a CDR2 containing the amino acid sequence set forth in SEQ ID NO:389, and a CDR3 containing the amino acid sequence set forth in SEQ ID NO:197 a CDR1 containing the amino acid sequence set forth in SEQ ID NO:195, a CDR2 containing the amino acid sequence set forth in SEQ ID NO:206, and a CDR3 containing the amino acid sequence set forth in SEQ ID NO:397; or a CDR1 containing the amino acid sequence set forth in SEQ ID NO:195, a CDR2 containing the amino acid sequence set forth in SEQ ID NO:206, and a CDR3 containing the amino acid sequence set forth in SEQ ID NO:398.

In some embodiments, the at least one CD28 sdAb contains a CDR1 comprising an the amino acid sequence set forth in SEQ ID NO:189, a CDR2 comprising the amino acid sequence set forth in SEQ ID NO:190, and a CDR3 comprising the amino acid sequence set forth in SEQ ID NO:191. In some embodiments, the at least one CD28 sdAb contains a CDR1 comprising an the amino acid sequence set forth in SEQ ID NO:192, a CDR2 comprising the amino acid sequence set forth in SEQ ID NO:193, and a CDR3 comprising the amino acid sequence set forth in SEQ ID NO:194. In some embodiments, the at least one CD28 sdAb contains a CDR1 comprising an the amino acid sequence set forth in SEQ ID NO:195, a CDR2 comprising the amino acid sequence set forth in SEQ ID NO:196, and a CDR3 comprising the amino acid sequence set forth in SEQ ID NO:197. In some embodiments, the at least one CD28 sdAb contains a CDR1 comprising an the amino acid sequence set forth in SEQ ID NO:198, a CDR2 comprising the amino acid sequence set forth in SEQ ID NO:196, and a CDR3 comprising the amino acid sequence set forth in SEQ ID NO:197. In some embodiments, the at least one CD28 sdAb contains a CDR1 comprising an the amino acid sequence set forth in SEQ ID NO:199, a CDR2 comprising the amino acid sequence set forth in SEQ ID NO:196, and a CDR3 comprising the amino acid sequence set forth in SEQ ID NO:197. In some embodiments, the at least one CD28 sdAb contains a CDR1 comprising an the amino acid sequence set forth in SEQ ID NO:200, a CDR2 comprising the amino acid sequence set forth in SEQ ID NO:196, and a CDR3 comprising the amino acid sequence set forth in SEQ ID NO:197. In some embodiments, the at least one CD28 sdAb contains CDR1 comprising an the amino acid sequence set forth in SEQ ID NO:201, a CDR2 comprising the amino acid sequence set forth in SEQ ID NO:196, and a CDR3 comprising the amino acid sequence set forth in SEQ ID NO:197. In some embodiments, the at least one CD28 sdAb contains a CDR1 comprising an the amino acid sequence set forth in SEQ ID NO:195, a CDR2 comprising the amino acid sequence set forth in SEQ ID NO:202, and a CDR3 comprising the amino acid sequence set forth in SEQ ID NO:197. In some embodiments, the at least one CD28 sdAb contains a CDR1 comprising an the amino acid sequence set forth in SEQ ID NO:195, a CDR2 comprising the amino acid sequence set forth in SEQ ID NO:203, and a CDR3 comprising the amino acid sequence set forth in SEQ ID NO:197. In some embodiments, the at least one CD28 sdAb contains CDR1 comprising an the amino acid sequence set forth in SEQ ID NO:195, a CDR2 comprising the amino acid sequence set forth in SEQ ID NO:204, and a CDR3 comprising the amino acid sequence set forth in SEQ ID NO:197. In some embodiments, the at least one CD28 sdAb contains CDR1 comprising an the amino acid sequence set forth in SEQ ID NO:195, a CDR2 comprising the amino acid sequence set forth in SEQ ID NO:205, and a CDR3 comprising the amino acid sequence set forth in SEQ ID NO:197. In some embodiments, the at least one CD28 sdAb contains CDR1 comprising an the amino acid sequence set forth in SEQ ID NO:195, a CDR2 comprising the amino acid sequence set forth in SEQ ID NO:206, and a CDR3 comprising the amino acid sequence set forth in SEQ ID NO:197. In some embodiments, the at least one CD28 sdAb contains a CDR1 comprising an the amino acid sequence set forth in SEQ ID NO:195, a CDR2 comprising the amino acid sequence set forth in SEQ ID NO:207, and a CDR3 comprising the amino acid sequence set forth in SEQ ID NO:197. In some embodiments, the at least one CD28 sdAb contains CDR1 comprising an the amino acid sequence set forth in SEQ ID NO:195, a CDR2 comprising the amino acid sequence set forth in SEQ ID NO:208, and a CDR3 comprising the amino acid sequence set forth in SEQ ID NO:197. In some embodiments, the at least one CD28 sdAb contains CDR1 comprising an the amino acid sequence set forth in SEQ ID NO:195, a CDR2 comprising the amino acid sequence set forth in SEQ ID NO:209, and a CDR3 comprising the amino acid sequence set forth in SEQ ID NO:197. In some embodiments, the at least one CD28 sdAb contains CDR1 comprising an the amino acid sequence set forth in SEQ ID NO:195, a CDR2 comprising the amino acid sequence set forth in SEQ ID NO:210, and a CDR3 comprising the amino acid sequence set forth in SEQ ID NO:197. In some embodiments, the at least one CD28 sdAb contains a CDR1 comprising an the amino acid sequence set forth in SEQ ID NO:195, a CDR2 comprising the amino acid sequence set forth in SEQ ID NO:211, and a CDR3 comprising the amino acid sequence set forth in SEQ ID NO:197. In some embodiments, the at least one CD28 sdAb contains a CDR1 comprising an the amino acid sequence set forth in SEQ ID NO:195, a CDR2 comprising the amino acid sequence set forth in SEQ ID NO:212, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:396. In some embodiments, the at least one CD28 sdAb contains a CDR1 comprising the amino acid sequence set forth in SEQ ID NO:201, a CDR2 comprising the amino acid sequence set forth in SEQ ID NO:386, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:387, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:397. In some embodiments, the at least one CD28 sdAb contains a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:398. In some embodiments, the at least one CD28 sdAb contains a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:396. In some embodiments, the at least one CD28 sdAb contains a CDR1 comprising the amino acid sequence set forth in SEQ ID NO:201, a CDR2 comprising the amino acid sequence set forth in SEQ ID NO:388, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:389, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:397. In some embodiments, the at least one CD28 sdAb contains a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:398. In some embodiments, the at least one CD28 sdAb contains a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:396. In some embodiments, the at least one CD28 sdAb contains a CDR1 comprising the amino acid sequence set forth in SEQ ID NO:201, a CDR2 comprising the amino acid sequence set forth in SEQ ID NO:390, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:391, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:397. In some embodiments, the at least one CD28 sdAb contains a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:398. In some embodiments, the at least one CD28 sdAb contains a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:396. In some embodiments, the at least one CD28 sdAb contains a CDR1 comprising the amino acid sequence set forth in SEQ ID NO:201, a CDR2 comprising the amino acid sequence set forth in SEQ ID NO:392, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:393, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:397. In some embodiments, the at least one CD28 sdAb contains a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:398. In some embodiments, the at least one CD28 sdAb contains a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:396. In some embodiments, the at least one CD28 sdAb contains a CDR1 comprising the amino acid sequence set forth in SEQ ID NO:201, a CDR2 comprising the amino acid sequence set forth in SEQ ID NO:394, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:395, and a CDR3 comprising the amino acid sequence set forth in SEQ ID NO:197. In some embodiments, the at least one CD28 sdAb contains a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:397. In some embodiments, the at least one CD28 sdAb contains a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:398. In some embodiments, the at least one CD28 sdAb contains a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:396. In some embodiments, the at least one CD28 sdAb contains a CDR1 comprising the amino acid sequence set forth in SEQ ID NO:195, a CDR2 comprising the amino acid sequence set forth in SEQ ID NO:388, and a CDR3 comprising the amino acid sequence set forth in SEQ ID NO:197. In some embodiments, the at least one CD28 sdAb contains a CDR1 comprising the amino acid sequence set forth in SEQ ID NO:195, a CDR2 comprising the amino acid sequence set forth in SEQ ID NO:389, and a CDR3 comprising the amino acid sequence set forth in SEQ ID NO:197. In some embodiments, the at least one CD28 sdAb contains a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:397; or a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:398.

In some embodiments, the at least one CD28 sdAb contains a complementarity determining region 1 (CDR1) having an amino acid sequence selected from the group consisting of SEQ ID NO:189, 192, 195, 198, 199, 200, and 201; a complementarity determining region 2 (CDR2) having an amino acid sequence selected from the group consisting of SEQ ID NO:190, 193, 196, 202, 204, 205, 206, 207, 208, 209, 210, 211, and 212; and a complementarity determining region 3 (CDR3) having an amino acid sequence selected from the group consisting of SEQ ID NO: 191, 194, and 197. In some embodiments, the at least one CD28 sdAb contains a complementarity determining region 1 (CDR1) comprising an amino acid sequence selected from the group consisting of SEQ ID NOS:189, 192, 195, 198, 199, 200, and 201; a complementarity determining region 2 (CDR2) comprising an amino acid sequence selected from the group consisting of SEQ ID NOS:190, 193, 196, 202, 204, 205, 206, 207, 208, 209, 210, 211, 212, 386, 387, 388, 389, 390, 391, 392, 393, 394, and 395; and a complementarity determining region 3 (CDR3) comprising an amino acid sequence selected from the group consisting of SEQ ID NOS: 191, 194, 197, 396, 397, and 398.

In some embodiments, the at least one CD28 sdAb contains: a CDR1 having an amino acid sequence set forth in SEQ ID NO:189, a CDR2 having the amino acid sequence set forth in SEQ ID NO:190, and a CDR3 having the amino acid sequence set forth in SEQ ID NO:191; a CDR1 having an amino acid sequence set forth in SEQ ID NO:192, a CDR2 having the amino acid sequence set forth in SEQ ID NO:193, and a CDR3 having the amino acid sequence set forth in SEQ ID NO:194; a CDR1 having an amino acid sequence set forth in SEQ ID NO:195, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:198, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:199, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:200, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:201, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:202, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:204, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:205, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:206, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:207, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:208, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:209, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:210, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:211, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:212, and a CDR3 having the amino acid sequence set forth in SEQ ID NO:197; a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:396; a CDR1 comprising the amino acid sequence set forth in SEQ ID NO:201, a CDR2 comprising the amino acid sequence set forth in SEQ ID NO:386, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:387, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:397; a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:398; a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:396; a CDR1 comprising the amino acid sequence set forth in SEQ ID NO:201, a CDR2 comprising the amino acid sequence set forth in SEQ ID NO:388, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:389, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:397; a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:398; a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:396; a CDR1 comprising the amino acid sequence set forth in SEQ ID NO:201, a CDR2 comprising the amino acid sequence set forth in SEQ ID NO:390, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:391, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:397; a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:398; a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:396; a CDR1 comprising the amino acid sequence set forth in SEQ ID NO:201, a CDR2 comprising the amino acid sequence set forth in SEQ ID NO:392, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:393, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:397; a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:398; a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:396; a CDR1 comprising the amino acid sequence set forth in SEQ ID NO:201, a CDR2 comprising the amino acid sequence set forth in SEQ ID NO:394, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:395, and a CDR3 comprising the amino acid sequence set forth in SEQ ID NO:197; a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:397; a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:398; a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:396; a CDR1 comprising the amino acid sequence set forth in SEQ ID NO:195, a CDR2 comprising the amino acid sequence set forth in SEQ ID NO:388, and a CDR3 comprising the amino acid sequence set forth in SEQ ID NO:197; a CDR1 comprising the amino acid sequence set forth in SEQ ID NO:195, a CDR2 comprising the amino acid sequence set forth in SEQ ID NO:389, and a CDR3 comprising the amino acid sequence set forth in SEQ ID NO:197 a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:397; or a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:398.

In some embodiments the at least one CD28 sdAb contains: a CDR1 having an amino acid sequence set forth in SEQ ID NO:189, a CDR2 having the amino acid sequence set forth in SEQ ID NO:190, and a CDR3 having the amino acid sequence set forth in SEQ ID NO:191; a CDR1 having an amino acid sequence set forth in SEQ ID NO:192, a CDR2 having the amino acid sequence set forth in SEQ ID NO:193, and a CDR3 having the amino acid sequence set forth in SEQ ID NO:194; a CDR1 having an amino acid sequence set forth in SEQ ID NO:195, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:198, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:199, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:200, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:201, a CDR2 having the amino acid sequence set forth in SEQ ID NO:196, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:202, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:204, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:205, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:206, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:207, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:208, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:209, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:210, and a CDR3 having the amino acid sequence set forth in SEQ ID NO:197; a CDR1 having an amino acid sequence set forth in SEQ ID NO:195, a CDR2 having the amino acid sequence set forth in SEQ ID NO:211, and a CDR3 having the amino acid sequence set forth in SEQ ID NO:197; or a CDR1 having an amino acid sequence set forth in SEQ ID NO:195, a CDR2 having the amino acid sequence set forth in SEQ ID NO:212, and a CDR3 having the amino acid sequence set forth in SEQ ID NO:197.

In some embodiments, the at least one CD28 sdAb (CD28 VHH) contains: a CDR1, a CDR2, and a CDR3 as contained in the VHH set forth in SEQ ID NO:186; a CDR1, a CDR2, and a CDR3 as contained in the VHH set forth in SEQ ID NO:187; a CDR1, a CDR2, and a CDR3 as contained in the VHH set forth in SEQ ID NO:188; a CDR1, a CDR2, and a CDR3 as contained in the VHH set forth in SEQ ID NO:213; a CDR1, a CDR2, and a CDR3 as contained in the VHH set forth in SEQ ID NO:214; a CDR1, a CDR2, and a CDR3 as contained in the VHH set forth in SEQ ID NO:215; a CDR1, a CDR2, and a CDR3 as contained in the VHH set forth in SEQ ID NO:216; a CDR1, a CDR2, and a CDR3 as contained in the VHH set forth in SEQ ID NO:217; a CDR1, a CDR2, and a CDR3 as contained in the VHH set forth in SEQ ID NO:218; a CDR1, a CDR2, and a CDR3 as contained in the VHH set forth in SEQ ID NO:219; a CDR1, a CDR2, and a CDR3 as contained in the VHH set forth in SEQ ID NO:220; a CDR1, a CDR2, and a CDR3 as contained in the VHH set forth in SEQ ID NO:221; a CDR1, a CDR2, and a CDR3 as contained in the VHH set forth in SEQ ID NO:222; a CDR1, a CDR2, and a CDR3 as contained in the VHH set forth in SEQ ID NO:223; a CDR1, a CDR2, and a CDR3 as contained in the VHH set forth in SEQ ID NO:224; a CDR1, a CDR2, and a CDR3 as contained in the VHH set forth in SEQ ID NO:225; a CDR1, a CDR2, and a CDR3 as contained in the VHH set forth in SEQ ID NO:226; a CDR1, a CDR2, and a CDR3 as contained in the VHH set forth in SEQ ID NO:227; a CDR1, a CDR2, and a CDR3 as contained in the VHH set forth in SEQ ID NO:228; a CDR1, a CDR2, and a CDR3 as contained in the VHH set forth in SEQ ID NO:229; a CDR1, a CDR2, and a CDR3 as contained in the VHH set forth in SEQ ID NO:230; a CDR1, a CDR2, and a CDR3 as contained in the VHH set forth in SEQ ID NO:231; a CDR1, a CDR2, and a CDR3 as contained in the VHH set forth in SEQ ID NO:232; a CDR1, a CDR2, and a CDR3 as contained in the VHH set forth in SEQ ID NO:233; a CDR1, a CDR2, and a CDR3 as contained in the VHH set forth in SEQ ID NO:234; a CDR1, a CDR2, and a CDR3 as contained in the VHH set forth in SEQ ID NO:235; a CDR1, a CDR2, and a CDR3 as contained in the VHH set forth in SEQ ID NO:236; a CDR1, a CDR2, and a CDR3 as contained in the VHH set forth in SEQ ID NO:237; a CDR1, a CDR2, and a CDR3 as contained in the VHH set forth in SEQ ID NO:238; a CDR1, a CDR2, and a CDR3 as contained in the VHH set forth in SEQ ID NO:239; or a CDR1, a CDR2, and a CDR3 as contained in the VHH set forth in SEQ ID NO:280.

In some embodiments, the at least one CD28 sdAb (CD28 VHH) contains: a CDR1, a CDR2, and a CDR3 as contained in the VHH set forth in SEQ ID NO:186; a CDR1, a CDR2, and a CDR3 as contained in the VHH set forth in SEQ ID NO:187; a CDR1, a CDR2, and a CDR3 as contained in the VHH set forth in SEQ ID NO:188; a CDR1, a CDR2, and a CDR3 as contained in the VHH set forth in SEQ ID NO:213; a CDR1, a CDR2, and a CDR3 as contained in the VHH set forth in SEQ ID NO:214; a CDR1, a CDR2, and a CDR3 as contained in the VHH set forth in SEQ ID NO:215; a CDR1, a CDR2, and a CDR3 as contained in the VHH set forth in SEQ ID NO:216; a CDR1, a CDR2, and a CDR3 as contained in the VHH set forth in SEQ ID NO:217; a CDR1, a CDR2, and a CDR3 as contained in the VHH set forth in SEQ ID NO:218; a CDR1, a CDR2, and a CDR3 as contained in the VHH set forth in SEQ ID NO:219; a CDR1, a CDR2, and a CDR3 as contained in the VHH set forth in SEQ ID NO:220; a CDR1, a CDR2, and a CDR3 as contained in the VHH set forth in SEQ ID NO:221; a CDR1, a CDR2, and a CDR3 as contained in the VHH set forth in SEQ ID NO:222; a CDR1, a CDR2, and a CDR3 as contained in the VHH set forth in SEQ ID NO:223; a CDR1, a CDR2, and a CDR3 as contained in the VHH set forth in SEQ ID NO:224; a CDR1, a CDR2, and a CDR3 as contained in the VHH set forth in SEQ ID NO:225; a CDR1, a CDR2, and a CDR3 as contained in the VHH set forth in SEQ ID NO:226; a CDR1, a CDR2, and a CDR3 as contained in the VHH set forth in SEQ ID NO:227; a CDR1, a CDR2, and a CDR3 as contained in the VHH set forth in SEQ ID NO:228; a CDR1, a CDR2, and a CDR3 as contained in the VHH set forth in SEQ ID NO:229; a CDR1, a CDR2, and a CDR3 as contained in the VHH set forth in SEQ ID NO:230; a CDR1, a CDR2, and a CDR3 as contained in the VHH set forth in SEQ ID NO:231; a CDR1, a CDR2, and a CDR3 as contained in the VHH set forth in SEQ ID NO:232; a CDR1, a CDR2, and a CDR3 as contained in the VHH set forth in SEQ ID NO:233; a CDR1, a CDR2, and a CDR3 as contained in the VHH set forth in SEQ ID NO:234; a CDR1, a CDR2, and a CDR3 as contained in the VHH set forth in SEQ ID NO:235; a CDR1, a CDR2, and a CDR3 as contained in the VHH set forth in SEQ ID NO:236; a CDR1, a CDR2, and a CDR3 as contained in the VHH set forth in SEQ ID NO:237; a CDR1, a CDR2, and a CDR3 as contained in the VHH set forth in SEQ ID NO:238; a CDR1, a CDR2, and a CDR3 as contained in the VHH set forth in SEQ ID NO:239; a CDR1, a CDR2, and a CDR3 as contained in the VHH set forth in SEQ ID NO:280; a CDR1, a CDR2, and a CDR3 as contained in the amino acid sequence set forth in SEQ ID NO:342; a CDR1, a CDR2, and a CDR3 as contained in the amino acid sequence set forth in SEQ ID NO:343; a CDR1, a CDR2, and a CDR3 as contained in the amino acid sequence set forth in SEQ ID NO:344; a CDR1, a CDR2, and a CDR3 as contained in the amino acid sequence set forth in SEQ ID NO:345; a CDR1, a CDR2, and a CDR3 as contained in the amino acid sequence set forth in SEQ ID NO:346; a CDR1, a CDR2, and a CDR3 as contained in the amino acid sequence set forth in SEQ ID NO:347; a CDR1, a CDR2, and a CDR3 as contained in the amino acid sequence set forth in SEQ ID NO:348; a CDR1, a CDR2, and a CDR3 as contained in the amino acid sequence set forth in SEQ ID NO:349; a CDR1, a CDR2, and a CDR3 as contained in the amino acid sequence set forth in SEQ ID NO:350; a CDR1, a CDR2, and a CDR3 as contained in the amino acid sequence set forth in SEQ ID NO:351; a CDR1, a CDR2, and a CDR3 as contained in the amino acid sequence set forth in SEQ ID NO:352; a CDR1, a CDR2, and a CDR3 as contained in the amino acid sequence set forth in SEQ ID NO:353; a CDR1, a CDR2, and a CDR3 as contained in the amino acid sequence set forth in SEQ ID NO:354; a CDR1, a CDR2, and a CDR3 as contained in the amino acid sequence set forth in SEQ ID NO:355; a CDR1, a CDR2, and a CDR3 as contained in the amino acid sequence set forth in SEQ ID NO:356; a CDR1, a CDR2, and a CDR3 as contained in the amino acid sequence set forth in SEQ ID NO:357; a CDR1, a CDR2, and a CDR3 as contained in the amino acid sequence set forth in SEQ ID NO:358; a CDR1, a CDR2, and a CDR3 as contained in the amino acid sequence set forth in SEQ ID NO:359; a CDR1, a CDR2, and a CDR3 as contained in the amino acid sequence set forth in SEQ ID NO:360; a CDR1, a CDR2, and a CDR3 as contained in the amino acid sequence set forth in SEQ ID NO:361; a CDR1, a CDR2, and a CDR3 as contained in the amino acid sequence set forth in SEQ ID NO:362; a CDR1, a CDR2, and a CDR3 as contained in the amino acid sequence set forth in SEQ ID NO:363; a CDR1, a CDR2, and a CDR3 as contained in the amino acid sequence set forth in SEQ ID NO:364; a CDR1, a CDR2, and a CDR3 as contained in the amino acid sequence set forth in SEQ ID NO:365; a CDR1, a CDR2, and a CDR3 as contained in the amino acid sequence set forth in SEQ ID NO:366; a CDR1, a CDR2, and a CDR3 as contained in the amino acid sequence set forth in SEQ ID NO:367; a CDR1, a CDR2, and a CDR3 as contained in the amino acid sequence set forth in SEQ ID NO:368; a CDR1, a CDR2, and a CDR3 as contained in the amino acid sequence set forth in SEQ ID NO:369; a CDR1, a CDR2, and a CDR3 as contained in the amino acid sequence set forth in SEQ ID NO:370; a CDR1, a CDR2, and a CDR3 as contained in the amino acid sequence set forth in SEQ ID NO:371; a CDR1, a CDR2, and a CDR3 as contained in the amino acid sequence set forth in SEQ ID NO:372; a CDR1, a CDR2, and a CDR3 as contained in the amino acid sequence set forth in SEQ ID NO:373; a CDR1, a CDR2, and a CDR3 as contained in the amino acid sequence set forth in SEQ ID NO:374; a CDR1, a CDR2, and a CDR3 as contained in the amino acid sequence set forth in SEQ ID NO:375; a CDR1, a CDR2, and a CDR3 as contained in the amino acid sequence set forth in SEQ ID NO:376; a CDR1, a CDR2, and a CDR3 as contained in the amino acid sequence set forth in SEQ ID NO:377; a CDR1, a CDR2, and a CDR3 as contained in the amino acid sequence set forth in SEQ ID NO:378; a CDR1, a CDR2, and a CDR3 as contained in the amino acid sequence set forth in SEQ ID NO:379; a CDR1, a CDR2, and a CDR3 as contained in the amino acid sequence set forth in SEQ ID NO:380; a CDR1, a CDR2, and a CDR3 as contained in the amino acid sequence set forth in SEQ ID NO:381; a CDR1, a CDR2, and a CDR3 as contained in the amino acid sequence set forth in SEQ ID NO:382; a CDR1, a CDR2, and a CDR3 as contained in the amino acid sequence set forth in SEQ ID NO:383; a CDR1, a CDR2, and a CDR3 as contained in the amino acid sequence set forth in SEQ ID NO:384; or a CDR1, a CDR2, and a CDR3 as contained in the amino acid sequence set forth in SEQ ID NO:385.

In some embodiments, the at least one CD28 sdAb domain comprises a CDR1, a CDR2, and a CDR3 as contained in the amino acid sequence set forth in SEQ ID NO:186. In some embodiments, the at least one CD28 sdAb domain comprises a CDR1, a CDR2, and a CDR3 as contained in the amino acid sequence set forth in SEQ ID NO:187. In some embodiments, the at least one CD28 sdAb domain comprises a CDR1, a CDR2, and a CDR3 as contained in the amino acid sequence set forth in SEQ ID NO:188. In some embodiments, the at least one CD28 sdAb domain comprises a CDR1, a CDR2, and a CDR3 as contained in the amino acid sequence set forth in SEQ ID NO:213. In some embodiments, the at least one CD28 sdAb domain comprises a CDR1, a CDR2, and a CDR3 as contained in the amino acid sequence set forth in SEQ ID NO:214. In some embodiments, the at least one CD28 sdAb domain comprises a CDR1, a CDR2, and a CDR3 as contained in the amino acid sequence set forth in SEQ ID NO:215. In some embodiments, the at least one CD28 sdAb domain comprises a CDR1, a CDR2, and a CDR3 as contained in the amino acid sequence set forth in SEQ ID NO:216. In some embodiments, the at least one CD28 sdAb domain comprises a CDR1, a CDR2, and a CDR3 as contained in the amino acid sequence set forth in SEQ ID NO:217. In some embodiments, the at least one CD28 sdAb domain comprises a CDR1, a CDR2, and a CDR3 as contained in the amino acid sequence set forth in SEQ ID NO:218. In some embodiments, the at least one CD28 sdAb domain comprises a CDR1, a CDR2, and a CDR3 as contained in the amino acid sequence set forth in SEQ ID NO:219. In some embodiments, the at least one CD28 sdAb domain comprises a CDR1, a CDR2, and a CDR3 as contained in the amino acid sequence set forth in SEQ ID NO:220. In some embodiments, the at least one CD28 sdAb domain comprises a CDR1, a CDR2, and a CDR3 as contained in the amino acid sequence set forth in SEQ ID NO:221. In some embodiments, the at least one CD28 sdAb domain comprises a CDR1, a CDR2, and a CDR3 as contained in the amino acid sequence set forth in SEQ ID NO:222. In some embodiments, the at least one CD28 sdAb domain comprises a CDR1, a CDR2, and a CDR3 as contained in the amino acid sequence set forth in SEQ ID NO:223. In some embodiments, the at least one CD28 sdAb domain comprises a CDR1, a CDR2, and a CDR3 as contained in the amino acid sequence set forth in SEQ ID NO:224. In some embodiments, the at least one CD28 sdAb domain comprises a CDR1, a CDR2, and a CDR3 as contained in the amino acid sequence set forth in SEQ ID NO:225. In some embodiments, the at least one CD28 sdAb domain comprises a CDR1, a CDR2, and a CDR3 as contained in the amino acid sequence set forth in SEQ ID NO:226. In some embodiments, the at least one CD28 sdAb domain comprises a CDR1, a CDR2, and a CDR3 as contained in the amino acid sequence set forth in SEQ ID NO:227. In some embodiments, the at least one CD28 sdAb domain comprises a CDR1, a CDR2, and a CDR3 as contained in the amino acid sequence set forth in SEQ ID NO:228. In some embodiments, the at least one CD28 sdAb domain comprises a CDR1, a CDR2, and a CDR3 as contained in the amino acid sequence set forth in SEQ ID NO:229. In some embodiments, the at least one CD28 sdAb domain comprises a CDR1, a CDR2, and a CDR3 as contained in the amino acid sequence set forth in SEQ ID NO:230. In some embodiments, the at least one CD28 sdAb domain comprises a CDR1, a CDR2, and a CDR3 as contained in the amino acid sequence set forth in SEQ ID NO:231. In some embodiments, the at least one CD28 sdAb domain comprises a CDR1, a CDR2, and a CDR3 as contained in the amino acid sequence set forth in SEQ ID NO:232. In some embodiments, the at least one CD28 sdAb domain comprises a CDR1, a CDR2, and a CDR3 as contained in the amino acid sequence set forth in SEQ ID NO:233. In some embodiments, the at least one CD28 sdAb domain comprises a CDR1, a CDR2, and a CDR3 as contained in the amino acid sequence set forth in SEQ ID NO:234. In some embodiments, the at least one CD28 sdAb domain comprises a CDR1, a CDR2, and a CDR3 as contained in the amino acid sequence set forth in SEQ ID NO:235. In some embodiments, the at least one CD28 sdAb domain comprises a CDR1, a CDR2, and a CDR3 as contained in the amino acid sequence set forth in SEQ ID NO:236. In some embodiments, the at least one CD28 sdAb domain comprises a CDR1, a CDR2, and a CDR3 as contained in the amino acid sequence set forth in SEQ ID NO:237. In some embodiments, the at least one CD28 sdAb domain comprises a CDR1, a CDR2, and a CDR3 as contained in the amino acid sequence set forth in SEQ ID NO:238. In some embodiments, the at least one CD28 sdAb domain comprises a CDR1, a CDR2, and a CDR3 as contained in the amino acid sequence set forth in SEQ ID NO:239. In some embodiments, the at least one CD28 sdAb domain comprises a CDR1, a CDR2, and a CDR3 as contained in the amino acid sequence set forth in SEQ ID NO:280. In some embodiments, the at least one CD28 sdAb domain comprises a CDR1, a CDR2, and a CDR3 as contained in the amino acid sequence set forth in SEQ ID NO:342. In some embodiments, the at least one CD28 sdAb domain comprises a CDR1, a CDR2, and a CDR3 as contained in the amino acid sequence set forth in SEQ ID NO:343. In some embodiments, the at least one CD28 sdAb domain comprises a CDR1, a CDR2, and a CDR3 as contained in the amino acid sequence set forth in SEQ ID NO:344. In some embodiments, the at least one CD28 sdAb domain comprises a CDR1, a CDR2, and a CDR3 as contained in the amino acid sequence set forth in SEQ ID NO:345. In some embodiments, the at least one CD28 sdAb domain comprises a CDR1, a CDR2, and a CDR3 as contained in the amino acid sequence set forth in SEQ ID NO:346. In some embodiments, the at least one CD28 sdAb domain comprises a CDR1, a CDR2, and a CDR3 as contained in the amino acid sequence set forth in SEQ ID NO:347. In some embodiments, the at least one CD28 sdAb domain comprises a CDR1, a CDR2, and a CDR3 as contained in the amino acid sequence set forth in SEQ ID NO:348. In some embodiments, the at least one CD28 sdAb domain comprises a CDR1, a CDR2, and a CDR3 as contained in the amino acid sequence set forth in SEQ ID NO:349. In some embodiments, the at least one CD28 sdAb domain comprises a CDR1, a CDR2, and a CDR3 as contained in the amino acid sequence set forth in SEQ ID NO:350. In some embodiments, the at least one CD28 sdAb domain comprises a CDR1, a CDR2, and a CDR3 as contained in the amino acid sequence set forth in SEQ ID NO:351. In some embodiments, the at least one CD28 sdAb domain comprises a CDR1, a CDR2, and a CDR3 as contained in the amino acid sequence set forth in SEQ ID NO:352. In some embodiments, the at least one CD28 sdAb domain comprises a CDR1, a CDR2, and a CDR3 as contained in the amino acid sequence set forth in SEQ ID NO:353. In some embodiments, the at least one CD28 sdAb domain comprises a CDR1, a CDR2, and a CDR3 as contained in the amino acid sequence set forth in SEQ ID NO:354. In some embodiments, the at least one CD28 sdAb domain comprises a CDR1, a CDR2, and a CDR3 as contained in the amino acid sequence set forth in SEQ ID NO:355. In some embodiments, the at least one CD28 sdAb domain comprises a CDR1, a CDR2, and a CDR3 as contained in the amino acid sequence set forth in SEQ ID NO:356. In some embodiments, the at least one CD28 sdAb domain comprises a CDR1, a CDR2, and a CDR3 as contained in the amino acid sequence set forth in SEQ ID NO:357. In some embodiments, the at least one CD28 sdAb domain comprises a CDR1, a CDR2, and a CDR3 as contained in the amino acid sequence set forth in SEQ ID NO:358. In some embodiments, the at least one CD28 sdAb domain comprises a CDR1, a CDR2, and a CDR3 as contained in the amino acid sequence set forth in SEQ ID NO:359. In some embodiments, the at least one CD28 sdAb domain comprises a CDR1, a CDR2, and a CDR3 as contained in the amino acid sequence set forth in SEQ ID NO:360. In some embodiments, the at least one CD28 sdAb domain comprises a CDR1, a CDR2, and a CDR3 as contained in the amino acid sequence set forth in SEQ ID NO:361. In some embodiments, the at least one CD28 sdAb domain comprises a CDR1, a CDR2, and a CDR3 as contained in the amino acid sequence set forth in SEQ ID NO:362. In some embodiments, the at least one CD28 sdAb domain comprises a CDR1, a CDR2, and a CDR3 as contained in the amino acid sequence set forth in SEQ ID NO:363. In some embodiments, the at least one CD28 sdAb domain comprises a CDR1, a CDR2, and a CDR3 as contained in the amino acid sequence set forth in SEQ ID NO:364. In some embodiments, the at least one CD28 sdAb domain comprises a CDR1, a CDR2, and a CDR3 as contained in the amino acid sequence set forth in SEQ ID NO:365. In some embodiments, the at least one CD28 sdAb domain comprises a CDR1, a CDR2, and a CDR3 as contained in the amino acid sequence set forth in SEQ ID NO:366. In some embodiments, the at least one CD28 sdAb domain comprises a CDR1, a CDR2, and a CDR3 as contained in the amino acid sequence set forth in SEQ ID NO:367. In some embodiments, the at least one CD28 sdAb domain comprises a CDR1, a CDR2, and a CDR3 as contained in the amino acid sequence set forth in SEQ ID NO:368. In some embodiments, the at least one CD28 sdAb domain comprises a CDR1, a CDR2, and a CDR3 as contained in the amino acid sequence set forth in SEQ ID NO:369. In some embodiments, the at least one CD28 sdAb domain comprises a CDR1, a CDR2, and a CDR3 as contained in the amino acid sequence set forth in SEQ ID NO:370. In some embodiments, the at least one CD28 sdAb domain comprises a CDR1, a CDR2, and a CDR3 as contained in the amino acid sequence set forth in SEQ ID NO:371. In some embodiments, the at least one CD28 sdAb domain comprises a CDR1, a CDR2, and a CDR3 as contained in the amino acid sequence set forth in SEQ ID NO:372. In some embodiments, the at least one CD28 sdAb domain comprises a CDR1, a CDR2, and a CDR3 as contained in the amino acid sequence set forth in SEQ ID NO:373. In some embodiments, the at least one CD28 sdAb domain comprises a CDR1, a CDR2, and a CDR3 as contained in the amino acid sequence set forth in SEQ ID NO:374. In some embodiments, the at least one CD28 sdAb domain comprises a CDR1, a CDR2, and a CDR3 as contained in the amino acid sequence set forth in SEQ ID NO:375. In some embodiments, the at least one CD28 sdAb domain comprises a CDR1, a CDR2, and a CDR3 as contained in the amino acid sequence set forth in SEQ ID NO:376. In some embodiments, the at least one CD28 sdAb domain comprises a CDR1, a CDR2, and a CDR3 as contained in the amino acid sequence set forth in SEQ ID NO:377. In some embodiments, the at least one CD28 sdAb domain comprises a CDR1, a CDR2, and a CDR3 as contained in the amino acid sequence set forth in SEQ ID NO:378. In some embodiments, the at least one CD28 sdAb domain comprises a CDR1, a CDR2, and a CDR3 as contained in the amino acid sequence set forth in SEQ ID NO:379. In some embodiments, the at least one CD28 sdAb domain comprises a CDR1, a CDR2, and a CDR3 as contained in the amino acid sequence set forth in SEQ ID NO:380. In some embodiments, the at least one CD28 sdAb domain comprises a CDR1, a CDR2, and a CDR3 as contained in the amino acid sequence set forth in SEQ ID NO:381. In some embodiments, the at least one CD28 sdAb domain comprises a CDR1, a CDR2, and a CDR3 as contained in the amino acid sequence set forth in SEQ ID NO:382. In some embodiments, the at least one CD28 sdAb domain comprises a CDR1, a CDR2, and a CDR3 as contained in the amino acid sequence set forth in SEQ ID NO:383. In some embodiments, the at least one CD28 sdAb domain comprises a CDR1, a CDR2, and a CDR3 as contained in the amino acid sequence set forth in SEQ ID NO:384; or a CDR1, a CDR2, and a CDR3 as contained in the amino acid sequence set forth in SEQ ID NO:385.

In some embodiments, the at least one CD28 sdAb (CD28 VHH) contains: a CDR1, a CDR2, and a CDR3 as contained in the VHH set forth in SEQ ID NO:186; a CDR1, a CDR2, and a CDR3 as contained in the VHH set forth in SEQ ID NO:187; a CDR1, a CDR2, and a CDR3 as contained in the VHH set forth in SEQ ID NO:188; a CDR1, a CDR2, and a CDR3 as contained in the VHH set forth in SEQ ID NO:213; a CDR1, a CDR2, and a CDR3 as contained in the VHH set forth in SEQ ID NO:214; a CDR1, a CDR2, and a CDR3 as contained in the VHH set forth in SEQ ID NO:215; a CDR1, a CDR2, and a CDR3 as contained in the VHH set forth in SEQ ID NO:216; a CDR1, a CDR2, and a CDR3 as contained in the VHH set forth in SEQ ID NO:217; a CDR1, a CDR2, and a CDR3 as contained in the VHH set forth in SEQ ID NO:218; a CDR1, a CDR2, and a CDR3 as contained in the VHH set forth in SEQ ID NO:219; a CDR1, a CDR2, and a CDR3 as contained in the VHH set forth in SEQ ID NO:221; a CDR1, a CDR2, and a CDR3 as contained in the VHH set forth in SEQ ID NO:222; a CDR1, a CDR2, and a CDR3 as contained in the VHH set forth in SEQ ID NO:223; a CDR1, a CDR2, and a CDR3 as contained in the VHH set forth in SEQ ID NO:224; a CDR1, a CDR2, and a CDR3 as contained in the VHH set forth in SEQ ID NO:225; a CDR1, a CDR2, and a CDR3 as contained in the VHH set forth in SEQ ID NO:226; a CDR1, a CDR2, and a CDR3 as contained in the VHH set forth in SEQ ID NO:227; a CDR1, a CDR2, and a CDR3 as contained in the VHH set forth in SEQ ID NO:228; a CDR1, a CDR2, and a CDR3 as contained in the VHH set forth in SEQ ID NO:229; a CDR1, a CDR2, and a CDR3 as contained in the VHH set forth in SEQ ID NO:230; a CDR1, a CDR2, and a CDR3 as contained in the VHH set forth in SEQ ID NO:231; a CDR1, a CDR2, and a CDR3 as contained in the VHH set forth in SEQ ID NO:232; a CDR1, a CDR2, and a CDR3 as contained in the VHH set forth in SEQ ID NO:233; a CDR1, a CDR2, and a CDR3 as contained in the VHH set forth in SEQ ID NO:234; a CDR1, a CDR2, and a CDR3 as contained in the VHH set forth in SEQ ID NO:235; a CDR1, a CDR2, and a CDR3 as contained in the VHH set forth in SEQ ID NO:236; a CDR1, a CDR2, and a CDR3 as contained in the VHH set forth in SEQ ID NO:237; a CDR1, a CDR2, and a CDR3 as contained in the VHH set forth in SEQ ID NO:238; a CDR1, a CDR2, and a CDR3 as contained in the VHH set forth in SEQ ID NO:239; or a CDR1, a CDR2, and a CDR3 as contained in the VHH set forth in SEQ ID NO:280.

In some embodiments, the at least one CD28 sdAb (CD28 VHH) contains: a CDR1, a CDR2, and a CDR3 as contained in the VHH set forth in SEQ ID NO:186; a CDR1, a CDR2, and a CDR3 as contained in the VHH set forth in SEQ ID NO:187; a CDR1, a CDR2, and a CDR3 as contained in the VHH set forth in SEQ ID NO:188; a CDR1, a CDR2, and a CDR3 as contained in the VHH set forth in SEQ ID NO:213; a CDR1, a CDR2, and a CDR3 as contained in the VHH set forth in SEQ ID NO:214; a CDR1, a CDR2, and a CDR3 as contained in the VHH set forth in SEQ ID NO:215; a CDR1, a CDR2, and a CDR3 as contained in the VHH set forth in SEQ ID NO:216; a CDR1, a CDR2, and a CDR3 as contained in the VHH set forth in SEQ ID NO:217; a CDR1, a CDR2, and a CDR3 as contained in the VHH set forth in SEQ ID NO:218; a CDR1, a CDR2, and a CDR3 as contained in the VHH set forth in SEQ ID NO:219; a CDR1, a CDR2, and a CDR3 as contained in the VHH set forth in SEQ ID NO:221; a CDR1, a CDR2, and a CDR3 as contained in the VHH set forth in SEQ ID NO:222; a CDR1, a CDR2, and a CDR3 as contained in the VHH set forth in SEQ ID NO:223; a CDR1, a CDR2, and a CDR3 as contained in the VHH set forth in SEQ ID NO:224; a CDR1, a CDR2, and a CDR3 as contained in the VHH set forth in SEQ ID NO:225; a CDR1, a CDR2, and a CDR3 as contained in the VHH set forth in SEQ ID NO:226; a CDR1, a CDR2, and a CDR3 as contained in the VHH set forth in SEQ ID NO:227; a CDR1, a CDR2, and a CDR3 as contained in the VHH set forth in SEQ ID NO:228; a CDR1, a CDR2, and a CDR3 as contained in the VHH set forth in SEQ ID NO:229; a CDR1, a CDR2, and a CDR3 as contained in the VHH set forth in SEQ ID NO:230; a CDR1, a CDR2, and a CDR3 as contained in the VHH set forth in SEQ ID NO:231; a CDR1, a CDR2, and a CDR3 as contained in the VHH set forth in SEQ ID NO:232; a CDR1, a CDR2, and a CDR3 as contained in the VHH set forth in SEQ ID NO:233; a CDR1, a CDR2, and a CDR3 as contained in the VHH set forth in SEQ ID NO:234; a CDR1, a CDR2, and a CDR3 as contained in the VHH set forth in SEQ ID NO:235; a CDR1, a CDR2, and a CDR3 as contained in the VHH set forth in SEQ ID NO:236; a CDR1, a CDR2, and a CDR3 as contained in the VHH set forth in SEQ ID NO:237; a CDR1, a CDR2, and a CDR3 as contained in the VHH set forth in SEQ ID NO:238; a CDR1, a CDR2, and a CDR3 as contained in the VHH set forth in SEQ ID NO:239; a CDR1, a CDR2, and a CDR3 as contained in the VHH set forth in SEQ ID NO:280; a CDR1, a CDR2, and a CDR3 as contained in the amino acid sequence set forth in SEQ ID NO:342; a CDR1, a CDR2, and a CDR3 as contained in the amino acid sequence set forth in SEQ ID NO:343; a CDR1, a CDR2, and a CDR3 as contained in the amino acid sequence set forth in SEQ ID NO:344; a CDR1, a CDR2, and a CDR3 as contained in the amino acid sequence set forth in SEQ ID NO:345; a CDR1, a CDR2, and a CDR3 as contained in the amino acid sequence set forth in SEQ ID NO:346; a CDR1, a CDR2, and a CDR3 as contained in the amino acid sequence set forth in SEQ ID NO:347; a CDR1, a CDR2, and a CDR3 as contained in the amino acid sequence set forth in SEQ ID NO:348; a CDR1, a CDR2, and a CDR3 as contained in the amino acid sequence set forth in SEQ ID NO:349; a CDR1, a CDR2, and a CDR3 as contained in the amino acid sequence set forth in SEQ ID NO:350; a CDR1, a CDR2, and a CDR3 as contained in the amino acid sequence set forth in SEQ ID NO:351; a CDR1, a CDR2, and a CDR3 as contained in the amino acid sequence set forth in SEQ ID NO:352; a CDR1, a CDR2, and a CDR3 as contained in the amino acid sequence set forth in SEQ ID NO:353; a CDR1, a CDR2, and a CDR3 as contained in the amino acid sequence set forth in SEQ ID NO:354; a CDR1, a CDR2, and a CDR3 as contained in the amino acid sequence set forth in SEQ ID NO:355; a CDR1, a CDR2, and a CDR3 as contained in the amino acid sequence set forth in SEQ ID NO:356; a CDR1, a CDR2, and a CDR3 as contained in the amino acid sequence set forth in SEQ ID NO:357; a CDR1, a CDR2, and a CDR3 as contained in the amino acid sequence set forth in SEQ ID NO:358; a CDR1, a CDR2, and a CDR3 as contained in the amino acid sequence set forth in SEQ ID NO:359; a CDR1, a CDR2, and a CDR3 as contained in the amino acid sequence set forth in SEQ ID NO:360; a CDR1, a CDR2, and a CDR3 as contained in the amino acid sequence set forth in SEQ ID NO:361; a CDR1, a CDR2, and a CDR3 as contained in the amino acid sequence set forth in SEQ ID NO:362; a CDR1, a CDR2, and a CDR3 as contained in the amino acid sequence set forth in SEQ ID NO:363; a CDR1, a CDR2, and a CDR3 as contained in the amino acid sequence set forth in SEQ ID NO:364; a CDR1, a CDR2, and a CDR3 as contained in the amino acid sequence set forth in SEQ ID NO:365; a CDR1, a CDR2, and a CDR3 as contained in the amino acid sequence set forth in SEQ ID NO:366; a CDR1, a CDR2, and a CDR3 as contained in the amino acid sequence set forth in SEQ ID NO:367; a CDR1, a CDR2, and a CDR3 as contained in the amino acid sequence set forth in SEQ ID NO:368; a CDR1, a CDR2, and a CDR3 as contained in the amino acid sequence set forth in SEQ ID NO:369; a CDR1, a CDR2, and a CDR3 as contained in the amino acid sequence set forth in SEQ ID NO:370; a CDR1, a CDR2, and a CDR3 as contained in the amino acid sequence set forth in SEQ ID NO:371; a CDR1, a CDR2, and a CDR3 as contained in the amino acid sequence set forth in SEQ ID NO:372; a CDR1, a CDR2, and a CDR3 as contained in the amino acid sequence set forth in SEQ ID NO:373; a CDR1, a CDR2, and a CDR3 as contained in the amino acid sequence set forth in SEQ ID NO:374; a CDR1, a CDR2, and a CDR3 as contained in the amino acid sequence set forth in SEQ ID NO:375; a CDR1, a CDR2, and a CDR3 as contained in the amino acid sequence set forth in SEQ ID NO:376; a CDR1, a CDR2, and a CDR3 as contained in the amino acid sequence set forth in SEQ ID NO:377; a CDR1, a CDR2, and a CDR3 as contained in the amino acid sequence set forth in SEQ ID NO:378; a CDR1, a CDR2, and a CDR3 as contained in the amino acid sequence set forth in SEQ ID NO:379; a CDR1, a CDR2, and a CDR3 as contained in the amino acid sequence set forth in SEQ ID NO:380; a CDR1, a CDR2, and a CDR3 as contained in the amino acid sequence set forth in SEQ ID NO:381; a CDR1, a CDR2, and a CDR3 as contained in the amino acid sequence set forth in SEQ ID NO:382; a CDR1, a CDR2, and a CDR3 as contained in the amino acid sequence set forth in SEQ ID NO:383; a CDR1, a CDR2, and a CDR3 as contained in the amino acid sequence set forth in SEQ ID NO:384; or a CDR1, a CDR2, and a CDR3 as contained in the amino acid sequence set forth in SEQ ID NO:385.

In some embodiments, the at least one CD28 sdAb contains the amino acid sequence set forth in any of SEQ ID NOS:186, 187, 188, 213, 214, 215, 216, 217, 218, 219, 220, 221, 222, 223, 224, 225, 226, 227, 228, 229, 230, 231, 232, 233, 234, 235, 236, 237, 238, 239, and 280, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS:186, 187, 188, 213, 214, 215, 216, 217, 218, 219, 220, 221, 222, 223, 224, 225, 226, 227, 228, 229, 230, 231, 232, 233, 234, 235, 236, 237, 238, 239, and 280. In some embodiments, the at least one CD28 sdAb contains the amino acid sequence set forth in any of SEQ ID NOS:186, 187, 188, 213, 214, 215, 216, 217, 218, 219, 220, 221, 222, 223, 224, 225, 226, 227, 228, 229, 230, 231, 232, 233, 234, 235, 236, 237, 238, 239, and 280. In some embodiments, the at least one CD28 sdAb contains the amino acid sequence set forth in any of SEQ ID NOS: 186, 187, 188, 213, 214, 215, 216, 217, 218, 219, 220, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS:186, 187, 188, 213, 214, 215, 216, 217, 218, 219, 220, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385. In some embodiments, the at least one CD28 sdAb contains the amino acid sequence set forth in any of SEQ ID NOS:

186, 187, 188, 213, 214, 215, 216, 217, 218, 219, 220, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385.

In some embodiments, the at least one CD28 sdAb comprises the amino acid sequence set forth in SEQ ID NO:186. In some embodiments, the at least one CD28 sdAb comprises the amino acid sequence set forth in SEQ ID NO:187. In some embodiments, the at least one CD28 sdAb comprises the amino acid sequence set forth in SEQ ID NO:188. In some embodiments, the at least one CD28 sdAb comprises the amino acid sequence set forth in SEQ ID NO:213. In some embodiments, the at least one CD28 sdAb comprises the amino acid sequence set forth in SEQ ID NO:214. In some embodiments, the at least one CD28 sdAb comprises the amino acid sequence set forth in SEQ ID NO:215. In some embodiments, the at least one CD28 sdAb comprises the amino acid sequence set forth in SEQ ID NO:216. In some embodiments, the at least one CD28 sdAb comprises the amino acid sequence set forth in SEQ ID NO:217. In some embodiments, the at least one CD28 sdAb comprises the amino acid sequence set forth in SEQ ID NO:218. In some embodiments, the at least one CD28 sdAb comprises the amino acid sequence set forth in SEQ ID NO:219. In some embodiments, the at least one CD28 sdAb comprises the amino acid sequence set forth in SEQ ID NO:220. In some embodiments, the at least one CD28 sdAb comprises the amino acid sequence set forth in SEQ ID NO:221. In some embodiments, the at least one CD28 sdAb comprises the amino acid sequence set forth in SEQ ID NO:222. In some embodiments, the at least one CD28 sdAb comprises the amino acid sequence set forth in SEQ ID NO:223. In some embodiments, the at least one CD28 sdAb comprises the amino acid sequence set forth in SEQ ID NO:224. In some embodiments, the at least one CD28 sdAb comprises the amino acid sequence set forth in SEQ ID NO:225. In some embodiments, the at least one CD28 sdAb comprises the amino acid sequence set forth in SEQ ID NO:226. In some embodiments, the at least one CD28 sdAb comprises the amino acid sequence set forth in SEQ ID NO:227. In some embodiments, the at least one CD28 sdAb comprises the amino acid sequence set forth in SEQ ID NO:228. In some embodiments, the at least one CD28 sdAb comprises the amino acid sequence set forth in SEQ ID NO:229. In some embodiments, the at least one CD28 sdAb comprises the amino acid sequence set forth in SEQ ID NO:230. In some embodiments, the at least one CD28 sdAb comprises the amino acid sequence set forth in SEQ ID NO:231. In some embodiments, the at least one CD28 sdAb comprises the amino acid sequence set forth in SEQ ID NO:232. In some embodiments, the at least one CD28 sdAb comprises the amino acid sequence set forth in SEQ ID NO:233. In some embodiments, the at least one CD28 sdAb comprises the amino acid sequence set forth in SEQ ID NO:234. In some embodiments, the at least one CD28 sdAb comprises the amino acid sequence set forth in SEQ ID NO:235. In some embodiments, the at least one CD28 sdAb comprises the amino acid sequence set forth in SEQ ID NO:236. In some embodiments, the at least one CD28 sdAb comprises the amino acid sequence set forth in SEQ ID NO:237. In some embodiments, the at least one CD28 sdAb comprises the amino acid sequence set forth in SEQ ID NO:238. In some embodiments, the at least one CD28 sdAb comprises the amino acid sequence set forth in SEQ ID NO:239. In some embodiments, the at least one CD28 sdAb comprises the amino acid sequence set forth in SEQ ID NO:280. In some embodiments, the at least one CD28 sdAb comprises the amino acid sequence set forth in SEQ ID NO:342. In some embodiments, the at least one CD28 sdAb comprises the amino acid sequence set forth in SEQ ID NO:343. In some embodiments, the at least one CD28 sdAb comprises the amino acid sequence set forth in SEQ ID NO:344. In some embodiments, the at least one CD28 sdAb comprises the amino acid sequence set forth in SEQ ID NO:345. In some embodiments, the at least one CD28 sdAb comprises the amino acid sequence set forth in SEQ ID NO:346. In some embodiments, the at least one CD28 sdAb comprises the amino acid sequence set forth in SEQ ID NO:347. In some embodiments, the at least one CD28 sdAb comprises the amino acid sequence set forth in SEQ ID NO:348. In some embodiments, the at least one CD28 sdAb comprises the amino acid sequence set forth in SEQ ID NO:349. In some embodiments, the at least one CD28 sdAb comprises the amino acid sequence set forth in SEQ ID NO:350. In some embodiments, the at least one CD28 sdAb comprises the amino acid sequence set forth in SEQ ID NO:351. In some embodiments, the at least one CD28 sdAb comprises the amino acid sequence set forth in SEQ ID NO:352. In some embodiments, the at least one CD28 sdAb comprises the amino acid sequence set forth in SEQ ID NO:353. In some embodiments, the at least one CD28 sdAb comprises the amino acid sequence set forth in SEQ ID NO:354. In some embodiments, the at least one CD28 sdAb comprises the amino acid sequence set forth in SEQ ID NO:355. In some embodiments, the at least one CD28 sdAb comprises the amino acid sequence set forth in SEQ ID NO:356. In some embodiments, the at least one CD28 sdAb comprises the amino acid sequence set forth in SEQ ID NO:357. In some embodiments, the at least one CD28 sdAb comprises the amino acid sequence set forth in SEQ ID NO:358. In some embodiments, the at least one CD28 sdAb comprises the amino acid sequence set forth in SEQ ID NO:359. In some embodiments, the at least one CD28 sdAb comprises the amino acid sequence set forth in SEQ ID NO:360. In some embodiments, the at least one CD28 sdAb comprises the amino acid sequence set forth in SEQ ID NO:361. In some embodiments, the at least one CD28 sdAb comprises the amino acid sequence set forth in SEQ ID NO:362. In some embodiments, the at least one CD28 sdAb comprises the amino acid sequence set forth in SEQ ID NO:363. In some embodiments, the at least one CD28 sdAb comprises the amino acid sequence set forth in SEQ ID NO:364. In some embodiments, the at least one CD28 sdAb comprises the amino acid sequence set forth in SEQ ID NO:365. In some embodiments, the at least one CD28 sdAb comprises the amino acid sequence set forth in SEQ ID NO:366. In some embodiments, the at least one CD28 sdAb comprises the amino acid sequence set forth in SEQ ID NO:367. In some embodiments, the at least one CD28 sdAb comprises the amino acid sequence set forth in SEQ ID NO:368. In some embodiments, the at least one CD28 sdAb comprises the amino acid sequence set forth in SEQ ID NO:369. In some embodiments, the at least one CD28 sdAb comprises the amino acid sequence set forth in SEQ ID NO:370. In some embodiments, the at least one CD28 sdAb comprises the amino acid sequence set forth in SEQ ID NO:371. In some embodiments, the at least one CD28 sdAb comprises the amino acid sequence set forth in SEQ ID NO:372. In some embodiments, the at least one CD28 sdAb comprises the amino acid sequence set forth in SEQ ID NO:373. In some embodiments, the at least one CD28 sdAb comprises the amino acid sequence set forth in SEQ ID NO:374. In some embodiments, the at least one CD28 sdAb comprises the amino acid sequence set forth in SEQ ID NO:375. In some embodiments, the at least one CD28 sdAb comprises the amino acid sequence set forth in SEQ ID NO:376. In some embodiments, the at least one CD28 sdAb comprises the amino acid sequence set forth in SEQ ID NO:377. In some embodiments, the at least one CD28 sdAb comprises the amino acid sequence set forth in SEQ ID NO:378. In some embodiments, the at least one CD28 sdAb comprises the amino acid sequence set forth in SEQ ID NO:379. In some embodiments, the at least one CD28 sdAb comprises the amino acid sequence set forth in SEQ ID NO:380. In some embodiments, the at least one CD28 sdAb comprises the amino acid sequence set forth in SEQ ID NO:381. In some embodiments, the at least one CD28 sdAb comprises the amino acid sequence set forth in SEQ ID NO:382. In some embodiments, the at least one CD28 sdAb comprises the amino acid sequence set forth in SEQ ID NO:383. In some embodiments, the at least one CD28 sdAb comprises the amino acid sequence set forth in SEQ ID NO:384. In some embodiments, the at least one CD28 sdAb comprises the amino acid sequence set forth in SEQ ID NO: and 385.

In some embodiments, the at least one CD28 sdAb contains the amino acid sequence set forth in any of SEQ ID NOS:186, 187, 188, 213, 214, 215, 216, 217, 218, 219, 221, 222, 223, 224, 225, 226, 227, 228, 229, 230, 231, 232, 233, 234, 235, 236, 237, 238, 239, and 280, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS:186, 187, 188, 213, 214, 215, 216, 217, 218, 219, 221, 222, 223, 224, 225, 226, 227, 228, 229, 230, 231, 232, 233, 234, 235, 236, 237, 238, 239, and 280. In some embodiments, the at least one CD28 sdAb contains the amino acid sequence set forth in any of SEQ ID NOS:186, 187, 188, 213, 214, 215, 216, 217, 218, 219, 221, 222, 223, 224, 225, 226, 227, 228, 229, 230, 231, 232, 233, 234, 235, 236, 237, 238, 239, and 280. In some embodiments, the at least one CD28 sdAb contains the amino acid sequence set forth in any of SEQ ID NOS: 186, 187, 188, 213, 214, 215, 216, 217, 218, 219, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS:186, 187, 188, 213, 214, 215, 216, 217, 218, 219, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385. In some embodiments, the at least one CD28 sdAb contains the amino acid sequence set forth in any of SEQ ID NOS: 186, 187, 188, 213, 214, 215, 216, 217, 218, 219, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385.

In some embodiments, the at least one CD28 sdAb contains the sequence set forth in (i) SEQ ID NO: 186, (ii) a humanized variant of SEQ ID NO:186, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 186. In some embodiments, the at least one CD28 sdAb contains the sequence set forth in SEQ ID NO: 186. In some embodiments, the at least one CD28 sdAb contains a humanized variant of SEQ ID NO:186. In some embodiments, the at least one CD28 sdAb contains a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 186. In some embodiments, the at least one CD28 sdAb contains a CDR1 having an amino acid sequence set forth in SEQ ID NO:189; a CDR2 having an amino acid sequence set forth in SEQ ID NO:190; and a CDR3 having an amino acid sequence set forth in SEQ ID NO:191.

In some embodiments, the at least one CD28 sdAb contains the sequence set forth in (i) SEQ ID NO: 187, (ii) a humanized variant of SEQ ID NO:187, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 187. In some embodiments, the at least one CD28 sdAb contains the sequence set forth in SEQ ID NO: 187. In some embodiments, the at least one CD28 sdAb contains a humanized variant of SEQ ID NO:187. In some embodiments, the at least one CD28 sdAb contains a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 187. In some embodiments, the at least one CD28 sdAb contains a CDR1 having an amino acid sequence set forth in SEQ ID NO:192; a CDR2 having an amino acid sequence set forth in SEQ ID NO:193; and a CDR3 having an amino acid sequence set forth in SEQ ID NO:194.

In some embodiments, the at least one CD28 sdAb contains the sequence set forth in (i) SEQ ID NO: 188, (ii) a humanized variant of SEQ ID NO:188, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 188. In some embodiments, the at least one CD28 sdAb contains the sequence set forth in SEQ ID NO: 188. In some embodiments, the at least one CD28 sdAb contains a humanized variant of SEQ ID NO:188. In some embodiments, the at least one CD28 sdAb contains a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 188.

In some embodiments, the at least one CD28 sdAb contains a CDR1 having an amino acid sequence set forth in any of SEQ ID NO:195, 198, 199, 200, and 201; a CDR2 having an amino acid sequence set forth in any of SEQ ID NO:196, 202, 203, 204, 205, 206, 207, 208, 209, 210, 211, and 212; and a CDR3 having an amino acid sequence set forth in SEQ ID NO:197. In some embodiments, the at least one CD28 sdAb contains a CDR1 comprising an amino acid sequence set forth in any of SEQ ID NOS:195, 198, 199, 200, and 201; a CDR2 comprising an amino acid sequence set forth in any of SEQ ID NOS:196, 202, 203, 204, 205, 206, 207, 208, 209, 210, 211, 212, 386, 387, 388, 389, 390, 391, 392, 393, 394, and 395; and a CDR3 comprising an amino acid sequence set forth in any of SEQ ID NOS:197, 396, 397, and 398.

In some embodiments, the at least one CD28 sdAb contains CDR1, CDR2 and CDR3 set forth in SEQ ID NOS: 195, 196, and 197, respectively; SEQ ID NOS: 198, 196, and 197, respectively; SEQ ID NOS: 199, 196, and 197, respectively; SEQ ID NOS: 200, 196, and 197, respectively; SEQ ID NOS: 201, 196, and 197, respectively; SEQ ID NOS: 195, 202, and 197, respectively; SEQ ID NOS: 195, 203, and 197, respectively; SEQ ID NOS: 195, 204, and 197, respectively; SEQ ID NOS: 195, 205, and 197, respectively; SEQ ID NOS: 195, 206, and 197, respectively; SEQ ID NOS: 195, 207, and 197, respectively; SEQ ID NOS: 195, 208, and 197, respectively; SEQ ID NOS: 195, 209, and 197, respectively; SEQ ID NOS: 195, 210, and 197, respectively; SEQ ID NOS: 195, 211, and 197, respectively; or SEQ ID NOS: 195, 212, and 197, respectively. In some embodiments, the at least one CD28 sdAb contains a CDR1, CDR2 and CDR3 set forth in: SEQ ID NOS: 195, 196, and 197, respectively; SEQ ID NOS: 198, 196, and 197, respectively; SEQ ID NOS: 199, 196, and 197, respectively; SEQ ID NOS: 200, 196, and 197, respectively; SEQ ID NOS: 201, 196, and 197, respectively; SEQ ID NOS: 195, 202, and 197, respectively; SEQ ID NOS: 195, 203, and 197, respectively; SEQ ID NOS: 195, 204, and 197, respectively; SEQ ID NOS: 195, 205, and 197, respectively; SEQ ID NOS: 195, 206, and 197, respectively; SEQ ID NOS: 195, 207, and 197, respectively; SEQ ID NOS: 195, 208, and 197, respectively; SEQ ID NOS: 195, 209, and 197, respectively; SEQ ID NOS: 195, 210, and 197, respectively; SEQ ID NOS: 195, 211, and 197, respectively; SEQ ID NOS: 195, 212, and 197, respectively; SEQ ID NOS: 201, 202, and 197, respectively; SEQ ID NOS: 201, 202, and 396, respectively; SEQ ID NOS: 201, 386, and 197, respectively; SEQ ID NOS: 201, 387, and 197, respectively; SEQ ID NOS: 201, 202, and 397, respectively; SEQ ID NOS: 201, 202, and 398, respectively; SEQ ID NOS: 201, 206, and 197, respectively; SEQ ID NOS: 201, 206, and 398, respectively; SEQ ID NOS: 201, 388, and 197, respectively; SEQ ID NOS: 201, 389, and 197, respectively; SEQ ID NOS: 201, 206, and 397, respectively; SEQ ID NOS: 201, 206, and 398, respectively; SEQ ID NOS: 201, 203, and 197, respectively; SEQ ID NOS: 201, 203, and 396, respectively; SEQ ID NOS: 201, 390, and 197, respectively; SEQ ID NOS: 201, 391, and 197, respectively; SEQ ID NOS: 201, 203, and 397, respectively; SEQ ID NOS: 201, 203, and 398, respectively; SEQ ID NOS: 201, 204, and 197, respectively; SEQ ID NOS: 201, 204, and 396, respectively; SEQ ID NOS: 201, 392, and 197, respectively; SEQ ID NOS: 201, 393, and 197, respectively; SEQ ID NOS: 201, 204, and 397, respectively; SEQ ID NOS: 201, 204, and 398, respectively; SEQ ID NOS: 201, 196, and 396, respectively; SEQ ID NOS: 201, 394, and 197, respectively; SEQ ID NOS: 201, 395, and 197, respectively; SEQ ID NOS: 201, 196, and 397, respectively; SEQ ID NOS: 201, 196, and 398, respectively; SEQ ID NOS: 195, 206, and 396, respectively; SEQ ID NOS: 195, 388, and 197, respectively; SEQ ID NOS: 195, 389, and 197, respectively; SEQ ID NOS: 195, 206, and 397, respectively; or SEQ ID NOS: 195, 206, and 398, respectively.

In some embodiments, the at least one CD28 sdAb contains the sequence of amino acids set forth in any one of SEQ ID NOs:213-239 and 280, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO:213-239 and 280. In some embodiments, the at least one CD28 sdAb contains the sequence of amino acids set forth in any one of SEQ ID NOS:213-239 and 280.

In some embodiments, the at least one CD28 sdAb contains the amino acid sequence set forth in any of SEQ ID NOS:213-239, 280, and 342-385, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO:213-239, 280, and 342-385. In some embodiments, the at least one CD28 sdAb contains the amino acid sequence set forth in any of SEQ ID NOS:213-239, 280, and 342-385.

In some embodiments, the at least one CD28 sdAb contains a CDR1 having an amino acid sequence set forth in any of SEQ ID NO:195, 198, 199, 200, and 201; a CDR2 having an amino acid sequence set forth in any of SEQ ID NO:196, 202, 204, 205, 206, 207, 208, 209, 210, 211, and 212; and a CDR3 having an amino acid sequence set forth in SEQ ID NO:197. In some embodiments, the at least one CD28 sdAb contains a CDR1 comprising an amino acid sequence set forth in any of SEQ ID NO:195, 198, 199, 200, and 201; a CDR2 comprising an amino acid sequence set forth in any of SEQ ID NO:196, 202, 204, 205, 206, 207, 208, 209, 210, 211, 212, 386, 387, 388, 389, 390, 391, 392, 393, 394, and 395; and a CDR3 comprising an amino acid sequence set forth in any of SEQ ID NO:197, 396, 397, and 398.

In some embodiments, the at least one CD28 sdAb contains a CDR1, CDR2 and CDR3 set forth in SEQ ID NOS: 195, 196, and 197, respectively; SEQ ID NOS: 198, 196, and 197, respectively; SEQ ID NOS: 199, 196, and 197, respectively; SEQ ID NOS: 200, 196, and 197, respectively; SEQ ID NOS: 201, 196, and 197, respectively; SEQ ID NOS: 195, 202, and 197, respectively; SEQ ID NOS: 195, 204, and 197, respectively; SEQ ID NOS: 195, 205, and 197, respectively; SEQ ID NOS: 195, 206, and 197, respectively; SEQ ID NOS: 195, 207, and 197, respectively; SEQ ID NOS: 195, 208, and 197, respectively; SEQ ID NOS: 195, 209, and 197, respectively; SEQ ID NOS: 195, 210, and 197, respectively; SEQ ID NOS: 195, 211, and 197, respectively; or SEQ ID NOS: 195, 212, and 197, respectively. In some embodiments, the at least one CD28 sdAb contains a CDR1, CDR2 and CDR3 set forth in: SEQ ID NOS: 195, 196, and 197, respectively; SEQ ID NOS: 198, 196, and 197, respectively; SEQ ID NOS: 199, 196, and 197, respectively; SEQ ID NOS: 200, 196, and 197, respectively; SEQ ID NOS: 201, 196, and 197, respectively; SEQ ID NOS: 195, 202, and 197, respectively; SEQ ID NOS: 195, 204, and 197, respectively; SEQ ID NOS: 195, 205, and 197, respectively; SEQ ID NOS: 195, 206, and 197, respectively; SEQ ID NOS: 195, 207, and 197, respectively; SEQ ID NOS: 195, 208, and 197, respectively; SEQ ID NOS: 195, 209, and 197, respectively; SEQ ID NOS: 195, 210, and 197, respectively; SEQ ID NOS: 195, 211, and 197, respectively; SEQ ID NOS: 195, 212, and 197, respectively; SEQ ID NOS: 201, 202, and 197, respectively; SEQ ID NOS: 201, 202, and 396, respectively; SEQ ID NOS: 201, 386, and 197, respectively; SEQ ID NOS: 201, 387, and 197, respectively; SEQ ID NOS: 201, 202, and 397, respectively; SEQ ID NOS: 201, 202, and 398, respectively; SEQ ID NOS: 201, 206, and 197, respectively; SEQ ID NOS: 201, 206, and 398, respectively; SEQ ID NOS: 201, 388, and 197, respectively; SEQ ID NOS: 201, 389, and 197, respectively; SEQ ID NOS: 201, 206, and 397, respectively; SEQ ID NOS: 201, 206, and 398, respectively; SEQ ID NOS: 201, 203, and 197, respectively; SEQ ID NOS: 201, 203, and 396, respectively; SEQ ID NOS: 201, 390, and 197, respectively; SEQ ID NOS: 201, 391, and 197, respectively; SEQ ID NOS: 201, 203, and 397, respectively; SEQ ID NOS: 201, 203, and 398, respectively; SEQ ID NOS: 201, 204, and 197, respectively; SEQ ID NOS:

201, 204, and 396, respectively; SEQ ID NOS: 201, 392, and 197, respectively; SEQ ID NOS: 201, 393, and 197, respectively; SEQ ID NOS: 201, 204, and 397, respectively; SEQ ID NOS: 201, 204, and 398, respectively; SEQ ID NOS: 201, 196, and 396, respectively; SEQ ID NOS: 201, 394, and 197, respectively; SEQ ID NOS: 201, 395, and 197, respectively; SEQ ID NOS: 201, 196, and 397, respectively; SEQ ID NOS: 201, 196, and 398, respectively; SEQ ID NOS: 195, 206, and 396, respectively; SEQ ID NOS: 195, 388, and 197, respectively; SEQ ID NOS: 195, 389, and 197, respectively; SEQ ID NOS: 195, 206, and 397, respectively; or SEQ ID NOS: 195, 206, and 398, respectively.

In some embodiments, the at least one CD28 sdAb contains the sequence of amino acids set forth in any one of SEQ ID NOs:213-219, 221-239, and 280, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO:213-219, 221-239, and 280. In some embodiments, the at least one CD28 sdAb contains the sequence of amino acids set forth in any one of SEQ ID NOS:213-219, 221-239, and 280. In some embodiments, the at least one CD28 sdAb contains the amino acid sequence set forth in any of SEQ ID NOS:213-239, 280, and 342-385, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO:213-239, 280, and 342-385. In some embodiments, the at least one CD28 sdAb comprises the amino acid sequence set forth in any of SEQ ID NOS:213-239, 280, and 342-385.

In any of the provided embodiments, the CD28-binding polypeptide contains a CD3 binding region. In some embodiments, the anti-CD28 sdAb-Fc fusion protein includes a CD3 binding region. In some embodiments, the homodimeric Fc fusion protein includes a CD3 binding region. In some embodiments, the heterodimeric Fc fusion protein includes a CD3 binding region. In some embodiments, the multi-specific binding polypeptide includes a CD3 binding region. In some embodiments, the homodimeric multi-specific binding polypeptide includes a CD3 binding region. In some embodiments, the heterodimeric multi-specific binding polypeptide includes a CD3 binding region. In some embodiments, the fusion protein includes a CD3 binding region.

Provided herein in a multi-specific construct containing at least one of the provided sdAbs, one or more binding domain (BD) that binds to an antigen other than CD28, and a CD3 binding region. In some embodiments, the BD binds to a tumor associated (antigen). In some embodiments, the BD is a single domain antibody.

In some embodiments, the CD3-binding region binds CD3 (CD3ε). In some embodiments, the CD3 binding region is an anti-CD3 antibody or antigen-binding fragment. In some embodiments, the CD3 binding region is an anti-CD3 antibody. In some embodiments, the CD3 binding region is an anti-CD3 antigen-binding fragment. In some embodiments, the anti-CD3 antibody or antigen-binding fragment contains a variable heavy chain region (VH) and a variable light chain region (VL). In some embodiments, the CD3 binding region is monovalent. In some embodiments, the CD3 binding region is an variable fragment (Fv) comprising a variable heavy chain region (VH) and a variable light chain region (VL). In some embodiments, the anti-CD3 antibody or antigen-binding fragment is not a single chain antibody. In some embodiments, the anti-CD3 antibody or antigen-binding fragment is not a single chain variable fragment (scFv).

In any of the provided embodiments, the CD28-binding polypeptide contains an immunoglobulin Fc region. In some embodiments, the Fc region is a homodimeric Fc region. In some embodiments, the Fc region contains a sequence of amino acids selected from the group consisting of SEQ ID NOS: 8, 10, 11, 12 and 13, or a sequence of amino acids that exhibits at least 85%, 86%, 87%, 88%, 89%, 90%, 91%, 92%, 93%, 94%, 95%, 96%, 97%, 98%, or 99% sequence identity to any one of SEQ ID NOS: 8, 10, 11, 12 and 13. In some embodiments, the Fc region consists of a sequence of amino acids selected from the group consisting of SEQ ID NOS: 8, 10, 11, 12 and 13. In some embodiments, the Fc region is a human IgG1. In some embodiments, the Fc region is a human IgG1. In some embodiments, the Fc region contains the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 8. In some embodiments, the Fc region consists of the sequence of amino acids set forth in SEQ ID NO: 8.

In some embodiments, the Fc region is a heterodimeric Fc region.

In some embodiments, the Fc region exhibits effector function.

In some embodiments, the Fc region contains a polypeptide having one or more amino acid modification that reduces effector function. In some embodiments, the Fc region contains a polypeptide having one or more amino acid modification that reduces binding to an effector molecule. In some embodiments, the Fc region contains a polypeptide having one or more amino acid modification that reduces binding to an effector molecule selected from an Fc gamma receptor and C1q. In some embodiments, the Fc region contains a polypeptide having one or more amino acid modification that reduces binding to Fc gamma receptor. In some embodiments, the Fc region contains a polypeptide having one or more amino acid modification that reduces binding to C1q. In some embodiments, the one or more amino acid modification is deletion of one or more of Glu233, Leu234 or Leu235. In some embodiments, the one or more amino acid modification is deletion of one or more of Glu233, Leu234 or Leu235. In some embodiments, the one or more amino acid modification is deletion of Glu233. In some embodiments, the one or more amino acid modification is deletion of Leu234. In some embodiments, the one or more amino acid modification is deletion of Leu235. In some embodiments, the Fc region contains the sequence of amino acids set forth in SEQ ID NO: 9 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 9. In some embodiments, the Fc region consists of the sequence of amino acids set forth in SEQ ID NO: 9.

In some embodiments, the CD28-binding polypeptide is a dimer. In some embodiments, the Fc is a heterodimeric Fc and the VH and VL that comprise the anti-CD3 antibody or antigen-binding fragment are linked to opposite polypeptides of the heterodimeric Fc.

In some embodiments, the CD3 binding region is not able to, or is not substantially able to, bind or engage CD3 unless at least one of the at least one CD28 sdAb is bound to CD28. In some embodiments, the CD3 binding region is not able to bind or engage CD3 unless at least one of the at least one CD28 sdAb is bound to CD28. In some embodiments, the CD3 binding region is not substantially able to bind or engage CD3 unless at least one of the at least one CD28 sdAb is bound to CD28. In some embodiments, the CD3 binding region is not able to, or is not substantially able, to bind or engage CD3 unless at least one of the one or more TAA sdAb is bound to its TAA. In some embodiments, the CD3 binding region is not able to bind or engage CD3 unless at least one of the one or more TAA sdAb is bound to its TAA. In some embodiments, the CD3 binding region is not substantially able to bind or engage CD3 unless at least one of the one or more TAA sdAb is bound to its TAA.

In some embodiments, the CD28-binding polypeptide includes a moiety that binds protein A.

In some embodiments, the at least one CD28 sdAb comprises an amino acid modification that reduces binding to protein A. In some embodiments, the at least one CD28 sdAb comprises the amino acid modification G65D by Kabat in framework region 3 (FR3).

Also provided herein are anti-CD28 single domain antibodies containing a complementarity determining region 1 (CDR1) having an amino acid sequence selected from the group consisting of SEQ ID NO:189, 192, 195, 198, 199, 200, and 201; a complementarity determining region 2 (CDR2) containing an amino acid sequence selected from the group consisting of SEQ ID NOS:190, 193, 196, 202, 203, 204, 205, 206, 207, 208, 209, 210, 211, and 212, 386, 387, 388, 389, 390, 391, 392, 393, 394, and 395; and a complementarity determining region 3 (CDR3) containing an amino acid sequence selected from the group consisting of SEQ ID NOS: 191, 194, and 197, 396, 397, and 398.

Also provided herein are anti-CD28 sdAbs containing a complementarity determining region 1 (CDR1) containing an amino acid sequence selected from the group consisting of SEQ ID NOS:189, 192, 195, 198, 199, 200, and 201; a complementarity determining region 2 (CDR2) containing an amino acid sequence selected from the group consisting of SEQ ID NOS:190, 193, 196, 202, 204, 205, 206, 207, 208, 209, 210, 211, and 212, 386, 387, 388, 389, 390, 391, 392, 393, 394, and 395; and a complementarity determining region 3 (CDR3) containing an amino acid sequence selected from the group consisting of SEQ ID NOS: 191, 194, and 197, 396, 397, and 398.

In some embodiments, the CD28 sdAb contains a CDR1 containing an the amino acid sequence set forth in SEQ ID NO:189, a CDR2 containing the amino acid sequence set forth in SEQ ID NO:190, and a CDR3 containing the amino acid sequence set forth in SEQ ID NO:191. In some embodiments, the CD28 sdAb contains a CDR1 containing an the amino acid sequence set forth in SEQ ID NO:192, a CDR2 containing the amino acid sequence set forth in SEQ ID NO:193, and a CDR3 containing the amino acid sequence set forth in SEQ ID NO:194. In some embodiments, the CD28 sdAb contains a CDR1 containing an the amino acid sequence set forth in SEQ ID NO:195, a CDR2 containing the amino acid sequence set forth in SEQ ID NO:196, and a CDR3 containing the amino acid sequence set forth in SEQ ID NO:197. In some embodiments, the CD28 sdAb contains a CDR1 containing an the amino acid sequence set forth in SEQ ID NO:198, a CDR2 containing the amino acid sequence set forth in SEQ ID NO:196, and a CDR3 containing the amino acid sequence set forth in SEQ ID NO:197. In some embodiments, the CD28 sdAb contains a CDR1 containing an the amino acid sequence set forth in SEQ ID NO:199, a CDR2 containing the amino acid sequence set forth in SEQ ID NO:196, and a CDR3 containing the amino acid sequence set forth in SEQ ID NO:197. In some embodiments, the CD28 sdAb contains a CDR1 containing an the amino acid sequence set forth in SEQ ID NO:200, a CDR2 containing the amino acid sequence set forth in SEQ ID NO:196, and a CDR3 containing the amino acid sequence set forth in SEQ ID NO:197. In some embodiments, the CD28 sdAb contains CDR1 containing an the amino acid sequence set forth in SEQ ID NO:201, a CDR2 containing the amino acid sequence set forth in SEQ ID NO:196, and a CDR3 containing the amino acid sequence set forth in SEQ ID NO:197. In some embodiments, the CD28 sdAb contains a CDR1 containing an the amino acid sequence set forth in SEQ ID NO:195, a CDR2 containing the amino acid sequence set forth in SEQ ID NO:202, and a CDR3 containing the amino acid sequence set forth in SEQ ID NO:197. In some embodiments, the CD28 sdAb contains a CDR1 containing an the amino acid sequence set forth in SEQ ID NO:195, a CDR2 containing the amino acid sequence set forth in SEQ ID NO:203, and a CDR3 containing the amino acid sequence set forth in SEQ ID NO:197. In some embodiments, the CD28 sdAb contains CDR1 containing an the amino acid sequence set forth in SEQ ID NO:195, a CDR2 containing the amino acid sequence set forth in SEQ ID NO:204, and a CDR3 containing the amino acid sequence set forth in SEQ ID NO:197. In some embodiments, the CD28 sdAb contains CDR1 containing an the amino acid sequence set forth in SEQ ID NO:195, a CDR2 containing the amino acid sequence set forth in SEQ ID NO:205, and a CDR3 containing the amino acid sequence set forth in SEQ ID NO:197. In some embodiments, the CD28 sdAb contains CDR1 containing an the amino acid sequence set forth in SEQ ID NO:195, a CDR2 containing the amino acid sequence set forth in SEQ ID NO:206, and a CDR3 containing the amino acid sequence set forth in SEQ ID NO:197. In some embodiments, the CD28 sdAb contains a CDR1 containing an the amino acid sequence set forth in SEQ ID NO:195, a CDR2 containing the amino acid sequence set forth in SEQ ID NO:207, and a CDR3 containing the amino acid sequence set forth in SEQ ID NO:197. In some embodiments, the CD28 sdAb contains CDR1 containing an the amino acid sequence set forth in SEQ ID NO:195, a CDR2 containing the amino acid sequence set forth in SEQ ID NO:208, and a CDR3 containing the amino acid sequence set forth in SEQ ID NO:197. In some embodiments, the CD28 sdAb contains CDR1 containing an the amino acid sequence set forth in SEQ ID NO:195, a CDR2 containing the amino acid sequence set forth in SEQ ID NO:209, and a CDR3 containing the amino acid sequence set forth in SEQ ID NO:197. In some embodiments, the CD28 sdAb contains CDR1 containing an the amino acid sequence set forth in SEQ ID NO:195, a CDR2 containing the amino acid sequence set forth in SEQ ID NO:210, and a CDR3 containing the amino acid sequence set forth in SEQ ID NO:197. In some embodiments, the CD28 sdAb contains a CDR1 containing an the amino acid sequence set forth in SEQ ID NO:195, a CDR2 containing the amino acid sequence set forth in SEQ ID NO:211, and a CDR3 containing the amino acid sequence set forth in SEQ ID NO:197. In some embodiments, the CD28 sdAb contains a CDR1 containing an the amino acid sequence set forth in SEQ ID NO:195, a CDR2 containing the amino acid sequence set forth in SEQ ID NO:212, and a CDR3 containing the amino acid sequence set forth in SEQ ID NO:197. In some embodiments, the CD28 sdAb contains a CDR1 containing the amino acid sequence set forth in SEQ ID NO:201, a CDR2 containing the amino acid sequence set forth in SEQ ID NO:202, and a CDR3 containing the amino acid sequence set forth in SEQ ID NO:197. In some embodiments, the CD28 sdAb contains a CDR1 containing the amino acid sequence set forth in SEQ ID NO:201, a CDR2 containing the amino acid sequence set forth in SEQ ID NO:202, and a CDR3 containing the amino acid sequence set forth in SEQ ID NO:396. In some embodiments, the CD28 sdAb contains a CDR1 containing the amino acid sequence set forth in SEQ ID NO:201, a CDR2 containing the amino acid sequence set forth in SEQ ID NO:386, and a CDR3 containing the amino acid sequence set forth in SEQ ID NO:197. In some embodiments, the CD28 sdAb contains a CDR1 containing the amino acid sequence set forth in SEQ ID NO:201, a CDR2 containing the amino acid sequence set forth in SEQ ID NO:387, and a CDR3 containing the amino acid sequence set forth in SEQ ID NO:197. In some embodiments, the CD28 sdAb contains a CDR1 containing the amino acid sequence set forth in SEQ ID NO:201, a CDR2 containing the amino acid sequence set forth in SEQ ID NO:202, and a CDR3 containing the amino acid sequence set forth in SEQ ID NO:397. In some embodiments, the CD28 sdAb contains a CDR1 containing the amino acid sequence set forth in SEQ ID NO:201, a CDR2 containing the amino acid sequence set forth in SEQ ID NO:202, and a CDR3 containing the amino acid sequence set forth in SEQ ID NO:398. In some embodiments, the CD28 sdAb contains a CDR1 containing the amino acid sequence set forth in SEQ ID NO:201, a CDR2 containing the amino acid sequence set forth in SEQ ID NO:206, and a CDR3 containing the amino acid sequence set forth in SEQ ID NO:197. In some embodiments, the CD28 sdAb contains a CDR1 containing the amino acid sequence set forth in SEQ ID NO:201, a CDR2 containing the amino acid sequence set forth in SEQ ID NO:206, and a CDR3 containing the amino acid sequence set forth in SEQ ID NO:396. In some embodiments, the CD28 sdAb contains a CDR1 containing the amino acid sequence set forth in SEQ ID NO:201, a CDR2 containing the amino acid sequence set forth in SEQ ID NO:388, and a CDR3 containing the amino acid sequence set forth in SEQ ID NO:197. In some embodiments, the CD28 sdAb contains a CDR1 containing the amino acid sequence set forth in SEQ ID NO:201, a CDR2 containing the amino acid sequence set forth in SEQ ID NO:389, and a CDR3 containing the amino acid sequence set forth in SEQ ID NO:197. In some embodiments, the CD28 sdAb contains a CDR1 containing the amino acid sequence set forth in SEQ ID NO:201, a CDR2 containing the amino acid sequence set forth in SEQ ID NO:206, and a CDR3 containing the amino acid sequence set forth in SEQ ID NO:397. In some embodiments, the CD28 sdAb contains a CDR1 containing the amino acid sequence set forth in SEQ ID NO:201, a CDR2 containing the amino acid sequence set forth in SEQ ID NO:206, and a CDR3 containing the amino acid sequence set forth in SEQ ID NO:398. In some embodiments, the CD28 sdAb contains a CDR1 containing the amino acid sequence set forth in SEQ ID NO:201, a CDR2 containing the amino acid sequence set forth in SEQ ID NO:203, and a CDR3 containing the amino acid sequence set forth in SEQ ID NO:197. In some embodiments, the CD28 sdAb contains a CDR1 containing the amino acid sequence set forth in SEQ ID NO:201, a CDR2 containing the amino acid sequence set forth in SEQ ID NO:203, and a CDR3 containing the amino acid sequence set forth in SEQ ID NO:396. In some embodiments, the CD28 sdAb contains a CDR1 containing the amino acid sequence set forth in SEQ ID NO:201, a CDR2 containing the amino acid sequence set forth in SEQ ID NO:390, and a CDR3 containing the amino acid sequence set forth in SEQ ID NO:197. In some embodiments, the CD28 sdAb contains a CDR1 containing the amino acid sequence set forth in SEQ ID NO:201, a CDR2 containing the amino acid sequence set forth in SEQ ID NO:391, and a CDR3 containing the amino acid sequence set forth in SEQ ID NO:197. In some embodiments, the CD28 sdAb contains a CDR1 containing the amino acid sequence set forth in SEQ ID NO:201, a CDR2 containing the amino acid sequence set forth in SEQ ID NO:203, and a CDR3 containing the amino acid sequence set forth in SEQ ID NO:397. In some embodiments, the CD28 sdAb contains a CDR1 containing the amino acid sequence set forth in SEQ ID NO:201, a CDR2 containing the amino acid sequence set forth in SEQ ID NO:203, and a CDR3 containing the amino acid sequence set forth in SEQ ID NO:398. In some embodiments, the CD28 sdAb contains a CDR1 containing the amino acid sequence set forth in SEQ ID NO:201, a CDR2 containing the amino acid sequence set forth in SEQ ID NO:204, and a CDR3 containing the amino acid sequence set forth in SEQ ID NO:197. In some embodiments, the CD28 sdAb contains a CDR1 containing the amino acid sequence set forth in SEQ ID NO:201, a CDR2 containing the amino acid sequence set forth in SEQ ID NO:204, and a CDR3 containing the amino acid sequence set forth in SEQ ID NO:396. In some embodiments, the CD28 sdAb contains a CDR1 containing the amino acid sequence set forth in SEQ ID NO:201, a CDR2 containing the amino acid sequence set forth in SEQ ID NO:392, and a CDR3 containing the amino acid sequence set forth in SEQ ID NO:197. In some embodiments, the CD28 sdAb contains a CDR1 containing the amino acid sequence set forth in SEQ ID NO:201, a CDR2 containing the amino acid sequence set forth in SEQ ID NO:393, and a CDR3 containing the amino acid sequence set forth in SEQ ID NO:197. In some embodiments, the CD28 sdAb contains a CDR1 containing the amino acid sequence set forth in SEQ ID NO:201, a CDR2 containing the amino acid sequence set forth in SEQ ID NO:204, and a CDR3 containing the amino acid sequence set forth in SEQ ID NO:397. In some embodiments, the CD28 sdAb contains a CDR1 containing the amino acid sequence set forth in SEQ ID NO:201, a CDR2 containing the amino acid sequence set forth in SEQ ID NO:204, and a CDR3 containing the amino acid sequence set forth in SEQ ID NO:398. In some embodiments, the CD28 sdAb contains a CDR1 containing the amino acid sequence set forth in SEQ ID NO:201, a CDR2 containing the amino acid sequence set forth in SEQ ID NO:196, and a CDR3 containing the amino acid sequence set forth in SEQ ID NO:396. In some embodiments, the CD28 sdAb contains a CDR1 containing the amino acid sequence set forth in SEQ ID NO:201, a CDR2 containing the amino acid sequence set forth in SEQ ID NO:394, and a CDR3 containing the amino acid sequence set forth in SEQ ID NO:197. In some embodiments, the CD28 sdAb contains a CDR1 containing the amino acid sequence set forth in SEQ ID NO:201, a CDR2 containing the amino acid sequence set forth in SEQ ID NO:395, and a CDR3 containing the amino acid sequence set forth in SEQ ID NO:197. In some embodiments, the CD28 sdAb contains a CDR1 containing the amino acid sequence set forth in SEQ ID NO:201, a CDR2 containing the amino acid sequence set forth in SEQ ID NO:196, and a CDR3 containing the amino acid sequence set forth in SEQ ID NO:397. In some embodiments, the CD28 sdAb contains a CDR1 containing the amino acid sequence set forth in SEQ ID NO:201, a CDR2 containing the amino acid sequence set forth in SEQ ID NO:196, and a CDR3 containing the amino acid sequence set forth in SEQ ID NO:398. In some embodiments, the CD28 sdAb contains a CDR1 containing the amino acid sequence set forth in SEQ ID NO:195, a CDR2 containing the amino acid sequence set forth in SEQ ID NO:206, and a CDR3 containing the amino acid sequence set forth in SEQ ID NO:396. In some embodiments, the CD28 sdAb contains a CDR1 containing the amino acid sequence set forth in SEQ ID NO:195, a CDR2 containing the amino acid sequence set forth in SEQ ID NO:388, and a CDR3 containing the amino acid sequence set forth in SEQ ID NO:197. In some embodiments, the CD28 sdAb contains a CDR1 containing the amino acid sequence set forth in SEQ ID NO:195, a CDR2 containing the amino acid sequence set forth in SEQ ID NO:389, and a CDR3 containing the amino acid sequence set forth in SEQ ID NO:197. In some embodiments, the CD28 sdAb contains a CDR1 containing the amino acid sequence set forth in SEQ ID NO:195, a CDR2 containing the amino acid sequence set forth in SEQ ID NO:206, and a CDR3 containing the amino acid sequence set forth in SEQ ID NO:397; or a CDR1 containing the amino acid sequence set forth in SEQ ID NO:195, a CDR2 containing the amino acid sequence set forth in SEQ ID NO:206, and a CDR3 containing the amino acid sequence set forth in SEQ ID NO:398.

In some embodiments, the CD28 sdAb contains the amino acid sequence set forth in SEQ ID NO:186. In some embodiments, the CD28 sdAb contains the amino acid sequence set forth in SEQ ID NO:187. In some embodiments, the CD28 sdAb contains the amino acid sequence set forth in SEQ ID NO:188. In some embodiments, the CD28 sdAb contains the amino acid sequence set forth in SEQ ID NO:213. In some embodiments, the CD28 sdAb contains the amino acid sequence set forth in SEQ ID NO:214. In some embodiments, the CD28 sdAb contains the amino acid sequence set forth in SEQ ID NO:215. In some embodiments, the CD28 sdAb contains the amino acid sequence set forth in SEQ ID NO:216. In some embodiments, the CD28 sdAb contains the amino acid sequence set forth in SEQ ID NO:217. In some embodiments, the CD28 sdAb contains the amino acid sequence set forth in SEQ ID NO:218. In some embodiments, the CD28 sdAb contains the amino acid sequence set forth in SEQ ID NO:219. In some embodiments, the CD28 sdAb contains the amino acid sequence set forth in SEQ ID NO:220. In some embodiments, the CD28 sdAb contains the amino acid sequence set forth in SEQ ID NO:221. In some embodiments, the CD28 sdAb contains the amino acid sequence set forth in SEQ ID NO:222. In some embodiments, the CD28 sdAb contains the amino acid sequence set forth in SEQ ID NO:223. In some embodiments, the CD28 sdAb contains the amino acid sequence set forth in SEQ ID NO:224. In some embodiments, the CD28 sdAb contains the amino acid sequence set forth in SEQ ID NO:225. In some embodiments, the CD28 sdAb contains the amino acid sequence set forth in SEQ ID NO:226. In some embodiments, the CD28 sdAb contains the amino acid sequence set forth in SEQ ID NO:227. In some embodiments, the CD28 sdAb contains the amino acid sequence set forth in SEQ ID NO:228. In some embodiments, the CD28 sdAb contains the amino acid sequence set forth in SEQ ID NO:229. In some embodiments, the CD28 sdAb contains the amino acid sequence set forth in SEQ ID NO:230. In some embodiments, the CD28 sdAb contains the amino acid sequence set forth in SEQ ID NO:231. In some embodiments, the CD28 sdAb contains the amino acid sequence set forth in SEQ ID NO:232. In some embodiments, the CD28 sdAb contains the amino acid sequence set forth in SEQ ID NO:233. In some embodiments, the CD28 sdAb contains the amino acid sequence set forth in SEQ ID NO:234. In some embodiments, the CD28 sdAb contains the amino acid sequence set forth in SEQ ID NO:235. In some embodiments, the CD28 sdAb contains the amino acid sequence set forth in SEQ ID NO:236. In some embodiments, the CD28 sdAb contains the amino acid sequence set forth in SEQ ID NO:237. In some embodiments, the CD28 sdAb contains the amino acid sequence set forth in SEQ ID NO:238. In some embodiments, the CD28 sdAb contains the amino acid sequence set forth in SEQ ID NO:239. In some embodiments, the CD28 sdAb contains the amino acid sequence set forth in SEQ ID NO:280. In some embodiments, the CD28 sdAb contains the amino acid sequence set forth in SEQ ID NO:342. In some embodiments, the CD28 sdAb contains the amino acid sequence set forth in SEQ ID NO:343. In some embodiments, the CD28 sdAb contains the amino acid sequence set forth in SEQ ID NO:344. In some embodiments, the CD28 sdAb contains the amino acid sequence set forth in SEQ ID NO:345. In some embodiments, the CD28 sdAb contains the amino acid sequence set forth in SEQ ID NO:346. In some embodiments, the CD28 sdAb contains the amino acid sequence set forth in SEQ ID NO:347. In some embodiments, the CD28 sdAb contains the amino acid sequence set forth in SEQ ID NO:348. In some embodiments, the CD28 sdAb contains the amino acid sequence set forth in SEQ ID NO:349. In some embodiments, the CD28 sdAb contains the amino acid sequence set forth in SEQ ID NO:350. In some embodiments, the CD28 sdAb contains the amino acid sequence set forth in SEQ ID NO:351. In some embodiments, the CD28 sdAb contains the amino acid sequence set forth in SEQ ID NO:352. In some embodiments, the CD28 sdAb contains the amino acid sequence set forth in SEQ ID NO:353. In some embodiments, the CD28 sdAb contains the amino acid sequence set forth in SEQ ID NO:354. In some embodiments, the CD28 sdAb contains the amino acid sequence set forth in SEQ ID NO:355. In some embodiments, the CD28 sdAb contains the amino acid sequence set forth in SEQ ID NO:356. In some embodiments, the CD28 sdAb contains the amino acid sequence set forth in SEQ ID NO:357. In some embodiments, the CD28 sdAb contains the amino acid sequence set forth in SEQ ID NO:358. In some embodiments, the CD28 sdAb contains the amino acid sequence set forth in SEQ ID NO:359. In some embodiments, the CD28 sdAb contains the amino acid sequence set forth in SEQ ID NO:360. In some embodiments, the CD28 sdAb contains the amino acid sequence set forth in SEQ ID NO:361. In some embodiments, the CD28 sdAb contains the amino acid sequence set forth in SEQ ID NO:362. In some embodiments, the CD28 sdAb contains the amino acid sequence set forth in SEQ ID NO:363. In some embodiments, the CD28 sdAb contains the amino acid sequence set forth in SEQ ID NO:364. In some embodiments, the CD28 sdAb contains the amino acid sequence set forth in SEQ ID NO:365. In some embodiments, the CD28 sdAb contains the amino acid sequence set forth in SEQ ID NO:366. In some embodiments, the CD28 sdAb contains the amino acid sequence set forth in SEQ ID NO:367. In some embodiments, the CD28 sdAb contains the amino acid sequence set forth in SEQ ID NO:368. In some embodiments, the CD28 sdAb contains the amino acid sequence set forth in SEQ ID NO:369. In some embodiments, the CD28 sdAb contains the amino acid sequence set forth in SEQ ID NO:370. In some embodiments, the CD28 sdAb contains the amino acid sequence set forth in SEQ ID NO:371. In some embodiments, the CD28 sdAb contains the amino acid sequence set forth in SEQ ID NO:372. In some embodiments, the CD28 sdAb contains the amino acid sequence set forth in SEQ ID NO:373. In some embodiments, the CD28 sdAb contains the amino acid sequence set forth in SEQ ID NO:374. In some embodiments, the CD28 sdAb contains the amino acid sequence set forth in SEQ ID NO:375. In some embodiments, the CD28 sdAb contains the amino acid sequence set forth in SEQ ID NO:376. In some embodiments, the CD28 sdAb contains the amino acid sequence set forth in SEQ ID NO:377. In some embodiments, the CD28 sdAb contains the amino acid sequence set forth in SEQ ID NO:378. In some embodiments, the CD28 sdAb contains the amino acid sequence set forth in SEQ ID NO:379. In some embodiments, the CD28 sdAb contains the amino acid sequence set forth in SEQ ID NO:380. In some embodiments, the CD28 sdAb contains the amino acid sequence set forth in SEQ ID NO:381. In some embodiments, the CD28 sdAb contains the amino acid sequence set forth in SEQ ID NO:382. In some embodiments, the CD28 sdAb contains the amino acid sequence set forth in SEQ ID NO:383. In some embodiments, the CD28 sdAb contains the amino acid sequence set forth in SEQ ID NO:384. In some embodiments, the CD28 sdAb contains the amino acid sequence set forth in SEQ ID NO: and 385.

In some embodiments, the anti-CD28 sdAb is isolated. In some embodiments, the anti-CD28 sdAb is purified.

In some embodiments, the CD28 sdAb comprises an amino acid modification that reduces binding to protein A. In some embodiments, the at least one CD28 sdAb comprises an amino acid modification that reduces binding to protein A. In some embodiments, the at least one CD28 sdAb comprises the amino acid modification G65D by Kabat in framework region 3 (FR3).

Provided herein is a polynucleotide(s) encoding any of the anti-CD28 sdAbs, CD28-binding polypeptides, fusion proteins, and multi-specific binding polypeptide, and multi-specific constructs described herein.

Also provided herein is a polynucleotide, containing a first nucleic acid sequence encoding a first polypeptide of any of the CD28-binding polypeptides provided herein and a second nucleic acid sequence encoding a second polypeptide of the CD28-binding polypeptide. In some embodiments, the first and second nucleic acid sequence are separated by an internal ribosome entry site (IRES), or a nucleic acid encoding a self-cleaving peptide or a peptide that causes ribosome skipping. Also provided herein is a polynucleotide, containing a first nucleic acid sequence encoding a first polypeptide of any of the CD28-binding polypeptides provided herein and a second nucleic acid sequence encoding a second polypeptide of the multispecific construct, wherein the first and second nucleic acid sequence are separated by an internal ribosome entry site (IRES), or a nucleic acid encoding a self-cleaving peptide or a peptide that causes ribosome skipping.

Also provided herein is a polynucleotide, containing a first nucleic acid sequence encoding a first polypeptide of any of the fusion proteins provided herein and a second nucleic acid sequence encoding a second polypeptide of the fusion protein. Also provided herein is a polynucleotide, containing a first nucleic acid sequence encoding a first polypeptide of any of the multi-specific binding polypeptide provided herein and a second nucleic acid sequence encoding a second polypeptide of the multi-specific binding polypeptide. Also provided herein is a polynucleotide, containing a first nucleic acid sequence encoding a first polypeptide of any of the multi-specific construct provided herein and a second nucleic acid sequence encoding a second polypeptide of the multi-specific construct.

In some embodiments, the first and second nucleic acid sequence are separated by an internal ribosome entry site (IRES), or a nucleic acid encoding a self-cleaving peptide or a peptide that causes ribosome skipping. In some embodiments, the first nucleic acid sequence and second nucleic acid sequence are operably linked to the same promoter. In some embodiments, the nucleic acid encoding a self-cleaving peptide or a peptide that causes ribosome skipping is selected from a T2A, a P2A, a E2A or a F2A.

Provided herein is a vector, comprising any of the polynucleotides described herein. In some embodiments, the vector is an expression vector. In some embodiments, the vector is a viral vector or a eukaryotic vector. In some embodiments, the eukaryotic vector is a mammalian vector.

Provided herein is a cell containing any of the polynucleotide or polynucleotides described herein. In some embodiments, the cell is a lymphocyte. In some embodiments, the cell is a T cell or a natural killer (NK) cells.

Provided herein are methods of producing a polypeptide, the method including introducing into a cell any polynucleotide or polynucleotides provided herein or any vector or vectors provided herein and culturing the cell under conditions to produce the anti-CD28 sdAb, CD28-binding polypeptide, fusion protein, multi-specific binding polypeptide, or multi-specific construct. In some embodiments, the method includes isolating or purifying the polypeptide from the cell. Also provided herein is a polypeptide produced by any of the methods described herein.

Provided herein are pharmaceutical compositions comprising any of the anti-CD28 sdAbs, CD28-binding polypeptides, fusion proteins, multi-specific binding polypeptides, and multi-specific constructs described. In some embodiments, the pharmaceutical composition includes a pharmaceutically acceptable carrier. In some embodiments, the pharmaceutical composition is sterile.

Provided herein are methods of stimulating an immune response in a subject, the methods including administering, to a subject in need thereof, any of the CD28 sdAbs, CD28-binding polypeptides, fusion proteins, multi-specific binding polypeptides, and multi-specific constructs or the pharmaceutical compositions described herein. In some embodiments, the immune response is increased against a tumor or cancer. In some embodiments, the method treats a disease or condition in the subject.

Also provided herein are methods of treating a disease or condition in a subject, the methods including administering, to a subject in need thereof, a therapeutically effective amount of any of the anti-CD28 sdAbs, CD28-binding polypeptides, fusion proteins, multi-specific binding polypeptides, and multi-specific constructs or the pharmaceutical compositions described herein.

Also provided herein are uses of any of the anti-CD28 sdAbs, CD28-binding polypeptides, fusion proteins, multi-specific binding polypeptides, and multi-specific constructs, or the pharmaceutical compositions described herein. Provided herein are uses of any of the provided multi-specific binding polypeptides. Provided herein are uses of any of the provided multi-specific constructs. Provided herein are uses of any of the provided pharmaceutical compositions.

Also provided are compositions comprising any of the anti-CD28 sdAbs, CD28-binding polypeptides, fusion proteins, multi-specific binding polypeptides, and multi-specific constructs, or the pharmaceutical compositions described herein for use treating a disease or condition in a subject. Provided herein are compositions comprising the multi-specific binding polypeptides for use in treating a disease or condition in a subject. Provided herein are compositions comprising the multi-specific conjugates for use in treating a disease or condition in a subject.

Also provided are any of the anti-CD28 sdAbs, CD28-binding polypeptides, fusion proteins, multi-specific binding polypeptides, and multi-specific constructs, or the pharmaceutical compositions described herein for use in the manufacture of a medicament for treating a disease or condition in a subject. Provided herein are compositions comprising the multi-specific binding polypeptides for use in the manufacture of a medicament for treating a disease or condition in a subject. Provided herein are compositions comprising the multi-specific conjugates for use in the manufacture of a medicament for treating a disease or condition in a subject.

In some embodiments, the disease or condition is a tumor or a cancer. In some embodiments, the disease or condition is a tumor. In some embodiments, the disease or condition is a cancer. In some embodiments, the subject is a human.

BRIEF DESCRIPTION OF THE DRAWINGS

FIG. 4C depicts the ability of cx694, a bispecific construct targeting PDL1 and CD28, to agonize CD28 on CD3 (IL-2) Jurkat reporter cells in a PDL1-dependent manner, as evidenced by increased activation of the reporter in the presence, but not absence, of PDL1-positive CHO-K1 cells (Promega™) Monospecific constructs individually targeting PDL1 (cx1204) or CD28 (cx698) did not significantly enhance activation of the reporter cell line compared to the untreated control in the presence or absence of the PDL1-expressing target cell line. FIG. 4D depicts the ability of cx8390, a bispecific construct targeting 5T4 and CD28, to agonize CD28 on CD3 (IL-2) Jurkat reporter cells in a 5T4-dependent manner, as evidenced by increased activation of the reporter in the presence, but not absence, of 5T4-positive T47D cells. Treatment of reporter cells alone or a co-culture of T47D cells and reporter cells with a monospecific protein targeting CD28 (cx8394) did not enhance activation of the reporter cell line compared to the untreated control.

FIG. 7A depicts the ability of cx8370, a bispecific construct targeting PDL1 and CD28, to enhance production of IFNγ produced by PBMCs treated with a CEF (Cytomegalovirus, Epstein-Barr virus, and Flu virus) peptide pool as assessed by FluoroSpot. Monospecific constructs individually targeting PDL1 (cx1204) or CD28 (cx984) did not impact the level of cytokine produced by the stimulated PBMCs. FIGS. 7B and 7C depict the ability of cx694, a bispecific construct targeting PDL1 and CD28, to induce production of TNFα by a co-culture of enriched T cells and autologous immature dendritic cells (iDCs). FIG. 7B and FIG. 7C depict responses by two different effector cell donor Leuko Packs. Monospecific constructs individually targeting PDL1 (cx1204) or CD28 (cx698) did not induce a robust cytokine response from either donor.

FIG. 8A and FIG. 8B depict responses by two different PBMC donor Leuko Packs.

DETAILED DESCRIPTION

Figure 1A:
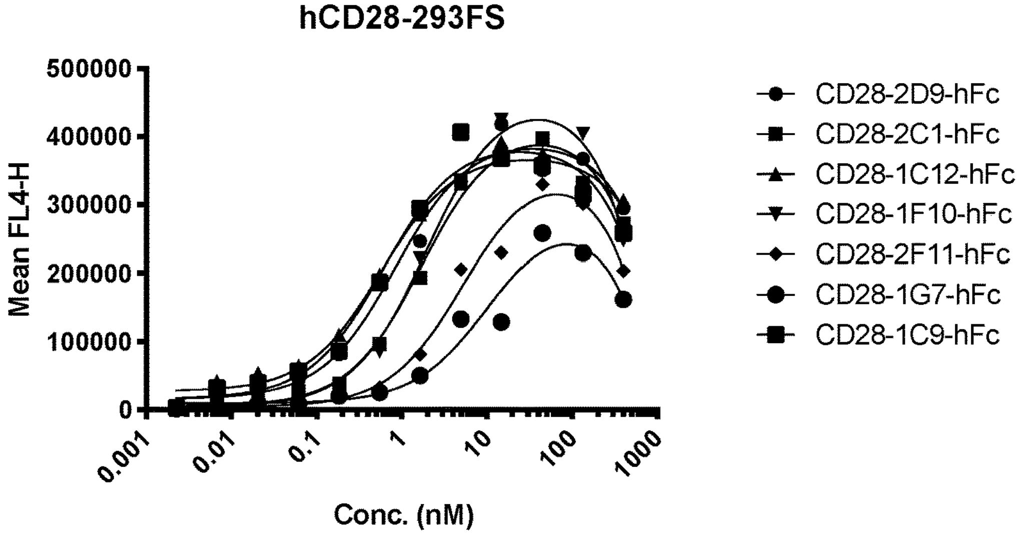
FIG. 1 depicts the ability of CD28-targeting single domain antibodies formatted as sdAb-IgG1 to bind cell-surface CD28. Binding was assessed by flow cytometry using HEK293FS (293FS) cells transiently transfected with full-length human (hCD28) or cynomolgus (cyCD28) antigen (FIGS. 1A and 1B, respectively). As a negative control, binding to CD28− untransfected 293FS cells was also tested (FIG. 1C). The single domain antibody 1C9 was formatted with an Fc domain having reduced effector function as sdAb-xELL and tested for binding to Jurkat cells or primary T cells enriched from PBMCs isolated from normal donor whole blood (FIGS. 1D and 1E, respectively), both of which endogenously express CD28.

Provided herein are polypeptides that specifically bind to CD28, hereinafter also called CD28-binding polypeptides. In some embodiments, the provided binding polypeptides contain at least one single domain antibody (sdAb; e.g. VHH domain) that binds CD28. The CD28-binding polypeptides provided herein include monovalent and multivalent (e.g.

bivalent) constructs. In some embodiments, a CD28-binding polypeptide provided herein contains one, two, three, four, five, six, seven, or eight VHH domains that each individually binds CD28. In some embodiments, a CD28-binding polypeptide provided herein contains one, two, three, or four VHH domains that bind CD28. In some embodiments, a CD28-binding polypeptide provided herein contains two VHH domains that bind CD28. In some embodiments, a CD28-binding polypeptide provided herein contains one VHH domain that binds CD28. In some embodiments, a CD28-binding polypeptide provided herein contains a single VHH domain that binds CD28.

In some embodiments, the CD28-binding polypeptides are monospecific. In some embodiments, the CD28-binding polypeptides are multispecific. For example, provided CD28-binding polypeptides include polypeptides that may contain at least one VHH domain that binds CD28 and one or more additional binding domains, such as one or more additional VHH domains that binds one or more target antigens other than CD28. In particular embodiments, the target antigen is a tumor-associated antigen (TAA).

In some embodiments, the CD28-binding polypeptides are provided as Fc fusion proteins. In some embodiments, a CD28-binding polypeptide contains at least one VHH domain that binds CD28 and an Fc domain. In some embodiments, a CD28-binding polypeptide contains at least one VHH domain that binds CD28, at least one other binding domain (e.g. VHH) that binds to another target antigen (e.g. TAA) and an Fc domain. In some embodiments, an Fc domain mediates dimerization of the CD28-binding polypeptide at physiological conditions such that a dimer is formed that doubles the number of CD28 binding sites and, if present, also may double the number of other antigen binding domains. For example, a CD28-binding polypeptide comprising one VHH domain that binds CD28 and an Fc region is monovalent as a monomer, but at physiological conditions, the Fc region may mediate dimerization, such that the CD28-binding polypeptide exists as a bivalent dimer under such conditions.

CD28 is a homodimeric transmembrane glycoprotein of the immunoglobulin (Ig) superfamily, constitutively expressed by T cells. The primary binding partners of CD28 are CD80 (B7-1) and CD86 (B7-2), which can in turn bind multiple receptors, such as CTLA4. Esensten et al., Immunity (2019) 44(5):973-88. CD28 provides a co-stimulatory, activating signal for T cells that is important for their proliferation and effector function. Id. The CD28 co-stimulation signal provides a secondary signal to potentiate primary signaling by the antigen-receptor complex (TCR/CD3) to activate CD8+ cytotoxic T cells (CTLs), which provide adaptive immune responses against cancer and execute tumor-specific immune responses. Huff et al., International Journal of Molecular Sciences (2019) 20(11):2810. Further, CD8+ T cells with low expression of CD28 have been identified in the context of ineffective CTL-mediated tumor killing. Id.

An exemplary sequence of canonical human CD28 is set forth as follows (SEQ ID NO:86, e.g. Uniprot No. P10747):

MLRLLLALNLFPSIQVTGNKILVKQSPMLVAYDNAVNLSCKYSYNLFSRE

FRASLHKGLDSAVEVCVVYGNYSQQLQVYSKTGFNCDGKLGNESVTFYLQ

NLYVNQTDIYFCKIEVMYPPPYLDNEKSNGTIIHVKGKHLCPSPLFPGPS

-continued

KPFWVLVVVGGVLACYSLLVTVAFIIFWVRSKRSRLLHSDYMNMTPRRPG

PTRKHYQPYAPPRDFAAYRS

Agonism of CD28 has been shown to promote activity of T cells, which may result in an effective immunotherapy to activate an efficient immune response against tumors for treating cancer. However, a problem with certain CD28 agonists is that they may have superagonist activity to result in CD28 agonism independent of TCR signaling. This can, in some cases, cause expansion of T cells in the absence of additional stimuli from the T-cell receptor and a measurable proinflammatory response. For example, the superagnonist monoclonal antibody TGN1412 resulted in a severe cytokine storm in healthy human patients to which it was administered (Suntharalingam et al. N Engl J Med 2006; 355:1018-1028). Thus, there is a need for improved CD28 agonists that are safer.

Provided herein are VHH domains that bind to CD28 but do not exhibit CD28 agonist activity in a monospecific/bivalent format. Such CD28-binding VHH domains can be incorporated in a number of binding formats to exhibit desired immune activity. A variety of CD28 polypeptide binding formats are provided, see e.g. FIGS. 3A and 3B.

Among provided CD28-binding polypeptides are polypeptides that are able to bind and mediate CD28-dependent signaling. In some cases, the provided CD28 binding polypeptides directly engage and/or agonize activity of CD28, which, in some aspects, can be used as a therapeutic to increase T cell antitumor activity.

In particular embodiments, provided herein are multispecific conditional CD28-binding polypeptides containing at least one VHH domain that binds CD28 and at least one binding domain that binds to another antigen, such as a tumor associated antigen (TAA; e.g. PD-L1 or 5T4) or another antigen present in the tumor microenvironment (TME). In some cases, the binding polypeptides include polypeptides that exhibit dual affinity for CD28 and a tumor associated antigen (TAA), such as PDL1 or 5T4. In some cases, the binding polypeptides include polypeptides that exhibit dual affinity for CD28 and another antigen present in the microenvironment, such as a T cell exhaustion marker, a T cell activation marker, or a TME marker. The provided multispecific conditional CD28-binding polypeptides exhibit CD28 agonist activity only when bound to the other antigen present on the surface of a cell (e.g. a tumor cell), and that T cell activity is independent of CD3 engagement. In some aspects, such dual affinity molecules are capable of engaging or activating T cells at the site of a tumor upon binding of a tumor-expressed TAA (e.g., PDL1 or 5T4). In some aspects, such dual affinity molecules are capable of engaging or activating T cells at the site of a tumor upon binding of a T cell-expressed activation or exhaustion marker. In some aspects, such dual affinity molecules are capable of engaging or activating T cells at the site of a tumor upon binding of an antigen expressed by a cell in the TME. In particular, among such molecules provided herein are molecules that exhibit conditional CD28 binding and/or engagement. In some embodiments, the CD28-binding polypeptide is multispecific, and its ability to co-stimulate a T cell is blocked or reduced in the absence of a TAA binding to the multispecific polypeptide. In some embodiments, the multispecific CD28-binding polypeptide can only co-stimulate a T cell when the multispecific polypeptide is bound to a TAA. In some embodiments, the multispecific CD28-binding polypeptide can only co-stimulate a T cell when the multispecific polypeptide is bound to an antigen in the TME.

In some embodiments, the multispecific conditional CD28-binding molecules include formats that are monovalent for CD28 and either monovalent or multivalent (e.g. bivalent) for the other antigen (e.g. TAA). In other embodiments, the multispecific conditional CD28-binding molecules include formats that are multivalent (e.g. bivalent) for CD28 and either monovalent or multivalent (e.g. bivalent) for the other antigen (e.g. TAA). In particular embodiments, provided multispecific conditional CD28-binding polypeptides are provided as a fusion protein with an Fc to result in a dimer of two polypeptide chains.

Also provided herein are T-cell engaging fusion proteins in the form of multispecific polypeptide constructs containing at least one (and typically only one) VHH that binds CD28, a CD3 binding region, and at least one other antigen (e.g. TAA). In particular embodiments, provided T-cell engaging fusion proteins are provided in a format with an Fc region N-terminal to the CD3-binding region. The provided multispecific polypeptide constructs exhibit constrained T-cell engaging activity because such constructs only substantially bind to CD3 once an antigen is bound via the antigen-bind domain. This unique property allows constrained CD3 engaging proteins to distribute to sites where another antigen (e.g. TAA) is present. This format is distinct from other CD3 engaging multispecific constructs, in that constitutive CD3 binding is disallowed or eliminated, providing a significant benefit by avoiding peripheral T-cell binding and permitting superior distribution to the site(s) where antigen is present as recognized by the antigen binding domain. The constrained T-cell engaging activity of the provided multispecific polypeptide constructs is due, in some aspects, to the positioning of the Fc region N-terminal to the CD3-binding region. In some embodiments, such positioning reduces, attenuates, dampens and/or prevents CD3 binding by the CD3 binding region. In the absence of antigen binding by the antigen binding domain, the multispecific polypeptide constructs provided herein demonstrate reduced or eliminated CD3 binding and T-cell activating capacity. The presence of a VHH that binds CD28 in the provided multispecific polypeptide constructs increases or potentiates T cell activity upon co-engagement of CD3 by the CD3 binding region and binding to other antigen (e.g. a TAA).

In any of the provided embodiments, the Fc is an Fc that exhibits reduced immune effector activity, such as via one or more mutations that reduces one or more effector functions such as antibody-dependent cellular cytotoxicity (ADCC), antibody-dependent cellular phagocytosis (ADCP) and/or complement-dependent cytotoxicity (CDC). Exemplary inert or effectorless Fc are described herein.

In some embodiments, the provided CD28-binding polypeptides can be used to stimulate an immune response in a subject, which, in some aspects, treats a disease or disorder, such as a cancer, in the subject. In some aspects, a CD28-binding polypeptide provided herein, such as a multispecific conditional CD28-binding polypeptide, can bind to CD28-expressing T cells and stimulate the T cells to induce antitumor activity. In some cases, the CD28 agonist stimulation and resulting antitumor activity can cause the death of the cancerous cells (e.g., a co-stimulated T cell kills a cancer cell).

Also provided herein are engineered cells, such as engineered T cells, that express any of the provided CD28 binding polypeptides. In some embodiments, the engineered cells produce and secrete a CD28 binding polypeptide.

All publications, including patent documents, scientific articles and databases, referred to in this application are incorporated by reference in their entirety for all purposes to the same extent as if each individual publication were individually incorporated by reference. If a definition set forth herein is contrary to or otherwise inconsistent with a definition set forth in the patents, applications, published applications and other publications that are herein incorporated by reference, the definition set forth herein prevails over the definition that is incorporated herein by reference.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. CURRENT PROTOCOLS IN MOLECULAR BIOLOGY (F. M. Ausubel, et al. eds., (2003)); the series METHODS IN ENZYMOLOGY (Academic Press, Inc.): PCR 2: A PRACTICAL APPROACH (M. J. MacPherson, B. D. Hames and G. R. Taylor eds. (1995)), Harlow and Lane, eds. (1988) ANTIBODIES, A LABORATORY MANUAL, and ANIMAL CELL CULTURE (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M. Zanetti and J. D. Capra, eds., Harwood Academic Publishers, 1995); and Cancer: Principles and Practice of Oncology (V. T. DeVita et al., eds., J.B. Lippincott Company, 1993); and updated versions thereof.

The section headings used herein are for organizational purposes only and are not to be construed as limiting the subject matter described.

I. Definitions

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

It is understood that embodiments of the invention described herein include "consisting" and/or "consisting essentially of" embodiments. As used herein, the singular form "a", "an", and "the" includes plural references unless indicated otherwise. Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X".

The terms "nucleic acid molecule", "nucleic acid" and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides comprised in the nucleic acid molecule or polynucleotide.

The term "isolated polynucleotide" as used herein shall mean a polynucleotide of genomic, cDNA, or synthetic origin or some combination thereof, which by virtue of its origin (1) is not associated with all or a portion of a polynucleotide found in nature, (2) is operably linked to a polynucleotide that it is not linked to in nature, or (3) does not occur in nature as part of a larger sequence.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The term "isolated protein" referred to herein means that a subject protein (1) is free of at least some other proteins with which it would typically be found in nature, (2) is essentially free of other proteins from the same source, e.g., from the same species, (3) is expressed by a cell from a different species, (4) has been separated from at least about 50 percent of polynucleotides, lipids, carbohydrates, or other materials with which it is associated in nature, (5) is not associated (by covalent or noncovalent interaction) with portions of a protein with which the "isolated protein" is associated in nature, (6) is operably associated (by covalent or noncovalent interaction) with a polypeptide with which it is not associated in nature, or (7) does not occur in nature. Such an isolated protein can be encoded by genomic DNA, cDNA, mRNA or other RNA, of may be of synthetic origin, or any combination thereof. In certain embodiments, the isolated protein is substantially pure or substantially free from proteins or polypeptides or other contaminants that are found in its natural environment that would interfere with its use (therapeutic, diagnostic, prophylactic, research or otherwise).

As used herein, "substantially pure" means an object species is the predominant species present (i.e., on a molar basis it is more abundant than any other individual species in the composition), and a substantially purified fraction is a composition wherein the object species comprises at least about 50 percent (on a molar basis) of all macromolecular species present. Generally, a substantially pure composition will comprise more than about 80 percent of all macromolecular species present in the composition, for example, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "specifically binds" to an antigen or epitope is a term that is well understood in the art, and methods to determine such specific binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. A single-domain antibody (sdAb) or VHH-containing polypeptide "specifically binds" or "preferentially binds" to a target if it binds with greater affinity, avidity, more readily, and/or with greater duration than it binds to other substances. For example, a sdAb or VHH-containing polypeptide that specifically or preferentially binds to a CD28 epitope is a sdAb or VHH-containing polypeptide that binds this epitope with greater affinity, avidity, more readily, and/or with greater duration than it binds to other CD28 epitopes or non-CD28 epitopes. It is also understood by reading this definition that; for example, a sdAb or VHH-containing polypeptide that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specificity" refers to the ability of a binding protein to selectively bind an antigen.

As used herein, the term "epitope" refers to a site on a target molecule (for example, an antigen, such as a protein, nucleic acid, carbohydrate or lipid) to which an antigen-binding molecule (for example, a sdAb or VHH-containing polypeptide) binds. Epitopes often include a chemically active surface grouping of molecules such as amino acids, polypeptides or sugar side chains and have specific three-dimensional structural characteristics as well as specific charge characteristics. Epitopes can be formed both from contiguous and/or juxtaposed noncontiguous residues (for example, amino acids, nucleotides, sugars, lipid moiety) of the target molecule. Epitopes formed from contiguous residues (for example, amino acids, nucleotides, sugars, lipid moiety) typically are retained on exposure to denaturing solvents whereas epitopes formed by tertiary folding typically are lost on treatment with denaturing solvents. An epitope may include but is not limited to at least 3, at least 5 or 8-10 residues (for example, amino acids or nucleotides). In some embodiments, an epitope is less than 20 residues (for example, amino acids or nucleotides) in length, less than 15 residues or less than 12 residues. Two antibodies may bind the same epitope within an antigen if they exhibit competitive binding for the antigen. In some embodiments, an epitope can be identified by a certain minimal distance to a CDR residue on the antigen-binding molecule. In some embodiments, an epitope can be identified by the above distance, and further limited to those residues involved in a bond (for example, a hydrogen bond) between a residue of the antigen-binding molecule and an antigen residue. An epitope can be identified by various scans as well, for example an alanine or arginine scan can indicate one or more residues that the antigen-binding molecule can interact with. Unless explicitly denoted, a set of residues as an epitope does not exclude other residues from being part of the epitope for a particular antigen-binding molecule. Rather, the presence of such a set designates a minimal series (or set of species) of epitopes. Thus, in some embodiments, a set of residues identified as an epitope designates a minimal epitope of relevance for the antigen, rather than an exclusive list of residues for an epitope on an antigen.

A "nonlinear epitope" or "conformational epitope" comprises noncontiguous polypeptides, amino acids and/or sugars within the antigenic protein to which an antigen-binding molecule specific to the epitope binds. In some embodiments, at least one of the residues will be noncontiguous with the other noted residues of the epitope; however, one or more of the residues can also be contiguous with the other residues.

A "linear epitope" comprises contiguous polypeptides, amino acids and/or sugars within the antigenic protein to which an antigen-binding molecule specific to the epitope binds. It is noted that, in some embodiments, not every one of the residues within the linear epitope need be directly bound (or involved in a bond) by the antigen-binding molecule. In some embodiments, linear epitopes can be from immunizations with a peptide that effectively consisted of the sequence of the linear epitope, or from structural sections of a protein that are relatively isolated from the remainder of the protein (such that the antigen-binding molecule can interact, at least primarily), just with that sequence section.

The terms "antibody" and "antigen-binding molecule" are used interchangeably in the broadest sense and encompass various polypeptides that comprise antibody-like antigen-binding domains, including but not limited to conventional antibodies (typically comprising at least one heavy chain and at least one light chain), single-domain antibodies (sdAbs, comprising just one chain, which is typically similar to a heavy chain), VHH-containing polypeptides (polypeptides comprising at least one heavy chain only antibody variable domain, or VHH), and fragments of any of the foregoing so long as they exhibit the desired antigen-binding activity. In some embodiments, an antibody comprises a dimerization domain. Such dimerization domains include, but are not limited to, heavy chain constant domains (comprising CH1, hinge, CH2, and CH3, where CH1 typically pairs with a light chain constant domain, CL, while the hinge mediates dimerization) and Fc domains (comprising hinge, CH2, and CH3, where the hinge mediates dimerization).

The term antibody also includes, but is not limited to, chimeric antibodies, humanized antibodies, and antibodies of various species such as camelid (including llama), shark, mouse, human, cynomolgus monkey, etc.

The term "variable region" or "variable domain" refers to the domain of an antibody heavy or light chain that is involved in binding the antibody to antigen. The variable regions of the heavy chain and light chain ($V_H$ and $V_L$, respectively) of a native antibody generally have similar structures, with each domain comprising four conserved framework regions (FRs) and three CDRs. (See, e.g., Kindt et al. Kuby Immunology, 6th ed., W.H. Freeman and Co., page 91 (2007). A single $V_H$ or $V_L$ domain may be sufficient to confer antigen-binding specificity, e.g. a single domain antibody, such as a VHH. Furthermore, antibodies that bind a particular antigen may be isolated using a $V_H$ or $V_L$ domain from an antibody that binds the antigen to screen a library of complementary $V_L$ or $V_H$ domains, respectively. See, e.g., Portolano et al., J. Immunol. 150:880-887 (1993); Clarkson et al., Nature 352:624-628 (1991).

An "antibody fragment" or "antigen-binding fragment" refers to a molecule other than a conventional or intact antibody that comprises a portion of an conventional or intact antibody containing at least a variable region that binds an antigen. Examples of antibody fragments include but are not limited to Fv, single chain Fvs (sdFvs), Fab, Fab', Fab'-SH, $F(ab')_2$; diabodies; linear antibodies; an single-domain antibodies comprising only the $V_H$ region (VHH).

As used herein, "monovalent" with reference to a binding molecule refers to binding molecules that have a single antigen recognition site that is specific for a target antigen. Examples of monovalent binding molecules include, for example, a monovalent antibody fragment, a proteinaceous binding molecule with antibody-like binding properties or an MHC molecule. Examples of monovalent antibody fragments include, but are not limited to, a Fab fragment, an Fv fragment, and a single-chain Fv fragment (scFv).

As used herein, "monovalent" with reference to a binding molecule refers to a binding molecule that has multiple (more than one) antigen recognition sites that are specific for a target antigen.

The terms "single domain antibody", "sdAb," "VHH" are used interchangeably herein to refer to an antibody having a single monomeric domain antigen binding/recognition domain. Such antibodies include a camelid antibody or shark antibody. In some embodiments, a VHH comprises three CDRs and four framework regions, designated FR1, CDR1, FR2, CDR2, FR3, CDR3, and FR4. In some embodiments, a VHH may be truncated at the N-terminus or C-terminus such that it comprise only a partial FR1 and/or FR4, or lacks one or both of those framework regions, so long as the VHH substantially maintains antigen binding and specificity.

The term "VHH-containing polypeptide" refers to a polypeptide that comprises at least one VHH domain. In some embodiments, a VHH polypeptide comprises two, three, or four or more VHH domains, wherein each VHH domain may be the same or different. In some embodiments, a VHH-containing polypeptide comprises an Fc domain. In some such embodiments, the VHH polypeptide may form a dimer. Nonlimiting structures of VHH-containing polypeptides include $VHH_1$-Fc, $VHH_1$-$VHH_2$-Fc, and $VHH_1$-$VHH_2$-$VHH_3$-Fc, wherein $VHH_1$, $VHH_2$, and $VHH_3$ may be the same or different. In some embodiments of such structures, one VHH may be connected to another VHH by a linker, or one VHH may be connected to the Fc by a linker. In some such embodiments, the linker comprises 1-20 amino acids, preferably 1-20 amino acids predominantly composed of glycine and, optionally, serine. In some embodiments, when a VHH-containing polypeptide comprises an Fc, it forms a dimer. Thus, the structure $VHH_1$-$VHH_2$-Fc, if it forms a dimer, is considered to be tetravalent (i.e., the dimer has four VHH domains). Similarly, the structure $VHH_1$-$VHH_2$-$VHH_3$-Fc, if it forms a dimer, is considered to be hexavalent (i.e., the dimer has six VHH domains).

As used herein, a CD28-binding polypeptide is a polypeptide or protein that specifically binds CD28. Typically, a CD28-binding polypeptide herein is a VHH-containing polypeptide containing at least one VHH domain that binds CD28. A CD28-binding polypeptide includes conjugates, including fusion proteins. A CD28-binding polypeptide includes fusion proteins, including those containing an Fc domain. In some embodiments, a CD28-binding polypeptide contains two, three, or four or more VHH domains that each specifically bind to CD28, wherein each VHH domain may be the same or different. In some embodiments, a CD28-binding polypeptide is multivalent. In some embodiments, a CD28-binding polypeptide is multispecific. In some cases, a CD28-binding polypeptide may contain one or more additional domains that bind to one or more further or additional antigens other than CD28.

The term "monoclonal antibody" refers to an antibody (including an sdAb or VHH-containing polypeptide) of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, Nature 348:552-554, for example.

The term "CDR" denotes a complementarity determining region as defined by at least one manner of identification to one of skill in the art. The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme); Al-Lazikani et al., (1997) JMB 273, 927-948 ("Chothia" numbering scheme); MacCallum et al., J. Mol. Biol. 262:732-745 (1996), "Antibody-antigen interactions: Contact analysis and binding site topography," J. Mol. Biol. 262, 732-745." ("Contact" numbering scheme); Lefranc M P et al., "IMGT unique numbering for immunoglobulin and T cell receptor variable domains and Ig superfamily V-like domains," Dev Comp Immunol, 2003 January; 27(1):55-77 ("IMGT" numbering scheme); Honegger A and Plückthun A, "Yet another numbering scheme for immunoglobulin variable domains: an automatic modeling and analysis tool," J Mol Biol, 2001 June 8; 309(3):657-70, ("Aho" numbering scheme); and Martin et al., "Modeling antibody hypervariable loops: a combined algorithm," PNAS, 1989, 86(23):9268-9272, ("AbM" numbering scheme).

The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. The AbM scheme is a compromise between Kabat and Chothia definitions based on that used by Oxford Molecular's AbM antibody modeling software.

In some embodiments, CDRs can be defined in accordance with any of the Chothia numbering schemes, the Kabat numbering scheme, a combination of Kabat and Chothia, the AbM definition, and/or the contact definition. A VHH comprises three CDRs, designated CDR1, CDR2, and CDR3. Table 1, below, lists exemplary position boundaries of CDR-H1, CDR-H2, CDR-H3 as identified by Kabat, Chothia, AbM, and Contact schemes, respectively. For CDR-H1, residue numbering is listed using both the Kabat and Chothia numbering schemes. FRs are located between CDRs, for example, with FR-H1 located before CDR-H1, FR-H2 located between CDR-H1 and CDR-H2, FR-H3 located between CDR-H2 and CDR-H3 and so forth. It is noted that because the shown Kabat numbering scheme places insertions at H35A and H35B, the end of the Chothia CDR-H1 loop when numbered using the shown Kabat numbering convention varies between H32 and H34, depending on the length of the loop.

TABLE 1

Boundaries of CDRs according to various numbering schemes.

| CDR | Kabat | Chothia | AbM | Contact |
|---|---|---|---|---|
| CDR-H1 (Kabat Numbering[1]) | H31--H35B | H26--H32 . . . 34 | H26--H35B | H30--H35B |
| CDR-H1 (Chothia Numbering[2]) | H31--H35 | H26--H32 | H26--H35 | H30--H35 |
| CDR-H2 | H50--H65 | H52--H56 | H50--H58 | H47--H58 |
| CDR-H3 | H95--H102 | H95--H102 | H95--H102 | H93--H101 |

[1]Kabat et al. (1991), "Sequences of Proteins of Immunological Interest," 5th Ed. Public Health Service, National Institutes of Health, Bethesda, MD
[2]Al-Lazikani et al., (1997) JMB 273, 927-948

Thus, unless otherwise specified, a "CDR" or "complementary determining region," or individual specified CDRs (e.g., CDR-H1, CDR-H2, CDR-H3), of a given antibody or region thereof, such as a variable region thereof, should be understood to encompass a (or the specific) complementary determining region as defined by any of the aforementioned schemes. For example, where it is stated that a particular CDR (e.g., a CDR-H3) contains the amino acid sequence of a corresponding CDR in a given VHH amino acid sequence, it is understood that such a CDR has a sequence of the corresponding CDR (e.g., CDR-H3) within the VHH, as defined by any of the aforementioned schemes. In some embodiments, specific CDR sequences are specified. Exemplary CDR sequences of provided antibodies are described using various numbering schemes (see e.g. Table 1), although it is understood that a provided antibody can include CDRs as described according to any of the other aforementioned numbering schemes or other numbering schemes known to a skilled artisan.

As used herein, "conjugate," "conjugation" or grammatical variations thereof refers the joining or linking together of two or more compounds resulting in the formation of another compound, by any joining or linking methods known in the art. It can also refer to a compound which is generated by the joining or linking together two or more compounds. For example, a VHH domain linked directly or indirectly to one or more chemical moieties or polypeptide is an exemplary conjugate. Such conjugates include fusion proteins, those produced by chemical conjugates and those produced by any other methods.

An immunoglobulin Fc fusion ("Fc-fusion"), such as VHH-Fc, is a molecule comprising one or more VHH domains operably linked to an Fc region of an immunoglobulin. An immunoglobulin Fc region may be linked indirectly or directly to one or more VHH domains. Various linkers are known in the art and can optionally be used to link an Fc to a fusion partner to generate an Fc-fusion. In some such embodiments, the linker comprises 1-20 amino acids, preferably 1-20 amino acids predominantly composed of glycine and, optionally, serine. Fc-fusions of identical species can be dimerized to form Fc-fusion homodimers, or using non-identical species to form Fc-fusion heterodimers. In some embodiments, the Fc is a mammalian Fc such as human Fc.

The term "heavy chain constant region" as used herein refers to a region comprising at least three heavy chain constant domains, $C_H1$, hinge, $C_H2$, and $C_H3$. Of course, non-function-altering deletions and alterations within the domains are encompassed within the scope of the term "heavy chain constant region," unless designated otherwise. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $\gamma_1$ constant region), IgG2 (comprising a $\gamma_2$ constant region), IgG3 (comprising a $\gamma_3$ constant region), and IgG4 (comprising a $\gamma_4$ constant region) antibodies; IgA antibodies include, but are not limited to, IgA1 (comprising an $\alpha_1$ constant region) and IgA2 (comprising an $\alpha_2$ constant region) antibodies; and IgM antibodies include, but are not limited to, IgM1 and IgM2.

A "Fc region" as used herein refers to a portion of a heavy chain constant region comprising CH2 and CH3. In some embodiments, an Fc region comprises a hinge, CH2, and CH3. In various embodiments, when an Fc region comprises a hinge, the hinge mediates dimerization between two Fc-containing polypeptides. An Fc region may be of any antibody heavy chain constant region isotype discussed herein. In some embodiments, an Fc region is an IgG1, IgG2, IgG3, or IgG4.

A "functional Fc region" possesses an "effector function" of a native sequence Fc region. Exemplary "effector functions" include Fc receptor binding; C1q binding and complement dependent cytotoxicity (CDC); Fc receptor binding; antibody-dependent cell-mediated cytotoxicity (ADCC); phagocytosis; down regulation of cell surface receptors (for example B-cell receptor); and B-cell activation, etc. Such effector functions generally require the Fc region to be combined with a binding domain (for example, an antibody variable domain) and can be assessed using various assays.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In some embodiments, a "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, for example, from about one to about ten amino acid substitutions, and preferably, from about one to about five amino acid substitutions in a native sequence Fc region or in the Fc region of the parent polypeptide. In some embodiments, the variant Fc region herein will possess at least about 80% sequence identity with a native sequence Fc region and/or with an Fc region of a parent polypeptide, at least about 90% sequence identity therewith, at least about 95%, at least about 96%, at least about 97%, at least about 98%, or at least about 99% sequence identity therewith.

In general, the numbering of the residues in an immunoglobulin heavy chain or portion thereof, such as an Fc region, is that of the EU index as in Kabat et al., Sequences of Proteins of Immunological Interest, 5th Ed. Public Health Service, National Institutes of Health, Bethesda, Md. (1991). The "EU index as in Kabat" refers to the residue numbering of the human IgG1 EU antibody.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. (See, for example, Daeron, Annu. Rev. Immunol. 15:203-234 (1997)). FcRs are reviewed, for example, in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. For example, the term "Fc receptor" or "FcR" also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)) and regulation of homeostasis of immunoglobulins. Methods of measuring binding to FcRn are known (see, for example, Ghetie and Ward, *Immunol. Today* 18(12):592-598 (1997);

Ghetie et al., *Nature Biotechnology,* 15(7):637-640 (1997); Hinton et al., *J. Biol. Chem.* 279(8):6213-6216 (2004); WO 2004/92219 (Hinton et al.).

An "acceptor human framework" as used herein is a framework comprising the amino acid sequence of a heavy chain variable domain ($V_H$) framework derived from a human immunoglobulin framework or a human consensus framework, as discussed herein. An acceptor human framework derived from a human immunoglobulin framework or a human consensus framework can comprise the same amino acid sequence thereof, or it can contain amino acid sequence changes. In some embodiments, the number of amino acid changes are fewer than 10, or fewer than 9, or fewer than 8, or fewer than 7, or fewer than 6, or fewer than 5, or fewer than 4, or fewer than 3, across all of the human frameworks in a single antigen binding domain, such as a VHH.

As used herein, a "chimeric antigen receptor" or "CAR" refers to an engineered receptor, which introduces an antigen specificity, via an antigen binding domain, onto cells to which it is engineered (for example T cells such as naive T cells, central memory T cells, effector memory T cells or combination thereof) thus combining the antigen binding properties of the antigen binding domain with the T cell activity (e.g. lytic capacity and self renewal) of T cells. A CAR typically includes an extracellular antigen-binding domain (ectodomain), a transmembrane domain and an intracellular signaling domain. The intracellular signaling domain generally contains at least one ITAM signaling domain, e.g. derived from CD3zeta, and optionally at least one costimulatory signaling domain, e.g. derived from CD28 or 4-1BB. In a CAR provided herein, a VHH domain forms the antigen binding domain and is located at the extracellular side when expressed in a cell.

"Affinity" refers to the strength of the sum total of noncovalent interactions between a single binding site of a molecule (for example, an antibody or VHH-containing polypeptide) and its binding partner (for example, an antigen). The affinity or the apparent affinity of a molecule X for its partner Y can generally be represented by the dissociation constant ($K_D$) or the $K_{D\text{-}apparent}$, respectively. Affinity can be measured by common methods known in the art (such as, for example, ELISA $K_D$, KinExA, flow cytometry, and/or surface plasmon resonance devices), including those described herein. Such methods include, but are not limited to, methods involving BIAcore®, Octet®, or flow cytometry.

The term "$K_D$", as used herein, refers to the equilibrium dissociation constant of an antigen-binding molecule/antigen interaction. When the term "$_K$D" is used herein, it includes $K_D$ and $K_{D\text{-}apparent}$.

In some embodiments, the $K_D$ of the antigen-binding molecule is measured by flow cytometry using an antigen-expressing cell line and fitting the mean fluorescence measured at each antibody concentration to a non-linear one-site binding equation (Prism Software graphpad). In some such embodiments, the $K_D$ is $K_{D\text{-}apparent}$.

The term "biological activity" refers to any one or more biological properties of a molecule (whether present naturally as found in vivo, or provided or enabled by recombinant means). Biological properties include, but are not limited to, binding a ligand, inducing or increasing cell proliferation (such as T cell proliferation), and inducing or increasing expression of cytokines.

An "affinity matured" VHH-containing polypeptide refers to a VHH-containing polypeptide with one or more alterations in one or more CDRs compared to a parent VHH-containing polypeptide that does not possess such alterations, such alterations resulting in an improvement in the affinity of the VHH-containing polypeptide for antigen.

A "humanized VHH" as used herein refers to a VHH in which one or more framework regions have been substantially replaced with human framework regions. In some instances, certain framework region (FR) residues of the human immunoglobulin are replaced by corresponding non-human residues. Furthermore, the humanized VHH can comprise residues that are found neither in the original VHH nor in the human framework sequences, but are included to further refine and optimize VHH or VHH-containing polypeptide performance. In some embodiments, a humanized VHH-containing polypeptide comprises a human Fc region. As will be appreciated, a humanized sequence can be identified by its primary sequence and does not necessarily denote the process by which the antibody was created.

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide.

As used herein, "percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table 2. Amino acid substitutions may be introduced into an antibody of interest and the products screened for a desired activity, for example, retained/improved antigen binding, decreased immunogenicity, or improved ADCC or CDC.

TABLE 2

| Original Residue | Exemplary Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:

(1) hydrophobic: Norleucine, Met, Ala, Val, Leu, Ile;

(2) neutral hydrophilic: Cys, Ser, Thr, Asn, Gln;

(3) acidic: Asp, Glu;

(4) basic: His, Lys, Arg;

(5) residues that influence chain orientation: Gly, Pro;

(6) aromatic: Trp, Tyr, Phe.

Non-conservative substitutions will entail exchanging a member of one of these classes for another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E, CHO-DG44, CHO-K1, CHO-S, and CHO-DS cells. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) a provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated".

The terms "individual" and "subject" are used interchangeably herein to refer to an animal; for example a mammal. The term patient includes human and veterinary subjects. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. The subject can be male or female and can be any suitable age, including infant, juvenile, adolescent, adult, and geriatric subjects. In some examples, an "individual" or "subject" refers to an individual or subject in need of treatment for a disease or disorder. In some embodiments, the subject to receive the treatment can be a patient, designating the fact that the subject has been identified as having a disorder of relevance to the treatment, or being at adequate risk of contracting the disorder. In particular embodiments, the subject is a human, such as a human patient.

A "disease" or "disorder" as used herein refers to a condition where treatment is needed and/or desired.

The term "tumor cell", "cancer cell", "cancer", "tumor", and/or "neoplasm", unless otherwise designated, are used herein interchangeably and refer to a cell (or cells) exhibiting an uncontrolled growth and/or abnormal increased cell survival and/or inhibition of apoptosis which interferes with the normal functioning of bodily organs and systems. Included in this definition are benign and malignant cancers, polyps, hyperplasia, as well as dormant tumors or micrometastases.

The terms "cancer" and "tumor" encompass solid and hematological/lymphatic cancers and also encompass malignant, pre-malignant, and benign growth, such as dysplasia. Also, included in this definition are cells having abnormal proliferation that is not impeded (e.g. immune evasion and immune escape mechanisms) by the immune system (e.g. virus infected cells). Exemplary cancers include, but are not limited to: adrenal cancer, astrocytoma, basal cell carcinoma, biliary tract cancer; bladder cancer; bone cancer; brain and central nervous system cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); melanoma; myeloma; neuroblastoma; oral cavity cancer (lip, tongue, mouth, and pharynx); ovarian cancer; pancreatic cancer; pituitary gland cancer, prostate cancer; retinoblastoma; rhabdomyo sarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; lymphoma including Hodgkin's and non-Hodgkin's lymphoma, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia; chronic lymphocytic leukemia (CLL); acute lymphoblastic leukemia (ALL); Hairy cell leukemia; chronic myeloblastic leukemia; as well as other carcinomas and sarcomas; and post-transplant lymphoproliferative disorder (PTLD), as well as abnormal vascular proliferation associated with phakomatoses, edema (such as that associated with brain tumors), and Meigs' syndrome.

The term "non-tumor cell" as used herein refers to a normal cells or tissue. Exemplary non-tumor cells include, but are not limited to: T-cells, B-cells, natural killer (NK) cells, natural killer T (NKT) cells, dendritic cells, monocytes, macrophages, epithelial cells, fibroblasts, hepatocytes, interstitial kidney cells, fibroblast-like synoviocytes, osteoblasts, and cells located in the breast, skeletal muscle, pancreas, stomach, ovary, small intestines, placenta, uterus, testis, kidney, lung, heart, brain, liver, prostate, colon, lymphoid organs, bone, and bone-derived mesenchymal stem cells. The term "a cell or tissue located in the periphery" as used herein refers to non-tumor cells not located near tumor cells and/or within the tumor microenvironment.

The term "cells or tissue within the tumor microenvironment" as used herein refers to the cells, molecules, extracellular matrix and/or blood vessels that surround and/or feed a tumor cell. Exemplary cells or tissue within the tumor microenvironment include, but are not limited to: tumor vasculature; tumor-infiltrating lymphocytes; fibroblast reticular cells; endothelial progenitor cells (EPC); cancer-associated fibroblasts; pericytes; other stromal cells; components of the extracellular matrix (ECM); dendritic cells; antigen presenting cells; T-cells; regulatory T-cells (Treg cells); macrophages; neutrophils; myeloid-derived suppressor cells (MDSCs) and other immune cells located proximal to a tumor. Methods for identifying tumor cells, and/or cells/tissues located within the tumor microenvironment are well known in the art, as described herein, below.

In some embodiments, an "increase" or "decrease" refers to a statistically significant increase or decrease, respectively. As will be clear to the skilled person, "modulating" can also involve effecting a change (which can either be an increase or a decrease) in affinity, avidity, specificity and/or selectivity of a target or antigen, for one or more of its ligands, binding partners, partners for association into a homomultimeric or heteromultimeric form, or substrates; effecting a change (which can either be an increase or a decrease) in the sensitivity of the target or antigen for one or more conditions in the medium or surroundings in which the target or antigen is present (such as pH, ion strength, the presence of co-factors, etc.); and/or cellular proliferation or cytokine production, compared to the same conditions but without the presence of a test agent. This can be determined in any suitable manner and/or using any suitable assay known per se or described herein, depending on the target involved.

As used herein, "an immune response" is meant to encompass cellular and/or humoral immune responses that are sufficient to inhibit or prevent onset or ameliorate the symptoms of disease (for example, cancer or cancer metastasis). "An immune response" can encompass aspects of both the innate and adaptive immune systems.

As used herein, the terms "treating," "treatment," or "therapy" of a disease, disorder or condition is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

As used herein in the context of cancer, the terms "treatment" or, "inhibit," "inhibiting" or "inhibition" of cancer refers to at least one of: a statistically significant decrease in the rate of tumor growth, a cessation of tumor growth, or a reduction in the size, mass, metabolic activity, or volume of the tumor, as measured by standard criteria such as, but not limited to, the Response Evaluation Criteria for Solid Tumors (RECIST), or a statistically significant increase in progression free survival (PFS) or overall survival (OS).

"Ameliorating" means a lessening or improvement of one or more symptoms as compared to not administering a therapeutic agent. "Ameliorating" also includes shortening or reduction in duration of a symptom.

"Preventing," "prophylaxis," or "prevention" of a disease or disorder refers to administration of a pharmaceutical composition, either alone or in combination with another compound, to prevent the occurrence or onset of a disease or disorder or some or all of the symptoms of a disease or disorder or to lessen the likelihood of the onset of a disease or disorder.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In some embodiments, by "reduce" or "inhibit" is meant the ability to cause an overall decrease of 10% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control over the same period of time.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. Unless otherwise specified, the terms "reduce", "inhibit", or "prevent" do not denote or require complete prevention over all time, but just over the time period being measured.

The term "anti-cancer agent" is used herein in its broadest sense to refer to agents that are used in the treatment of one or more cancers. Exemplary classes of such agents in include, but are not limited to, chemotherapeutic agents, anti-cancer biologics (such as cytokines, receptor extracellular domain-Fc fusions, and antibodies), radiation therapy, CAR-T therapy, therapeutic oligonucleotides (such as antisense oligonucleotides and siRNAs) and oncolytic viruses.

The term "biological sample" means a quantity of a substance from a living thing or formerly living thing. Such substances include, but are not limited to, blood, (for example, whole blood), plasma, serum, urine, amniotic fluid, synovial fluid, endothelial cells, leukocytes, monocytes, other cells, organs, tissues, bone marrow, lymph nodes and spleen.

The term "control" or "reference" refers to a composition known to not contain an analyte ("negative control") or to contain an analyte ("positive control"). A positive control can comprise a known concentration of analyte.

The terms "effective amount" or "therapeutically effective amount" refer to a quantity and/or concentration of a composition containing an active ingredient (e.g. sdAb or VHH-containing polypeptide) that when administered into a patient either alone (i.e., as a monotherapy) or in combination with additional therapeutic agents, yields a statistically significant decrease in disease progression as, for example, by ameliorating or eliminating symptoms and/or the cause of the disease. An effective amount may be an amount that relieves, lessens, or alleviates at least one symptom or biological response or effect associated with a disease or disorder, prevents progression of the disease or disorder, or improves physical functioning of the patient. A therapeutically effective amount of a composition containing an active agent may vary according to factors such as the disease state, age, sex, and weight of the individual, and the ability of the active agent to elicit a desired response in the individual. A therapeutically effective amount is also one in which any toxic or detrimental effects of the active agent are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result.

As used herein, a composition refers to any mixture of two or more products, substances, or compounds, including cells. It may be a solution, a suspension, liquid, powder, a paste, aqueous, non-aqueous or any combination thereof.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Hence, it is a composition suitable for pharmaceutical use in a mammalian subject, often a human. A pharmaceutical composition typically comprises an effective amount of an active agent (e.g., sdAb or VHH-containing polypeptide) and a carrier, excipient, or diluent. The carrier, excipient, or diluent is typically a pharmaceutically acceptable carrier, excipient or diluent, respectively. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and are compatible with other ingredients of the formulation. The pharmaceutically acceptable carrier is appropriate for the formulation employed.

Administration "in combination with" one or more further therapeutic agents includes simultaneous (concurrent) and sequential administration in any order.

The term "concurrently" is used herein to refer to administration of two or more therapeutic agents, where at least part of the administration overlaps in time, or where the administration of one therapeutic agent falls within a short period of time relative to administration of the other therapeutic agent, or wherein the therapeutic effect of both agents overlap for at least a period of time.

The term "sequentially" is used herein to refer to administration of two or more therapeutic agents that does not overlap in time, or wherein the therapeutic effects of the agents do not overlap.

As used herein, "in conjunction with" refers to administration of one treatment modality in addition to another treatment modality. As such, "in conjunction with" refers to administration of one treatment modality before, during, or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (for example, a package or container) or kit comprising at least one reagent, for example, a medicament for treatment of a disease or disorder (for example, cancer), or a probe for specifically detecting a biomarker described herein. In some embodiments, the manufacture or kit is promoted, distributed, or sold as a unit for performing the methods described herein.

The terms "label" and "detectable label" mean a moiety attached, for example, to an antibody or antigen to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^{3}H$ $^{14}C$, $^{35}S$, $^{90}Y$, $^{99}Tc$, $^{111}In$, $^{125}I$, $^{131}I$, $^{177}Lu$, $^{166}Ho$, or $^{153}Sm$); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

II. Single Domain Antibodies (e.g. VHH Domains) Binding CD28

Provided herein are CD28-binding polypeptides that are single domain antibody (sdAb; e.g. VHH)-containing polypeptides containing at least one sdAb (e.g. VHH domain) that specifically binds to CD28. In some embodiments, the sdAb is a VHH. In some embodiments, the VHH domain binds human CD28. In some of any of the provided embodiments, the VHH domain binds CD28 having the sequence set forth in SEQ ID NO:86 or a mature form thereof.

In some embodiments, the VHH-containing polypeptides incorporate multiple copies of a VHH domain provided herein. In such embodiments, the VHH-containing polypeptide may incorporate multiple copies of the same VHH domain. In some embodiments, the VHH-containing polypeptides may incorporate multiple copies of a VHH domain that are different but that recognize the same epitope on CD28. The VHH-containing polypeptides can be formatted in a variety of formats, including any as described in Section III below.

A VHH domain is an antibody fragment that is a single monomeric variable antibody domain that is able to bind selectively to a specific antigen. With a molecular weight of only 12-15 kDa, VHH domains (also called single-domain antibodies) are much smaller than common antibodies (150-160 kDa) which are composed of two heavy protein chains and two light chains, and even smaller than Fab fragments (~50 kDa, one light chain and half a heavy chain) and single-chain variable fragments (~25 kDa, two variable domains, one from a light and one from a heavy chain).

Single domain antibodies are antibodies whose complementary determining regions are part of a single domain polypeptide. Examples include, but are not limited to, heavy chain antibodies, antibodies naturally devoid of light chains, single domain antibodies derived from conventional 4-chain antibodies, engineered antibodies and single domain scaffolds other than those derived from antibodies. Single domain antibodies may be derived from any species including, but not limited to mouse, human, camel, llama, alpaca, vicuna, guanaco, shark, goat, rabbit, and/or bovine. In some embodiments, a single domain antibody as used herein is a naturally occurring single domain antibody known as heavy chain antibody devoid of light chains. For clarity reasons, this variable domain derived from a heavy chain antibody naturally devoid of light chain is known herein as a VHH to distinguish it from the conventional VH of four chain immunoglobulins. Such a VHH molecule can be derived from antibodies raised in Camelidae species, for example in camel, llama, dromedary, alpaca, vicuna and guanaco. Other species besides Camelidae may produce heavy chain antibodies naturally devoid of light chain; such VHHs are within the scope of the disclosure.

Methods for the screening of VHH domains, including VHH-binding polypeptides, that possess the desired specificity for CD28 include, but are not limited to, enzyme linked immunosorbent assay (ELISA), enzymatic assays, flow cytometry, and other immunologically mediated techniques known within the art.

Among the provided VHH domains provided herein are CD28 VHH (llama-derived) and humanized sequences, such as any described below.

In some embodiments, a VHH domain that binds CD28 may be humanized. Humanized antibodies (such as VHH-containing polypeptides) are useful as therapeutic molecules because humanized antibodies reduce or eliminate the human immune response to non-human antibodies, which can result in an immune response to an antibody therapeutic, and decreased effectiveness of the therapeutic. Generally, a humanized antibody comprises one or more variable domains in which CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (for example, the antibody from which the CDR residues are derived), for example, to restore or improve antibody specificity or affinity.

Humanized antibodies and methods of making them are reviewed, for example, in Almagro and Fransson, (2008) Front. Biosci. 13: 1619-1633, and are further described, for example, in Riechmann et al., (1988) Nature 332:323-329; Queen et al., (1989) Proc. Natl Acad. Sci. USA 86: 10029-10033; U.S. Pat. Nos. 5,821,337, 7,527,791, 6,982,321, and 7,087,409; Kashmiri et al., (2005) Methods 36:25-34; Padlan, (1991) Mol. Immunol. 28:489-498 (describing “resurfacing”); Dall’Acqua et al., (2005) Methods 36:43-60 (describing “FR shuffling”); and Osbourn et al., (2005) Methods 36:61-68 and Klimka et al., (2000) Br. J. Cancer, 83:252-260 (describing the “guided selection” approach to FR shuffling).

Human framework regions that can be used for humanization include but are not limited to: framework regions selected using the “best-fit” method (see, for example, Sims et al. (1993) J. Immunol. 151:2296); framework regions derived from the consensus sequence of human antibodies of a particular subgroup of heavy chain variable regions (see, for example, Carter et al. (1992) Proc. Natl. Acad. Sci. USA, 89:4285; and Presta et al. (1993) J. Immunol, 151:2623); human mature (somatically mutated) framework regions or human germline framework regions (see, for example, Almagro and Fransson, (2008) Front. Biosci. 13:1619-1633); and framework regions derived from screening FR libraries (see, for example, Baca et al., (1997) J. Biol. Chem. 272: 10678-10684 and Rosok et al., (1996) J. Biol. Chem. 271:22611-22618). Typically, the FR regions of a VHH are replaced with human FR regions to make a humanized VHH. In some embodiments, certain FR residues of the human FR are replaced in order to improve one or more properties of the humanized VHH. VHH domains with such replaced residues are still referred to herein as “humanized.”

Provided herein is a VHH domain that binds CD28 in which the VHH domain comprises a CDR1, CDR2, and CDR3 contained in a VHH amino acid sequence selected from any one of SEQ ID NO:186-188, 213-239, and 280, or an amino acid sequence that has at least 90%, 91%, 92%, 93%, 94%, 95%, 96%, 97%, 98%, or 99% sequence identity to the VHH region amino acid selected from any one of SEQ ID NOs:186-188, 213-239, and 280. In some embodiments, a CD28 VHH domain provided herein contains a CDR1 set forth in any one of SEQ ID NOS:189, 192, 195, and 198-201, a CDR2 set forth in any one of SEQ ID NOS:190, 193, 196, and 202-212, and a CDR3 set forth in any one of SEQ ID NOS:191, 194, and 197.

Also provided herein is a VHH domain that binds CD28 in which the VHH domain comprises a CDR1, CDR2, and CDR3 contained in a VHH amino acid sequence selected from any one of SEQ ID NO:186-188, 213-239, 280, and 342-385, or an amino acid sequence that has at least 90%, 91%, 92%, 93%, 94%, 95%, 96%, 97%, 98%, or 99% sequence identity to the VHH region amino acid selected from any one of SEQ ID NOs:186-188, 213-239, 280, and 342-385. In some embodiments, a CD28 VHH domain provided herein contains a CDR1 set forth in any one of SEQ ID NOS:189, 192, 195, and 198-201; a CDR2 set forth in any one of SEQ ID NOS:190, 193, 196, 202-212, and 386-395; and a CDR3 set forth in any one of SEQ ID NOS:191, 194, 197, and 396-398.

Also provided herein is a VHH domain that binds CD28 in which the VHH domain comprises a CDR1, CDR2, and CDR3 contained in a VHH amino acid sequence selected from any one of SEQ ID NO:186-188, 213-219, 221-239, and 280, or an amino acid sequence that has at least 90%, 91%, 92%, 93%, 94%, 95%, 96%, 97%, 98%, or 99% sequence identity to the VHH region amino acid selected from any one of SEQ ID NOs:186-188, 213-219, 221-239, and 280. In some embodiments, a CD28 VHH domain provided herein contains a CDR1 set forth in any one of SEQ ID NOS:189, 192, 195, and 198-201, a CDR2 set forth in any one of SEQ ID NOS:190, 193, 196, 202, and 204-212, and a CDR3 set forth in any one of SEQ ID NOS:191, 194, and 197.

Also provided herein is a VHH domain that binds CD28 in which the VHH domain comprises a CDR1, CDR2, and CDR3 contained in a VHH amino acid sequence selected from any one of SEQ ID NO:186-188, 213-219, 221-239, 280, and 342-385, or or an amino acid sequence that has at least 90%, 91%, 92%, 93%, 94%, 95%, 96%, 97%, 98%, or 99% sequence identity to the VHH region amino acid selected from any one of SEQ ID NOs:186-188, 213-219, 221-239, 280, and 342-385. In some embodiments, a CD28 VHH domain provided herein contains a CDR1 set forth in any one of SEQ ID NOS:189, 192, 195, and 198-201; a CDR2 set forth in any one of SEQ ID NOS:190, 193, 196, 202, 204-212, and 386-395; and a CDR3 set forth in any one of SEQ ID NOS:191, 194, 197, 396, 397, and 398.

In some embodiments, a CD28 VHH domain has the amino acid sequence set forth in any of SEQ ID NOS:186-188, 213-239, and 280, or an amino acid sequence that has at least 90%, 91%, 92%, 93%, 94%, 95%, 96%, 97%, 98%, or 99% sequence identity to the VHH region amino acid selected from any one of SEQ ID NO:186-188, 213-239, and 280. In some embodiments, the CD28 VHH domain has the sequence of amino acids set forth in any one of SEQ ID NO:186-188, 213-239, and 280. In some embodiments, a CD28 VHH domain has the amino acid sequence set forth in any of SEQ ID NOS:186-188, 213-239, 280, and 342-385, or an amino acid sequence that has at least 90%, 91%, 92%, 93%, 94%, 95%, 96%, 97%, 98%, or 99% sequence identity to the VHH region amino acid selected from any one of SEQ ID NO:186-188, 213-239, 280, and 342-385. In some embodiments, the CD28 VHH domain has the sequence of amino acids set forth in any one of SEQ ID NO:186-188, 213-239, 280, and 342-385.

In some embodiments, a CD28 VHH domain has the amino acid sequence set forth in any of SEQ ID NOS:186-188, 213-219, 221-239, and 280, or an amino acid sequence that has at least 90%, 91%, 92%, 93%, 94%, 95%, 96%, 97%, 98%, or 99% sequence identity to the VHH region amino acid selected from any one of SEQ ID NO:186-188, 213-219, 221-239, and 280. In some embodiments, the CD28 VHH domain has the sequence of amino acids set forth in any one of SEQ ID NO:186-188, 213-219, 221-239, and 280. In some embodiments, a CD28 VHH domain has the amino acid sequence set forth in any of SEQ ID NOS:186-188, 213-219, 221-239, 280, and 342-385, or an amino acid sequence that has at least 90%, 91%, 92%, 93%, 94%, 95%, 96%, 97%, 98%, or 99% sequence identity to the VHH region amino acid selected from any one of SEQ ID NO:186-188, 213-219, 221-239, 280, and 342-385. In some embodiments, the CD28 VHH domain has the sequence of amino acids set forth in any one of SEQ ID NO:186-188, 213-219, 221-239, 280, and 342-385.

In some embodiments, a CD28 VHH domain provided herein contains a CDR1, CDR2, CDR3 contained in a VHH domain set forth in SEQ ID NO:186 or an amino acid sequence that has at least 90%, 91%, 92%, 93%, 94%, 95%, 96%, 97%, 98%, or 99% sequence identity to the VHH region amino acid set forth in SEQ ID NO:186. In some embodiments, the CD28 VHH domain has the amino acid sequence set forth in SEQ ID NO:186 or an amino acid sequence that has at least 90%, 91%, 92%, 93%, 94%, 95%, 96%, 97%, 98%, or 99% sequence identity to the amino acid set forth in SEQ ID NO:186. In some embodiments, the CD28 VHH domain is a humanized variant of the amino acid sequence set forth in SEQ ID NO:186.

In some embodiments, a CD28 VHH domain provided herein contains a CDR1 set forth in SEQ ID NO: 189, a CDR2 set forth in SEQ ID NO: 190, and a CDR3 set forth in SEQ ID NO:191.

In some embodiments, a CD28 VHH domain provided herein contains a CDR1, CDR2, CDR3 contained in a VHH domain set forth in SEQ ID NO:187 or an amino acid sequence that has at least 90%, 91%, 92%, 93%, 94%, 95%, 96%, 97%, 98%, or 99% sequence identity to the VHH region amino acid set forth in SEQ ID NO:187. In some embodiments, the CD28 VHH domain has the amino acid sequence set forth in SEQ ID NO:187 or an amino acid sequence that has at least 90%, 91%, 92%, 93%, 94%, 95%, 96%, 97%, 98%, or 99% sequence identity to the amino acid set forth in SEQ ID NO:187. In some embodiments, the CD28 VHH domain is a humanized variant of the amino acid sequence set forth in SEQ ID NO:187.

In some embodiments, a CD28 VHH domain provided herein contains a CDR1 set forth in SEQ ID NO: 192, a CDR2 set forth in SEQ ID NO: 193, and a CDR3 set forth in SEQ ID NO:194.

In some embodiments, a CD28 VHH domain provided herein contains a CDR1, CDR2, CDR3 contained in a VHH domain set forth in SEQ ID NO:188 or an amino acid sequence that has at least 90%, 91%, 92%, 93%, 94%, 95%, 96%, 97%, 98%, or 99% sequence identity to the VHH region amino acid set forth in SEQ ID NO:188. In some embodiments, the CD28 VHH domain has the amino acid sequence set forth in SEQ ID NO:188 or an amino acid sequence that has at least 90%, 91%, 92%, 93%, 94%, 95%, 96%, 97%, 98%, or 99% sequence identity to the amino acid set forth in SEQ ID NO:188. In some embodiments, the CD28 VHH domain is a humanized variant of the amino acid sequence set forth in SEQ ID NO:188.

In some embodiments, a CD28 VHH domain provided herein contains a CDR1 set forth in any of SEQ ID NO: 195 and 198-201, a CDR2 set forth in any of SEQ ID NO: 196 and 202-212, and a CDR3 set forth in SEQ ID NO:197. In some embodiments, a CD28 VHH domain provided herein contains a CDR1 set forth in any of SEQ ID NO: 195 and 198-201; a CDR2 set forth in any of SEQ ID NO: 196, 202-212, and 386-395; and a CDR3 set forth in any of SEQ ID NO:197 and 396-398. In some embodiments, a CD28 VHH domain provided herein contains a CDR1 set forth in any of SEQ ID NO: 195 and 198-201, a CDR2 set forth in any of SEQ ID NO: 196, 202, and 204-212, and a CDR3 set forth in SEQ ID NO:197. In some embodiments, a CD28 VHH domain provided herein contains a CDR1 set forth in any of SEQ ID NO: 195 and 198-201; a CDR2 set forth in any of SEQ ID NO: 196, 202, 204-212, and 386-395; and a CDR3 set forth in any of SEQ ID NO:197 and 396-398.

In some embodiments, the CD28 VHH domain provided herein contains a CDR1, CDR2, and CDR3 set forth in SEQ ID NO: 195, 196, and 197, respectively. In some embodiments, the CD28 VHH domain provided herein contains a CDR1, CDR2, and CDR3 set forth in SEQ ID NO: 198, 196, and 197, respectively. In some embodiments, the CD28 VHH domain provided herein contains a CDR1, CDR2, and CDR3 set forth in SEQ ID NO: 199, 196, and 197, respectively. In some embodiments, the CD28 VHH domain provided herein contains a CDR1, CDR2, and CDR3 set forth in SEQ ID NO: 195, 202, and 197, respectively. In some embodiments, the CD28 VHH domain provided herein contains a CDR1, CDR2, and CDR3 set forth in SEQ ID NO: 195, 203, and 197, respectively. In some embodiments, the CD28 VHH domain provided herein contains a CDR1, CDR2, and CDR3 set forth in SEQ ID NO: 195, 204, and 197, respectively. In some embodiments, the CD28 VHH domain provided herein contains a CDR1, CDR2, and CDR3 set forth in SEQ ID NO: 200, 196, and 197, respectively. In some embodiments, the CD28 VHH domain provided herein contains a CDR1, CDR2, and CDR3 set forth in SEQ ID NO: 201, 196, and 197, respectively. In some embodiments, the CD28 VHH domain provided herein contains a CDR1, CDR2, and CDR3 set forth in SEQ ID NO: 195, 205, and 197, respectively. In some embodiments, the CD28 VHH domain provided herein contains a CDR1, CDR2, and CDR3 set forth in SEQ ID NO: 195, 206, and 197, respectively. In some embodiments, the CD28 VHH domain provided herein contains a CDR1, CDR2, and CDR3 set forth in SEQ ID NO: 195, 207, and 197, respectively. In some embodiments, the CD28 VHH domain provided herein contains a CDR1, CDR2, and CDR3 set forth in SEQ ID NO: 195, 208, and 197, respectively. In some embodiments, the CD28 VHH domain provided herein contains a CDR1, CDR2, and CDR3 set forth in SEQ ID NO: 195, 209, and 197, respectively. In some embodiments, the CD28 VHH domain provided herein contains a CDR1, CDR2, and CDR3 set forth in SEQ ID NO: 195, 210, and 197, respectively. In some embodiments, the CD28 VHH domain provided herein contains a CDR1, CDR2, and CDR3 set forth in SEQ ID NO: 195, 211, and 197, respectively. In some embodiments, the CD28 VHH domain provided herein contains a CDR1, CDR2, and CDR3 set forth in SEQ ID NO: 195, 212, and 197, respectively. In some embodiments, the CD28 VHH domain provided herein contains a CDR1, CDR2, and CDR3 set forth in SEQ ID NO: 201, 202, and 197, respectively. In some embodiments, the CD28 VHH domain provided herein contains a CDR1, CDR2, and CDR3 set forth in SEQ ID NO: 201, 202, and 396, respectively. In some embodiments, the CD28 VHH domain provided herein contains a CDR1, CDR2, and CDR3 set forth in SEQ ID NO: 201, 386, and 197, respectively. In some embodiments, the CD28 VHH domain provided herein contains a CDR1, CDR2, and CDR3 set forth in SEQ ID NO: 201, 387, and 197, respectively. In some embodiments, the CD28 VHH domain provided herein contains a CDR1, CDR2, and CDR3 set forth in SEQ ID NO: 201, 202, and 397, respectively. In some embodiments, the CD28 VHH domain provided herein contains a CDR1, CDR2, and CDR3 set forth in SEQ ID NO: 201, 202, and 398, respectively. In some embodiments, the CD28 VHH domain provided herein contains a CDR1, CDR2, and CDR3 set forth in SEQ ID NO: 201, 206, and 197, respectively. In some embodiments, the CD28 VHH domain provided herein contains a CDR1, CDR2, and CDR3 set forth in SEQ ID NO: 201, 206, and 396, respectively. In some embodiments, the CD28 VHH domain provided herein contains a CDR1, CDR2, and CDR3 set forth in SEQ ID NO: 201, 388, and 197, respectively. In some embodiments, the CD28 VHH domain provided herein contains a CDR1, CDR2, and CDR3 set forth in SEQ ID NO: 201, 389, and 197, respectively. In some embodiments, the CD28 VHH domain provided herein contains a CDR1, CDR2, and CDR3 set forth in SEQ ID NO: 201, 206, and 397, respectively. In some embodiments, the CD28 VHH domain provided herein contains a CDR1, CDR2, and CDR3 set forth in SEQ ID NO: 201, 206, and 398, respectively. In some embodiments, the CD28 VHH domain provided herein contains a CDR1, CDR2, and CDR3 set forth in SEQ ID NO: 201, 203, and 197, respectively. In some embodiments, the CD28 VHH domain provided herein contains a CDR1, CDR2, and CDR3 set forth in SEQ ID NO: 201, 203, and 396, respectively. In some embodiments, the CD28 VHH domain provided herein contains a CDR1, CDR2, and CDR3 set forth in SEQ ID NO: 201, 390, and 197, respectively. In some embodiments, the CD28 VHH domain provided herein contains a CDR1, CDR2, and CDR3 set forth in SEQ ID NO: 201, 391, and 197, respectively. In some embodiments, the CD28 VHH domain provided herein contains a CDR1, CDR2, and CDR3 set forth in SEQ ID NO: 201, 203, and 397, respectively. In some embodiments, the CD28 VHH domain provided herein contains a CDR1, CDR2, and CDR3 set forth in SEQ ID NO: 201, 203, and 398, respectively. In some embodiments, the CD28 VHH domain provided herein contains a CDR1, CDR2, and CDR3 set forth in SEQ ID NO: 201, 204, and 197, respectively. In some embodiments, the CD28 VHH domain provided herein contains a CDR1, CDR2, and CDR3 set forth in SEQ ID NO: 201, 204, and 396, respectively. In some embodiments, the CD28 VHH domain provided herein contains a CDR1, CDR2, and CDR3 set forth in SEQ ID NO: 201, 392, and 197, respectively. In some embodiments, the CD28 VHH domain provided herein contains a CDR1, CDR2, and CDR3 set forth in SEQ ID NO: 201, 393, and 197, respectively. In some embodiments, the CD28 VHH domain provided herein contains a CDR1, CDR2, and CDR3 set forth in SEQ ID NO: 201, 204, and 397, respectively. In some embodiments, the CD28 VHH domain provided herein contains a CDR1, CDR2, and CDR3 set forth in SEQ ID NO: 201, 204, and 398, respectively. In some embodiments, the CD28 VHH domain provided herein contains a CDR1, CDR2, and CDR3 set forth in SEQ ID NO: 201, 196, and 396, respectively. In some embodiments, the CD28 VHH domain provided herein contains a CDR1, CDR2, and CDR3 set forth in SEQ ID NO: 201, 394, and 197, respectively. In some embodiments, the CD28 VHH domain provided herein contains a CDR1, CDR2, and CDR3 set forth in SEQ ID NO: 201, 395, and 197, respectively. In some embodiments, the CD28 VHH domain provided herein contains a CDR1, CDR2, and CDR3 set forth in SEQ ID NO: 201, 196, and 397, respectively. In some embodiments, the CD28 VHH domain provided herein contains a CDR1, CDR2, and CDR3 set forth in SEQ ID NO: 201, 196, and 398, respectively. In some embodiments, the CD28 VHH domain provided herein contains a CDR1, CDR2, and CDR3 set forth in SEQ ID NO: 195, 206, and 396, respectively. In some embodiments, the CD28 VHH domain provided herein contains a CDR1, CDR2, and CDR3 set forth in SEQ ID NO: 195, 388, and 197, respectively. In some embodiments, the CD28 VHH domain provided herein contains a CDR1, CDR2, and CDR3 set forth in SEQ ID NO: 195, 389, and 197, respectively. In some embodiments, the CD28 VHH domain provided herein contains a CDR1, CDR2, and CDR3 set forth in SEQ ID NO: 195, 206, and 397, respectively. In some embodiments, the CD28 VHH domain provided herein contains a CDR1, CDR2, and CDR3 set forth in SEQ ID NO: 195, 206, and 398, respectively.

In some aspects, a VHH domain that binds CD28 comprises a CDR1, CDR2, and CDR3 contained in a VHH amino acid sequence set forth in any one of SEQ ID NOS:213-239 and 280, or an amino acid sequence that has at least 90%, 91%, 92%, 93%, 94%, 95%, 96%, 97%, 98%, or 99% sequence identity to the VHH region amino acid sequence set forth in any one of SEQ ID NOS:213-239 and 280. In some aspects, a VHH domain that binds CD28 comprises a CDR1, CDR2, and CDR3 contained in a VHH amino acid sequence set forth in any one of SEQ ID NOS:213-239, 280, and 342-385, or an amino acid sequence that has at least 90%, 91%, 92%, 93%, 94%, 95%, 96%, 97%, 98%, or 99% sequence identity to the VHH region amino acid sequence set forth in any one of SEQ ID NOS:213-239, 280, and 342-385.

In some cases, the provided CD28 VHH domain is a humanized variant that has the amino acid sequence set forth in any one of SEQ ID NOS:213-239 and 280 or an amino acid sequence that has at least 90%, 91%, 92%, 93%, 94%, 95%, 96%, 97%, 98%, or 99% sequence identity to the VHH region amino acid sequence set forth in any one of SEQ ID NO:213-239 and 280. In some embodiments, the CD28 humanized VHH domain has the sequence of amino acids set forth in any one of SEQ ID NO:213-239 and 280. In some cases, the provided CD28 VHH domain is a humanized variant that has the amino acid sequence set forth in any one of SEQ ID NOS:213-239, 280, and 342-385, or an amino acid sequence that has at least 90%, 91%, 92%, 93%, 94%, 95%, 96%, 97%, 98%, or 99% sequence identity to the VHH region amino acid sequence set forth in any one of SEQ ID NO:213-239, 280, and 342-385. In some embodiments, the CD28 humanized VHH domain has the sequence of amino acids set forth in any one of SEQ ID NO:213-239, 280, and 342-385.

In some aspects, a VHH domain that binds CD28 comprises a CDR1, CDR2, and CDR3 contained in a VHH amino acid sequence set forth in any one of SEQ ID NOS:213-219, 221-239 and 280, or an amino acid sequence that has at least 90%, 91%, 92%, 93%, 94%, 95%, 96%, 97%, 98%, or 99% sequence identity to the VHH region amino acid sequence set forth in any one of SEQ ID NOS:213-219, 221-239 and 280. In some aspects, a VHH domain that binds CD28 comprises a CDR1, CDR2, and CDR3 contained in a VHH amino acid sequence set forth in any one of SEQ ID NOS:213-219, 221-239, 280, and 342-385, or an amino acid sequence that has at least 90%, 91%, 92%, 93%, 94%, 95%, 96%, 97%, 98%, or 99% sequence identity to the VHH region amino acid sequence set forth in any one of SEQ ID NOS:213-219, 221-239, 280, and 342-385.

In some cases, the provided CD28 VHH domain is a humanized variant that has the amino acid sequence set forth in any one of SEQ ID NOS:213-219, 221-239 and 280 or an amino acid sequence that has at least 90%, 91%, 92%, 93%, 94%, 95%, 96%, 97%, 98%, or 99% sequence identity to the VHH region amino acid sequence set forth in any one of SEQ ID NO:213-219, 221-239 and 280. In some embodiments, the CD28 humanized VHH domain has the sequence of amino acids set forth in any one of SEQ ID NO:213-219, 221-239 and 280. In some cases, the provided CD28 VHH domain is a humanized variant that has the amino acid sequence set forth in any one of SEQ ID NOS:213-219, 221-239, 280, and 342-385, or an amino acid sequence that has at least 90%, 91%, 92%, 93%, 94%, 95%, 96%, 97%, 98%, or 99% sequence identity to the VHH region amino acid sequence set forth in any one of SEQ ID NO:213-219, 221-239, 280, and 342-485. In some embodiments, the CD28 humanized VHH domain has the sequence of amino acids set forth in any one of SEQ ID NO:213-219, 221-239, 280, and 342-385.

In some embodiments, the CD28 VHH domain has a mutation to prevent or reduce binding of the VHH to protein A. In some embodiments, the mutation is G73D. In some embodiments, the CD28 VHH is SEQ ID NO:280.

In some embodiments, at least one CD28 sdAb comprises an amino acid modification that reduces binding to protein A. In some embodiments, the amino acid modification is G65D by Kabat in framework region 3 (FR3).

In some embodiments, the CD28 binding domain, or independently each of the antigen binding domains that binds CD28 results in monovalent, bivalent, trivalent, tetravalent, pentavalent, or hexavalent binding to CD28. In some embodiments, bivalent binding to CD28 comprises two CD28 binding domains that bind the same epitope of CD28 (e.g. mono-epitopic). In some embodiments, bivalent binding to CD28 comprises two CD28 binding domains that bind different epitopes of CD28 (e.g. bi-epitopic). In some embodiments, monovalent binding to CD28 comprises one CD28 binding domain that binds one epitope of CD28 (e.g. mono-epitopic).

In some embodiments, a CD28 VHH domain is linked, directly or indirectly, to a moiety that binds protein A. In some embodiments, the protein A-binding moiety assists in purification of CD28 VHH domains.

In some embodiments, the ability of a CD28 VHH domain to bind or engage CD28 is prevented or reduced in the absence of an additional binding domain being bound to an antigen. In some embodiments, the additional binding domain binds a tumor associated antigen (TAA). In some embodiments, the CD28 VHH domain is linked, directly or indirectly, to a TAA antigen binding domain. Thus, in some embodiments, the ability of a CD28 VHH domain to bind or engage CD28 is prevented or reduced in the absence of a directly or indirectly linked TAA binding domain being bound to its antigen.

III. Fusion Proteins and Conjugates Containing CD28-Binding Polypeptides

Provided herein are fusion proteins and conjugates containing CD28-binding polypeptides containing at least one VHH domain that specifically binds CD28 linked, directly or indirectly, to one or more additional domains or moieties. In some embodiments, the fusion protein or conjugate of the present disclosure is composed of a single polypeptide. In other embodiments, the fusion protein or conjugate of the present disclosure is composed of more than one polypeptide. In some embodiments, the CD28-binding polypeptide of the present disclosure incorporates at least one VHH domain that specifically binds CD28. In some aspects, the CD28-binding polypeptide is multivalent for CD28. In some embodiments, the CD28-binding polypeptides include two or more CD28 VHH domains that specifically bind CD28, for example, three or more, four or more, five or more, or six or more VHH domains that specifically bind CD28.

In any of the provided embodiments, a CD28-binding polypeptide includes an Fc domain. In some embodiments, the CD28-binding polypeptide includes at least one CD28 sdAb and an Fc domain.

In certain aspects, the CD28-binding polypeptide contains one or more additional binding domain and is multispecific for CD28 and another antigen that is not CD28. For example, in some cases, the one or more additional domain may be one or more additional binding domain that binds to one or more further antigen, such as a tumor associated antigen (TAA). In some embodiments, the multispecific CD28-binding polypeptide is multivalent for the additional antigen. For example, in some embodiments, a multispecific CD28-binding polypeptide includes two or more VHH domains that bind the additional antigen. In some embodiments, a multispecific CD28-binding polypeptide further includes an Fc domain, such that the multispecific CD28-binding polypeptide further includes at least one TAA sdAb, at least one CD28 sdAB, and an Fc domain.

In some embodiments, a multispecific CD28-binding polypeptide further includes a CD3 binding region, such that the multispecific CD28-binding polypeptide further includes at least one TAA sdAb, at least one CD28 sdAB, an Fc domain, and a CD3 binding region.

In some embodiments, the CD28-binding polypeptides of the present disclosure include two or more polypeptide sequences that are operably linked via amino acid linkers. In some embodiments, these linkers are composed predominately of the amino acids Glycine and Serine, denoted as GS-linkers herein. The GS-linkers of the fusion proteins of the present disclosure can be of various lengths, for example, 5, 6, 7, 8, 9, 10, 11, 12, 13, 14, 15, 16, 17, 18, 19, 20 amino acids in length. In some embodiments, the GS-linker comprises an amino acid sequence selected from the group consisting of GGSGGS, i.e., (GGS)2 (SEQ ID NO: 1); GGSGGSGGS, i.e., (GGS)3 (SEQ ID NO: 2); GGSGGSGGSGGS, i.e., (GGS)4 (SEQ ID NO: 3); GGSGGGGS (SEQ ID NO:89); and GGSGGSGGSGGSGGS, i.e., (GGS)5 (SEQ ID NO: 4). In some embodiments, the linker is a flexible linker comprising Glycine residues, such as, by way of non-limiting example, GG (SEQ ID NO:249), GGG (SEQ ID NO:87), GGGG (SEQ ID NO: 5), GGGGG (SEQ ID NO: 6), and GGGGGG (SEQ ID NO: 7). In some embodiments, the CD28-binding polypeptide includes a combination of a GS-linker and a Glycine linker. In some embodiments, the linker is (GGGGS)n, wherein n is 1 to 5 (SEQ ID NO:123); (GGGGGS)n, wherein n is 1 to 4 (SEQ ID NO:124); GGGGS (SEQ ID NO:125); GGGGGS (SEQ ID NO:126); GGGGGSGGGGGSGGGGGS (SEQ ID NO:127); GGGGSGGGGSGGGGS (SEQ ID NO:128); GGSGGGGSGGGGSGGGGS (SEQ ID NO:129); or PGGGG (SEQ ID NO:250). In some embodiments, the linker is a GG linker. In some embodiments, the CD28-binding polypeptide includes a combination of a GS-linker and a Glycine linker.

A. Fc Fusions

Provided herein is a CD28-binding polypeptide that is a fusion protein containing at least one VHH domain that binds CD28. In some embodiments, a CD28-binding polypeptide provided herein contains one, two, three, or four VHH domains that bind CD28. In some embodiments, the fusion protein contains an Fc domain. In some embodiments, the fusion protein contains at least one VHH domain that binds CD28 provided herein and an Fc domain. In some embodiments, the fusion protein contains one, two, three, or four VHH domains that bind CD28 and an Fc domain.

In some embodiments, incorporation of an immunoglobulin Fc region into the fusion protein can, in some aspects, be composed of two polypeptides that together form a dimer. In some embodiments, an Fc domain mediates dimerization of the CD28-binding polypeptide at physiological conditions, such as when expressed from a cell, such that a dimer is formed that doubles the number of CD28 binding sites. For example, a CD28-binding polypeptide comprising one VHH domain that binds CD28 and an Fc region is monovalent as a monomer, but the Fc region may mediate dimerization, such that the CD28-binding polypeptide exists as a bivalent dimer under such conditions. In some embodiments, a CD28 VHH domain is fused to an IgG Fc region, and in these embodiments, the fusion protein is bivalent having two CD28 VHH domains per molecule. In some embodiments, two CD28 binding domains (2×) are fused to an IgG Fc region and in these embodiments, the fusion protein is tetravalent having four CD28 VHH domains per molecule. In some embodiments, three CD28 VHH domain (3×) are fused to an IgG Fc region and in these embodiments, the fusion protein is hexavalent having six CD28 VHH domains per molecule. In some embodiments, a CD28-binding polypeptide incorporates an IgG Fc region and in these embodiments, the fusion protein is bivalent having two CD28 VHH domains per molecule. In some embodiments, a CD28-binding polypeptide having two CD28 binding domains (2×) incorporates an IgG Fc region and in these embodiments, the fusion protein is tetravalent having four CD28 VHH domains per molecule. In some embodiments, a CD28-binding polypeptide having three CD28 VHH domain (3×) incorporates an IgG Fc region and in these embodiments, the fusion protein is hexavalent having six CD28 VHH domains per molecule.

In some embodiments, the multivalent CD28-binding polypeptide is bivalent. In some embodiments, the bivalent CD28-binding polypeptide of the disclosure includes two copies of a CD28-binding polypeptide having the following structure: (CD28 VHH)-Fc. In some embodiments, the CD28 VHH is or contains the amino acid sequence set forth in SEQ ID NO:188, 220, or 280. In some embodiments, the CD28 VHH is or contains the amino acid sequence set forth in SEQ ID NO:188. In some embodiments, the CD28 VHH is or contains the amino acid sequence set forth in SEQ ID NO:220. In some embodiments, the CD28 VHH is or contains the amino acid sequence set forth in SEQ ID NO:280. In some embodiments, the Fc is or contains the amino acid sequence SEQ ID NO:8 or 9. In some embodiments, the Fc is or contains the amino acid sequence set forth in SEQ ID NO:8. In some embodiments, the Fc is or contains the amino acid sequence set forth in SEQ ID NO:9. In some embodiments, the CD28 VHH is or contains the amino acid sequence set forth in SEQ ID NO:188 and the Fc domain is or contains the amino acid sequence set forth in SEQ ID NO:9.

In some embodiments, the multivalent CD28-binding polypeptide is tetravalent. In some embodiments, the tetravalent CD28-binding polypeptide of the disclosure includes two copies of a CD28-polypeptide having the following structure: (CD28 VHH)-Linker-(CD28 VHH)-Fc. In some embodiments, the multivalent CD28-binding polypeptide is hexavalent. In some embodiments, the hexavalent CD28-binding polypeptide of the disclosure includes two copies of a CD28-binding polypeptide having the following structure: (CD28 VHH)-Linker-(CD28 VHH)-Linker-(CD28 VHH)-Fc.

In some cases, the CH3 domain of the Fc region can be used as homodimerization domain, such that the resulting fusion protein is formed from two identical polypeptides. In other cases, the CH3 dimer interface region of the Fc region can be mutated so as to enable heterodimerization. For example, a heterodimerization domain can be incorporated into the fusion protein such that the construct is an asymmetric fusion protein.

In any of the provided embodiments, a CD28 VHH domain can be any as described above. In some embodiments, the CD28 VHH domain is a humanized VHH domain that binds CD28.

In various embodiments, an Fc domain included in a CD28-binding polypeptide is a human Fc domain, or is derived from a human Fc domain. In some embodiments, the fusion protein contains an immunoglobulin Fc region. In some embodiments, the immunoglobulin Fc region is an IgG isotype selected from the group consisting of IgG1 isotype, IgG2 isotype, IgG3 isotype, and IgG4 subclass.

In some embodiments, the immunoglobulin Fc region or immunologically active fragment thereof is an IgG isotype. For example, the immunoglobulin Fc region of the fusion protein is of human IgG1 isotype, having an amino acid sequence:

```
                                          (SEQ ID NO: 8)
PAPELLGGPS VFLFPPKPKD TLMISRTPEV TCVVVDVSHE

DPEVKFNWYV DGVEVHNAKT KPREEQYNST YRVVSVLTVL

HQDWLNGKEY KCKVSNKALP APIEKTISKA KGQPREPQVY

TLPPSRDELT KNQVSLTCLV KGFYPSDIAV EWESNGQPEN

NYKTTPPVLD SDGSFFLYSK LTVDKSRWQQ GNVFSCSVMH

EALHNHYTQK SLSLSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 8.

In some embodiments where the fusion protein of the disclosure includes an Fc polypeptide, the Fc polypeptide is mutated or modified. In some cases, the mutations include one or more amino acid substitutions to reduce an effector function of the Fc polypeptide. Various examples of mutations to Fc polypeptides to alter, such as reduce, effector function are known, including any as described below. In some embodiments, reference to amino acid substitutions in an Fc region is by EU numbering by Kabat (also called Kabat numbering) unless described with reference to a specific SEQ ID NO. EU numbering is known and is according to the most recently updated IMGT Scientific Chart (IMGT®, the international ImMunoGeneTics information System®, http://www.imgt.org/IMGTScientificChart/Numbering/Hu_IGHGnber.html (created: 17 May 2001, last updated: 10 Jan. 2013) and the EU index as reported in Kabat, E. A. et al. Sequences of Proteins of Immunological interest. 5th ed. US Department of Health and Human Services, NIH publication No. 91-3242 (1991).

In some embodiments, an Fc region that exhibits reduced effector functions may be a desirable candidate for applications in which CD28 binding is desired yet certain effector functions (such as CDC and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the multispecific polypeptide constructs and/or cleaved components thereof lack FcγR binding (hence likely lacking ADCC activity), but retains FcRn binding ability. The primary cells for mediating ADCC, NK cells, express FcγRIII only, whereas monocytes express FcγRI, FcγRII and FcγRIII Non-limiting examples of in vitro assays to assess ADCC activity of a molecule of interest is described in U.S. Pat. No. 5,500,362 (see, e.g., Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assay methods may be employed (see, for example, ACTI™ non-radioactive cytotoxicity assay for flow cytometry (CellTechnology, Inc. Mountain View, Calif.; and CytoTox 96™ non-radioactive cytotoxicity assay (Promega™, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the multispecific polypeptide construct or cleaved components thereof is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half-life determinations can also be performed using methods known in the art (see, e.g., Petkova, S. B. et al., *Intl. Immunol.* 18(12):1759-1769 (2006)).

In some embodiments, the human IgG Fc region is modified to alter antibody-dependent cellular cytotoxicity (ADCC) and/or complement-dependent cytotoxicity (CDC), e.g., the amino acid modifications described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1):1-11.

Examples of mutations that enhance ADCC include modification at Ser239 and Ile332, for example Ser239Asp and Ile332Glu (S239D, 1332E). Examples of mutations that enhance CDC include modifications at Lys326 and Glu333. In some embodiments, the Fc region is modified at one or both of these positions, for example Lys326Ala and/or Glu333Ala (K326A and E333A) using the Kabat numbering system.

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325), Ala327 (A327) or Pro329 (P329). For example, Leu 234Ala (L234A), Leu235Ala (L235A), Leu235Glu (L235E), Asp265Asn (D265N), Asp265Ala (D265A), Asp270Asn (D270N), Ser298Asn (S298N), Asn297Ala (N297A), Pro329Ala (P329A) or Pro239Gly (P329G), Asn325Glu (N325E) or Ala327Ser (A327S). In preferred embodiments, modifications within the Fc region reduce binding to Fc-receptor-gamma receptors while have minimal impact on binding to the neonatal Fc receptor (FcRn).

In some embodiments, the human IgG1 Fc region is modified at amino acid Asn297 (Kabat Numbering) to prevent glycosylation of the fusion protein, e.g., Asn297Ala (N297A) or Asn297Asp (N297D). In some embodiments, the Fc region of the fusion protein is modified at amino acid Leu235 (Kabat Numbering) to alter Fc receptor interactions, e.g., Leu235Glu (L235E) or Leu235Ala (L235A). In some embodiments, the Fc region of the fusion protein is modified at amino acid Leu234 (Kabat Numbering) to alter Fc receptor interactions, e.g., Leu234Ala (L234A). In some embodiments, the Fc region of the fusion protein is modified at amino acid Leu234 (Kabat Numbering) to alter Fc receptor interactions, e.g., Leu235Glu (L235E). In some embodiments, the Fc region of the fusion protein is altered at both amino acids 234 and 235, e.g., Leu234Ala and Leu235Ala (L234A/L235A) or Leu234Val and Leu235Ala (L234V/L235A). In some embodiments, the Fc region of the fusion protein is altered at amino acids 234, 235, and 297, e.g., Leu234Ala, Leu235Ala, Asn297Ala (L234A/L235A/N297A). In some embodiments, the Fc region of the fusion protein is altered at amino acids at 234, 235, and 329, e.g., Leu234Ala, Leu235Ala, Pro239Ala (L234A/L235A/P329A). In some embodiments, the Fc region of the fusion protein is modified at amino acid Asp265 (Kabat Numbering) to alter Fc receptor interactions, e.g. Asp265Ala (D265A). In some embodiments, the Fc region of the fusion protein is modified at amino acid Pro329 (Kabat Numbering) to alter Fc receptor interactions, e.g. Pro329Ala (P329A) or Pro329Gly (P329G). In some embodiments, the Fc region of the fusion protein is altered at both amino acids 265 and 329, e.g., Asp265Ala and Pro329Ala (D265A/P329A) or Asp265Ala and Pro329Gly (D265A/P329G). In some embodiments, the Fc region of the fusion protein is altered at amino acids at 234, 235, and 265, e.g., Leu234Ala, Leu235Ala, Asp265Ala (L234A/L235A/D265A). In some embodiments, the Fc region of the fusion protein is altered at amino acids at 234, 235, and 329, e.g., Leu234Ala, Leu235Ala, Pro329Gly (L234A/L235A/P329G). In some embodiments, the Fc region of the fusion protein is altered at amino acids at 234, 235, 265 and 329, e.g., Leu234Ala, Leu235Ala, Asp265Ala, Pro329Gly (L234A/L235A/D265A/P329G). In some embodiments, the Fc region of the fusion protein is altered at Gly235 to reduce Fc receptor binding. For example, wherein Gly235 is deleted from the fusion protein. In some embodiments, the human IgG1 Fc region is modified at amino acid Gly236 to enhance the interaction with CD32A, e.g., Gly236Ala (G236A). In some embodiments, the human IgG1 Fc region lacks Lys447 (EU index of Kabat et al 1991 Sequences of Proteins of Immunological Interest).

In some embodiments, the Fc region of the fusion protein is lacking an amino acid at one or more of the following positions to reduce Fc receptor binding: Glu233 (E233), Leu234 (L234), or Leu235 (L235). In some embodiments, the Fc region of the fusion protein is lacking an amino acid at one or more of the following positions Glu233 (E233), Leu234 (L234), or Leu235 (L235), and is modified at one or more of Asp265 (D265), Asn297 (N297), or Pro329 (P329), to reduce Fc receptor binding. For example, an Fc region included in a CD28-binding polypeptide is derived from a human Fc domain, and comprises a three amino acid deletion in the lower hinge corresponding to IgG1 E233, L234, and L235. In some aspects, such Fc polypeptides do not engage FcγRs and thus are referred to as "effector silent" or "effector null." For example, Fc deletion of these three amino acids reduces the complement protein C1q binding. In some embodiments, a polypeptide with an Fc region with Fc deletion of these three amino acids retains binding to FcRn and therefore has extended half-life and transcytosis associated with FcRn mediated recycling. Such a modified Fc region is referred to as "Fc xELL" or "Fc deletion" and has the following amino acid sequence:

```
                                        (SEQ ID NO: 9)
PAPGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPI

EKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEAL

HNHYTQKSLSLSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 9.

In some embodiments, the human IgG Fc region is modified to enhance FcRn binding. Examples of Fc mutations that enhance binding to FcRn are Met252Tyr, Ser254Thr, Thr256Glu (M252Y, S254T, T256E, respectively) (Kabat numbering, Dall'Acqua et al 2006, J. Biol Chem Vol. 281(33) 23514-23524), Met428Leu and Asn434Ser (M428L, N434S) (Zalevsky et al 2010 Nature Biotech, Vol. 28(2) 157-159), or Met252Ile, Thr256Asp, Met428Leu (M252I, T256D, M428L, respectively), (EU index of Kabat et al 1991 Sequences of Proteins of Immunological Interest).

In some embodiments, the Fc domain included in a CD28-binding polypeptide is derived from a human Fc domain and comprises mutations M252Y and M428V, herein referred to as "Fc-YV". In some embodiments, the mutated or modified Fc polypeptide includes the following mutations: M252Y and M428L using the Kabat numbering system. In some embodiments, such mutations enhance binding to FcRn at the acidic pH of the endosome (near 6.5), while losing detectable binding at neutral pH (about 7.2), allowing for enhanced FcRn mediated recycling and extended half-life.

In particular embodiments of multispecific polypeptide constructs provides herein, the Fc domain included in a CD28-binding polypeptide is derived from a human Fc domain and comprises mutations to induce heterodimerization. In some embodiments, such mutations include those referred to as "knob" and "hole" mutations. For example, having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). In some embodiments, the "knob" Fc domain comprises the mutation T366W. In some embodiments, the "hole" Fc domain comprises mutations T366S, L368A, and Y407V. Heterodimerization via CH3 modifications can be further stabilized by the introduction of a disulfide bond, for example by changing Ser354 to Cys (S354C) and Y349 to Cys (Y349C) on opposite CH3 domains (Reviewed in Carter, 2001 Journal of Immunological Methods, 248: 7-15). In some embodiments, Fc domains used for heterodimerization comprise additional mutations, such as the mutation S354C on a first member of a heterodimeric Fc pair that forms an asymmetric disulfide with a corresponding mutation Y349C on the second member of a heterodimeric Fc pair. In some embodiments, one member of a heterodimeric Fc pair comprises the modification H435R or H435K to prevent protein A binding while maintaining FcRn binding. In some embodiments, one member of a heterodimeric Fc pair comprises the modification H435R or H435K, while the second member of the heterodimeric Fc pair is not modified at H435. In various embodiments, the hole Fc domain comprises the modification H435R or H435K (referred to as "hole-R" in some instances when the modification is H435R), while the knob Fc domain does not. In some instances, the hole-R mutation improves purification of the heterodimer over homodimeric hole Fc domains that may be present.

In some embodiments, the human IgG Fc region is modified to prevent dimerization. In these embodiments, the fusion proteins of the present disclosure are monomeric. For example modification at residue Thr366 to a charged residue, e.g. Thr366Lys, Thr366Arg, Thr366Asp, or Thr366Glu (T366K, T366R, T366D, or T366E, respectively), prevents CH3-CH3 dimerization.

In some embodiments, the immunoglobulin Fc region or immunologically active fragment of the fusion protein is of human IgG2 isotype, having an amino acid sequence:

(SEQ ID NO: 10)

PAPPVAGPSVFLFPPKPKDTLMISRTPEVTCVVVDVSHEDPEVQFNWYVD

GVEVHNAKTKPREEQFNSTFRVVSVLTVVHQDWLNGKEYKCKVSNKGLPA

PIEKTISKTKGQPREPQVYTLPPSREEMTKNQVSLTCLVKGFYPSDISVE

WESNGQPENNYKTTPPMLDSDGSFFLYSKLTVDKSRWQQGNVFSCSVMHE

ALHNHYTQKSLSLSPGK

In some embodiments, the fusion or immunologically active fragment thereof comprises a human IgG2 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 10.

In some embodiments, the human IgG2 Fc region is modified at amino acid Asn297 (e.g. to prevent to glycosylation of the antibody, e.g., Asn297Ala (N297A) or Asn297Asp (N297D). In some embodiments, the human IgG2 Fc region is lacks Lys447 (EU index of Kabat et al 1991 Sequences of Proteins of Immunological Interest).

In some embodiments, the immunoglobulin Fc region or immunologically active fragment of the fusion protein is of human IgG3 isotype, having an amino acid sequence:

(SEQ ID NO: 11)

PAPELLGGPS VFLFPPKPKD TLMISRTPEV TCVVVDVSHE

DPEVQFKWYV DGVEVHNAKT KPREEQYNST FRVVSVLTVL

HQDWLNGKEY KCKVSNKALP APIEKTISKT KGQPREPQVY

TLPPSREEMT KNQVSLTCLV KGFYPSDIAV EWESSGQPEN

-continued

NYNTTPPMLD SDGSFFLYSK LTVDKSRWQQ GNIFSCSVMH

EALHNRFTQK SLSLSPGK

In some embodiments, the antibody or immunologically active fragment thereof comprises a human IgG3 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 11.

In some embodiments, the human IgG3 Fc region is modified at amino acid Asn297 (Kabat Numbering) to prevent to glycosylation of the antibody, e.g., Asn297Ala (N297A) or Asn297Asp (N297D). In some embodiments, the human IgG3 Fc region is modified at amino acid 435 to extend the half-life, e.g., Arg435His (R435H). In some embodiments, the human IgG3 Fc region is lacks Lys447 (EU index of Kabat et al 1991 Sequences of Proteins of Immunological Interest).

In some embodiments, the immunoglobulin Fc region or immunologically active fragment of the fusion protein is of human IgG4 isotype, having an amino acid sequence:

(SEQ ID NO: 12)

PAPEFLGGPS VFLFPPKPKD TLMISRTPEV TCVVVDVSQE

DPEVQFNWYV DGVEVHNAKT KPREEQFNST YRVVSVLTVL

HQDWLNGKEY KCKVSNKGLP SSIEKTISKA KGQPREPQVY

TLPPSQEEMT KNQVSLTCLV KGFYPSDIAV EWESNGQPEN

NYKTTPPVLD SDGSFFLYSR LTVDKSRWQE GNVFSCSVMH

EALHNHYTQK SLSLSLGK

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 12.

In some embodiments, the immunoglobulin Fc region or immunologically active fragment of the fusion protein is of human IgG4 isotype, having an amino acid sequence:

(SEQ ID NO: 13)

PAPELLGGPS VFLFPPKPKD TLMISRTPEV TCVVVDVSQE

DPEVQFNWYV DGVEVHNAKT KPREEQFNST YRVVSVLTVL

HQDWLNGKEY KCKVSNKGLP SSIEKTISKA KGQPREPQVY

TLPPSQEEMT KNQVSLTCLV KGFYPSDIAV EWESNGQPEN

NYKTTPPVLD SDGSFFLYSR LTVDKSRWQE GNVFSCSVMH

EALHNHYTQK SLSLSLGK

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 13.

In some embodiments, the human IgG4 Fc region is modified at amino acid 235 to alter Fc receptor interactions, e.g., Leu235Glu (L235E). In some embodiments, the human IgG4 Fc region is modified at amino acid Asn297 (Kabat Numbering) to prevent to glycosylation of the antibody, e.g., Asn297Ala (N297A) or Asn297Asp (N297D). In some embodiments, the human IgG4 Fc region is lacks Lys447 (EU index of Kabat et al 1991 Sequences of Proteins of Immunological Interest).

In some embodiments, the fusion protein contains a polypeptide derived from an immunoglobulin hinge region. The hinge region can be selected from any of the human IgG subclasses. For example, the fusion protein may contain a modified IgG1 hinge having the sequence of EPKSSDKTHTCPPC (SEQ ID NO: 14), where in the Cys220 that forms a disulfide with the C-terminal cysteine of the light chain is mutated to serine, e.g., Cys220Ser (C220S). In other embodiments, the fusion protein contains a truncated hinge having a sequence DKTHTCPPC (SEQ ID NO: 15).

In some embodiments, the fusion protein has a modified hinge from IgG4, which is modified to prevent or reduce strand exchange, e.g., Ser228Pro (S228P), having the sequence ESKYGPPCPPC (SEQ ID NO: 16). In some embodiments, the fusion protein contains linker polypeptides. In other embodiments, the fusion protein contains linker and hinge polypeptides.

In some embodiments, the Fc region lacks or has reduced Fucose attached to the N-linked glycan-chain at N297. There are numerous ways to prevent fucosylation, including but not limited to production in a FUT8 deficient cell line; addition inhibitors to the mammalian cell culture media, for example Castanospermine; and metabolic engineering of the production cell line.

In some embodiments, the Fc region is engineered to eliminate recognition by pre-existing antibodies found in humans. In some embodiments, the VHH-containing polypeptides of the present disclosure are modified by mutation of position 11 and by changes in carboxy-terminal region. In some embodiments, VHH-containing polypeptides of the present disclosure are modified by mutation of position Leu11, for example Leu11Glu (L11E) or Leu11Lys (L11K). In some embodiments, VHH-containing polypeptides of the present disclosure contain the carboxy terminal modifications of Ser112Lys (S112K) and Ser113Pro (S113P). For example, humanized variants of single domain antibodies of the present disclosure can contain the modification of Leu11Glu (L11E) and the carboxy terminal modifications of Ser112Lys (S112K) and Ser113Pro (S113P), as these are known prevent or reduce the recognition of pre-existing ADA directed toward sdAbs (as described in US20160207981). In other embodiments, single domain antibodies of the present disclosure are modified by changes in carboxy-terminal region, for example the terminal sequence has the sequence GQGTLVTVKPGG (SEQ ID NO: 17) or GQGTLVTVEPGG (SEQ ID NO: 18) or modification thereof.

In some embodiments, the one or more polypeptides of the fusion proteins of the present disclosure are operably linked via amino acid linkers. In some embodiments, these linkers are composed predominately of the amino acids Glycine and Serine, denoted as GS-linkers herein. The GS-linkers of the fusion proteins of the present disclosure can be of various lengths, for example, 5, 6, 7, 8, 9, 10, 11, 12, 13, 14, 15, 16, 17, 18, 19, 20 amino acids in length.

In some embodiments, the GS-linker comprises an amino acid sequence selected from the group consisting of GGSGGS, i.e., (GGS)2 (SEQ ID NO: 1); GGSGGSGGS, i.e., (GGS)3 (SEQ ID NO: 2); GGSGGSGGSGGS, i.e., (GGS)4 (SEQ ID NO: 3); and GGSGGSGGSGGSGGS, i.e., (GGS)5 (SEQ ID NO: 4). In some embodiments, the linker is a flexible linker comprising Glycine residues, such as, by way of non-limiting example, GG (SEQ ID NO:249), GGG (SEQ ID NO:87), GGGG (SEQ ID NO: 5), GGGGG (SEQ ID NO: 6), and GGGGGG (SEQ ID NO: 7). In some embodiments, the linker is (GGGGS)n, wherein n is 1 to 5 (SEQ ID NO:123); (GGGGGS)n, wherein n is 1 to 4 (SEQ ID NO:124); GGGGS (SEQ ID NO:125); GGGGGS (SEQ ID NO:126); GGGGGSGGGGGSGGGGGS (SEQ ID NO:127); GGGGSGGGGSGGGGS (SEQ ID NO:128); GGSGGGGSGGGGSGGGGS (SEQ ID NO:129); or PGGGG (SEQ ID NO:250). In some embodiments, the linker is GGSGGGGS (SEQ ID NO:89). In some embodiments, the fusion proteins can include a combination of a GS-linker and a Glycine linker.

B. Conjugates

Provided herein are conjugates containing at least one VHH domain that specifically binds CD28 provided herein and one or more further moiety. The further moiety can be a therapeutic agent, such as a cytotoxic agent, or can be a detection agent. In some embodiments, the moiety can be a targeting moiety, a small molecule drug (non-polypeptide drug of less than 500 Daltons molar mass), a toxin, a cytostatic agent, a cytotoxic agent, an immunosuppressive agent, a radioactive agent suitable for diagnostic purposes, a radioactive metal ion for therapeutic purposes, a prodrug-activating enzyme, an agent that increases biological half-life, or a diagnostic or detectable agent.

In some embodiments, the conjugate is an antibody drug conjugate (ADC, also called immunoconjugates) containing one or more CD28 VHH domain provided herein conjugated to a therapeutic agent, which is either cytotoxic, cytostatic or otherwise provides some therapeutic benefit. In some embodiments, the cytotoxic agent is a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate). In some embodiments, provided antibody drug conjugates of the present disclosure allow targeted-delivery of the drug moiety to tumors. In some cases, this can result in targeted killing of the tumor cell.

In some embodiments, there is provided a CD28-binding conjugate comprising at least one CD28 VHH domain provided herein conjugated with a therapeutic agent. In some embodiments, the therapeutic agent includes, for example, daunomycin, doxorubicin, methotrexate, and vindesine (Rowland et al., Cancer Immunol. Immunother. 21:183-187, 1986). In some embodiments, the therapeutic agent has an intracellular activity. In some embodiments, the CD28-binding conjugate is internalized and the therapeutic agent is a cytotoxin that blocks the protein synthesis of the cell, therein leading to cell death. In some embodiments, the therapeutic agent is a cytotoxin comprising a polypeptide having ribosome-inactivating activity including, for example, gelonin, bouganin, saporin, ricin, ricin A chain, bryodin, diphtheria toxin, restrictocin, *Pseudomonas* exotoxin A and variants thereof. In some embodiments, where the therapeutic agent is a cytotoxin comprising a polypeptide having a ribosome-inactivating activity, the CD28-binding conjugate must be internalized upon binding to the target cell in order for the protein to be cytotoxic to the cells.

In some embodiments, there is provided a CD28-binding conjugate comprising at least one CD28 VHH domain provided herein conjugated with a toxin. In some embodiments, the toxin includes, for example, bacterial toxins such as diphtheria toxin, plant toxins such as ricin, small molecule toxins such as geldanamycin (Mandler et al., J. Nat. Cancer Inst. 92(19):1573-1581 (2000); Mandler et al., Bioorganic & Med. Chem. Letters 10:1025-1028 (2000); Mandler et al., Bioconjugate Chem. 13:786-791 (2002)), maytansinoids (EP 1391213; Liu et al., Proc. Natl. Acad. Sci. USA 93:8618-8623 (1996)), and calicheamicin (Lode et al., Cancer Res. 58:2928 (1998); Hinman et al., Cancer Res. 53:3336-3342 (1993)). The toxins may exert their cytotoxic and cytostatic effects by mechanisms including tubulin binding, DNA binding, or topoisomerase inhibition.

In some embodiments, there is provided a CD28-binding conjugate comprising at least one CD28 VHH domain provided herein conjugated with a label, which can generate a detectable signal, indirectly or directly. These IgSF conjugates can be used for research or diagnostic applications, such as for the in vivo detection of cancer. The label is preferably capable of producing, either directly or indirectly, a detectable signal. For example, the label may be radio-opaque or a radioisotope, such as 3H, 14C, 32P, 35S, 123I, 125I, 131I; a fluorescent (fluorophore) or chemiluminescent (chromophore) compound, such as fluorescein isothiocyanate, rhodamine or luciferin; an enzyme, such as alkaline phosphatase, β-galactosidase or horseradish peroxidase; an imaging agent; or a metal ion. In some embodiments, the label is a radioactive atom for scintigraphic studies, for example 99Tc or 123I, or a spin label for nuclear magnetic resonance (NMR) imaging (also known as magnetic resonance imaging, MRI), such as zirconium-89, iodine-123, iodine-131, indium-111, fluorine-19, carbon-13, nitrogen-15, oxygen-17, gadolinium, manganese or iron. Zirconium-89 may be complexed to various metal chelating agents and conjugated to antibodies, e.g., for PET imaging (WO 2011/056983).

The CD28-binding conjugates may be prepared using any methods known in the art. See, e.g., WO 2009/067800, WO 2011/133886, and U.S. Patent Application Publication No. 2014322129, incorporated by reference herein in their entirety.

In some embodiments, the attachment can be covalent or non-covalent, e.g., via a biotin-streptavidin non-covalent interaction. In some embodiments, 1, 2, 3, 4, 5 or more moieties, which can be the same or different, are conjugated, linked or fused to a CD28 VHH domain to form a CD28-binding conjugate. In some embodiments, such moieties can be attached to the VHH domain using various molecular biological or chemical conjugation and linkage methods known in the art and described below. In some embodiments, linkers such as peptide linkers, cleavable linkers, non-cleavable linkers or linkers that aid in the conjugation reaction, can be used to link or conjugate the effector moieties to the variant polypeptide or immunomodulatory protein.

In some embodiments, a CD28 VHH domain is conjugated to one or more moieties, e.g. about 1 to about 20 drug moieties per VHH, through a linker (L). In some embodiments, the CD28-binding conjugate comprises the following components: (VHH domain), $(L)_q$ and $(\text{moiety})_m$, wherein the VHH domain is any of the described VHH domains capable of specifically binding CD28 as described; L is a linker for linking the protein or polypeptide to the moiety; m is at least 1; q is 0 or more; and the resulting CD28-binding conjugate binds to CD28. In particular embodiments, m is 1 to 4 and q is 0 to 8.

The linker may be composed of one or more linker components. For covalent attachment of the antibody and the drug moiety the linker typically has two reactive functional groups, i.e. bivalency in a reactive sense. Bivalent linker reagents which are useful to attach two or more functional or biologically active moieties, such as peptides, nucleic acids, drugs, toxins, antibodies, haptens, and reporter groups are known, and methods have been described their resulting conjugates (Hermanson, G. T. (1996) Bioconjugate Techniques; Academic Press: New York, p 234-242).

Exemplary linker components include 6-maleimidocaproyl ("MC"), maleimidopropanoyl ("MP"), valine-citrulline ("val-cit"), a alanine-phenylalanine ("ala-phe"), p-aminobenzyloxycarbonyl ("PAB"), N-Succinimidyl 4-(2-pyridylthio)pentanoate ("SPP"), N-Succinimidyl 4-(N-maleimidomethyl)cyclohexane-I carboxylate ("SMCC"), and N-Succinimidyl (4-iodo-acetyl)aminobenzoate ("STAB").

In some embodiments, the linker may comprise amino acid residues. Exemplary amino acid linker components include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline (gly-val-cit) and glycine-glycine-glycine (gly-gly-gly). Amino acid residues which comprise an amino acid linker component include those occurring naturally, as well as minor amino acids and non-naturally occurring amino acid analogs, such as citrulline. Amino acid linker components can be designed and optimized in their selectivity for enzymatic cleavage by a particular enzymes, for example, a tumor-associated protease, cathepsin B, C and D, at a plasmin protease.

Conjugates of a VHH domain and cytotoxic agent can be made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl substrate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene).

The antibody drug conjugate can be prepared by a variety of methods, such as organic chemistry reactions, conditions, and reagents known to those skilled in the art. In one embodiments, methods include: (1) reaction of a nucleophilic group of a VHH domain with a bivalent linker reagent, to form VHH-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of a VHH domain.

Nucleophilic groups on antibodies, including VHH domains, include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by introducing one, two, three, four, or more cysteine residues (e.g., preparing mutant antibodies comprising one or more non-native cysteine amino acid residues).

Conjugates, such as antibody drug conjugates, may also be produced by modification of an antibody, such as a VHH domain, to introduce electrophilic moieties, which can react with nucleophilic substituents on the linker reagent or drug. The sugars of glycosylated antibodies may be oxidized, e.g., with periodate oxidizing reagents, to form aldehyde or ketone groups which may lead with the amine group of linker reagents or drug moieties. The resulting imine Schiff base groups may form a stable linkage, or may be reduced, e.g., by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, Bioconjugate Techniques). In another embodiment, proteins containing N-terminal serine or threonine residues can react with sodium meta-periodate, resulting in production of an aldehyde in place of the first amino acid. Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBi esters, haloformates, and acid halides; (ii) alkyl and benzyl halides such as haloacetamides; (iii) aldehydes, ketones, carboxyl, and maleimide groups.

Alternatively, a fusion protein containing a VHH domain and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

C. Multispecific Formats

Provided herein are CD28-binding polypeptides that are multispecific containing at least one VHH domain that binds CD28 and one or more additional binding domains (BD). In some embodiments, the ability of the multispecific CD28-binding polypeptide to engage CD28 is conditioned upon binding of the one or more additional binding domains to its binding partner. Typically, the one or more additional binding domains binds to an antigen other than CD28. In some embodiments, that one or more additional binding domain is an antibody or antigen binding fragment specific for the other antigen, such as an antigen expressed by an activated T cell, an exhausted T cell, or another type of cell in the tumor microenvironment (TME). In some embodiments, the one or more additional binding domain is an antibody or antigen binding fragment specific for the other antigen, such as a tumor associated antigen (TAA). In some embodiments, the additional domain is a VHH domain, such as a TAA VHH (sdAb).

In some examples, the multispecific CD28-binding polypeptides additionally include an Fc domain. In some embodiments, the inclusion of an Fc domain allows for dimerization of two CD28-binding polypeptides, thereby doubling the number of CD28 VHHs and/or BDs. In some embodiments, the inclusion of an Fc domain allows for dimerization of two CD28-binding polypeptides, thereby doubling the number of CD28 VHHs and/or TAA VHHs.

In some embodiments, the multispecific CD28-binding polypeptides additionally include a CD3 binding region. In some embodiments, the CD3 binding region is not able to engage, or is not able to substantially engage, CD3, unless the one or more additional binding domain (e.g. TAA sdAb) to its binding partner (e.g. a TAA or other antigen).

Non-limiting exemplary multispecific CD28-binding polypeptides are described below.

a. Conditional CD28 Multispecific Constructs

In some embodiments, the CD28-binding polypeptide is a multispecific CD28-binding polypeptide having at least one CD28 VHH and one or more additional binding domains (BD) that binds to an antigen other than CD28 (e.g. a single domain antibody that binds a tumor associated antigen or other antigen present in the TME). In some embodiments, the multispecific CD28-binding polypeptide is a conditional multispecific CD28-binding polypeptide. For example, the conditional multispecific CD28-binding peptides are not able to, or not substantially able to, engage CD28, unless the one or more additional binding domain is bound to its binding partner. In some embodiments, when the binding partner (e.g. a TAA or other antigen present in the TME) binds to the one or more additional binding domain (e.g. a BD sdAb, such as a TAA sdAb), the CD28-multispecific polypeptide is capable of engaging CD28.

In some embodiments, the conditional multispecific CD28-binding polypeptides provided herein exist in two states in terms of capacity to engage CD28 and subsequently stimulate T-cells: (1) the "inactive" state occurs when there is no binding of any or all of the antigen binding domain(s) to its antigen (e.g. a TAA), such that the CD28 binding is conditional and T-cell stimulation is obviated or reduced, and (2) the "active" state occurs upon antigen binding by any or all of the antigen binding domain(s) to its antigen (e.g. a TAA), such that the CD28 binding region is able to engage CD28 and the T-cell stimulation is allowed.

In some embodiments, the conditional multispecific CD28-binding polypeptides provided herein exist in two states in terms of capacity to agonize CD28 and subsequently stimulate T-cells: (1) the "inactive" state occurs when there is binding to CD28, but signaling is not elicited and T-cell stimulation is obviated or reduced, and (2) the "active" state occurs upon engagement of the construct through the one or more additional antigen binding domain(s) that bind an antigen other than CD28, such that the CD28 binding region is able to agonized CD28 and the T-cell stimulation is allowed. In some embodiments, CD28 agonism is conditional, meaning it is dependent on co-engagement of the one or more binding domain that binds an antigen other than CD28 by its antigen.

a. CD28 Binding Domain

The multispecific CD28-binding polypeptides include at least one CD28 binding domain, such as single domain antibody (VHH domain) that binds CD28, and one or more additional binding domain (BD; e.g. a sdAb) that binds an antigen that is not CD28. In some embodiments, this different antigen is a tumor associated antigen (TAA) or tumor microenvironment associated antigen (TMEAA). In some embodiments, this second antigen is an immunomodulatory antigen, wherein said antigen is involved with enhancing or dampening a signaling pathway in an immune cell. Thus, in some embodiments, the provided multispecific CD28-binding polypeptides include at least one CD28 sdAb (VHH) and one or more TAA sdAbs. In some embodiments, the provided multispecific CD28-binding polypeptides include at least one CD28 sdAb (VHH) and one or more BDs that binds an antigen in the TME. In some embodiments, the antigen in the TME is an antigen expressed by activated and/or exhausted T cells. In some embodiments, the antigen in the TME is an antigen expressed by other T cells in the TME.

In some embodiments, a multispecific CD28-binding polypeptide includes one CD28 sdAb (i.e. the multispecific C28-binding polypeptide is monovalent for CD28). The one CD28 may be or contain any of the CD28 sdAb sequences as described in Section II. In some embodiments, the one CD28 sdAb is or contains the sequence set forth in SEQ ID NO:188, 220, or 280. In some embodiments, the one CD28 sdAb is or contains the sequence set forth in SEQ ID NO:188. In some embodiments, the one CD28 sdAb is or contains the sequence set forth in SEQ ID NO:220. In some embodiments, the one CD28 sdAb is or contains the sequence set forth in SEQ ID NO:280.

In some embodiments, the multispecific CD28-binding polypeptide is multivalent for CD28. In some embodiments, the multispecific CD28-binding polypeptide includes two or more CD28 sdAb, for example, three or more, four or more, five or more, or six of more CD28 sdAb. In some embodiments, the CD28-binding polypeptide includes two CD28 sdAbs. In some embodiments, the two CD28 sdAbs are identical. In some embodiments, the two CD28 antibodies are different, for example, they bind to different epitopes of CD28. In some embodiments, the CD28-binding polypeptide includes four CD28 sdAbs. In some embodiments, all four CD28 sdAbs are identical. In some embodiments, the first two of the 4 CD28 sdAbs are identical and the other two of the four CD28 sdAbs are identical. In some embodiments, three of the four CD28 sdAbs are identical and the fourth of the four CD28 sdAbs is different from the other three. In any of the provided embodiments, the incorporated CD28 sdAbs (VHH) are or contain any of the CD28 VHH sequences as described in Section II.

In some embodiments, the multispecific CD28-binding polypeptide includes at least one CD28 sdAb having the amino acid sequence set forth in SEQ ID NO:188. In some embodiments, the multispecific CD28-binding polypeptide includes two CD28 sdAbs having the amino acid sequence set forth in SEQ ID NO:188. In some embodiments, the multispecific CD28-binding polypeptide includes four CD28 sdAbs having the amino acid sequence set forth in SEQ ID NO:188. In some embodiments, the multispecific CD28-binding polypeptide includes at least one CD28 sdAb having the amino acid sequence set forth in SEQ ID NO:220. In some embodiments, the multispecific CD28-binding polypeptide includes two CD28 sdAbs having the amino acid sequence set forth in SEQ ID NO:220. In some embodiments, the multispecific CD28-binding polypeptide includes four CD28 sdAbs having the amino acid sequence set forth in SEQ ID NO:280.

b. TAA Binding Domain

The provided multispecific CD28-binding polypeptides contain one or more TAA binding domain. In some embodiments, the one or more TAA binding domain is one or more TAA sdAbs. In some embodiments, the TAA is any as described in Section IIIC(c)(ii). The one TAA sdAb may be or contain any of the TAA sdAb sequences as described in Section IIIC(c)(ii).

In some embodiments, a multispecific CD28-binding polypeptide is monovalent for a TAA, in that the multispecific CD28-binding polypeptide includes one single domain antibody (or VHH) that binds a tumor associated antigen (TAA).

In some embodiments, the TAA is PDL1. In some embodiments, the TAA sdAB contains a CDR1, CDR2, and CDR3 having the sequence set forth in SEQ ID NO:100, 101, and 102, respectively. In some embodiments, the TAA sdAb is or contains the sequence set forth in SEQ ID NO:99.

In some embodiments, the TAA is 5T4. In some embodiments, the TAA sdAB contains a CDR1, CDR2, and CDR3 having the sequence set forth in SEQ ID NO:241, 242, and 243, respectively. In some embodiments, the TAA sdAb is or contains the sequence set forth in SEQ ID NO:240. In some embodiments, the TAA sdAB contains a CDR1, CDR2, and CDR3 having the sequence set forth in SEQ ID NO:246, 247, and 248, respectively. In some embodiments, the TAA sdAb is or contains the sequence set forth in SEQ ID NO:245.

In some embodiments, the multispecific CD28-binding polypeptide contains one or more TAA binding domains, such as one or more TAA sdAbs. In some embodiments, the multispecific CD28-binding polypeptide includes two or more TAA VHH domains, for example, three or more, four or more, five or more, or six of more TAA VHH domains. In some embodiments, the multispecific CD28-binding polypeptide includes 2 TAA sdAbs. In some embodiments, the two TAA sdAbs bind the same TAA. In some embodiments, the two TAA sdAbs bind the same epitope of the same TAA. In some embodiments, the two TAA sdAbs bind different epitopes of the same TAA. In some embodiments, the two TAA sdAbs bind different TAAs. In some embodiments, the CD28-binding polypeptide includes four TAA sdAbs. In some embodiments, all four TAA sdAbs bind the same TAA. In some embodiments, the first two of the 4 TAA sdAbs bind a first TAA and the other two of the four TAA sdAbs bind another TAA. In some embodiments, three of the four TAAs sdAbs bind the same TA and the fourth of the four TAA sdAbs binds a different TAA. In any of the provided embodiments, the TAA is any as described in Section IIIC(c)(ii). In any of the provided embodiments, the incorporated TAA sdAbs (VHH) are or contain any of the TAA VHH sequences as described in Section IIIC(c)(ii).

In some embodiments, the multispecific CD28-binding polypeptide includes at least one TAA sdAb having the amino acid sequence set forth in SEQ ID NO:99. In some embodiments, the multispecific CD28-binding polypeptide includes two TAA sdAb having the amino acid sequence set forth in SEQ ID NO:99.

In some embodiments, the multispecific CD28-binding polypeptide includes at least one TAA sdAb having the amino acid sequence set forth in SEQ ID NO:240. In some embodiments, the multispecific CD28-binding polypeptide includes two TAA sdAb having the amino acid sequence set forth in SEQ ID NO:245. In some embodiments, the multispecific CD28-binding polypeptide includes a TAA sdAb having the amino acid sequence set forth in SEQ ID NO:240 and a TAA sdAb having the amino acid sequence set forth in SEQ ID NO:245.

In some embodiments, the multispecific CD28-binding polypeptide contains from N-terminal to C-terminal: (TAA sdAb)-linker-(CD28 sdAb). In some embodiments, the multispecific CD28-binding polypeptide contains from N-terminal to C-terminal: (TAA sdAb)-linker-(TAA sdAb)-linker-(CD28 sdAb). In some embodiments, the multispecific CD28-binding polypeptide contains from N-terminal to C-terminal: (TAA sdAb)-linker-(CD28 sdAb)-linker-(CD28 sdAb). In some embodiments, the multispecific CD28-binding polypeptide contains from N-terminal to C-terminal: (TAA sdAb)-linker-(TAA sdAb)-linker-(CD28 sdAb)-linker-(CD28 sdAb).

In some embodiments, a multispecific polypeptide construct includes a moiety that binds protein A. In some embodiments, the protein A-binding moiety assists in purification of multispecific polypeptide constructs, particularly those without an Fc region.

c. Fc Region

In some embodiments, the conditional multispecific CD28-binding polypeptide further includes an immunoglobulin Fc region, such as any described in Section IIIA or IIIC(c)(iii).

In some embodiments, the Fc region is linked to the at least one CD28 sdAb via a linker or linkers. In some embodiments, the Fc region is linked to the at least one CD28 sdAb via a non-cleavable linker or linkers. In some embodiments, the Fc region is linked to the at least one CD28 VHH binding region via a cleavable linker or an otherwise labile linker or linkers.

The provided conditional multispecific polypeptide constructs include a configuration in which the Fc region is C-terminal to at least one of the at least one CD28 sdAbs. In such an embodiment, the Fc domain and the CD28 sdAb are joined via a linker that is N-terminal to the Fc region. In some embodiments, the Fc domain is positioned on the carboxy-terminal (C-term) region of the multispecific polypeptide construct.

In some embodiments, the multispecific CD28-binding polypeptide contains one or more TAA binding domains. In some embodiments, at least one of the one or more TAA sdAbs is linked to at least one of the at least one CD28 sdAbs. In some embodiments, the TAA sdAb is N-terminal to the CD28 sdAb, such that the TAA sdAb linked to the CD28 sdAb at the C-terminal of the TAA sdAb.

Thus, in some embodiments, the multispecific CD28-binding polypeptide includes from N-terminal to C-terminal: (TAA sdAb)-linker-(CD28 sdAb)-linker-Fc. In some embodiments, the multispecific CD28-binding polypeptide includes from N-terminal to C-terminal: (TAA sdAb)-linker-(TAA sdAb)-linker-(CD28 sdAb)-linker-Fc. In some embodiments, the multispecific CD28-binding polypeptide includes from N-terminal to C-terminal: (TAA sdAb)-linker-(CD28 sdAb)-linker-(CD28 sdAb)-linker-Fc. In some embodiments, the multispecific CD28-binding polypeptide includes from N-terminal to C-terminal: (TAA sdAb)-linker-(TAA sdAb)-linker-(CD28 sdAb)-linker-(CD28 sdAb)-linker-Fc.

In some embodiments, a multispecific CD28-binding polypeptide is a dimer formed by polypeptides, each containing an Fc.

In some embodiments, the conditional multispecific polypeptide construct is a dimer, in which dimerization is formed by covalent or non-covalent interactions between two polypeptide chains. In some embodiments, the two polypeptide chains are covalently bonded to each other by, for example, interchain disulfide bonds. In some embodiments, the Fc region mediates dimerization via interchain disulfide bonds.

In some embodiments, a conditional multispecific polypeptide construct contains a homodimeric Fc region (such as any described in Section IIIA or IIIC(c)(iii)), which mediates dimerization of CD28-binding polypeptide chains that are the same, such as any of those described above. Thus, in some embodiments, the multispecific CD28-binding polypeptide comprises two polypeptide chains that each include, from N-terminal to C-terminal: (TAA sdAb)-linker-(CD28 sdAb)-linker-Fc. In some embodiments, the multispecific CD28-binding polypeptide comprises two polypeptide chains that each include, from N-terminal to C-terminal: (TAA sdAb)-linker-(TAA sdAb)-linker-(CD28 sdAb)-linker-Fc. In some embodiments, the multispecific CD28-binding polypeptide comprises two polypeptide chains that each include, from N-terminal to C-terminal: (TAA sdAb)-linker-(CD28 sdAb)-linker-(CD28 sdAb)-linker-Fc. In some embodiments, the multispecific CD28-binding polypeptide comprises two polypeptide chains that each include, from N-terminal to C-terminal: (TAA sdAb)-linker-(TAA sdAb)-linker-(CD28 sdAb)-linker-(CD28 sdAb)-linker-Fc.

In particular embodiments, a conditional multispecific polypeptide construct contains a heterodimeric Fc region (such as any described in Section IIIA or IIIC(c)(iii)) in which, in some cases, the polypeptide chains of the multispecific polypeptide construct are different (heterodimer).

In some embodiments, a multispecific CD28-binding polypeptide is formed from or includes two polypeptides, including a first polypeptide comprising a first Fc polypeptide of a heterodimeric Fc region, and optionally at least one CD28 VHH and/or one or more TAA binding domain; and a second polypeptide comprising a second Fc polypeptide of the heterodimeric Fc region, and optionally at least one CD28 VHH and/or one or more TAA binding domain. In some embodiments, the first and/or the second polypeptide comprises at least one CD28 VHH and one or more TAA binding domain, which are joined by linker. In some embodiments, the first polypeptide contains zero, one, two, or three sdAb that bind to CD28. In some embodiments, the second polypeptide contains zero, one, two, or three sdAbs that bind to CD28. In some embodiments, the first polypeptide contains zero, one, two, or three TAA binding domains that bind to a TAA. In some embodiments, the second polypeptide contains zero, one, two, or three TAA binding domains that bind to a TAA. In some embodiments, a conditional multispecific polypeptide construct contains at least one CD28 sdAb. In some embodiments, a conditional multispecific polypeptide construct contains at least two CD28 sdAb. In some embodiments, a conditional multispecific polypeptide construct contains one or more TAA binding domain. In some embodiments, a conditional multispecific polypeptide construct contains at least two TAA binding domains.

In some cases, at least one of the at least one CD28 sdAb is located N-terminally to the Fc polypeptide. In some cases, at least one of the one or more TAA binding domain is located N-terminally to the Fc polypeptide. In some cases, at least one of the one or more TAA binding domain is located N-terminally to at least one of the at least one CD28 sdAbs. In some cases, at least one of the one or more TAA binding domain and at least one CD28 VHH domain are located N-terminally to the Fc polypeptide.

In some embodiments, the multispecific CD28-binding polypeptide is formed from or includes two polypeptides, including a first polypeptide having a first TAA sdAb, a CD28 VHH, and a first Fc polypeptide of a heterodimeric Fc region; and a second polypeptide having a second TAA sdAb, optionally, the same or different TAA, a CD28 VHH, optionally, the same or different VHH, and the second Fc polypeptide of the heterodimeric Fc region. The sdAb that binds to a TAA can be positioned amino terminally relative to an Fc polypeptide of the heterodimeric Fc and/or amino terminally relative to a CD28 VHH. The sdAb that binds to a TAA can be positioned amino terminally relative to an Fc polypeptide of the heterodimeric Fc and amino terminally relative to at least one of the at least one CD28 VHH.

In some embodiments, the multispecific CD28-binding polypeptide is formed from or includes two polypeptides, including a first polypeptide having one or more TAA sdAb, at least one CD28 VHH, and a first Fc polypeptide of a heterodimeric Fc region; and a second polypeptide having the second Fc polypeptide of the heterodimeric Fc region. In some embodiments, the multispecific polypeptide construct is formed from or includes two polypeptides, including a first polypeptide having at least one CD28 VHH and a first Fc polypeptide of a heterodimeric Fc region; and a second polypeptide having one or more TAA sdAb and the second Fc polypeptide of the heterodimeric Fc region. In some embodiments, the multispecific polypeptide construct is formed from or includes two polypeptides, including a first polypeptide having one or more TAA sdAb, at least one CD28 VHH and a first Fc polypeptide of a heterodimeric Fc region; and a second polypeptide having one or more TAA sdAb and the second Fc polypeptide of the heterodimeric Fc region. In some embodiments, the multispecific CD28-binding polypeptide is formed from or includes two polypeptides, including a first polypeptide having one or more TAA sdAb, at least one CD28 VHH and a first Fc polypeptide of a heterodimeric Fc region; and a second polypeptide having at least one CD28 VHH and the second Fc polypeptide of the heterodimeric Fc region. In some embodiments, the multispecific CD28-binding polypeptide is formed from or includes two polypeptides, including a first polypeptide having one or more TAA sdAb and a first Fc polypeptide of a heterodimeric Fc region; and a second polypeptide having at least one CD28 VHH and the second Fc polypeptide of the heterodimeric Fc region.

In some embodiments, a multispecific CD28-binding polypeptide does not contain a CD3-binding domain. In some embodiments, a multispecific CD28-binding polypeptide engages CD28 independently of CD3.

b. Constrained CD3 Multispecific Constructs

In any of the provided embodiments, the multispecific CD28-binding polypeptides additionally contain a CD3 binding region. Thus, in some embodiments, the multispecific CD28-binding polypeptides include at least one CD28 binding domain (e.g. sdAb), one or more TAA binding domain (e.g. sdAb), an Fc region, and a CD3 binding region. In some embodiments, the CD3 binding region is C-terminal to the Fc region. For example, in some embodiments, a multispecific CD28-biding polypeptide includes from N-terminal to C-terminal: (TAA sdAb)-linker-(CD28 sdAb)-linker-Fc-CD3 binding region.

In some embodiments, the CD3 binding region is not able to, or is not substantially able, to bind or engage CD3 unless the one or more TAA binding regions, or each of the one or more TAA binding regions, is bound to its antigen. Thus, in some embodiments, the multispecific CD28-binding polypeptides provided herein exist in two states in terms of capacity to bind and/or engage CD3: (1) the "inactive" state occurs when there is no binding of any or all of the antigen binding domain(s) to a TAA, such that the CD3 binding is conditional and CD3 engagement is obviated or reduced, and (2) the "active" state occurs upon antigen binding by any or all of the antigen binding domain(s) to a TAA, such that the CD3 binding region is able to engage CD3.

In some embodiments, a multispecific CD28-binding polypeptide additionally includes one or more copies of an anti-CD3 binding domain. The anti-CD3 binding domains of the disclosure activate T cells via engagement of CD3 or a member of the CD3 complex on the T cells. In some embodiments, the anti-CD3 binding domains of the disclosure specifically bind the epsilon chain of CD3, also known as CD3ε. The anti-CD3ε binding domains of the disclosure activate T cells via engagement of CD3ε on the T cells. The anti-CD3 binding domains of the disclosure agonize, stimulate, activate, and/or otherwise augment CD3-mediated T cell activation. Biological activities of CD3 include, for example, T cell activation and other signaling through interaction between CD3 and the antigen-binding subunits of the T-Cell Receptor (TCR). For example, the anti-CD3 binding domains of the disclosure completely or partially activate T cells via engagement of CD3ε on T cells by partially or completely modulating, e.g., agonizing, stimulating, activating or otherwise augmenting CD3-mediated T cell activation.

The CD3 binding domain can be any as described above. In particular embodiments, the CD3 binding domain is an Fv antibody fragment that binds CD3ε (referred to herein as an anti-CD3ε Fv fragment). In some embodiments, the anti-CD3ε Fv antibody fragment is a disulfide stabilized anti-CD3 binding Fv fragment (dsFv). In some embodiments, the anti-CD3 binding domain is monovalent for binding CD3.

In some embodiments, the CD3 binding region is an Fv antibody fragment containing a variable heavy chain (Hv, also called VH) and variable light chain (Lv, also called VL), such as any as described. In aspects of such embodiments, the immunoglobulin Fc region is a heterodimeric Fc region containing two different Fc polypeptides capable of heterodimeric association between both polypeptides of the Fc heterodimer, such as any as described herein. In such embodiments, the variable heavy chain (VH) and variable light chain (VL) of the CD3 binding region are linked on opposite chains of the heterodimeric Fc.

In some embodiments, the CD3 binding region is an Fv or dsFv of SP34 (Pessano et ai. The EMBO Journal. 4: 337-344, 1985) or a humanized variant of SP34 (WO2015001085).

In some embodiments, the anti-CD3ε binding domain thereof is an Fv, such as a dsFv fragment, that includes a combination of heavy chain variable amino acid sequence and a light chain variable amino acid sequence. In some embodiments, the CD3-binding domain is an Fv or dsFv fragment in which is contained a VH CDR1 sequence that includes at least the amino acid sequence TYAMN (SEQ ID NO: 29); a VH CDR2 sequence that includes at least the amino acid sequence RIRSKYNNYATYYADSVKD (SEQ ID NO: 30); a VH CDR3 sequence that includes at least the amino acid sequence HGNFGNSYVSWFAY (SEQ ID NO: 31), a VL CDR1 sequence that includes at least the amino acid sequence RSSTGAVTTSNYAN (SEQ ID NO: 32); a VL CDR2 sequence that includes at least the amino acid sequence GTNKRAP (SEQ ID NO: 33); and a VL CDR3 sequence that includes at least the amino acid sequence ALWYSNLWV (SEQ ID NO: 34). In some embodiments, the anti-CD3ε binding domain thereof is an Fv, such as a dsFv fragment, that includes a heavy chain variable amino acid sequence selected from the group of SEQ ID NO: 35-65, 340, 341, or 283 and a light chain variable amino acid sequence selected from the group consisting of SEQ ID NO: 66-84, 281, 338, or 339.

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence TYAMN (SEQ ID NO: 29); a VH CDR2 sequence that is at least 90%, 91%, 92%, 93%, 94%, 95%, 96%, 97%, 98%, 99% or more identical to the amino acid sequence RIRSKYNNYATYYADSVKD (SEQ ID NO: 30); a VH CDR3 sequence that is at least 90%, 91%, 92%, 93%, 94%, 95%, 96%, 97%, 98%, 99% or more identical to the amino acid sequence HGNFGNSYVSWFAY (SEQ ID NO: 31), a VL CDR1 sequence that is at least 90%, 91%, 92%, 93%, 94%, 95%, 96%, 97%, 98%, 99% or more identical to the amino acid sequence RSSTGAVTTSNYAN (SEQ ID NO: 32); a VL CDR2 sequence that is at least 90%, 91%, 92%, 93%, 94%, 95%, 96%, 97%, 98%, 99% or more identical to the amino acid sequence GTNKRAP (SEQ ID NO: 33); and a VL CDR3 sequence that is at least 90%, 91%, 92%, 93%, 94%, 95%, 96%, 97%, 98%, 99% or more identical to the amino acid sequence ALWYSNLWV (SEQ ID NO: 34).

In some embodiments, the anti-CD3ε binding domain includes a VH CDR1 sequence that includes at least the amino acid sequence GFTFNTYAMN (SEQ ID NO: 252); a VH CDR2 sequence that includes at least the amino acid sequence RIRSKYNNYATY (SEQ ID NO: 286); a VH CDR3 sequence that includes at least the amino acid sequence HGNFGNSYVSWFAY (SEQ ID NO: 31), a VL CDR1 sequence that includes at least the amino acid sequence RSSTGAVTTSNYAN (SEQ ID NO: 32); a VL CDR2 sequence that includes at least the amino acid sequence GTNKRAP (SEQ ID NO: 33); and a VL CDR3 sequence that includes at least the amino acid sequence ALWYSNLWV (SEQ ID NO: 34).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence GFTFNTYAMN (SEQ ID NO: 252); a VH CDR2 sequence that is at least 90%, 91%, 92%, 93%, 94%, 95%, 96%, 97%, 98%, 99% or more identical to the amino acid sequence RIRSKYNNYATY (SEQ ID NO: 286); a VH CDR3 sequence that is at least 90%, 91%, 92%, 93%, 94%, 95%, 96%, 97%, 98%, 99% or more identical to the amino acid sequence HGNFGNSYVSWFAY (SEQ ID NO: 31), a VL CDR1 sequence that is at least 90%, 91%, 92%, 93%, 94%, 95%, 96%, 97%, 98%, 99% or more identical to the amino acid sequence RSSTGAVTTSNYAN (SEQ ID NO: 32); a VL CDR2 sequence that is at least 90%, 91%, 92%, 93%, 94%, 95%, 96%, 97%, 98%, 99% or more identical to the amino acid sequence GTNKRAP (SEQ ID NO: 33); and a VL CDR3 sequence that is at least 90%, 91%, 92%, 93%, 94%, 95%, 96%, 97%, 98%, 99% or more identical to the amino acid sequence ALWYSNLWV (SEQ ID NO: 34).

In some embodiments, the anti-CD3ε binding domain includes a VH CDR1 sequence that includes at least the amino acid sequence GFTFNTYAMN (SEQ ID NO: 252); a VH CDR2 sequence that includes at least the amino acid sequence RIRSKYNNYATY (SEQ ID NO: 286); a VH CDR3 sequence that includes at least the amino acid sequence HGNFGNSYVSWFAY (SEQ ID NO: 31), a VL CDR1 sequence that includes at least the amino acid sequence GSSTGAVTTSNYAN (SEQ ID NO: 304); a VL CDR2 sequence that includes at least the amino acid sequence GTNKRAP (SEQ ID NO: 33); and a VL CDR3 sequence that includes at least the amino acid sequence ALWYSNHWV (SEQ ID NO: 288).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence GFTFNTYAMN (SEQ ID NO: 252); a VH CDR2 sequence that is at least 90%, 91%, 92%, 93%, 94%, 95%, 96%, 97%, 98%, 99% or more identical to the amino acid sequence RIRSKYNNYATY (SEQ ID NO: 286); a VH CDR3 sequence that is at least 90%, 91%, 92%, 93%, 94%, 95%, 96%, 97%, 98%, 99% or more identical to the amino acid sequence HGNFGNSYVSWFAY (SEQ ID NO: 31), a VL CDR1 sequence that is at least 90%, 91%, 92%, 93%, 94%, 95%, 96%, 97%, 98%, 99% or more identical to the amino acid sequence GSSTGAVTTSNYAN (SEQ ID NO: 304); a VL CDR2 sequence that is at least 90%, 91%, 92%, 93%, 94%, 95%, 96%, 97%, 98%, 99% or more identical to the amino acid sequence GTNKRAP (SEQ ID NO: 33); and a VL CDR3 sequence that is at least 90%, 91%, 92%, 93%, 94%, 95%, 96%, 97%, 98%, 99% or more identical to the amino acid sequence ALWYSNHWV (SEQ ID NO: 288).

In some embodiments, the anti-CD3ε binding domain includes a VH CDR1 sequence that includes at least the amino acid sequence GFTFSTYAMN (SEQ ID NO: 302); a VH CDR2 sequence that includes at least the amino acid sequence RIRSKYNNYATY (SEQ ID NO: 303); a VH CDR3 sequence that includes at least the amino acid sequence HGNFGDSYVSWFAY (SEQ ID NO: 287), a VL CDR1 sequence that includes at least the amino acid sequence GSSTGAVTTSNYAN (SEQ ID NO: 304); a VL CDR2 sequence that includes at least the amino acid sequence GTNKRAP (SEQ ID NO: 33); and a VL CDR3 sequence that includes at least the amino acid sequence ALWYSNHWV (SEQ ID NO: 288).

In some embodiments, the anti-CD3ε binding domain includes a VH CDR1 sequence that is at least 90%, 91%, 92%, 93%, 94%, 95%, 96%, 97%, 98%, 99% or more identical to the amino acid sequence GFTFSTYAMN (SEQ ID NO: 302); a VH CDR2 sequence that is at least 90%, 91%, 92%, 93%, 94%, 95%, 96%, 97%, 98%, 99% or more identical to the amino acid sequence RIRSKYNNYATY (SEQ ID NO: 303); a VH CDR3 sequence that is at least 90%, 91%, 92%, 93%, 94%, 95%, 96%, 97%, 98%, 99% or more identical to the amino acid sequence HGNFGDSYVSWFAY (SEQ ID NO: 287), a VL CDR1 sequence that is at least 90%, 91%, 92%, 93%, 94%, 95%, 96%, 97%, 98%, 99% or more identical to the amino acid sequence GSSTGAVTTSNYAN (SEQ ID NO: 304); a VL CDR2 sequence that is at least 90%, 91%, 92%, 93%, 94%, 95%, 96%, 97%, 98%, 99% or more identical to the amino acid sequence GTNKRAP (SEQ ID NO: 33); and a VL CDR3 sequence that is at least 90%, 91%, 92%, 93%, 94%, 95%, 96%, 97%, 98%, 99% or more identical to the amino acid sequence ALWYSNHWV (SEQ ID NO: 288).

In some embodiments, the anti-CD3ε binding domain includes a CDR3 that includes at least amino acids VLWYSNRWV (SEQ ID NO:289). In some embodiments, the anti-CD3ε binding domain includes a CDR3 that is at least 90%, 91%, 92%, 93%, 94%, 95%, 96%, 97%, 98%, 99% or more identical to the amino acids VLWYSNRWV (SEQ ID NO:289).

In some embodiments, the anti-CD3ε binding domain includes one or more copies of an antibody or an antigen-binding fragment thereof selected from the group consisting of a Fab fragment, a $F(ab')_2$ fragment, an Fv fragment, a scFv, a scAb, a dAb, a single domain heavy chain antibody, and a single domain light chain antibody. In some embodiments, the anti-CD3 binding domain includes an Fv antibody fragment that binds CD3ε (referred to herein as an anti-CD3ε Fv fragment). In some embodiments, the anti-CD3ε Fv antibody fragment is a disulfide stabilized anti-CD3 binding Fv fragment (dsFv). In some embodiments, the anti-CD3 binding domain is monovalent for binding CD3.

In some embodiments, the CD3 binding region is not a single chain antibody. For example, in some aspects, the CD3 binding region is not a single chain variable fragment (scFv).

In some embodiments, the CD3 binding region is an Fv antibody fragment containing a variable heavy chain (Hv, also called VH) and variable light chain (Lv, also called VL), such as any as described. In aspects of such embodiments, the immunoglobulin Fc region is a heterodimeric Fc region containing two different Fc polypeptides capable of heterodimeric association between both polypeptides of the Fc heterodimer, such as any as described in Section III.C.2.b. In such embodiments, the variable heavy chain (VH) and variable light chain (VL) of the CD3 binding region are linked on opposite chains of the heterodimeric Fc.

In some embodiments, the anti-CD3ε binding domain thereof includes a combination of a heavy chain variable region amino acid sequence and a light chain variable region amino acid sequence comprising an amino acid sequence selected from the group of SEQ ID NO: 27, 28, 35-84, 281, 338-341, and 283. In some embodiments, the anti-CD3ε binding domain thereof includes a combination of a heavy chain variable region amino acid sequence selected from the group of SEQ ID NO: 27, 35-65, 340, 341, and 283 and a light chain variable region amino acid sequence comprising an amino acid sequence selected from the group of SEQ ID NO: 28, 66-84, 281, 338, and 339.

In some embodiments, the anti-CD3ε binding domain thereof is an Fv fragment that includes a combination of heavy chain variable amino acid sequence and a light chain variable amino acid sequence. In some embodiments, the anti-CD3ε binding domain thereof is an Fv fragment that includes a combination of heavy chain variable amino acid sequence and a light chain variable amino acid sequence comprising an amino acid sequence that is at least 90%, 91%, 92%, 93%, 94%, 95%, 96%, 97%, 98%, 99% or more identical to an amino acid sequence selected from the group consisting of SEQ ID NOs: 35-84, 281, 338-341, and 283. In some embodiments, the anti-CD3ε binding domain thereof is an Fv fragment that includes a combination of heavy chain variable amino acid sequence and a light chain variable amino acid sequence comprising an amino acid sequence selected from the group consisting of SEQ ID NOs: 35-84, 281, 338-341, and 283. In some embodiments, the anti-CD3ε binding domain thereof is an Fv fragment that includes a combination of heavy chain variable amino acid sequence selected from the group of SEQ ID NO: 35-65, 340, 341, and 283 and light chain variable amino acid sequence selected from the group consisting of SEQ ID NO: 66-84, 281, 338 and 339. In some embodiments, the anti-CD3ε binding domain thereof is an Fv fragment that includes a combination of heavy chain variable amino acid sequence that is at least 90%, 91%, 92%, 93%, 94%, 95%, 96%, 97%, 98%, 99% or more identical to an amino acid sequence selected from the group consisting of SEQ ID NO: 35-65, 340, 341, and 283 and a light chain variable amino acid sequence that is at least 90%, 91%, 92%, 93%, 94%, 95%, 96%, 97%, 98%, 99% or more identical to an amino acid sequence selected from the group consisting of SEQ ID NO: 66-84, 281, 338, and 339.

In some embodiments, the anti-CD3ε binding domain thereof is an Fv or dsFv fragment that includes a heavy chain variable amino acid sequence that is at least 90%, 91%, 92%, 93%, 94%, 95%, 96%, 97%, 98%, 99% or more identical to an amino acid sequence selected from the group consisting of SEQ ID NO: 35-65, 340, 341, and 283 and an amino acid sequence that is at least 90%, 91%, 92%, 93%, 94%, 95%, 96%, 97%, 98%, 99% or more identical to an amino acid sequence selected from the group consisting of SEQ ID NO: 66-84, 281, 338, and 339. In some embodiments, the anti-CD3 binding domain is an Fv or dsFv, in which is contained a variable heavy chain (VH) comprising the amino acid sequence of SEQ ID NO: 47 and a variable light chain (VL) comprising the amino acid sequence of SEQ ID NO: 75. In some embodiments, the anti-CD3 binding domain is an Fv or dsFv, in which is contained a variable heavy chain (VH) comprising the amino acid sequence of SEQ ID NO: 47 and a variable light chain (VL) comprising the amino acid sequence of SEQ ID NO: 281.

In some embodiments, the anti-CD3ε binding domain thereof is an Fv fragment that includes a combination of heavy chain variable amino acid sequence and a light chain variable amino acid sequence. In some embodiments, the anti-CD3ε binding domain thereof is an Fv fragment that includes a combination of heavy chain variable amino acid sequence and a light chain variable amino acid sequence comprising an amino acid sequence that is at least 90%, 91%, 92%, 93%, 94%, 95%, 96%, 97%, 98%, 99% or more identical to an amino acid sequence selected from the group consisting of SEQ ID NOs: 27, 28, 35-84, 281, 338-341, 283. In some embodiments, the anti-CD3ε binding domain thereof is an Fv fragment that includes a combination of heavy chain variable amino acid sequence and a light chain variable amino acid sequence comprising an amino acid sequence selected from the group consisting of SEQ ID NOs: 27, 28, 35-84, 281, 338-341, and 283. In some embodiments, the anti-CD3ε Fv antibody fragment includes a combination of a heavy chain variable amino acid sequence that is at least 90%, 91%, 92%, 93%, 94%, 95%, 96%, 97%, 98%, 99% or more identical to an amino acid sequence selected from the group consisting of SEQ ID NO: 27, 35-65, 340, 341, and 283 and a light chain variable amino acid sequence that is at least 90%, 91%, 92%, 93%, 94%, 95%, 96%, 97%, 98%, 99% or more identical to an amino acid sequence selected from the group consisting of SEQ ID NO: 28, 66-84, 281, 338, and 339. In some embodiments, the anti-CD3ε Fv antibody fragment includes a combination of a heavy chain variable amino acid sequence selected from the group of SEQ ID NO: 27, 35-65, 340, 341, and 283 and a light chain variable amino acid sequence selected from the group consisting of SEQ ID NO: 28, 66-84, 281, 338, and 339.

In some embodiments, the anti-CD3ε Fv antibody fragment includes a combination of a heavy chain variable amino acid sequence that is at least 90%, 91%, 92%, 93%, 94%, 95%, 96%, 97%, 98%, 99% or more identical to an amino acid sequence selected from the group consisting of SEQ ID NO: 27, 35-46, 48-50, 340, 341, and 283 and a light chain variable amino acid sequence that is at least 90%, 91%, 92%, 93%, 94%, 95%, 96%, 97%, 98%, 99% or more identical to an amino acid sequence selected from the group consisting of SEQ ID NO: 28, 66, 68-74, 76, 78, 80, 281, 338, and 339. In some embodiments, the anti-CD3ε Fv antibody fragment includes a combination of a heavy chain variable amino acid sequence selected from the group of SEQ ID NO: 27, 35-46, 48-50, 340, 341, and 283 and a light chain variable amino acid sequence selected from the group consisting of SEQ ID NO: 28, 66, 68-74, 76, 78, 80, 338, and 339.

In some embodiments, the anti-CD3ε Fv antibody fragment includes a combination of a heavy chain variable amino acid sequence that is at least 90%, 91%, 92%, 93%, 94%, 95%, 96%, 97%, 98%, 99% or more identical to an amino acid sequence selected from the group consisting of SEQ ID NO: 27, 35-46, 48-50, 340, 341, and 283 and a light chain variable amino acid sequence that is at least 90%, 91%, 92%, 93%, 94%, 95%, 96%, 97%, 98%, 99% or more identical to an amino acid sequence selected from the group consisting of SEQ ID NO: 28, 66, 68-74, 76, 78, 80, 281, 338, and 339. In some embodiments, the anti-CD3ε Fv antibody fragment includes a combination of a heavy chain variable amino acid sequence selected from the group of SEQ ID NO: 27, 35-46, 48-50, 340, 341, and 283 and a light chain variable amino acid sequence selected from the group consisting of SEQ ID NO: 28, 66, 68-74, 76, 78, 80, 281, 338, and 339.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO:27. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 28. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 27 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 28. In some embodiments, the anti-CD3ε binding domain thereof includes a variable heavy chain (VH) comprising the amino acid sequence of SEQ ID NO: 27. In some embodiments, the anti-CD3ε binding domain includes a variable light chain (VL) comprising the amino acid sequence of SEQ ID NO: 28. In some embodiments, the anti-CD3ε binding domain thereof includes a variable heavy chain (VH) comprising the amino acid sequence of SEQ ID NO: 27 and a variable light chain (VL) comprising the amino acid sequence of SEQ ID NO: 28.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 340. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 338. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 340 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 338. In some embodiments, the anti-CD3ε binding domain thereof includes a variable heavy chain (VH) comprising the amino acid sequence of SEQ ID NO: 340. In some embodiments, the anti-CD3ε binding domain includes a variable light chain (VL) comprising the amino acid sequence of SEQ ID NO: 338. In some embodiments, the anti-CD3ε binding domain thereof includes a variable heavy chain (VH) comprising the amino acid sequence of SEQ ID NO: 340 and a variable light chain (VL) comprising the amino acid sequence of SEQ ID NO: 338.

In particular embodiments, the Fv is a disulfide stabilized Fv fragment (dsFv) in which the $V_H$-$V_L$ heterodimer is stabilized by an interchain disulfide bond. In some embodiments, the interchain disulfide bond is engineered by mutation of position in framework positions of the VH and/or VL chain. In some embodiments, the disulfide stabilized anti-CD3 Fv comprises an anti-CD3 VH with the mutation 44 to Cys and an anti-CD3 VL with the mutation 100 to Cys by Kabat numbering. For example, in some embodiments, the VH chain contains the mutation G44C and the VL chain contains the mutation G100C, each by kabat numbering. In some embodiments, the disulfide stabilized anti-CD3 Fv comprises an anti-CD3 VH with the mutation at position 105 to Cys and an anti-CD3 VL with the mutation position 43 to Cys by Kabat numbering.

In some embodiments, the anti-CD3ε Fv antibody fragment includes a combination of a heavy chain variable amino acid sequence that is at least 90%, 91%, 92%, 93%, 94%, 95%, 96%, 97%, 98%, 99% or more identical to an amino acid sequence selected from the group consisting of SEQ ID NO: 47, 52-65, 341, or 283 and a light chain variable amino acid sequence that is at least 90%, 91%, 92%, 93%, 94%, 95%, 96%, 97%, 98%, 99% or more identical to an amino acid sequence selected from the group consisting of SEQ ID NO: 67, 75, 77, 79, 81-84, 281, or 339. In some of any such embodiments, the anti-CD3 Fv is a dsFv that has a VH chain containing the mutation G44C and a VL chain containing the mutation G100C, each by kabat numbering. In some embodiments, the anti-CD3ε Fv antibody fragment includes a combination of a heavy chain variable amino acid sequence selected from the group of SEQ ID NO: 47, 52-65, 341, or 283 and a light chain variable amino acid sequence selected from the group consisting of SEQ ID NO: 67, 75, 77, 79, 81-84, 281, or 339.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 47 In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 75. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 47 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 75. In some of any such embodiments, the anti-CD3 Fv is a dsFv that has a VH chain containing the mutation G44C and a VL chain containing the mutation G100C, each by kabat numbering. In some embodiments, the anti-CD3ε binding domain thereof includes a variable heavy chain (VH) comprising the amino acid sequence of SEQ ID NO: 47. In some embodiments, the anti-CD3ε binding domain includes a variable light chain (VL) comprising the amino acid sequence of SEQ ID NO: 75. In some embodiments, the anti-CD3ε binding domain thereof includes a variable heavy chain (VH) comprising the amino acid sequence of SEQ ID NO: 47 and a variable light chain (VL) comprising the amino acid sequence of SEQ ID NO: 75.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 341. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 339. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 341 and a variable light chain (VL) comprising an amino acid sequence that is at least 90%, 91%, 92%, 93%, 94%, 95%, 96%, 97%, 98%, 99% or more identical to the amino acid sequence of SEQ ID NO: 339. In some of any such embodiments, the anti-CD3 Fv is a dsFv that has a VH chain containing the mutation G44C and a VL chain containing the mutation G100C, each by kabat numbering. In some embodiments, the anti-CD3ε binding domain thereof includes a variable heavy chain (VH) comprising the amino acid sequence of SEQ ID NO: 341. In some embodiments, the anti-CD3ε binding domain includes a variable light chain (VL) comprising the amino acid sequence of SEQ ID NO: 339. In some embodiments, the anti-CD3ε binding domain thereof includes a variable heavy chain (VH) comprising the amino acid sequence of SEQ ID NO: 341 and a variable light chain (VL) comprising the amino acid sequence of SEQ ID NO: 339.

In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 283. In some embodiments, the anti-CD3ε binding domain includes a variable light chain (VL) comprising an amino acid sequence that is at least 90%, 91%, 92%, 93%, 94%, 95%, 96%, 97%, 98%, 99% or more identical to the amino acid sequence of SEQ ID NO: 339. In some embodiments, the anti-CD3ε binding domain thereof includes a variable heavy chain (VH) comprising an amino acid sequence that is at least 90%, 91%, 92%, 93%, 94%, 95%, 96%, 97%, 98%, 99% or more identical to the amino acid sequence of SEQ ID NO: 283 and a variable light chain (VL) comprising an amino acid sequence that is at least 90%, 91%, 92%, 93%, 94%, 95%, 96%, 97%, 98%, 99% or more identical to the amino acid sequence of SEQ ID NO:339. In some of any such embodiments, the anti-CD3 Fv is a dsFv that has a VH chain containing the mutation G44C and a VL chain containing the mutation G100C, each by kabat numbering. In some embodiments, the anti-CD3ε binding domain thereof includes a variable heavy chain (VH) comprising the amino acid sequence of SEQ ID NO: 283. In some embodiments, the anti-CD3ε binding domain includes a variable light chain (VL) comprising the amino acid sequence of SEQ ID NO: 339. In some embodiments, the anti-CD3ε binding domain thereof includes a variable heavy chain (VH) comprising the amino acid sequence of SEQ ID NO: 283 and a variable light chain (VL) comprising the amino acid sequence of SEQ ID NO: 339.

c. Components of Multispecific Formats i. CD28 VHH Antigen Binding Domain

The multispecific CD28-binding polypeptides described herein include at least one CD28 VHH domain from among any provided herein, such as any of those described in Section II. In some embodiments, the CD28 VHH domain comprises a sequence of amino acids set forth in any of SEQ ID NOS:186-188, 213-239, and 280. In some embodiments, the CD28 VHH domain comprises a sequence of amino acids set forth in any of SEQ ID NOS:186-188, 213-239, 280, and 342-385. In some embodiments, the CD28 VHH domain comprises a sequence of amino acids set forth in any of SEQ ID NOS:186-188, 213-219, 221-239, and 280. In some embodiments, the CD28 VHH domain comprises a sequence of amino acids set forth in any of SEQ ID NOS:186-188, 213-219, 221-239, 280, and 342-385. In some cases, the at least one CD28 VHH is or comprises the sequence set forth in SEQ ID NO:188. In some cases, the at least one CD28 VHH is or comprises the sequence set forth in SEQ ID NO:220. In some cases, the at least one CD28 VHH is or comprises the sequence set forth in SEQ ID NO:280.

In particular embodiments, a multispecific CD28-binding polypeptide contains at least two CD28 domains. In particular embodiments, the multispecific CD28-binding polypeptide construct contains at least three or at least four CD28 domains. In some embodiments, the CD28 VHH domain comprises the sequence of amino acids set forth in any of SEQ ID NOS:186-188, 213-239, and 280. In some embodiments, the CD28 VHH domain comprises the sequence of amino acids set forth in any of SEQ ID NOS:186-188, 213-239, 280, and 342-385. In some embodiments, the CD28 VHH domain comprises the sequence of amino acids set forth in any of SEQ ID NOS:186-188, 213-219, 221-239, and 280. In some embodiments, the CD28 VHH domain comprises the sequence of amino acids set forth in any of SEQ ID NOS:186-188, 213-219, 221-239, 280, and 342-385.

In some cases, at least one CD28 VHH domain is positioned carboxy terminally relative to at least one TAA binding domain. In some cases, at least one CD28 VHH domain is positioned carboxy terminally relative to at least two TAA binding domains. In some cases, at least two CD28 VHH domains are positioned carboxy terminally relative to at least one TAA binding domain. In some cases, at least two CD28 VHH domains are positioned carboxy terminally relative to at least two TAA binding domains.

In some cases, at least one CD28 VHH domain is positioned amino terminally relative to an Fc region In some cases, at least one CD28 VHH domain is positioned amino terminally relative to an Fc region of a homodimeric Fc. In some cases, at least one CD28 VHH domain is positioned amino-terminally relative to an Fc region of a heterodimeric Fc. In some cases, at least two CD28 VHH domains are positioned amino terminally relative to an Fc region. In some cases, at least two CD28 VHH domains are positioned amino terminally relative to an Fc region of a homodimeric Fc. In some cases, at least two CD28 VHH domains are positioned amino-terminally relative to an Fc region of a heterodimeric Fc.

In some embodiments, at least one CD28 VHH is positioned carboxy terminally relative to a TAA binding domain and amino terminally relative to an Fc region. In some embodiments, at least two CD28 VHHs are positioned carboxy terminally relative to a TAA binding domain and amino terminally relative to an Fc region.

In aspects of a multispecific CD28-binding polypeptide construct containing at least two or containing two CD28 VHH domains, each of the CD28 VHH domains can bind to the same or an overlapping epitope on CD28.

In aspects of a polypeptide construct containing at least two or containing two CD28 VHH domains, each of the CD28 VHH domains can bind to a different or a non-overlapping epitope on CD28.

In some cases, the first sdAb VHH domain comprises the amino acid sequence set forth in SEQ ID NO:188, or a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:188, and binds CD28; and the second sdAbVHH domain comprises the amino acid sequence set forth in SEQ ID NO:188, or a humanized variant thereof, or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO:188 and binds CD28.

In some cases, the first sdAb VHH domain comprises the amino acid sequence set forth in SEQ ID NO:188 or a humanized variant thereof set forth in any of SEQ ID NOS:213-239 and 280; and the second sdAbVHH domain comprises the amino acid sequence set forth in SEQ ID NO:188 or a humanized variant thereof set forth in any of SEQ ID NOS:213-239 and 280. In some cases, the first sdAb VHH domain comprises the amino acid sequence set forth in SEQ ID NO:188 or a humanized variant thereof set forth in any of SEQ ID NOS:213-239, 280, and 342-385; and the second sdAbVHH domain comprises the amino acid sequence set forth in SEQ ID NO:188 or a humanized variant thereof set forth in any of SEQ ID NOS:213-239, 280, and 342-385. In some cases, the first sdAb VHH domain comprises the amino acid sequence set forth in SEQ ID NO:188 or a humanized variant thereof set forth in any of SEQ ID NOS:213-219, 221-239 and 280; and the second sdAbVHH domain comprises the amino acid sequence set forth in SEQ ID NO:188 or a humanized variant thereof set forth in any of SEQ ID NOS:213-219, 221-239 and 280. In some cases, the first sdAb VHH domain comprises the amino acid sequence set forth in SEQ ID NO:188 or a humanized variant thereof set forth in any of SEQ ID NOS:213-219, 221-239, 280, and 342-385; and the second sdAbVHH domain comprises the amino acid sequence set forth in SEQ ID NO:188 or a humanized variant thereof set forth in any of SEQ ID NOS:213-219, 221-239, 280, and 342-385.

In some embodiments, the first sdAbVHH domain and second sdAbVHH domain comprise the amino acid sequence set forth in SEQ ID NO: 188 and SEQ ID NO: 188, respectively. In some embodiments, the first sdAbVHH domain and second sdAbVHH domain comprise the amino acid sequence set forth in SEQ ID NO: 220 and SEQ ID NO: 220, respectively. In some embodiments, the first sdAbVHH domain and second sdAbVHH domain comprise the amino acid sequence set forth in SEQ ID NO: 280 and SEQ ID NO: 280, respectively. In some embodiments, the first sdAbVHH domain and second sdAbVHH domain comprise amino acid sequences selected from SEQ ID NO: 188 and SEQ ID NO: 220. In some embodiments, the first sdAbVHH domain and second sdAbVHH domain comprise the amino acid sequences set forth in SEQ ID NO: 188 and SEQ ID NO: 220, respectively. In some embodiments, the first sdAbVHH domain and second sdAbVHH domain comprise amino acid sequences selected from SEQ ID NO: 188 and SEQ ID NO: 280. In some embodiments, the first sdAbVHH domain and second sdAbVHH domain comprise the amino acid sequences set forth in SEQ ID NO: 188 and SEQ ID NO: 280, respectively. In some embodiments, the first sdAbVHH domain and second sdAbVHH domain comprise amino acid sequences selected from SEQ ID NO: 220 and SEQ ID NO: 280. In some embodiments, the first sdAbVHH domain and second sdAbVHH domain comprise the amino acid sequences set forth in SEQ ID NO: 220 and SEQ ID NO: 280, respectively.

ii. Binding Domain (e.g. TAA Binding Domain)

The multispecific CD28-binding polypeptides of the present disclosure include one or more additional binding domain (BD) that binds an antigen that is not CD28.

In some embodiments, the one or more BD is one BD. In some embodiments, the one or more BD is two, three, four, or more BDs. In some embodiments, the one or more BD is two BDs. In some embodiments, the one or more BD is three BDs. In some embodiments, the one or more BD is four BDs.

In some aspects, the one or more BD binds a T cell activation marker. In some aspects, the one or more BD binds a T cell exhaustion marker. In some aspects, the one or more BD binds a tumor microenvironment marker.

In some embodiments, the T cell activation marker is selected from CD25, CD44, CD69, CD71, CD107a, CD137, HLA-DR, and/or KLRG1. In some embodiments, the T cell exhaustion marker is selected from 2B4, CD160, LAGS, PD-1, and/or TIGIT. In some embodiments, the tumor microenvironment marker is selected from alpha-SMA, EDB, FAP, FSP-1, PDGFRalpha, and/or PDGFRbeta.

In some aspects, the one or more additional binding domain is a binding domain that binds a tumor associated antigen (TAA), such as one or more, two or more, three or more, or four or more TAA binding domains. In some aspects, the one or more antigen binding domain, or independently each of the antigen binding domains, is selected from an antibody or antigen binding fragment, a natural (or native) cognate binding partner, an Anticalin (engineered lipocalin), a Darpin, a Fynomer, a Centyrin (engineered fibroneticin III domain), a cysteine-knot domain, an Affilin, an Affibody, or an engineered CH3 domain. In some embodiments, the natural cognate binding partner comprises an extracellular domain or binding fragment thereof of the native cognate binding partner of the TAA, or a variant thereof that exhibits binding activity to the TAA.

In some embodiments, the one or more antigen binding domains, or independently each of the antigen binding domains, includes an antibody or an antigen-binding fragment thereof. In some embodiments, the antigen binding domain or independently each of the antigen binding domains, includes an antibody or an antigen-binding fragment thereof selected from the group consisting of a Fab fragment, a $F(ab')_2$ fragment, an Fv fragment, a scFv, a scAb, a dAb, a single domain heavy chain antibody, and a single domain light chain antibody. In some embodiments, the one or more antigen binding domain, or independently each of the antigen binding domains, is a single chain antibody. In some examples, the single chain is an scFv, a scAb, a single domain heavy chain antibody, or a single domain light chain antibody.

In some embodiments, the one or more antigen binding domain, or independently each of the antigen binding domains, is a single chain antibody. In some examples, the single chain is an scFv, a scAb, a single domain heavy chain antibody, or a single domain light chain antibody.

In some embodiments, the one or more antigen binding domain or independently each of the antigen binding domains, includes a single domain antibody (sdAb) fragments, for example $V_HH$, $V_{NAR}$, engineered $V_H$ or $V_K$ domains. $V_HH$s can be generated from natural camelid heavy chain only antibodies, genetically modified rodents that produce heavy chain only antibodies, or naïve/synthetic camelid or humanized camelid single domain antibody libraries. $V_{NAR}$s can be generated from cartilaginous fish heavy chain only antibodies. Various methods have been implemented to generate monomeric sdAbs from conventionally heterodimeric $V_H$ and $V_K$ domains, including interface engineering and selection of specific germline families.

In some embodiments, the one or more BD, or independently each of the BDs, of the contains an sdAb that binds an antigen other than CD28. In some embodiments, the one or more BD is positioned amino-terminally relative to a CD28 VHH. In some embodiments, the one or more BD is positioned amino-terminally relative to an Fc region. In some embodiments, the one or more BD is positioned amino-terminally relative to a CD28 VHH and an Fc region.

In some embodiments, the multispecific polypeptide construct contains only one BD, which can be positioned amino-terminally relative to a CD28 VHH or carboxy-terminally relative to a CD28 VHH. In some embodiments, the multispecific CD28-binding polypeptide contains two BDs positioned amino-terminally relative to a CD28 VHH and/or carboxy-terminally relative to a CD28 VHH. In some embodiments, the multispecific CD28-binding polypeptide construct contains three BDs, in which two are positioned amino-terminally relative to a CD28 VHH, and the third is positioned at the other end of the multispecific CD28-binding polypeptide construct.

In some embodiments, the one or more antigen binding domain, or independently each of the antigen binding domains, of the multispecific CD28-binding polypeptides contains an sdAb that binds a TAA. In some embodiments, the one or more scFv or sdAb that binds a TAA is positioned amino-terminally relative to a CD28 VHH. In some embodiments, the one or more sdAb that binds a TAA is positioned amino-terminally relative to an Fc region. In some embodiments, the one or more sdAb that binds a TAA is positioned amino-terminally relative to a CD28 VHH and an Fc region. In some embodiments, the multispecific polypeptide construct contains only one sdAb that binds to a TAA, which can be positioned amino-terminally relative to a CD28 VHH or carboxy-terminally relative to a CD28 VHH. In some embodiments, the multispecific CD28-binding polypeptide contains two sdAbs that bind to a TAA, positioned amino-terminally relative to a CD28 VHH and/or carboxy-terminally relative to a CD28 VHH. In some embodiments, the multispecific CD28-binding polypeptide construct contains three sdAb, in which two are positioned amino-terminally relative to a CD28 VHH, and the third is positioned at the other end of the multispecific CD28-binding polypeptide construct.

In some embodiments, the one or more antigen binding domain or independently each of the antigen binding domains, contains binding domains as single domain antibodies (sdAbs).

In some embodiments, the one or more antigen binding domain or independently each of the antigen binding domains, contains more than one chain. In some embodiments, the one or more antigen binding domain or independently each of the antigen binding domains, contains VH and VL sequences assembled as FABs.

In some embodiments, the one or more BD, or independently each of the BDs, is or includes an extracellular domain or binding fragment thereof of the natural (or native) cognate binding partner of the antigen, or a variant thereof that exhibits binding activity to the antigen.

In some embodiments, the one or more antigen binding domain, or independently each of the antigen binding domains, is or includes an extracellular domain or binding fragment thereof of the natural (or native) cognate binding partner of the TAA, or a variant thereof that exhibits binding activity to the TAA.

In some embodiments, the one or more BD or independently each of the BDs, bind the same antigen. In some embodiments, there is more than one BD that binds an antigen, and each of the BDs binds a different antigen. In some embodiments, each of the BDs binds the same antigen. In some embodiments, each of the BDs binds a different antigen. In some embodiments, each of the BDs binds a different epitope on the same antigen. In some embodiments, each of the BDs the same epitope on the same antigen.

In some embodiments, the one or more antigen binding domain or independently each of the antigen binding domains, bind the same antigen. In some embodiments, there is more than one antigen binding domain that binds a TAA, and each of the antigen binding domains binds a different antigen. In some embodiments, each of the antigen binding domains binds the same tumor associated antigen (TAA). In some embodiments, each of the antigen binding domains binds a different TAA. In some embodiments, each of the antigen binding domains binds a different epitope on the same TAA. In some embodiments, each of the antigen binding domains binds the same epitope on the same TAA.

In some embodiments, the one or more BD, or independently each of the BDs that binds an antigen results in monovalent, bivalent, trivalent, or tetravalent binding to the antigen. In some embodiments, bivalent binding to the antigen comprises two BDs that bind the same epitope of the same antigen (e.g. mono-epitopic). In some embodiments, bivalent binding to the antigen comprises two BDs that bind different epitopes of the same antigen (e.g. bi-epitopic). In some embodiments, monovalent binding to the antigen comprises one BD that binds one epitope of the antigen (e.g. mono-epitopic).

In some embodiments, the one or more antigen binding domain, or independently each of the antigen binding domains that binds TAA results in monovalent, bivalent, trivalent, or tetravalent binding to the TAA. In some embodiments, bivalent binding to the TAA comprises two antigen binding domains that bind the same epitope of the same antigen (e.g. mono-epitopic). In some embodiments, bivalent binding to the TAA comprises two antigen binding domains that bind different epitopes of the same antigen (e.g. bi-epitopic). In some embodiments, monovalent binding to the TAA comprises one antigen binding domain that binds one epitope of the antigen (e.g. mono-epitopic).

In some embodiments, the antigen to which the one or more BD binds is selected from the group consisting of: 1-92-LFA-3, 2B4, 5T4, Alpha-4 integrin, Alpha-V integrin, alpha4beta1 integrin, alpha4beta7 integrin, alpha-SMA, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD69, CD70, CD71, CD74, CD80, CD81, CD86, CD95, CD107a, CD117, CD123, CD125, CD132, (IL-2RG), CD133, CD137, CD138, CD160, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRalpha), FSP-1, GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HLA-DR, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL13Ra2, IL15, IL17, IL18, IL21, IL23, IL23R, IL27/IL27R (wsx1), IL29, IL-31R, IL31/IL31R, IL2R, IL4, IL4R, IL6, IL6R, IL1 receptor accessory protein (IL1RAP), Insulin Receptor, Jagged Ligands, Jagged 1, Jagged 2, KISS1-R, KLRG1, LAG-3, LIF-R, Lewis X, LIGHT, LRP4, LRRC26, Ly6G6D, LyPD1, MCSP, Mesothelin, MRP4, MUC1, Mucin-16

(MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidyl-serine, P1GF, PSCA, PSMA, PSGR, RAAG12, RAGE, SLC44A4, Siglec15, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

In some embodiments, the TAA is selected from the group consisting of 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRα), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL13Ra2, IL15, IL17, IL18, IL21, IL23, IL23R, IL27/IL27R (wsx1), IL29, IL-31R, IL31/IL31R, IL2R, IL4, IL4R, IL6, IL6R, IL1 receptor accessory protein (IL1RAP), Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidyl-serine, P1GF, PSCA, PSMA, PSGR, RAAG12, RAGE, SLC44A4, Siglec15, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

In some embodiments, the TAA is PDL1. In some embodiments, the TAA is Siglec15. In some embodiments, the TAA is B7H3. In some embodiments, the TAA is B7H4. In some embodiments, the TAA is IL1RaP. In some embodiments, the TAA is IL13Ra2. In some embodiments, the TAA is gpNMB. In some embodiments, the TAA is mesothelin. In some embodiments, the TAA is EGFR. In some embodiments, the TAA is cMET. In some embodiments, the TAA is HER2. In some embodiments, the TAA is ENPP3.

In some embodiments, at least one antigen binding domain, or independently each antigen binding domain, binds the tumor associated antigen (TAA) folate receptor alpha (FRα). For example, the antigen binding domain contains the binding domain as an sdAb that binds FRα. Exemplary FRα-binding sdAbs are set forth in any one of SEQ ID NOS: 253, 254, and 255. The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID NOS and bind FRα.

In some embodiments, at least one antigen binding domain, or independently each antigen binding domain, binds the tumor associated antigen (TAA) 5T4. In some embodiments, the antigen binding domain is a sdAb, such as a VHH. Exemplary 5T4-binding sdAbs are set forth in any of SEQ ID NO:240 or 245. In some embodiments, the VHH contains a CDR1, a CDR2, and a CDR3 as set forth in SEQ ID NOS: 241, 242, and 243, respectively. In some embodiments, the 5T4-binding sdAb is set forth in SEQ ID NO:240. In some embodiments, the VHH contains a CDR1, a CDR2, and a CDR3 as set forth in SEQ ID NOS: 246, 247, and 248, respectively. In some embodiments, the 5T4-binding sdAb is set forth in SEQ ID NO:245. In some embodiments, the antigen binding domain is or contains a Fab antibody fragment comprising a Fd and LC that binds 5T4. An exemplary 5T4 Fd is set forth in SEQ ID NO: 256 and an exemplary 5T4 LC is set forth in SEQ ID NO: 257. In some embodiments, the antibody binding domain comprises a VH-CH1 (Fd) or VL-CL as set forth in SEQ ID NOS: 258 and 259 (U.S. Pat. No. 8,044,178). The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID NOS and bind 5T4.

In some embodiments, at least one antigen binding domain, or independently each antigen binding domain, binds the tumor associated antigen (TAA) PDL1. In some embodiments, the antigen binding domain is a sdAb, such as a VHH. An exemplary PDL1- binding sdAb is set forth in SEQ ID NO:99. In some embodiments, the VHH contains a CDR1, a CDR2, and a CDR3 as set forth in SEQ ID NOS: 100, 101, and 102, respectively. In some embodiments, the antigen binding domain is or contains a Fab antibody fragment comprising a Fd and LC that binds PDL1. The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID NOS and bind PDL1.

In some embodiments, at least one antigen binding domain, or independently each antigen binding domain, binds the tumor associated antigen (TAA) cMET. For example, the antigen binding domain contains the binding domain as a sdAb that binds cMET. An exemplary cMET-binding sdAb is set forth in SEQ ID NO: 260 (U.S. Pat. No. 9,346,884). The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID NOS and bind cMET.

In some embodiments, at least one antigen binding domain, or independently each antigen binding domain, binds the tumor associated antigen (TAA) B7H3. For example, the antigen binding domain contains the binding domain as an scFv that binds B7H3. An exemplary B7H3-binding scFv is set forth in SEQ ID NO:261. In some embodiments, the antigen binding domain is a sdAb, such as a VHH. Exemplary B7H3-binding sdAbs are set forth in any of SEQ ID NOS: 262-266. In some embodiments, the antigen binding domain is or contains a Fab antibody fragment comprising a VH-CH1 (Fd) and LC. An exemplary B7H3 Fd is set forth in SEQ ID NO: 267 and an exemplary B7H3 LC is set forth in SEQ ID NO: 268 (PCT Publication No, WO2017/030926). The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID Nos and bind B7H3.

In some embodiments, at least one antigen binding domain, or independently each antigen binding domain, binds the tumor associated antigen (TAA) CD20. In some embodiments, such an antigen-binding domain contains a VH set forth in SEQ ID NO: 269 and a VL set forth in SEQ ID NO: 270 or a sequence that exhibits at least at or about 85%, 90%, 95%, 96%, 97%, 98%, 98%, or 99% sequence identity to SEQ ID NO: 269 and SEQ ID NO:270. For example, the antigen binding domain contains the binding domain as an scFv that binds CD20. Exemplary CD20-binding scFvs are set forth in SEQ ID NO: 271 (U.S. Pub. No. US 2005/0123546). The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID NOS and bind CD20.

In some embodiments, at least one antigen binding domain, or independently each antigen binding domain, binds the tumor associated antigen (TAA) DLL3. For example, the antigen binding domain contains the binding domain as an scFv that binds DLL3. Exemplary DLL3-binding scFv is set forth in SEQ ID NO: 272 and 273 (U.S. Pub. No. US 2017/0037130). In some embodiments, the antigen binding domain is a sdAb, such as a VHH. Exemplary DLL3-binding sdAbs are set forth in any of SEQ ID NO: 274 or SEQ ID NO:275. In some embodiments, the antigen binding domain is or contains a Fab antibody fragment comprising a Fd and LC that binds DLL3. An exemplary DLL3 Fd is set forth in SEQ ID NO: 276 and an exemplary DLL3 LC is set forth in SEQ ID NO: 277 (U.S. Pat. No. 8,044,178). The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID NOS and bind DLL3.

In some embodiments, at least one antigen binding domain, or independently each antigen binding domain, binds the tumor associated antigen (TAA) gpNMB. In some embodiments, the antigen binding domain is or contains a Fab fragment comprising a Fd and LC chain. An exemplary gpNMB Fd is set forth in SEQ ID NO: 278 and an exemplary gpNMB LC is set forth in SEQ ID NO: 279. The antigen binding domain, or independently each antigen binding domain, in a provided multispecific polypeptide construct can have at least 85%, 85%, 87%, 88%, 89%, 90%, 91%, 92%, 93%, 94%, 95%, 96%, 97%, 98% or 99% sequence identity to any of the foregoing SEQ ID NOS and bind gpNMB.

In some embodiments, the antigen binding domain is linked, directly or indirectly via a linker, to a CD28 VHH region and/or to an Fc peptide. In some embodiments, the antigen binding domain is linked, directly or indirectly via a linker, to a CD28 VHH region. In some embodiments, the antigen binding domain is linked, directly or indirectly to an Fc peptide. In some embodiments, linkage is via a linker. In some embodiments, the linker is a linking peptide (LP), which can include any flexible or rigid linker as described in Section IIIC(d), although generally peptides linking the antigen binding domain or domains is not a cleavable liker.

In some embodiments, the linking peptide is a peptide of about 1 to 20 amino acids in length. In some embodiments, the linking peptide is a peptide that is or comprises any Gly-Ser linker as set forth in any one of SEQ ID NOs: 1-7, 89, 90, 123-129, 142, 244, and 249.

iii. Fc Region

In some embodiments, a CD28-binding polypeptide provided herein includes an immunoglobulin Fc region. The Fc polypeptide can be any as set forth in Section IIIA. In some embodiments, the Fc region is a homodimeric Fc region. In particular embodiments, the Fc region is formed by Fc domains that are mutated or modified to promote heterodimerization in which different polypeptides can be dimerized to yield a heterodimer. Thus, in some embodiments, the dimer is a heterodimer in which two polypeptide chains of the multispecific polypeptide construct are different.

Various methods are known for promoting heterodimerization of complementary Fc polypeptides, see e.g. Ridgway et al, Protein Eng. 9:617-621 (1996); Merchant et al, Nat. Biotechnol. 16(7): 677-81 (1998); Moore et al. (2011) MAbs, 3:546-57; Von Kreudenstein et al. MAbs, (2013) 5:646-54; Gunasekaran et al. (2010) J. Biol. Chem., 285:19637-46; Leaver-Fay et al. (2016) Structure, 24:641-51; Ha et al. (2016) Frontiers in Immunology, 7:1; Davis et al. (2010) Protein Eng Des Sel, 23:195-202; published international PCT Appl. No. WO 1998/050431, WO 2009/089004, WO2011143545 WO 2014/067011, WO 2012/058768, WO2018027025; published U.S. patent Appl. No. US20140363426, US20150307628, US20180016354, US20150239991; and U.S. patent Nos. U.S. Pat. Nos. 5,731,168, 7,183,076, 9,701,759, 9,605,084, and 9,650,446. Methods to promote heterodimerization of Fc chains include mutagenesis of the Fc region, such as by including a set of "knob-into-hole" mutations or including mutations to effect electrostatic steering of the Fc to favor attractive interactions among different polypeptide chains. For example, in some embodiments, the Fc polypeptides of a heterodimer includes a mutation to alter charge polarity across the Fc dimer interface such that coexpression of electrostatically matched Fc chains support favorable attractive interactions thereby promoting desired Fc heterodimer formation, whereas unfavorable repulsive charge interactions suppress unwanted Fc homodimer formation (Guneskaran et al. (2010) JBC, 285:19637-19646). When co-expressed in a cell, association between the chains is possible but the chains do not substantially self-associate due to charge repulsion. Other strategies for generating a heterodimeric Fc include mixing human IgG and IgA CH3 domain segments to create a complementary CH3 heterodimer, which is referred to as a SEED Fc.

Methods and variants for heterodimerization also include those described in published international PCT App. WO2014/145806, including "knobs and holes" mutations (also called "skew" variants), mutations that relate to "electrostatic steering" or "charge pairs," and pI variants. Heterodimeric variants also include any as described in U.S. published Appl. No. US2012/0149876 or US2018/011883.

In some embodiments, to promote heterodimerization both polypeptides of the Fc heterodimer contain paired or complementary amino acid modifications. Exemplary paired amino acid modification of polypeptides of an Fc fusion are set forth in Table 3.

TABLE 3

| Paired amino acids of Heterodimeric Fc | |
|---|---|
| First Fc polypeptide | Second Fc Polypeptide |
| T366W | T366S/L368W/Y407V |
| T366W/S354C | T366S/L368A/Y407V/Y349C |
| S364H/F405A | Y349T/Y349F |
| T350V/L351Y/F405A/Y407V | T350V/T366L/K392L/T394W |
| K360D/D399M/Y407A | E345R/Q347R/T366V/K409V |
| K409D/K392D | D399K/E356K |
| K360E/K409W | Q347R/D399V/F405T |
| L360E/K409W/Y349C | Q347R/399V/F405T/S354C |
| K370E/K409W | E357N/D399V/F405T |

In some embodiments, modifications include introduction of a protuberance (knob) into a first Fc polypeptide and a cavity (hole) into a second Fc polypeptide such that the protuberance is positionable in the cavity to promote complexing of the first and second Fc-containing polypeptides. Amino acids targeted for replacement and/or modification to create protuberances or cavities in a polypeptide are typically interface amino acids that interact or contact with one or more amino acids in the interface of a second polypeptide.

In some embodiments, a first Fc polypeptide that is modified to contain protuberance (knob) amino acids include replacement of a native or original amino acid with an amino acid that has at least one side chain which projects from the interface of the first Fc polypeptide and is therefore positionable in a compensatory cavity (hole) in an adjacent interface of a second polypeptide. Most often, the replacement amino acid is one which has a larger side chain volume than the original amino acid residue. One of skill in the art knows how to determine and/or assess the properties of amino acid residues to identify those that are ideal replacement amino acids to create a protuberance. In some embodiments, the replacement residues for the formation of a protuberance are naturally occurring amino acid residues and include, for example, arginine (R), phenylalanine (F), tyrosine (Y), or tryptophan (W). In some examples, the original residue identified for replacement is an amino acid residue that has a small side chain such as, for example, alanine, asparagine, aspartic acid, glycine, serine, threonine, or valine.

In some embodiments, a second Fc polypeptide that is modified to contain a cavity (hole) is one that includes replacement of a native or original amino acid with an amino acid that has at least one side chain that is recessed from the interface of the second polypeptide and thus is able to accommodate a corresponding protuberance from the interface of a first polypeptide. Most often, the replacement amino acid is one which has a smaller side chain volume than the original amino acid residue. One of skill in the art knows how to determine and/or assess the properties of amino acid residues to identify those that are ideal replacement residues for the formation of a cavity. Generally, the replacement residues for the formation of a cavity are naturally occurring amino acids and include, for example, alanine (A), serine (S), threonine (T) and valine (V). In some examples, the original amino acid identified for replacement is an amino acid that has a large side chain such as, for example, tyrosine, arginine, phenylalanine, or tryptophan.

The CH3 interface of human IgG1, for example, involves sixteen residues on each domain located on four anti-parallel β-strands which buries 1090 Å2 from each surface (see e.g., Deisenhofer et al. (1981) Biochemistry, 20:2361-2370; Miller et al., (1990) J Mol. Biol., 216, 965-973; Ridgway et al., (1996) Prot. Engin., 9: 617-621; U.S. Pat. No. 5,731, 168). Modifications of a CH3 domain to create protuberances or cavities are described, for example, in U.S. Pat. No. 5,731,168; International Patent Applications WO98/50431 and WO 2005/063816; and Ridgway et al., (1996) Prot. Engin., 9: 617-621. In some examples, modifications of a CH3 domain to create protuberances or cavities are typically targeted to residues located on the two central anti-parallel β-strands. The aim is to minimize the risk that the protuberances which are created can be accommodated by protruding into the surrounding solvent rather than being accommodated by a compensatory cavity in the partner CH3 domain.

For example, in some embodiments the heterodimeric Fc includes a polypeptide having an amino acid modification within the CH3 domain at Thr366, which when replaced with a more bulky amino acid, e.g., Try (T366W), is able to preferentially pair with a second CH3 domain having amino acid modifications to less bulky amino acids at positions Thr366, Leu368, and Tyr407, e.g., Ser, Ala and Val, respectively (T366S/L368A/Y407V). Heterodimerization via CH3 modifications can be further stabilized by the introduction of a disulfide bond, for example by changing Ser354 to Cys (S354C) and Tyr349 to Cys (Y349C) on opposite CH3 domains (Reviewed in Carter, 2001 Journal of Immunological Methods, 248: 7-15).

In particular embodiments, a multispecific CD28-binding polypeptide contains a first Fc and a second Fc able to mediate Fc heterodimerization containing a first Fc polypeptide containing mutations T366W and S354C and a second Fc polypeptide containing mutations T366S, L368A, Y407V and Y349C. In some embodiments, the first Fc polypeptide is selected from an Fc polypeptide comprising the sequence set forth in SEQ ID NO: 328 or 334 and the second Fc polypeptide is selected from an Fc polypeptide comprising the sequence set forth in SEQ ID NO: 329, 332 or 336. In some embodiments, the first Fc polypeptide is or comprises the sequence of amino acids set forth in any of SEQ ID NOS:103, 107, 115 or 117 and the second Fc polypeptide is or comprises the sequence of amino acids set forth in any of SEQ ID NOS:104, 108, 111, 113, 119 or 121.

In some embodiments, the Fc polypeptide exhibits features providing Fc-mediated effector functions. In particular examples, the first Fc polypeptide is or comprises the sequence set forth in SEQ ID NO:328 and a second Fc polypeptide that is or comprises SEQ ID NO: 329 or 332. In some embodiments, the first Fc polypeptide is or comprises the sequence set forth in SEQ ID NO: 103 and the second Fc polypeptide is or comprises the sequence set forth in SEQ ID NO: 104 or 111. In some embodiments, the first Fc polypeptide is or comprises the sequence set forth in SEQ ID NO: 107 and the second Fc polypeptide is or comprises the sequence set forth in SEQ ID NO: 108 or 113. The first and second Fc polypeptide can be formatted on either polypeptide chain of the construct.

In some embodiments, one or both of the first and second Fc polypeptides can further include one or more amino acid mutations to further reduce one or more Fc effector functions, such as reduced Fc receptor binding. Exemplary mutations to reduce Fc effector functions include any as described. In some embodiments, the modification can be a deletion of one or more positions Glu233 (E233), Leu234 (L234), or Leu235 (L235), such as a deletion of amino acids Glu233 (E233), Leu234 (L234), and Leu235 (L235). In some embodiments, the first Fc polypeptide is selected from an Fc polypeptide comprising the sequence set forth in SEQ ID NO: 328 or 334 and the second Fc polypeptide is selected from an Fc polypeptide comprising the sequence set forth in SEQ ID NO: 329, 332 or 336. In some embodiments, the first Fc polypeptide is or comprises the sequence of amino acids set forth in any of SEQ ID NOS:105, 109, 116 or 118 and the second Fc polypeptide is or comprises the sequence of amino acids set forth in any of SEQ ID NOS: 106, 110, 112, 114, 120 or 122.

In particular examples, the first Fc polypeptide is or comprises the sequence set forth in SEQ ID NOs:330 and a second Fc polypeptide that is or comprises SEQ ID NO: 331 or 333. In some embodiments, the first Fc polypeptide is or comprises the sequence set forth in SEQ ID NO: 105 and the second Fc polypeptide is or comprises the sequence set forth in SEQ ID NO: 106 or 112. In some embodiments, the first Fc polypeptide is or comprises the sequence set forth in SEQ ID NO: 109 and the second Fc polypeptide is or comprises the sequence set forth in SEQ ID NO: 110 or 114. The first and second Fc polypeptide can be formatted on either polypeptide chain of the construct.

In some embodiments, the first Fc polypeptide or second Fc polypeptide further includes mutations M252Y and/or M428V. In particular examples, the first Fc polypeptide is or comprises the sequence set forth in SEQ ID NO:334 and the second Fc polypeptide is or comprises the sequence set forth in SEQ ID NO:336. In some embodiments, the first Fc polypeptide is or comprises the sequence set forth in SEQ ID NO:115 and the second Fc polypeptide is or comprises the sequence set forth in SEQ ID NO: 119. In some embodiments, the first Fc polypeptide is or comprises the sequence set forth in SEQ ID NO:117 and the second Fc polypeptide is or comprises the sequence set forth in SEQ ID NO: 121. In other examples, the first Fc polypeptide is or comprises the sequence set forth in SEQ ID NO:335 and the second Fc polypeptide is or comprises the sequence set forth in SEQ ID NO:337. In some embodiments, the first Fc polypeptide is or comprises the sequence set forth in SEQ ID NO:116 and the second Fc polypeptide is or comprises the sequence set forth in SEQ ID NO: 120. In some embodiments, the first Fc polypeptide is or comprises the sequence set forth in SEQ ID NO:118 and the second Fc polypeptide is or comprises the sequence set forth in SEQ ID NO: 122. The first and second Fc polypeptide can be formatted on either polypeptide chain of the construct.

Additional examples of variants that can facilitate the promotion of heterodimers are any combination or pair of steric variants (e.g. skew variants) of a first Fc polypeptide and a second Fc polypeptide from among: S364K/E357Q and L368D/K370S; L368D/K370S and S364K; L368E/K370S and S364K; T411T/E360E/Q362E and D401K; L368D/K370S and S364K/E357L, K370S and S364K/E357Q and T366S/L368A/Y407V and T366W or 366S/L368A/Y407V/Y349C and T366W/S354C), where each pair represents mutations in the first Fc polypeptide and second Fc polypeptide. In particular embodiments, a provided construct contains a first and second Fc polypeptide containing the pair of mutations L368D/K370S and S364K and E357Q.

An additional mechanism that can be used in the generation of heterodimers is sometimes referred to as "electrostatic steering" as described in Gunasekaran et al., J. Biol. Chem. 285(25):19637 (2010). This is sometimes referred to herein as "charge pairs". In this embodiment, electrostatics are used to skew the formation towards heterodimerization. As those in the art will appreciate, these may also have an effect on pI, and thus on purification, and thus could in some cases also be considered pI variants. However, as these were generated to force heterodimerization and were not used as purification tools, they are classified as "steric variants". In one embodiments, a first Fc polypeptide can contain mutations D221E/P228E/L368E and a second Fc polypeptide can contain mutations D221R/P228R/K409R. In another embodiments, a first Fc polypeptide can contain mutations C220E/P228E/368E and a second Fc polypeptide can contain mutations C220R/E224R/P228R/K409R.

In some embodiments, heterodimerization can be facilitated by pI variants. In some aspects, a pI variant can include those that increase the pI of the protein (basic changes). In other aspects, the pI variant can include those that decrease the pI of the protein (acidic changes). In some cases, all combinations of these variants can be done, including combinations in which one Fc polypeptide may be wild type, or a variant that does not display a significantly different pI from wild-type, and the other Fc polypeptide can be either more basic or more acidic. Alternatively, each Fc polypeptide can be changed, one to more basic and one to more acidic. In some embodiments, at least one Fc polypeptide is a negative pI variant Fc containing mutations Q295E/N384D/Q418E/N421D.

In some embodiments, a combination of steric heterodimerization variants (e.g. knob and hole) and pI or charge pair variants can be used.

In particular embodiments, the provided constructs contains (a) a first Fc polypeptide comprising the skew variants S364K/E357Q; and b) a second Fc polypeptide containing skew variants L368D/K370S and the pI variants N208D/Q295E/N384D/Q418E/N421D. In some embodiments, one or both of the first and second polypeptide can contain further mutations to reduce Fc effector activity, such as the exemplary mutations E233P/L234V/L235A/G236del/S267K. An example of such a first Fc polypeptide and a second Fc polypeptide able to mediate Fc heterodimerization comprise the sequences set forth in SEQ ID NOs:284 and 285. The first and second Fc polypeptide can be formatted on either polypeptide chain of the construct.

The resulting conditional multispecific polypeptide constructs can be purified by any suitable method such as, for example, by affinity chromatography over Protein A or Protein G columns. Where two nucleic acid molecules encoding different polypeptides are transformed into cells, formation of homo- and heterodimers will occur. Conditions for expression can be adjusted so that heterodimer formation is favored over homodimer formation.

Techniques for recovery of heterodimers from homodimers based on a differential affinity of the heterodimers for an affinity reagent are known. In some aspects, such techniques include designing a heterodimer so that one of the Fc polypeptide chains does not bind to the affinity reagent protein A. In some cases, one of the polypeptide chain can contain one or more amino acid substitution to abrogate or reduce affinity for the protein A reagent in one of the polypeptides of the Fc heterodimer, see e.g. WO2017134440, WO2010151792, Jendeberg et al. (Jendeberg et al., (1997) J. Immunol. Methods, 201(1): 25-34. In some of these embodiments, the Fc region may be modified at the protein-A binding site on one member of the heterodimer so as to prevent protein-A binding and thereby enable more efficient purification of the heterodimeric fusion protein. An exemplary modification within this binding site is Ile253, for example Ile253Arg (I253R). In some embodiments, the modification may be H435R or H435R/Y436F. In some embodiments, an Fc polypeptide of an Fc heterodimer can contain a modification so that it is capable of binding protein A but not protein G (pA+/pG−). Exemplary pA+/pG− amino acid modifications include an Fc containing serine at position 428, serine at position 434 and optionally histidine at position 436, with reference to human IgG1 or comprising these residues at the corresponding positions in human IgG 2, 3, or 4. In some aspects, such amino acid modifications in one IgG Fc polypeptide at positions 428, 434 and optionally 436 reduces or prevents the binding of protein G, enhancing the purification of the protein.

In some embodiments, any of such modifications to confer differential affinity to an affinity reagent can be combined with any one or more other amino acid modifications described above. For example, the I253R modification may be combined with either the T366S/L368A/Y407V modifications or with the T366W modifications. The T366S/L368A/Y407V modified Fc is capable of forming homodimers as there is no steric occlusion of the dimerization interface as there is in the case of the T336W modified Fc. Therefore, in some embodiments, the I253R modification is combined with the T366S/L368A/Y407V modified Fc to disallow purification any homodimeric Fc that may have formed. Similar modifications can be employed by combining T366S/L368A/Y407V and H453R.

In some embodiments, the Fc regions of the heterodimeric molecule additionally can contain one or more other Fc mutation, such as any described above. In some embodiments, the heterodimer molecule contains an Fc region with a mutation that reduces effector function. In some embodiments, the Fc region is altered to provide reduced Fc-mediated effector functions, such as via reduced Fc receptor binding, e.g. binding to FcγR binding but generally not FcRn binding.

In some embodiments, the Fc region is mutated in one or more of the following positions to reduce Fc receptor binding: Glu233 (E233), Leu234 (L234), or Leu235 (L235). The one or more mutations can include E233P, L234V and/or L235A.

In particular embodiments, the mutations of the Fc region to reduce Fc effector function, e.g. via reducing Fc receptor binding to FcγR, include mutations from among any of G236R/L328R, E233P/L234V/L235A/G236del/S239K, E233P/L234V/L235A/G236del/S267K, E233P/L234V/L235A/G236del/S239K/A327G, E233P/L234V/L235A/G236del/S267K/A327G or E233P/L234V/L235A/G236del, D265A/P329A, D265A/P329G, D265A/N297A, L234V/L235A/D265A, L234V/L235A/N297A, L234V/L235A/P329A, or L234V/L235A/P329G.

In some embodiments, one Fc polypeptide of a heterodimeric Fc comprises the sequence of amino acids set forth in any of SEQ ID NOS: 328 (e.g. SEQ ID NO:103 or 107), 334 (e.g. SEQ ID NO:115 or 117), and the other Fc polypeptide of the heterodimeric Fc contains the sequence of amino acids set forth in any of SEQ ID NOS: 329 (e.g. SEQ ID NO:104 or 108), 332 (e.g. SEQ ID NO:111 or 113), 336 (e.g. SEQ ID NO:119 or 121). In some embodiments, one Fc polypeptide of a heterodimeric Fc comprises the sequence of amino acids set forth in any of SEQ ID NOS: 330 (SEQ ID NO:105 or 109), 335 (e.g. SEQ ID NO:116 or 118) and the other Fc polypeptide of the heterodimeric Fc comprises the sequence of amino acids set forth in any of SEQ ID NOS: 331 (e.g. SEQ ID NO:106 or 110), 333 (e.g. SEQ ID NO:112 or 114), 337 (e.g. SEQ ID NO:120 or 122).

In some embodiments, the Fc region of the provided multispecific polypeptide constructs exhibit one or more effector functions. In some cases, the Fc region is capable of providing Fc-mediated effector functions, such as for example, ADCC (e.g., release of granzyme B by NK cells), ADCP, and/or CDC. In general, the Fc region is responsible for effector functions, such as complement-dependent cytotoxicity (CDC) and antibody-dependent cell cytotoxicity (ADCC), in addition to the antigen-binding capacity, which is the main function of immunoglobulins. Additionally, the FcRn sequence present in the Fc region plays the role of regulating the IgG level in serum by increasing the in vivo half-life by conjugation to an in vivo FcRn receptor. In some embodiments in which the multispecific polypeptide constructs contain a cleavable linker, cleavage of the linker can produce two components that each have biological activity: the CD3-binding region that is able to bind and engage CD3 on a T cell; and the Fc region linked to the CD28 VHH domain that can exhibit target-specific effector function. In particular embodiments provided herein, the multispecific polypeptide constructs contain a non-cleavable linker and may, in some aspects, not exhibit an independent Fc-mediated effector function.

In some embodiments, the Fc region includes an Fc polypeptide that is mutated or modified to alter one or more effector functions. Thus, in some cases, effector functions such as on or more of ADCC, ADCP and/or CDC can be altered, such as reduced or enhanced, in an Fc for use with the provided conditional multispecific polypeptide constructs. Exemplary mutations to reduce effector function include any as described above.

In some embodiments, an IgG1 Fc polypeptide or a variant thereof such as any described below can be made in a G1 ml or G1 m3 allotype. In some embodiments, the Fc region can contain amino acids of the human G1 ml allotype, such as residues containing Asp (D) and Leu (L) at positions 356 and 358, e.g. as set forth in SEQ ID NO:8. In some cases, an Fc polypeptide can contain amino acid substitutions E356D and M358L to reconstitute residues of allotype G1 ml. In other embodiments, the Fc region can contain amino acids of the human G1 m3 allotype, such as residues Glu (E) and Met (M) at positions 356 and 358 by EU numbering, e.g. as set forth in SEQ ID NOS: 284 and 285. In some cases, an Fc polypeptide can contain amino acid substitutions D356E and L358M to reconstitute residues of allotype G1 m3.

In some embodiments, a multispecific CD28-binding polypeptide does not include an Fc region.

d. Linker

In any of the provided embodiments, a CD28-binding polypeptide contains a linker. In some embodiments, the linker joins or couples a first component and a second component.

For example, a CD28 VHH-Fc fusion contains a linker that joins or couples at least one of the at least one CD28 sdAbs with the Fc region. In some embodiments, the linker is positioned at the end of the C-terminal region of the first component, such that the first component containing the at least one CD28 VHH is N-terminal to the Fc region.

In any of the provided embodiments, a multispecific CD28-binding polypeptide containing the one or more TAA sdAbs and the at least one CD28 sdAbs includes a linker that joins or couples at least one of the one or more TAA sdAbs and at least one of the at least one CD28 sdAbs. In some embodiments, the linker is positioned at the end of the C-terminal region of the first component, such that the first component containing the one or more TAA sdAb is N-terminal to the at least one CD28 sdAb.

In some embodiments, the provided CD28-binding polypeptides are multimers, such as dimers containing a first and second polypeptide, such that the provided constructs include a linker joining the first component and the at least one CD28 VHH of the first polypeptide and a linker joining the first component and the at least one CD28 VHH of the second polypeptide.

In some embodiments, the first polypeptide includes at least one TAA binding domain and/or at least one CD28 VHH, and a first Fc polypeptide of a heterodimeric Fc region, and the second polypeptide includes at least one TAA binding domain and/or at least one CD28 VHH, and a second Fc polypeptide of the heterodimeric Fc region. In some embodiments, the first polypeptide includes at least one TAA binding domain and at least one CD28 VHH, wherein the TAA binding domain and the CD28 VHH are joined by a linker. In some embodiments, the second polypeptide includes at least one TAA binding domain and at least one CD28 VHH, wherein the TAA binding domain and the CD28 VHH are joined by a linker. In some embodiments, the first and the second polypeptide each include at least one TAA binding domain and at least one CD28 VHH, wherein the TAA binding domain and the CD28 VHH of each polypeptide are joined by a linker. In some embodiments, the linkers present in the first and second polypeptides of the conditional multispecific CD28-binding polypeptide are the same.

In some embodiments, a conditional multispecific CD28-binding polypeptide contains an Fc domain. In some embodiments, the Cd28-binding polypeptide contains a linker that joins or couples a CD28 VHH and the Fc domain. In some embodiments, the linker is positioned at the end of the C-terminal region of the CD28 VHH, such that the CD28 VHH is N-terminal to the Fc domain. It is understood that because the provided conditional multispecific polypeptide constructs are multimers, such as dimers containing a first and second polypeptide, the provided constructs include a linker joining a CD28 VHH and a Fc domain of the first polypeptide and a linker joining the CD28 VHH and a Fc domain of the second polypeptide. In some embodiments, the first polypeptide includes at least one TAA binding domain and/or at least one CD28 VHH, and a first Fc polypeptide of a heterodimeric Fc region, and the second polypeptide includes at least one TAA binding domain and/or at least one CD28 VHH, and a second Fc polypeptide of the heterodimeric Fc region. In some embodiments, the first polypeptide includes least one CD28 VHH, wherein the CD28 VHH and the Fc domain are joined by a linker. In some embodiments, the second polypeptide includes at least one CD28 VHH, wherein the CD28 VHH and the Fc domain are joined by a linker. In some embodiments, the first and the second polypeptide each include at least one CD28 VHH, wherein the CD28 VHH and the Fc domain of each polypeptide are joined by a linker. In some embodiments, the linkers present in the first and second polypeptides of the CD28-binding polypeptide construct are the same.

Various polypeptide linkers for use in fusion proteins are known (see e.g. Chen et al. (2013) Adv. Drug. Deliv. 65:1357-1369; and International PCT publication No. WO 2014/099997, WO2000/24884; U.S. Pat. Nos. 5,258,498; 5,525,491; 5,525,491, 6,132,992).

In some embodiments, a conditional multispecific polypeptide construct of the disclosure includes a linker that joins at least one of the one or more TAA sdAb and at least one of the at least one CD28 sdAb. In some embodiments, the linker is not a cleavable linker.

In some embodiments, a conditional multispecific polypeptide construct of the disclosure includes a linker that joins at least one of the at least one CD28 sdAb and an Fc region. In some embodiments, the linker is not a cleavable linker.

Typically, the linker also is one that ensures correct folding of the polypeptide construct, does not exhibit a charge that would be inconsistent with the activity or function of the linked polypeptides or form bonds or other interactions with amino acid residues in one or more of the domains that would impede or alter activity of the linked polypeptides.

In some embodiments, the linker is a polypeptide linker. The polypeptide linker can be a flexible linker or a rigid linker or a combination of both. In some aspects, the linker is a short, medium or long linker. In some embodiments, the linker is up to 40 amino acids in length. In some embodiments, the linker is up to 25 amino acids in length. In some embodiments, the linker is at least or is at least about 2 amino acids in length. In some aspects, a suitable length is, e.g., a length of at least one and typically fewer than about 40 amino acid residues, such as 2-25 amino acid residues, 5-20 amino acid residues, 5-15 amino acid residues, 8-12 amino acid residues. In some embodiments, the linker is from or from about 2 to 24 amino acids, 2 to 20 amino acids, 2 to 18 amino acids, 2 to 14 amino acids, 2 to 12 amino acids, 2 to 10 amino acids, 2 to 8 amino acids, 2 to 6 amino acids, 6 to 24 amino acids, 6 to 20 amino acids, 6 to 18 amino acids, 6 to 14 amino acids, 6 to 12 amino acids, 6 to 10 amino acids, 6 to 8 amino acids, 8 to 24 amino acids, 8 to 20 amino acids, 8 to 18 amino acids, 8 to 14 amino acids, 8 to 12 amino acids, 8 to 10 amino acids, 10 to 24 amino acids, 10 to 20 amino acids, 10 to 18 amino acids, 10 to 14 amino acids, 10 to 12 amino acids, 12 to 24 amino acids, 12 to 20 amino acids, 12 to 18 amino acids, 12 to 14 amino acids, 14 to 24 amino acids, 14 to 20 amino acids, 14 to 18 amino acids, 18 to 24 amino acids, 18 to 20 amino acids or 20 to 24 amino acids. In some embodiments, the linker is 2, 3, 4, 5, 6, 7, 8, 9, 10, 11, 12, 13, 14, 15, 16, 17, 18, 19 or 20 amino acids in length.

The linkers can be naturally-occurring, synthetic or a combination of both. Particularly suitable linker polypeptides predominantly include amino acid residues selected from Glycine (Gly), Serine (Ser), Alanine (Ala), and Threonine (Thr). For example, the linker may contain at least 75% (calculated on the basis of the total number of residues present in the peptide linker), such as at least 80%, at least 85%, or at least 90% of amino acid residues selected from Gly, Ser, Ala, and Thr. The linker may also consist of Gly, Ser, Ala and/or Thr residues only. In some embodiments, the linker contains 1-25 glycine residues, 5-20 glycine residues, 5-15 glycine residues, or 8-12 glycine residues. In some aspects, suitable peptide linkers typically contain at least 50% glycine residues, such as at least 75% glycine residues. In some embodiments, a peptide linker comprises glycine residues only. In some embodiments, a peptide linker comprises glycine and serine residues only.

In some embodiments, these linkers are composed predominately of the amino acids Glycine and Serine, denoted as GS-linkers herein. In some embodiments, the linker contains (GGS)n, wherein n is 1 to 10, such as 1 to 5, for example 1 to 3, such as GGS(GGS)n (SEQ ID NO:244), wherein n is 0 to 10. In particular embodiments, the linker contains the sequence (GGGGS)n (SEQ ID NO: 123), wherein n is 1 to 10 or n is 1 to 5, such as 1 to 3. In further embodiments, the linker contains (GGGGGS)n (SEQ ID NO:124), wherein n is 1 to 4, such as 1 to 3. The linker can include combinations of any of the above, such as repeats of 2, 3, 4, or 5 GS, GGS, GGGGS, and/or GGGGGS linkers may be combined. In some embodiments, such a linker is 2, 3, 4, 5, 6, 7, 8, 9, 10, 11, 12, 13, 14, 15, 16, 17, 18 or 19 amino acids in length.

In some embodiments, the linker is (in one-letter amino acid code): GGS (SEQ ID NO:244), GGGGS (SEQ ID NO: 125), GGGGGS (SEQ ID NO: 126), or GGSGGGGS (SEQ ID NO:89). In some embodiments, the GS-linker comprises an amino acid sequence of GGSGGS, i.e., (GGS)2 (SEQ ID NO: 1); GGSGGSGGS, i.e., (GGS)3 (SEQ ID NO: 2); GGSGGSGGSGGS, i.e., (GGS)4 (SEQ ID NO: 3); GGSGGSGGSGGSGGS, i.e., (GGS)5 (SEQ ID NO: 4); GGSGGGGS (SEQ ID NO:89); GGGGGSGGGGGSGGGGGS, i.e., (G5S)3 (SEQ ID NO: 127), GGSGGGGSGGGGSGGGGS (SEQ ID NO: 129) and GGGGSGGGGSGGGGS (SEQ ID NO:128). In some embodiments, the linker is GG (SEQ ID NO:249). In some embodiments, the linker is GGS (SEQ ID NO:244). In some embodiments, the linker is GGGSGS (SEQ ID NO:90). In some embodiments, the linker is GGG (SEQ ID NO:87). In some embodiments, the linker is GGGG (SEQ ID NO:5). In some embodiments, the linker is GGSGGS (SEQ ID NO:1). In some embodiments, the linker is GGSGGGGS (SEQ ID NO:89). In some embodiments, the linker is GGGGGSGGGGGSGGGGGS (SEQ ID NO:127). In some of any of the above examples, serine can be replaced with alanine (e.g., (Gly4Ala) or (Gly3Ala)).

In some embodiments, the linker includes a peptide linker having the amino acid sequence Glyx-Xaa-Glyy-Xaa-Glyz (SEQ ID NO:130), wherein each Xaa is independently selected from Alanine (Ala), Valine (Val), Leucine (Leu), Isoleucine (Ile), Methionine (Met), Phenylalanine (Phe), Tryptophan (Trp), Proline (Pro), Glycine (Gly), Serine (Ser), Threonine (Thr), Cysteine (Cys), Tyrosine (Tyr), Asparagine (Asn), Glutamine (Gln), Lysine (Lys), Arginine (Arg), Histidine (His), Aspartate (Asp), and Glutamate (Glu), and wherein x, y, and z are each integers in the range from 1-5. In some embodiments, each Xaa is independently selected from the group consisting of Ser, Ala, and Thr. In a specific variation, each of x, y, and z is equal to 3 (thereby yielding a peptide linker having the amino acid sequence Gly-Gly-Gly-Xaa-Gly-Gly-Gly-Xaa-Gly-Gly-Gly (SEQ ID NO:131), wherein each Xaa is selected as above.

In some embodiments, the linker is serine-rich linkers based on the repetition of a (SSSSG)y (SEQ ID NO:132) motif where y is at least 1, though y can be 2, 3, 4, 5, 6, 7, 8 and 9.

In some cases, it may be desirable to provide some rigidity into the peptide linker. This may be accomplished by including proline residues in the amino acid sequence of the peptide linker. Thus, in some embodiments, a linker comprises at least one proline residue in the amino acid sequence of the peptide linker. For example, a peptide linker can have an amino acid sequence wherein at least 25% (e.g., at least 50% or at least 75%) of the amino acid residues are proline residues. In one particular embodiment, the peptide linker comprises proline residues only.

In some aspects, a peptide linker comprises at least one cysteine residue, such as one cysteine residue. For example, in some embodiments, a linker comprises at least one cysteine residue and amino acid residues selected from the group consisting of Gly, Ser, Ala, and Thr. In some such embodiments, a linker comprises glycine residues and cysteine residues, such as glycine residues and cysteine residues only. Typically, only one cysteine residue will be included per peptide linker. One example of a specific linker comprising a cysteine residue includes a peptide linker having the amino acid sequence Glym-Cys-Glyn, wherein n and m are each integers from 1-12, e.g., from 3-9, from 4-8, or from 4-7. In a specific variation, such a peptide linker has the amino acid sequence GGGGG-C-GGGGG (SEQ ID NO: 133).

In some embodiments, the linker of the fusion protein is a structured linker. In particular embodiments, the structured linker contains the sequence (AP)n or (EAAAK)n (SEQ ID NO:134), wherein n is 2 to 20, preferably 4 to 10, including but not limited to, AS-(AP)n-GT (SEQ ID NO:135) or AS-(EAAAK)n-GT (SEQ ID NO:136), wherein n is 2 to 20, such as 2, 3, 4, 5, 6, 7, 8, 9, 10, 11, 12, 13, 14 or 15. In other embodiments, the linker comprises the sequences (GGGGA)n (SEQ ID NO:137), (PGGGS)n (SEQ ID NO:138), (AGGGS)n (SEQ ID NO:139) or GGS-(EGKSSGSGSESKST)n-GGS (SEQ ID NO:140, wherein n is 2 to 20), (ADAAP)n (SEQ ID NO:313, wherein n is 2 to 20), (ADAAP)n-G (SEQ ID NO:314, wherein n is 2 to 20), (GEPQG)n (SEQ ID NO:315, wherein n is 2 to 20), (GEPQG)n-G (SEQ ID NO:316, wherein n is 2 to 20), (AGGEP)n (SEQ ID NO:317, wherein n is 2 to 20), (AGGEP)n-G (SEQ ID NO:318, wherein n is 2 to 20), (AGSEP)n (SEQ ID NO:319, wherein n is 2 to 20), (AGSEP)n-G (SEQ ID NO:320, wherein n is 2 to 20), (GGGEQ)n (SEQ ID NO:321, wherein n is 2 to 20), (GGGEQ)n-G (SEQ ID NO:322, wherein n is 2 to 20). In some embodiments, the linker is SSSASASSA (SEQ ID NO:141), GSPGSPG (SEQ ID NO:142), ATTTGSSPGPT (SEQ ID NO:143), ADAAPADAAPG (SEQ ID NO:323), GEPQGGEPQGG (SEQ ID NO:324), AGGEPAGGEPG (SEQ ID NO:325), AGSEPAGSEPG (SEQ ID NO:326), or GGGEQGGGEQG (SEQ ID NO:327).

In some embodiments, such linkers, by virtue of their structure, may be more resistant to proteolytic degradation, thereby offering an advantage when injected in vivo.

In some embodiments, the linker is not a cleavable linker, also called a non-cleavable linker. In some embodiments, the linker is not a cleavable by a protease. In some embodiments, a linker that is not a cleavable linker or that is not cleavable by a protease is one that is generally stable for in vivo delivery or recombinant production. In some aspects, a linker that is not cleavable by a protease includes those that do not contain at least one peptide bond which preferably lies within a cleavable peptide sequence or recognition site of a protease. In particular embodiments, a non-cleavable linker is not a target substrate for a protease, such that it is not preferentially or specifically cleaved by a protease compared to a linker that contains a substrate recognition site for the same protease.

In some embodiments, the linker does not contains a substrate recognition site or cleavage site for a particular protease, which is the sequence recognized by the active site of a protease that is cleaved by a protease. Typically, for example, for a serine protease, a cleavage sequence is made up of the P1-P4 and P1'-P4' amino acids in a substrate, where cleavage occurs after the P1 position. Typically, a cleavage sequence for a serine protease is six residues in length to match the extended substrate specificity of many proteases, but can be longer or shorter depending upon the protease. Typically, the linker does not include a P1-P1' scissile bond sequence that is recognized by a protease. In some aspects, a non-cleavable linker or a linker that does not contain a substrate recognition site that is specifically recognized for cleavage by a protease is one whose cleavage by a protease is substantially less than cleavage of a target substrate of the protease.

In some embodiments, the linker is a cleavable linker. In some aspects, a cleavable linker is a linker, such as any described above, that further includes a sequence that is a substrate for a protease due to the presence of at least one bond that can be broken under physiological conditions. In some cases, a cleavable linker is susceptible to or sensitive to cleavage under specific conditions that exist in vivo, such as following exposure to an extracellular protease, including those present in cellular environments in vivo. In some cases, the protease may be present in a particular physiological microenvironment, such as the tumor microenvironment, thereby restricting the sites at which cleavage may occur.

A protease typically exhibits specificity or preference for cleavage of a particular target substrate compared to another non-target substrate. Such a degree of specificity can be determined based on the rate constant of cleavage of a sequence, e.g. linker, which is a measure of preference of a protease for its substrate and the efficiency of the enzyme. Any method to determine the rate of increase of cleavage over time in the presence of various concentrations of substrate can be used to calculate the specificity constant. For example, a substrate is linked to a fluorogenic moiety, which is released upon cleavage by a protease. By determining the rate of cleavage at different protease concentrations the specificity constant for cleavage ($k_{cat}/K_M$) can be determined for a particular protease towards a particular linker. In some embodiments, a cleavable linker is a linker that is capable of being specifically cleaved by a protease at a rate of about at least $1\times10^4$ $M^{-1}$ $S^{-1}$, or at least $5\times10^4$ $M^{-1}$ $S^{-1}$, at least $10\times10^4$ $M^{-1}$ $S^{-1}$, at least $10\times10^5$ $M^{-1}$ $S^{-1}$ or more.

In some embodiments, the cleavable linker includes an amino acid sequence that can serve as a substrate for a protease, usually an extracellular protease. For example, the cleavable linker may include a cleavage sequence containing at least one peptide bond which preferably lies within a cleavable peptide sequence of a protease. Suitable proteases include, for example, matrix metalloproteases (MMP), cysteine proteases, serine proteases and plasmin activators, which are formed or activated in intensified manner in diseases such as rheumatoid arthritis or cancer, leading to excessive tissue degradation, inflammations and metastasis. In particular embodiments, the protease is a protease that is produced by a tumor, an activated immune effector cell (e.g. a T cell or a NK cell), or a cell in a tumor microenvironment. In some embodiments, the protease is a granzyme B, a matriptase or an MMP, such as MMP-2.

The cleavable linker may be selected based on a protease that is produced by a tumor that is in proximity to cells that express the target and/or produced by a tumor that is co-localized in tissue with the desired target of the multispecific polypeptide constructs. There are reports in the literature of increased levels of proteases having known substrates in a number of cancers, e.g., solid tumors. See, e.g., La Rocca et al, (2004) British J. of Cancer 90(7): 1414-1421.

In some embodiments, the cleavable linker that joins a CD3 and an Fc domain of a CD3 constrained multispecific polypeptide construct is cleaved by a protease produced by an immune effector cell that is activated by one of the components. For example, multispecific polypeptide constructs that encompass an effector enabled or enhanced IgG Fc region are capable of eliciting ADCC when engaged with the target antigen. Central to ADCC is the release of granzyme B and perforin from the effector cells, namely NK cells and cytotoxic T-cells. Upon release granzyme B enters the target cell in a perforin dependent manner wherein it mediates apoptosis. Importantly, granzyme B is active within the extracellular synapse between the effector cell and the target cell. In some embodiments, the cleavable linker that joins a CD28 VHH and an Fc domain of a multispecific polypeptide construct is cleaved by granzyme B. Granzyme B is released during effector cell activation mediated by one of the components of the multispecific polypeptide construct. In some embodiments, granzyme B and other proteases can be produced by immune effector cells, including activated T cells or NK cells. In some embodiments, activation of T cells by CD3 engagement upon binding of a TAA by a multispecific polypeptide construct may release such proteases, which then can cleave a specific cleavable linker thereby potentiating or increasing activity of the CD3 binding molecule to engage CD3. In some embodiments, the cleavage can amplify or increase the activity achieved by the multispecific construct when bound to TAA in an uncleaved state.

Exemplary substrates include but are not limited to substrates cleavable by one or more of the following enzymes or proteases: ADAMS, ADAMTS, e.g. ADAMS; ADAMS; ADAM10; ADAM12; ADAM15; ADAM17/TACE; ADAMDEC1; ADAMTS1; ADAMTS4; ADAMTS5; aspartate proteases, e.g., BACE or Renin; aspartic cathepsins, e.g., Cathepsin D or Cathepsin E; Caspases, e.g., Caspase 1, Caspase 2, Caspase 3, Caspase 4, Caspase 5, Caspase 6, Caspase 7, Caspase 8, Caspase 9, Caspase 10, or Caspase 14; cysteine cathepsins, e.g., Cathepsin B, Cathepsin C, Cathepsin K, Cathepsin L, Cathepsin S, Cathepsin V/L2, Cathepsin X/Z/P; Cysteine proteinases, e.g., Cruzipain; Legumain; Otubain-2; KLKs, e.g., KLK4, KLK5, KLK6, KLK7, KLK8, KLK10, KLK11, KLK13, or KLK14; Metallo proteinases, e.g., Meprin; Neprilysin; PSMA; BMP-1; MMPs, e.g., MMP1, MMP2, MMP3, MMP7, MMP8, MMP9, MMP10, MMP11, MMP12, MMP13, MMP14, MMP15, MMP16, MMP17, MMP19, MMP20, MMP23, MMP24, MMP26, or MMP27, serine proteases, e.g., activated protein C, Cathepsin A, Cathepsin G, Chymase, coagulation factor proteases (e.g., FVIIa, FIXa, FXa, FXIa, FXIIa), Elastase, granzyme B, Guanidinobenzoatase, HtrA1, Human Neutrophil Elastase, Lactoferrin, Marapsin, NS3/4A, PACE4, Plasmin, PSA, tPA, Thrombin, Tryptase, uPA; Type II Transmembrane Serine Proteases (TTSPs), e.g., DESC1, DPP-4, FAP, Hepsin, Matriptase-2, Matriptase, TMPRSS2, TMPRSS3, or TMPRSS4; and any combination thereof.

In some embodiments, the cleavable linker is cleaved by multiple proteases, e.g., 2 or more proteases, 3 or more proteases, 4 or more proteases, and so on.

In some embodiments, the cleavable linker is selected for use with a specific protease, for example a protease that is known to be produced by a tumor that is in proximity to cells that express the target and/or produced by a tumor that is co-localized with the target of the multispecific polypeptide construct.

In some embodiments, the cleavable linker contains a substrate recognition site or cleavage site for a particular protease, which is the sequence recognized by the active site of a protease that is cleaved by a protease. Typically, for example, for a serine protease, a cleavage sequence is made up of the P1-P4 and P1'-P4' amino acids in a substrate, where cleavage occurs after the P1 position. Typically, a cleavage sequence for a serine protease is six residues in length to match the extended substrate specificity of many proteases, but can be longer or shorter depending upon the protease. Typically, the cleavable linker includes a P1-P1' scissile bond sequence that is recognized by a protease. In some aspects, the cleavable linker is engineered to introduce a peptide bond able to be cleaved by a specific protease, for example by introducing a substrate recognition site sequence or cleavage sequence of the protease.

In some embodiments, the cleavable linker includes a combination of two or more substrate sequences. In some embodiments, each substrate sequence is cleaved by the same protease. In some embodiments, at least two of the substrate sequences are cleaved by different proteases. In some embodiments, the cleavable linker comprises an amino acid that is a substrate for granzyme B. In some embodiments, a granzyme B cleavable linker contains an amino acid sequence having the general formula P4 P3 P2 P1↓P1' (SEQ ID NO: 144), wherein P4 is amino acid I, L, Y, M, F, V, or A; P3 is amino acid A, G, S, V, E, D, Q, N, or Y; P2 is amino acid H, P, A, V, G, S, or T; P1 is amino acid D or E; and P1' is amino acid I, L, Y, M, F, V, T, S, G or A. In some embodiments, a granzyme B cleavable linker contains an amino acid sequence having the general formula P4 P3 P2 P1↓P1' (SEQ ID NO: 145), wherein P4 is amino acid I or L; P3 is amino acid E; P2 is amino acid P or A; P1 is amino acid D; and P1' is amino acid I, V, T, S, or G.

In some embodiments, the substrate for granzyme B comprises the amino acid sequence LEAD (SEQ ID NO: 146), LEPD (SEQ ID NO: 147), or LEAE (SEQ ID NO:148). In some embodiments, the cleavable linker contains the amino acid sequence the cleavable linker comprises the amino acid sequence IEPDI (SEQ ID NO:149), LEPDG (SEQ ID NO:150), LEADT (SEQ ID NO:151), IEPDG (SEQ ID NO:152), IEPDV (SEQ ID NO:153), IEPDS (SEQ ID NO:154), IEPDT (SEQ ID NO:155), IEPDP (SEQ ID NO:251), or LEADG (SEQ ID NO:144).

In some embodiments, the cleavable linker comprises an amino acid that is a substrate for matriptase. In some embodiments, the cleavable linker comprises the sequence P1QAR↓(A/V) (SEQ ID NO: 156), wherein P1 is any amino acid. In some embodiments, the cleavable linker comprises the sequence RQAR(A/V) (SEQ ID NO: 157). In some embodiments, the substrate for matriptase comprises the amino acid sequence RQAR (SEQ ID NO: 158). In some embodiments, the cleavable linker comprises the amino acid sequence RQARV (SEQ ID NO: 159).

In some embodiments, the cleavable linker comprises an amino acid that is a substrate for one or more matrix metalloproteases (MMPs). In some embodiments, the MMP is MMP-2. In some embodiments, the cleavable linker contains. the general formula P3 P2 P1↓P1' (SEQ ID NO: 160), wherein P3 is P, V or A; P2 is Q or D; P1 is A or N; and P1' is L, I or M. In some embodiments, the cleavable linker contains the general formula P3 P2 P1↓P1' (SEQ ID NO: 161), wherein P3 is P; P2 is Q or D; P1 is A or N; and P1' is L or I. In some embodiments, the substrate for MMP comprises the amino acid sequence PAGL (SEQ ID NO: 162).

In some embodiments, the cleavable linker comprises a combination of an amino acid sequence that is a substrate for granzyme B and an amino acid sequence that is a substrate for matriptase. In some embodiments, the cleavable linker comprises a combination of the amino acid sequence LEAD (SEQ ID NO: 146) and the amino acid sequence RQAR (SEQ ID NO: 158).

In some embodiments, the cleavable linker comprises a combination of an amino acid sequence that is a substrate for granzyme B and an amino acid sequence that is a substrate for MMP. In some embodiments, the cleavable linker comprises a combination of the amino acid sequence LEAD (SEQ ID NO: 146) and the amino acid sequence PAGL (SEQ ID NO: 162).

In some embodiments, the cleavable linker comprises a combination of an amino acid sequence that is a substrate for matriptase and an amino acid sequence that is a substrate for MMP. In some embodiments, the cleavable linker comprises a combination of the amino acid sequence RQAR (SEQ ID NO: 158) and the amino acid sequence PAGL (SEQ ID NO: 162).

In some embodiments, the cleavable linker comprises a combination of an amino acid sequence that is a substrate for granzyme B, an amino acid sequence that is a substrate for matriptase, and an amino acid sequence that is a substrate for MMP. In some embodiments, the cleavable linker comprises a combination of an amino acid sequence that is a substrate for granzyme B and an amino acid sequence that is a substrate for MMP. In some embodiments, the cleavable linker comprises a combination of the amino acid sequence LEAD (SEQ ID NO: 146), the amino acid sequence RQAR (SEQ ID NO: 158), and the amino acid sequence PAGL (SEQ ID NO: 162).

The cleavable linker can include any known linkers. Examples of cleavable linkers are described in Be'liveau et al. (2009) FEBS Journal, 276; U.S. published application Nos. US20160194399; US20150079088; US20170204139; US20160289324; US20160122425; US20150087810; US20170081397; U.S. Pat. No. 9,644,016.

In some embodiments, the cleavable linker comprises an amino acid sequence selected from the group consisting of TGLEADGSPAGLGRQARVG (SEQ ID NO: 163); TGLEADGSRQARVGPAGLG (SEQ ID NO: 164); TGSPAGLEADGSRQARVGS (SEQ ID NO: 165); TGPAGLGLEADGSRQARVG (SEQ ID NO: 166); TGRQARVGLEADGSPAGLG (SEQ ID NO: 167); TGSRQARVGPAGLEADGS (SEQ ID NO: 168); and TGPAGLGSRQARVGLEADGS (SEQ ID NO:169); GPAGLGLEPDGSRQARVG (SEQ ID NO: 170); GGSGGGGIEPDIGGSGGS (SEQ ID NO: 171); GGSGGGGLEADTGGSGGS (SEQ ID NO: 172); GSIEPDIGS (SEQ ID NO: 173); GSLEADTGS (SEQ ID NO: 174); GGSGGGGIEPDGGGSGGS (SEQ ID NO: 175); GGSGGGGIEPDVGGSGGS (SEQ ID NO: 176); GGSGGGGIEPDSGGSGGS (SEQ ID NO: 177); GGSGGGGIEPDTGGSGGS (SEQ ID NO: 178); GGGSLEPDGSGS (SEQ ID NO: 179); and GPAGLGLEADGSRQARVG (SEQ ID NO: 180), GGEGGGGSGGSGGGS (SEQ ID NO: 181); GSSAGSEAGGSGQAGVGS (SEQ ID NO: 182); GGSGGGGLEAEGSGGGGS (SEQ ID NO: 183); GGSGGGIEPDPGGSGGS(SEQ ID NO: 184); TGGSGGGGIEPDIGGSGGS (SEQ ID NO: 185).

D. Engineered Cells

Provided herein are engineered cells expressing any of the provided CD28-binding polypeptides. In some embodiments, the cells, such as immune cells, e.g. T cells or NK cells, are engineered to produce any of the provided CD28-binding polypeptides. In some embodiments, the engineered cells express and are capable of or are able to secrete the CD28-binding polypeptides from the cells under conditions suitable for secretion of the protein. In one embodiment, the cell is selected from the group consisting of a T cell, a Natural Killer (NK) cell, a cytotoxic T lymphocyte (CTL), a regulatory T cell, hematopoietic stem cells and/or pluripotent embryonic/induced stem cells. In some embodiments, engineered cell is a lymphocyte such as a tumor infiltrating lymphocyte (TIL), T-cell or NK cell. In some cases, the cell is a T cell, such as a CD4 and/or CD8 T cell. In some embodiments, the engineered cells are primary cells obtained from a subject, such as a patient. In particular embodiments, the subject is a human subject. In some embodiments, the cells are autologous to the subject. For example, in some embodiments, cells, e.g. T cells, may be isolated from a patient (also called primary cells) for engineering, e.g. transfection or transduction, with a nucleic acid construct encoding the CD28-binding polypeptide.

In some embodiments, engineered T-cells include, but are not limited to, T helper cell, cytotoxic T-cell (alternatively, cytotoxic T lymphocyte or CTL), natural killer T-cell, regulatory T-cell, memory T-cell, or gamma delta T-cell. In some embodiments, the engineered T cells are CD4+ or CD8+.

In some embodiments, the engineered cells express CD28-binding polypeptides that are secreted from the cell. In some embodiments, such a CD28-binding polypeptide is encoded by a nucleic acid molecule encoding the CD28-binding polypeptide under the operable control of a signal sequence for secretion. In some embodiments, the encoded CD28-binding polypeptide is secreted when expressed from a cell. In some embodiments, the signal peptide is a non-native signal peptide. In some embodiments, the signal peptide is a signal peptide from an immunoglobulin (such as IgG heavy chain or IgG-kappa light chain), a cytokine (such as interleukin-2 (IL-2), or CD33), a serum albumin protein (e.g., HSA or albumin), a human azurocidin preprotein signal sequence, a luciferase, a trypsinogen (e.g., chymotrypsinogen or trypsinogen) or other signal peptide able to efficiently secrete a protein from a cell.

In some embodiments, the provided engineered cells also express or are engineered to express an antigen-binding receptor, such as a recombinant receptor, such as a chimeric antigen receptor (CAR) or T cell receptor (TCR). In some embodiments, the engineered cell, such as an engineered T cell, recognizes a desired antigen associated with cancer. In specific embodiments, the antigen-binding receptor contains an antigen-binding moiety that specifically binds a tumor specific antigen or a tumor associated antigen. In some embodiments, the antigen-binding receptor is a CAR (chimeric antigen receptor) that contains an antigen-binding domain (e.g., scFv) that specifically binds to an antigen, such as a tumor specific antigen or tumor associated antigen, in which the CAR contains an antigen-binding domain (e.g., scFv) that specifically binds to an antigen, such as a tumor specific antigen or tumor associated antigen, and also contains a transmembrane domain and an intracellular signaling region (endodomain) containing an activating domain (e.g. CD3zeta signaling domain) and, in some cases, a costimulatory domain is capable of inducing or mediating an activation signal to the T cell after the antigen is bound. In another embodiment, the engineered cell possesses a TCR, such as a recombinant or engineered TCR. In some embodiments, the TCR can be a native TCR. Those of skill in the art will recognize that generally native mammalian T-cell receptors comprise an alpha and a beta chain (or a gamma and a delta chain) involved in antigen specific recognition and binding. In some embodiments, the TCR is an engineered TCR that is modified. In some embodiments, the TCR of an engineered T-cell specifically binds to a tumor associated or tumor specific antigen presented as a peptide on a major histocompatibility complex (MHC) molecule.

In some embodiments, the CD28-binding polypeptides can be incorporated into engineered cells, such as engineered T cells, by a variety of strategies such as those employed for recombinant host cells. A variety of methods to introduce a DNA construct into cells, such as primary cells, e.g. T cells, are known in the art. In some embodiments, viral transduction or plasmid electroporation are employed. In typical embodiments, the nucleic acid molecule encoding the CD28-binding polypeptide, or the expression vector, comprises a signal peptide that localizes the CD28-binding polypeptide for secretion. In some embodiments, a nucleic acid encoding a CD28-binding polypeptide is sub-cloned into a viral vector, such as a retroviral vector, which allows expression in the host mammalian cell. The expression vector can be introduced into a mammalian host cell and, under host cell culture conditions, the CD28-binding polypeptide is expressed on or in the cell, and, in some cases, is secreted.

Also provided herein are methods for the prevention and/or treatment of a disease or condition in a subject, such as a cancer, that includes administering to a subject engineered cells provided herein. Generally, the subject is in need of treatment for the disease or condition, such as a pharmaceutically active amount of a cell and/or of a pharmaceutical composition provided herein.

IV. Polypeptide Expression and Production

Nucleic acid molecules comprising polynucleotides that encode any of the provided sdAb and CD28-binding polypeptides, such as fusion proteins and multi-specific binding polypeptides, are provided. In some embodiments, the provided nucleic acid sequences and particularly DNA sequences encode fusion proteins as provided herein. In any of the foregoing embodiments, the nucleic acid molecule may also encode a leader sequence that directs secretion of the CD28-binding polypeptide, which leader sequence is typically cleaved such that it is not present in the secreted polypeptide. The leader sequence may be a native heavy chain (or VHH) leader sequence, or may be another heterologous leader sequence.

Nucleic acid molecules can be constructed using recombinant DNA techniques conventional in the art. In some embodiments, a nucleic acid molecule is an expression vector that is suitable for expression in a selected host cell.

Vectors comprising nucleic acids that encode the CD28-binding polypeptides, such as a fusion protein or a multi-specific binding polypeptide, described herein are provided. Such vectors include, but are not limited to, DNA vectors, phage vectors, viral vectors, retroviral vectors, etc. In some embodiments, a vector is selected that is optimized for expression of polypeptides in a desired cell type, such as CHO or CHO-derived cells, or in NSO cells. Exemplary such vectors are described, for example, in Running Deer et al., Biotechnol. Prog. 20:880-889 (2004).

In particular, a DNA vector that encodes a desired CD28-binding polypeptides, such as a fusion protein or multi-specific binding polypeptide, can be used to facilitate the methods of preparing the CD28-binding polypeptides described herein and to obtain significant quantities. The DNA sequence can be inserted into an appropriate expression vector, i.e., a vector which contains the necessary elements for the transcription and translation of the inserted protein-coding sequence. A variety of host-vector systems may be utilized to express the protein-coding sequence. These include mammalian cell systems infected with virus (e.g., vaccinia virus, adenovirus, etc.); insect cell systems infected with virus (e.g., baculovirus); microorganisms such as yeast containing yeast vectors, or bacteria transformed with bacteriophage DNA, plasmid DNA or cosmid DNA.

Depending on the host-vector system utilized, any one of a number of suitable transcription and translation elements may be used.

The disclosure also provides methods of producing a CD28-binding polypeptides, such as a fusion protein or a multi-specific binding polypeptide, by culturing a cell under conditions that lead to expression of the polypeptide, wherein the cell comprises an isolated nucleic acid molecule encoding a CD28-binding polypeptide described herein, and/or vectors that include these isolated nucleic acid sequences.

In some embodiments, a CD28-binding polypeptide, such as a fusion protein or a multi-specific binding polypeptide, may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. In some embodiments, the CD28-binding polypeptides may be expressed in yeast. See, e.g., U.S. Publication No. US 2006/0270045 A1. In some embodiments, a particular eukaryotic host cell is selected based on its ability to make desired post-translational modifications to the polypeptide. For example, in some embodiments, CHO cells produce polypeptides that have a higher level of sialylation than the same polypeptide produced in 293 cells.

Introduction of one or more nucleic acids (such as vectors) into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, for example, in Sambrook et al., Molecular Cloning, A Laboratory Manual, 3rd ed. Cold Spring Harbor Laboratory Press (2001). Nucleic acids may be transiently or stably transfected in the desired host cells, according to any suitable method.

Host cells comprising any of the nucleic acids or vectors described herein are also provided. In some embodiments, a host cell that expresses a CD28-binding polypeptide, such as a fusion protein or a multi-specific binding polypeptide, described herein is provided. The CD28-binding polypeptides expressed in host cells can be purified by any suitable method. Such methods include, but are not limited to, the use of affinity matrices or hydrophobic interaction chromatography. Suitable affinity ligands include CD80 or CD86 and agents that bind Fc regions. For example, a Protein A, Protein G, Protein A/G, or an antibody affinity column may be used to bind the Fc region and to purify a CD28-binding polypeptide that comprises an Fc region. Hydrophobic interactive chromatography, for example, a butyl or phenyl column, may also suitable for purifying some polypeptides such as antibodies. Ion exchange chromatography (for example anion exchange chromatography and/or cation exchange chromatography) may also suitable for purifying some polypeptides such as antibodies. Mixed-mode chromatography (for example reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

In some embodiments, the CD28-binding polypeptide, such as a fusion protein or a multi-specific binding polypeptide, is produced in a cell-free system. Nonlimiting exemplary cell-free systems are described, for example, in Sitaraman et al., Methods Mol. Biol. 498: 229-44 (2009); Spirin, Trends Biotechnol. 22: 538-45 (2004); Endo et al., Biotechnol. Adv. 21: 695-713 (2003).

In some embodiments, CD28-binding polypeptides, such as fusion proteins or multi-specific binding polypeptides, prepared by the methods described above are provided. In some embodiments, the CD28-binding polypeptide is prepared in a host cell. In some embodiments, the CD28-binding polypeptide is prepared in a cell-free system. In some embodiments, the anti-CD28 sdAb is purified. In some embodiments, the fusion protein is purified. In some embodiments, the CD28-binding polypeptide is purified. In some embodiments, the multi-specific binding polypeptide is purified. In some embodiments, a cell culture media comprising an CD28-binding polypeptide is provided.

In some embodiments, compositions comprising antibodies prepared by the methods described above are provided. In some embodiments, the composition comprises a CD28-binding polypeptide prepared in a host cell. In some embodiments, the composition comprises a CD28-binding polypeptide prepared in a cell-free system. In some embodiments, the composition comprises a purified CD28-binding polypeptide, such as a fusion protein or a multi-specific binding polypeptide.

V. Pharmaceutical Compositions and Formulations

Provided herein are pharmaceutical compositions containing any of the anti-CD28 sdAbs, CD28-binding polypeptides, fusion proteins, and/or multi-specific binding polypeptides provided herein or engineered cells expressing the same. In some embodiments, CD28-binding polypeptides, such as fusion proteins and/or multi-specific binding polypeptides of the disclosure (also referred to herein as "active compounds"), and derivatives, fragments, analogs and homologs thereof, can be incorporated into pharmaceutical compositions suitable for administration. In some embodiments, engineered cells expressing a chimeric receptor, such as a chimeric antigen receptor, containing a CD28-binding polypeptide provided herein can be incorporated into pharmaceutical compositions suitable for administration.

Such compositions typically contain a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, intratumoral, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a kit, container, pack, or dispenser together with instructions for administration. These pharmaceutical compositions can be included in diagnostic kits with instructions for use.

Pharmaceutical compositions are administered in an amount effective for treatment or prophylaxis of the specific indication. The therapeutically effective amount is typically dependent on the weight of the subject being treated, his or her physical or health condition, the extensiveness of the condition to be treated, or the age of the subject being treated. In some embodiments, the pharmaceutical composition may be administered in an amount in the range of about 50 μg/kg body weight to about 50 mg/kg body weight per dose. In some embodiments, the pharmaceutical composition may be administered in an amount in the range of about 100 μg/kg body weight to about 50 mg/kg body weight per dose. In some embodiments, the pharmaceutical composition may be administered in an amount in the range of about 100 μg/kg body weight to about 20 mg/kg body weight per dose. In some embodiments, the pharmaceutical composition may be administered in an amount in the range of about 0.5 mg/kg body weight to about 20 mg/kg body weight per dose.

In some embodiments, the pharmaceutical composition may be administered in an amount in the range of about 10 mg to about 1,000 mg per dose. In some embodiments, the pharmaceutical composition may be administered in an amount in the range of about 20 mg to about 500 mg per dose. In some embodiments, the pharmaceutical composition may be administered in an amount in the range of about 20 mg to about 300 mg per dose. In some embodiments, the pharmaceutical composition may be administered in an amount in the range of about 20 mg to about 200 mg per dose.

The pharmaceutical composition may be administered as needed to subjects. In some embodiments, an effective dose of the pharmaceutical composition is administered to a subject one or more times. In various embodiments, an effective dose of the pharmaceutical composition is administered to the subject once a month, less than once a month, such as, for example, every two months, every three months, or every six months. In other embodiments, an effective dose of the pharmaceutical composition is administered more than once a month, such as, for example, every two weeks, every week, twice per week, three times per week, daily, or multiple times per day. An effective dose of the pharmaceutical composition is administered to the subject at least once. In some embodiments, the effective dose of the pharmaceutical composition may be administered multiple times, including for periods of at least a month, at least six months, or at least a year. In some embodiments, the pharmaceutical composition is administered to a subject as-needed to alleviate one or more symptoms of a condition.

VI. Methods of Treatment and Uses

The CD28-binding polypeptides, such as fusion proteins and multi-specific binding polypeptides, or engineered cells expressing the same described herein are useful in a variety of therapeutic, diagnostic and prophylactic indications. For example, the CD28-binding polypeptides or engineered cells are useful in treating a variety of diseases and disorders in a subject. Such methods and uses include therapeutic methods and uses, for example, involving administration of the molecules or engineered cells, or compositions containing the same, to a subject having a disease, condition, or disorder, such as a tumor or cancer. In some embodiments, the molecule ore engineered cell is administered in an effective amount to effect treatment of the disease or disorder. Uses include uses of molecules containing the CD28-binding polypeptides, such as fusion proteins and multi-specific binding polypeptides, or engineered cells in such methods and treatments, and in the preparation of a medicament in order to carry out such therapeutic methods. In some embodiments, the methods are carried out by administering the CD28-binding polypeptides or engineered cells, or compositions comprising the same, to the subject having or suspected of having the disease or condition. In some embodiments, the methods thereby treat the disease or condition or disorder in the subject.

In one embodiment, a CD28-binding polypeptide, such as a fusion protein or a multi-specific binding polypeptide, or engineered cell of the disclosure may be used as therapeutic agents. Such agents will generally be employed to diagnose, prognose, monitor, treat, alleviate, and/or prevent a disease or pathology in a subject. A therapeutic regimen is carried out by identifying a subject, e.g., a human patient or other mammal suffering from (or at risk of developing) a disorder using standard methods. A CD28-binding polypeptide or engineered cell is administered to the subject. A CD28-binding polypeptide or engineered cell is administered to the subject and will generally have an effect due to its binding with the target(s).

In some embodiments, a provided CD28 polypeptide multi-specific polypeptide construct or engineered cell is capable of modulating, e.g. increasing, an immune response when administered to a subject, such as by co-stimulation of T cells to induce antitumor activity. In some embodiments, provided herein is a method of modulating an immune response in a subject by administering a therapeutically effective amount of a provided multispecific construction or engineered cell, or pharmaceutical compositions thereof. In some embodiments, the method of modulating an immune response increases or enhances an immune response in a subject. For example, the increase or enhanced response may be an increase in cell-mediated immunity. In some examples, the method increases T-cell activity, such as cytolytic T-cell (CTL) activity. In some embodiments, the modulated (e.g., increased) immune response is against a tumor or cancer.

In some embodiments, administration of a CD28-binding polypeptide, such as an CD28-Fc fusion protein or a multispecific binding polypeptide containing an Fc region, may activate innate immune cells via engagement of FcγRs through the Fc-region of the multispecific polypeptide construct. Administration of such multispecific polypeptide constructs may agonize, stimulate, activate, and/or augment innate immune cell effector functions, including ADCC, cytokine release, degranulation and/or ADCP. In the case of a conditional multispecific polypeptide construct, administration of such multispecific polypeptide constructs may activate T-cells upon binding of a tumor associated antigen on a target cell (e.g. a tumor cell), thereby allowing the anti-CD28 binding portion to bind CD28 on T cells. In some cases, administration of the multispecific polypeptide constructs may agonize, stimulate, activate, and/or augment CD28-mediated T cell activation, cytotoxicity, cytokine release and/or proliferation.

In some embodiments, the provided methods are for treating a disease or condition in a subject by administering a therapeutically effective amount of any of the provided CD28-binding polypeptides, such as fusion proteins and multi-specific binding polypeptides, or engineered cells or pharmaceutical compositions thereof. In some embodiments, the disease or condition is a tumor or a cancer. Generally, alleviation or treatment of a disease or disorder involves the lessening of one or more symptoms or medical problems associated with the disease or disorder. For example, in the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition of this disclosure can be used to prevent the onset or reoccurrence of the disease or disorder in a subject, e.g., a human or other mammal, such as a non-human primate, companion animal (e.g., cat, dog, horse), farm animal, work animal, or zoo animal. The terms subject and patient are used interchangeably herein.

In some embodiments, the CD28-binding polypeptides or engineered cells, or pharmaceutical compositions thereof, can be used to inhibit growth of mammalian cancer cells (such as human cancer cells). A method of treating cancer can include administering an effective amount of any of the pharmaceutical compositions described herein to a subject with cancer. The effective amount of the pharmaceutical composition can be administered to inhibit, halt, or reverse progression of cancers. Human cancer cells can be treated in vivo, or ex vivo. In ex vivo treatment of a human patient, tissue or fluids containing cancer cells are treated outside the body and then the tissue or fluids are reintroduced back into the patient. In some embodiments, the cancer is treated in a human patient in vivo by administration of the therapeutic composition into the patient.

Non-limiting examples of disease include: all types of cancers (breast, lung, colorectal, prostate, melanomas, head and neck, pancreatic, etc.), rheumatoid arthritis, Crohn's disuse, SLE, cardiovascular damage, ischemia, etc. For example, indications would include leukemias, including T-cell acute lymphoblastic leukemia (T-ALL), lymphoblastic diseases including multiple myeloma, and solid tumors, including lung, colorectal, prostate, pancreatic, and breast, including triple negative breast cancer. For example, indications include bone disease or metastasis in cancer, regardless of primary tumor origin; adrenal cancer; breast cancer, including by way of non-limiting example, basal-like breast cancer, ER/PR+ breast cancer, Her2+ breast cancer, triple-negative breast cancer; colorectal cancer; endometrial cancer; gastric cancer; brain cancer, such as by way of non-limiting example, astrocytoma, glioblastoma; head and neck cancer, such as esophageal cancer; liver cancer; lung cancer, such as by way of non-limiting example, non-small cell lung cancer; multiple myeloma ovarian cancer; pancreatic cancer; prostate cancer; sarcoma, such as osteosarcoma; renal cancer, such as by way of nonlimiting example, renal cell carcinoma; skin cancer, such as by way of nonlimiting example, squamous cell cancer, basal cell carcinoma, or melanoma; and/or testicular cancer. In some embodiments, the cancer is a melanoma. In some embodiments, the cancer is a brain cancer, such as an astrocytoma or glioblastoma. In some embodiments, the cancer is a breast cancer, such as a basal-like breast cancer. In some embodiments, the cancer is a gastric cancer. In some embodiments, the cancer is an adrenal cancer. In some embodiments, the cancer is a gastric cancer. In some embodiments, the cancer is a renal cancer. In some embodiments, the cancer is a liver cancer. In some embodiments, the cancer is a testicular cancer.

In some embodiments, the CD28-binding polypeptides, such as fusion proteins and multi-specific binding polypeptides, or engineered cells, or pharmaceutical compositions thereof, or are useful in treating, alleviating a symptom of, ameliorating and/or delaying the progression of a cancer or other neoplastic condition. In some embodiments, the cancer is adrenal cancer, bladder cancer, brain cancer, breast cancer, uterine/cervical cancer, ovarian cancer, prostate cancer, testicular cancer, esophageal cancer, gastrointestinal cancer, pancreatic cancer, colorectal cancer, colon cancer, kidney cancer, head and neck cancer, lung cancer, stomach cancer, germ cell cancer, bone cancer, liver cancer, thyroid cancer, skin cancer, neoplasm of the central nervous system, lymphoma, leukemia, myeloma, sarcoma, and virus-related cancer. In certain embodiments, the cancer is a metastatic cancer, refractory cancer, or recurrent cancer.

In some embodiments, a therapeutically effective amount of a CD28-binding polypeptide, such as a fusion protein or multispecific polypeptide construct, of the disclosure relates generally to the amount needed to achieve a therapeutic objective. Typically, precise amount of the compositions of the present disclosure to be administered can be determined by a physician with consideration of individual differences in age, weight, tumor size, extent of infection or metastasis, and condition of the patient (subject).

In some embodiments, a therapeutically effective dose may be, by way of nonlimiting example, from about 0.01 μg/kg body weight to about 10 mg/kg body weight. In some embodiments, the therapeutically effective dose may be, by way of nonlimiting example, from about 0.01 mg/kg body weight to about 5-10 mg/kg body weight. Common dosing frequencies may range, for example, from twice daily to once a week.

In some embodiments, a therapeutic amount of an engineered cell composition of the present disclosure is administered. It can generally be stated that a pharmaceutical composition comprising engineered cells, e.g., T cells, as described herein may be administered at a dosage of $10^4$ to $10^9$ cells/kg body weight, such as $10^5$ to $10^6$ cells/kg body weight, including all integer values within those ranges. Engineered cell compositions, such as T cell compositions, may also be administered multiple times at these dosages. The cells can be administered by using infusion techniques that are commonly known in immunotherapy (see, e.g., Rosenberg et al, New Eng. J. of Med. 319: 1676, 1988). The optimal dosage and treatment regime for a particular patient can readily be determined by one skilled in the art of medicine by monitoring the patient for signs of disease and adjusting the treatment accordingly.

Efficaciousness of treatment is determined in association with any known method for diagnosing or treating the particular disorder. Methods for the screening of CD28-binding polypeptides, or engineered cells containing the same, that possess the desired specificity include, but are not limited to, enzyme linked immunosorbent assay (ELISA) and other immunologically mediated techniques known within the art. A variety of means are known for determining if administration of the provided CD28-binding polypeptides or engineered cells sufficiently modulates immunological activity by eliminating, sequestering, or inactivating immune cells mediating or capable of mediating an undesired immune response; inducing, generating, or turning on immune cells that mediate or are capable of mediating a protective immune response; changing the physical or functional properties of immune cells; or a combination of these effects. Examples of measurements of the modulation of immunological activity include, but are not limited to, examination of the presence or absence of immune cell populations (using flow cytometry, immunohistochemistry, histology, electron microscopy, polymerase chain reaction (PCR)); measurement of the functional capacity of immune cells including ability or resistance to proliferate or divide in response to a signal (such as using T-cell proliferation assays and pepscan analysis based on 3H-thymidine incorporation following stimulation with anti-CD3 antibody, anti-T-cell receptor antibody, anti-CD28 antibody, calcium ionophores, PMA (phorbol 12-myristate 13-acetate) antigen presenting cells loaded with a peptide or protein antigen; B cell proliferation assays); measurement of the ability to kill or lyse other cells (such as cytotoxic T cell assays); measurements of the cytokines, chemokines, cell surface molecules, antibodies and other products of the cells (e.g., by flow cytometry, enzyme-linked immunosorbent assays, Western blot analysis, protein microarray analysis, immunoprecipitation analysis); measurement of biochemical markers of activation of immune cells or signaling pathways within immune cells (e.g., Western blot and immunoprecipitation analysis of tyrosine, serine or threonine phosphorylation, polypeptide cleavage, and formation or dissociation of protein complexes; protein array analysis; DNA transcriptional, profiling using DNA arrays or subtractive hybridization); measurements of cell death by apoptosis, necrosis, or other mechanisms (e.g., annexin V staining, TUNEL assays, gel electrophoresis to measure DNA laddering, histology; fluorogenic caspase assays, Western blot analysis of caspase substrates); measurement of the genes, proteins, and other molecules produced by immune cells (e.g., Northern blot analysis, polymerase chain reaction, DNA microarrays, protein microarrays, 2-dimensional gel electrophoresis, Western blot analysis, enzyme linked immunosorbent assays, flow cytometry); and measurement of clinical symptoms or outcomes such as improvement of autoimmune, neurodegenerative, and other diseases involving self-proteins or self-polypeptides (clinical scores, requirements for use of additional therapies, functional status, imaging studies) for example, by measuring relapse rate or disease severity.

The provided CD28-binding polypeptides are also useful in a variety of diagnostic and prophylactic formulations. In one embodiment, a CD28-binding polypeptide is administered to patients that are at risk of developing one or more of the aforementioned disorders. A patient's or organ's predisposition to one or more of the disorders can be determined using genotypic, serological or biochemical markers.

In another embodiment of the disclosure, a CD28-binding polypeptide or engineered cell is administered to human individuals diagnosed with a clinical indication associated with one or more of the aforementioned disorders. Upon diagnosis, such a therapeutic agent is administered to mitigate or reverse the effects of the clinical indication.

Combination Therapy

CD28-binding polypeptides, such as fusion proteins and multi-specific binding polypeptides, or engineered cells of the present disclosure can be administered alone or in combination with other modes of treatment, such as other anti-cancer agents. They can be provided before, substantially contemporaneous with, or after other modes of treatment (i.e., concurrently or sequentially). In some embodiments, the method of treatment described herein can further include administering: radiation therapy, chemotherapy, vaccination, targeted tumor therapy, CAR-T therapy, oncolytic virus therapy, cancer immunotherapy, cytokine therapy, surgical resection, chromatin modification, ablation, cryotherapy, an antisense agent against a tumor target, a siRNA agent against a tumor target, a microRNA agent against a tumor target or an anti-cancer/tumor agent, or a biologic, such as an antibody, cytokine, or receptor extracellular domain-Fc fusion.

In some embodiments, a CD28-binding polypeptide provided herein is given concurrently with one or more chemotherapeutic agent, CAR-T (chimeric antigen receptor T-cell) therapy, oncolytic virus therapy, cytokine therapy, and/or agents that target other checkpoint molecules, such as PD1, PD-L1, LAG3, TIM3, VISTA, gpNMB, B7H4, HHLA2, CD73, CTLA4, TIGIT, etc.

In some embodiments, the CD28-binding polypeptide or engineered cells of the present disclosure is used in combination with other anti-tumor agents, such as anti-HER-2 antibodies, anti-CD20 antibodies, an epidermal growth factor receptor (EGFR) antagonist (e.g., a tyrosine kinase inhibitor), HER1/EGFR inhibitor (e.g., erlotinib (TARCEVA®), platelet derived growth factor inhibitors (e.g., GLEEVEC® (Imatinib Mesylate)), a COX-2 inhibitor (e.g., celecoxib), interferons, CTLA4 inhibitors (e.g., anti-CTLA antibody ipilimumab (YERVOY®)), PD-1 inhibitors (e.g., anti-PD1 antibodies, BMS-936558), PDL1 inhibitors (e.g., anti-PDL1 antibodies, MPDL3280A), PDL2 inhibitors (e.g., anti-PDL2 antibodies) cytokines, antagonists (e.g., neutralizing antibodies) that bind to one or more of the following targets ErbB2, ErbB3, ErbB4, PDGFR-beta, BlyS, APRIL, BCMA, PD-1, PDL1, PDL2, CTLA4, or VEGF receptor(s), TRAIL/Apo2, and other bioactive and organic chemical agents, etc.

In some embodiments, a CD28-binding polypeptide or engineered cell provided herein is given concurrently with a PD-1/PD-L1 therapy. Examples of PD-1/PD-L1 therapy include nivolumab (BMS); pidilizumab (CureTech, CT-011), pembrolizumab (Merck); durvalumab (Medimmune/AstraZeneca); atezolizumab (Genentech/Roche); avelumab (Pfizer); AMP-224 (Amplimmune); BMS-936559; AMP-514 (Amplimmune); MDX-1105 (Merck); TSR-042 (Tesaro/AnaptysBio, ANB-011); STI-A1010 (Sorrento Therapeutics); STI-A1110 (Sorrento Therapeutics); and other agents that are directed against programmed death-1 (PD-1) or programmed death ligand 1 (PD-L1).

In some embodiments, the CD28-binding polypeptide or engineered cell of the present disclosure may be used in combination with a chemotherapeutic agent. Examples of chemotherapeutic agents include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, *Chem Intl. Ed. Engl.,* 33: 183-186 (1994)); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, OR); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Illinois), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (VL); oxaliplatin, including the oxaliplatin treatment regimen (FOLFOX); inhibitors of PKC-alpha, Raf, H-Ras, EGFR (e.g., erlotinib (TARCEVA®)) and VEGF-A that reduce cell proliferation and pharmaceutically acceptable salts, acids or derivatives of any of the above.

Further nonlimiting exemplary chemotherapeutic agents include anti-hormonal agents that act to regulate or inhibit hormone action on cancers such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® (aldesleukin) rIL-2; LURTOTECAN® topoisomerase 1 inhibitor; ABARELIX® GnRH agonist; and pharmaceutically acceptable salts, acids or derivatives of any of the above.

In some embodiments, the CD28-binding polypeptide and the additional agent are formulated into a single therapeutic composition, and the CD28-binding polypeptide and additional agent are administered simultaneously. Alternatively, the CD28-binding polypeptide or engineered cell and the additional agent are separate from each other, e.g., each is formulated into a separate therapeutic composition, and the CD28-binding polypeptide or engineered cell and the additional agent are administered simultaneously, or the CD28-binding polypeptide or engineered cell and the additional agent are administered at different times during a treatment regimen. For example, the CD28-binding polypeptide or engineered cell is administered prior to the administration of the additional agent, the CD28-binding polypeptide or engineered cell is administered subsequent to the administration of the additional agent, or the CD28-binding polypeptide or engineered cell and the additional agent are administered in an alternating fashion. The CD28-binding polypeptide and additional agent may be administered in single doses or in multiple doses.

In some embodiments, the CD28-binding polypeptide or engineered cell and the additional agent(s) are administered simultaneously. For example, the CD28-binding polypeptide and the additional agent(s) can be formulated in a single composition or administered as two or more separate compositions. In some embodiments, the CD28-binding polypeptide or engineered cell and the additional agent(s) are administered sequentially, or the CD28-binding polypeptide or engineered cell and the additional agent are administered at different times during a treatment regimen.

VII. Exemplary Embodiments

Among the provided embodiments are:

1. A CD28-binding polypeptide comprising at least one single domain antibody (sdAb) that binds CD28, wherein the at least one CD28 sdAb comprises a complementarity determining region 1 (CDR1) comprising an amino acid sequence selected from the group consisting of SEQ ID NO:189, 192, 195, 198, 199, 200, and 201; a complementarity determining region 2 (CDR2) comprising an amino acid sequence selected from the group consisting of SEQ ID NO:190, 193, 196, 202, 203, 204, 205, 206, 207, 208, 209, 210, 211, and 212; and a complementarity determining region 3 (CDR3) comprising an amino acid sequence selected from the group consisting of SEQ ID NO: 191, 194, and 197.
2. The CD28-binding polypeptide of embodiment 1, wherein the at least one CD28 sdAb comprises:

a CDR1 comprising an amino acid sequence set forth in SEQ ID NO:189, a CDR2 comprising the amino acid sequence set forth in SEQ ID NO:190, and a CDR3 comprising the amino acid sequence set forth in SEQ ID NO:191;

a CDR1 comprising an amino acid sequence set forth in SEQ ID NO:192, a CDR2 comprising the amino acid sequence set forth in SEQ ID NO:193, and a CDR3 comprising the amino acid sequence set forth in SEQ ID NO:194;

a CDR1 comprising an amino acid sequence set forth in SEQ ID NO:195, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:198, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:199, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:200, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:201, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:202, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:203, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:204, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:205, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:206, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:207, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:208, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:209, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:210, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:211, and a CDR3 comprising the amino acid sequence set forth in SEQ ID NO:197; or a CDR1 comprising an amino acid sequence set forth in SEQ ID NO:195, a CDR2 comprising the amino acid sequence set forth in SEQ ID NO:212, and a CDR3 comprising the amino acid sequence set forth in SEQ ID NO:197.

3. A CD28-binding polypeptide comprising at least one single domain antibody (sdAb) that binds CD28, wherein the at least one CD28 sdAb comprises a complementarity determining region 1 (CDR1) comprising an amino acid sequence selected from the group consisting of SEQ ID NO:189, 192, 195, 198, 199, 200, and 201; a complementarity determining region 2 (CDR2) comprising an amino acid sequence selected from the group consisting of SEQ ID NO:190, 193, 196, 202, 204, 205, 206, 207, 208, 209, 210, 211, and 212; and a complementarity determining region 3 (CDR3) comprising an amino acid sequence selected from the group consisting of SEQ ID NO: 191, 194, and 197.

4. The CD28-binding polypeptide of embodiment 3, wherein the at least one CD28 sdAb comprises:

a CDR1 comprising an amino acid sequence set forth in SEQ ID NO:189, a CDR2 comprising the amino acid sequence set forth in SEQ ID NO:190, and a CDR3 comprising the amino acid sequence set forth in SEQ ID NO:191;

a CDR1 comprising an amino acid sequence set forth in SEQ ID NO:192, a CDR2 comprising the amino acid sequence set forth in SEQ ID NO:193, and a CDR3 comprising the amino acid sequence set forth in SEQ ID NO:194;

a CDR1 comprising an amino acid sequence set forth in SEQ ID NO:195, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:198, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:199, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:200, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:201, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:202, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:204, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:205, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:206, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:207, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:208, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:209, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:210, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:211, and a CDR3 comprising the amino acid sequence set forth in SEQ ID NO:197; or a CDR1 comprising an amino acid sequence set forth in SEQ ID NO:195, a CDR2 comprising the amino acid sequence set forth in SEQ ID NO:212, and a CDR3 comprising the amino acid sequence set forth in SEQ ID NO:197.

5. A CD28-binding polypeptide comprising at least one single domain antibody (sdAb) that binds CD28, wherein the CD28 VHH domain comprises:

a CDR1, a CDR2, and a CDR3 as contained in the VHH set forth in SEQ ID NO:186;

a CDR1, a CDR2, and a CDR3 as contained in the VHH set forth in SEQ ID NO:187;

a CDR1, a CDR2, and a CDR3 as contained in the VHH set forth in SEQ ID NO:188;

a CDR1, a CDR2, and a CDR3 as contained in the VHH set forth in SEQ ID NO:213;

a CDR1, a CDR2, and a CDR3 as contained in the VHH set forth in SEQ ID NO:214;

a CDR1, a CDR2, and a CDR3 as contained in the VHH set forth in SEQ ID NO:215;

a CDR1, a CDR2, and a CDR3 as contained in the VHH set forth in SEQ ID NO:216;

a CDR1, a CDR2, and a CDR3 as contained in the VHH set forth in SEQ ID NO:217;

a CDR1, a CDR2, and a CDR3 as contained in the VHH set forth in SEQ ID NO:218;

a CDR1, a CDR2, and a CDR3 as contained in the VHH set forth in SEQ ID NO:219;

a CDR1, a CDR2, and a CDR3 as contained in the VHH set forth in SEQ ID NO:220;

a CDR1, a CDR2, and a CDR3 as contained in the VHH set forth in SEQ ID NO:221;

a CDR1, a CDR2, and a CDR3 as contained in the VHH set forth in SEQ ID NO:222;

a CDR1, a CDR2, and a CDR3 as contained in the VHH set forth in SEQ ID NO:223;

a CDR1, a CDR2, and a CDR3 as contained in the VHH set forth in SEQ ID NO:224;

a CDR1, a CDR2, and a CDR3 as contained in the VHH set forth in SEQ ID NO:225;

a CDR1, a CDR2, and a CDR3 as contained in the VHH set forth in SEQ ID NO:226;

a CDR1, a CDR2, and a CDR3 as contained in the VHH set forth in SEQ ID NO:227;

a CDR1, a CDR2, and a CDR3 as contained in the VHH set forth in SEQ ID NO:228;

a CDR1, a CDR2, and a CDR3 as contained in the VHH set forth in SEQ ID NO:229;

a CDR1, a CDR2, and a CDR3 as contained in the VHH set forth in SEQ ID NO:230;

a CDR1, a CDR2, and a CDR3 as contained in the VHH set forth in SEQ ID NO:231;

a CDR1, a CDR2, and a CDR3 as contained in the VHH set forth in SEQ ID NO:232;

a CDR1, a CDR2, and a CDR3 as contained in the VHH set forth in SEQ ID NO:233;

a CDR1, a CDR2, and a CDR3 as contained in the VHH set forth in SEQ ID NO:234;

a CDR1, a CDR2, and a CDR3 as contained in the VHH set forth in SEQ ID NO:235;

a CDR1, a CDR2, and a CDR3 as contained in the VHH set forth in SEQ ID NO:236;

a CDR1, a CDR2, and a CDR3 as contained in the VHH set forth in SEQ ID NO:237;

a CDR1, a CDR2, and a CDR3 as contained in the VHH set forth in SEQ ID NO:238;

a CDR1, a CDR2, and a CDR3 as contained in the VHH set forth in SEQ ID NO:239; or a CDR1, a CDR2, and a CDR3 as contained in the VHH set forth in SEQ ID NO:280.

6. A CD28-binding polypeptide comprising at least one single domain antibody (sdAb) that binds CD28 (CD28 VHH), wherein the CD28 VHH domain comprises:

a CDR1, a CDR2, and a CDR3 as contained in the VHH set forth in SEQ ID NO:186;

a CDR1, a CDR2, and a CDR3 as contained in the VHH set forth in SEQ ID NO:187;

a CDR1, a CDR2, and a CDR3 as contained in the VHH set forth in SEQ ID NO:188;

a CDR1, a CDR2, and a CDR3 as contained in the VHH set forth in SEQ ID NO:213;

a CDR1, a CDR2, and a CDR3 as contained in the VHH set forth in SEQ ID NO:214;

a CDR1, a CDR2, and a CDR3 as contained in the VHH set forth in SEQ ID NO:215;

a CDR1, a CDR2, and a CDR3 as contained in the VHH set forth in SEQ ID NO:216;

a CDR1, a CDR2, and a CDR3 as contained in the VHH set forth in SEQ ID NO:217;
a CDR1, a CDR2, and a CDR3 as contained in the VHH set forth in SEQ ID NO:218;
a CDR1, a CDR2, and a CDR3 as contained in the VHH set forth in SEQ ID NO:219;
a CDR1, a CDR2, and a CDR3 as contained in the VHH set forth in SEQ ID NO:221;
a CDR1, a CDR2, and a CDR3 as contained in the VHH set forth in SEQ ID NO:222;
a CDR1, a CDR2, and a CDR3 as contained in the VHH set forth in SEQ ID NO:223;
a CDR1, a CDR2, and a CDR3 as contained in the VHH set forth in SEQ ID NO:224;
a CDR1, a CDR2, and a CDR3 as contained in the VHH set forth in SEQ ID NO:225;
a CDR1, a CDR2, and a CDR3 as contained in the VHH set forth in SEQ ID NO:226;
a CDR1, a CDR2, and a CDR3 as contained in the VHH set forth in SEQ ID NO:227;
a CDR1, a CDR2, and a CDR3 as contained in the VHH set forth in SEQ ID NO:228;
a CDR1, a CDR2, and a CDR3 as contained in the VHH set forth in SEQ ID NO:229;
a CDR1, a CDR2, and a CDR3 as contained in the VHH set forth in SEQ ID NO:230;
a CDR1, a CDR2, and a CDR3 as contained in the VHH set forth in SEQ ID NO:231;
a CDR1, a CDR2, and a CDR3 as contained in the VHH set forth in SEQ ID NO:232;
a CDR1, a CDR2, and a CDR3 as contained in the VHH set forth in SEQ ID NO:233;
a CDR1, a CDR2, and a CDR3 as contained in the VHH set forth in SEQ ID NO:234;
a CDR1, a CDR2, and a CDR3 as contained in the VHH set forth in SEQ ID NO:235;
a CDR1, a CDR2, and a CDR3 as contained in the VHH set forth in SEQ ID NO:236;
a CDR1, a CDR2, and a CDR3 as contained in the VHH set forth in SEQ ID NO:237;
a CDR1, a CDR2, and a CDR3 as contained in the VHH set forth in SEQ ID NO:238;
a CDR1, a CDR2, and a CDR3 as contained in the VHH set forth in SEQ ID NO:239; or
a CDR1, a CDR2, and a CDR3 as contained in the VHH set forth in SEQ ID NO:280.

7. The CD28-binding polypeptide of any of embodiments 1-6, wherein the at least one CD28 sdAb comprises the amino acid sequence set forth in any of SEQ ID NOS:186, 187, 188, 213, 214, 215, 216, 217, 218, 219, 220, 221, 222, 223, 224, 225, 226, 227, 228, 229, 230, 231, 232, 233, 234, 235, 236, 237, 238, 239, and 280, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS:186, 187, 188, 213, 214, 215, 216, 217, 218, 219, 220, 221, 222, 223, 224, 225, 226, 227, 228, 229, 230, 231, 232, 233, 234, 235, 236, 237, 238, 239, and 280.

8. The CD28-binding polypeptide of any of embodiments 1-6, wherein the at least one CD28 sdAb comprises the amino acid sequence set forth in any of SEQ ID NOS:186, 187, 188, 213, 214, 215, 216, 217, 218, 219, 221, 222, 223, 224, 225, 226, 227, 228, 229, 230, 231, 232, 233, 234, 235, 236, 237, 238, 239, and 280, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS:186, 187, 188, 213, 214, 215, 216, 217, 218, 219, 221, 222, 223, 224, 225, 226, 227, 228, 229, 230, 231, 232, 233, 234, 235, 236, 237, 238, 239, and 280.

9. The CD28-binding polypeptide of any of embodiments 1-8, wherein the at least one CD28 sdAb comprises the sequence set forth in (i) SEQ ID NO: 186, (ii) a humanized variant of SEQ ID NO:186, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 186.

10. The CD28-binding polypeptide of any of embodiments 1-9, wherein the at least one CD28 sdAb comprises a CDR1 comprising an amino acid sequence set forth in SEQ ID NO:189; a CDR2 comprising an amino acid sequence set forth in SEQ ID NO:190; and a CDR3 comprising an amino acid sequence set forth in SEQ ID NO:191.

11. The CD28-binding polypeptide of any of embodiments 1-8, wherein the at least one CD28 sdAb comprises the sequence set forth in (i) SEQ ID NO: 187, (ii) a humanized variant of SEQ ID NO:187, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 187.

12. The CD28-binding polypeptide of any of embodiments 1-8 and 11, wherein the at least one CD28 sdAb comprises a CDR1 comprising an amino acid sequence set forth in SEQ ID NO:192; a CDR2 comprising an amino acid sequence set forth in SEQ ID NO:193; and a CDR3 comprising an amino acid sequence set forth in SEQ ID NO:194.

13. The CD28-binding polypeptide of any of embodiments 1-8, wherein the at least one CD28 sdAb comprises the sequence set forth in (i) SEQ ID NO: 188, (ii) a humanized variant of SEQ ID NO:188, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 188.

14. The CD28-binding polypeptide of any of embodiments 1-8 and 13, wherein the at least one CD28 sdAb comprises a CDR1 comprising an amino acid sequence set forth in any of SEQ ID NO:195, 198, 199, 200, and 201; a CDR2 comprising an amino acid sequence set forth in any of SEQ ID NO:196, 202, 203, 204, 205, 206, 207, 208, 209, 210, 211, and 212; and a CDR3 comprising an amino acid sequence set forth in SEQ ID NO:197.

15. The CD28-binding polypeptide of any of embodiments 1-8, 13 and 14, wherein the at least one CD28 sdAb comprises a CDR1, CDR2 and CDR3 set forth in SEQ ID NOS: 195, 196, and 197, respectively; SEQ ID NOS: 198, 196, and 197, respectively; SEQ ID NOS: 199, 196, and 197, respectively; SEQ ID NOS: 200, 196, and 197, respectively; SEQ ID NOS: 201, 196, and 197, respectively; SEQ ID NOS: 195, 202, and 197, respectively; SEQ ID NOS: 195, 203, and 197, respectively; SEQ ID NOS: 195, 204, and 197, respectively; SEQ ID NOS: 195, 205, and 197, respectively; SEQ ID NOS: 195, 206, and 197, respectively; SEQ ID NOS: 195, 207, and 197, respectively; SEQ ID NOS: 195, 208, and 197, respectively; SEQ ID NOS: 195, 209, and 197, respectively; SEQ ID NOS: 195, 210, and 197, respectively; SEQ ID NOS: 195, 211, and 197, respectively; or SEQ ID NOS: 195, 212, and 197, respectively.

16. The CD28-binding polypeptide of any of embodiments 1-8 and 13, wherein the at least one CD28 sdAb comprises a CDR1 comprising an amino acid sequence set forth in any of SEQ ID NO:195, 198, 199, 200, and 201; a CDR2 comprising an amino acid sequence set forth in any of SEQ ID NO:196, 202, 204, 205, 206, 207, 208, 209, 210, 211, and 212; and a CDR3 comprising an amino acid sequence set forth in SEQ ID NO:197.

17. The CD28-binding polypeptide of any of embodiments 1-8, 13 and 16, wherein the at least one CD28 sdAb comprises a CDR1, CDR2 and CDR3 set forth in SEQ ID NOS: 195, 196, and 197, respectively; SEQ ID NOS: 198, 196, and 197, respectively; SEQ ID NOS: 199, 196, and 197, respectively; SEQ ID NOS: 200, 196, and 197, respectively; SEQ ID NOS: 201, 196, and 197, respectively; SEQ ID NOS: 195, 202, and 197, respectively; SEQ ID NOS: 195, 204, and 197, respectively; SEQ ID NOS: 195, 205, and 197, respectively; SEQ ID NOS: 195, 206, and 197, respectively; SEQ ID NOS: 195, 207, and 197, respectively; SEQ ID NOS: 195, 208, and 197, respectively; SEQ ID NOS: 195, 209, and 197, respectively; SEQ ID NOS: 195, 210, and 197, respectively; SEQ ID NOS: 195, 211, and 197, respectively; or SEQ ID NOS: 195, 212, and 197, respectively.

18. The CD28-binding polypeptide of any of embodiments 1-8 and 13-15, wherein the at least one CD28 sdAb comprises the sequence of amino acids set forth in any one of SEQ ID NOs:213-239 and 280, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO:213-239 and 280.

19. The CD28-binding polypeptide of any of embodiments 1-8, 13-15, and 18, wherein the at least one CD28 sdAb comprises the sequence of amino acids set forth in any one of SEQ ID NOS:213-239 and 280.

20. The CD28-binding polypeptide of any of embodiments 1-8, 13, 16, and 17, wherein the at least one CD28 sdAb comprises the sequence of amino acids set forth in any one of SEQ ID NOs:213-219, 221-239, and 280, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO:213-219, 221-239, and 280.

21. The CD28-binding polypeptide of any of embodiments 1-7, 13, 16, 17, and 20, wherein the at least one CD28 sdAb comprises the sequence of amino acids set forth in any one of SEQ ID NOS:213-219, 221-239, and 280.

22. The CD28-binding polypeptide of any of embodiments 1-21, wherein the at least one sdAb is one CD28 sdAb and/or the CD28-binding polypeptide is monovalent for CD28.

23. The CD28-binding polypeptide of any of embodiments 1-21, wherein the at least one sdAb is two, three, or four CD28 sdAbs and/or the CD28-binding polypeptide is multivalent for CD28.

24. The CD28-binding polypeptide of any of embodiments 1-21 and 23, wherein the at least one sdAb is two CD28 sdAbs and/or the CD28-binding polypeptide is bivalent for CD28.

25. The CD28-binding polypeptide of embodiment 24, wherein the two CD28 sdAbs are the same CD28 sdAb.

26. The CD28-binding polypeptide of embodiment 24 or embodiment 25, wherein both of the CD28 sdAbs comprise the amino acid sequence set forth in SEQ ID NO:188.

27. The CD28-binding polypeptide of embodiment 24 or embodiment 25, wherein both of the CD28 sdAbs comprise the amino acid sequence set forth in SEQ ID NO:220.

28. The CD28-binding polypeptide of embodiment 24 or embodiment 25, wherein both of the CD28 sdAbs comprise the amino acid sequence set forth in SEQ ID NO:280.

29. The CD28-binding polypeptide of embodiment 24, wherein the two CD28 sdAbs are different CD28 sdAbs.

30. The CD28-binding polypeptide of embodiment 24 or embodiment 29, wherein one of the two CD28 sdAbs comprises the amino acid sequence set forth in SEQ ID NO:188 and the other of the two CD28 sdAbs comprises the amino acid sequence set forth in SEQ ID NOS:220.

31. The CD28-binding polypeptide of embodiment 24 or embodiment 29, wherein one of the two CD28 sdAbs comprises the amino acid sequence set forth in SEQ ID NO:188 and the other of the two CD28 sdAbs comprises the amino acid sequence set forth in SEQ ID NOS:280.

32. The CD28-binding polypeptide of embodiment 24 or embodiment 29, wherein one of the two CD28 sdAbs comprises the amino acid sequence set forth in SEQ ID NO:220 and the other of the two CD28 sdAbs comprises the amino acid sequence set forth in SEQ ID NOS:280.

33. The CD28-binding polypeptide of any of embodiments 1-32, wherein the CD28-binding polypeptide comprises an immunoglobulin Fc region.

34. The CD28-binding polypeptide of embodiment 33, wherein the Fc region is linked by a linking peptide (LP) to at least one of the at least one CD28 sdAb.

35. The CD28-binding polypeptide of embodiment 32 or embodiment 32, wherein the at least one CD28 sdAb is linked by a linking peptide (LP) to the Fc region at the N-terminal of the Fc region.

36. The CD28-binding polypeptide of any of embodiments 33-35, wherein the LP is a non-cleavable linker.

37. The CD28-binding polypeptide of any of embodiments 33-36, wherein the LP is a peptide of about 1 to 20 amino acids in length.

38. The CD28-binding polypeptide of any of embodiments 33-37, wherein the CD28-binding polypeptide comprises from N-terminal to C-terminal: (CD28 sdAb)-LP-Fc.

39. The CD28-binding polypeptide of any of embodiments 33-37, wherein the CD28-binding polypeptide comprises from N-terminal to C-terminal: (CD28 sdAb)-LP-(CD28 sdAb)-LP-Fc.

40. The CD28-binding polypeptide of any of embodiments 1-39 that is a dimer.

41. The CD28-binding polypeptide of any of embodiments 38-40, wherein the Fc region is a homodimeric Fc region.

42. The CD28-binding polypeptide of any of embodiments 38-41, wherein the Fc region comprises a sequence of amino acids selected from the group consisting of SEQ ID NOS: 8, 10, 11, 12 or 13, or a sequence of amino acids that exhibits at least 85%, 86%, 87%, 88%, 89%, 90%, 91%, 92%, 93%, 94%, 95%, 96%, 97%, 98%, or 99% sequence identity to any one of SEQ ID NOS: 8, 10, 11, 12 or 13.

43. The CD28-binding polypeptide of any of embodiments 38-42, wherein the Fc region is a human IgG1.

44. The CD28-binding polypeptide of any of embodiments 38-43, wherein the Fc region is a human IgG1, optionally wherein the Fc region comprises the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 8.

45. The CD28-binding polypeptide of any of embodiments 38-40, wherein the Fc region is a heterodimeric Fc region.

46. The CD28-binding polypeptide of any of embodiments 38-45, wherein the Fc region exhibits effector function.

47. The CD28-binding polypeptide of any of embodiments 38-45, wherein the Fc region comprises a polypeptide comprising one or more amino acid modification that reduces effector function and/or reduces binding to an effector molecule selected from an Fc gamma receptor or C1q.

48. The CD28-binding polypeptide of embodiment 47, wherein the one or more amino acid modification is deletion of one or more of Glu233, Leu234 or Leu235.

49. The CD28-binding polypeptide of embodiment 47 or embodiment 48, wherein the one or more amino acid modification is deletion of one or more of Glu233, Leu234 or Leu235, optionally wherein the Fc region comprises the sequence of amino acids set forth in SEQ ID NO: 9 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 9.

50. The CD28-binding polypeptide of any of embodiments 1-49, wherein the CD28-binding polypeptide comprises one or more binding domain that binds to a target antigen other than CD28.

51. The CD28-binding polypeptide of embodiment 50, wherein the one or more binding domain is one or more single domain antibody (sdAb) that binds a tumor associated antigen (TAA).

52. The CD28-binding polypeptide of any of embodiments 1-51, wherein the CD28-binding polypeptide comprises a moiety that binds protein A.

53. A CD28-binding polypeptide comprising from N-terminal to C-terminal:
 - one or more antigen binding domain comprising a single domain antibody (sdAb) that binds a tumor associated antigen (TAA);
 - at least one CD28-binding domain comprising a sdAb that binds CD28; and
 - an Fc region.

54. The CD28-binding polypeptide of any of embodiments 51-54, wherein at least one of the one or more TAA sdAb is joined by a linking peptide (LP) to at least one of the at least one CD28 sdAb.

55. The CD28-binding polypeptide of any of embodiments 51-54, wherein the CD28-binding polypeptide comprises from N-terminal to C-terminal: (TAA sdAb)-LP-(CD28 sdAb)-LP-Fc.

56. The CD28-binding polypeptide of any of embodiments 50-54 that is a dimer.

57. The CD28-binding polypeptide of any of embodiments 50-55, wherein the Fc region is a homodimeric Fc region.

58. A CD28-binding polypeptide comprising, from the N-terminal to the C-terminal:
 - one or more antigen binding domain comprising a single domain antibody (sdAb) that binds a tumor associated antigen (TAA);
 - at least one CD28-binding domain that comprises a sdAb that binds CD28; and
 - an Fc region, wherein the CD28-binding polypeptide is a dimer comprising a homodimeric Fc region.

59. The CD28-binding polypeptide of any of embodiments 50-59, wherein the Fc region comprises a sequence of amino acids selected from the group consisting of SEQ ID NOS: 8, 10, 11, 12 or 13, or a sequence of amino acids that exhibits at least 85%, 86%, 87%, 88%, 89%, 90%, 91%, 92%, 93%, 94%, 95%, 96%, 97%, 98%, or 99% sequence identity to any one of SEQ ID NOS: 8, 10, 11, 12 or 13.

60. The CD28-binding polypeptide of any of embodiments 50-60, wherein the Fc region is a human IgG1.

61. The CD28-binding polypeptide of any of embodiments 50-60, wherein the Fc region is a human IgG1, optionally wherein the Fc region comprises the sequence of amino acids set forth in SEQ ID NO: 8 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 8.

62. The CD28-binding polypeptide of any of embodiments 50-55 and 57, wherein the Fc region is a heterodimeric Fc region.

63. The CD28-binding polypeptide of any of embodiments 50-62, wherein the Fc region exhibits effector function.

64. The CD28-binding polypeptide of any of embodiments 50-62, wherein the Fc region comprises a polypeptide comprising one or more amino acid modification that reduces effector function and/or reduces binding to an effector molecule selected from an Fc gamma receptor or C1q.

65. The CD28-binding polypeptide of embodiment 64, wherein the one or more amino acid modification is deletion of one or more of Glu233, Leu234 or Leu235.

66. The CD28-binding polypeptide of embodiment 64 or embodiment 65, wherein the one or more amino acid modification is deletion of one or more of Glu233, Leu234 or Leu235, optionally wherein the Fc region comprises the sequence of amino acids set forth in SEQ ID NO: 9 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 9.

67. The CD28-binding polypeptide of any of embodiments 51-66, wherein the TAA is selected from the group consisting of: 1-92-LFA-3, 5T4, Alpha-4 integrin, Alpha-V integrin, alpha4beta1 integrin, alpha4beta7 integrin, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD70, CD71, CD74, CD80, CD81, CD86, CD95, CD117, CD123, CD125, CD132, (IL-2RG), CD133, CD137, CD138, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRalpha), GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HVEM, Hyaluronidase, ICOS, IFNalpha, IFN-beta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL13Ra2, IL15, IL17, IL18, IL21, IL23, IL23R, IL27/IL27R (wsx1), IL29, IL-31R, IL31/IL31R, IL2R, IL4, IL4R, IL6, IL6R, IL1 receptor accessory protein (IL1RAP), Insulin Receptor, Jagged Ligands, Jagged 1, Jagged 2, KISS1-R, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFR-beta, PD-1, PD-L1, PD-L2, Phosphatidyl-serine, P1GF, PSCA, PSMA, PSGR, RAAG12, RAGE, SLC44A4, Siglec15, Sphingosine 1 Phosphate, STEAP1, STEAP2, TAG-72, TAPA1, TEM-8, TGFbeta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

68. The CD28-binding polypeptide of any of embodiments 51-67, wherein the one or more TAA sdAb is one TAA sdAb and/or the CD28-binding polypeptide is monovalent for the TAA.

69. The CD28-binding polypeptide of any of embodiments 51-67, wherein the one or more TAA sdAb is two, three, or four TAA sdAbs and/or the CD28-binding polypeptide is multivalent for one or more TAA.

70. The CD28-binding polypeptide of any of embodiments 51-67 and 69, wherein the one or more TAA sdAb is two TAA sdAbs and/or the CD28-binding polypeptide is bivalent for a TAA.

71. The CD28-binding polypeptide of embodiment 70, wherein the two TAA sdAbs are the same TAA sdAbs.

72. The CD28-binding polypeptide of embodiment 70, wherein the two TAA sdAbs are different TAA sdAbs that bind the same TAA, optionally that bind different epitopes of the same TAA.

73. The CD28-binding polypeptide of embodiment 70, wherein the two TAA sdAbs are different TAA sdAbs that bind different TAAs.

74. The CD28-binding polypeptide of any of embodiments 33-73, wherein the CD28-binding polypeptide comprises a linking peptide (LP) between at least one of the at least one CD28 sdAb and the Fc region.

75. The CD28-binding polypeptide of any of embodiments 33-74, wherein the CD28-binding polypeptide comprises a linking peptide (LP) between at least one of the one or more TAA sdAb and the Fc region.

76. The CD28-binding polypeptide of embodiment 74 or embodiment 75, wherein the LP is a non-cleavable linker.

77. The CD28-binding polypeptide of any of embodiments 74-76, wherein the LP is a peptide of about 1 to 20 amino acids in length.

78. The CD28-binding polypeptide of any of embodiments 74-77, wherein the LP is or comprises a sequence set forth in any of SEQ ID NOS:1-7, 89, 90, 123-129, 244, or 249.

79. The CD28-binding polypeptide of any of embodiments 51-78, wherein the at least one CD28 sdAb is not able to, or is not substantially able to, bind or engage CD28 unless at least one of the one or more TAA sdAb is bound to its TAA.

80. The CD28-binding polypeptide of any of embodiments 51-78, wherein the at least one CD28 sdAb not able to, or is not substantially able to, bind or engage CD28 unless each of the one or more TAA sdAb is bound to its TAA.

81. The CD28-binding polypeptide of any of embodiments 1-80, wherein the CD-28 binding polypeptide does not comprise a CD3 binding region.

82. The CD28-binding polypeptide of any of embodiments 50-81, wherein the CD28-binding polypeptide comprises a CD3 binding region.

83. A CD28-binding polypeptide comprising at least one CD28 sdAb and a CD3 binding region.

84. The CD28 binding polypeptide of embodiment 83, wherein the at least one CD28 sdAb comprises a complementarity determining region 1 (CDR1) comprising an amino acid sequence selected from the group consisting of SEQ ID NO:189, 192, 195, 198, 199, 200, and 201; a complementarity determining region 2 (CDR2) comprising an amino acid sequence selected from the group consisting of SEQ ID NO:190, 193, 196, 202, 203, 204, 205, 206, 207, 208, 209, 210, 211, and 212; and a complementarity determining region 3 (CDR3) comprising an amino acid sequence selected from the group consisting of SEQ ID NO: 191, 194, and 197.

85. The CD28-binding polypeptide of embodiment 83 or embodiment 84, wherein the at least one CD28 sdAb comprises:

a CDR1 comprising an amino acid sequence set forth in SEQ ID NO:189, a CDR2 comprising the amino acid sequence set forth in SEQ ID NO:190, and a CDR3 comprising the amino acid sequence set forth in SEQ ID NO:191;

a CDR1 comprising an amino acid sequence set forth in SEQ ID NO:192, a CDR2 comprising the amino acid sequence set forth in SEQ ID NO:193, and a CDR3 comprising the amino acid sequence set forth in SEQ ID NO:194;

a CDR1 comprising an amino acid sequence set forth in SEQ ID NO:195, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:198, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:199, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:200, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:201, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:202, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:203, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:204, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:205, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:206, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:207, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:208, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:209, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:210, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:211, and a CDR3 comprising the amino acid sequence set forth in SEQ ID NO:197; or a CDR1 comprising an amino acid sequence set forth in SEQ ID NO:195, a CDR2 comprising the amino acid sequence set forth in SEQ ID NO:212, and a CDR3 comprising the amino acid sequence set forth in SEQ ID NO:197.

86. The CD28-binding polypeptide of embodiment 83, wherein the at least one CD28 sdAb comprises a complementarity determining region 1 (CDR1) comprising an amino acid sequence selected from the group consisting of SEQ ID NO:189, 192, 195, 198, 199, 200, and 201; a complementarity determining region 2 (CDR2) comprising an amino acid sequence selected from the group consisting of SEQ ID NO:190, 193, 196, 202, 204, 205, 206, 207, 208, 209, 210, 211, and 212; and a complementarity determining region 3 (CDR3) comprising an amino acid sequence selected from the group consisting of SEQ ID NO: 191, 194, and 197.

87. The CD28-binding polypeptide of embodiment 83 or embodiment 86, wherein the at least one CD28 sdAb comprises:

a CDR1 comprising an amino acid sequence set forth in SEQ ID NO:189, a CDR2 comprising the amino acid sequence set forth in SEQ ID NO:190, and a CDR3 comprising the amino acid sequence set forth in SEQ ID NO:191;

a CDR1 comprising an amino acid sequence set forth in SEQ ID NO:192, a CDR2 comprising the amino acid sequence set forth in SEQ ID NO:193, and a CDR3 comprising the amino acid sequence set forth in SEQ ID NO:194;

a CDR1 comprising an amino acid sequence set forth in SEQ ID NO:195, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:198, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:199, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:200, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:201, a CDR2 comprising the amino acid sequence set forth in SEQ ID NO:196, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:202, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:204, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:205, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:206, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:207, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:208, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:209, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:210, and a CDR3 comprising the amino acid sequence set forth in SEQ ID NO:197;

a CDR1 comprising an amino acid sequence set forth in SEQ ID NO:195, a CDR2 comprising the amino acid sequence set forth in SEQ ID NO:211, and a CDR3 comprising the amino acid sequence set forth in SEQ ID NO:197; or a CDR1 comprising an amino acid sequence set forth in SEQ ID NO:195, a CDR2 comprising the amino acid sequence set forth in SEQ ID NO:212, and a CDR3 comprising the amino acid sequence set forth in SEQ ID NO:197.

88. The CD28-binding polypeptide of any of embodiments 83-85, wherein the at least one CD28 sdAb (CD288 VHH) comprises:

a CDR1, a CDR2, and a CDR3 as contained in the VHH set forth in SEQ ID NO:186;

a CDR1, a CDR2, and a CDR3 as contained in the VHH set forth in SEQ ID NO:187;

a CDR1, a CDR2, and a CDR3 as contained in the VHH set forth in SEQ ID NO:188;

a CDR1, a CDR2, and a CDR3 as contained in the VHH set forth in SEQ ID NO:213;

a CDR1, a CDR2, and a CDR3 as contained in the VHH set forth in SEQ ID NO:214;

a CDR1, a CDR2, and a CDR3 as contained in the VHH set forth in SEQ ID NO:215;

a CDR1, a CDR2, and a CDR3 as contained in the VHH set forth in SEQ ID NO:216;

a CDR1, a CDR2, and a CDR3 as contained in the VHH set forth in SEQ ID NO:217;

a CDR1, a CDR2, and a CDR3 as contained in the VHH set forth in SEQ ID NO:218;

a CDR1, a CDR2, and a CDR3 as contained in the VHH set forth in SEQ ID NO:219;

a CDR1, a CDR2, and a CDR3 as contained in the VHH set forth in SEQ ID NO:220;

a CDR1, a CDR2, and a CDR3 as contained in the VHH set forth in SEQ ID NO:221;

a CDR1, a CDR2, and a CDR3 as contained in the VHH set forth in SEQ ID NO:222;

a CDR1, a CDR2, and a CDR3 as contained in the VHH set forth in SEQ ID NO:223;

a CDR1, a CDR2, and a CDR3 as contained in the VHH set forth in SEQ ID NO:224;

a CDR1, a CDR2, and a CDR3 as contained in the VHH set forth in SEQ ID NO:225;

a CDR1, a CDR2, and a CDR3 as contained in the VHH set forth in SEQ ID NO:226;

a CDR1, a CDR2, and a CDR3 as contained in the VHH set forth in SEQ ID NO:227;

a CDR1, a CDR2, and a CDR3 as contained in the VHH set forth in SEQ ID NO:228;

a CDR1, a CDR2, and a CDR3 as contained in the VHH set forth in SEQ ID NO:229;

a CDR1, a CDR2, and a CDR3 as contained in the VHH set forth in SEQ ID NO:230;

a CDR1, a CDR2, and a CDR3 as contained in the VHH set forth in SEQ ID NO:231;

a CDR1, a CDR2, and a CDR3 as contained in the VHH set forth in SEQ ID NO:232;

a CDR1, a CDR2, and a CDR3 as contained in the VHH set forth in SEQ ID NO:233;

a CDR1, a CDR2, and a CDR3 as contained in the VHH set forth in SEQ ID NO:234;

a CDR1, a CDR2, and a CDR3 as contained in the VHH set forth in SEQ ID NO:235;

a CDR1, a CDR2, and a CDR3 as contained in the VHH set forth in SEQ ID NO:236;

a CDR1, a CDR2, and a CDR3 as contained in the VHH set forth in SEQ ID NO:237;

a CDR1, a CDR2, and a CDR3 as contained in the VHH set forth in SEQ ID NO:238;

a CDR1, a CDR2, and a CDR3 as contained in the VHH set forth in SEQ ID NO:239; or a CDR1, a CDR2, and a CDR3 as contained in the VHH set forth in SEQ ID NO:280.

89. The CD28-binding polypeptide of any of embodiments 83, 86, and 87, wherein the at least one CD28 sdAb (CD28 VHH) comprises:

a CDR1, a CDR2, and a CDR3 as contained in the VHH set forth in SEQ ID NO:186;

a CDR1, a CDR2, and a CDR3 as contained in the VHH set forth in SEQ ID NO:187;

a CDR1, a CDR2, and a CDR3 as contained in the VHH set forth in SEQ ID NO:188;

a CDR1, a CDR2, and a CDR3 as contained in the VHH set forth in SEQ ID NO:213;

a CDR1, a CDR2, and a CDR3 as contained in the VHH set forth in SEQ ID NO:214;

a CDR1, a CDR2, and a CDR3 as contained in the VHH set forth in SEQ ID NO:215;

a CDR1, a CDR2, and a CDR3 as contained in the VHH set forth in SEQ ID NO:216;

a CDR1, a CDR2, and a CDR3 as contained in the VHH set forth in SEQ ID NO:217;

a CDR1, a CDR2, and a CDR3 as contained in the VHH set forth in SEQ ID NO:218;

a CDR1, a CDR2, and a CDR3 as contained in the VHH set forth in SEQ ID NO:219;

a CDR1, a CDR2, and a CDR3 as contained in the VHH set forth in SEQ ID NO:221;

a CDR1, a CDR2, and a CDR3 as contained in the VHH set forth in SEQ ID NO:222;

a CDR1, a CDR2, and a CDR3 as contained in the VHH set forth in SEQ ID NO:223;

a CDR1, a CDR2, and a CDR3 as contained in the VHH set forth in SEQ ID NO:224;

a CDR1, a CDR2, and a CDR3 as contained in the VHH set forth in SEQ ID NO:225;
a CDR1, a CDR2, and a CDR3 as contained in the VHH set forth in SEQ ID NO:226;
a CDR1, a CDR2, and a CDR3 as contained in the VHH set forth in SEQ ID NO:227;
a CDR1, a CDR2, and a CDR3 as contained in the VHH set forth in SEQ ID NO:228;
a CDR1, a CDR2, and a CDR3 as contained in the VHH set forth in SEQ ID NO:229;
a CDR1, a CDR2, and a CDR3 as contained in the VHH set forth in SEQ ID NO:230;
a CDR1, a CDR2, and a CDR3 as contained in the VHH set forth in SEQ ID NO:231;
a CDR1, a CDR2, and a CDR3 as contained in the VHH set forth in SEQ ID NO:232;
a CDR1, a CDR2, and a CDR3 as contained in the VHH set forth in SEQ ID NO:233;
a CDR1, a CDR2, and a CDR3 as contained in the VHH set forth in SEQ ID NO:234;
a CDR1, a CDR2, and a CDR3 as contained in the VHH set forth in SEQ ID NO:235;
a CDR1, a CDR2, and a CDR3 as contained in the VHH set forth in SEQ ID NO:236;
a CDR1, a CDR2, and a CDR3 as contained in the VHH set forth in SEQ ID NO:237;
a CDR1, a CDR2, and a CDR3 as contained in the VHH set forth in SEQ ID NO:238;
a CDR1, a CDR2, and a CDR3 as contained in the VHH set forth in SEQ ID NO:239; or
a CDR1, a CDR2, and a CDR3 as contained in the VHH set forth in SEQ ID NO:280.

90. The CD28-binding polypeptide of any of embodiments 83-85 and 88, wherein the at least one CD28 sdAb comprises the amino acid sequence set forth in any of SEQ ID NOS:186, 187, 188, 213, 214, 215, 216, 217, 218, 219, 220, 221, 222, 223, 224, 225, 226, 227, 228, 229, 230, 231, 232, 233, 234, 235, 236, 237, 238, 239, and 280, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS:186, 187, 188, 213, 214, 215, 216, 217, 218, 219, 220, 221, 222, 223, 224, 225, 226, 227, 228, 229, 230, 231, 232, 233, 234, 235, 236, 237, 238, 239, and 280.

91. The CD28-binding polypeptide of any of embodiments 83, 86, 88, and 89, wherein the at least one CD28 sdAb comprises the amino acid sequence set forth in any of SEQ ID NOS:186, 187, 188, 213, 214, 215, 216, 217, 218, 219, 221, 222, 223, 224, 225, 226, 227, 228, 229, 230, 231, 232, 233, 234, 235, 236, 237, 238, 239, and 280, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS:186, 187, 188, 213, 214, 215, 216, 217, 218, 219, 221, 222, 223, 224, 225, 226, 227, 228, 229, 230, 231, 232, 233, 234, 235, 236, 237, 238, 239, and 280.

92. The CD28-binding polypeptide of any of embodiments 83-91, wherein the at least one CD28 sdAb comprises the sequence set forth in (i) SEQ ID NO: 186, (ii) a humanized variant of SEQ ID NO:186, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 186.

93. The CD28-binding polypeptide of any of embodiments 83-92, wherein the at least one CD28 sdAb comprises a CDR1 comprising an amino acid sequence set forth in SEQ ID NO:189; a CDR2 comprising an amino acid sequence set forth in SEQ ID NO:190; and a CDR3 comprising an amino acid sequence set forth in SEQ ID NO:191.

94. The CD28-binding polypeptide of any of embodiments 83-91, wherein the at least one CD28 sdAb comprises the sequence set forth in (i) SEQ ID NO: 187, (ii) a humanized variant of SEQ ID NO:187, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 187.

95. The CD28-binding polypeptide of any of embodiments 83-91 and 94, wherein the at least one CD28 sdAb comprises a CDR1 comprising an amino acid sequence set forth in SEQ ID NO:192; a CDR2 comprising an amino acid sequence set forth in SEQ ID NO:193; and a CDR3 comprising an amino acid sequence set forth in SEQ ID NO:194.

96. The CD28-binding polypeptide of any of embodiments 83-91, wherein the at least one CD28 sdAb comprises the sequence set forth in (i) SEQ ID NO: 188, (ii) a humanized variant of SEQ ID NO:188, or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 188.

97. The CD28-binding polypeptide of any of embodiments 83-91 and embodiment 96, wherein the at least one CD28 sdAb comprises a CDR1 comprising an amino acid sequence set forth in any of SEQ ID NO:195, 198, 199, 200, and 201; a CDR2 comprising an amino acid sequence set forth in any of SEQ ID NO:196, 202, 203, 204, 205, 206, 207, 208, 209, 210, 211, and 212; and a CDR3 comprising an amino acid sequence set forth in SEQ ID NO:197.

98. The CD28-binding polypeptide of any of embodiments 83-91, 96, and 97, wherein the at least one CD28 sdAb comprises a CDR1, CDR2 and CDR3 set forth in SEQ ID NOS: 195, 196, and 197, respectively; SEQ ID NOS: 198, 196, and 197, respectively; SEQ ID NOS: 199, 196, and 197, respectively; SEQ ID NOS: 200, 196, and 197, respectively; SEQ ID NOS: 201, 196, and 197, respectively; SEQ ID NOS: 195, 202, and 197, respectively; SEQ ID NOS: 195, 203, and 197, respectively; SEQ ID NOS: 195, 204, and 197, respectively; SEQ ID NOS: 195, 205, and 197, respectively; SEQ ID NOS: 195, 206, and 197, respectively; SEQ ID NOS: 195, 207, and 197, respectively; SEQ ID NOS: 195, 208, and 197, respectively; SEQ ID NOS: 195, 209, and 197, respectively; SEQ ID NOS: 195, 210, and 197, respectively; SEQ ID NOS: 195, 211, and 197, respectively; or SEQ ID NOS: 195, 212, and 197, respectively.

99. The CD28-binding polypeptide of any of embodiments 83-91 and 96, wherein the at least one CD28 sdAb comprises a CDR1 comprising an amino acid sequence set forth in any of SEQ ID NO:195, 198, 199, 200, and 201; a CDR2 comprising an amino acid sequence set forth in any of SEQ ID NO:196, 202, 204, 205, 206, 207, 208, 209, 210, 211, and 212; and a CDR3 comprising an amino acid sequence set forth in SEQ ID NO:197.

100. The CD28-binding polypeptide of any of embodiments 83-91, 96, and 99, wherein the at least one CD28 sdAb comprises a CDR1, CDR2 and CDR3 set forth in SEQ ID NOS: 195, 196, and 197, respectively; SEQ ID NOS: 198, 196, and 197, respectively; SEQ ID NOS: 199, 196, and 197, respectively; SEQ ID NOS: 200, 196, and 197, respectively; SEQ ID NOS: 201, 196, and 197, respectively; SEQ ID NOS: 195, 202, and 197, respectively; SEQ ID NOS: 195, 204, and 197, respectively; SEQ ID NOS: 195, 205, and 197, respectively; SEQ ID NOS: 195, 206, and 197, respectively; SEQ ID NOS: 195, 207, and 197, respectively; SEQ ID NOS: 195, 208, and 197, respectively; SEQ ID NOS: 195, 209, and 197, respectively; SEQ ID NOS: 195, 210, and 197, respectively; SEQ ID NOS: 195, 211, and 197, respectively; or SEQ ID NOS: 195, 212, and 197, respectively.
101. The CD28-binding polypeptide of any of embodiments 83-91 and 96-98, wherein the at least one CD28 sdAb comprises the sequence of amino acids set forth in any one of SEQ ID NOs:213-239 and 280, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO:213-239 and 280.
102. The CD28-binding polypeptide of any of embodiments 83-91, 96-98, and 101, wherein the at least one CD28 sdAb comprises the sequence of amino acids set forth in any one of SEQ ID NOS:213-239 and 280.
103. The CD28-binding polypeptide of any of embodiments 83-91, 96, 99, and 100, wherein the at least one CD28 sdAb comprises the sequence of amino acids set forth in any one of SEQ ID NOs:213-219, 221-239, and 280, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO:213-219, 221-239, and 280.
104. The CD28-binding polypeptide of any of embodiments 83-91, 96, 99, 100, and 103, wherein the at least one CD28 sdAb comprises the sequence of amino acids set forth in any one of SEQ ID NOS:213-219, 221-239, and 280.
105. The CD28-binding polypeptide of any of embodiments 82-104, wherein the CD3-binding region binds CD3 (CD3ε).
106. The CD28-binding polypeptide of any of embodiments 82-105, wherein the CD3 binding region is an anti-CD3 antibody or anti-binding fragment.
107. The CD28-binding polypeptide of embodiment 106, wherein the anti-CD3 antibody or antigen binding fragment comprises a variable heavy chain region (VH) and a variable light chain region (VL).
108. The CD28-binding polypeptide of any of embodiments 82-107, wherein the CD3 binding region is monovalent.
109. The CD28-binding polypeptide of any of embodiments 82-108, wherein the CD3 binding region is an variable fragment (Fv) comprising a variable heavy chain region (VH) and a variable light chain region (VL).
110. The CD28-binding polypeptide of any of embodiments 82-108, wherein the anti-CD3 antibody or antigen binding fragment is not a single chain antibody, optionally is not a single chain variable fragment (scFv).
111. The CD28-binding polypeptide of any of embodiments 82-110, wherein the CD28-binding polypeptide comprises an immunoglobulin Fc region.
112. The CD28-binding polypeptide of embodiment 111, wherein the CD28-binding polypeptide is a dimer.
113. The CD28-binding polypeptide of embodiment 111 or embodiment 112, wherein the Fc is a heterodimeric Fc and the VH and VL that comprise the anti-CD3 antibody or antigen binding fragment are linked to opposite polypeptides of the heterodimeric Fc.
114. The CD28-binding polypeptide of any of embodiments 82-113, wherein the CD3 binding region is not able to, or is not substantially able to, bind or engage CD3 unless at least one of the one or more TAA sdAb is bound to a TAA.
115. The CD28-binding polypeptide of any of embodiments 82-114, wherein the CD3 binding region is not able to, or is not substantially able, to bind or engage CD3 unless at least one of the at least one CD28 sdAb is bound to CD28.
116. A polynucleotide(s) encoding the CD28-binding polypeptide construct of any of embodiments 1-115.
117. A polynucleotide, comprising a first nucleic acid sequence encoding a first polypeptide of a CD28-binding polynucleotide of any of embodiments 1-115 and a second nucleic acid sequence encoding a second polypeptide of the multispecific construct, wherein the first and second nucleic acid sequence are separated by an internal ribosome entry site (IRES), or a nucleic acid encoding a self-cleaving peptide or a peptide that causes ribosome skipping.
118. The polynucleotide of embodiment 117, wherein the first nucleic acid sequence and second nucleic acid sequence are operably linked to the same promoter.
119. The polynucleotide of embodiment 118, wherein the nucleic acid encoding a self-cleaving peptide or a peptide that causes ribosome skipping is selected from a T2A, a P2A, a E2A or a F2A.
120. A vector, comprising the polynucleotide of any of embodiments 116-119.
121. The vector of embodiment 120 that is an expression vector.
122. The vector of embodiment 120 or embodiment 121 that is a viral vector or a eukaryotic vector, optionally wherein the eukaryotic vector is a mammalian vector.
123. A cell comprising the polynucleotide or polynucleotides of any of embodiments 116-119 or the vector or vectors of any of embodiments 120-122.
124. The cell of embodiment 123, wherein the cell is a lymphocyte.
125. The cell of embodiment 123 or embodiment 124, wherein the cell is a T cell or a natural killer (NK) cells.
126. A method of producing a polypeptide, the method comprising introducing into a cell a polynucleotide or polynucleotides of any of embodiments 116-119 or a vector or vectors of any of embodiments 120-122 and culturing the cell under conditions to produce the multispecific polypeptide construct.
127. The method of embodiment 126, further comprising isolating or purifying the polypeptide from the cell.
128. A polypeptide produced by the method of embodiment 126 or embodiment 127.
129. A pharmaceutical composition comprising the CD28-binding polypeptide construct of any of embodiments 1-115.
130. The pharmaceutical composition of embodiment 129, comprising a pharmaceutically acceptable carrier.

131. The pharmaceutical composition of embodiment 129 or embodiment 130 that is sterile.
132. A method of stimulating an immune response in a subject, the method comprising administering, to a subject in need thereof, the CD28-binding polypeptide construct of any of embodiments 1-115 or the pharmaceutical composition of any of embodiments 129-131.
133. The method of embodiment 132, wherein the immune response is increased against a tumor or cancer.
134. The method of embodiment 132 or embodiment 133, wherein the method treats a disease or condition in the subject.
135. A method of treating a disease or condition in a subject, the method comprising administering, to a subject in need thereof, a therapeutically effective amount of the CD28-binding polypeptide construct of any of embodiments 1-115 or the pharmaceutical composition of any of embodiments 129-131.
136. The method of embodiment 134 or embodiment 135, wherein the disease or condition is a tumor or a cancer.
137. The method of any of embodiments 132-136, wherein said subject is a human.

Among the provided embodiments also are:

1. A CD28-binding polypeptide comprising at least one single domain antibody (sdAb) that binds CD28, wherein the at least one CD28 sdAb comprises a complementarity determining region 1 (CDR1) comprising an amino acid sequence selected from the group consisting of SEQ ID NOS:189, 192, 195, 198, 199, 200, and 201; a complementarity determining region 2 (CDR2) comprising an amino acid sequence selected from the group consisting of SEQ ID NOS:190, 193, 196, 202, 203, 204, 205, 206, 207, 208, 209, 210, 211, 212, 386, 387, 388, 389, 390, 391, 392, 393, 394, and 395; and a complementarity determining region 3 (CDR3) comprising an amino acid sequence selected from the group consisting of SEQ ID NOS: 191, 194, 197, 396, 397, and 398.
2. The CD28-binding polypeptide of embodiment 1, wherein the at least one CD28 sdAb comprises:

a CDR1 comprising the amino acid sequence set forth in SEQ ID NO:189, a CDR2 comprising the amino acid sequence set forth in SEQ ID NO:190, and a CDR3 comprising the amino acid sequence set forth in SEQ ID NO:191;

a CDR1 comprising the amino acid sequence set forth in SEQ ID NO:192, a CDR2 comprising the amino acid sequence set forth in SEQ ID NO:193, and a CDR3 comprising the amino acid sequence set forth in SEQ ID NO:194;

a CDR1 comprising the amino acid sequence set forth in SEQ ID NO:195, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:198, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:199, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:200, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:202, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:203, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:204, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:205, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:207, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:208, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:209, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:210, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:211, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:212, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:386, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:387, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:398;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:388, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:389, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:398;

a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:390, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:391, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:398;

a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:392, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:393, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:398;

a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:394, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:395, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:398;

a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:396;

a CDR1 comprising the amino acid sequence set forth in SEQ ID NO:195, a CDR2 comprising the amino acid sequence set forth in SEQ ID NO:388, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:389, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:397; or a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:398.

3. A CD28-binding polypeptide comprising at least one single domain antibody (sdAb) that binds CD28, wherein the at least one CD28 sdAb comprises a complementarity determining region 1 (CDR1) comprising an amino acid sequence selected from the group consisting of SEQ ID NOS:189, 192, 195, 198, 199, 200, and 201; a complementarity determining region 2 (CDR2) comprising an amino acid sequence selected from the group consisting of SEQ ID NOS:190, 193, 196, 202, 204, 205, 206, 207, 208, 209, 210, 211, 212, 386, 387, 388, 389, 390, 391, 392, 393, 394, and 395; and a complementarity determining region 3 (CDR3) comprising an amino acid sequence selected from the group consisting of SEQ ID NOS: 191, 194, and 197, 396, 397, and 398.

4. The CD28-binding polypeptide of embodiment 3, wherein the at least one CD28 sdAb comprises:

a CDR1 comprising the amino acid sequence set forth in SEQ ID NO:189, a CDR2 comprising the amino acid sequence set forth in SEQ ID NO:190, and a CDR3 comprising the amino acid sequence set forth in SEQ ID NO:191;

a CDR1 comprising the amino acid sequence set forth in SEQ ID NO:192, a CDR2 comprising the amino acid sequence set forth in SEQ ID NO:193, and a CDR3 comprising the amino acid sequence set forth in SEQ ID NO:194;

a CDR1 comprising the amino acid sequence set forth in SEQ ID NO:195, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:198, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:199, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:200, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:202, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:204, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:205, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:207, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:208, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:209, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:210, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:211, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:212, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:386, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:387, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:398;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:388, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:389, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:398;

a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:390, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:391, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:398;

a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:392, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:393, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:398;

a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:394, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:395, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:398;

a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:396;

a CDR1 comprising the amino acid sequence set forth in SEQ ID NO:195, a CDR2 comprising the amino acid sequence set forth in SEQ ID NO:388, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:389, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:397; or a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:398.

5. A CD28-binding polypeptide comprising at least one single domain antibody (sdAb) that binds CD28, wherein the at least one CD28 sdAb (CD28 VHH) domain comprises:

a CDR1, a CDR2, and a CDR3 as contained in the amino acid sequence set forth in SEQ ID NO:186; a CDR1, a CDR2, and a CDR3 as contained in the amino acid sequence set forth in SEQ ID NO:187; a CDR1, a CDR2, and a CDR3 as contained in the amino acid sequence set forth in SEQ ID NO:188; a CDR1, a CDR2, and a CDR3 as contained in the amino acid sequence set forth in SEQ ID NO:213; a CDR1, a CDR2, and a CDR3 as contained in the amino acid sequence set forth in SEQ ID NO:214; a CDR1, a CDR2, and a CDR3 as contained in the amino acid sequence set forth in SEQ ID NO:215; a CDR1, a CDR2, and a CDR3 as contained in the amino acid sequence set forth in SEQ ID NO:216; a CDR1, a CDR2, and a CDR3 as contained in the amino acid sequence set forth in SEQ ID NO:217; a CDR1, a CDR2, and a CDR3 as contained in the amino acid sequence set forth in SEQ ID NO:218; a CDR1, a CDR2, and a CDR3 as contained in the amino acid sequence set forth in SEQ ID NO:219; a CDR1, a CDR2, and a CDR3 as contained in the amino acid sequence set forth in SEQ ID NO:220; a CDR1, a CDR2, and a CDR3 as contained in the amino acid sequence set forth in SEQ ID NO:221; a CDR1, a CDR2, and a CDR3 as contained in the amino acid sequence set forth in SEQ ID NO:222; a CDR1, a CDR2, and a CDR3 as contained in the amino acid sequence set forth in SEQ ID NO:223; a CDR1, a CDR2, and a CDR3 as contained in the amino acid sequence set forth in SEQ ID NO:224; a CDR1, a CDR2, and a CDR3 as contained in the amino acid sequence set forth in SEQ ID NO:225; a CDR1, a CDR2, and a CDR3 as contained in the amino acid sequence set forth in SEQ ID NO:226; a CDR1, a CDR2, and a CDR3 as contained in the amino acid sequence set forth in SEQ ID NO:227; a CDR1, a CDR2, and a CDR3 as contained in the amino acid sequence set forth in SEQ ID NO:228; a CDR1, a CDR2, and a CDR3 as contained in the amino acid sequence set forth in SEQ ID NO:229; a CDR1, a CDR2, and a CDR3 as contained in the amino acid sequence set forth in SEQ ID NO:230; a CDR1, a CDR2, and a CDR3 as contained in the amino acid sequence set forth in SEQ ID NO:231; a CDR1, a CDR2, and a CDR3 as contained in the amino acid sequence set forth in SEQ ID NO:232; a CDR1, a CDR2, and a CDR3 as contained in the amino acid sequence set forth in SEQ ID NO:233; a CDR1, a CDR2, and a CDR3 as contained in the amino acid sequence set forth in SEQ ID NO:234; a CDR1, a CDR2, and a CDR3 as contained in the amino acid sequence set forth in SEQ ID NO:235; a CDR1, a CDR2, and a CDR3 as contained in the amino acid sequence set forth in SEQ ID NO:236; a CDR1, a CDR2, and a CDR3 as contained in the amino acid sequence set forth in SEQ ID NO:237; a CDR1, a CDR2, and a CDR3 as contained in the amino acid sequence set forth in SEQ ID NO:238; a CDR1, a CDR2, and a CDR3 as contained in the amino acid sequence set forth in SEQ ID NO:239; a CDR1, a CDR2, and a CDR3 as contained in the amino acid sequence set forth in SEQ ID NO:280; a CDR1, a CDR2, and a CDR3 as contained in the amino acid sequence set forth in SEQ ID NO:342; a CDR1, a CDR2, and a CDR3 as contained in the amino acid sequence set forth in SEQ ID NO:343; a CDR1, a CDR2, and a CDR3 as contained in the amino acid sequence set forth in SEQ ID NO:344; a CDR1, a CDR2, and a CDR3 as contained in the amino acid sequence set forth in SEQ ID NO:345; a CDR1, a CDR2, and a CDR3 as contained in the amino acid sequence set forth in SEQ ID NO:346; a CDR1, a CDR2, and a CDR3 as contained in the amino acid sequence set forth in SEQ ID NO:347; a CDR1, a CDR2, and a CDR3 as contained in the amino acid sequence set forth in SEQ ID NO:348; a CDR1, a CDR2, and a CDR3 as contained in the amino acid sequence set forth in SEQ ID NO:349; a CDR1, a CDR2, and a CDR3 as contained in the amino acid sequence set forth in SEQ ID NO:350; a CDR1, a CDR2, and a CDR3 as contained in the amino acid sequence set forth in SEQ ID NO:351; a CDR1, a CDR2, and a CDR3 as contained in the amino acid sequence set forth in SEQ ID NO:352; a CDR1, a CDR2, and a CDR3 as contained in the amino acid sequence set forth in SEQ ID NO:353; a CDR1, a CDR2, and a CDR3 as contained in the amino acid sequence set forth in SEQ ID NO:354; a CDR1, a CDR2, and a CDR3 as contained in the amino acid sequence set forth in SEQ ID NO:355; a CDR1, a CDR2, and a CDR3 as contained in the amino acid sequence set forth in SEQ ID NO:356; a CDR1, a CDR2, and a CDR3 as contained in the amino acid sequence set forth in SEQ ID NO:357; a CDR1, a CDR2, and a CDR3 as contained in the amino acid sequence set forth in SEQ ID NO:358; a CDR1, a CDR2, and a CDR3 as contained in the amino acid sequence set forth in SEQ ID NO:359; a CDR1, a CDR2, and a CDR3 as contained in the amino acid sequence set forth in SEQ ID NO:360; a CDR1, a CDR2, and a CDR3 as contained in the amino acid sequence set forth in SEQ ID NO:361; a CDR1, a CDR2, and a CDR3 as contained in the amino acid sequence set forth in SEQ ID NO:362; a CDR1, a CDR2, and a CDR3 as contained in the amino acid sequence set forth in SEQ ID NO:363; a CDR1, a CDR2, and a CDR3 as contained in the amino acid sequence set forth in SEQ ID NO:364; a CDR1, a CDR2, and a CDR3 as contained in the amino acid sequence set forth in SEQ ID NO:365; a CDR1, a CDR2, and a CDR3 as contained in the amino acid sequence set forth in SEQ ID NO:366; a CDR1, a CDR2, and a CDR3 as contained in the amino acid sequence set forth in SEQ ID NO:367; a CDR1, a CDR2, and a CDR3 as contained in the amino acid sequence set forth in SEQ ID NO:368; a CDR1, a CDR2, and a CDR3 as contained in the amino acid sequence set forth in SEQ ID NO:369; a CDR1, a CDR2, and a CDR3 as contained in the amino acid sequence set forth in SEQ ID NO:370; a CDR1, a CDR2, and a CDR3 as contained in the amino acid sequence set forth in SEQ ID NO:371; a CDR1, a CDR2, and a CDR3 as contained in the amino acid sequence set forth in SEQ ID NO:372; a CDR1, a CDR2, and a CDR3 as contained in the amino acid sequence set forth in SEQ ID NO:373; a CDR1, a CDR2, and a CDR3 as contained in the amino acid sequence set forth in SEQ ID NO:374; a CDR1, a CDR2, and a CDR3 as contained in the amino acid sequence set forth in SEQ ID NO:375; a CDR1, a CDR2, and a CDR3 as contained in the amino acid sequence set forth in SEQ ID NO:376; a CDR1, a CDR2, and a CDR3 as contained in the amino acid sequence set forth in SEQ ID NO:377; a CDR1, a CDR2, and a CDR3 as contained in the amino acid sequence set forth in SEQ ID NO:378; a CDR1, a CDR2, and a CDR3 as contained in the amino acid sequence set forth in SEQ ID NO:379; a CDR1, a CDR2, and a CDR3 as contained in the amino acid sequence set forth in SEQ ID NO:380; a CDR1, a CDR2, and a CDR3 as contained in the amino acid sequence set forth in SEQ ID NO:381; a CDR1, a CDR2, and a CDR3 as contained in the amino acid sequence set forth in SEQ ID NO:382; a CDR1, a CDR2, and a CDR3 as contained in the amino acid sequence set forth in SEQ ID NO:383; a CDR1, a CDR2, and a CDR3 as contained in the amino acid sequence set forth in SEQ ID NO:384; or a CDR1, a CDR2, and a CDR3 as contained in the amino acid sequence set forth in SEQ ID NO:385.

6. A CD28-binding polypeptide comprising at least one single domain antibody (sdAb) that binds CD28, wherein the at least one CD28 sdAb (CD28 VHH) domain comprises:

a CDR1, a CDR2, and a CDR3 as contained in the amino acid sequence set forth in SEQ ID NO:186; a CDR1, a CDR2, and a CDR3 as contained in the amino acid sequence set forth in SEQ ID NO:187; a CDR1, a CDR2, and a CDR3 as contained in the amino acid sequence set forth in SEQ ID NO:188; a CDR1, a CDR2, and a CDR3 as contained in the amino acid sequence set forth in SEQ ID NO:213; a CDR1, a CDR2, and a CDR3 as contained in the amino acid sequence set forth in SEQ ID NO:214; a CDR1, a CDR2, and a CDR3 as contained in the amino acid sequence set forth in SEQ ID NO:215; a CDR1, a CDR2, and a CDR3 as contained in the amino acid sequence set forth in SEQ ID NO:216; a CDR1, a CDR2, and a CDR3 as contained in the amino acid sequence set forth in SEQ ID NO:217; a CDR1, a CDR2, and a CDR3 as contained in the amino acid sequence set forth in SEQ ID NO:218; a CDR1, a CDR2, and a CDR3 as contained in the amino acid sequence set forth in SEQ ID NO:219; a CDR1, a CDR2, and a CDR3 as contained in the amino acid sequence set forth in SEQ ID NO:221; a CDR1, a CDR2, and a CDR3 as contained in the amino acid sequence set forth in SEQ ID NO:222; a CDR1, a CDR2, and a CDR3 as contained in the amino acid sequence set forth in SEQ ID NO:223; a CDR1, a CDR2, and a CDR3 as contained in the amino acid sequence set forth in SEQ ID NO:224; a CDR1, a CDR2, and a CDR3 as contained in the amino acid sequence set forth in SEQ ID NO:225; a CDR1, a CDR2, and a CDR3 as contained in the amino acid sequence set forth in SEQ ID NO:226; a CDR1, a CDR2, and a CDR3 as contained in the amino acid sequence set forth in SEQ ID NO:227; a CDR1, a CDR2, and a CDR3 as contained in the amino acid sequence set forth in SEQ ID NO:228; a CDR1, a CDR2, and a CDR3 as contained in the amino acid sequence set forth in SEQ ID NO:229; a CDR1, a CDR2, and a CDR3 as contained in the amino acid sequence set forth in SEQ ID NO:230; a CDR1, a CDR2, and a CDR3 as contained in the amino acid sequence set forth in SEQ ID NO:231; a CDR1, a CDR2, and a CDR3 as contained in the amino acid sequence set forth in SEQ ID NO:232; a CDR1, a CDR2, and a CDR3 as contained in the amino acid sequence set forth in SEQ ID NO:233; a CDR1, a CDR2, and a CDR3 as contained in the amino acid sequence set forth in SEQ ID NO:234; a CDR1, a CDR2, and a CDR3 as contained in the amino acid sequence set forth in SEQ ID NO:235; a CDR1, a CDR2, and a CDR3 as contained in the amino acid sequence set forth in SEQ ID NO:236; a CDR1, a CDR2, and a CDR3 as contained in the amino acid sequence set forth in SEQ ID NO:237; a CDR1, a CDR2, and a CDR3 as contained in the amino acid sequence set forth in SEQ ID NO:238; a CDR1, a CDR2, and a CDR3 as contained in the amino acid sequence set forth in SEQ ID NO:239; a CDR1, a CDR2, and a CDR3 as contained in the amino acid sequence set forth in SEQ ID NO:280; a CDR1, a CDR2, and a CDR3 as contained in the amino acid sequence set forth in SEQ ID NO:342; a CDR1, a CDR2, and a CDR3 as contained in the amino acid sequence set forth in SEQ ID NO:343; a CDR1, a CDR2, and a CDR3 as contained in the amino acid sequence set forth in SEQ ID NO:344; a CDR1, a CDR2, and a CDR3 as contained in the amino acid sequence set forth in SEQ ID NO:345; a CDR1, a CDR2, and a CDR3 as contained in the amino acid sequence set forth in SEQ ID NO:346; a CDR1, a CDR2, and a CDR3 as contained in the amino acid sequence set forth in SEQ ID NO:347; a CDR1, a CDR2, and a CDR3 as contained in the amino acid sequence set forth in SEQ ID NO:348; a CDR1, a CDR2, and a CDR3 as contained in the amino acid sequence set forth in SEQ ID NO:349; a CDR1, a CDR2, and a CDR3 as contained in the amino acid sequence set forth in SEQ ID NO:350; a CDR1, a CDR2, and a CDR3 as contained in the amino acid sequence set forth in SEQ ID NO:351; a CDR1, a CDR2, and a CDR3 as contained in the amino acid sequence set forth in SEQ ID NO:352; a CDR1, a CDR2, and a CDR3 as contained in the amino acid sequence set forth in SEQ ID NO:353; a CDR1, a CDR2, and a CDR3 as contained in the amino acid sequence set forth in SEQ ID NO:354; a CDR1, a CDR2, and a CDR3 as contained in the amino acid sequence set forth in SEQ ID NO:355; a CDR1, a CDR2, and a CDR3 as contained in the amino acid sequence set forth in SEQ ID NO:356; a CDR1, a CDR2, and a CDR3 as contained in the amino acid sequence set forth in SEQ ID NO:357; a CDR1, a CDR2, and a CDR3 as contained in the amino acid sequence set forth in SEQ ID NO:358; a CDR1, a CDR2, and a CDR3 as contained in the amino acid sequence set forth in SEQ ID NO:359; a CDR1, a CDR2, and a CDR3 as contained in the amino acid sequence set forth in SEQ ID NO:360; a CDR1, a CDR2, and a CDR3 as contained in the amino acid sequence set forth in SEQ ID NO:361; a CDR1, a CDR2, and a CDR3 as contained in the amino acid sequence set forth in SEQ ID NO:362; a CDR1, a CDR2, and a CDR3 as contained in the amino acid sequence set forth in SEQ ID NO:363; a CDR1, a CDR2, and a CDR3 as contained in the amino acid sequence set forth in SEQ ID NO:364; a CDR1, a CDR2, and a CDR3 as contained in the amino acid sequence set forth in SEQ ID NO:365; a CDR1, a CDR2, and a CDR3 as contained in the amino acid sequence set forth in SEQ ID NO:366; a CDR1, a CDR2, and a CDR3 as contained in the amino acid sequence set forth in SEQ ID NO:367; a CDR1, a CDR2, and a CDR3 as contained in the amino acid sequence set forth in SEQ ID NO:368; a CDR1, a CDR2, and a CDR3 as contained in the amino acid sequence set forth in SEQ ID NO:369; a CDR1, a CDR2, and a CDR3 as contained in the amino acid sequence set forth in SEQ ID NO:370; a CDR1, a CDR2, and a CDR3 as contained in the amino acid sequence set forth in SEQ ID NO:371; a CDR1, a CDR2, and a CDR3 as contained in the amino acid sequence set forth in SEQ ID NO:372; a CDR1, a CDR2, and a CDR3 as contained in the amino acid sequence set forth in SEQ ID NO:373; a CDR1, a CDR2, and a CDR3 as contained in the amino acid sequence set forth in SEQ ID NO:374; a CDR1, a CDR2, and a CDR3 as contained in the amino acid sequence set forth in SEQ ID NO:375; a CDR1, a CDR2, and a CDR3 as contained in the amino acid sequence set forth in SEQ ID NO:376; a CDR1, a CDR2, and a CDR3 as contained in the amino acid sequence set forth in SEQ ID NO:377; a CDR1, a CDR2, and a CDR3 as contained in the amino acid sequence set forth in SEQ ID NO:378; a CDR1, a CDR2, and a CDR3 as contained in the amino acid sequence set forth in SEQ ID NO:379; a CDR1, a CDR2, and a CDR3 as contained in the amino acid sequence set forth in SEQ ID NO:380; a CDR1, a CDR2, and a CDR3 as contained in the amino acid sequence set forth in SEQ ID NO:381; a CDR1, a CDR2, and a CDR3 as contained in the amino acid sequence set forth in SEQ ID NO:382; a CDR1, a CDR2, and a CDR3 as contained in the amino acid sequence set forth in SEQ ID NO:383; a CDR1, a CDR2, and a CDR3 as contained in the amino acid sequence set forth in SEQ ID NO:384; or a CDR1, a CDR2, and a CDR3 as contained in the amino acid sequence set forth in SEQ ID NO:385.

7. The CD28-binding polypeptide of any of embodiments 1-6, wherein the at least one CD28 sdAb comprises the amino acid sequence set forth in any of SEQ ID NOS:186, 187, 188, 213, 214, 215, 216, 217, 218, 219, 220, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS:186, 187, 188, 213, 214, 215, 216, 217, 218, 219, 220, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385.
8. The CD28-binding polypeptide of any of embodiments 1-6, wherein the at least one CD28 sdAb comprises the amino acid sequence set forth in any of SEQ ID NOS:186, 187, 188, 213, 214, 215, 216, 217, 218, 219, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS:186, 187, 188, 213, 214, 215, 216, 217, 218, 219, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385.
9. The CD28-binding polypeptide of any of embodiments 1-8, wherein the at least one CD28 sdAb comprises the amino acid sequence set forth in (i) SEQ ID NO: 186, (ii) a humanized variant of SEQ ID NO: 186, and/or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 186.

10. The CD28-binding polypeptide of any of embodiments 1-9, wherein the at least one CD28 sdAb comprises a CDR1 comprising the amino acid sequence set forth in SEQ ID NO: 189; a CDR2 comprising the amino acid sequence set forth in SEQ ID NO: 190; and a CDR3 comprising the amino acid sequence set forth in SEQ ID NO: 191.

11. The CD28-binding polypeptide of any of embodiments 1-8, wherein the at least one CD28 sdAb comprises the amino acid sequence set forth in (i) SEQ ID NO: 187, (ii) a humanized variant of SEQ ID NO: 187, and/or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 187.

12. The CD28-binding polypeptide of any of embodiments 1-8 and 11, wherein the at least one CD28 sdAb comprises a CDR1 comprising the amino acid sequence set forth in SEQ ID NO: 192; a CDR2 comprising the amino acid sequence set forth in SEQ ID NO: 193; and a CDR3 comprising the amino acid sequence set forth in SEQ ID NO: 194.

13. The CD28-binding polypeptide of any of embodiments 1-8, wherein the at least one CD28 sdAb comprises the amino acid sequence set forth in (i) SEQ ID NO: 188, (ii) a humanized variant of SEQ ID NO: 188, and/or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 188.

14. The CD28-binding polypeptide of any of embodiments 1-8 and 13, wherein the at least one CD28 sdAb comprises a CDR1 comprising the amino acid sequence set forth in any of SEQ ID NOS:195, 198, 199, 200, and 201; a CDR2 comprising the amino acid sequence set forth in any of SEQ ID NOS:196, 202, 203, 204, 205, 206, 207, 208, 209, 210, 211, 212, 386, 387, 388, 389, 390, 391, 392, 393, 394, and 395; and a CDR3 comprising the amino acid sequence set forth in any of SEQ ID NOS:197, 396, 397, and 398.

15. The CD28-binding polypeptide of any of embodiments 1-8, 13 and 14, wherein the at least one CD28 sdAb comprises a CDR1, CDR2 and CDR3 set forth in: SEQ ID NOS: 195, 196, and 197, respectively; SEQ ID NOS: 198, 196, and 197, respectively; SEQ ID NOS: 199, 196, and 197, respectively; SEQ ID NOS: 200, 196, and 197, respectively; SEQ ID NOS: 201, 196, and 197, respectively; SEQ ID NOS: 195, 202, and 197, respectively; SEQ ID NOS: 195, 203, and 197, respectively; SEQ ID NOS: 195, 204, and 197, respectively; SEQ ID NOS: 195, 205, and 197, respectively; SEQ ID NOS: 195, 206, and 197, respectively; SEQ ID NOS: 195, 207, and 197, respectively; SEQ ID NOS: 195, 208, and 197, respectively; SEQ ID NOS: 195, 209, and 197, respectively; SEQ ID NOS: 195, 210, and 197, respectively; SEQ ID NOS: 195, 211, and 197, respectively; SEQ ID NOS: 195, 212, and 197, respectively; SEQ ID NOS: 201, 202, and 197, respectively; SEQ ID NOS: 201, 202, and 396, respectively; SEQ ID NOS: 201, 386, and 197, respectively; SEQ ID NOS: 201, 387, and 197, respectively; SEQ ID NOS: 201, 202, and 397, respectively; SEQ ID NOS: 201, 202, and 398, respectively; SEQ ID NOS: 201, 206, and 197, respectively; SEQ ID NOS: 201, 206, and 398, respectively; SEQ ID NOS: 201, 388, and 197, respectively; SEQ ID NOS: 201, 389, and 197, respectively; SEQ ID NOS: 201, 206, and 397, respectively; SEQ ID NOS: 201, 206, and 398, respectively; SEQ ID NOS: 201, 203, and 197, respectively; SEQ ID NOS: 201, 203, and 396, respectively; SEQ ID NOS: 201, 390, and 197, respectively; SEQ ID NOS: 201, 391, and 197, respectively; SEQ ID NOS: 201, 203, and 397, respectively; SEQ ID NOS: 201, 203, and 398, respectively; SEQ ID NOS: 201, 204, and 197, respectively; SEQ ID NOS: 201, 204, and 396, respectively; SEQ ID NOS: 201, 392, and 197, respectively; SEQ ID NOS: 201, 393, and 197, respectively; SEQ ID NOS: 201, 204, and 397, respectively; SEQ ID NOS: 201, 204, and 398, respectively; SEQ ID NOS: 201, 196, and 396, respectively; SEQ ID NOS: 201, 394, and 197, respectively; SEQ ID NOS: 201, 395, and 197, respectively; SEQ ID NOS: 201, 196, and 397, respectively; SEQ ID NOS: 201, 196, and 398, respectively; SEQ ID NOS: 195, 206, and 396, respectively; SEQ ID NOS: 195, 388, and 197, respectively; SEQ ID NOS: 195, 389, and 197, respectively; SEQ ID NOS: 195, 206, and 397, respectively; or SEQ ID NOS: 195, 206, and 398, respectively.

16. The CD28-binding polypeptide of any of embodiments 1-8 and 13, wherein the at least one CD28 sdAb comprises a CDR1 comprising the amino acid sequence set forth in any of SEQ ID NOS:195, 198, 199, 200, and 201; a CDR2 comprising the amino acid sequence set forth in any of SEQ ID NOS:196, 202, 204, 205, 206, 207, 208, 209, 210, 211, 212, 386, 387, 388, 389, 390, 391, 392, 393, 394, and 395; and a CDR3 comprising the amino acid sequence set forth in any of SEQ ID NOS:197, 396, 397, and 398.

17. The CD28-binding polypeptide of any of embodiments 1-8, 13 and 16, wherein the at least one CD28 sdAb comprises a CDR1, CDR2 and CDR3 set forth in SEQ ID NOS: 195, 196, and 197, respectively; SEQ ID NOS: 198, 196, and 197, respectively; SEQ ID NOS: 199, 196, and 197, respectively; SEQ ID NOS: 200, 196, and 197, respectively; SEQ ID NOS: 201, 196, and 197, respectively; SEQ ID NOS: 195, 202, and 197, respectively; SEQ ID NOS: 195, 204, and 197, respectively; SEQ ID NOS: 195, 205, and 197, respectively; SEQ ID NOS: 195, 206, and 197, respectively; SEQ ID NOS: 195, 207, and 197, respectively; SEQ ID NOS: 195, 208, and 197, respectively; SEQ ID NOS: 195, 209, and 197, respectively; SEQ ID NOS: 195, 210, and 197, respectively; SEQ ID NOS: 195, 211, and 197, respectively; SEQ ID NOS: 195, 212, and 197, respectively; SEQ ID NOS: 201, 202, and 197, respectively; SEQ ID NOS: 201, 202, and 396, respectively; SEQ ID NOS: 201, 386, and 197, respectively; SEQ ID NOS: 201, 387, and 197, respectively; SEQ ID NOS: 201, 202, and 397, respectively; SEQ ID NOS: 201, 202, and 398, respectively; SEQ ID NOS: 201, 206, and 197, respectively; SEQ ID NOS: 201, 206, and 398, respectively; SEQ ID NOS: 201, 388, and 197, respectively; SEQ ID NOS: 201, 389, and 197, respectively; SEQ ID NOS: 201, 206, and 397, respectively; SEQ ID NOS: 201, 206, and 398, respectively; SEQ ID NOS: 201, 203, and 197, respectively; SEQ ID NOS: 201, 203, and 396, respectively; SEQ ID NOS: 201, 390, and 197, respectively; SEQ ID NOS: 201, 391, and 197, respectively; SEQ ID NOS: 201, 203, and 397, respectively; SEQ ID NOS: 201, 203, and 398, respectively; SEQ ID NOS: 201, 204, and 197, respectively; SEQ ID NOS: 201, 204, and 396, respectively; SEQ ID NOS: 201, 392, and 197, respectively; SEQ ID NOS: 201, 393, and 197, respectively; SEQ ID NOS: 201, 204, and 397, respectively; SEQ ID NOS: 201, 204, and 398, respectively; SEQ ID NOS: 201, 196, and 396, respectively; SEQ ID NOS: 201, 394, and 197, respectively; SEQ ID NOS: 201, 395, and 197, respectively; SEQ ID NOS: 201, 196, and 397, respectively; SEQ ID NOS: 201, 196, and 398, respectively; SEQ ID NOS: 195, 206, and 396, respectively; SEQ ID NOS: 195, 388, and 197, respectively; SEQ ID NOS: 195, 389, and 197, respectively; SEQ ID NOS: 195, 206, and 397, respectively; or SEQ ID NOS: 195, 206, and 398, respectively.

18. The CD28-binding polypeptide of any of embodiments 1-8 and 13-15, wherein the at least one CD28 sdAb comprises the amino acid sequence set forth in any of SEQ ID NOS:213-239, 280, and 342-385, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS:213-239, 280, and 342-385.
19. The CD28-binding polypeptide of any of embodiments 1-8, 13-15, and 18, wherein the at least one CD28 sdAb comprises the amino acid sequence set forth in any of SEQ ID NOS:213-239, 280, and 342-385.
20. The CD28-binding polypeptide of any of embodiments 1-8, 13, 16, and 17, wherein the at least one CD28 sdAb comprises the amino acid sequence set forth in any of SEQ ID NOS:213-219, 221-239, 280, and 342-385, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS:213-219, 221-239, 280, and 342-385.
21. The CD28-binding polypeptide of any of embodiments 1-7, 13, 16, 17, and 20, wherein the at least one CD28 sdAb comprises the amino acid sequence set forth in any of SEQ ID NOS:213-219, 221-239, 280, and 342-385.
22. The CD28-binding polypeptide of any of embodiments 1-21, wherein the at least one CD28 sdAb is one CD28 sdAb and/or the CD28-binding polypeptide is monovalent for CD28.
23. The CD28-binding polypeptide of any of embodiments 1-21, wherein the at least one CD28 sdAb is two, three, or four CD28 sdAbs and/or the CD28-binding polypeptide is multivalent for CD28.
24. The CD28-binding polypeptide of any of embodiments 1-21 and 23, wherein the at least one CD28 sdAb is two CD28 sdAbs and/or the CD28-binding polypeptide is bivalent for CD28.
25. The CD28-binding polypeptide of embodiment 24, wherein the two CD28 sdAbs are the same CD28 sdAb.
26. The CD28-binding polypeptide of embodiment 24 or embodiment 25, wherein each of the two CD28 sdAbs comprise the amino acid sequence set forth in SEQ ID NO:188.
27. The CD28-binding polypeptide of embodiment 24 or embodiment 25, wherein each of the two CD28 sdAbs comprise the amino acid sequence set forth in SEQ ID NO:220.
28. The CD28-binding polypeptide of embodiment 24 or embodiment 25, wherein each of the two CD28 sdAbs comprise the amino acid sequence set forth in SEQ ID NO:280.
29. The CD28-binding polypeptide of embodiment 24, wherein the two CD28 sdAbs are different CD28 sdAbs.
30. The CD28-binding polypeptide of embodiment 24 or embodiment 29, wherein one of the two CD28 sdAbs comprises the amino acid sequence set forth in SEQ ID NO:188 and the other of the two CD28 sdAbs comprises the amino acid sequence set forth in SEQ ID NOS:220.
31. The CD28-binding polypeptide of embodiment 24 or embodiment 29, wherein one of the two CD28 sdAbs comprises the amino acid sequence set forth in SEQ ID NO:188 and the other of the two CD28 sdAbs comprises the amino acid sequence set forth in SEQ ID NOS:280.
32. The CD28-binding polypeptide of embodiment 24 or embodiment 29, wherein one of the two CD28 sdAbs comprises the amino acid sequence set forth in SEQ ID NO:220 and the other of the two CD28 sdAbs comprises the amino acid sequence set forth in SEQ ID NOS:280.
33. The CD28-binding polypeptide of any of embodiments 1-32, wherein the CD28-binding polypeptide comprises a moiety that binds protein A.
34. The CD28-binding polypeptide of any of embodiments 1-33, wherein the at least one CD28 sdAb comprises an amino acid modification that reduces binding to protein A.
35. The CD28-binding polypeptide of embodiment 34, wherein the amino acid modification is G65D by Kabat in framework region 3 (FR3).
36. An anti-CD28 sdAb-Fc fusion protein, comprising a CD28-binding polypeptide of any of embodiments 1-35 and an immunoglobulin Fc region.
37. The anti-CD28 sdAb-Fc fusion protein of embodiment 36, wherein the Fc region is linked by a linking peptide (LP) to at least one of the at least one CD28 sdAb.
38. The anti-CD28 sdAb-Fc fusion protein of embodiment 36 or embodiment 37, wherein the at least one CD28 sdAb is linked by a linking peptide (LP) to the Fc region at the N-terminal of the Fc region.
39. The anti-CD28 sdAb-Fc fusion protein of embodiment 37 or embodiment 38, wherein the LP is a non-cleavable linker.
40. The anti-CD28 sdAb-Fc fusion protein of any of embodiments 37-39, wherein the LP is a peptide of about 1 to 20 amino acids in length.
41. The anti-CD28 sdAb-Fc fusion protein of any of embodiments 38-40, wherein the CD28-binding polypeptide comprises from N-terminal to C-terminal: (CD28 sdAb)-LP-Fc.
42. The anti-CD28 sdAb-Fc fusion protein of any of embodiments 37-40, wherein the CD28-binding polypeptide comprises from N-terminal to C-terminal: (CD28 sdAb)-LP-(CD28 sdAb)-LP-Fc.
43. The anti-CD28 sdAb-Fc fusion protein of any of embodiments 1-42 that is a dimer.
44. The anti-CD28 sdAb-Fc fusion protein of any of embodiments 36-43, wherein the Fc region is a homodimeric Fc region.
45. The anti-CD28 sdAb-Fc fusion protein of any of embodiments 36-44, wherein the Fc region comprises an amino acid sequence selected from the group consisting of SEQ ID NOS: 8, 10, 11, 12 and 13, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 8, 10, 11, 12 and 13.

46. The anti-CD28 sdAb-Fc fusion protein of any of embodiments 36-45, wherein the Fc region is a human IgG 1.

47. The anti-CD28 sdAb-Fc fusion protein of any of embodiments 36-46, wherein the Fc region is a human IgG1, optionally wherein the Fc region comprises the amino acid sequence set forth in SEQ ID NO: 8 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 8.

48. The anti-CD28 sdAb-Fc fusion protein of any of embodiments 36-43, wherein the Fc region is a heterodimeric Fc region.

49. The anti-CD28 sdAb-Fc fusion protein of any of embodiments 36-48, wherein the Fc region exhibits effector function.

50. The anti-CD28 sdAb-Fc fusion protein of any of embodiments 36-48, wherein the Fc region comprises a polypeptide comprising one or more amino acid modification that reduces effector function and/or reduces binding to an effector molecule selected from an Fc gamma receptor and C1q.

51. The anti-CD28 sdAb-Fc fusion protein of embodiment 50, wherein the one or more amino acid modification is deletion of one or more of Glu233, Leu234 or Leu235.

52. The anti-CD28 sdAb-Fc fusion protein of embodiment 50 or embodiment 51, wherein the one or more amino acid modification is deletion of one or more of Glu233, Leu234 or Leu235, optionally wherein the Fc region comprises the amino acid sequence set forth in SEQ ID NO: 9 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 9.

53. A homodimeric Fc fusion protein, comprising two identical copies of the anti-CD28 sdAb-Fc fusion protein of any of embodiments 33-49.

54. A heterodimeric fusion protein, comprising two of the anti-CD28 sdAb-Fc fusion proteins of any of embodiments 33-49.

55. A multi-specific binding polypeptide comprising the anti-CD28 sdAb-Fc fusion protein of any of embodiments 36-52 and one or more binding domain (BD) that binds to a target antigen other than CD28.

56. The multi-specific-binding polypeptide of embodiment 55, wherein the one or more BD binds a tumor associated antigen (TAA).

57. The multi-specific binding polypeptide of embodiment 55, wherein the one or more BD binds a T cell surface marker that is a T cell activation marker or a T cell exhaustion marker.

58. The multi-specific binding polypeptide of embodiment 55, wherein the one or more BD binds a cell surface marker that is a tumor microenvironment marker.

59. The multi-specific binding polypeptide of any of embodiments 55-58, wherein the one or more BD, optionally each of the one or more BD, in a single domain antibody (sdAb).

60. The multi-specific binding polypeptide of any of embodiments 55-59, wherein the multi-specific binding polypeptide is an Fc fusion protein, wherein at least one of the one or more BD and/or the at least one CD28 sdAb is linked to the immunoglobulin Fc region.

61. The multi-specific binding polypeptide of embodiment 60, wherein the Fc fusion protein comprises from N-terminus to C-terminus:

the one or more BD;

the at least one CD28-binding domain comprising a sdAb that binds CD28; and the Fc region.

62. The multi-specific binding polypeptide of any of embodiments 55-61, wherein at least one of the one or more BD is joined by a linking peptide (LP) to at least one of the at least one CD28 sdAb.

63. The multi-specific binding polypeptide of any of embodiments 55-62, comprising from N-terminus to C-terminus: (BD)-LP-(CD28 sdAb)-LP-Fc.

64. The CD28-binding polypeptide of any of embodiments 55-63 that is a dimer.

65. The multi-specific binding polypeptide of any of embodiments 55-64, wherein the Fc region is a homodimeric Fc region.

66 The multi-specific binding polypeptide of any of embodiments 55-65, wherein the Fc region comprises an amino acid sequence selected from the group consisting of SEQ ID NOS: 8, 10, 11, 12 and 13, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 8, 10, 11, 12 and 13.

67. The multi-specific binding polypeptide of any of embodiments 55-66, wherein the Fc region is a human IgG 1.

68. The multi-specific binding polypeptide of any of embodiments 55-67, wherein the Fc region is a human IgG1, optionally wherein the Fc region comprises the amino acid sequence set forth in SEQ ID NO: 8 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 8.

69. The multi-specific binding polypeptide of any of embodiments 55-64 and 66-68, wherein the Fc region is a heterodimeric Fc region.

70. The multi-specific binding polypeptide of any of embodiments 55-69, wherein the Fc region exhibits effector function.

71. The multi-specific binding polypeptide of any of embodiments 55-69, wherein the Fc region comprises a polypeptide comprising one or more amino acid modification that reduces effector function and/or reduces binding to an effector molecule selected from an Fc gamma receptor and C1q.

72. The multi-specific binding polypeptide of embodiment 71, wherein the one or more amino acid modification is deletion of one or more of Glu233, Leu234 or Leu235.

73. The multi-specific binding polypeptide of embodiment 71 or embodiment 72, wherein the one or more amino acid modification is deletion of one or more of Glu233, Leu234 or Leu235, optionally wherein the Fc region comprises the amino acid sequence set forth in SEQ ID NO: 9 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 9.

74. The multi-specific binding polypeptide of any of embodiments 55-73, wherein the antigen to which the BD binds is selected from the group consisting of: 1-92-LFA-3, 2B4, 5T4, Alpha-4 integrin, Alpha-V integrin, alpha4beta1 integrin, alpha4beta7 integrin, alpha-SMA, AGR2, Anti-Lewis-Y, Apelin J receptor, APRIL, B7-H3, B7-H4, BAFF, BTLA, C5 complement, C-242, CA9, CA19-9, (Lewis a), Carbonic anhydrase 9, CD2, CD3, CD6, CD9, CD11a, CD19, CD20, CD22, CD24, CD25, CD27, CD28, CD30, CD33, CD38, CD40, CD40L, CD41, CD44, CD44v6, CD47, CD51, CD52, CD56, CD64, CD69, CD70, CD71, CD74, CD80, CD81, CD86, CD95, CD107a, CD117, CD123, CD125, CD132, (IL-2RG), CD133, CD137, CD138, CD160, CD166, CD172A, CD248, CDH6, CEACAM5 (CEA), CEACAM6 (NCA-90), CLAUDIN-3, CLAUDIN-4, cMet, Collagen, Cripto, CSFR, CSFR-1, CTLA-4, CTGF, CXCL10, CXCL13, CXCR1, CXCR2, CXCR4, CYR61, DL44, DLK1, DLL3, DLL4, DPP-4, DSG1, EDA, EDB, EGFR, EGFRviii, Endothelin B receptor (ETBR), ENPP3, EpCAM, EPHA2, EPHB2, ERBB3, F protein of RSV, FAP, FGF-2, FGF8, FGFR1, FGFR2, FGFR3, FGFR4, FLT-3, Folate receptor alpha (FRalpha), FSP-1, GAL3ST1, G-CSF, G-CSFR, GD2, GITR, GLUT1, GLUT4, GM-CSF, GM-CSFR, GP IIb/IIIa receptors, Gp130, GPIIB/IIIA, GPNMB, GRP78, HER2/neu, HER3, HER4, HGF, hGH, HLA-DR, HVEM, Hyaluronidase, ICOS, IFNalpha, IFNbeta, IFNgamma, IgE, IgE Receptor (FceRI), IGF, IGF1R, IL1B, IL1R, IL2, IL11, IL12, IL12p40, IL-12R, IL-12Rbeta1, IL13, IL13R, IL13Ra2, IL15, IL17, IL18, IL21, IL23, IL23R, IL27/IL27R (wsx1), IL29, IL-31R, IL31/IL31R, IL2R, IL4, IL4R, IL6, IL6R, IL1 receptor accessory protein (IL1RAP), Insulin Receptor, Jagged Ligands, Jagged 1, Jagged 2, KISS1-R, KLRG1, LAG-3, LIF-R, Lewis X, LIGHT, LRP4, LRRC26, Ly6G6D, LyPD1, MCSP, Mesothelin, MRP4, MUC1, Mucin-16 (MUC16, CA-125), Na/K ATPase, NGF, Nicastrin, Notch Receptors, Notch 1, Notch 2, Notch 3, Notch 4, NOV, OSM-R, OX-40, PAR2, PDGF-AA, PDGF-BB, PDGFRalpha, PDGFRbeta, PD-1, PD-L1, PD-L2, Phosphatidyl-serine, P1GF, PSCA, PSMA, PSGR, RAAG12, RAGE, SLC44A4, Siglec15, Sphingosine 1 Phosphate, STEAP1, STEAP2, TAG-72, TAPA1, TEM-8, TGF-beta, TIGIT, TIM-3, TLR2, TLR4, TLR6, TLR7, TLR8, TLR9, TMEM31, TNFalpha, TNFR, TNFRS12A, TRAIL-R1, TRAIL-R2, Transferrin, Transferrin receptor, TRK-A, TRK-B, uPAR, VAP1, VCAM-1, VEGF, VEGF-A, VEGF-B, VEGF-C, VEGF-D, VEGFR1, VEGFR2, VEGFR3, VISTA, WISP-1, WISP-2, and WISP-3.

75. The multi-specific binding polypeptide of any of embodiments 55-74, wherein the one or more BD is one BD and/or the multi-specific binding polypeptide is monovalent for the antigen.

76. The multi-specific binding polypeptide of any of embodiments 55-74, wherein the one or more BD is two, three, or four BDs and/or the multi-specific binding polypeptide is multivalent for one or more antigen.

77. The multi-specific binding polypeptide of any of embodiments 55-74 and 76, wherein the one or more BD is two BDs and/or the multi-specific binding polypeptide is bivalent for one or more antigen.

78. The multi-specific binding polypeptide of embodiment 77, wherein the two BDs are single domain antibodies (sdAbs), and the two sdAbs are the same sdAbs.

79. The multi-specific binding polypeptide of embodiment 77, wherein the two BDs are single domain antibodies (sdAbs), and the two sdAbs are different sdAbs that bind the same antigen, optionally that bind different epitopes of the same antigen.

80. The multi-specific binding polypeptide of embodiment 77, wherein the two BDs are single domain antibodies (sdAbs) and the two sdAbs are different sdAbs that bind different antigen.

81. A homodimeric multi-specific Fc fusion protein, comprising two identical copies of the multi-specific binding polypeptide of any of embodiments 55-80.

82. A heterodimeric multi-specific Fc fusion protein, comprising two of the multi-specific binding polypeptides of any of embodiments 55-80.

83. The multi-specific Fc fusion protein of embodiment 81 or embodiment 82, comprising a linking peptide (LP) between at least one of the at least one CD28 sdAb and the Fc region.

84. The multi-specific Fc fusion protein of any of embodiments 81-83, wherein the CD28-binding polypeptide comprises a linking peptide (LP) between at least one of the one or more BD and the Fc region.

85. The multi-specific Fc fusion protein of embodiment 83 or embodiment 84, wherein the LP is a non-cleavable linker.

86. The multi-specific Fc fusion protein of any of embodiments 83-85, wherein the LP is a peptide of about 1 to 20 amino acids in length. 87. The multi-specific Fc fusion protein of any of embodiments 83-86, wherein the LP is or comprises the amino acid sequence set forth in any of SEQ ID NOS: 1-7, 89, 90, 123-129, 244, and 249.

88. The multi-specific binding polypeptide of any of embodiments 55-80 or the multi-specific Fc fusion protein of any of embodiments 81-87, wherein the at least one CD28 sdAb is not able to, or is not substantially able to, bind or engage CD28 unless at least one of the one or more BD is bound to its antigen.

89. The multi-specific binding polypeptide of any of embodiments 55-80 or the multi-specific Fc fusion protein of any of embodiments 81-87, wherein the at least one CD28 sdAb not able to, or is not substantially able to, bind or engage CD28 unless each of the one or more BD is bound to its antigen.

90. An anti-CD28 single domain antibody (sdAb) comprising: a complementarity determining region 1 (CDR1) comprising an amino acid sequence selected from the group consisting of SEQ ID NOS:189, 192, 195, 198, 199, 200, and 201; a complementarity determining region 2 (CDR2) comprising an amino acid sequence selected from the group consisting of SEQ ID NOS:190, 193, 196, 202, 203, 204, 205, 206, 207, 208, 209, 210, 211, 212, 386, 387, 388, 389, 390, 391, 392, 393, 394, and 395; and a complementarity determining region 3 (CDR3) comprising an amino acid sequence selected from the group consisting of SEQ ID NOS: 191, 194, 197, 396, 397, and 398.

91. The anti-CD28 sdAb of embodiment 90, comprising:

a CDR1 comprising the amino acid sequence set forth in SEQ ID NO:189, a CDR2 comprising the amino acid sequence set forth in SEQ ID NO:190, and a CDR3 comprising the amino acid sequence set forth in SEQ ID NO:191;

a CDR1 comprising the amino acid sequence set forth in SEQ ID NO:192, a CDR2 comprising the amino acid sequence set forth in SEQ ID NO:193, and a CDR3 comprising the amino acid sequence set forth in SEQ ID NO:194;

a CDR1 comprising the amino acid sequence set forth in SEQ ID NO:195, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:198, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:199, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:200, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:202, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:203, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:204, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:205, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:207, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:208, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:209, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:210, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:211, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:212, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:386, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:387, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:398;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:388, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:389, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:398;

a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:390, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:391, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:398;

a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:392, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:393, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:398;

a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:394, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:395, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:398;

a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:396;

a CDR1 comprising the amino acid sequence set forth in SEQ ID NO:195, a CDR2 comprising the amino acid sequence set forth in SEQ ID NO:388, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:389, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:397; or a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:398.

92. An anti-CD28 single domain antibody (sdAb) comprising: a complementarity determining region 1 (CDR1) comprising an amino acid sequence selected from the group consisting of SEQ ID NOS:189, 192, 195, 198, 199, 200, and 201; a complementarity determining region 2 (CDR2) comprising an amino acid sequence selected from the group consisting of SEQ ID NOS:190, 193, 196, 202, 204, 205, 206, 207, 208, 209, 210, 211, 212, 386, 387, 388, 389, 390, 391, 392, 393, 394, and 395; and a complementarity determining region 3 (CDR3) comprising an amino acid sequence selected from the group consisting of SEQ ID NOS: 191, 194, 197, 396, 397, and 398.

93. The anti-CD28 sdAb of embodiment 92, wherein the anti-CD28 sdAb comprises:

a CDR1 comprising the amino acid sequence set forth in SEQ ID NO:189, a CDR2 comprising the amino acid sequence set forth in SEQ ID NO:190, and a CDR3 comprising the amino acid sequence set forth in SEQ ID NO:191;

a CDR1 comprising the amino acid sequence set forth in SEQ ID NO:192, a CDR2 comprising the amino acid sequence set forth in SEQ ID NO:193, and a CDR3 comprising the amino acid sequence set forth in SEQ ID NO:194;

a CDR1 comprising the amino acid sequence set forth in SEQ ID NO:195, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:198, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:199, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:200, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:202, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:204, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:205, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:207, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:208, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:209, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:210, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:211, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:212, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:386, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:387, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:398;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:388, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:389, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO:398;

a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:390, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:391, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:203, and a CDR3 comprising the amino acid sequence set forth in SEQ ID NO:398;

a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:392, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:393, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO:398;

a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:396;

a CDR1 comprising the amino acid sequence set forth in SEQ ID NO:201, a CDR2 comprising the amino acid sequence set forth in SEQ ID NO:394, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:395, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:397;

a CDR1 comprising the amino acid sequence set forth in SEQ ID NO:201, a CDR2 comprising the amino acid sequence set forth in SEQ ID NO:196, and a CDR3 comprising the amino acid sequence set forth in SEQ ID NO:398;

a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:396;

a CDR1 comprising the amino acid sequence set forth in SEQ ID NO:195, a CDR2 comprising the amino acid sequence set forth in SEQ ID NO:388, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:389, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:397; or a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO:398.

94. An anti-CD28 single domain antibody (sdAb) comprising:

a CDR1, a CDR2, and a CDR3 as contained in the amino acid sequence set forth in SEQ ID NO:186; a CDR1, a CDR2, and a CDR3 as contained in the amino acid sequence set forth in SEQ ID NO:187; a CDR1, a CDR2, and a CDR3 as contained in the amino acid sequence set forth in SEQ ID NO:188; a CDR1, a CDR2, and a CDR3 as contained in the amino acid sequence set forth in SEQ ID NO:213; a CDR1, a CDR2, and a CDR3 as contained in the amino acid sequence set forth in SEQ ID NO:214; a CDR1, a CDR2, and a CDR3 as contained in the amino acid sequence set forth in SEQ ID NO:215; a CDR1, a CDR2, and a CDR3 as contained in the amino acid sequence set forth in SEQ ID NO:216; a CDR1, a CDR2, and a CDR3 as contained in the amino acid sequence set forth in SEQ ID NO:217; a CDR1, a CDR2, and a CDR3 as contained in the amino acid sequence set forth in SEQ ID NO:218; a CDR1, a CDR2, and a CDR3 as contained in the amino acid sequence set forth in SEQ ID NO:219; a CDR1, a CDR2, and a CDR3 as contained in the amino acid sequence set forth in SEQ ID NO:220; a CDR1, a CDR2, and a CDR3 as contained in the amino acid sequence set forth in SEQ ID NO:221; a CDR1, a CDR2, and a CDR3 as contained in the amino acid sequence set forth in SEQ ID NO:222; a CDR1, a CDR2, and a CDR3 as contained in the amino acid sequence set forth in SEQ ID NO:223; a CDR1, a CDR2, and a CDR3 as contained in the amino acid sequence set forth in SEQ ID NO:224; a CDR1, a CDR2, and a CDR3 as contained in the amino acid sequence set forth in SEQ ID NO:225; a CDR1, a CDR2, and a CDR3 as contained in the amino acid sequence set forth in SEQ ID NO:226; a CDR1, a CDR2, and a CDR3 as contained in the amino acid sequence set forth in SEQ ID NO:227; a CDR1, a CDR2, and a CDR3 as contained in the amino acid sequence set forth in SEQ ID NO:228; a CDR1, a CDR2, and a CDR3 as contained in the amino acid sequence set forth in SEQ ID NO:229; a CDR1, a CDR2, and a CDR3 as contained in the amino acid sequence set forth in SEQ ID NO:230; a CDR1, a CDR2, and a CDR3 as contained in the amino acid sequence set forth in SEQ ID NO:231; a CDR1, a CDR2, and a CDR3 as contained in the amino acid sequence set forth in SEQ ID NO:232; a CDR1, a CDR2, and a CDR3 as contained in the amino acid sequence set forth in SEQ ID NO:233; a CDR1, a CDR2, and a CDR3 as contained in the amino acid sequence set forth in SEQ ID NO:234; a CDR1, a CDR2, and a CDR3 as contained in the amino acid sequence set forth in SEQ ID NO:235; a CDR1, a CDR2, and a CDR3 as contained in the amino acid sequence set forth in SEQ ID NO:236; a CDR1, a CDR2, and a CDR3 as contained in the amino acid sequence set forth in SEQ ID NO:237; a CDR1, a CDR2, and a CDR3 as contained in the amino acid sequence set forth in SEQ ID NO:238; a CDR1, a CDR2, and a CDR3 as contained in the amino acid sequence set forth in SEQ ID NO:239; a CDR1, a CDR2, and a CDR3 as contained in the amino acid sequence set forth in SEQ ID NO:280; a CDR1, a CDR2, and a CDR3 as contained in the amino acid sequence set forth in SEQ ID NO:342; a CDR1, a CDR2, and a CDR3 as contained in the amino acid sequence set forth in SEQ ID NO:343; a CDR1, a CDR2, and a CDR3 as contained in the amino acid sequence set forth in SEQ ID NO:344; a CDR1, a CDR2, and a CDR3 as contained in the amino acid sequence set forth in SEQ ID NO:345; a CDR1, a CDR2, and a CDR3 as contained in the amino acid sequence set forth in SEQ ID NO:346; a CDR1, a CDR2, and a CDR3 as contained in the amino acid sequence set forth in SEQ ID NO:347;

a CDR1, a CDR2, and a CDR3 as contained in the amino acid sequence set forth in SEQ ID NO:348; a CDR1, a CDR2, and a CDR3 as contained in the amino acid sequence set forth in SEQ ID NO:349; a CDR1, a CDR2, and a CDR3 as contained in the amino acid sequence set forth in SEQ ID NO:350; a CDR1, a CDR2, and a CDR3 as contained in the amino acid sequence set forth in SEQ ID NO:351; a CDR1, a CDR2, and a CDR3 as contained in the amino acid sequence set forth in SEQ ID NO:352; a CDR1, a CDR2, and a CDR3 as contained in the amino acid sequence set forth in SEQ ID NO:353; a CDR1, a CDR2, and a CDR3 as contained in the amino acid sequence set forth in SEQ ID NO:354; a CDR1, a CDR2, and a CDR3 as contained in the amino acid sequence set forth in SEQ ID NO:355; a CDR1, a CDR2, and a CDR3 as contained in the amino acid sequence set forth in SEQ ID NO:356; a CDR1, a CDR2, and a CDR3 as contained in the amino acid sequence set forth in SEQ ID NO:357; a CDR1, a CDR2, and a CDR3 as contained in the amino acid sequence set forth in SEQ ID NO:358; CDR1, a CDR2, and a CDR3 as contained in the amino acid sequence set forth in SEQ ID NO:359; a CDR1, a CDR2, and a CDR3 as contained in the amino acid sequence set forth in SEQ ID NO:360; a CDR1, a CDR2, and a CDR3 as contained in the amino acid sequence set forth in SEQ ID NO:361; a CDR1, a CDR2, and a CDR3 as contained in the amino acid sequence set forth in SEQ ID NO:362; a CDR1, a CDR2, and a CDR3 as contained in the amino acid sequence set forth in SEQ ID NO:363; a CDR1, a CDR2, and a CDR3 as contained in the amino acid sequence set forth in SEQ ID NO:364; a CDR1, a CDR2, and a CDR3 as contained in the amino acid sequence set forth in SEQ ID NO:365; a CDR1, a CDR2, and a CDR3 as contained in the amino acid sequence set forth in SEQ ID NO:366; a CDR1, a CDR2, and a CDR3 as contained in the amino acid sequence set forth in SEQ ID NO:367; a CDR1, a CDR2, and a CDR3 as contained in the amino acid sequence set forth in SEQ ID NO:368; a CDR1, a CDR2, and a CDR3 as contained in the amino acid sequence set forth in SEQ ID NO:369; a CDR1, a CDR2, and a CDR3 as contained in the amino acid sequence set forth in SEQ ID NO:370; a CDR1, a CDR2, and a CDR3 as contained in the amino acid sequence set forth in SEQ ID NO:371; a CDR1, a CDR2, and a CDR3 as contained in the amino acid sequence set forth in SEQ ID NO:372; a CDR1, a CDR2, and a CDR3 as contained in the amino acid sequence set forth in SEQ ID NO:373; a CDR1, a CDR2, and a CDR3 as contained in the amino acid sequence set forth in SEQ ID NO:374; a CDR1, a CDR2, and a CDR3 as contained in the amino acid sequence set forth in SEQ ID NO:375; a CDR1, a CDR2, and a CDR3 as contained in the amino acid sequence set forth in SEQ ID NO:376; a CDR1, a CDR2, and a CDR3 as contained in the amino acid sequence set forth in SEQ ID NO:377; a CDR1, a CDR2, and a CDR3 as contained in the amino acid sequence set forth in SEQ ID NO:378; a CDR1, a CDR2, and a CDR3 as contained in the amino acid sequence set forth in SEQ ID NO:379; a CDR1, a CDR2, and a CDR3 as contained in the amino acid sequence set forth in SEQ ID NO:380; a CDR1, a CDR2, and a CDR3 as contained in the amino acid sequence set forth in SEQ ID NO:381; a CDR1, a CDR2, and a CDR3 as contained in the amino acid sequence set forth in SEQ ID NO:382; CDR1, a CDR2, and a CDR3 as contained in the amino acid sequence set forth in SEQ ID NO:383; a CDR1, a CDR2, and a CDR3 as contained in the amino acid sequence set forth in SEQ ID NO:384; or a CDR1, a CDR2, and a CDR3 as contained in the amino acid sequence set forth in SEQ ID NO:385.

95. An anti-CD28 single domain antibody (sdAb) comprising:

a CDR1, a CDR2, and a CDR3 as contained in the amino acid sequence set forth in SEQ ID NO:186; a CDR1, a CDR2, and a CDR3 as contained in the amino acid sequence set forth in SEQ ID NO:187; a CDR1, a CDR2, and a CDR3 as contained in the amino acid sequence set forth in SEQ ID NO:188; a CDR1, a CDR2, and a CDR3 as contained in the amino acid sequence set forth in SEQ ID NO:213; CDR1, a CDR2, and a CDR3 as contained in the amino acid sequence set forth in SEQ ID NO:214; a CDR1, a CDR2, and a CDR3 as contained in the amino acid sequence set forth in SEQ ID NO:215; a CDR1, a CDR2, and a CDR3 as contained in the amino acid sequence set forth in SEQ ID NO:216; a CDR1, a CDR2, and a CDR3 as contained in the amino acid sequence set forth in SEQ ID NO:217; a CDR1, a CDR2, and a CDR3 as contained in the amino acid sequence set forth in SEQ ID NO:218; a CDR1, a CDR2, and a CDR3 as contained in the amino acid sequence set forth in SEQ ID NO:219; a CDR1, a CDR2, and a CDR3 as contained in the amino acid sequence set forth in SEQ ID NO:221; a CDR1, a CDR2, and a CDR3 as contained in the amino acid sequence set forth in SEQ ID NO:222; a CDR1, a CDR2, and a CDR3 as contained in the amino acid sequence set forth in SEQ ID NO:223; a CDR1, a CDR2, and a CDR3 as contained in the amino acid sequence set forth in SEQ ID NO:224; a CDR1, a CDR2, and a CDR3 as contained in the amino acid sequence set forth in SEQ ID NO:225; a CDR1, a CDR2, and a CDR3 as contained in the amino acid sequence set forth in SEQ ID NO:226; a CDR1, a CDR2, and a CDR3 as contained in the amino acid sequence set forth in SEQ ID NO:227; a CDR1, a CDR2, and a CDR3 as contained in the amino acid sequence set forth in SEQ ID NO:228; a CDR1, a CDR2, and a CDR3 as contained in the amino acid sequence set forth in SEQ ID NO:229; a CDR1, a CDR2, and a CDR3 as contained in the amino acid sequence set forth in SEQ ID NO:230; a CDR1, a CDR2, and a CDR3 as contained in the amino acid sequence set forth in SEQ ID NO:231; a CDR1, a CDR2, and a CDR3 as contained in the amino acid sequence set forth in SEQ ID NO:232; a CDR1, a CDR2, and a CDR3 as contained in the amino acid sequence set forth in SEQ ID NO:233; a CDR1, a CDR2, and a CDR3 as contained in the amino acid sequence set forth in SEQ ID NO:234; a CDR1, a CDR2, and a CDR3 as contained in the amino acid sequence set forth in SEQ ID NO:235; a CDR1, a CDR2, and a CDR3 as contained in the amino acid sequence set forth in SEQ ID NO:236; a CDR1, a CDR2, and a CDR3 as contained in the amino acid sequence set forth in SEQ ID NO:237; a CDR1, a CDR2, and a CDR3 as contained in the amino acid sequence set forth in SEQ ID NO:238; a CDR1, a CDR2, and a CDR3 as contained in the amino acid sequence set forth in SEQ ID NO:239; a CDR1, a CDR2, and a CDR3 as contained in the amino acid sequence set forth in SEQ ID NO:280; a CDR1, a CDR2, and a CDR3 as contained in the amino acid sequence set forth in SEQ ID NO:342; a CDR1, a CDR2, and a CDR3 as contained in the amino acid sequence set forth in SEQ ID NO:343; a CDR1, a CDR2, and a CDR3 as contained in the amino acid sequence set forth in SEQ ID NO:344; a CDR1, a CDR2, and a CDR3 as contained in the amino acid sequence set forth in SEQ ID NO:345; a CDR1, a CDR2, and a CDR3 as contained in the amino acid sequence set forth in SEQ ID NO:346; a CDR1, a CDR2, and a CDR3 as contained in the amino acid sequence set forth in SEQ ID NO:347; a CDR1, a CDR2, and a CDR3 as contained in the amino acid sequence set forth in SEQ ID NO:348; a CDR1, a CDR2, and a CDR3 as contained in the amino acid sequence set forth in SEQ ID NO:349; a CDR1, a CDR2, and a CDR3 as contained in the amino acid sequence set forth in SEQ ID NO:350; a CDR1, a CDR2, and a CDR3 as contained in the amino acid sequence set forth in SEQ ID NO:351; a CDR1, a CDR2, and a CDR3 as contained in the amino acid sequence set forth in SEQ ID NO:352; a CDR1, a CDR2, and a CDR3 as contained in the amino acid sequence set forth in SEQ ID NO:353; a CDR1, a CDR2, and a CDR3 as contained in the amino acid sequence set forth in SEQ ID NO:354; a CDR1, a CDR2, and a CDR3 as contained in the amino acid sequence set forth in SEQ ID NO:355; a CDR1, a CDR2, and a CDR3 as contained in the amino acid sequence set forth in SEQ ID NO:356; a CDR1, a CDR2, and a CDR3 as contained in the amino acid sequence set forth in SEQ ID NO:357; a CDR1, a CDR2, and a CDR3 as contained in the amino acid sequence set forth in SEQ ID NO:358; a CDR1, a CDR2, and a CDR3 as contained in the amino acid sequence set forth in SEQ ID NO:359; a CDR1, a CDR2, and a CDR3 as contained in the amino acid sequence set forth in SEQ ID NO:360; a CDR1, a CDR2, and a CDR3 as contained in the amino acid sequence set forth in SEQ ID NO:361; a CDR1, a CDR2, and a CDR3 as contained in the amino acid sequence set forth in SEQ ID NO:362; a CDR1, a CDR2, and a CDR3 as contained in the amino acid sequence set forth in SEQ ID NO:363; a CDR1, a CDR2, and a CDR3 as contained in the amino acid sequence set forth in SEQ ID NO:364; a CDR1, a CDR2, and a CDR3 as contained in the amino acid sequence set forth in SEQ ID NO:365; a CDR1, a CDR2, and a CDR3 as contained in the amino acid sequence set forth in SEQ ID NO:366; a CDR1, a CDR2, and a CDR3 as contained in the amino acid sequence set forth in SEQ ID NO:367; a CDR1, a CDR2, and a CDR3 as contained in the amino acid sequence set forth in SEQ ID NO:368; a CDR1, a CDR2, and a CDR3 as contained in the amino acid sequence set forth in SEQ ID NO:369; a CDR1, a CDR2, and a CDR3 as contained in the amino acid sequence set forth in SEQ ID NO:370; a CDR1, a CDR2, and a CDR3 as contained in the amino acid sequence set forth in SEQ ID NO:371; a CDR1, a CDR2, and a CDR3 as contained in the amino acid sequence set forth in SEQ ID NO:372; a CDR1, a CDR2, and a CDR3 as contained in the amino acid sequence set forth in SEQ ID NO:373; a CDR1, a CDR2, and a CDR3 as contained in the amino acid sequence set forth in SEQ ID NO:374; a CDR1, a CDR2, and a CDR3 as contained in the amino acid sequence set forth in SEQ ID NO:375; a CDR1, a CDR2, and a CDR3 as contained in the amino acid sequence set forth in SEQ ID NO:376; a CDR1, a CDR2, and a CDR3 as contained in the amino acid sequence set forth in SEQ ID NO:377; a CDR1, a CDR2, and a CDR3 as contained in the amino acid sequence set forth in SEQ ID NO:378; a CDR1, a CDR2, and a CDR3 as contained in the amino acid sequence set forth in SEQ ID NO:379; a CDR1, a CDR2, and a CDR3 as contained in the amino acid sequence set forth in SEQ ID NO:380; a CDR1, a CDR2, and a CDR3 as contained in the amino acid sequence set forth in SEQ ID NO:381; a CDR1, a CDR2, and a CDR3 as contained in the amino acid sequence set forth in SEQ ID NO:382; a CDR1, a CDR2, and a CDR3 as contained in the amino acid sequence set forth in SEQ ID NO:383; a CDR1, a CDR2, and a CDR3 as contained in the amino acid sequence set forth in SEQ ID NO:384; a CDR1, a CDR2, and a CDR3 as contained in the amino acid sequence set forth in SEQ ID NO:385.

96. The anti-CD28 sdAb of any of embodiments 90-95, wherein the anti-CD28 sdAb comprises the amino acid sequence set forth in any of SEQ ID NOS:186, 187, 188, 213, 214, 215, 216, 217, 218, 219, 220, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS:186, 187, 188, 213, 214, 215, 216, 217, 218, 219, 220, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385.

97. The anti-CD28 sdAb of any of embodiments 90-95, wherein the anti-CD28 sdAb comprises the amino acid sequence set forth in any of SEQ ID NOS:186, 187, 188, 213, 214, 215, 216, 217, 218, 219, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385, or a sequence of amino acids that exhibits at least 85%, 86%, 87%, 88%, 89%, 90%, 91%, 92%, 93%, 94%, 95%, 96%, 97%, 98%, or 99% sequence identity to any of any of SEQ ID NOS:186, 187, 188, 213, 214, 215, 216, 217, 218, 219, 221, 222, 223, 224, 225, 226, 227, 228, 229, 230, 231, 232, 233, 234, 235, 236, 237, 238, 239, 280, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, and 385.

98. The anti-CD28 sdAb of any of embodiments 90-97, wherein the anti-CD28 sdAb comprises the amino acid sequence set forth in (i) SEQ ID NO: 186, (ii) a humanized variant of SEQ ID NO:186, and/or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 186.

99. The anti-CD28 sdAb of any of embodiments 90-98, wherein the anti-CD28 sdAb comprises a CDR1 comprising the amino acid sequence set forth in SEQ ID NO:189; a CDR2 comprising the amino acid sequence set forth in SEQ ID NO:190; and a CDR3 comprising the amino acid sequence set forth in SEQ ID NO:191.

100. The anti-CD28 sdAb of any of embodiments 90-97, wherein the anti-CD28 sdAb comprises the amino acid sequence set forth in (i) SEQ ID NO: 187, (ii) a humanized variant of SEQ ID NO:187, and/or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 187.

101. The anti-CD28 sdAb of any of embodiments 90-97 and 100, wherein the anti-CD28 sdAb comprises a CDR1 comprising the amino acid sequence set forth in SEQ ID NO:192; a CDR2 comprising the amino acid sequence set forth in SEQ ID NO:193; and a CDR3 comprising the amino acid sequence set forth in SEQ ID NO:194.

102. The anti-CD28 sdAb of any of embodiments 90-97, wherein the anti-CD28 sdAb comprises the amino acid sequence set forth in (i) SEQ ID NO: 188, (ii) a humanized variant of SEQ ID NO:188, and/or (iii) a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 188.

103. The anti-CD28 sdAb of any of embodiments 90-97 and 102, wherein the anti-CD28 sdAb comprises a CDR1 comprising an amino acid sequence set forth in any of SEQ ID NOS:195, 198, 199, 200, and 201; a CDR2 comprising an amino acid sequence set forth in any of SEQ ID NOS:196, 202, 203, 204, 205, 206, 207, 208, 209, 210, 211, 212, 386, 387, 388, 389, 390, 391, 392, 393, 394, and 395; and a CDR3 comprising an amino acid sequence set forth in any of SEQ ID NOS:197, 396, 397, and 398.

104. The anti-CD28 sdAb of any of embodiments 90-97, 102, and 103, wherein the anti-CD28 sdAb comprises a CDR1, CDR2 and CDR3 set forth in: SEQ ID NOS: 195, 196, and 197, respectively; SEQ ID NOS: 198, 196, and 197, respectively; SEQ ID NOS: 199, 196, and 197, respectively; SEQ ID NOS: 200, 196, and 197, respectively; SEQ ID NOS: 201, 196, and 197, respectively; SEQ ID NOS: 195, 202, and 197, respectively; SEQ ID NOS: 195, 203, and 197, respectively; SEQ ID NOS: 195, 204, and 197, respectively; SEQ ID NOS: 195, 205, and 197, respectively; SEQ ID NOS: 195, 206, and 197, respectively; SEQ ID NOS: 195, 207, and 197, respectively; SEQ ID NOS: 195, 208, and 197, respectively; SEQ ID NOS: 195, 209, and 197, respectively; SEQ ID NOS: 195, 210, and 197, respectively; SEQ ID NOS: 195, 211, and 197, respectively; SEQ ID NOS: 195, 212, and 197, respectively;

SEQ ID NOS: 201, 202, and 197, respectively; SEQ ID NOS: 201, 202, and 396, respectively; SEQ ID NOS: 201, 386, and 197, respectively; SEQ ID NOS: 201, 387, and 197, respectively; SEQ ID NOS: 201, 202, and 397, respectively; SEQ ID NOS: 201, 202, and 398, respectively; SEQ ID NOS: 201, 206, and 197, respectively; SEQ ID NOS: 201, 206, and 398, respectively; SEQ ID NOS: 201, 388, and 197, respectively; SEQ ID NOS: 201, 389, and 197, respectively; SEQ ID NOS: 201, 206, and 397, respectively; SEQ ID NOS: 201, 206, and 398, respectively; SEQ ID NOS: 201, 203, and 197, respectively; SEQ ID NOS: 201, 203, and 396, respectively; SEQ ID NOS: 201, 390, and 197, respectively; SEQ ID NOS: 201, 391, and 197, respectively; SEQ ID NOS: 201, 203, and 397, respectively; SEQ ID NOS: 201, 203, and 398, respectively; SEQ ID NOS: 201, 204, and 197, respectively; SEQ ID NOS: 201, 204, and 396, respectively; SEQ ID NOS: 201, 392, and 197, respectively; SEQ ID NOS: 201, 393, and 197, respectively; SEQ ID NOS: 201, 204, and 397, respectively; SEQ ID NOS: 201, 204, and 398, respectively; SEQ ID NOS: 201, 196, and 396, respectively; SEQ ID NOS: 201, 394, and 197, respectively; SEQ ID NOS: 201, 395, and 197, respectively; SEQ ID NOS: 201, 196, and 397, respectively; SEQ ID NOS: 201, 196, and 398, respectively; SEQ ID NOS: 195, 206, and 396, respectively; SEQ ID NOS: 195, 388, and 197, respectively; SEQ ID NOS: 195, 389, and 197, respectively; SEQ ID NOS: 195, 206, and 397, respectively; or SEQ ID NOS: 195, 206, and 398, respectively.

105. The anti-CD28 sdAb of any of embodiments 90-97 and 102, wherein the anti-CD28 sdAb comprises a CDR1 comprising an amino acid sequence set forth in any of SEQ ID NO:195, 198, 199, 200, and 201; a CDR2 comprising an amino acid sequence set forth in any of SEQ ID NO:196, 202, 204, 205, 206, 207, 208, 209, 210, 211, 212, 386, 387, 388, 389, 390, 391, 392, 393, 394, and 395; and a CDR3 comprising an amino acid sequence set forth in any of SEQ ID NO:197, 396, 397, and 398.

106. The anti-CD28 sdAb of any of embodiments 90-07, 102, and 105, wherein the anti-CD28 sdAb comprises a CDR1, CDR2 and CDR3 set forth in: SEQ ID NOS: 195, 196, and 197, respectively; SEQ ID NOS: 198, 196, and 197, respectively; SEQ ID NOS: 199, 196, and 197, respectively; SEQ ID NOS: 200, 196, and 197, respectively; SEQ ID NOS: 201, 196, and 197, respectively; SEQ ID NOS: 195, 202, and 197, respectively; SEQ ID NOS: 195, 204, and 197, respectively; SEQ ID NOS: 195, 205, and 197, respectively; SEQ ID NOS: 195, 206, and 197, respectively; SEQ ID NOS: 195, 207, and 197, respectively; SEQ ID NOS: 195, 208, and 197, respectively; SEQ ID NOS: 195, 209, and 197, respectively; SEQ ID NOS: 195, 210, and 197, respectively; SEQ ID NOS: 195, 211, and 197, respectively; SEQ ID NOS: 195, 212, and 197, respectively; SEQ ID NOS: 201, 202, and 197, respectively; SEQ ID NOS: 201, 202, and 396, respectively; SEQ ID NOS: 201, 386, and 197, respectively; SEQ ID NOS: 201, 387, and 197, respectively; SEQ ID NOS: 201, 202, and 397, respectively; SEQ ID NOS: 201, 202, and 398, respectively; SEQ ID NOS: 201, 206, and 197, respectively; SEQ ID NOS: 201, 206, and 398, respectively; SEQ ID NOS: 201, 388, and 197, respectively; SEQ ID NOS: 201, 389, and 197, respectively; SEQ ID NOS: 201, 206, and 397, respectively; SEQ ID NOS: 201, 206, and 398, respectively; SEQ ID NOS: 201, 203, and 197, respectively; SEQ ID NOS: 201, 203, and 396, respectively; SEQ ID NOS: 201, 390, and 197, respectively; SEQ ID NOS: 201, 391, and 197, respectively; SEQ ID NOS: 201, 203, and 397, respectively; SEQ ID NOS: 201, 203, and 398, respectively; SEQ ID NOS: 201, 204, and 197, respectively; SEQ ID NOS: 201, 204, and 396, respectively; SEQ ID NOS: 201, 392, and 197, respectively; SEQ ID NOS: 201, 393, and 197, respectively; SEQ ID NOS: 201, 204, and 397, respectively; SEQ ID NOS: 201, 204, and 398, respectively; SEQ ID NOS: 201, 196, and 396, respectively; SEQ ID NOS: 201, 394, and 197, respectively; SEQ ID NOS: 201, 395, and 197, respectively; SEQ ID NOS: 201, 196, and 397, respectively; SEQ ID NOS: 201, 196, and 398, respectively; SEQ ID NOS: 195, 206, and 396, respectively; SEQ ID NOS: 195, 388, and 197, respectively; SEQ ID NOS: 195, 389, and 197, respectively; SEQ ID NOS: 195, 206, and 397, respectively; or SEQ ID NOS: 195, 206, and 398, respectively.

107. The anti-CD28 sdAb of any of embodiments 90-97 and 102-104, wherein the anti-CD28 sdAb comprises the amino acid sequence set forth in any of SEQ ID NOS:213-239, 280, and 342-385, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NO:213-239, 280, and 342-385.

108. The anti-CD28 sdAb of any of embodiments 90-97, 102-104, and 107, wherein the anti-CD28 sdAb comprises the amino acid sequence set forth in any of SEQ ID NOS:213-239, 280, and 342-385.

109. The anti-CD28 sdAb of any of embodiments 90-97, 102, 105, and 106, wherein the anti-CD28 sdAb comprises the amino acid sequence set forth in any of SEQ ID NOS:213-219, 221-239, 280, and 342-385, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS:213-219, 221-239, 280, and 342-385.

110. The anti-CD28 sdAb of any of embodiments 90-97, 102, 105, 106, and 109, wherein the anti-CD28 sdAb comprises the amino acid sequence set forth in any of SEQ ID NOS:213-219, 221-239, 280, and 342-385.

111. The anti-CD28 sdAb of any of embodiments 90-110, wherein the anti-CD28 sdAb comprises an amino acid modification that reduces binding to protein A.

112. The anti-CD28 sdAb of embodiment 111, wherein the amino acid modification is G65D by Kabat in framework region 3 (FR3).

113. The CD28-binding polypeptide of any of embodiments 1-35; the fusion protein of any of embodiments 36-54 and 81-89; the multi-specific binding protein of any of embodiments 55-80 and 88-89; or the anti-CD28 single domain antibody of any of embodiments 90-112, which does not comprise a CD3 binding region.

114. The CD28-binding polypeptide of any of embodiments 1-35; the fusion protein of any of embodiments 36-54 and 81-89; the multi-specific binding protein of any of embodiments 55-80 and 88-89; or the anti-CD28 single domain antibody of any of embodiments 90-112, which comprises a CD3 binding region.

115. A multi-specific construct comprising at least one anti-CD28 single domain antibody (sdAb) of any of embodiments 90-112, one or more binding domain (BD) that binds an antigen other than CD28, and a CD3 binding region.

116. The multi-specific construct of embodiment 115, wherein the BD binds a TAA. 117. The multi-specific construct of embodiment 115 or embodiment 116, wherein the BD is a single domain antibody (sdAb).

118. The CD28-binding polypeptide of embodiment 114; the fusion protein of embodiment 114; the multi-specific binding protein of embodiment 114; the anti-CD28 single domain antibody of embodiment 114; or the multi-specific construct of any of embodiments 115-117, wherein the CD3-binding region binds CD3 (CD3ε).

119. The CD28-binding polypeptide of embodiment 114 or embodiment 118; the fusion protein of embodiment 114 or embodiment 118; the multi-specific binding protein of embodiment 114 or embodiment 118; the anti-CD28 single domain antibody of embodiment 114 or embodiment 118; or the multi-specific construct of any of embodiments 115-118, wherein the CD3 binding region is an anti-CD3 antibody or antigen-binding fragment.

120. The CD28-binding polypeptide, the fusion protein, the multi-specific binding protein, the anti-CD28 single domain antibody, or the multi-specific construct of embodiment 1 of embodiment 120, wherein the anti-CD3 antibody or antigen-binding fragment comprises a variable heavy chain region (VH) and a variable light chain region (VL).

121. The CD28-binding polypeptide of any of embodiments 114 and 118-120; the fusion protein of any of embodiments 114 and 118-120; the multi-specific binding protein of any of embodiments 114 and 118-120; the anti-CD28 single domain antibody of any of embodiments 114 and 118-120; or the multi-specific construct of any of embodiments 115-120, wherein the CD3 binding region is monovalent.

122. The CD28-binding polypeptide of any of embodiments 114 and 118-121; the fusion protein of any of embodiments 114 and 118-121; the multi-specific binding protein of any of embodiments 114 and 118-121; the anti-CD28 single domain antibody of any of embodiments 114 and 118-121; or the multi-specific construct of any of embodiments 115-121, wherein the CD3 binding region is an variable fragment (Fv) comprising a variable heavy chain region (VH) and a variable light chain region (VL).

123. The CD28-binding polypeptide of any of embodiments 114 and 118-121; the fusion protein of any of embodiments 114 and 118-121; the multi-specific binding protein of any of embodiments 114 and 118-121; the anti-CD28 single domain antibody of any of embodiments 114 and 118-121; or the multi-specific construct of any of embodiments 115-121, wherein the anti-CD3 antibody or antigen binding fragment is not a single chain antibody, optionally is not a single chain variable fragment (scFv).

124. The CD28-binding polypeptide of any of embodiments 114 and 118-123; the fusion protein of any of embodiments 114 and 118-123; the multi-specific binding protein of any of embodiments 114 and 118-123; the anti-CD28 single domain antibody of any of embodiments 114 and 118-123; or the multi-specific construct of any of embodiments 115-123, wherein the CD28-binding polypeptide comprises an immunoglobulin Fc region.

125. The CD28-binding polypeptide; the fusion protein; the multi-specific binding protein; the anti-CD28 single domain antibody; or the multi-specific construct of embodiment 124, wherein the Fc region comprises an amino acid sequence selected from the group consisting of SEQ ID NOS: 8, 10, 11, 12 and 13, or a sequence of amino acids that exhibits at least 85%, 86%, 87%, 88%, 89%, 90%, 91%, 92%, 93%, 94%, 95%, 96%, 97%, 98%, or 99% sequence identity to any of SEQ ID NOS: 8, 10, 11, 12 and 13.

126. The CD28-binding polypeptide; the fusion protein; the multi-specific binding protein; the anti-CD28 single domain antibody; or the multi-specific construct of embodiment 124 or embodiment 125, wherein the Fc region is a human IgG1.

127. The CD28-binding polypeptide; the fusion protein; the multi-specific binding protein; the anti-CD28 single domain antibody; or the multi-specific construct of any of embodiments 124-126, wherein the Fc region is a human IgG1, optionally wherein the Fc region comprises the amino acid sequence set forth in SEQ ID NO: 8 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 8.

128. The CD28-binding polypeptide; the fusion protein; the multi-specific binding protein; the anti-CD28 single domain antibody; or the multi-specific construct of any of embodiments 124-127, wherein the Fc region is a heterodimeric Fc region.

129. The CD28-binding polypeptide of any of embodiments The CD28-binding polypeptide; the fusion protein; the multi-specific binding protein; the anti-CD28 single domain antibody; or the multi-specific construct of any of embodiments 124-128, wherein the Fc region exhibits effector function.

130. The CD28-binding polypeptide; the fusion protein; the multi-specific binding protein; the anti-CD28 single domain antibody; or the multi-specific construct of any of embodiments 124-128, wherein the Fc region comprises a polypeptide comprising one or more amino acid modification that reduces effector function and/or reduces binding to an effector molecule selected from an Fc gamma receptor and C1q.

131. The CD28-binding polypeptide; the fusion protein; the multi-specific binding protein; the anti-CD28 single domain antibody; or the multi-specific construct of embodiment 130, wherein the one or more amino acid modification is deletion of one or more of Glu233, Leu234 or Leu235.

132. The CD28-binding polypeptide; the fusion protein; the multi-specific binding protein; the anti-CD28 single domain antibody; or the multi-specific construct of embodiment 130 or embodiment 131, wherein the one or more amino acid modification is deletion of one or more of Glu233, Leu234 or Leu235, optionally wherein the Fc region comprises the amino acid sequence set forth in SEQ ID NO: 9 or a sequence of amino acids that exhibits at least 85%, 86%, 87%, 88%, 89%, 90%, 91%, 92%, 93%, 94%, 95%, 96%, 97%, 98%, or 99% sequence identity to SEQ ID NO: 9.

133. The CD28-binding polypeptide; the fusion protein; the multi-specific binding protein; the anti-CD28 single domain antibody; or the multi-specific construct of any of embodiments 124-132, wherein the CD28-binding polypeptide is a dimer.

134. The CD28-binding polypeptide; the fusion protein; the multi-specific binding protein; the anti-CD28 single domain antibody; or the multi-specific construct of any of embodiments 124-133, wherein the Fc is a heterodimeric Fc and the VH and VL that comprise the anti-CD3 antibody or antigen-binding fragment are linked to opposite polypeptides of the heterodimeric Fc.
135. The CD28-binding polypeptide of any of embodiments 114 and 118-134; the fusion protein of any of embodiments 114 and 118-134; the multi-specific binding protein of any of embodiments 114 and 118-134; the anti-CD28 single domain antibody of any of embodiments 114 and 118-134; or the multi-specific construct of any of embodiments 115-134, wherein the CD3 binding region is not able to, or is not substantially able to, bind or engage CD3 unless at least one of the one or more BD is bound to its antigen.
136. The CD28-binding polypeptide of any of embodiments 114 and 118-135; the fusion protein of any of embodiments 114 and 118-135; the multi-specific binding protein of any of embodiments 114 and 118-135; the anti-CD28 single domain antibody of any of embodiments 114 and 118-135; or the multi-specific construct of any of embodiments 115-135, wherein the CD3 binding region is not able to, or is not substantially able, to bind or engage CD3 unless at least one of the at least one CD28 sdAb is bound to CD28.
137. A polynucleotide(s) encoding: the CD28-binding polypeptide of any of embodiments 1-35 and 113-136; the fusion protein of any of embodiments 36-42, 45-47, 49-52, and 113-136; the multi-specific binding polypeptide of any of embodiments 55-63, 66-68, 70-80, 88-89, and 113-136; or the anti-CD28 sdAb of any of embodiments 90-136.
138. A polynucleotide, comprising a first nucleic acid sequence encoding a first polypeptide of a CD28-binding polypeptide of any of embodiments 1-35 and 113-136; a fusion protein of any of embodiments 36-55, 81-89 and 113-136; or a multi-specific binding polypeptide of any of embodiments 55-80, 88-89, and 113-136 and a second nucleic acid sequence encoding a second polypeptide, wherein the first and second nucleic acid sequence are separated by an internal ribosome entry site (IRES), or a nucleic acid encoding a self-cleaving peptide or a peptide that causes ribosome skipping.
139. The polynucleotide of embodiment 138, wherein the first nucleic acid sequence and the second nucleic acid sequence are operably linked to the same promoter.
140. The polynucleotide of embodiment 138 or embodiment 139, wherein the nucleic acid encoding a self-cleaving peptide or a peptide that causes ribosome skipping is selected from a T2A, a P2A, a E2A, and a F2A.
141. A vector, comprising the polynucleotide of any of embodiments 137-140.
142. The vector of embodiment 141 that is an expression vector.
143. The vector of embodiment 141 or embodiment 142 that is a viral vector or a eukaryotic vector, optionally wherein the eukaryotic vector is a mammalian vector.
144. A cell comprising the polynucleotide or polynucleotides of any of embodiments 137-140 or the vector or vectors of any of embodiments 141-143.
145. The cell of embodiment 144, wherein the cell is a lymphocyte.
146. The cell of embodiment 144 or embodiment 145, wherein the cell is a T cell or a natural killer (NK) cells.
147. A method of producing a polypeptide, the method comprising introducing into a cell a polynucleotide or polynucleotides of any of embodiments 137-140 or a vector or vectors of any of embodiments 141-143 and culturing the cell under conditions to produce the polypeptide.
148. The method of embodiment 147, further comprising isolating or purifying the polypeptide from the cell.
149. A polypeptide produced by the method of embodiment 147 or embodiment 148.
150. A pharmaceutical composition comprising a CD28-binding polypeptide of any of embodiments 1-35 and 113-136; a fusion protein of any of embodiments 36-55, 81-89 and 113-136; a multi-specific binding polypeptide of any of embodiments 55-80, 88-89, and 113-136; or an anti-CD28 sdAb of any of embodiments 90-136.
151. The pharmaceutical composition of embodiment 150, comprising a pharmaceutically acceptable carrier.
152. The pharmaceutical composition of embodiment 150 or embodiment 151 that is sterile.
153. A method of stimulating an immune response in a subject, the method comprising administering, to a subject in need thereof, a CD28-binding polypeptide of any of embodiments 1-35 and 113-136; a fusion protein of any of embodiments 36-55, 81-89 and 113-136; a multi-specific binding polypeptide of any of embodiments 55-80, 88-89, and 113-136; an anti-CD28 sdAb of any of embodiments 90-136; or a pharmaceutical composition of any of embodiments 150-152.
154. The method of embodiment 153, wherein the immune response is increased against a tumor or cancer.
155. The method of embodiment 153 or embodiment 154, wherein the method treats a disease or condition in the subject.
156. A method of treating a disease or condition in a subject, the method comprising administering to a subject in need thereof a therapeutically effective amount of a CD28-binding polypeptide of any of embodiments 1-35 and 113-136; a fusion protein of any of embodiments 36-55, 81-89 and 113-136; a multi-specific binding polypeptide of any of embodiments 55-80, 88-89, and 113-136; an anti-CD28 sdAb of any of embodiments 90-136; or a pharmaceutical composition of any of embodiments 150-152.
157. Use of a CD28-binding polypeptide of any of embodiments 1-35 and 113-136; a fusion protein of any of embodiments 36-55, 81-89 and 113-136; a multi-specific binding polypeptide of any of embodiments 55-80, 88-89, and 113-136; an anti-CD28 sdAb of any of embodiments 90-136; or a pharmaceutical composition of any of embodiments 150-152.
158. A composition comprising a CD28-binding polypeptide of any of embodiments 1-35 and 113-136; a fusion protein of any of embodiments 36-55, 81-89 and 113-136; a multi-specific binding polypeptide of any of embodiments 55-80, 88-89, and 113-136; or an anti-CD28 sdAb of any of embodiments 90-136; or a pharmaceutical composition of any of embodiments 150-152 for use treating a disease or condition in a subject.
159. A composition comprising a CD28-binding polypeptide of any of embodiments 1-35 and 113-136; a fusion protein of any of embodiments 36-55, 81-89 and 113-136; a multi-specific binding polypeptide of any of embodiments 55-80, 88-89, and 113-136; or an anti-CD28 sdAb of any of embodiments 90-136; or a pharmaceutical composition of any of embodiments 150-152 for use in the manufacture of a medicament for treating a disease or condition in a subject.
160. The method of embodiment 155 or embodiment 156, the use of embodiment 157, or the composition of embodiment 158 or embodiment 159, wherein the disease or condition is a tumor or a cancer.

161. The method of embodiment 155 or embodiment 156, the use of embodiment 157, or the composition of embodiment 158 or embodiment 159, wherein the subject is a human.

VIII. Examples

The following examples are included for illustrative purposes only and are not intended to limit the scope of the invention.

Example 1: Generation of CD28 sdAbs

A single domain antibody targeting human CD28 was generated via immunization of llamas and alpacas. Llamas and alpacas were immunized with a recombinant version of human CD28 extracellular domain (ECD; amino acids 19-152 of human CD28 set forth in SEQ ID NO:86, e.g. UniProt No. P10747) set forth as follows:

NKILVKQSPMLVAYDNAVNLSCKYSYNLFSREFRASLHKGLDSAVEVCVV

YGNYSQQLQVYSKTGFNCDGKLGNESVTFYLQNLYVNQTDIYFCKIEVMY

PPPYLDNEKSNGTIIHVKGKHLCPSPLFPGPSKP

Following the development of specific anti-CD28 antibody titers, llama/alpaca peripheral blood mononuclear cells (PBMCs) were isolated from 500 mL of blood from the immunized animal and total mRNA was isolated using the Qiagen RNeasy® Maxi Kit and subsequently converted to first strand cDNA using Thermo SuperScript™ IV Reverse Transcriptase and oligo-dT priming. The exemplary single domain antibody (sdAb; also called VHH) sequence was specifically amplified via PCR using the cDNA as template and cloned into a yeast surface display vector as a sdAb-Fc-AGA2 fusion protein. The Fc was a human IgG1 Fc (hFc; set forth in SEQ ID NO:8) or, in some cases, a variant thereof with reduced effector function (Fc xELL; set forth in SEQ ID NO:9).

Yeast libraries displaying the sdAb were enriched using recombinant forms of CD28 via magnetic bead isolation followed by fluorescence activated cell sorting (FACS). Sorted yeast were plated out and isolated colonies were picked into 96-well blocks and grown in media that switched the expression from surface displayed sdAb-Fc to secretion into the media. Supernatants from the 96-well yeast secretion cultures were applied to CD28 positive and negative cells. The cells were washed, treated with fluorophore labeled anti-human Fc secondary antibody, and analyzed by 96-well flow cytometry.

The nucleic acid sequence encoding the sdAb that bound to CD28 positive cells and not to CD28 negative cells was cloned in-frame with a human Fc encoding region into a mammalian expression vector, and expressed by transient transfection in HEK293 freestyle cells (293FS cells) or CHO cells using polyethylenimine. Supernatant was collected after 3-7 days, secreted recombinant protein was purified by protein A chromatography, and concentration was calculated from the absorbance at 280 nm and extinction coefficient.

A number of sdAbs were identified by the screen. Based on further screening assays, selected clones were identified that did not stimulate or agonize CD28 in monospecific formats bivalent for CD28 (see e.g. Example 5A). Exemplary identified sdAbs are set forth in Table E1.

TABLE E1

| CD28 sdAbs | | | | | | | |
|---|---|---|---|---|---|---|---|
| Clone name | CDR1 | SEQ ID NO | CDR2 | SEQ ID NO | CDR3 | SEQ ID NO | VHH SEQ ID NO |
| 1G7 | RTIGLISLMG | 189 | TIIASGRTN | 190 | NAETAPWSRRGF | 191 | 186 |
| 2F11 | GISFNVVDMD | 192 | GITRGGATY | 193 | RWPSRYQNY | 194 | 187 |
| 1C9 | GRMFSNYAMG | 195 | AINYRRDSAD | 196 | TYAGWASSRRDDYNY | 197 | 188 |

Example 2: Binding of sdAb to CD28-Expressing Cells by Flow Cytometry

The specificity, relative affinity, and cynomolgus cross-reactivity of identified and purified CD28 sdAbs (including those selected as described in Table E1) formatted with a human IgG1 (hFc; e.g., SEQ ID NO:8) were assessed by flow cytometry using cells expressing CD28. HEK293FS transiently transfected with full-length human CD28 or cynomolgus CD28 were used as CD28-positive cells. Untransfected HEK293FS cells were used as CD28-negative cells. Cells were seeded in 96-well round-bottom plates at $3\times10^3$ cells/well in FACS buffer. The exemplary generated sdAb-hFcs were titrated onto cells and assay plates were incubated for 30 minutes at 4° C. Cells were washed two time with FACS buffer and then resuspended in diluted Alexa Fluor 647-conjugated anti-human IgG secondary antibody (1:2000 in FACS buffer). Assay plates were incubated for 30 minutes at 4° C. and then cells were washed two times with FACS buffer and resuspended in FACS buffer for analysis using an Intellicyt iQue®.

Figure 1B:
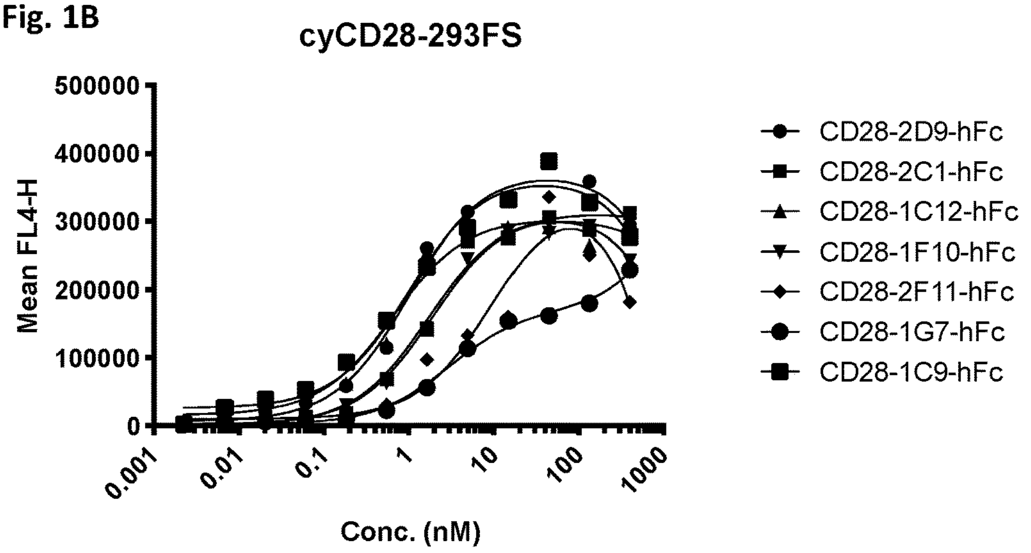
Figure 1C:
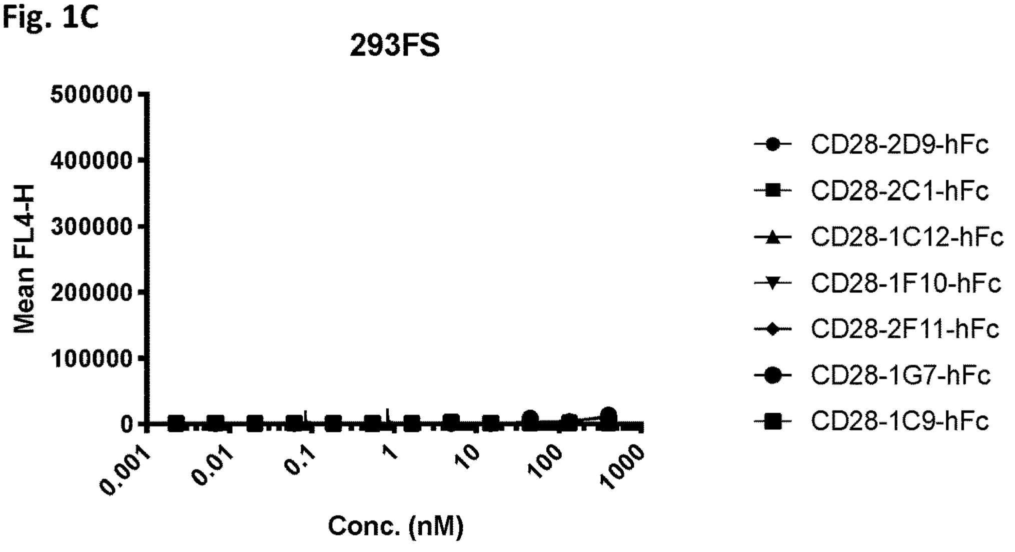
Figure 1D:
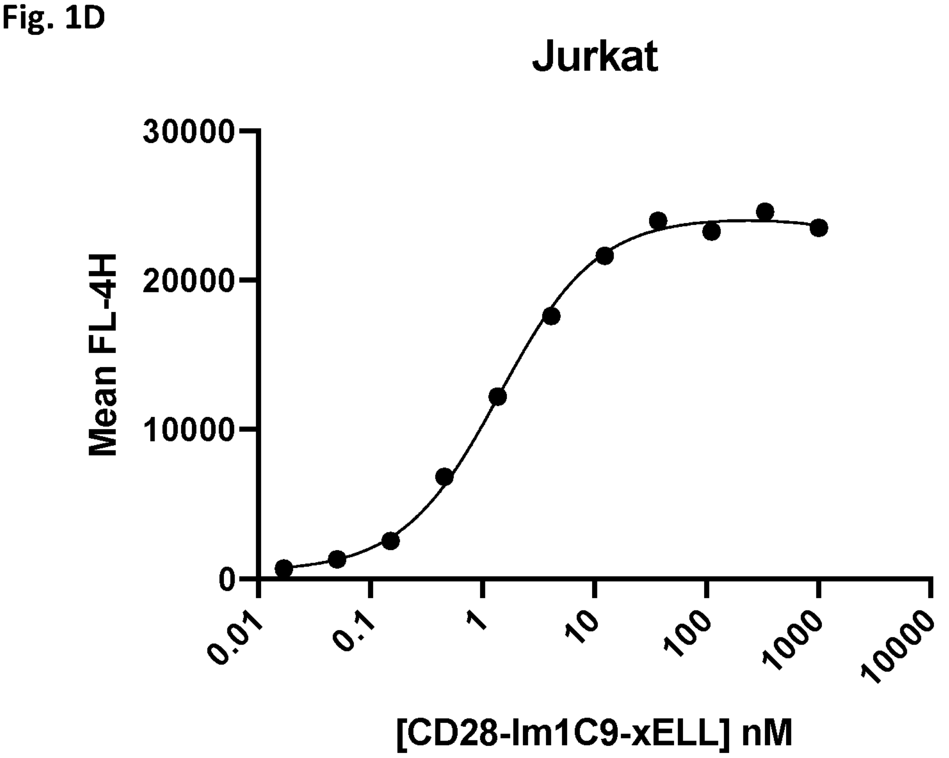
Figure 1E:
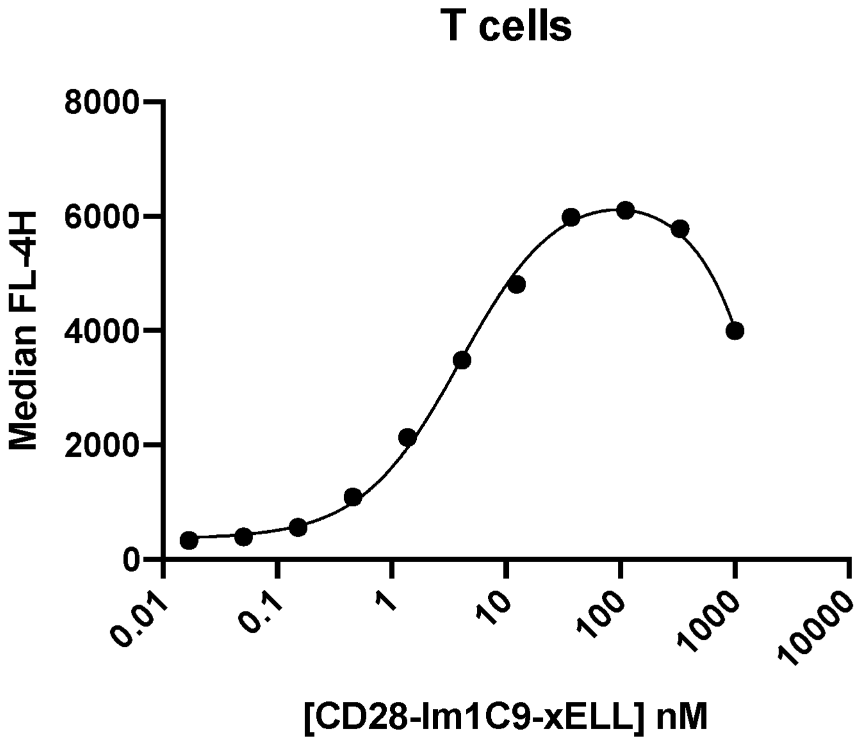
Figure 2A:
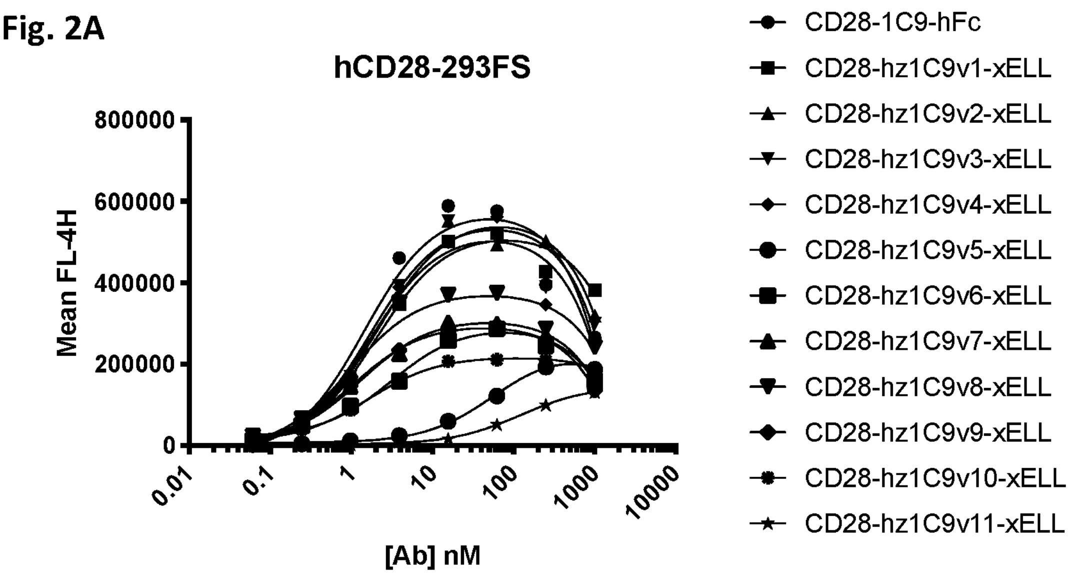
FIGS. 2A-I depict the ability of 1C9 and humanized variants thereof to bind cell-surface CD28. Binding was assessed by flow cytometry to HEK293FS (293FS) cells transiently transfected with full-length human (hCD28) or cynomolgous (cyCD28) antigen (FIGS. 2A, B, D, E), untransfected HEK293FS cells (FIGS. 2C and 2F), Jurkat cells, which endogenously express CD28 (FIG. 2G-H), or primary T cells enriched from PBMCs isolated from normal donor whole blood (FIG. 2I).
Figure 2B:
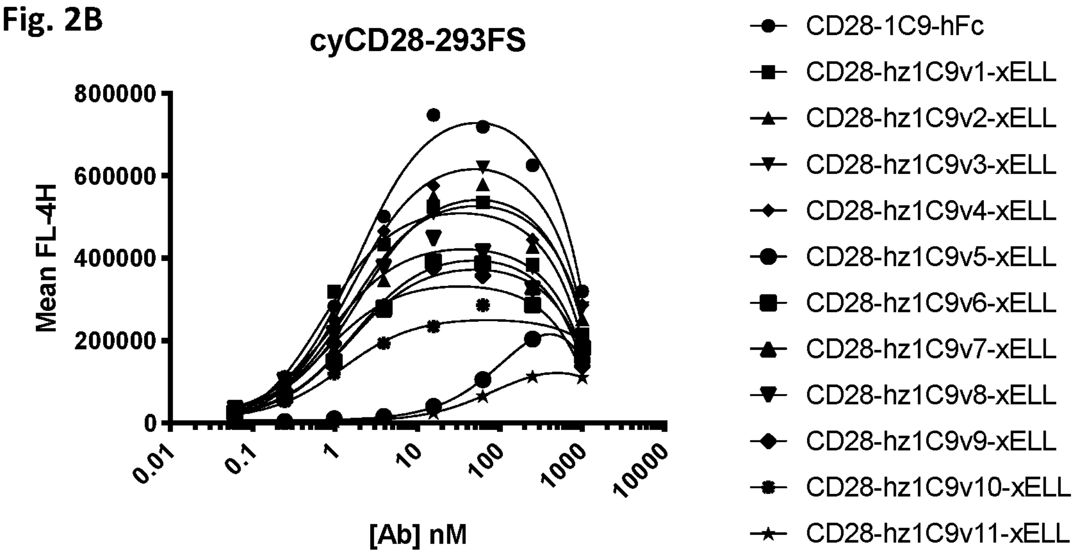
Figure 2C:
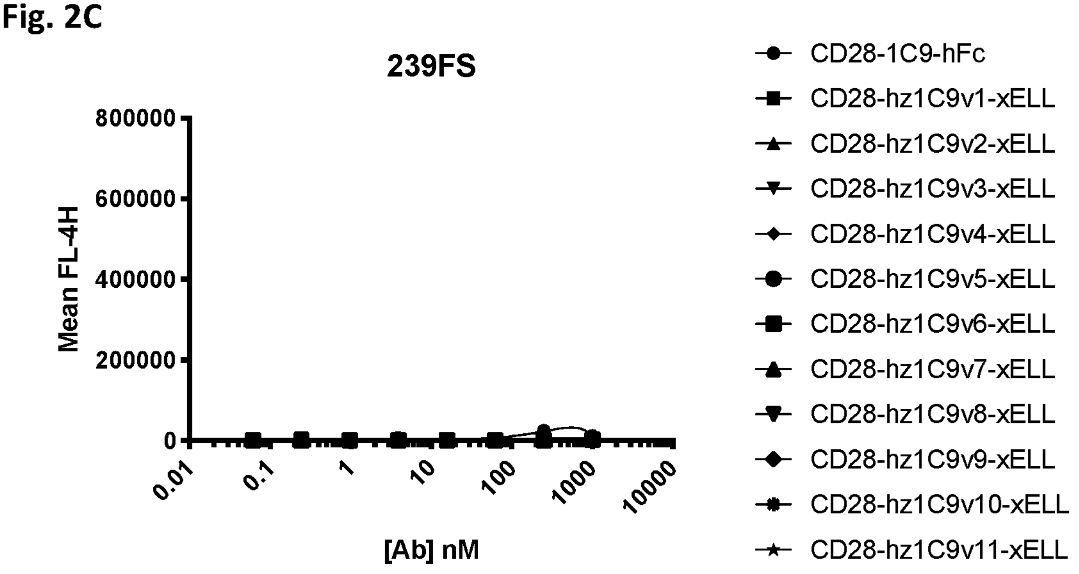
Figure 2D:
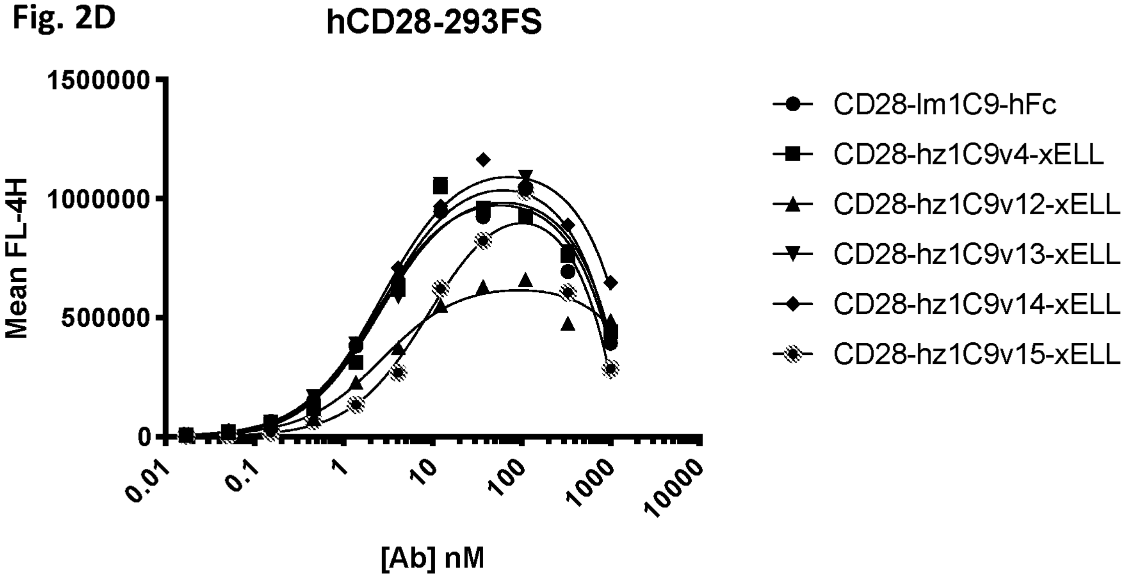
Figure 2E:
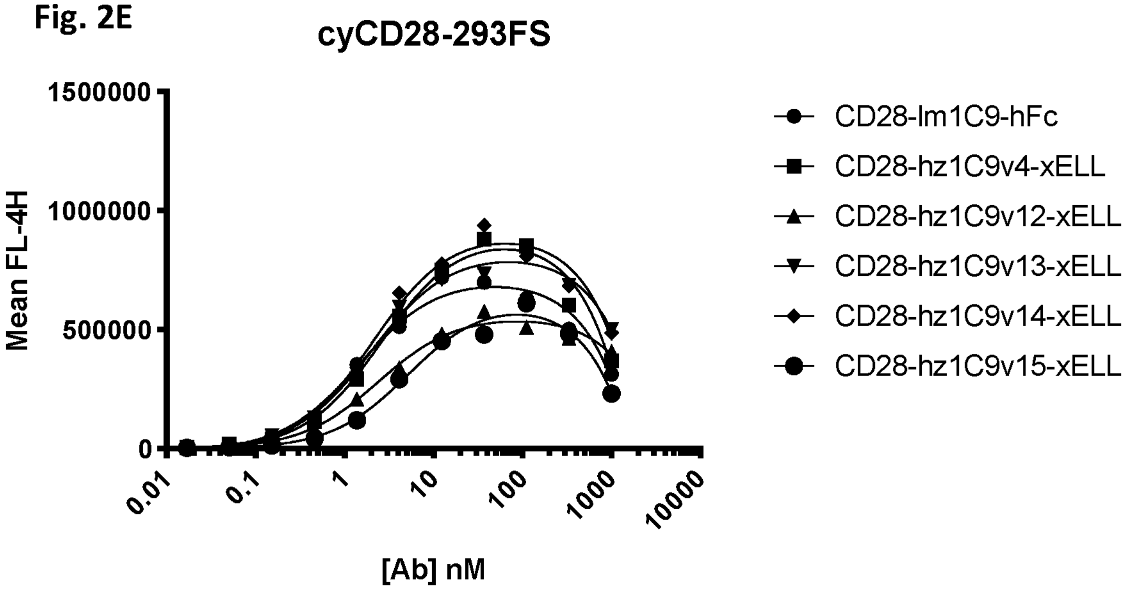
Figure 2F:
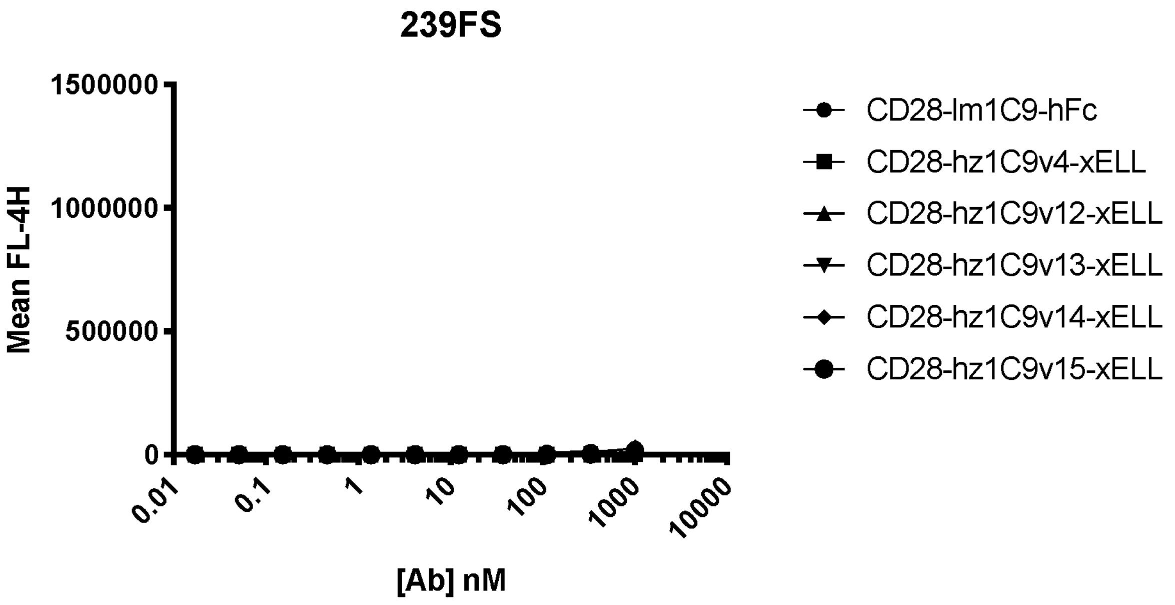
Figure 2G:
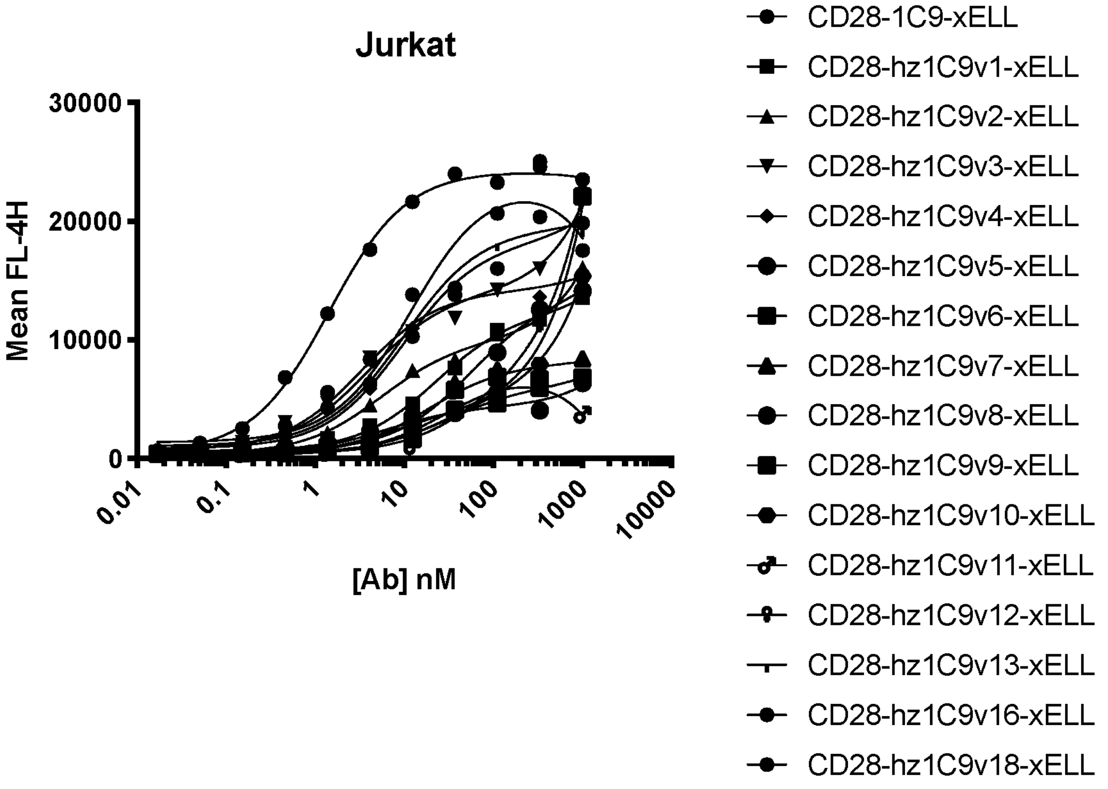
Figure 2H:
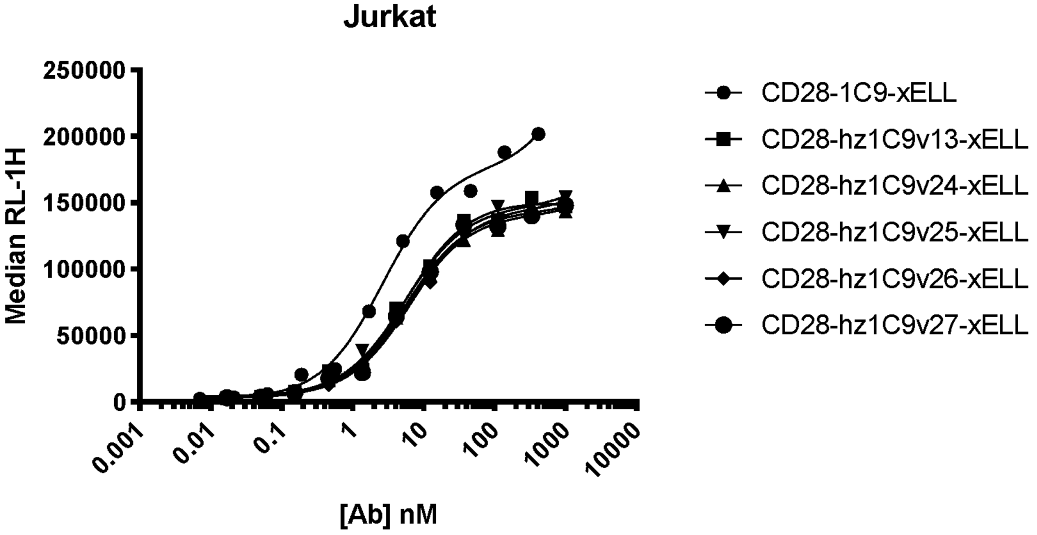
Figure 2I:
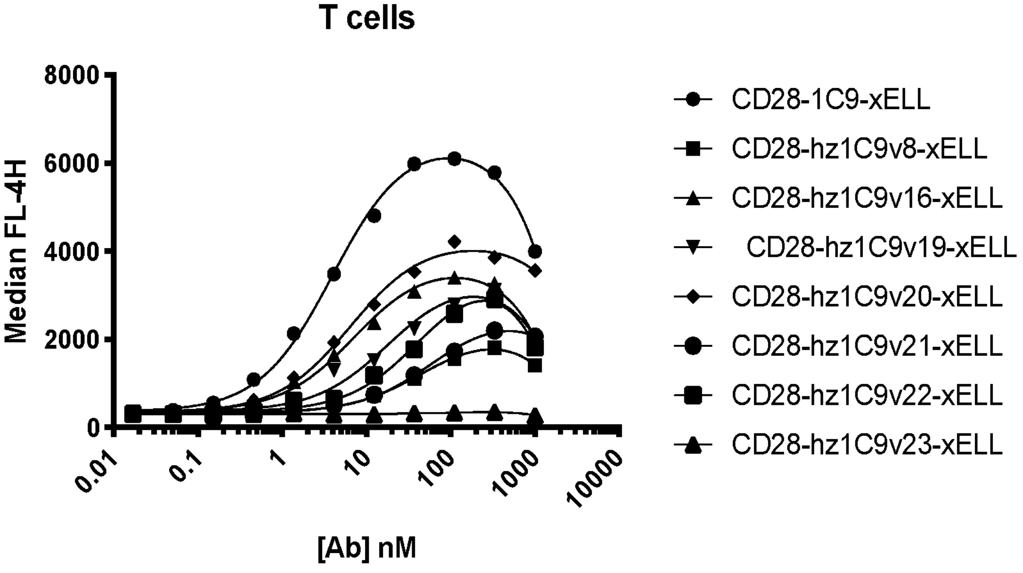

FIGS. 1A-1C set forth results for exemplary generated CD28 sdAb-hFcs. All sdAbs tested exhibited specific binding to CD28-expressing cells and were cross-reactive to cynomolgus CD28.

The exemplary CD28 sdAb 1C9 was also formatted with a variant human IgG1 Fe having reduced effector function (Fe xELL; e.g. SEQ H) NO:9) and tested for binding to the human T lymphocyte cell line Jurkat, and primary T cells enriched from PBMCs. As shown in FIGS. 1D-E, 1C9-xELL bound cells that endogenously expressed CD28 with single-digit nanomolar affinity.

Example 3: Humanization of Exemplary Camelid Derived CD28 sdAbs

The exemplary camelid derived CD28 sdAb 1C9 (SEQ ID NO:188), was humanized using the human VH3-23 germline as scaffold. Camelid residues that contribute to solubility, specificity, stability and/or affinity remained unmodified. In addition all humanized variants contained the modification of Leu11Glu (L11E) and the carboxy-terminal modifications of Ser112Lys (S112K) and Ser113Pro (S113P), as these are known prevent or reduce the recognition of pre-existing anti-human sdAb antibodies (ASDA) directed toward sdAbs (as described in US20160207981). In some cases, humanized variants contained a G73D amino acid mutation (e.g., 1C9v8D).

Table E2 sets forth exemplary humanized variants of the CD28 sdAb 1C9.

TABLE E2

CD28 sdAb Humanized Variants

| Clone name | CDR1 | SEQ ID NO | CDR2 | SEQ ID NO | CDR3 | SEQ ID NO | VHH SEQ ID NO |
|---|---|---|---|---|---|---|---|
| 1C9 Humanized Variants | | | | | | | |
| hz1C9v1 | GRMFSNYAMG | 195 | AINYRRDSAD | 196 | TYAGWASSRRDDYNY | 197 | 213 |
| hz1C9v2 | GRMFSNYAMG | 195 | AINYRRDSAD | 196 | TYAGWASSRRDDYNY | 197 | 214 |
| hz1C9v3 | GRMFSNYAMG | 195 | AINYRRDSAD | 196 | TYAGWASSRRDDYNY | 197 | 215 |
| hz1C9v4 | GRMFSNYAMG | 195 | AINYRRDSAD | 196 | TYAGWASSRRDDYNY | 197 | 216 |
| hz1C9v5 | GRIFSNYAMG | 198 | AINYRRDSAD | 196 | TYAGWASSRRDDYNY | 197 | 217 |
| hz1C9v6 | GRLFSNYAMG | 199 | AINYRRDSAD | 196 | TYAGWASSRRDDYNY | 197 | 218 |
| hz1C9v7 | GRMFSNYAMG | 195 | AINYRRESAD | 202 | TYAGWASSRRDDYNY | 197 | 219 |
| hz1C9v7.1 | GFTFSNYAMG | 201 | AINYRRESAD | 202 | TYAGWASSRRDDYNY | 197 | 358 |
| hz1C9v7.2 | GFTFSNYAMG | 201 | AINYRRESAD | 202 | TYAGWASSRRDDYDY | 396 | 359 |
| hz1C9v7.3 | GFTFSNYAMG | 201 | AINYRRESAD | 202 | TYAGWASSRRDDYNY | 197 | 360 |
| hz1C9v7.5 | GFTFSNYAMG | 201 | AINYGRESAD | 386 | TYAGWASSRRDDYNY | 197 | 361 |
| hz1C9v7.6 | GFTFSNYAMG | 201 | AINYRGESAD | 387 | TYAGWASSRRDDYNY | 197 | 362 |
| hz1C9v7.7 | GFTFSNYAMG | 201 | AINYRRESAD | 202 | TYAGWASSGRDDYNY | 397 | 363 |
| hz1C9v7.8 | GFTFSNYAMG | 201 | AINYRRESAD | 202 | TYAGWASSRGDDYNY | 398 | 364 |
| hz1C9v7.9 | GFTFSNYAMG | 201 | AINYRRDDAD | 206 | TYAGWASSRRDDYNY | 197 | 365 |
| hz1C9v7.10 | GFTFSNYAMG | 201 | AINYRRDDAD | 206 | TYAGWASSRRDDYDY | 396 | 366 |
| hz1C9v7.11 | GFTFSNYAMG | 201 | AINYRRDDAD | 206 | TYAGWASSRRDDYNY | 197 | 367 |
| hz1C9v7.12 | GFTFSNYAMG | 201 | AINYGRDDAD | 388 | TYAGWASSRRDDYNY | 197 | 368 |
| hz1C9v7.13 | GFTFSNYAMG | 201 | AINYRGDDAD | 389 | TYAGWASSRRDDYNY | 197 | 369 |
| hz1C9v7.14 | GFTFSNYAMG | 201 | AINYRRDDAD | 206 | TYAGWASSGRDDYNY | 397 | 370 |
| hz1C9v7.15 | GFTFSNYAMG | 201 | AINYRRDDAD | 206 | TYAGWASSRGDDYNY | 398 | 371 |
| hz1C9v7.16 | GFTFSNYAMG | 201 | AINYRRDAAD | 203 | TYAGWASSRRDDYNY | 197 | 372 |
| hz1C9v7.17 | GFTFSNYAMG | 201 | AINYRRDAAD | 203 | TYAGWASSRRDDYDY | 396 | 373 |
| hz1C9v7.18 | GFTFSNYAMG | 201 | AINYRRDAAD | 203 | TYAGWASSRRDDYNY | 197 | 374 |
| hz1C9v7.19 | GFTFSNYAMG | 201 | AINYGRDAAD | 390 | TYAGWASSRRDDYNY | 197 | 375 |
| hz1C9v7.20 | GFTFSNYAMG | 201 | AINYRGDAAD | 391 | TYAGWASSRRDDYNY | 197 | 376 |
| hz1C9v7.21 | GFTFSNYAMG | 201 | AINYRRDAAD | 203 | TYAGWASSGRDDYNY | 397 | 377 |
| hz1C9v7.22 | GFTFSNYAMG | 201 | AINYRRDAAD | 203 | TYAGWASSRGDDYNY | 398 | 378 |
| hz1C9v7.23 | GFTFSNYAMG | 201 | AINYRRDTAD | 204 | TYAGWASSRRDDYNY | 197 | 379 |
| hz1C9v7.24 | GFTFSNYAMG | 201 | AINYRRDTAD | 204 | TYAGWASSRRDDYDY | 396 | 380 |
| hz1C9v7.25 | GFTFSNYAMG | 201 | AINYRRDTAD | 204 | TYAGWASSRRDDYNY | 197 | 381 |
| hz1C9v7.26 | GFTFSNYAMG | 201 | AINYGRDTAD | 392 | TYAGWASSRRDDYNY | 197 | 382 |
| hz1C9v7.27 | GFTFSNYAMG | 201 | AINYRGDTAD | 393 | TYAGWASSRRDDYNY | 197 | 383 |
| hz1C9v7.28 | GFTFSNYAMG | 201 | AINYRRDTAD | 204 | TYAGWASSGRDDYNY | 397 | 384 |
| hz1C9v7.29 | GFTFSNYAMG | 201 | AINYRRDTAD | 204 | TYAGWASSRGDDYNY | 398 | 385 |
| hz1C9v8 | GRMFSNYAMG | 195 | AINYRRDAAD | 203 | TYAGWASSRRDDYNY | 197 | 220 |

TABLE E2-continued

CD28 sdAb Humanized Variants

| Clone name | CDR1 | SEQ ID NO | CDR2 | SEQ ID NO | CDR3 | SEQ ID NO | VHH SEQ ID NO |
|---|---|---|---|---|---|---|---|
| hz1C9v8D | GRMFSNYAMG | 195 | AINYRRDAAD | 203 | TYAGWASSRRDDYNY | 197 | 280 |
| hz1C9v9 | GRMFSNYAMG | 195 | AINYRRDTAD | 204 | TYAGWASSRRDDYNY | 197 | 221 |
| hz1C9v10 | GRTFSNYAMG | 200 | AINYRRDSAD | 196 | TYAGWASSRRDDYNY | 197 | 222 |
| hz1C9v11 | GFTFSNYAMG | 201 | AINYRRDSAD | 196 | TYAGWASSRRDDYNY | 197 | 223 |
| hz1C9v11.1 | GFTFSNYAMG | 201 | AINYRRDSAD | 196 | TYAGWASSRRDDYNY | 197 | 351 |
| hz1C9v11.2 | GFTFSNYAMG | 201 | AINYRRDSAD | 196 | TYAGWASSRRDDYDY | 396 | 352 |
| hz1C9v11.3 | GFTFSNYAMG | 201 | AINYRRDSAD | 196 | TYAGWASSRRDDYNY | 197 | 353 |
| hz1C9v11.4 | GFTFSNYAMG | 201 | AINYGRDSAD | 394 | TYAGWASSRRDDYNY | 197 | 354 |
| hz1C9v11.5 | GFTFSNYAMG | 201 | AINYRGDSAD | 395 | TYAGWASSRRDDYNY | 197 | 355 |
| hz1C9v11.6 | GFTFSNYAMG | 201 | AINYRRDSAD | 196 | TYAGWASSGRDDYNY | 397 | 356 |
| hz1C9v11.7 | GFTFSNYAMG | 201 | AINYRRDSAD | 196 | TYAGWASSRGDDYNY | 398 | 357 |
| hz1C9v12 | GRMFSNYAMG | 195 | AINYRRDVAD | 205 | TYAGWASSRRDDYNY | 197 | 224 |
| hz1C9v13 | GRMFSNYAMG | 195 | AINYRRDDAD | 206 | TYAGWASSRRDDYNY | 197 | 225 |
| hz1C9v13.1 | GRMFSNYAMG | 195 | AINYRRDDAD | 206 | TYAGWASSRRDDYNY | 197 | 342 |
| hz1C9v13.2 | GRMFSNYAMG | 195 | AINYRRDDAD | 206 | TYAGWASSRRDDYDY | 396 | 343 |
| hz1C9v13.3 | GRMFSNYAMG | 195 | AINYRRDDAD | 206 | TYAGWASSRRDDYNY | 197 | 344 |
| hz1C9v13.4 | GRMFSNYAMG | 195 | AINYRRDDAD | 206 | TYAGWASSRRDDYNY | 197 | 345 |
| hz1C9v13.5 | GRMFSNYAMG | 195 | AINYRRDDAD | 206 | TYAGWASSRRDDYDY | 396 | 346 |
| hz1C9v13.6 | GRMFSNYAMG | 195 | AINYGRDDAD | 388 | TYAGWASSRRDDYNY | 197 | 347 |
| hz1C9v13.7 | GRMFSNYAMG | 195 | AINYRGDDAD | 389 | TYAGWASSRRDDYNY | 197 | 348 |
| hz1C9v13.8 | GRMFSNYAMG | 195 | AINYRRDDAD | 206 | TYAGWASSGRDDYNY | 397 | 349 |
| hz1C9v13.9 | GRMFSNYAMG | 195 | AINYRRDDAD | 206 | TYAGWASSRGDDYNY | 398 | 350 |
| hz1C9v14 | GRMFSNYAMG | 195 | AINYRRSDAD | 207 | TYAGWASSRRDDYNY | 197 | 226 |
| hz1C9v15 | GRMFSNYAMG | 195 | AINYRRTCAD | 208 | TYAGWASSRRDDYNY | 197 | 227 |
| hz1C9v16 | GRMFSNYAMG | 195 | AINYRRDDAD | 206 | TYAGWASSRRDDYNY | 197 | 228 |
| hz1C9v17 | GRMFSNYAMG | 195 | AINYRRDDAD | 206 | TYAGWASSRRDDYNY | 197 | 229 |
| hz1C9v18 | GRMFSNYAMG | 195 | AINYRRDDAA | 209 | TYAGWASSRRDDYNY | 197 | 230 |
| hz1C9v19 | GRMFSNYAMG | 195 | AINYRRSSAD | 210 | TYAGWASSRRDDYNY | 197 | 231 |
| hz1C9v20 | GRMFSNYAMG | 195 | AINYRRDDTD | 211 | TYAGWASSRRDDYNY | 197 | 232 |
| hz1C9v21 | GRMFSNYAMG | 195 | AINYRRDEAD | 212 | TYAGWASSRRDDYNY | 197 | 233 |
| hz1C9v22 | GRMFSNYAMG | 195 | AINYRRDDAD | 206 | TYAGWASSRRDDYNY | 197 | 234 |
| hz1C9v23 | GRMFSNYAMG | 195 | AINYRRDDAD | 206 | TYAGWASSRRDDYNY | 197 | 235 |
| hz1C9v24 | GRMFSNYAMG | 195 | AINYRRDDAD | 206 | TYAGWASSRRDDYNY | 197 | 236 |
| hz1C9v25 | GRMFSNYAMG | 195 | AINYRRDDAD | 206 | TYAGWASSRRDDYNY | 197 | 237 |
| hz1C9v26 | GRMFSNYAMG | 195 | AINYRRDDAD | 206 | TYAGWASSRRDDYNY | 197 | 238 |
| hz1C9v27 | GRMFSNYAMG | 195 | AINYRRDDAD | 206 | TYAGWASSRRDDYNY | 197 | 239 |

Humanized variants of the CD28 sdAb 1C9 were tested for their ability to bind CD28 expressing cells, and binding was compared to the parental 1C9 sdAb. Binding of CD28-sdAb-Fc fusion proteins was assessed by flow cytometry using a CD28 non-expressing cell line (293FS), 293FS cells transiently transfected with full-length human (hCD28-293FS) or cynomolgus (cyCD28-293FS) CD28, the CD28+ Jurkat cell line, or primary human T cells isolated from normal donor whole blood. A titration series of the fusion protein was incubated with the various cell lines ($3\times10^3$ cells/well in 96-well round-bottom plates) for 30 minutes at 4° C. in FACS Buffer (PBS 1% BSA, 0.1% NaN3 pH 7.4) in 96-well plates. Following two washes with FACS buffer, cells were resuspended in diluted. Alexa Fluor 647-conjugated anti-human IgG secondary antibody (1:2000 in FACS buffer), and cells were incubated for 30 minutes at 4° C. Following two additional washes in FACS buffer, bound antibody was detected via flow cytometry (Intellicyt iQue®).

FIGS. 2A-2I set forth results for the humanized variants of the exemplary CD28 sdAb 1C9. All humanized variants tested bound both human and cynomolgus CD28.

Example 4: Generation and Testing of CD28-Targeted Constructs

Exemplary CD28-binding constructs were generated to contain an exemplary CD28 sdAb described above, for example, 1C9 (SEQ ID NO:188), 1C9v8 (SEQ ID NO:220), or 1C9v8D (SEQ ID NO:280). In some cases, various constructs were generated that were monospecific for CD28. In other cases, constructs were engineered to be multispecific and additionally contained at least one tumor associated antigen (TAA) TAA binding domain. For example, at least one TAA binding domain can bind PDL1 (e.g. CDR1, CDR2, CDR3 as set forth in SEQ ID NOS:100, 101, and 102, respectively; e.g. set forth in SEQ ID NO:99) or 5T4 (e.g. CDR1, CDR2, and CDR3 as set forth in SEQ ID NOS: 241, 242, and 243, respectively; or 246, 247, and 248, respectively, e.g. set forth in SEQ ID NOS:240 or 245, respectively). Multispecific constructs generally contained a linker separating the CD28 sdAb and TAA binding domain (e.g. sdAb). In these constructs, the polypeptide chain generally included in order, from the N-terminus to C-terminus, one or more TAA sdAbs, a linker, and one or more CD28 sdAbs. In some cases, the constructs were generated with the exemplary linker GGSGGS (SEQ ID NO:1), GGSGGGGS (SEQ ID NO:89), or GGGSGS (SEQ ID NO:90). As controls, monospecific constructs containing only the TAA sdAb were also generated.

In addition, constructs were generated that were either monovalent or bivalent for CD28. Further among, bispecific constructs that contained at least one TAA sdAb, the constructs were generated to be bivalent for the TAA.

In some cases, the multivalent formats were generated to contain a Fc domain, thereby resulting in the formation of dimers incorporating either a homodimeric or heterodimeric Fc domain. The Fc domain was engineered as a variant having decreased effector function (xELL).

The exemplary generated constructs are summarized in Table E3. For generation of the exemplary constructs, polynucleotides encoding a polypeptide chain were generated and cloned into a plasmid for expression. Plasmid encoding the polypeptide chain(s) was transiently transfected into mammalian cells (either HEK293 or CHO) using polyethylenimine. For constructs with heterodimeric Fc domains, separate plasmids encoding each chain of a heterodimeric CD28-binding protein were transiently transfected at an equimolar ratio into mammalian cells (either HEK293 or CHO) using polyethylenimine. Supernatant was collected after 3-7 days, and secreted recombinant protein was purified by protein A chromatography, followed by preparative size exclusion chromatography (SEC) or flow-through hydrophobic interaction chromatography (HIC). Heterodimeric protein was selectively purified owing to a mutation designed into one chain of the heterodimeric Fc at position I253R or H435R (usually the hole-Fc) such that it did not bind protein A. The second chromatography step on SEC (AKTA with Superdex-200 resin) or FT-HIC (AKTA with butyl/phenyl sepharose) was used to remove undesired cross-paired species containing two heterodimeric Fcs that were more hydrophobic and twice the expected molecular weight. The method allowed for production of heterodimeric multispecific polypeptide constructs containing properly paired species of heterodimeric. Purified heterodimeric CD28-binding protein was stable and did not accumulate cross-paired species upon prolonged incubation at 4° C. or increased protein concentration.

In some cases, exemplary constructs without Fc domains (e.g. cx8390 and cx8394), were engineered to contain a domain that binds protein A (PA) to assist with purification.

Figure 3A:
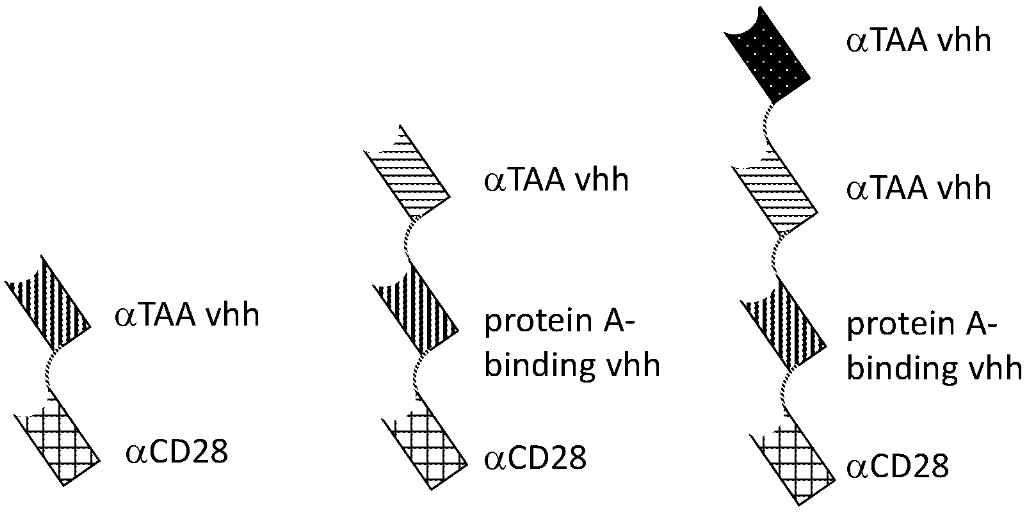
FIGS. 3A and 3B depict exemplary CD28-binding polypeptides without and with Fc domains, respectively.
Figure 3B:
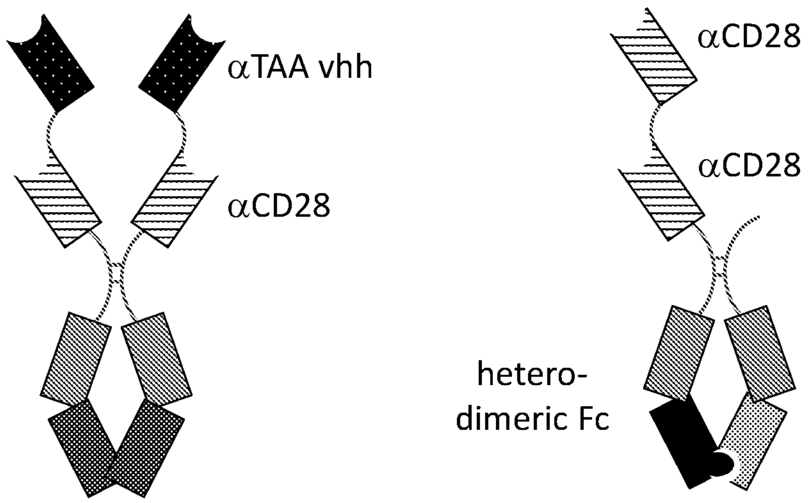

The generated constructs are among those shown in FIGS. 3A and 3B, and Table E3.

TABLE E3

CD28-Targeted Constructs

| Construct | Chain | N-term sdAb TAA (SEQ ID NO) | Linker (SEQ ID NO) | CD28 sdAb (SEQ ID NO) | Fc (SEQ ID NO) |
|---|---|---|---|---|---|
| cx8394 (monospecific) | 1 | PA | GGGSGS (90) | 1C9v8D (280) | — |
| cx8390 (bispecific) | 1 | 5T4, 5T4, PA (240, 245) | GGGSGS (90) | 1C9v8D (280) | — |
| cx8370 (bispecific) | 1 | PDL1 (99) | GGSGGS (1) | 1C9 (188) | xELL (9) |
| | 2 | PDL1 (99) | GGSGGS (1) | 1C9 (188) | xELL (9) |
| cx694 (bispecific) | 1 | PDL1 (99) | GGSGGGGS (89) | 1C9 (188) | xELL (9) |

TABLE E3-continued

CD28-Targeted Constructs

| Construct | Chain | N-term sdAb TAA (SEQ ID NO) | Linker (SEQ ID NO) | CD28 sdAb (SEQ ID NO) | Fc (SEQ ID NO) |
|---|---|---|---|---|---|
| | 2 | PDL1 (99) | GGSGGGGS (89) | 1C9 (188) | xELL (9) |
| cx984 (monospecific) | 1 | — | — | 1C9 (188) | xELL (9) |
| | 2 | — | — | 1C9 (188) | xELL (9) |
| cx698 (monospecific) | 1 | — | — | 1C9, 1C9 (188, 188) | xELL knob (109) |
| | 2 | — | — | 1C9, 1C9 (188, 188) | xELL hole (110) |
| cx1204 (monospecific) | 1 | PDL1 (99) | — | — | xELL (9) |
| | 2 | PDL1 (99) | — | — | xELL (9) |

The exemplary generated constructs were tested for their ability to bind cells expressing CD28, PDL1, and/or 5T4. Binding of the exemplary generated constructs was assessed substantially as described in Example 3, except compared using CD28-293FS cells transiently transfected with PDL1 (PDL1-293FS), a 5T4+/CD28− cell line (T47D), a 5T4−/PDL1−/CD28+ cell line (Jurkat), or a 5T4−/PDL1−/CD28− cell line (Raji).

Figure 3C:
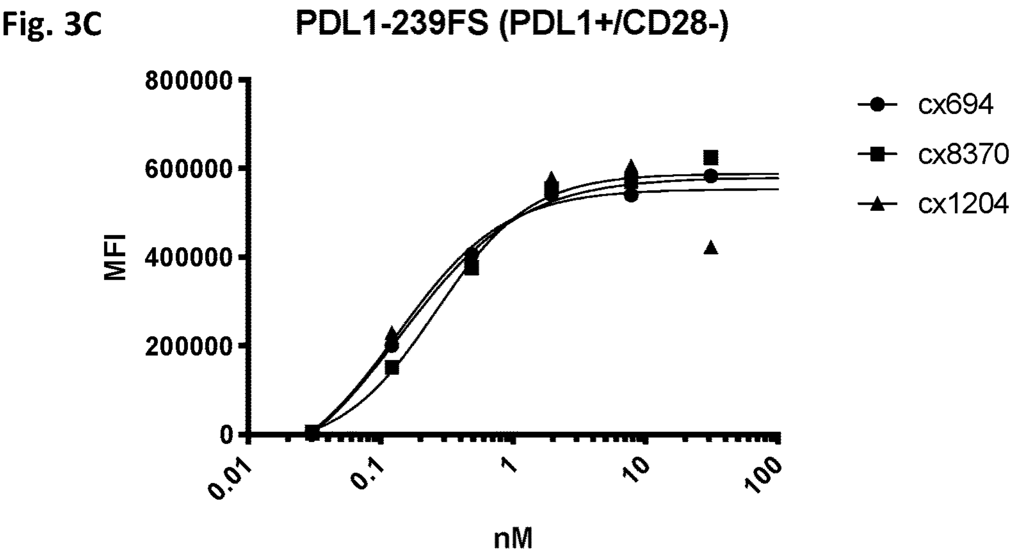
FIGS. 3C-3H depict the ability of exemplary generated constructs to bind cell-surface CD28, PDL1, and/or 5T4. Binding was assessed by flow cytometry to HEK293FS (293FS) cells transiently transfected with PDL1 (FIG. 3C), T47D cells, which endogenously express 5T4 (FIG. 3F), Jurkat cells, which endogenously express CD28 (FIGS. 3D and 3G), or Raji cells, which do not express PDL1, 5T4, or CD28 (FIGS. 3E and 3H).
Figure 3D:
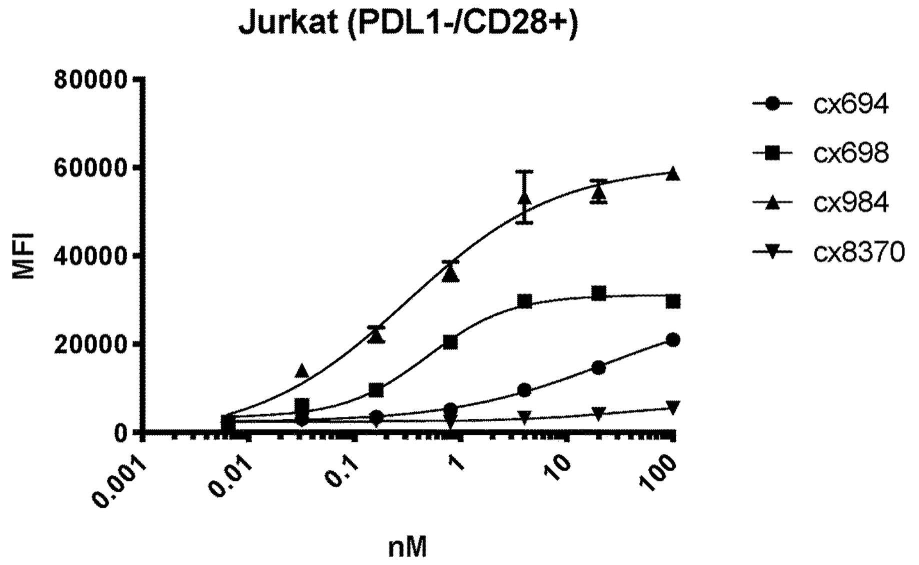
Figure 3E:
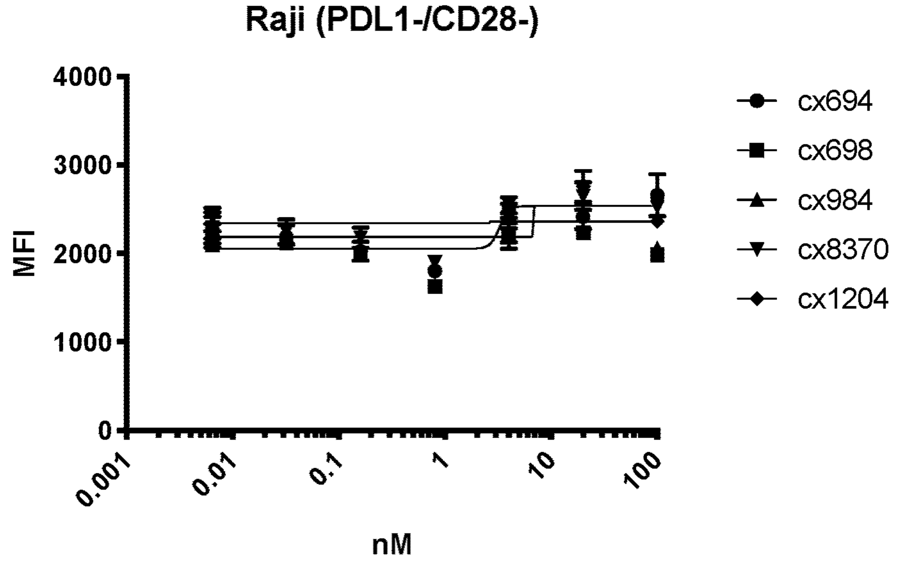
Figure 3F:
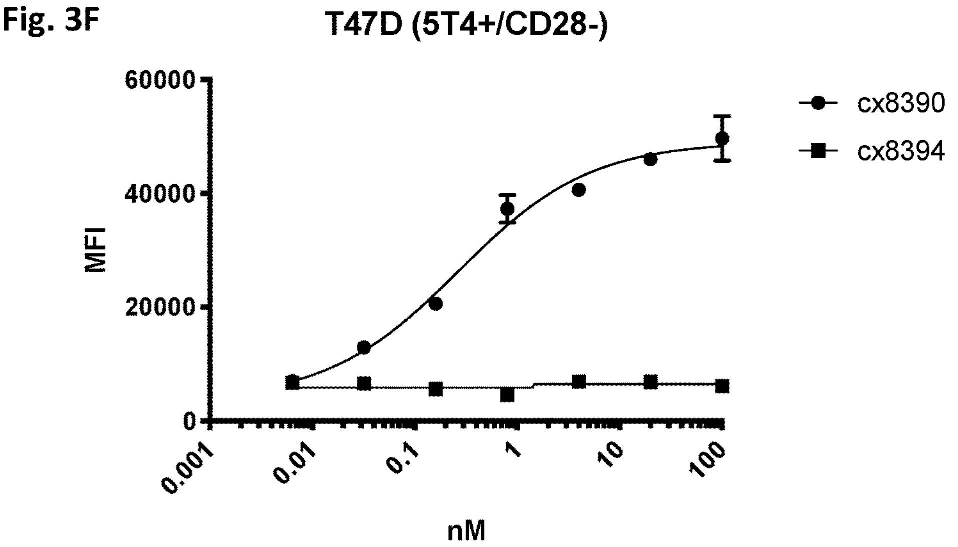
Figure 3G:
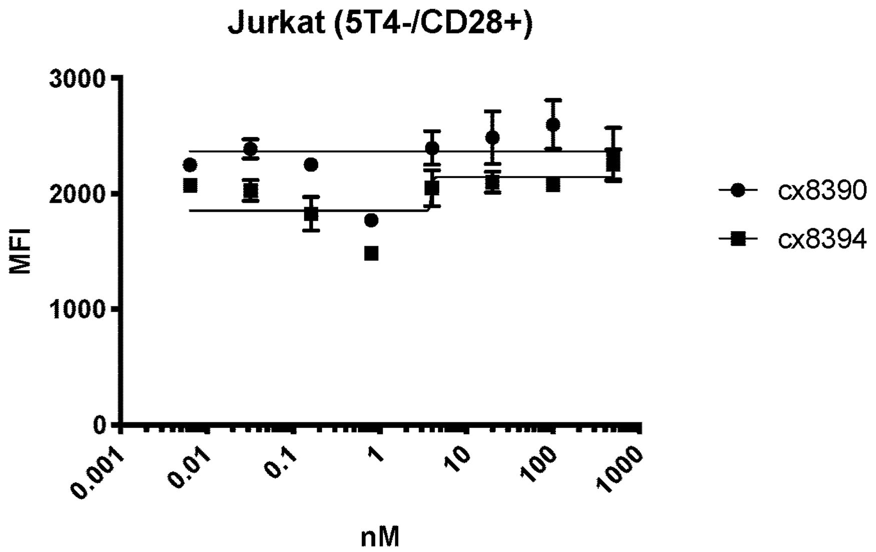
Figure 3H:
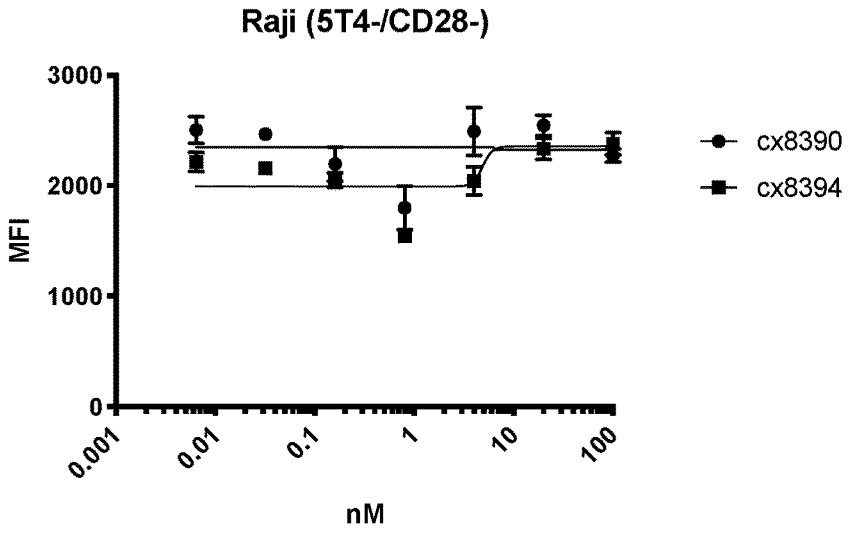

FIGS. 3C-3H set forth results of the exemplary generated CD28-targeted constructs. As shown in FIG. 3C, the exemplary constructs engineered to bind PDL1 in a bivalent format (cx694, cx8370, and cx1204) each bound cells expressing PDL1 in dose-dependent manner. As shown in FIG. 3D, the exemplary constructs monospecific for CD28, cx984 and cx698, bound CD28-expressing Jurkat cells, whereas the exemplary constructs bispecific for CD28 and PDL1 (cx694 and cx8370) were not able to bind CD28-expressing cells in the absence of PDL1. As shown in FIG. 3F, the exemplary construct formatted in bivalent 5T4 binding format (cx8390) bound T47D cells, whereas a construct formatted without the 5T4 sdAbs (cx8394) was not able to bind T47D cells. Neither of the constructs were able to bind Jurkat cells, consisting with an observation that binding of the CD28 sdAb in cx8390 is conditioned on binding of the 5T4 sdAb to 5T4 (FIG. 3G). None of the exemplary constructs were capable of binding Raji cells, which served as a negative control (FIGS. 3E and 3H).

Example 5: Activation of IL-2 Promoter-Driven Luciferase Reporter Cells by CD28-Targeted Constructs A. CD28-Targeted Monospecific Constructs CD28 agonism by monospecific CD28-targeted constructs was assessed using a Jurkat-based reporter cell line (Promega™) engineered to produce IL-2 promoter-driven luciferase. Activation of CD3 on reporter cells leads to production of luciferase, which can be enhanced with concurrent CD28 agonism.

CD28 sdAbs identified as 1G7 and 1C9 in Example 1, as well as additional exemplary CD28 sdAbs (1C12, 1F10, 2F12) were formatted as bivalent, CD28 monospecific constructs with a human IgG1 Fc domain. CD3 (IL-2) reporter cells were seeded in wells of a 96-well plate at $10^5$ cells/well. The exemplary bivalent sdAb-hFc constructs were either incubated with an anti-human Fc antibody at a 1:3 molar ratio for 10 minutes at room temperature or incubated alone under the same conditions. The bivalent constructs were then titrated onto the reporter cells along with the anti-CD3 activating clone OKT3 at a fixed concentration of 1 μg/mL. Assay plates were incubated for 6 hours at 37° C. and then equilibrated to room temperature. Bio-Glo™ reagent was added to all wells, and luminescence was measured using a SpectraMax® L.

Figure 4A:
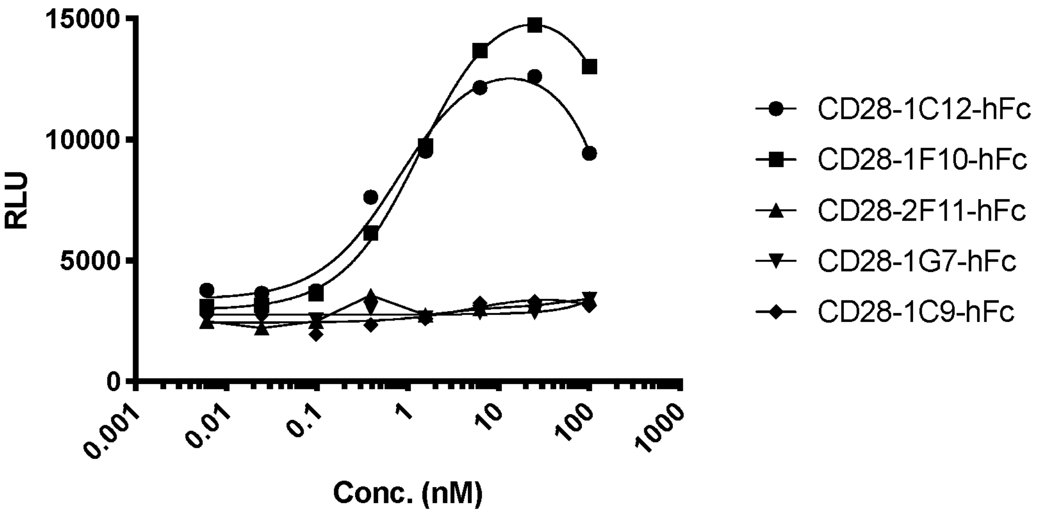
FIG. 4A depicts the ability of CD28-targeting single domain antibodies 1C12 and 1F10, but not 2F11, 1G7, and 1C9, formatted as bivalent sdAb-IgG1, to enhance activation of a Jurkat-based reporter cell line, in which production of luciferase is driven by the IL-2 promoter, by an activating anti-CD3 antibody.
Figure 4B:
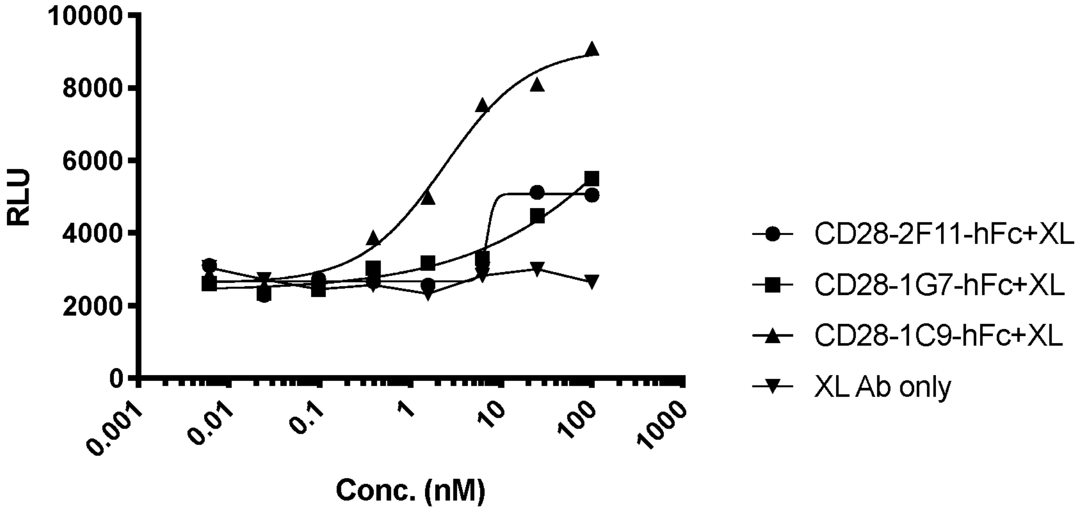
FIG. 4B depicts the ability of cross-linked (XL) 1C9-IgG1, representing a multimer of 1C9 with a valency greater than 2, to stimulate the reporter cells.

As shown in FIG. 4A, bivalent formats of sdAbs 1C12 and 1F10, but not 2F12, 1G7, and 1C9, were able to enhance reporter activation by OKT3, and therefore agonize CD28. While single domain antibodies 2F12, 1G7, and 1C9 do not agonize CD28 when formatted as bivalent sdAb-IgG1, when crosslinked using an anti-Fc antibody (XL) to permit higher-order valency constructs, all three clones were able to enhance reporter activation by OKT3, with crosslinked 1C9 exhibiting the greatest activation (FIG. 4B). These results led to the selection of sdAb clones 1G7, 2F11, and 1C9, as described in Example 1.

B. CD28-Targeted Bispecific Constructs

CD28 agonism by bispecific constructs targeting CD28 and a tumor associated antigen (TAA), as described in Example 4, were assessed using a Jurkat-based reporter cell line (Promega™) engineered to produce IL-2 promoter-driven luciferase. Activation of CD3 on reporter cells leads to production of luciferase, which can be enhanced with concurrent CD28 agonism.

To assess PDL1-dependent agonism of CD28 by an exemplary PDL1×CD28 bispecific construct in bivalent format, CD3 (IL-2) Jurkat reporter cells were seeded in wells of a 96-well plate at $5\times10^4$ cells/well, with or without an equal number of PDL1-CHO-K1 cells (Promega™). The latter cell line was engineered to express not only PDL1, but also a cell-surface protein that activates the T cell receptor (TCR) in an antigen-dependent manner. Thus, co-culture of PDL1-CHO-K1 cells and CD3 (IL-2) Jurkat reporter cells resulted in a low level of reporter cell activation, which can be enhanced by the addition of a CD28-agonizing antibody. Exemplary constructs were added and assay plates were incubated for 6 hours at 37° C. and then equilibrated to room temperature. Bio-Glo™ reagent was added to all wells, and luminescence was measured using a SpectraMax® L.

Figure 4C:
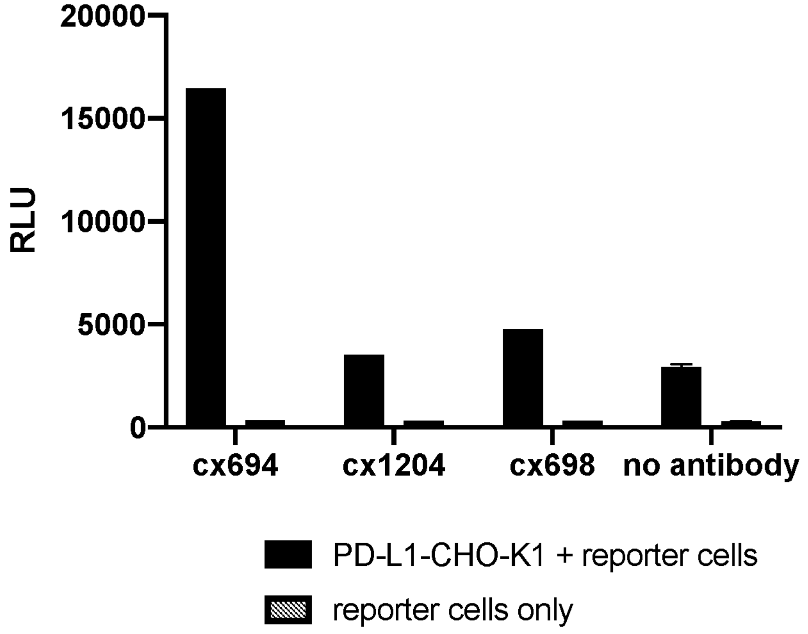
FIGS. 4C and 4D depict the ability of TAAxCD28 bispecific proteins to agonize CD28 on CD3 (IL-2) Jurkat reporter cells in a TAA-dependent manner.

As shown in FIG. 4C, the PDL1×CD28 bispecific protein (cx694) agonized CD28 on the CD3 (IL-2) Jurkat reporter cell line in a PDL1-dependent manner, as evidenced by an increase in reporter cell activation in the presence, but not absence, of PDL1+ cells. Monospecific constructs individually targeting PDL1 (cx1204) or CD28 (cx698) did not increase reporter cell activation relative to the untreated control.

To assess 5T4-dependent agonism of CD28 by an exemplary 5T4×CD28 bispecific construct, as described in Example 4, CD3 (IL-2) reporter cells were seeded in wells of a 96-well plate at $10^5$ cells/well, with or without 5T4-positive T47D cells. Exemplary constructs and the anti-CD3 activating clone OKT3 were added at final concentrations of 100 nM and 1 μg/mL, respectively. Assay plates were incubated for 6 hours at 37° C. and then equilibrated to room temperature. Bio-Glo™ reagent was added to all wells, and luminescence was measured using a SpectraMax® L.

Figure 4D:
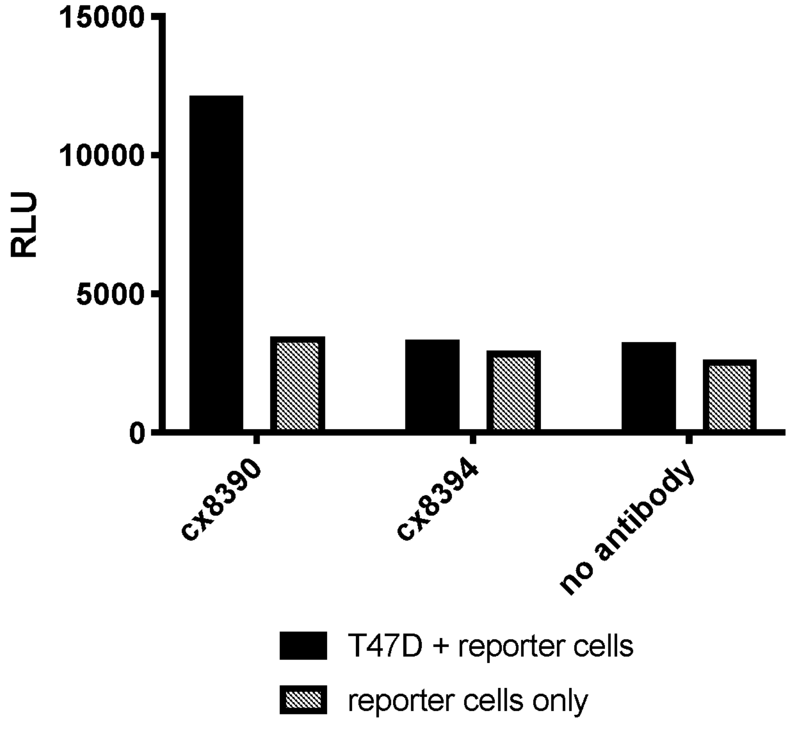

As shown in FIG. 4D, the 5T4×CD28 bispecific construct (cx8390) agonized CD28 on the CD3 (IL-2) Jurkat reporter cell line in a 5T4-dependent manner, as evidenced by an increase in reporter cell activation in the presence, but not absence, of 5T4+ cells. A monospecific protein targeting CD28 (cx8394) did not increase reporter cell activation relative to the untreated control.

Example 6: Assessment of PDL1×CD28 Bispecific Construct Functional Activity

A. T Cell-Mediated Cytotoxicity

Target-dependent cytotoxicity of an exemplary PDL1×CD28 bispecific construct (cx694) was assessed using A549 and untransfected HEK293FS cells as PDL1+ and PDL1− target cells, respectively. Target cells were fluorescently labeled with CytoID red and seeded in wells of a 96-well flat-bottom plate at $1.5\times10^3$ cells/well in assay media (RPMI supplemented with 10% FBS and 1% antibiotic-antimycotic). Cells were allowed to settle at room temperature for uniform distribution, and incubated for 24 hours at 37° C. to permit adherence prior to addition of other assay components. Titrations of the exemplary bispecific construct and primary T cells negatively enriched from PBMCs were then added to the assay plates along with a green caspase-3/7 reagent, which fluorescently labeled nuclear DNA of cells undergoing apoptosis. Monospecific constructs targeting either CD28 (cx698) or PDL1 (cx1204) were also assessed as controls. Assay plates were serially imaged for 5 days using an IncuCyte®. Target cell death was determined by measuring total red/green overlap object area. Following the final imaging time point, suspension cells and supernatants were collected for analysis of activation markers and cytokine production, respectively. Remaining adherent (viable target) cells were gently washed with PBS and then analyzed using CellTiter-Glo® 2.0, a luciferase-based reagent that results in bioluminescence in presence of ATP (viable cells).

Figure 5A:
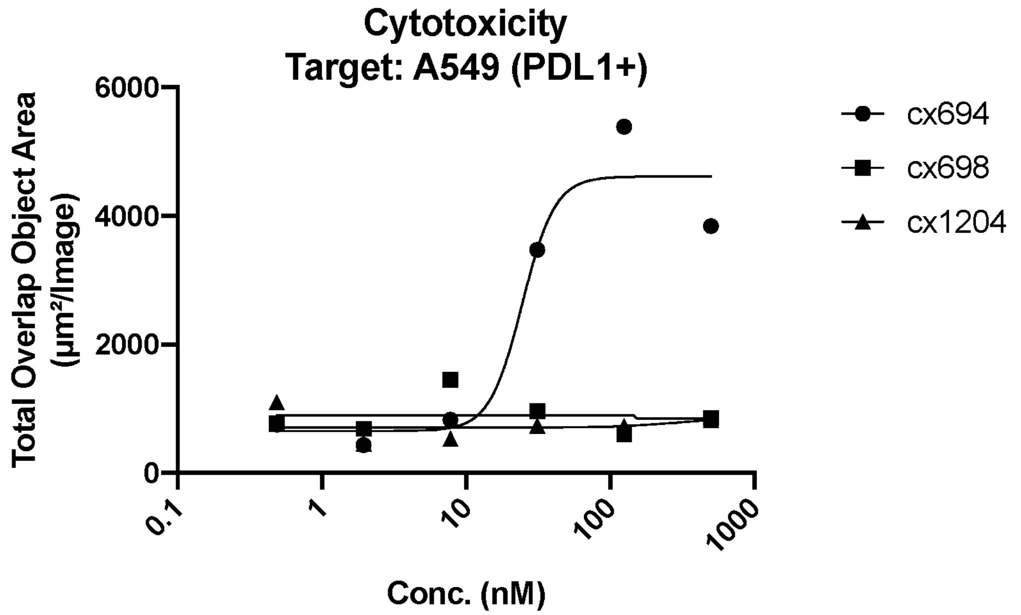
FIG. 5 depicts the ability of cx694, a bispecific construct targeting PDL1 and CD28, to induce T cell-mediated cytotoxicity of a PDL1+ cell line, A549 (FIGS. 5A and 5C), but not HEK293FS (293FS), a PDL1− cell line (FIGS. 5B and 5D) as assessed by caspase-3/7 activation using a cell imaging system (FIGS. 5A and 5B) and cell survival using a CellTiter-Glo assay (FIGS. 5C and 5D). Monospecific constructs individually targeting PDL1 (cx1204) or CD28 (cx698) lacked cytotoxic activity against both A549 and 239FS cells (FIGS. 5A-5D).
Figure 5B:
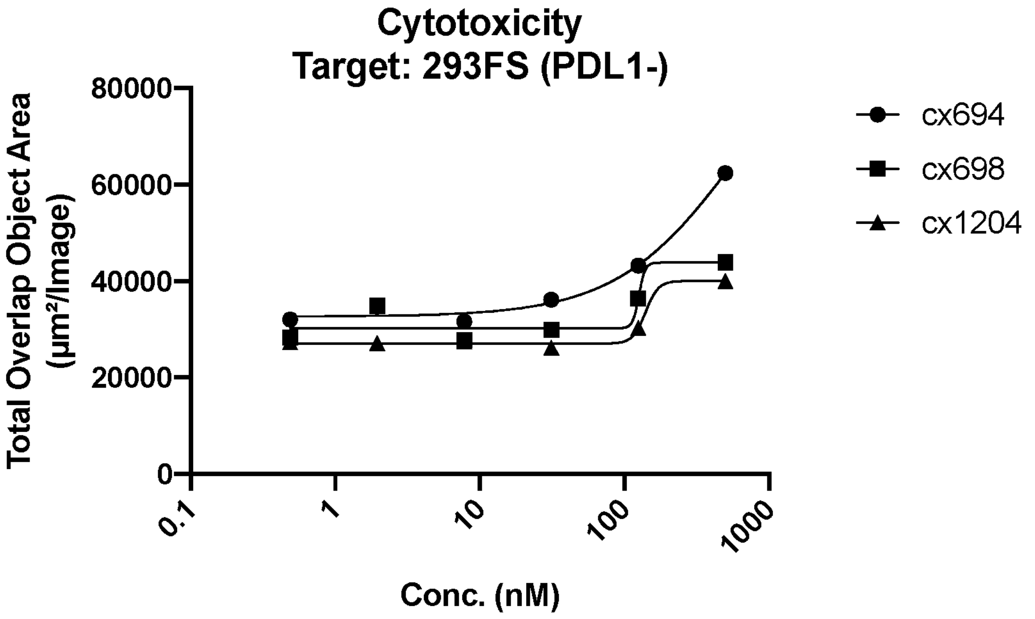
Figure 5C:
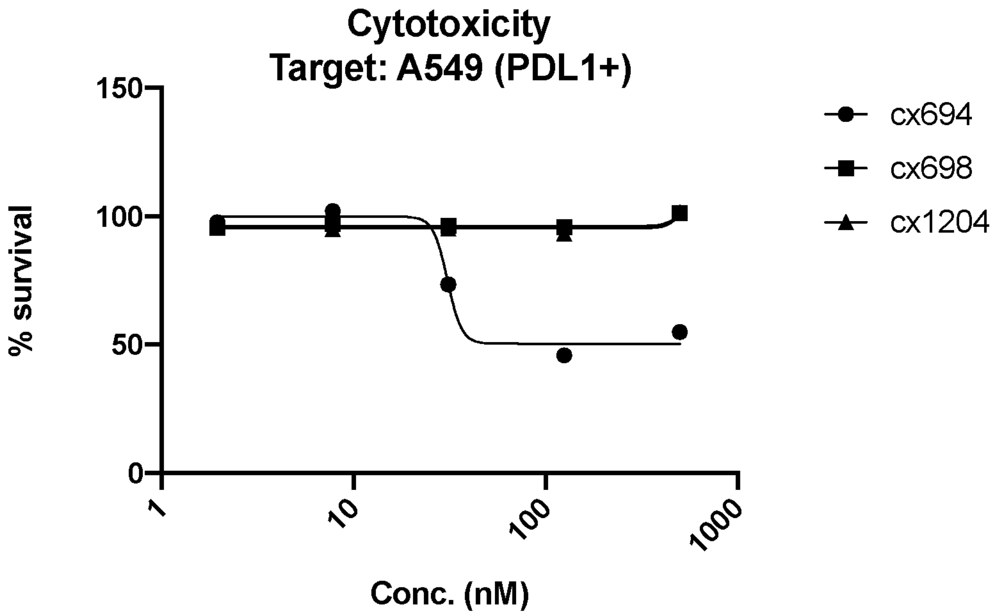
Figure 5D:
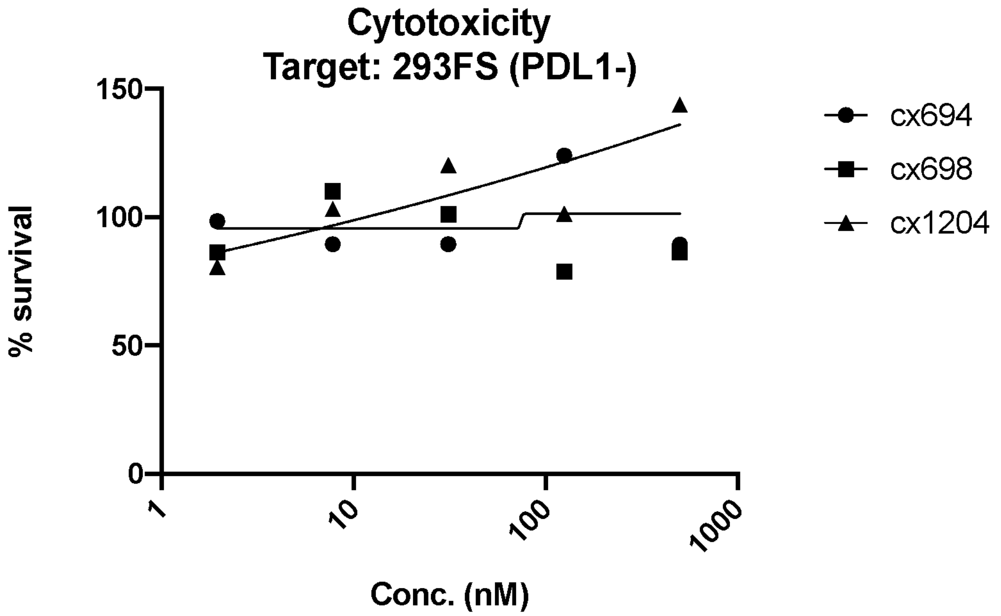

As shown in FIGS. 5A and 5B, the exemplary PDL1×CD28 bispecific construct cx694 induced T cell-mediated caspase-3/7 activation in PDL1+ A549 cells, but not PDL1− 293FS cells, while monospecific constructs targeting PDL1 or CD28 alone (cx1204 and cx698, respectively) did not induce caspase-3/7 activation in either cell type. As shown in FIGS. 5C and 5D, the target-dependent caspase activation induced by the exemplary PDL1×CD28 bispecific construct correlated with target-dependent, T cell-mediated cytotoxicity (as assessed by cell survival).

B. T Cell Activation

To assess T cell activation, cells from T cell-mediated cytotoxicity assays were collected and centrifuged at 400 g for five minutes and supernatants were discarded. Cells were resuspended in FACS buffer containing a live/dead stain and fluorophore-conjugated anti-human CD4, anti-human CD8, anti-human CD25, anti-human CD69, and/or anti-human CD71 antibodies. Cells were analyzed using a Novocyte and CD4+ or CD8+ T cell activation was determined by measuring expression levels of CD25, CD69, or CD71, or the percent of CD25+, CD69+, or CD71+ cells.

Figure 6A:
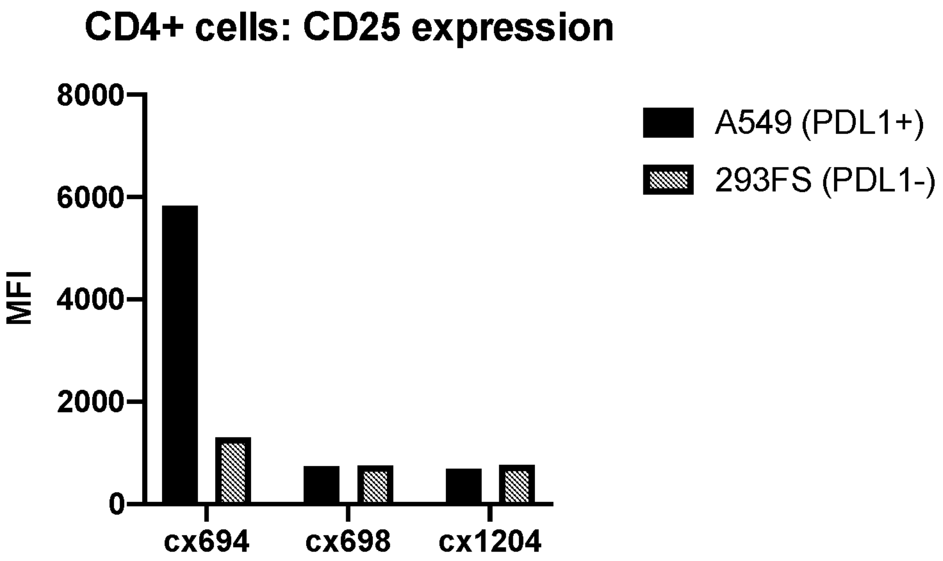
FIGS. 6A-D depict the ability of cx694, a bispecific protein targeting PDL1 and CD28, to induce antigen-specific activation of CD4+ (FIGS. 6A-6C) and CD8+ (FIG. 6D) T cells as assessed by flow cytometry by analyzing the activation markers CD25 (FIG. 6A), CD69 (FIGS. 6B and 6D), and CD71 (FIG. 6C). Monospecific constructs individually targeting PDL1 (cx1204) or CD28 (cx698) did not activate either T cell subset in the presence of either target cell line. A549 and 293FS cells were used as PDL1+ and PDL1− cells, respectively.
Figure 6B:
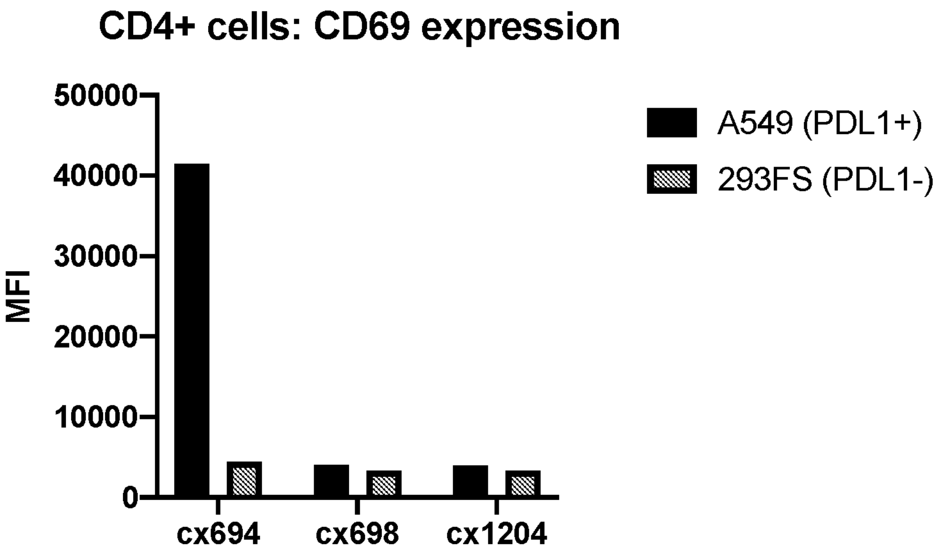
Figure 6C:
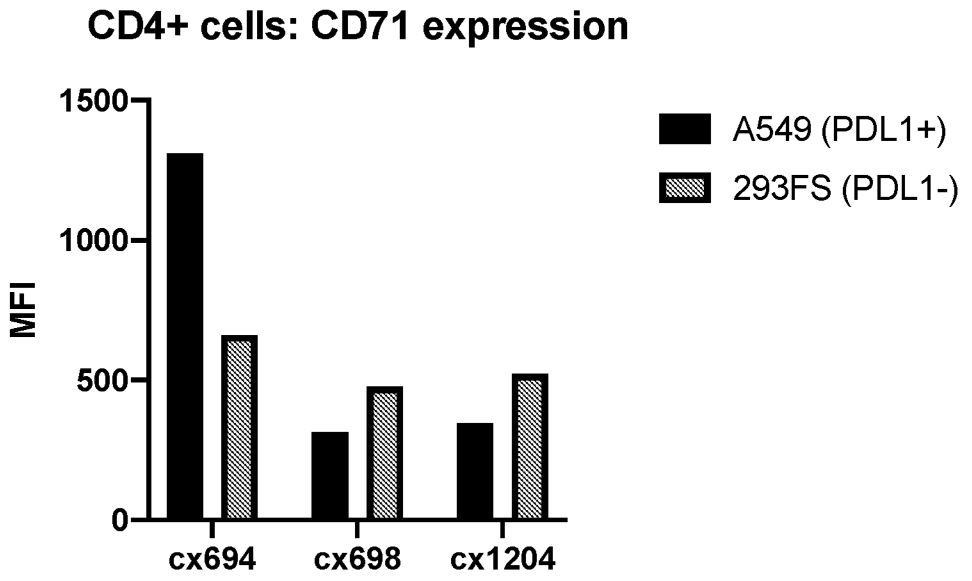
Figure 6D:
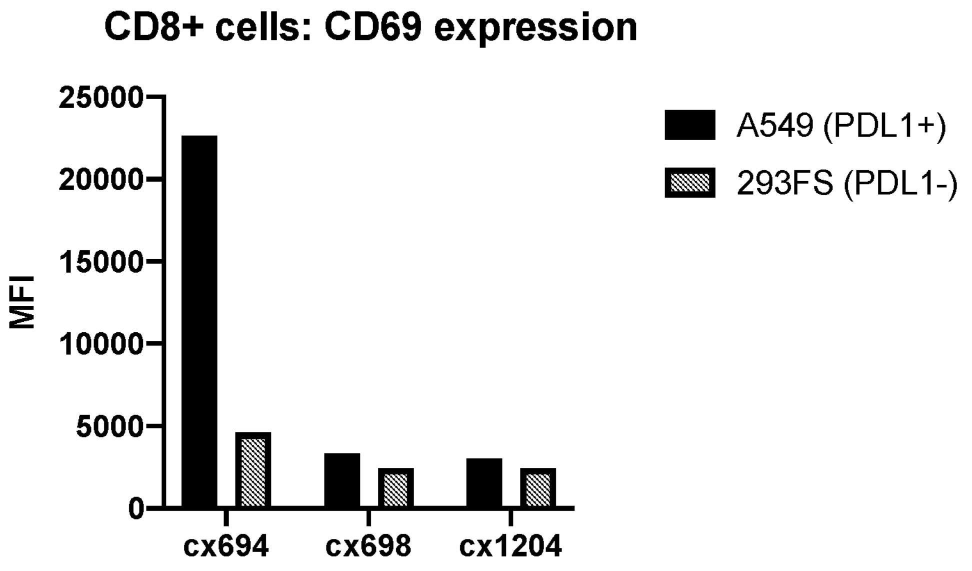

FIGS. 6A, 6B, and 6C depict results for CD25, CD69, and CD71 expression, respectively, by CD4+ T cells following culture of T cells with PDL1+ (A549) or PDL1− (293FS) cells in the presence of 125 nM of a PDL1×CD28 bispecific construct (cx694) or a monospecific construct individually targeting PDL1 (cx1204) or CD28 (cx698). FIG. 6D depicts results for CD69 expression by CD8+ T cells following culture of T cells with PDL1+(A549) or PDL1− (293FS) cells in the presence of a PDL1×CD28 bispecific construct (cx694) or monospecific constructs individually targeting PDL1 (cx1204) or CD28 (cx698). The results show that the exemplary PDL1×CD28 bispecific construct induced PDL1-dependent activation of both CD4+ and CD8+ T cells, as evidenced by increased expression of CD25, CD69, and CD71 on CD4+ T cells (FIGS. 6A-6C), and CD69 on CD8+ T cells (FIG. 6D).

C. T Cell Cytokine Production (ELISA)

Figure 6E:
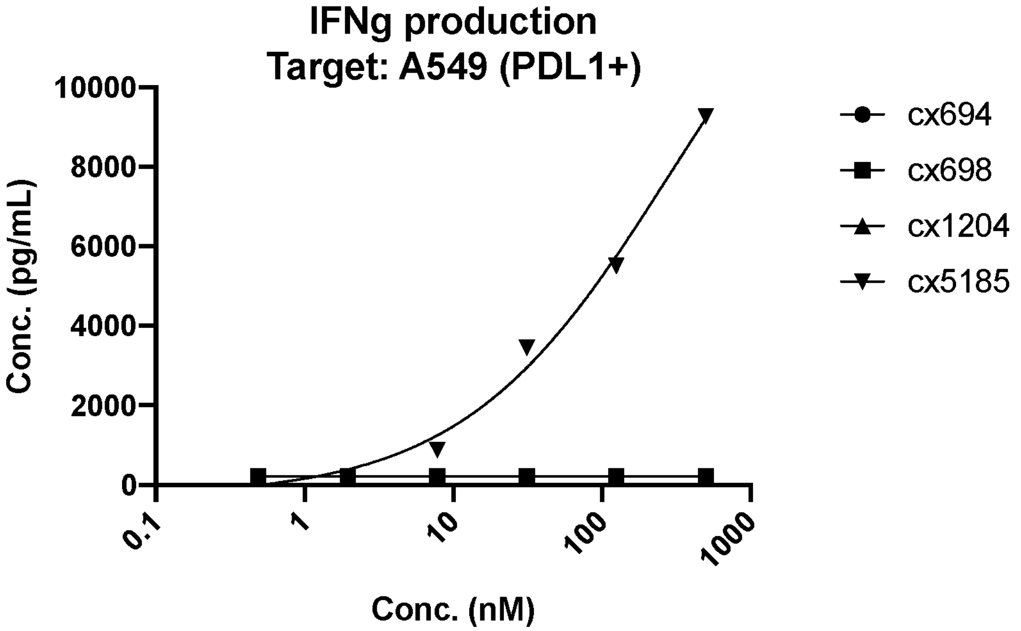
FIG. 6E depicts the lack of IFNγ production by A549/T cell co-cultures treated with cx694. cx5185 is a CD3-stimulating protein that served as a positive control for the experiment.

A T cell-mediated cytotoxicity assay was carried out substantially as described above, and supernatant was collected and analyzed for IFNγ content by sandwich ELISA (BioLegend®, USA). For ELISA analysis, the manufacturer's instructions were followed and a standard curve was generated from which cytokine concentration values of supernatant samples were interpolated. Samples that had absorbance values below the lower limit of detection were assigned a cytokine concentration equal to half that of the lowest standard concentration. As shown in FIG. 6E, the exemplary PDL1×CD28 bispecific construct (cx694) did not elicit IFNγ production by T cells co-cultured with either PDL1+ or PDL1− cells. cx5185 is a CD3-targeting construct that was used as a positive control, and was the only construct tested that yielded values above the lower limit of quantification (LLOQ). Taken together with the cytotoxicity data, this shows that the exemplary PDL1×CD28 bispecific construct has the capacity to induce T cell-mediated killing of PDL1+ cells without leading to production of detectable IFNγ.

D. T Cell Cytokine Production (Immunospot)

T cell co-stimulation by exemplary PDL1×CD28 bispecific constructs was assessed in both a Cytomegalovirus, Epstein-Barr Virus, and Flu Virus (CEF) peptide pool stimulation assay and an autologous mixed lymphocyte reaction (aMLR) assay.

CEF Peptide Pool Stimulation Assay

T cell co-stimulation by an exemplary PDL1×CD28 bispecific construct, cx8370, was assessed by measuring IFNγ production by PBMCs treated with a CEF peptide pool, which contains epitopes from Cytomegalovirus, Epstein-Barr Virus, and Flu Virus, in combination with a titration of the bispecific construct. IFNγ production was measured using an Immunospot Analyzer.

PBMCs isolated from whole blood from a normal human donor were seeded in wells of a 96-well plate coated with an IFNγ capture antibody. The CEF peptide pool and a titration of the bispecific construct or monospecific constructs individually targeting PDL1 (cx1204) or CD28 (cx984), were added. The assay plate was incubated for 24 hours at 37° C., washed, and anti-IFNγ detection antibody was added. The assay plate was incubated for 2 hours at room temperature, washed, and then fluorescent tertiary detection antibody was added. The plate was incubated for an hour at room temperature, washed, and then incubated for an additional hour at room temperature to dry the membrane. The membrane was imaged and IFNγ spot count was determined using an Immunospot Analyzer.

Figure 7A:
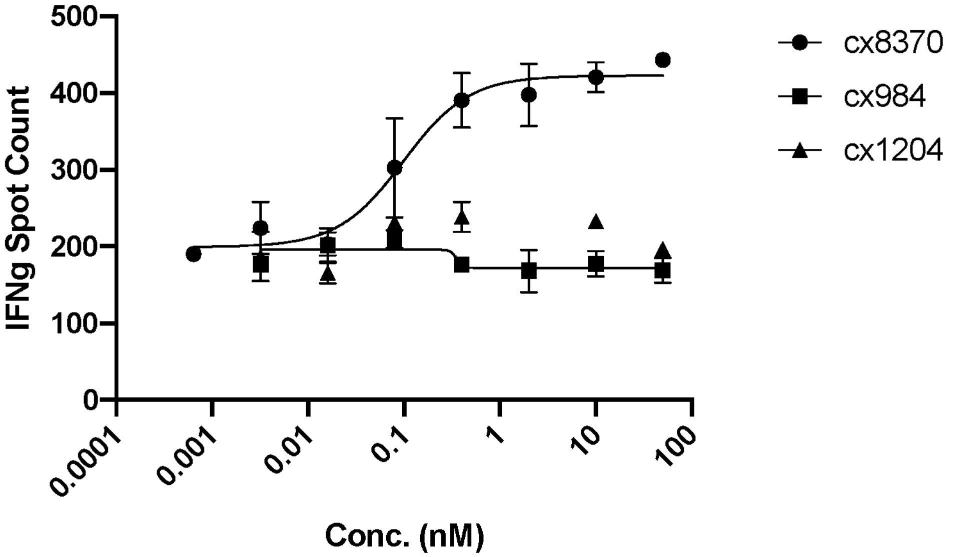
FIGS. 7A-7C depict the ability of bispecific constructs targeting PDL1 and CD28 to co-stimulate primary T cells.

As shown in FIG. 7A, addition of the exemplary PDL1×CD28 bispecific construct cx8370 to CET peptide pool-treated PBMCs resulted in co-stimulation, as evidenced by dose-dependent IFNγ production. Targeting PDL1 or CD28 individually with the monospecific constructs cx1204 and cx984, respectively, did not impact the level of IFNγ production by treated. PBMCs.

Autologous Mixed Lymphocyte (aMLR) Assay

T cell co-stimulation by an exemplary PDL1×CD28 bispecific construct, cx694, was assessed by measuring TNFα production by treated co-cultures of enriched T cells and autologous immature dendritic cells (iDC). TNFα production was measured using an Immunospot Analyzer.

T cells were negatively enriched from PBMCs isolated from normal human donor leukapheresis packs (STEMCELL Technologies). Immature dendritic cells were generated by isolating monocytes from the PBMCs using an adherence-based protocol followed by treatment with recombinant GM-CSF (500 U/mL) and IL-4 (250 U/mL) for 6-7 days. T cells were seeded in wells of a 96-well plate coated with a TNFα capture antibody at $3\times10^5$ cells/well. Autologous iDCs were added at $1.5\times10^4$ cells/well for a 1:20 iDC-to-T cell ratio. Exemplary mono- and bispecific constructs (10 nM) and recombinant IL-7 (5 ng/mL) were added to the co-cultures and the assay plate was incubated at 37° C. for 4 days. The membrane was washed and incubations with secondary and tertiary detection antibodies were performed according to the manufacturer's instructions (Immunospot®). The membrane was imaged and TNFα spot count was determined using an Immunospot® Analyzer.

Figure 7B:
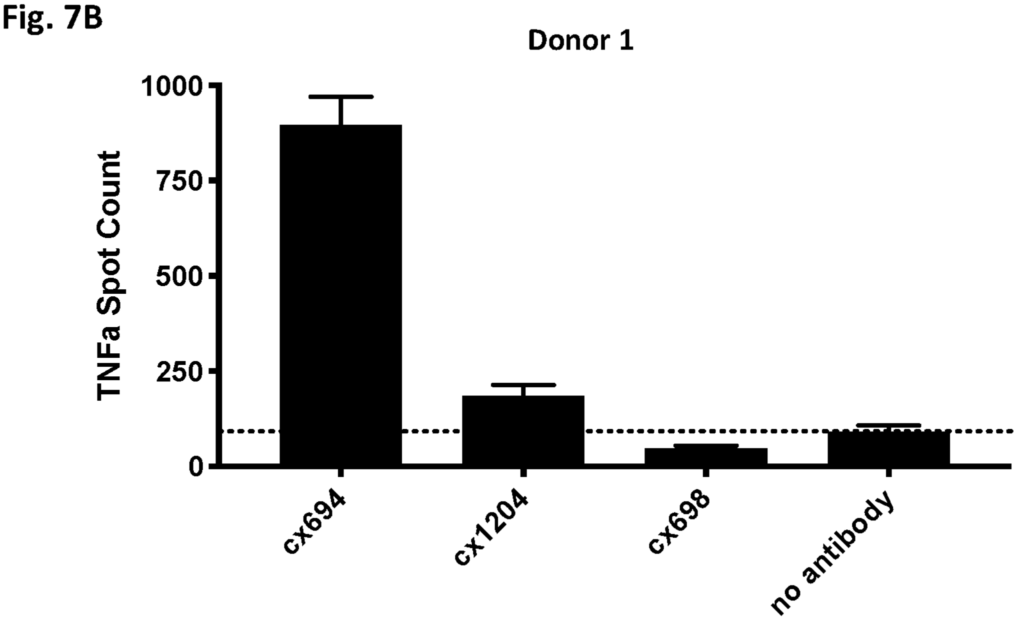
Figure 7C:
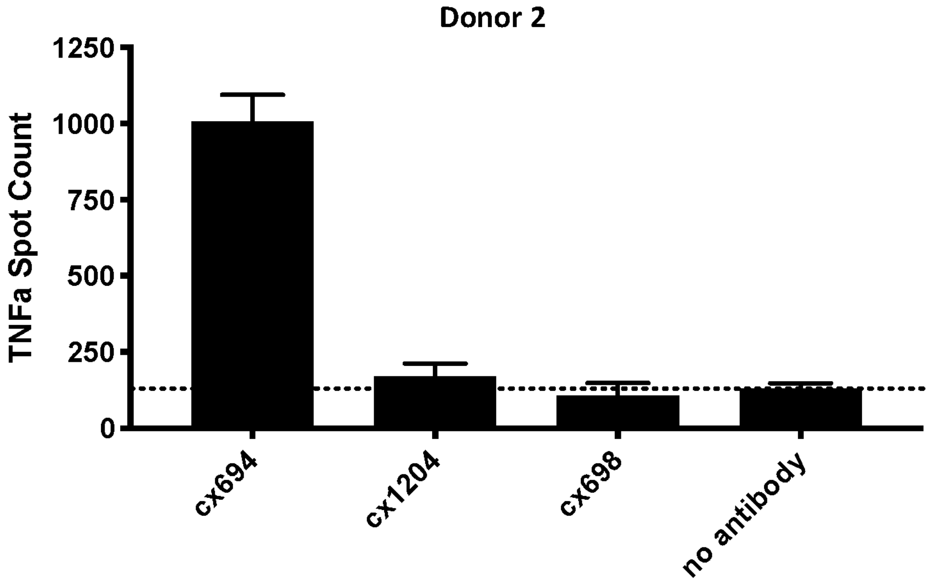

As shown in FIGS. 7B and 7C, addition of the exemplary PDL1×CD28 bispecific construct cx694 to autologous mixed lymphocyte cultures resulted in co-stimulation, as evidenced by the production of TNFα. Targeting PDL1 or CD28 individually with monospecific antibodies cx1204 and cx698, respectively, did not impact the level of cytokine produced by the co-culture of primary cells.

Example 7: Predictive Assay for In Vivo CRS

TGN1412 is a CD28-targeted superagonist antibody that induced severe and rapid cytokine release syndrome (CRS) in healthy volunteers in a clinical trial in 2006 (see e.g., Attarwala, J. Young Pharm. (2010) 2(3):332-36). This response was not predicted from preclinical in vitro experiments with PBMCs cultured under normal physiological conditions. Subsequent method development led to an assay in which cytokine production was measured by PBMCs pre-cultured at high-density, a condition that better mimics conditions in tissues in vivo. Under these modified conditions, TGN1412 induces robust production of TNFα by CD4+ T cells. This assay has become a standard for testing the potential toxicity of T cell activating antibodies.

PBMCs isolated from normal human donor leukapheresis packs (STEMCELL Technologies) were cultured in XVIVO™-15 media at high-density ($10^7$ cells/mL) for 2 days at 37° C. Cells were collected, washed, resuspended in fresh assay media, and seeded in wells of a 96-well plate coated with exemplary generated mono- and bispecific constructs at 10 μg/mL ($2\times10^5$ cells/well). The assay plate was incubated for 2 hours at 37° C., a protein transport inhibitor was added to all wells, and then the assay plate was incubated for an additional 4 hours at 37° C. Cells were washed with PBS, stained with a viability dye, treated with an FcR blocking reagent, and then stained with fluorophore-conjugated anti-human CD3, CD4, CD8, CD56, and CD16 antibodies. The assay plate was incubated for 20 minutes at 4° C. and then cells were washed and resuspended in fixation/permeabilization buffer and incubated for 30 minutes at 4° C. Cells were washed with permeabilization wash buffer and resuspended in permeabilization buffer containing fluorophore-conjugated anti-TNFα antibody. The assay plate was incubated overnight at 4° C. and then cells were washed and resuspended in FACS buffer for analysis using a Quanteon flow cytometer.

Figure 8A:
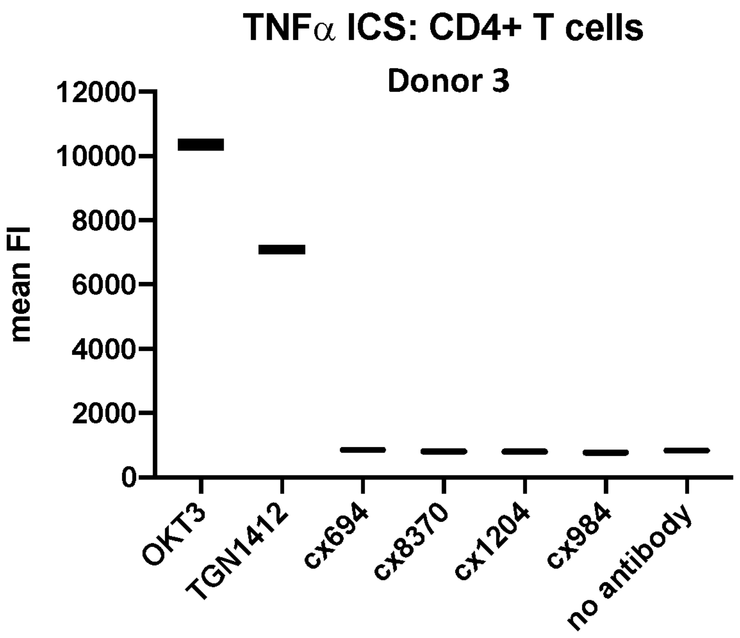
FIGS. 8A and 8B depict the ability of immobilized positive control anti-CD3 (OKT3) and anti-CD28 (TGN1412) antibodies to induce production of TNFα by CD4+ T cells in PBMCs pre-cultured at high density, whereas immobilized proteins containing the exemplary sdAb 1C9 (cx694, cx8370, and cx984) did not induce production of TNFα in this cell population at levels above that of the untreated control sample.
Figure 8B:
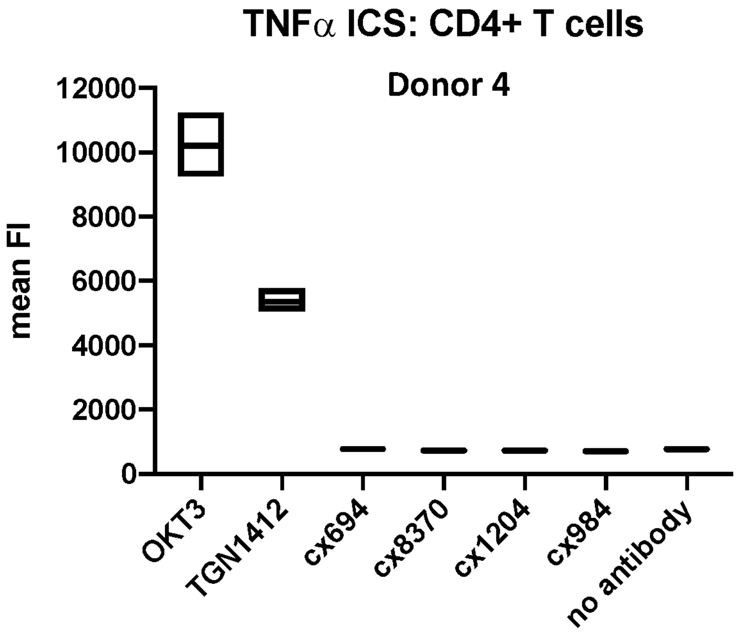

As shown in FIGS. 8A and 8B, both immobilized anti-CD3 antibody and the anti-CD28 superagonist TGN1412 antibody induced production of TNFα in CD4+ T cells from PBMCs pre-cultured at high-density, as expected. Unlike TGN1412, the exemplary monospecific, bivalent CD28 sdAb cx984 did not induce production of TNFα in this cell population at a level above that of the untreated control sample. Likewise, neither of the PDL1×CD28 bispecific constructs (cx694 and cx8370), each bivalent for PDL1 and CD28, induced production of TNFα in this cell population at levels above that of the untreated control sample. Without wishing to be bound by theory, the results indicate that the exemplary generated bivalent mono- and bispecific CD28-targeting constructs do not induce robust production of TNFα by CD4+ T cells, which may indicate a reduced risk of in vivo CRS.

The present invention is not intended to be limited in scope to the particular disclosed embodiments, which are provided, for example, to illustrate various aspects of the invention. Various modifications to the compositions and methods described will become apparent from the description and teachings herein. Such variations may be practiced without departing from the true scope and spirit of the disclosure and are intended to fall within the scope of the present disclosure.

Sequences

| # | SEQUENCE | ANNOTATION |
|---|---|---|
| 1 | GGSGGS | (GGS)2 linker |
| 2 | GGSGGSGGS | (GGS)3 linker |
| 3 | GGSGGSGGSGGS | (GGS)4 linker |
| 4 | GGSGGSGGSGGSGGS | (GGS)5 linker |
| 5 | GGGG | glycine linker |

-continued

Sequences

| # | SEQUENCE | ANNOTATION |
|---|---|---|
| 6 | GGGGG | glycine linker |
| 7 | GGGGGG | glycine linker |
| 8 | PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSRDELT KNQVSLTCLV KGFYPSDIAV EWESNGQPEN NYKTTPPVLD SDGSFFLYSK LTVDKSRWQQ GNVFSCSVMH EALHNHYTQK SLSLSPGK | human IgG1 Fc |
| 9 | PAPGGPSVFLFPPKPKDTLMISRTPEVTCVVVDVSHEDPEVKFNWYVD GVEVHNAKTKPREEQYNSTYRVVSVLTVLHQDWLNGKEYKCKVSN KALPAPIEKTISKAKGQPREPQVYTLPPSRDELTKNQVSLTCLVKGFYP SDIAVEWESNGQPENNYKTTPPVLDSDGSFFLYSKLTVDKSRWQQGN VFSCSVMHEALHNHYTQKSLSLSPGK | Fc xELL |
| 10 | PAPPVAGPSV FLFPPKPKDT LMISRTPEVT CVVVDVSHED PEVQFNWYVD GVEVHNAKTK PREEQFNSTF RVVSVLTVVH QDWLNGKEYK CKVSNKGLPA PIEKTISKTK GQPREPQVYT LPPSREEMTK NQVSLTCLVK GFYPSDISVE WESNGQPENN YKTTPPMLDS DGSFFLYSKL TVDKSRWQQG NVFSCSVMHE ALHNHYTQKS LSLSPGK | human IgG2 Fc |
| 11 | PAPELLGGPS VFLFPPKPKD TLMISRTPEV TCVVVDVSHE DPEVQFKWYV DGVEVHNAKT KPREEQYNST FRVVSVLTVL HQDWLNGKEY KCKVSNKALP APIEKTISKT KGQPREPQVY TLPPSREEMT KNQVSLTCLV KGFYPSDIAV EWESSGQPEN NYNTTPPMLD SDGSFFLYSK LTVDKSRWQQ GNIFSCSVMH EALHNRFTQK SLSLSPGK | human IgG3 Fc |
| 12 | PAPEFLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK | human IgG4 Fc |
| 13 | PAPELLGGPS VFLFPPKPKD TLMISRTPEV TCVVVDVSQE DPEVQFNWYV DGVEVHNAKT KPREEQFNST YRVVSVLTVL HQDWLNGKEY KCKVSNKGLP SSIEKTISKA KGQPREPQVY TLPPSQEEMT KNQVSLTCLV KGFYPSDIAV EWESNGQPEN NYKTTPPVLD SDGSFFLYSR LTVDKSRWQE GNVFSCSVMH EALHNHYTQK SLSLSLGK | human IgG4 Fc |
| 14 | EPKSSDKTHTCPPC | modified IgG1 hinge |
| 15 | DKTHTCPPC | truncated IgG1 hinge |
| 16 | ESKYGPPCPPC | modified IgG4 hinge |
| 17 | GQGTLVTVKPGG | carboxy-terminal sequence |
| 18 | GQGTLVTVEPGG | carboxy-terminal sequence |
| 19 | QVQLVQSGGG VVQPGRSLRL SCKASGYTFT RYTMHWVRQA PGKGLEWIGY INPSRGYTNY NQKVKDRFTI SRDNSKNTAF LQMDSLRPED TGVYFCARYY DDHYCLDYWG QGTPVTVSS | OKT3 VH |
| 20 | DIQMTQSPSS LSASVGDRVT ITCSASSSVS YMNWYQQTPG KAPKRWIYDT SKLASGVPSR FSGSGSGTDY TFTISSLOPE DIATYYCQQW SSNPFTFGQG TKLQIT | OKT3 VL |
| 21 | QVQLVQSGGG VVQPGRSLRL SCKASGYTFT RYTMHWVRQA PGKGLEWIGY INPSRGYTNY NQKVKDRFTI SRDNSKNTAF LQMDSLRPED TGVYFCARYY DDHYSLDYWG QGTPVTVSS | OKT3 humanized VH |

-continued

Sequences

| # | SEQUENCE | ANNOTATION |
|---|---|---|
| 22 | DVQLVQSGAE VKKPGASVKV SCKASGYTFT RYTMHWVRQA PGQGLEWIGY INPSRGYTNY ADSVKGRFTI TTDKSTSTAY MELSSLRSED TATYYCARYY DDHYCLDYWG QGTTVTVSS | OKT3 humanized VH |
| 23 | QVQLVQSGAE LKKPGASVKV SCKASGYTFT RYTMHWVRQA PGQCLEWMGY INPSRGYTNY NQKFKDKATL TADKSTSTAY MELRSLRSDD TAVYYCARYY DDHYSLDYWG QGTLVTVSS | OKT3 humanized VH |
| 24 | QIVLTQSPAI MSASPGEKVT MTCSASSSVS YMNWYQQKSG TSPKRWIYDT SKLASGVPAH FRGSGSGTSY SLTISGMEAE DAATYYCQQW SSNPFTFGSG TKLEIN | OKT3 humanized VL |
| 25 | DIQMTQSPSS LSASVGDRVT ITCRASQSVS YMNWYQQKPG KAPKRWIYDT SKVASGVPAR FSGSGSGTDY SLTINSLEAE DAATYYCQQW SSNPLTFGGG TKVEIK | OKT3 humanized VL |
| 26 | DIQLTQSPSI LSASVGDRVT ITCRASSSVS YMNWYQQKPG KAPKRWIYDT SKVASGVPYR FSGSGSGTEY TLTISSMQPE DFATYYCQQW SSNPLTFGCG TKVEIKRT | OKT3 humanized VL |
| 27 | EVQLVESGGGLVQPKGSLKLSCAASGFTFNTYAMNWVRQAPGKGLE WVARIRSKYNNYATYYADSVKDRFTISRDDSQSILYLQMNNLKTEDT AMYYCVRHGNFGNSYVSWFAYWGQGTLVTVSA | anti-CD3 Hv |
| 28 | QAVVTQESALTTSPGETVTLTCRSSTGAVTTSNYANWVQEKPDHLFT GLIGGTNKRAPGVPARFSGSLIGDKAALTITGAQTEDEAIYFCALWYS NLWVFGGGTKLTVL | anti-CD3 Lv |
| 29 | TYAMN | anti-CD3 VH CDR1 |
| 30 | RIRSKYNNYATYYADSVKD | anti-CD3 VH CDR2 |
| 31 | HGNFGNSYVSWFAY | anti-CD3 VH CDR3 |
| 32 | RSSTGAVTTSNYAN | anti-CD3 VL CDR1 |
| 33 | GTNKRAP | anti-CD3 VL CDR2 |
| 34 | ALWYSNLWV | anti-CD3 VL CDR3 |
| 35 | EVQLVESGGGLVQPGGSLRLSCAASGFTFSTYAMNWVRQAPGKGLE WVGRIRSKYNNYATYYADSVKDRFTISRDDSKNSLYLQMNSLKTEDT AVYYCVRHGNFGNSYVSWFAYWGQGTLVTVSS | anti-CD3 VH1 |
| 36 | EVKLVESGGGLVQPGGSLRLSCAASGFTFNTYAMNWVRQAPGKGLE WVARIRSKYNNYATYYADSVKDRFTISRDDSKSSLYLQMNNLKTEDT AMYYCVRHGNFGNSYVSWFAYWGQGTLVTVSS | anti-CD3 VH2 |
| 37 | EVKLVESGGGLVKPGRSLRLSCAASGFTFNTYAMNWVRQAPGKGLE WVARIRSKYNNYATYYADSVKDRFTISRDDSKSILYLQMNNLKTEDT AMYYCVRHGNFGNSYVSWFAYWGQGTLVTVSS | anti-CD3 VH3 |
| 38 | EVKLVESGGGLVKPGRSLRLSCAASGFTFNTYAMNWVRQAPGKGLE WVARIRSKYNNYATYYADSVKDRFTISRDDSKSILYLQMNSLKTEDT AMYYCVRHGNFGNSYVSWFAYWGQGTLVTVSS | anti-CD3 VH4 |
| 39 | EVKLVESGGGLVKPGRSLRLSCAASGFTFNTYAMNWVRQAPGKGLE WVARIRSKYNNYATYYADSVKDRFTISRDDSKSILYLQMNSLKTEDT AMYYCVRHGNFGNSYVSWFAYWGQGTLVTVSS | anti-CD3 VH5 |
| 40 | EVQLLESGGGLVQPGGSLRLSCAASGFTFSTYAMNWVRQAPGKGLE WVSRIRSKYNNYATYYADSVKGRFTISRDDSKNTLYLQMNSLRAEDT AVYYCVRHGNFGNSYVSWFAYWGQGTLVTVSS | anti-CD3 VH6 |
| 41 | EVQLVESGGGLVQPGGSLRLSCAASGFTFSTYAMSWVRQAPGKGLE | anti-CD3 VH7 |

-continued

Sequences

| # | SEQUENCE | ANNOTATION |
|---|---|---|
| | WVGRIRSKYNNYATYYADSVKGRFTISRDDSKNTLYLQMNSLRAED TAVYYCVRHGNFGDSYVSWFAYWGQGTLVTVSS | |
| 42 | EVQLVESGGGLVQPGGSLKLSCAASGFTFNKYAMNWVRQAPGKGLE WVARIRSKYNNYATYYADSVKDRFTISRDDSKNTAYLQMNNLKTED TAVYYCVRHGNFGNSYISYWAYWGQGTLVTVS | anti-CD3 VH8 |
| 43 | EVQLVESGGGLVQPGGSLRLSCAASGFTFNTYAMNWVRQAPGKGLE WVARIRSKYNNYATYYADSVKGRFTISRDDSKNTLYLQMNSLRAED TAVYYCVRHGNFGNSYVSWFAYWGQGTTVTVSS | anti-CD3 VH9 |
| 44 | EVQLVESGGGLVQPGGSLRLSCAASGFTFNTYAMNWVRQAPGKGLE WVARIRSKYNNYATYYADSVKGRFTISRDDSKNTLYLQMNSLRAED TAVYYCVRHGNFGNSYVSYFAYWGQGTTVTVSS | anti-CD3 VH10 |
| 45 | EVQLVESGGGLVQPKGSLKLSCAASGFTFNTYAMNWVRQAPGKGLE WVARIRSKYNNYATYYADSVKDRFTISRDDSQSILYLQMNNLKTEDT AMYYCVRHGNFGNSYVSWFAYWGQGTLVTVSS | anti-CD3 VH11 |
| 46 | EVQLVESGGGLVQPGGSLRLSCAASGFTFNTYAMNWVRQAPGKGLE WVARIRSKYNNYATYYADSVKGRFTISRDDAKNTLYLQMSSLRAED TAVYYCVRHGNFGNSYVSWFAYWGQGTLVTVKP | anti-CD3 VH12 |
| 47 | EVQLVESGGGLVQPGGSLRLSCAASGFTFNTYAMNWVRQAPGKCLE WVARIRSKYNNYATYYADSVKGRFTISRDDAKNTLYLQMSSLRAED TAVYYCVRHGNFGNSYVSWFAYWGQGTLVTVKP | anti-CD3 VH13 |
| 48 | EVQLVESGGGLVQPGGSLRLSCAASGFTFNTYAMNWVRQAPGKGLE WVARIRSKYNNYATYYADSVKGRFTISRDDAKNTLYLQMSSLRAED TAVYYCVRHGNFGNSYVSWFAYWGCGTLVTVKP | anti-CD3 VH14 |
| 49 | EVQLVESGGGLVQPGGSLRLSCAASGFTFSTYAMNWVRQAPGKGLE WVARIRSKYNNYATYYADSVKGRFTISRDDAKNTLYLQMSSLRAED TAVYYCVRHGNFGNSYVSWFAYWGQGTLVTVSS | anti-CD3 VH15 |
| 50 | EVQLVESGGGLVQPGGSLRLSCAASGFTFNTYAMNWVRQAPGKGLE WVSRIRSKYNNYATYYADSVKGRFTISRDDAKNTLYLQMSSLRAEDT AVYYCVRHGNFGNSYVSWFAYWGQGTLVTVSS | anti-CD3 VH16 |
| 51 | EVQLVESGGGLVQPGGSLRLSCAASGFTFSTYAMNWVRQAPGKGLE WVSRIRSKYNNYATYYADSVKGRFTISRDDAKNTLYLQMSSLRAEDT AVYYCVRHGNFGNSYVSWFAYWGQGTLVTVSS | anti-CD3 VH17 |
| 52 | EVQLVESGGGLVQPGGSLRLSCAASGFTFSTYAMNWVRQAPGKCLE WVARIRSKYNNYATYYADSVKGRFTISRDDAKNTLYLQMSSLRAED TAVYYCVRHGNFGNSYVSWFAYWGQGTLVTVSS | anti-CD3 VH18 |
| 53 | EVQLVESGGGLVQPGGSLRLSCAASGFTFNTYAMNWVRQAPGKCLE WVSRIRSKYNNYATYYADSVKGRFTISRDDAKNTLYLQMSSLRAEDT AVYYCVRHGNFGNSYVSWFAYWGQGTLVTVSS | anti-CD3 VH19 |
| 54 | EVQLVESGGGLVQPGGSLRLSCAASGFTFSTYAMNWVRQAPGKCLE WVSRIRSKYNNYATYYADSVKGRFTISRDDAKNTLYLQMSSLRAEDT AVYYCVRHGNFGNSYVSWFAYWGQGTLVTVSS | anti-CD3 VH20 |
| 55 | EVQLVESGGGLVQPGGSLRLSCAASGFTFSTYAMNWVRQAPGKCLE WVGRIRSKYNNYATYYADSVKDRFTISRDDSKNSLYLQMNSLKTEDT AVYYCVRHGNFGNSYVSWFAYWGQGTLVTVSS | anti-CD3 VH21 |
| 56 | EVKLVESGGGLVQPGGSLRLSCAASGFTFNTYAMNWVRQAPGKCLE WVARIRSKYNNYATYYADSVKDRFTISRDDSKSSLYLQMNNLKTEDT AMYYCVRHGNFGNSYVSWFAYWGQGTLVTVSS | anti-CD3 VH22 |
| 57 | EVKLVESGGGLVKPGRSLRLSCAASGFTFNTYAMNWVRQAPGKCLE WVARIRSKYNNYATYYADSVKDRFTISRDDSKSILYLQMNNLKTEDT AMYYCVRHGNFGNSYVSWFAYWGQGTLVTVSS | anti-CD3 VH23 |
| 58 | EVKLVESGGGLVKPGRSLRLSCAASGFTFNTYAMNWVRQAPGKCLE WVARIRSKYNNYATYYADSVKDRFTISRDDSKSILYLQMNSLKTEDT AMYYCVRHGNFGNSYVSWFAYWGQGTLVTVSS | anti-CD3 VH24 |
| 59 | EVKLVESGGGLVKPGRSLRLSCAASGFTFNTYAMNWVRQAPGKCLE WVARIRSKYNNYATYYADSVKDRFTISRDDSKSILYLQMNSLKTEDT AMYYCVRHGNFGNSYVSWFAYWGQGTLVTVSS | anti-CD3 VH25 |

-continued

Sequences

| # | SEQUENCE | ANNOTATION |
|---|---|---|
| 60 | EVQLLESGGGLVQPGGSLRLSCAASGFTFSTYAMNWVRQAPGKCLE WVSRIRSKYNNYATYYADSVKGRFTISRDDSKNTLYLQMNSLRAEDT AVYYCVRHGNFGNSYVSWFAYWGQGTLVTVSS | anti-CD3 VH26 |
| 61 | EVQLVESGGGLVQPGGSLRLSCAASGFTFSTYAMSWVRQAPGKCLE WVGRIRSKYNNYATYYADSVKGRFTISRDDSKNTLYLQMNSLRAED TAVYYCVRHGNFGDSYVSWFAYWGQGTLVTVSS | anti-CD3 VH27 |
| 62 | EVQLVESGGGLVQPGGSLKLSCAASGFTFNKYAMNWVRQAPGKCLE WVARIRSKYNNYATYYADSVKDRFTISRDDSKNTAYLQMNNLKTED TAVYYCVRHGNFGNSYISYWAYWGQGTLVTVS | anti-CD3 VH28 |
| 63 | EVQLVESGGGLVQPGGSLRLSCAASGFTFNTYAMNWVRQAPGKCLE WVARIRSKYNNYATYYADSVKGRFTISRDDSKNTLYLQMNSLRAED TAVYYCVRHGNFGNSYVSWFAYWGQGTTVTVSS | anti-CD3 VH29 |
| 64 | EVQLVESGGGLVQPGGSLRLSCAASGFTFNTYAMNWVRQAPGKCLE WVARIRSKYNNYATYYADSVKGRFTISRDDSKNTLYLQMNSLRAED TAVYYCVRHGNFGNSYVSYFAYWGQGTTVTVSS | anti-CD3 VH30 |
| 65 | EVQLVESGGGLVQPKGSLKLSCAASGFTFNTYAMNWVRQAPGKCLE WVARIRSKYNNYATYYADSVKDRFTISRDDSQSILYLQMNNLKTEDT AMYYCVRHGNFGNSYVSWFAYWGQGTLVTVSS | anti-CD3 VH31 |
| 66 | QAVVTQESALTTSPGETVTLTCRSSTGAVTTSNYANWVQEKPDHLFT GLIGGTNKRAPGVPARFSGSLIGDKAALTITGAQTEDEAIYFCALWYS NLWVFGGGTKLTVL | anti-CD3 VL1 |
| 67 | QAVVTQEPSLTVSPGGTVTLTCGSSTGAVTTSNYANWVQQKPGKSPR GLIGGTNKRAPGVPARFSGSLLGGKAALTISGAQPEDEADYYCALWY SNHWVFGCGTKLEIK | anti-CD3 VL2 |
| 68 | QAVVTQEPSLTVSPGGTVTLTCRSSTGAVTTSNYANWVQQKPGQAPR GLIGGTNKRAPWTPARFSGSLLGGKAALTITGAQAEDEADYYCALW YSNLWVFGGGTKLTVL | anti-CD3 VL3 |
| 69 | QAVVTQEPSFSVSPGGTVTLTCRSSTGAVTTSNYANWVQQTPGQAFR GLIGGTNKRAPGVPARFSGSLIGDKAALTITGAQADDESIYFCALWYS NLWVFGGGTKLTVL | anti-CD3 VL4 |
| 70 | QAVVTQEPSFSVSPGGTVTLTCRSSTGAVTTSNYANWVQQTPGQAFR GLIGGTNKRAPGVPARFSGSILGNKAALTITGAQADDESIYFCALWYS NLWVFGGGTKLTVL | anti-CD3 VL5 |
| 71 | QAVVTQEPSFSVSPGGTVTLTCRSSTGAVTTSNYANWVQQTPGQAFR GLIGGTNKRAPGVPARFSGSILGNKAALTITGAQADDESDYYCALWY SNLWVFGGGTKLTVL | anti-CD3 VL6 |
| 72 | QAVVTQEPSLTVSPGGTVTLTCGSSTGAVTTSNYANWVQEKPGQAFR GLIGGTNKRAPGTPARFSGSLLGGKAALTLSGAQPEDEAEYYCALWY SNLWVFGGGTKLTVL | anti-CD3 VL7 |
| 73 | QTVVTQEPSLTVSPGGTVTLTCGSSTGAVTSGNYPNWVQQKPGQAPR GLIGGTKFLAPGTPARFSGSLLGGKAALTLSGVQPEDEAEYYCVLWY SNRWVFGGGTKLTVL | anti-CD3 VL8 |
| 74 | QAVVTQEPSLTVSPGGTVTLTCGSSTGAVTTSNYANWVQQKPGQAFR GLIGGTNKRAPGVPARFSGSLLGGKAALTISGAQPEDEADYYCALWY SNHWVFGGGTKLEIK | anti-CD3 VL9 |
| 75 | QAVVTQEPSLTVSPGGTVTLTCGSSTGAVTTSNYANWVQQKPGQAFR GLIGGTNKRAPGVPARFSGSLLGGKAALTISGAQPEDEADYYCALWY SNHWVFGCGTKLEIK | anti-CD3 VL10 |
| 76 | QAVVTQEPSLTVSPGGTVTLTCGSSTGAVTTSNYANWVQQKPGQCFR GLIGGTNKRAPGVPARFSGSLLGGKAALTISGAQPEDEADYYCALWY SNHWVFGEGTKLEIK | anti-CD3 VL11 |
| 77 | QAVVTQESALTTSPGETVTLTCRSSTGAVTTSNYANWVQEKPDHLFT GLIGGTNKRAPGVPARFSGSLIGDKAALTITGAQTEDEAIYFCALWYS NLWVFGCGTKLTVL | anti-CD3 VL12 |
| 78 | QAVVTQEPSLTVSPGGTVTLTCGSSTGAVTTSNYANWVQQKPGKSPR GLIGGTNKRAPGVPARFSGSLLGGKAALTISGAQPEDEADYYCALWY SNHWVFGGGTKLEIK | anti-CD3 VL13 |

-continued

| Sequences | | |
|---|---|---|
| # | SEQUENCE | ANNOTATION |
| 79 | QAVVTQEPSLTVSPGGTVTLTCRSSTGAVTTSNYANWVQQKPGQAPR GLIGGTNKRAPWTPARFSGSLLGGKAALTITGAQAEDEADYYCALW YSNLWVFGCGTKLTVL | anti-CD3 VL14 |
| 80 | QAVVTQEPSFSVSPGGTVTLTCRSSTGAVTTSNYANWVQQTPGQAFR GLIGGTNKRAPGVPARFSGSLIGDKAALTITGAQADDESIYFCALWYS NLWVFGGGTKLTVL | anti-CD3 VL15 |
| 81 | QAVVTQEPSFSVSPGGTVTLTCRSSTGAVTTSNYANWVQQTPGQAFR GLIGGTNKRAPGVPARFSGSILGNKAALTITGAQADDESIYFCALWYS NLWVFGCGTKLTVL | anti-CD3 VL16 |
| 82 | QAVVTQEPSFSVSPGGTVTLTCRSSTGAVTTSNYANWVQQTPGQAFR GLIGGTNKRAPGVPARFSGSILGNKAALTITGAQADDESDYYCALWY SNLWVFGCGTKLTVL | anti-CD3 VL17 |
| 83 | QAVVTQEPSLTVSPGGTVTLTCGSSTGAVTTSNYANWVQEKPGQAFR GLIGGTNKRAPGTPARFSGSLLGGKAALTLSGAQPEDEAEYYCALWY SNLWVFGCGTKLTVL | anti-CD3 VL18 |
| 84 | QTVVTQEPSLTVSPGGTVTLTCGSSTGAVTSGNYPNWVQQKPGQAPR GLIGGTKFLAPGTPARFSGSLLGGKAALTLSGVQPEDEAEYYCVLWY SNRWVFGCGTKLTVL | anti-CD3 VL19 |
| 85 | QVQLQESGGG LVQAGGSLRL SCAASGRTFS NYHMGWFRQA PGKERELVAA ISGSGGSTYY TDSVKGRFTI SRNNAKNTMS LQMSNLKPED TGVYYCTTPT EKGSSIDYWG QGTQVTVSSG RYPYDVPDY | anti-CD3 VHH |
| 86 | MLRLLLALNLFPSIQVTGNKILVKQSPMLVAYDNAVNLSCKYSYNLF SREFRASLHKGLDSAVEVCVVYGNYSQQLQVYSKTGFNCDGKLGNE SVTFYLQNLYVNQTDIYFCKIEVMYPPPYLDNEKSNGTIIHVKGKHLC PSPLFPGPSKPFWVLVVVGGVLACYSLLVTVAFIIFWVRSKRSRLLHS DYMNMTPRRPGPTRKHYQPYAPPRDFAAYRS | Canonical CD28 sequence (e.g., UniProt No. P10747) |
| 87 | GGG | linker |
| 88 | NKILVKQSPMLVAYDNAVNLSCKYSYNLFSREFRASLHKGLDSAVEV CVVYGNYSQQLQVYSKTGFNCDGKLGNESVTFYLQNLYVNQTDIYF CKIEVMYPPPYLDNEKSNGTIIHVKGKHLCPSPLFPGPSKP | CD28 ECD (aa 19-152 of human CD28, e.g., UniProt No. P10747) |
| 89 | GGSGGGGS | linker |
| 90 | GGGSGS | linker |
| 91 | RVKFSRSADAPAYQQGQNQLYNELNLGRREEYDVLDKRRGRDPEMG GKPRRKNPQEGLYNELQKDKMAEAYSEIGMKGERRRGKGHDGLYQ GLSTATKDTYDALHMQALPPR | CD3zeta signaling domain |
| 92 | KRGRKKLLYIFKQPFMRPVQTTQEEDGCSCRFPEEEEGGCEL | 4-1BB-derived costimulatory domain |
| 93 | SKRSRLLHSDYMNMTPRRPGPTRKHYQPYAPPRDFAAYRS | CD28-derived costimulatory domain |
| 94 | RSKRSRLLHSDYMNMTPRRPGPTRKHYQPYAPPRDFAAYRS | CD28-derived costimulatory domain 2 |
| 95 | FWVRSKRSRLLHSDYMNMTPRRPGPTRKHYQPYAPPRDFAAYRS | CD28-derived costimulatory domain 3 |
| 96 | KPTTTPAPRPPTPAPTIASQPLSLRPEASRPAAGGAVHTRGLDFASDIYI WAPLAGTCGVLLLSLVITLYC | CD8-derived hinge and transmembrane domain |
| 97 | AKPTTTPAPRPPTPAPTIASQPLSLRPEACRPAAGGAVHTRGLDFACDI YIWAPLAGTCG VLLLSLVIT | CD8-derived hinge and transmembrane domain |

-continued

Sequences

| # | SEQUENCE | ANNOTATION |
|---|---|---|
| 98 | KPTTTPAPRPPTPAPTIASQPLSLRPEACRPAAGGAVHTRGLDFACDIYI WAPLAGTCGVLLLSLVIT | CD8 hinge and transmembrane domain |
| 99 | EVQLLESGGGEVQPGGSLRLSCAASGGIFAIKPISWYRQAPGKQREWV STTTSSGATNYAESVKGRFTISRDNAKNTLYLQMSSLRAEDTAVYYC NVFEYWGQGTLVTVKP | PDL1 sdAb |
| 100 | GGIFAIKPIS | CDR1 PDL1 |
| 101 | TTTSSGATN | CDR2 PDL1 |
| 102 | FEY | CDR3 PDL1 |
| 103 | DKTHTCPPCPAPELLGGPSVFLFPPKPKDTLMISRTPEVTCVVVDVSHE DPEVKFNWYVDGVEVHNAKTKPREEQYNSTYRVVSVLTVLHQDWL NGKEYKCKVSNKALPAPIEKTISKAKGQPREPQVYTLPPCRDELTKNQ VSLWCLVKGFYPSDIAVEWESNGQPENNYKTTPPVLDSDGSFFLYSK LTVDKSRWQQGNVFSCSVMHEALHNHYTQKSLSLSPT | Knob Fc |
| 104 | DKTHTCPPCPAPELLGGPSVFLFPPKPKDTLMRSRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVCTLPPSRDELTKN QVSLSCAVKGFYPSDIAVEWESNGQPENNYKTTPPVLDSDGSFFLVSK LTVDKSRWQQGNVFSCSVMHEALHNHYTQKSLSLSPT | Hole Fc |
| 105 | DKTHTCPPCPAPGGPSVFLFPPKPKDTLMISRTPEVTCVVVDVSHEDPE VKFNWYVDGVEVHNAKTKPREEQYNSTYRVVSVLTVLHQDWLNGK EYKCKVSNKALPAPIEKTISKAKGQPREPQVYTLPPCRDELTKNQVSL WCLVKGFYPSDIAVEWESNGQPENNYKTTPPVLDSDGSFFLYSKLTV DKSRWQQGNVFSCSVMHEALHNHYTQKSLSLSPT | Knob Fc |
| 106 | DKTHTCPPCPAPGGPSVFLFPPKPKDTLMRSRTPEVTCVVVDVSHEDP EVKFNWYVDGVEVHNAKTKPREEQYNSTYRVVSVLTVLHQDWLNG KEYKCKVSNKALPAPIEKTISKAKGQPREPQVCTLPPSRDELTKNQVS LSCAVKGFYPSDIAVEWESNGQPENNYKTTPPVLDSDGSFFLVSKLTV DKSRWQQGNVFSCSVMHEALHNHYTQKSLSLSPT | Hole Fc |
| 107 | DKTHTCPPCPAPELLGGPSVFLFPPKPKDTLMISRTPEVTCVVVDVSHE DPEVKFNWYVDGVEVHNAKTKPREEQYNSTYRVVSVLTVLHQDWL NGKEYKCKVSNKALPAPIEKTISKAKGQPREPQVYTLPPCRDELTKNQ VSLWCLVKGFYPSDIAVEWESNGQPENNYKTTPPVLDSDGSFFLYSK LTVDKSRWQQGNVFSCSVMHEALHNHYTQKSLSLSPG | Knob Fc |
| 108 | DKTHTCPPCPAPELLGGPSVFLFPPKPKDTLMRSRTPEVTCVVVDVSH EDPEVKFNWYVDGVEVHNAKTKPREEQYNSTYRVVSVLTVLHQDW LNGKEYKCKVSNKALPAPIEKTISKAKGQPREPQVCTLPPSRDELTKN QVSLSCAVKGFYPSDIAVEWESNGQPENNYKTTPPVLDSDGSFFLVSK LTVDKSRWQQGNVFSCSVMHEALHNHYTQKSLSLSPG | Hole Fc |
| 109 | DKTHTCPPCPAPGGPSVFLFPPKPKDTLMISRTPEVTCVVVDVSHEDPE VKFNWYVDGVEVHNAKTKPREEQYNSTYRVVSVLTVLHQDWLNGK EYKCKVSNKALPAPIEKTISKAKGQPREPQVYTLPPCRDELTKNQVSL WCLVKGFYPSDIAVEWESNGQPENNYKTTPPVLDSDGSFFLYSKLTV DKSRWQQGNVFSCSVMHEALHNHYTQKSLSLSPG | Knob Fc |
| 110 | DKTHTCPPCPAPGGPSVFLFPPKPKDTLMRSRTPEVTCVVVDVSHEDP EVKFNWYVDGVEVHNAKTKPREEQYNSTYRVVSVLTVLHQDWLNG KEYKCKVSNKALPAPIEKTISKAKGQPREPQVCTLPPSRDELTKNQVS LSCAVKGFYPSDIAVEWESNGQPENNYKTTPPVLDSDGSFFLVSKLTV DKSRWQQGNVFSCSVMHEALHNHYTQKSLSLSPG | Hole Fc |
| 111 | DKTHTCPPCPAPELLGGPSVFLFPPKPKDTLMISRTPEVTCVVVDVSHE DPEVKFNWYVDGVEVHNAKTKPREEQYNSTYRVVSVLTVLHQDWL NGKEYKCKVSNKALPAPIEKTISKAKGQPREPQVCTLPPSRDELTKNQ VSLSCAVKGFYPSDIAVEWESNGQPENNYKTTPPVLDSDGSFFLVSKL TVDKSRWQQGNVFSCSVMHEALHNRYTQKSLSLSPT | Hole Fc |
| 112 | DKTHTCPPCPAPGGPSVFLFPPKPKDTLMISRTPEVTCVVVDVSHEDPE VKFNWYVDGVEVHNAKTKPREEQYNSTYRVVSVLTVLHQDWLNGK EYKCKVSNKALPAPIEKTISKAKGQPREPQVCTLPPSRDELTKNQVSLS CAVKGFYPSDIAVEWESNGQPENNYKTTPPVLDSDGSFFLVSKLTVD KSRWQQGNVFSCSVMHEALHNRYTQKSLSLSPT | Hole Fc |

-continued

Sequences

| # | SEQUENCE | ANNOTATION |
|---|---|---|
| 113 | DKTHTCPPCPAPELLGGPSVFLFPPKPKDTLMISRTPEVTCVVVDVSHE DPEVKFNWYVDGVEVHNAKTKPREEQYNSTYRVVSVLTVLHQDWL NGKEYKCKVSNKALPAPIEKTISKAKGQPREPQVCTLPPSRDELTKNQ VSLSCAVKGFYPSDIAVEWESNGQPENNYKTTPPVLDSDGSFFLVSKL TVDKSRWQQGNVFSCSVMHEALHNRYTQKSLSLSPG | Hole Fc |
| 114 | DKTHTCPPCPAPGGPSVFLFPPKPKDTLMISRTPEVTCVVVDVSHEDPE VKFNWYVDGVEVHNAKTKPREEQYNSTYRVVSVLTVLHQDWLNGK EYKCKVSNKALPAPIEKTISKAKGQPREPQVCTLPPSRDELTKNQVSLS CAVKGFYPSDIAVEWESNGQPENNYKTTPPVLDSDGSFFLVSKLTVD KSRWQQGNVFSCSVMHEALHNRYTQKSLSLSPG | Hole Fc |
| 115 | DKTHTCPPCPAPELLGGPSVFLFPPKPKDTLYISRTPEVTCVVVDVSHE DPEVKFNWYVDGVEVHNAKTKPREEQYNSTYRVVSVLTVLHQDWL NGKEYKCKVSNKALPAPIEKTISKAKGQPREPQVYTLPPCRDELTKNQ VSLWCLVKGFYPSDIAVEWESNGQPENNYKTTPPVLDSDGSFFLYSK LTVDKSRWQQGNVFSCSVVHEALHNHYTQKSLSLSPT | Knob Fc |
| 116 | DKTHTCPPCPAPGGPSVFLFPPKPKDTLYISRTPEVTCVVVDVSHEDPE VKFNWYVDGVEVHNAKTKPREEQYNSTYRVVSVLTVLHQDWLNGK EYKCKVSNKALPAPIEKTISKAKGQPREPQVYTLPPCRDELTKNQVSL WCLVKGFYPSDIAVEWESNGQPENNYKTTPPVLDSDGSFFLYSKLTV DKSRWQQGNVFSCSVVHEALHNHYTQKSLSLSPT | Knob Fc |
| 117 | DKTHTCPPCPAPELLGGPSVFLFPPKPKDTLYISRTPEVTCVVVDVSHE DPEVKFNWYVDGVEVHNAKTKPREEQYNSTYRVVSVLTVLHQDWL NGKEYKCKVSNKALPAPIEKTISKAKGQPREPQVYTLPPCRDELTKNQ VSLWCLVKGFYPSDIAVEWESNGQPENNYKTTPPVLDSDGSFFLYSK LTVDKSRWQQGNVFSCSVVHEALHNHYTQKSLSLSPG | Knob Fc |
| 118 | DKTHTCPPCPAPGGPSVFLFPPKPKDTLYISRTPEVTCVVVDVSHEDPE VKFNWYVDGVEVHNAKTKPREEQYNSTYRVVSVLTVLHQDWLNGK EYKCKVSNKALPAPIEKTISKAKGQPREPQVYTLPPCRDELTKNQVSL WCLVKGFYPSDIAVEWESNGQPENNYKTTPPVLDSDGSFFLYSKLTV DKSRWQQGNVFSCSVVHEALHNHYTQKSLSLSPG | Knob Fc |
| 119 | DKTHTCPPCPAPELLGGPSVFLFPPKPKDTLYISRTPEVTCVVVDVSHE DPEVKFNWYVDGVEVHNAKTKPREEQYNSTYRVVSVLTVLHQDWL NGKEYKCKVSNKALPAPIEKTISKAKGQPREPQVCTLPPSRDELTKNQ VSLSCAVKGFYPSDIAVEWESNGQPENNYKTTPPVLDSDGSFFLVSKL TVDKSRWQQGNVFSCSVVHEALHNRYTQKSLSLSPT | Hole Fc |
| 120 | DKTHTCPPCPAPGGPSVFLFPPKPKDTLYISRTPEVTCVVVDVSHEDPE VKFNWYVDGVEVHNAKTKPREEQYNSTYRVVSVLTVLHQDWLNGK EYKCKVSNKALPAPIEKTISKAKGQPREPQVCTLPPSRDELTKNQVSLS CAVKGFYPSDIAVEWESNGQPENNYKTTPPVLDSDGSFFLVSKLTVD KSRWQQGNVFSCSVVHEALHNRYTQKSLSLSPT | Hole Fc |
| 121 | DKTHTCPPCPAPELLGGPSVFLFPPKPKDTLYISRTPEVTCVVVDVSHE DPEVKFNWYVDGVEVHNAKTKPREEQYNSTYRVVSVLTVLHQDWL NGKEYKCKVSNKALPAPIEKTISKAKGQPREPQVCTLPPSRDELTKNQ VSLSCAVKGFYPSDIAVEWESNGQPENNYKTTPPVLDSDGSFFLVSKL TVDKSRWQQGNVFSCSVVHEALHNRYTQKSLSLSPG | Hole Fc |
| 122 | DKTHTCPPCPAPGGPSVFLFPPKPKDTLYISRTPEVTCVVVDVSHEDPE VKFNWYVDGVEVHNAKTKPREEQYNSTYRVVSVLTVLHQDWLNGK EYKCKVSNKALPAPIEKTISKAKGQPREPQVCTLPPSRDELTKNQVSLS CAVKGFYPSDIAVEWESNGQPENNYKTTPPVLDSDGSFFLVSKLTVD KSRWQQGNVFSCSVVHEALHNRYTQKSLSLSPG | Hole Fc |
| 123 | (GGGGS)n, wherein n is 1 to 5 | Linker |
| 124 | (GGGGGS)n, wherein n is 1 to 4 | Linker |
| 125 | GGGGS | Linker |
| 126 | GGGGGS | Linker |
| 127 | GGGGGSGGGGGSGGGGGS | Linker |
| 128 | GGGGSGGGGSGGGGS | Linker |
| 129 | GGSGGGGSGGGGSGGGGS | Linker |
| 130 | Glyx-Xaa-Glyy-Xaa-Glyz | Linker |

-continued

Sequences

| # | SEQUENCE | ANNOTATION |
|---|---|---|
| | Xaa is indepen-<br>dently selected from A, V, L, I, M, F, W, P, G, S, T, C, Y, N, Q,<br>K, R, H, D, or E<br>x, y, and z are each integers in the range from 1-5 | |
| 131 | Gly-Gly-Gly-Xaa-Gly-Gly-Gly-Xaa-Gly-Gly-Gly<br>Xaa is indepen-<br>dently selected from A, V, L, I, M, F, W, P, G, S, T, C, Y, N, Q,<br>K, R, H, D, or E | Linker |
| 132 | (SSSSG)n<br>n = 1-9 | Linker |
| 133 | GGGGG-C-GGGGG | Linker |
| 134 | (EAAAK)n | Linker |
| 135 | AS-(AP)n-GT<br>n = 2-20 | Linker |
| 136 | AS-(EAAAK)n-GT<br>n = 2-20 | Linker |
| 137 | (GGGGA)n<br>n = 2-20 | Linker |
| 138 | (PGGGS)n<br>n = 2-20 | Linker |
| 139 | (AGGGS)n<br>n = 2-20 | Linker |
| 140 | GGS-(EGKSSGSGSESKST)n-GGS<br>n = 2-20 | Linker |
| 141 | SSSASASSA | Linker |
| 142 | GSPGSPG | Linker |
| 143 | ATTTGSSPGPT | Linker |
| 144 | X1 X2 X3 X4 X5 (P4 P3 P2 P1 ↓ P1')<br>X1 = I, L, Y, M, F, V, or A; (P4 = I, L, Y, M, F, V, or A)<br>X2 = A, G, S, V, E, D, Q, N, or Y; (P3 = A, G, S, V, E, D, Q, N, or Y)<br>X3 = H, P, A, V, G, S, or T; (P2 = H, P, A, V, G, S, or T)<br>X4 = D or E; (P1 = D or E)<br>X5 = I, L, Y, M, F, V, T, S, G or A (P1' = I, L, Y, M, F, V, T, S, G or A) | Linker consensus |
| 145 | X1 E X3 D X5 (P4 P3 P2 P1 ↓ P1')<br>X1 = I or L; (P4 = I or L)<br>(P3 = E)<br>X3 = P or A; (P2 = P or A)<br>X5 = I, V, T, S, or G (P1' = I, V, T, S, or G) | Linker consensus |
| 146 | LEAD | granzyme B<br>substrate |
| 147 | LEPD | Linker |
| 148 | LEAE | Linker |
| 149 | IEPDI | Linker |
| 150 | LEPDG | Linker |
| 151 | LEADT | Linker |
| 152 | IEPDG | Linker |
| 153 | IEPDV | Linker |
| 154 | IEPDS | Linker |
| 155 | IEPDT | Linker |
| 156 | X1QARX5 (P1QAR↓(A/V)) | Linker consensus |

-continued

Sequences

| # | SEQUENCE | ANNOTATION |
|---|---|---|
| | X1 = any amino acid; (P1 is any amino acid)<br>X5 = A or V | |
| 157 | RQARX5 (RQAR(A/V))<br>X5 = A or V | Linker |
| 158 | RQAR | matriptase substrate |
| 159 | RQARV | linker |
| 160 | X1X2 X3 X4 (P3 P2 P1 ↓ P1')<br>X1 = P, V or A; (P3 = P, V or A)<br>X2 = Q or D; (P2 = Q or D)<br>X3 = A or N; (P1 = A or N)<br>X4 = L, I or M (P1' = L, I or M) | Linker consensus |
| 161 | PX2X3X4 (P3 P2 P1 ↓ P1')<br>(P3 = P)<br>X2 = Q or D; (P2 = Q or D)<br>X3 = A or N; (P1 is A or N)<br>X4 = L or I (P1' is L or I) | Linker consensus |
| 162 | PAGL | MMP substrate |
| 163 | TGLEADGSPAGLGRQARVG | Linker |
| 164 | TGLEADGSRQARVGPAGLG | Linker |
| 165 | TGSPAGLEADGSRQARVGS | Linker |
| 166 | TGPAGLGLEADGSRQARVG | Linker |
| 167 | TGRQARVGLEADGSPAGLG | Linker |
| 168 | TGSRQARVGPAGLEADGS | Linker |
| 169 | TGPAGLGSRQARVGLEADGS | Linker |
| 170 | GPAGLGLEPDGSRQARVG | Linker |
| 171 | GGSGGGGIEPDIGGSGGS | Linker |
| 172 | GGSGGGGLEADTGGSGGS | Linker |
| 173 | GSIEPDIGS | Linker |
| 174 | GSLEADTGS | Linker |
| 175 | GGSGGGGIEPDGGGSGGS | Linker |
| 176 | GGSGGGGIEPDVGGSGGS | Linker |
| 177 | GGSGGGGIEPDSGGSGGS | Linker |
| 178 | GGSGGGGIEPDTGGSGGS | Linker |
| 179 | GGGSLEPDGSGS | Linker |
| 180 | GPAGLGLEADGSRQARVG | Linker |
| 181 | GGEGGGGSGGSGGGS | Linker |
| 182 | GSSAGSEAGGSGQAGVGS | Linker |
| 183 | GGSGGGGLEAEGSGGGGS | Linker |
| 184 | GGSGGGGIEPDPGGSGGS | Linker |
| 185 | TGGSGGGGIEPDIGGSGGS | Linker |
| 186 | EVQLVQSGGALVQAGGSLRLSCVAPRTIGLISLMGWYRQAPGKQREL<br>VATIIASGRTNYAESVKDRFTISRDNAENKVYLQVNSLKPEDTAVYYC<br>RVNAETAPWSRRGFWGQGTQVTVKP | 1G7 CD28 sdAb |
| 187 | QVQLQQSGGGLVQAGGSLRLSCVASGISFNVVDMDWHRQAPGKERE | 2F11 CD28 sdAb |

-continued

| Sequences | | |
|---|---|---|
| # | SEQUENCE | ANNOTATION |
| | LVAGITRGGATYYADSVKGRFTISRDNAKNSAYLQLANLKPEDTAVYYCNARWPSRYQNYWGQGTQVTVKP | |
| 188 | EVQLVQSGGGLVQTGGSLRLSCAASGRMFSNYAMGWFRQAPGKEREFVAAINYRRDSADYADSVKGRFTISRDNAKNTVYLEMNSLKPEDTAIYYCGFTYAGWASSRRDDYNYWGQGTQVTVKP | 1C9 CD28 sdAb |
| 189 | RTIGLISLMG | CDR1 (1G7) |
| 190 | TIIASGRTN | CDR2 (1G7) |
| 191 | NAETAPWSRRGF | CDR3 (1G7) |
| 192 | GISFNVVDMD | CDR1 (2F11) |
| 193 | GITRGGATY | CDR2 (2F11) |
| 194 | RWPSRYQNY | CDR3 (2F11) |
| 195 | GRMFSNYAMG | CDR1 (1C9, v1-v4, v7-v9, v12-v27) |
| 196 | AINYRRDSAD | CDR2 (1C9, v1-v6, v10, v11) |
| 197 | TYAGWASSRRDDYNY | CDR3 (1C9, v1-v27) |
| 198 | GRIFSNYAMG | CDR1 (1C9v5) |
| 199 | GRLFSNYAMG | CDR1 (1C9v6) |
| 200 | GRTFSNYAMG | CDR1 (1C9v10) |
| 201 | GFTFSNYAMG | CDR1 (1C9v11) |
| 202 | AINYRRESAD | CDR2 (1C9v7) |
| 203 | AINYRRDAAD | CDR2 (1C9v8) |
| 204 | AINYRRDTAD | CDR2 (1C9v9) |
| 205 | AINYRRDVAD | CDR2 (1C9v12) |
| 206 | AINYRRDDAD | CDR2 (1C9v13, 16, 17, 22-27) |
| 207 | AINYRRSDAD | CDR2 (1C9v14) |
| 208 | AINYRRTCAD | CDR2 (1C9v15) |
| 209 | AINYRRDDAA | CDR2 (1C9v18) |
| 210 | AINYRRSSAD | CDR2 (1C9v19) |
| 211 | AINYRRDDTD | CDR2 (1C9v20) |
| 212 | AINYRRDEAD | CDR2 (1C9v21) |
| 213 | EVQLVESGGGEVQPGGSLRLSCAASGRMFSNYAMGWFRQAPGKGREFVSAINYRRDSADYAESVKGRFTISRDNAKNTLYLQMNSLRAEDTAVYYCGFTYAGWASSRRDDYNYWGQGTLVTVKP | 1C9v1 CD28 sdAb |
| 214 | EVQLVESGGGEVQPGGSLRLSCAASGRMFSNYAMGWFRQAPGKEREFVSAINYRRDSADYAESVKGRFTISRDNAKNTLYLQMNSLRAEDTAVYYCGFTYAGWASSRRDDYNYWGQGTLVTVKP | 1C9v2 CD28 sdAb |
| 215 | EVQLVESGGGEVQPGGSLRLSCAASGRMFSNYAMGWFRQAPGKEREFVSAINYRRDSADYAESVKGRFTISRDNAKNTVYLQMNSLRAEDTAVYYCGFTYAGWASSRRDDYNYWGQGTLVTVKP | 1C9v3 CD28 sdAb |
| 216 | EVQLVESGGGEVQPGGSLRLSCAASGRMFSNYAMGWFRQAPGKEREFVAAINYRRDSADYAESVKGRFTISRDNAKNTVYLQMNSLRAEDTAVYYCGFTYAGWASSRRDDYNYWGQGTLVTVKP | 1C9v4 CD28 sdAb |
| 217 | EVQLVESGGGEVQPGGSLRLSCAASGRIFSNYAMGWFRQAPGKEREFVAAINYRRDSADYAESVKGRFTISRDNAKNTVYLQMNSLRAEDTAV | 1C9v5 CD28 sdAb |

-continued

Sequences

| # | SEQUENCE | ANNOTATION |
|---|---|---|
| | YYCGFTYAGWASSRRDDYNYWGQGTLVTVKP | |
| 218 | EVQLVESGGGEVQPGGSLRLSCAASGRLFSNYAMGWFRQAPGKERE FVAAINYRRDSADYAESVKGRFTISRDNAKNTVYLQMNSLRAEDTAV YYCGFTYAGWASSRRDDYNYWGQGTLVTVKP | 1C9v6 CD28 sdAb |
| 219 | EVQLVESGGGEVQPGGSLRLSCAASGRMFSNYAMGWFRQAPGKERE FVAAINYRRESADYAESVKGRFTISRDNAKNTVYLQMNSLRAEDTAV YYCGFTYAGWASSRRDDYNYWGQGTLVTVKP | 1C9v7 CD28 sdAb |
| 220 | EVQLVESGGGEVQPGGSLRLSCAASGRMFSNYAMGWFRQAPGKERE FVAAINYRRDAADYAESVKGRFTISRDNAKNTVYLQMNSLRAEDTA VYYCGFTYAGWASSRRDDYNYWGQGTLVTVKP | 1C9v8 CD28 sdAb |
| 221 | EVQLVESGGGEVQPGGSLRLSCAASGRMFSNYAMGWFRQAPGKERE FVAAINYRRDTADYAESVKGRFTISRDNAKNTVYLQMNSLRAEDTAV YYCGFTYAGWASSRRDDYNYWGQGTLVTVKP | 1C9v9 CD28 sdAb |
| 222 | EVQLVESGGGEVQPGGSLRLSCAASGRTFSNYAMGWFRQAPGKERE FVAAINYRRDSADYAESVKGRFTISRDNAKNTVYLQMNSLRAEDTAV YYCGFTYAGWASSRRDDYNYWGQGTLVTVKP | 1C9v10 CD28 sdAb |
| 223 | EVQLVESGGGEVQPGGSLRLSCAASGFTFSNYAMGWFRQAPGKEREF VAAINYRRDSADYAESVKGRFTISRDNAKNTVYLQMNSLRAEDTAV YYCGFTYAGWASSRRDDYNYWGQGTLVTVKP | 1C9v11 CD28 sdAb |
| 224 | EVQLVESGGGEVQPGGSLRLSCAASGRMFSNYAMGWFRQAPGKERE FVAAINYRRDVADYAESVKGRFTISRDNAKNTVYLQMNSLRAEDTA VYYCGFTYAGWASSRRDDYNYWGQGTLVTVKP | 1C9v12 CD28 sdAb |
| 225 | EVQLVESGGGEVQPGGSLRLSCAASGRMFSNYAMGWFRQAPGKERE FVAAINYRRDDADYAESVKGRFTISRDNAKNTVYLQMNSLRAEDTA VYYCGFTYAGWASSRRDDYNYWGQGTLVTVKP | 1C9v13 CD28 sdAb |
| 226 | EVQLVESGGGEVQPGGSLRLSCAASGRMFSNYAMGWFRQAPGKERE FVAAINYRRSDADYAESVKGRFTISRDNAKNTVYLQMNSLRAEDTAV YYCGFTYAGWASSRRDDYNYWGQGTLVTVKP | 1C9v14 CD28 sdAb |
| 227 | EVQLVESGGGEVQPGGSLRLSCAASGRMFSNYAMGWFRQAPGKERE FVAAINYRRTCADYAESVKGRFTISRDNAKNTVYLQMNSLRAEDTAV YYCGFTYAGWASSRRDDYNYWGQGTLVTVKP | 1C9v15 CD28 sdAb |
| 228 | EVQLVESGGGEVQPGGSLRLSCAASGRMFSNYAMGWFRQAPGKGRE FVAAINYRRDDADYAESVKGRFTISRDNAKNTVYLQMNSLRAEDTA VYYCGFTYAGWASSRRDDYNYWGQGTLVTVKP | 1C9v16 CD28 sdAb |
| 229 | EVQLVESGGGEVQPGGSLRLSCAASGRMFSNYAMGWFRQAPGKGRE FVAAINYRRDDADYAESVKDRFTISRDNAKNTVYLQMNSLRAEDTA VYYCGFTYAGWASSRRDDYNYWGQGTLVTVKP | 1C9v17 CD28 sdAb |
| 230 | EVQLVESGGGEVQPGGSLRLSCAASGRMFSNYAMGWFRQAPGKERE FVAAINYRRDDAAYAESVKGRFTISRDNAKNTVYLQMNSLRAEDTA VYYCGFTYAGWASSRRDDYNYWGQGTLVTVKP | 1C9v18 CD28 sdAb |
| 231 | EVQLVESGGGEVQPGGSLRLSCAASGRMFSNYAMGWFRQAPGKERE FVAAINYRRSSADYAESVKGRFTISRDNAKNTVYLQMNSLRAEDTAV YYCGFTYAGWASSRRDDYNYWGQGTLVTVKP | 1C9v19 CD28 sdAb |
| 232 | EVQLVESGGGEVQPGGSLRLSCAASGRMFSNYAMGWFRQAPGKERE FVAAINYRRDDTDYAESVKGRFTISRDNAKNTVYLQMNSLRAEDTAV YYCGFTYAGWASSRRDDYNYWGQGTLVTVKP | 1C9v20 CD28 sdAb |
| 233 | EVQLVESGGGEVQPGGSLRLSCAASGRMFSNYAMGWFRQAPGKERE FVAAINYRRDEADYAESVKGRFTISRDNAKNTVYLQMNSLRAEDTAV YYCGFTYAGWASSRRDDYNYWGQGTLVTVKP | 1C9v21 CD28 sdAb |
| 234 | EVQLVESGGGEVQPGGSLRLSCAASGRMFSNYAMGWFRQAPGKERE WVAAINYRRDDADYAESVKGRFTISRDNAKNTVYLQMNSLRAEDTA VYYCGFTYAGWASSRRDDYNYWGQGTLVTVKP | 1C9v22 CD28 sdAb |
| 235 | EVQLVESGGGEVQPGGSLRLSCAASGRMFSNYAMGWVRQAPGKERE FVAAINYRRDDADYAESVKGRFTISRDNAKNTVYLQMNSLRAEDTA VYYCGFTYAGWASSRRDDYNYWGQGTLVTVKP | 1C9v23 CD28 sdAb |
| 236 | EVQLVESGGGEVQTGGSLRLSCAASGRMFSNYAMGWFRQAPGKERE | 1C9v24 CD28 sdAb |

-continued

| Sequences | | |
|---|---|---|
| # | SEQUENCE | ANNOTATION |
| | FVAAINYRRDDADYAESVKGRFTISRDNAKNTVYLQMNSLRAEDTA VVYYCGFTYAGWASSRRDDYNYWGQGTLVTVKP | |
| 237 | EVQLVESGGGEVQPGGSLRLSCAASGRMFSNYAMGWFRQAPGKERE FVAAINYRRDDADYAESVKGRFTISRDNAKNTVYLEMNSLRAEDTAV YYCGFTYAGWASSRRDDYNYWGQGTLVTVKP | 1C9v25 CD28 sdAb |
| 238 | EVQLVESGGGEVQTGGSLRLSCAASGRMFSNYAMGWFRQAPGKERE FVAAINYRRDDADYAESVKGRFTISRDNAKNTVYLEMNSLRAEDTAV YYCGFTYAGWASSRRDDYNYWGQGTLVTVKP | 1C9v26 CD28 sdAb |
| 239 | EVQLVESGGGEVQPGGSLRLSCAASGRMFSNYAMGWFRQAPGKERE FVAAINYRRDDADYAESVKGRFTISRDNAKNTVYLQMNSLRAEDTAI YYCGFTYAGWASSRRDDYNYWGQGTLVTVKP | 1C9v27 CD28 sdAb |
| 240 | EVQLVESGGGEVQPGGSLRLSCAASGRPFSSKTMAWFRQAPGKEREF VAAVRWIGGATRYTESVKGRFTISRDNAKNTVYLQMSSLRAEDTAV YYCAAGQAWGTKFTDYSDWGQGTLVTVKP | 5T4 sdAb |
| 241 | GRPFSSKTMA | CDR1 5T4 sdAb |
| 242 | AVRWIGGATR | CDR2 5T4 sdAb |
| 243 | GQAWGTKFTDYSD | CDR3 5T4 sdAb |
| 244 | GGS(GGS)n, wherein n is 0 to 10 | Linker |
| 245 | EVQLVESGGGEVQPGGSLRLSCAASGRPFSSYAMGWFRQAPGKERET VAAVSRNAGSSYYAESVKGRFTISRDNAKNTVYLQMSSLRAEDTAV YYCAARSAAYSRSSETYTEKHDYTYWGQGTLVTVKP | 5T4 sdAb |
| 246 | GRPFSSYAMG | CDR1 5T4 sdAb |
| 247 | AVSRNAGSSY | CDR2 5T4 sdAb |
| 248 | WGQGTLVTVKP | CDR3 5T4 sdAb |
| 249 | GG | linker |
| 250 | PGGGG | linker |
| 251 | IEPDP | Linker |
| 252 | GFTFNTYAMN | anti-CD3 VH CDR1 |
| 253 | QLQLQESGGGLVQPGGSLRLSCAASGFTLDNYAIGWFRQAPGKEREG VSCISSSDGSTYYADSVKGRFTISRNNAKGTVYLLMNSLKPEDTAVYY CATELVPACTYSNGRGPLDGMDYWGKGTQVTVKP | FRalpha sdAb |
| 254 | EVQLLESGGGEVQPGGSLRLSCAASGSIFSIDATAWYRQAPGKQRELV AIITSSGSTNYPESVKGRFTISRDNAKNTVYLQMSSLRAEDTAVYYCN AITRYGGSTYDFWGQGTLVTVKP | FRalpha sdAb |
| 255 | EVQPGGSLRLSCAASETFGVVFTLGWYRQAPGKGREFVARVTGTDTV DYAESVKGRFTISSDFARNTVYLQMNSLRAEDTAVYYCNTGAYWGQ GTLVTVKP | FRalpha sdAb |
| 256 | EVQLVESGGGLVQPKGSLKLSCAASGFTFNTYAMNWVRQAPGKGLE WVARIRSKSNNYATYYADSVKDRFTISRDDSQSMLYLQMNNLKTED TAMYYCVRQWDYDVRAMNYWGQGTSVTVSSASTKGPSVFPLAPSS KSTSGGTAALGCLVKDYFPEPVTVSWNSGALTSGVHTFPAVLQSSGL YSLSSVVTVPSSSLGTQTYICNVNHKPSNTKVDKKVEPKSC | 5T4 Fd |
| 257 | DIVMTQSHIFMSTSVGDRVSITCKASQDVDTAVAWYQQKPGQSPKLL IYWASTRLTGVPDRFTGSGSGTDFTLTISNVQSEDLADYFCQQYSSYP YTFGGGTKLEIKRTVAAPSVFIFPPSDEQLKSGTASVVCLLNNFYPREA KVQWKVDNALQSGNSQESVTEQDSKDSTYSLSSTLTLSKADYEKHK VYACEVTHQGLSSPVTKSFNRGEC | 5T4 LC |
| 258 | EVQLVESGGGLVQPKGSLKLSCAASGFTFNTYAMNWVRQAPGKGLE WVARIRSKSNNYATYYADSVKDRFTISRDDSQSMLYLQMNNLKTED TAMYXCVRQWDYDVRAMNYWGQGTSVTVSS X = C or Y | anti-5T4 VH |
| 259 | DIVMTQSHIFMSTSVGDRVSITCKASQDVDTAVAWYQQKPGQSPKLL | anti-5T4 VL |

-continued

Sequences

| # | SEQUENCE | ANNOTATION |
|---|---|---|
| | IYWASTRLTGVPDRFTGSGSGTDFTLTISNVQSEDLADYFCQQYSSYP YTFGG GTKLEIK | |
| 260 | EVQLVESGGGLVQPGGSLRLSCAASGFILDYYAIGWFRQAPGKEREG VLCIDASDDITYYADSVKGRFTISRDNAKNTVYLQMNSLKPEDTGVY YCATPIGLSSSCLLEYDYDYWGQGTLVTVKP | cMET sdAb |
| 261 | EVQLVESGGGLVQPGGSLRLSCAASGFTFSSFGMHWVRQAPGKGLE WVAYISSDSSAIYYADTVKGRFTISRDNAKNSLYLQMNSLRDEDTAV YYCGRGRENIYYGSRLDYWGQGTTVTVSSSGGGGSGGGGSGGGGSD IQLTQSPSFLSASVGDRVTITCKASQNVDTNVAWYQQKPGKAPKALIY SASYRYSGVPSRFSGSGSGTDFTLTISSLQPEDFATYYCQQYNNYPFTF GQGTKLEIK | B7H3 scFv |
| 262 | EVQLVESGGGEVQPGGSLRLSCAASGFSFSSNVMMWVRQAPGKGLE WVSTIYSSGTGTFYAESVKGRFTISRDNAKNTLYLQMSSLRPEDTAVY YCATSGPVRGWGPRSQGTLVTVKP | B7H3 sdAb |
| 263 | EVQLVESGGGEVQPGGSLRLSCAASGSTFSSYHMSWFRQAPGKQREP VATSHHGGTTNYAGSVKGRFTISRDNAKNTVYLQMNTLRAEDTAVY YCKADHGYQGRGYWGQGTLVTVKP | B7H3 sdAb |
| 264 | EVQLVESGGGEVQPGGSLRLSCAASGFTFSSYHMSWFRQAPGKQREL VATSHHGGTTNYAGSVKGRFTISRDNAKNTVYLQMNTLRAEDTAVY YCKADHGYQGRGYWGQGTLVTVKP | B7H3 sdAb |
| 265 | EVQLVESGGGEVQPGGSLRLSCAASGFTFSSYHMSWFRQAPGKQREP VATSHHGGTTNYAGSVKGRFTISRDNAKNTVYLQMNTLRAEDTAVY YCKADHGYQGRGYWGQGTLVTVKP | B7H3sdAb |
| 266 | EVQLVESGGGEVQPGGSLRLSCAPSERTFSTYTMGWFRQAPGKEREF VAVVNWGGGSKYYAESVKGRFTISRDNAKNTVYLQMSSLRAEDTAV YYCAAGGAYSGPYYDTRQYTYWGQGTLVTVKP | B7H3 sdAb |
| 267 | EVQLVESGGGLVQPGGSLRLSCAASGFTFSSFGMHWVRQAPGKGLE WVAYISSDSSAIYYADTVKGRFTISRDNAKNSLYLQMNSLRDEDTAV YYCGRGRENIYYGSRLDYWGQGTTVTVSSASTKGPSVFPLAPSSKSTS GGTAALGCLVKDYFPEPVTVSWNSGALTSGVHTFPAVLQSSGLYSLS SVVTVPSSSLGTQTYICNVNHKPSNTKVDKKVEPKSC | B7H3 Fd |
| 268 | DIQLTQSPSFLSASVGDRVTITCKASQNVDTNVAWYQQKPGKAPKALI YSASYRYSGVPSRFSGSGSGTDFTLTISSLQPEDFATYYCQQYNNYPFT FGQGTKLEIKRTVAAPSVFIFPPSDEQLKSGTASVVCLLNNFYPREAKV QWKVDNALQSGNSQESVTEQDSKDSTYSLSSTLTLSKADYEKHKVY ACEVTHQGLSSPVTKSFNRGEC | B7H3 LC |
| 269 | QVQLVQSGAE VKKPGSSVKV SCKASGYAFS YSWINWVRQA PGQGLEWMGR IFPGDGDTDY NGKFKGRVTI TADKSTSTAY MELSSLRSED TAVYYCARNV FDGYWLVYWG QGTLVTVSS | CD20 VH |
| 270 | DIVMTQTPLSLPVTPGEPASISCRSSKSLLHSNGITYLYWYLQKPGQSP QLLIYQMSNLVSGVPDRFSGSGSGTDFTLKISRVEAEDVGVYYCAQN LELP YTFGGGTKVEIKRTV | CD20 VL |
| 271 | QVQLVQSGAEVKKPGSSVKVSCKASGYAFSYSWINWVRQAPGQGLE WMGRIFPGDGDTDYNGKFKGRVTITADKSTSTAYMELSSLRSEDTAV YYCARNVFDGYWLVYWGQGTLVTVSGSGGGGSGGGGTGGGGSDIV MTQTPLSLPVTPGEPASISCRSSKSLLHSNGITYLYWYLQKPGQSPQLL IYQMSNLVSGVPDRFSGSGSGTDFTLKISRVEAEDVGVYYCAQNLELP YTFGGGTKVEIK | CD20 scFv |
| 272 | QVQLQESGPGLVKPSETLSLTCTVSGGSISSYYWSWIRQPPGKGLEWI GYVYYSGTTNYNPSLKSRVTISVDTSKNQFSLKLSSVTAADTAVYYC ASIAVTGFYFDYWGQGTLVTVSSGGGGSGGGGSGGGGSEIVLTQSPG TLSLSPGERVTLSCRASQRVNNNYLAWYQQRPGQAPRLLIYGASSRA TGIPDRFSGSGSGTDFTLTISRLEPEDFAVYYCQQYDRSPLTFGGGTKL EIK | DLL3 scFv |
| 273 | QVQLQESGPG LVKPSETLSL TCTVSGGSIS SYYWSWIRQP PGKGLEWIGYVYYSGTTNYN PSLKSRVTIS VDTSKNQFSL KLSSVTAADT AVYYCASIAVTGFYFDYWGQ GTLVTVSSGG GGSGGGGSGG GGSEIVLTQS PGTLSLSPGERVTLSCRASQ RVNNNYLAWY QQRPGQAPRL LIYGASSRAT GIPDRFSGSG SGTDFTLTIS RLEPEDFAVY YCQQYDRSPL TFGGGTKLEI K | DLL3 scFv |

-continued

Sequences

| # | SEQUENCE | ANNOTATION |
|---|---|---|
| 274 | EVQLVESGGGEVQPGGSLRLSCAASGSIFSINAMGWYRQAPGKQREL VAGFTGDTNTIYAESVKGRFTISRDNAKNTVYLQMSSLRAEDTAVYY CAADVQLFSRDYEFYWGQGTLVTVKP | DLL3 sdAb |
| 275 | EVQLVESGGGEVQPGGSLRLSCGPSEIITSDKSMGWVRQAPGKQRNL VAGISNVGSTNYAQSVKGRFTISRDNAKNTVYLQMSSLRAEDTAVYY CYARDFENEYWGQGTLVTVKP | DLL3 sdAb |
| 276 | QIQLVQSGPELKKPGETVKISCKASGYTFTNYGMNWVKQAPGKGLK WMAWINTYTGEPTYADDFKGRFAFSLETSASTASLQIINLKNEDTATY FCARIGDSSPSDYWGQGTTLTVSSSSASTKGPSVFPLAPSSKSTSGGTA ALGCLVKDYFPEPVTVSWNSGALTSGVHTFPAVLQSSGLYSLSSVVT VPSSSLGTQTYICNVNHKPSNTKVDKKVEPKSC | DLL3 Fd |
| 277 | SIVMTQTPKFLLVSAGDRVTITCKASQSVSNDVVWYQQKPGQSPKLLI YYASNRYTGVPDRFAGSGYGTDFSFTISTVQAEDLAVYFCQQDYTSP WTFGGGTKLEIRRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC | DLL3 LC |
| 278 | QVQLQESGPGLVKPSQTLSLTCTVSGGSISSFNYYWSWIRHHPGKGLE WIGYIYYSGSTYSNPSLKSRVTISVDTSKNQFSLTLSSVTAADTAVYYC ARGYNWNYFDYWGQGTLVTVSSASTKGPSVFPLAPSSKSTSGGTAAL GCLVKDYFPEPVTVSWNSGALTSGVHTFPAVLQSSGLYSLSSVVTVPS SSLGTQTYICNVNHKPSNTKVDKKVEPKSC | gpNMB Fd |
| 279 | EIVMTQSPATLSVSPGERATLSCRASQSVDNNLVWYQQKPGQAPRLLI YGASTRATGIPARFSGSGSGTEFTLTISSLQSEDFAVYYCQQYNNWPP WTFGQGTKVEIKRTVAAPSVFIFPPSDEQLKSGTASVVCLLNNFYPRE AKVQWKVDNALQSGNSQESVTEQDSKDSTYSLSSTLTLSKADYEKH KVYACEVTHQGLSSPVTKSFNRGEC | gpNMB LC |
| 280 | EVQLVESGGGEVQPGGSLRLSCAASGRMFSNYAMGWFRQAPGKERE FVAAINYRRDAADYAESVKDRFTISRDNAKNTVYLQMNSLRAEDTA VYYCGFTYAGWASSRRDDYNYWGQGTLVTVKP | 1C9v8D CD28 sdAb |
| 281 | QAVVTQEPSLTVSPGGTVTLTCGSSTGAVTTSNYANWVQQKPGQAFR GLIGGTNKRAPGVPARFSGSLLGGKAALTISGAQPEDEADYYCALWY SNHWVFGCGTKLTVL | anti-CD3 VL (CON) |
| 282 | EIITSDKSMG | CDR1 |
| 283 | EVQLVESGGGLVQPGGSLRLSCAASGFTFSTYAMNWVRQAPGKCLE WVGRIRSKYNNYATYYADSVKGRFTISRDDSKNTLYLQMNSLRAED TAVYYCVRHGNFGDSYVSWFAYWGQGTLVTVSS | CD3-VH33 |
| 284 | DKTHTCPPCPAPPVAGPSVFLFPPKPKDTLMISRTPEVTCVVVDVKHE DPEVKFNWYVDGVEVHNAKTKPREEEYNSTYRVVSVLTVLHQDWL NGKEYKCKVSNKALPAPIEKTISKAKGQPREPQVYTLPPSREEMTKNQ VSLTCDVSGFYPSDIAVEWESDGQPENNYKTTPPVLDSDGSFFLYSKL TVDKSRWEQGDVFSCSVMHEALHNHYTQKSLSLSPGK | Fc-Het-1 |
| 285 | DKTHTCPPCPAPPVAGPSVFLFPPKPKDTLMISRTPEVTCVVVDVKHE DPEVKFNWYVDGVEVHNAKTKPREEQYNSTYRVVSVLTVLHQDWL NGKEYKCKVSNKALPAPIEKTISKAKGQPREPQVYTLPPSREQMTKN QVKLTCLVKGFYPSDIAVEWESNGQPENNYKTTPPVLDSDGSFFLYSK LTVDKSRWQQGNVFSCSVMHEALHNHYTQKSLSLSPGK | Fc-Het-2 |
| 286 | RIRSKYNNYATY | anti-CD3 VH CDR2 |
| 287 | HGNFGDSYVSWFAY | CD3-VH7, VH33 CDR3 |
| 288 | ALWYSNHWV | CD3-VL2, VL21 CDR3 |
| 289 | VLWYSNRWV | CD3-VL8 CDR3 |
| 290 | GSIFRINVMG | CDRH1 (C05) |
| 291 | RIFSGGSPN | CDRH2 (C05) |
| 292 | LIASRAAPGLKYDY | CDRH3 (C05) |

-continued

| Sequences | | |
|---|---|---|
| # | SEQUENCE | ANNOTATION |
| 293 | ISIFSINRMG | CDRH1 (E08) |
| 294 | AMTSGGSTN | CDRH2 (E08) |
| 295 | ASRRELY | CDRH3 (E08) |
| 296 | GAIFSKTEVQ | CDRH1 (B11) |
| 297 | TISAGDRIN | CDRH2 (B11) |
| 298 | RRGDTIL | CDRH3 (B11) |
| 299 | GIIFREYAMG | CDRH1 (B10) |
| 300 | VISKTGTTI | CDRH2 (B10) |
| 301 | TRGQLDY | CDRH3 (B10) |
| 302 | GFTFSTYAMN | CD3 VH33 CDR1 |
| 303 | RIRSKYNNYATY | CD3 VH33 CDR2 |
| 304 | GSSTGAVTTSNYAN | CD3 VL21 CDR1 |
| 305 | EVQLVESGGGLVQPGRSLRLSCAASGFTFDDYAMHWVRQAPGKGLE WVSGISWNSGSIGYADSVKGFTISRDNAKNSLYLQMNSLRAEDTALY YCAKDSRGYGDYRLGGAYWGQGTLVTVSS | Anti-CD3 VH 312557 |
| 306 | EVQLVESGGGLVQPGRSLRLSCAASGFTFDDYAMHWVRQAPGKCLE WVSGISWNSGSIGYADSVKGFTISRDNAKNSLYLQMNSLRAEDTALY YCAKDSRGYGDYRLGGAYWGQGTLVTVSS | Anti-CD3 VH 312557 G44C |
| 307 | EIVMTQSPATLSVSPGERATLSCRASQSVSSNLAWYQQKPGQAPRLLI YGASTRATGIPARFSGSGSGTEFTLTISSLQSEDFAVYYCQQYNNWPW TFGQGTKVEIK | Anti-CD3 VL 312557 |
| 308 | EIVMTQSPATLSVSPGERATLSCRASQSVSSNLAWYQQKPGQAPRLLI YGASTRATGIPARFSGSGSGTEFTLTISSLQSEDFAVYYCQQYNNWPW TFGCGTKVEIK | Anti-CD3 VL 312557Q100C |
| 309 | EVQLVESGGGLVQPGRSLRLSCVASGFTFDDYSMHWVRQAPGKGLE WVSGISWNSGSKDYADSVKGRFTISRDNAKNSLYLQMNSLRAEDTAL YYCAKYGSGYGKFYHYGLDVWGQGTTVTVSS | CD3-VH-G |
| 310 | EVQLVESGGGLVQPGRSLRLSCVASGFTFDDYSMHWVRQAPGKCLE WVSGISWNSGSKDYADSVKGRFTISRDNAKNSLYLQMNSLRAEDTAL YYCAKYGSGYGKFYHYGLDVWGQGTTVTVSS | CD3-VH-G |
| 311 | DIQMTQSPSSLSASVGDRVTITCRASQSISSYLNWYQQKPGKAPKLLIY AASSLQSGVPSRFSGSGSGTDFTLTISSLQPEDFATYYCQQSYSTPPITF GQGTRLEIK | $V_{K1}$-39JK5 |
| 312 | DIQMTQSPSSLSASVGDRVTITCRASQSISSYLNWYQQKPGKAPKLLIY AASSLQSGVPSRFSGSGSGTDFTLTISSLQPEDFATYYCQQSYSTPPITF GCGTRLEIK | $V_{K1}$-39JK5Q100C |
| 313 | (ADAAP)n n = 2-20 | linker |
| 314 | (ADAAP)n-G n = 2-20 | linker |
| 315 | (GEPQG)n n = 2-20 | linker |
| 316 | (GEPQG)n-G n = 2-20 | linker |
| 317 | (AGGEP)n n = 2-20 | linker |
| 318 | (AGGEP)n-G n = 2-20 | linker |
| 319 | (AGSEP)n | linker |

-continued

Sequences

| # | SEQUENCE | ANNOTATION |
|---|---|---|
| | n = 2-20 | |
| 320 | (AGSEP)n-G<br>n = 2-20 | linker |
| 321 | (GGGEQ)n<br>n = 2-20 | linker |
| 322 | (GGGEQ)n-G<br>n = 2-20 | linker |
| 323 | ADAAPADAAPG | linker |
| 324 | GEPQGGEPQGG | linker |
| 325 | AGGEPAGGEPG | linker |
| 326 | AGSEPAGSEPG | linker |
| 327 | GGGEQGGGEQG | linker |
| 328 | DKTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWL<br>NGKEYKCKVSNKALPAPIEKTISKAKGQPREPQVYTLPPCRDELTKNQ<br>VSLWCLVKGFYPSDIAVEWESNGQPENNYKTTPPVLDSDGSFFLYSK<br>LTVDKSRWQQGNVFSCSVMHEALHNHYTQKSLSLSP | Knob Fc |
| 329 | DKTHTCPPCPAPELLGGPSVFLFPPKPKDTLMRSRTPEVTCVVVDVSH<br>EDPEVKFNWYVDGVEVHNAKTKPREEQYNSTYRVVSVLTVLHQDW<br>LNGKEYKCKVSNKALPAPIEKTISKAKGQPREPQVCTLPPSRDELTKN<br>QVSLSCAVKGFYPSDIAVEWESNGQPENNYKTTPPVLDSDGSFFLVSK<br>LTVDKSRWQQGNVFSCSVMHEALHNHYTQKSLSLSP | Hole Fc |
| 330 | DKTHTCPPCPAPGGPSVFLFPPKPKDTLMISRTPEVTCVVVDVSHEDPE<br>VKFNWYVDGVEVHNAKTKPREEQYNSTYRVVSVLTVLHQDWLNGK<br>EYKCKVSNKALPAPIEKTISKAKGQPREPQVYTLPPCRDELTKNQVSL<br>WCLVKGFYPSDIAVEWESNGQPENNYKTTPPVLDSDGSFFLYSKLTV<br>DKSRWQQGNVFSCSVMHEALHNHYTQKSLSLSP | Knob Fc |
| 331 | DKTHTCPPCPAPGGPSVFLFPPKPKDTLMRSRTPEVTCVVVDVSHEDP<br>EVKFNWYVDGVEVHNAKTKPREEQYNSTYRVVSVLTVLHQDWLNG<br>KEYKCKVSNKALPAPIEKTISKAKGQPREPQVCTLPPSRDELTKNQVS<br>LSCAVKGFYPSDIAVEWESNGQPENNYKTTPPVLDSDGSFFLVSKLTV<br>DKSRWQQGNVFSCSVMHEALHNHYTQKSLSLSP | Hole Fc |
| 332 | DKTHTCPPCPAPELLGGPSVFLFPPKPKDTLMISRTPEVTCVVVDVSHE<br>DPEVKFNWYVDGVEVHNAKTKPREEQYNSTYRVVSVLTVLHQDWL<br>NGKEYKCKVSNKALPAPIEKTISKAKGQPREPQVCTLPPSRDELTKNQ<br>VSLSCAVKGFYPSDIAVEWESNGQPENNYKTTPPVLDSDGSFFLVSKL<br>TVDKSRWQQGNVFSCSVMHEALHNRYTQKSLSLSP | Hole Fc |
| 333 | DKTHTCPPCPAPGGPSVFLFPPKPKDTLMISRTPEVTCVVVDVSHEDPE<br>VKFNWYVDGVEVHNAKTKPREEQYNSTYRVVSVLTVLHQDWLNGK<br>EYKCKVSNKALPAPIEKTISKAKGQPREPQVCTLPPSRDELTKNQVSLS<br>CAVKGFYPSDIAVEWESNGQPENNYKTTPPVLDSDGSFFLVSKLTVD<br>KSRWQQGNVFSCSVMHEALHNRYTQKSLSLSP | Hole Fc |
| 334 | DKTHTCPPCPAPELLGGPSVFLFPPKPKDTLYISRTPEVTCVVVDVSHE<br>DPEVKFNWYVDGVEVHNAKTKPREEQYNSTYRVVSVLTVLHQDWL<br>NGKEYKCKVSNKALPAPIEKTISKAKGQPREPQVYTLPPCRDELTKNQ<br>VSLWCLVKGFYPSDIAVEWESNGQPENNYKTTPPVLDSDGSFFLYSK<br>LTVDKSRWQQGNVFSCSVVHEALHNHYTQKSLSLSP | Knob Fc |
| 335 | DKTHTCPPCPAPGGPSVFLFPPKPKDTLYISRTPEVTCVVVDVSHEDPE<br>VKFNWYVDGVEVHNAKTKPREEQYNSTYRVVSVLTVLHQDWLNGK<br>EYKCKVSNKALPAPIEKTISKAKGQPREPQVYTLPPCRDELTKNQVSL<br>WCLVKGFYPSDIAVEWESNGQPENNYKTTPPVLDSDGSFFLYSKLTV<br>DKSRWQQGNVFSCSVVHEALHNHYTQKSLSLSP | Knob Fc |
| 336 | DKTHTCPPCPAPELLGGPSVFLFPPKPKDTLYISRTPEVTCVVVDVSHE<br>DPEVKFNWYVDGVEVHNAKTKPREEQYNSTYRVVSVLTVLHQDWL<br>NGKEYKCKVSNKALPAPIEKTISKAKGQPREPQVCTLPPSRDELTKNQ<br>VSLSCAVKGFYPSDIAVEWESNGQPENNYKTTPPVLDSDGSFFLVSKL<br>TVDKSRWQQGNVFSCSVVHEALHNRYTQKSLSLSP | Hole Fc |

-continued

Sequences

| # | SEQUENCE | ANNOTATION |
|---|---|---|
| 337 | DKTHTCPPCPAPGGPSVFLFPPKPKDTLYISRTPEVTCVVVDVSHEDPE VKFNWYVDGVEVHNAKTKPREEQYNSTYRVVSVLTVLHQDWLNGK EYKCKVSNKALPAPIEKTISKAKGQPREPQVCTLPPSRDELTKNQVSLS CAVKGFYPSDIAVEWESNGQPENNYKTTPPVLDSDGSFFLVSKLTVD KSRWQQGNVFSCSVVHEALHNRYTQKSLSLSP | Hole Fc |
| 338 | QAVVTQEPSLTVSPGGTVTLTCGSSTGAVTTSNYANWVQQKPGKSPR GLIGGTNKRAPGVPARFSGSLLGGKAALTISGAQPEDEADYYCALWY SNHWVFGGGTKLTVL | CD3-VL20 |
| 339 | QAVVTQEPSLTVSPGGTVTLTCGSSTGAVTTSNYANWVQQKPGKSPR GLIGGTNKRAPGVPARFSGSLLGGKAALTISGAQPEDEADYYCALWY SNHWVFGCGTKLTVL | CD3-VL21 |
| 340 | EVQLVESGGGLVQPGGSLRLSCAASGFTFSTYAMNWVRQAPGKGLE WVGRIRSKYNNYATYYADSVKGRFTISRDDSKNTLYLQMNSLRAED TAVYYCVRHGNFGDSYVSWFAYWGQGTLVTVSS | CD3-VH32 |
| 341 | EVQLVESGGGLVQPGGSLRLSCAASGFTFSTYAMNWVRQAPGKCLE WVARIRSKYNNYATYYADTVKGRFTISRDDAKNTLYLQMSSLRAED TAVYYCVRHGNFGDSYVSWFAYWGQGTLVTV | CD3-VH34 |
| 342 | EVQLVESGGGEVQPGGSLRLSCAASGRMFSNYAMGWFRQAPGKERE FVAAINYRRDDADYAESVKGRFTISRDNAKNTVYLQMSSLRAEDTAV YYCGFTYAGWASSRRDDYNYWGQGTLVTVKP | 1C9v13.1 CD28 sdAb |
| 343 | EVQLVESGGGEVQPGGSLRLSCAASGRMFSNYAMGWFRQAPGKERE FVAAINYRRDDADYAESVKGRFTISRDNAKNTVYLQMSSLRAEDTAV YYCGFTYAGWASSRRDDYDYWGQGTLVTVKP | 1C9v13.2 CD28 sdAb |
| 344 | EVQLVESGGGEVQPGGSLRLSCAASGRMFSNYAMGWFRQAPGKERE FVAAINYRRDDADYAESVKDRFTISRDNAKNTVYLQMSSLRAEDTAV YYCGFTYAGWASSRRDDYNYWGQGTLVTVKP | 1C9v13.3 CD28 sdAb |
| 345 | EVQLVESGGGEVQPGGSLRLSCAASGRMFSNYAMGWFRQAPGKERE FVAAINYRRDDADYAESVKDRFTISRDNAKNTVYLQMSSLRAEDTAI YYCGFTYAGWASSRRDDYNYWGQGTLVTVKP | 1C9v13.4 CD28 sdAb |
| 346 | EVQLVESGGGEVQPGGSLRLSCAASGRMFSNYAMGWFRQAPGKERE FVAAINYRRDDADYAESVKGRFTISRDNAKNTVYLQMSSLRAEDTAI YYCGFTYAGWASSRRDDYDYWGQGTLVTVKP | 1C9v13.5 CD28 sdAb |
| 347 | EVQLVESGGGEVQPGGSLRLSCAASGRMFSNYAMGWFRQAPGKERE FVAAINYGRDDADYAESVKGRFTISRDNAKNTVYLQMSSLRAEDTAV YYCGFTYAGWASSRRDDYNYWGQGTLVTVKP | 1C9v13.6 CD28 sdAb |
| 348 | EVQLVESGGGEVQPGGSLRLSCAASGRMFSNYAMGWFRQAPGKERE FVAAINYRGDDADYAESVKGRFTISRDNAKNTVYLQMSSLRAEDTAV YYCGFTYAGWASSRRDDYNYWGQGTLVTVKP | 1C9v13.7 CD28 sdAb |
| 349 | EVQLVESGGGEVQPGGSLRLSCAASGRMFSNYAMGWFRQAPGKERE FVAAINYRRDDADYAESVKGRFTISRDNAKNTVYLQMSSLRAEDTAV YYCGFTYAGWASSGRDDYNYWGQGTLVTVKP | 1C9v13.8 CD28 sdAb |
| 350 | EVQLVESGGGEVQPGGSLRLSCAASGRMFSNYAMGWFRQAPGKERE FVAAINYRRDDADYAESVKGRFTISRDNAKNTVYLQMSSLRAEDTAV YYCGFTYAGWASSRGDDYNYWGQGTLVTVKP | 1C9v13.9 CD28 sdAb |
| 351 | EVQLVESGGGEVQPGGSLRLSCAASGFTFSNYAMGWFRQAPGKEREF VAAINYRRDSADYAESVKGRFTISRDNAKNTVYLQMSSLRAEDTAVY YCGFTYAGWASSRRDDYNYWGQGTLVTVKP | 1C9v11.1 CD28 sdAb |
| 352 | EVQLVESGGGEVQPGGSLRLSCAASGFTFSNYAMGWFRQAPGKEREF VAAINYRRDSADYAESVKGRFTISRDNAKNTVYLQMSSLRAEDTAVY YCGFTYAGWASSRRDDYDYWGQGTLVTVKP | 1C9v11.2 CD28 sdAb |
| 353 | EVQLVESGGGEVQPGGSLRLSCAASGFTFSNYAMGWFRQAPGKEREF VAAINYRRDSADYAESVKDRFTISRDNAKNTVYLQMSSLRAEDTAVY YCGFTYAGWASSRRDDYNYWGQGTLVTVKP | 1C9v11.3 CD28 sdAb |
| 354 | EVQLVESGGGEVQPGGSLRLSCAASGFTFSNYAMGWFRQAPGKEREF VAAINYGRDSADYAESVKGRFTISRDNAKNTVYLQMSSLRAEDTAVY YCGFTYAGWASSRRDDYNYWGQGTLVTVKP | 1C9v11.4 CD28 sdAb |
| 355 | EVQLVESGGGEVQPGGSLRLSCAASGFTFSNYAMGWFRQAPGKEREF | 1C9v11.5 CD28 |

-continued

| Sequences | | |
|---|---|---|
| # | SEQUENCE | ANNOTATION |
| | VAAINYRGDSADYAESVKGRFTISRDNAKNTVYLQMSSLRAEDTAVY YCGFTYAGWASSRRDDYNYWGQGTLVTVKP | sdAb |
| 356 | EVQLVESGGGEVQPGGSLRLSCAASGFTFSNYAMGWFRQAPGKEREF VAAINYRRDSADYAESVKGRFTISRDNAKNTVYLQMSSLRAEDTAVY YCGFTYAGWASSGRDDYNYWGQGTLVTVKP | 1C9v11.6 CD28 sdAb |
| 357 | EVQLVESGGGEVQPGGSLRLSCAASGFTFSNYAMGWFRQAPGKEREF VAAINYRRDSADYAESVKGRFTISRDNAKNTVYLQMSSLRAEDTAVY YCGFTYAGWASSRGDDYNYWGQGTLVTVKP | 1C9v11.7 CD28 sdAb |
| 358 | EVQLVESGGGEVQPGGSLRLSCAASGFTFSNYAMGWFRQAPGKEREF VAAINYRRESADYAESVKGRFTISRDNAKNTVYLQMSSLRAEDTAVY YCGFTYAGWASSRRDDYNYWGQGTLVTVKP | 1C9v7.1 CD28 sdAb |
| 359 | EVQLVESGGGEVQPGGSLRLSCAASGFTFSNYAMGWFRQAPGKEREF VAAINYRRESADYAESVKGRFTISRDNAKNTVYLQMSSLRAEDTAVY YCGFTYAGWASSRRDDYDYWGQGTLVTVKP | 1C9v7.2 CD28 sdAb |
| 360 | EVQLVESGGGEVQPGGSLRLSCAASGFTFSNYAMGWFRQAPGKEREF VAAINYRRESADYAESVKDRFTISRDNAKNTVYLQMSSLRAEDTAVY YCGFTYAGWASSRRDDYNYWGQGTLVTVKP | 1C9v7.3 CD28 sdAb |
| 361 | EVQLVESGGGEVQPGGSLRLSCAASGFTFSNYAMGWFRQAPGKEREF VAAINYGRESADYAESVKGRFTISRDNAKNTVYLQMSSLRAEDTAVY YCGFTYAGWASSRRDDYNYWGQGTLVTVKP | 1C9v7.5 CD28 sdAb |
| 362 | EVQLVESGGGEVQPGGSLRLSCAASGFTFSNYAMGWFRQAPGKEREF VAAINYRGESADYAESVKGRFTISRDNAKNTVYLQMSSLRAEDTAVY YCGFTYAGWASSRRDDYNYWGQGTLVTVKP | 1C9v7.6 CD28 sdAb |
| 363 | EVQLVESGGGEVQPGGSLRLSCAASGFTFSNYAMGWFRQAPGKEREF VAAINYRRESADYAESVKGRFTISRDNAKNTVYLQMSSLRAEDTAVY YCGFTYAGWASSGRDDYNYWGQGTLVTVKP | 1C9v7.7 CD28 sdAb |
| 364 | EVQLVESGGGEVQPGGSLRLSCAASGFTFSNYAMGWFRQAPGKEREF VAAINYRRESADYAESVKGRFTISRDNAKNTVYLQMSSLRAEDTAVY YCGFTYAGWASSRGDDYNYWGQGTLVTVKP | 1C9v7.8 CD28 sdAb |
| 365 | EVQLVESGGGEVQPGGSLRLSCAASGFTFSNYAMGWFRQAPGKEREF VAAINYRRDDADYAESVKGRFTISRDNAKNTVYLQMSSLRAEDTAV YYCGFTYAGWASSRRDDYNYWGQGTLVTVKP | 1C9v7.9 CD28 sdAb |
| 366 | EVQLVESGGGEVQPGGSLRLSCAASGFTFSNYAMGWFRQAPGKEREF VAAINYRRDDADYAESVKGRFTISRDNAKNTVYLQMSSLRAEDTAV YYCGFTYAGWASSRRDDYDYWGQGTLVTVKP | 1C9v7.10 CD28 sdAb |
| 367 | EVQLVESGGGEVQPGGSLRLSCAASGFTFSNYAMGWFRQAPGKEREF VAAINYRRDDADYAESVKDRFTISRDNAKNTVYLQMSSLRAEDTAV YYCGFTYAGWASSRRDDYNYWGQGTLVTVKP | 1C9v7.11 CD28 sdAb |
| 368 | EVQLVESGGGEVQPGGSLRLSCAASGFTFSNYAMGWFRQAPGKEREF VAAINYGRDDADYAESVKGRFTISRDNAKNTVYLQMSSLRAEDTAV YYCGFTYAGWASSRRDDYNYWGQGTLVTVKP | 1C9v7.12 CD28 sdAb |
| 369 | EVQLVESGGGEVQPGGSLRLSCAASGFTFSNYAMGWFRQAPGKEREF VAAINYRGDDADYAESVKGRFTISRDNAKNTVYLQMSSLRAEDTAV YYCGFTYAGWASSRRDDYNYWGQGTLVTVKP | 1C9v7.13 CD28 sdAb |
| 370 | EVQLVESGGGEVQPGGSLRLSCAASGFTFSNYAMGWFRQAPGKEREF VAAINYRRDDADYAESVKGRFTISRDNAKNTVYLQMSSLRAEDTAV YYCGFTYAGWASSGRDDYNYWGQGTLVTVKP | 1C9v7.14 CD28 sdAb |
| 371 | EVQLVESGGGEVQPGGSLRLSCAASGFTFSNYAMGWFRQAPGKEREF VAAINYRRDDADYAESVKGRFTISRDNAKNTVYLQMSSLRAEDTAV YYCGFTYAGWASSRGDDYNYWGQGTLVTVKP | 1C9v7.15CD28 sdAb |
| 372 | EVQLVESGGGEVQPGGSLRLSCAASGFTFSNYAMGWFRQAPGKEREF VAAINYRRDAADYAESVKGRFTISRDNAKNTVYLQMSSLRAEDTAV YYCGFTYAGWASSRRDDYNYWGQGTLVTVKP | 1C9v7.16 CD28 sdAb |
| 373 | EVQLVESGGGEVQPGGSLRLSCAASGFTFSNYAMGWFRQAPGKEREF VAAINYRRDAADYAESVKGRFTISRDNAKNTVYLQMSSLRAEDTAV YYCGFTYAGWASSRRDDYDYWGQGTLVTVKP | 1C9v7.17 CD28 sdAb |

-continued

| Sequences | | |
|---|---|---|
| # | SEQUENCE | ANNOTATION |
| 374 | EVQLVESGGGEVQPGGSLRLSCAASGFTFSNYAMGWFRQAPGKEREF VAAINYRRDAADYAESVKDRFTISRDNAKNTVYLQMSSLRAEDTAV YYCGFTYAGWASSRRDDYNYWGQGTLVTVKP | 1C9v7.18 CD28 sdAb |
| 375 | EVQLVESGGGEVQPGGSLRLSCAASGFTFSNYAMGWFRQAPGKEREF VAAINYGRDAADYAESVKGRFTISRDNAKNTVYLQMSSLRAEDTAV YYCGFTYAGWASSRRDDYNYWGQGTLVTVKP | 1C9v7.19 CD28 sdAb |
| 376 | EVQLVESGGGEVQPGGSLRLSCAASGFTFSNYAMGWFRQAPGKEREF VAAINYRGDAADYAESVKGRFTISRDNAKNTVYLQMSSLRAEDTAV YYCGFTYAGWASSRRDDYNYWGQGTLVTVKP | 1C9v7.20 CD28 sdAb |
| 377 | EVQLVESGGGEVQPGGSLRLSCAASGFTFSNYAMGWFRQAPGKEREF VAAINYRRDAADYAESVKGRFTISRDNAKNTVYLQMSSLRAEDTAV YYCGFTYAGWASSGRDDYNYWGQGTLVTVKP | 1C9v7.21 CD28 sdAb |
| 378 | EVQLVESGGGEVQPGGSLRLSCAASGFTFSNYAMGWFRQAPGKEREF VAAINYRRDAADYAESVKGRFTISRDNAKNTVYLQMSSLRAEDTAV YYCGFTYAGWASSRGDDYNYWGQGTLVTVKP | 1C9v7.22 CD28 sdAb |
| 379 | EVQLVESGGGEVQPGGSLRLSCAASGFTFSNYAMGWFRQAPGKEREF VAAINYRRDTADYAESVKGRFTISRDNAKNTVYLQMSSLRAEDTAVY YCGFTYAGWASSRRDDYNYWGQGTLVTVKP | 1C9v7.23 CD28 sdAb |
| 380 | EVQLVESGGGEVQPGGSLRLSCAASGFTFSNYAMGWFRQAPGKEREF VAAINYRRDTADYAESVKGRFTISRDNAKNTVYLQMSSLRAEDTAVY YCGFTYAGWASSRRDDYDYWGQGTLVTVKP | 1C9v7.24 CD28 sdAb |
| 381 | EVQLVESGGGEVQPGGSLRLSCAASGFTFSNYAMGWFRQAPGKEREF VAAINYRRDTADYAESVKDRFTISRDNAKNTVYLQMSSLRAEDTAVY YCGFTYAGWASSRRDDYNYWGQGTLVTVKP | 1C9v7.25 CD28 sdAb |
| 382 | EVQLVESGGGEVQPGGSLRLSCAASGFTFSNYAMGWFRQAPGKEREF VAAINYGRDTADYAESVKGRFTISRDNAKNTVYLQMSSLRAEDTAV YYCGFTYAGWASSRRDDYNYWGQGTLVTVKP | 1C9v7.26 CD28 sdAb |
| 383 | EVQLVESGGGEVQPGGSLRLSCAASGFTFSNYAMGWFRQAPGKEREF VAAINYRGDTADYAESVKGRFTISRDNAKNTVYLQMSSLRAEDTAV YYCGFTYAGWASSRRDDYNYWGQGTLVTVKP | 1C9v7.27 CD28 sdAb |
| 384 | EVQLVESGGGEVQPGGSLRLSCAASGFTFSNYAMGWFRQAPGKEREF VAAINYRRDTADYAESVKGRFTISRDNAKNTVYLQMSSLRAEDTAVY YCGFTYAGWASSGRDDYNYWGQGTLVTVKP | 1C9v7.28 CD28 sdAb |
| 385 | EVQLVESGGGEVQPGGSLRLSCAASGFTFSNYAMGWFRQAPGKEREF VAAINYRRDTADYAESVKGRFTISRDNAKNTVYLQMSSLRAEDTAVY YCGFTYAGWASSRGDDYNYWGQGTLVTVKP | 1C9v7.29 CD28 sdAb |
| 386 | AINYGRESAD | CDR2 (1C9v7.5) |
| 387 | AINYRGESAD | CDR2 (1C9v7.6) |
| 388 | AINYGRDDAD | CDR2 (1C9v7.12; 1C9v13.6) |
| 389 | AINYRGDDAD | CDR2 (1C9v7.13; 1C9v13.7) |
| 390 | AINYGRDAAD | CDR2 (1C9v7.19) |
| 391 | AINYRGDAAD | CDR2 (1C9v7.20) |
| 392 | AINYGRDTAD | CDR2 (1C9v7.26) |
| 393 | AINYRGDTAD | CDR2 (C9v7.27) |
| 394 | AINYGRDSAD | CDR2 (1C9v11.4) |
| 395 | AINYRGDSAD | CDR2 (1C9v11.5) |
| 396 | TYAGWASSRRDDYDY | CDR3 (1C9v7.2, 10, 17, 24; 1C9v11.2; 1C9v13.2, 5) |
| 397 | TYAGWASSGRDDYNY | CDR3 (1C9v7.7, 14, |

-continued

| Sequences | |
|---|---|
| # SEQUENCE | ANNOTATION |
| | 21, 28; 1C9v11.6; 1C9v13.8) |
| 398 TYAGWASSRGDDYNY | CDR3 (1C9v7.8, 15, 22, 29; 1C9v11.7; 1C9v13.9) |

The invention claimed is:

1. A CD28-binding polypeptide comprising at least one VHH domain that binds CD28, wherein the at least one VHH domain comprises:

(a) a complementarity determining region 1 (CDR1) comprising an amino acid sequence selected from the group consisting of SEQ ID NOS: 195, 198, 199, 200, and 201; a complementarity determining region 2 (CDR2) comprising an amino acid sequence selected from the group consisting of SEQ ID NOS: 196, 202, 204, 205, 206, 207, 208, 209, 210, 211, and 212; and a complementarity determining region 3 (CDR3) comprising an amino acid sequence set forth in SEQ ID NO: 197;

(b) a CDR1 comprising an amino acid sequence set forth in SEQ ID NO: 189; a CDR2 comprising an amino acid sequence set forth in SEQ ID NO:190; and a CDR3 comprising an amino acid sequence set forth in SEQ ID NO: 191; or (c) a CDR1 comprising an amino acid sequence set forth in SEQ ID NO:192; a CDR2 comprising an amino acid sequence set forth in SEQ ID NO: 193; and a CDR3 comprising an amino acid sequence set forth in SEQ ID NO: 194.

2. The CD28-binding polypeptide of claim 1, wherein the at least one VHH domain comprises:

a CDR1 comprising the amino acid sequence set forth in SEQ ID NO:195, a CDR2 comprising the amino acid sequence set forth in SEQ ID NO:206, and a CDR3 comprising the amino acid sequence set forth in SEQ ID NO: 197;

a CDR1 comprising the amino acid sequence set forth in SEQ ID NO:189, a CDR2 comprising the amino acid sequence set forth in SEQ ID NO:190, and a CDR3 comprising the amino acid sequence set forth in SEQ ID NO:191;

a CDR1 comprising the amino acid sequence set forth in SEQ ID NO:192, a CDR2 comprising the amino acid sequence set forth in SEQ ID NO: 193, and a CDR3 comprising the amino acid sequence set forth in SEQ ID NO:194;

a CDR1 comprising the amino acid sequence set forth in SEQ ID NO:195, a CDR2 comprising the amino acid sequence set forth in SEQ ID NO:196, and a CDR3 comprising the amino acid sequence set forth in SEQ ID NO:197;

a CDR1 comprising the amino acid sequence set forth in SEQ ID NO:198, a CDR2 comprising the amino acid sequence set forth in SEQ ID NO: 196, and a CDR3 comprising the amino acid sequence set forth in SEQ ID NO:197;

a CDR1 comprising the amino acid sequence set forth in SEQ ID NO:198, a CDR2 comprising the amino acid sequence set forth in SEQ ID NO:206, and a CDR3 comprising the amino acid sequence set forth in SEQ ID NO: 197;

a CDR1 comprising the amino acid sequence set forth in SEQ ID NO:199, a CDR2 comprising the amino acid sequence set forth in SEQ ID NO: 196, and a CDR3 comprising the amino acid sequence set forth in SEQ ID NO:197;

a CDR1 comprising the amino acid sequence set forth in SEQ ID NO: 199, a CDR2 comprising the amino acid sequence set forth in SEQ ID NO:206, and a CDR3 comprising the amino acid sequence set forth in SEQ ID NO:197;

a CDR1 comprising the amino acid sequence set forth in SEQ ID NO:200, a CDR2 comprising the amino acid sequence set forth in SEQ ID NO: 196, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO: 196, and a CDR3 comprising the amino acid sequence set forth in SEQ ID NO:197;

a CDR1 comprising the amino acid sequence set forth in SEQ ID NO: 195, a CDR2 comprising the amino acid sequence set forth in SEQ ID NO:202, and a CDR3 comprising the amino acid sequence set forth in SEQ ID NO:197;

a CDR1 comprising the amino acid sequence set forth in SEQ ID NO: 195, a CDR2 comprising the amino acid sequence set forth in SEQ ID NO:204, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:205, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:207, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:208, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:209, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:210, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:211, and a CDR3 comprising the amino acid sequence set forth in SEQ ID NO:197;

a CDR1 comprising the amino acid sequence set forth in SEQ ID NO:195, a CDR2 comprising the amino acid sequence set forth in SEQ ID NO:212, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:202, and a CDR3 comprising the amino acid sequence set forth in SEQ ID NO:197;

a CDR1 comprising the amino acid sequence set forth in SEQ ID NO:201, a CDR2 comprising the amino acid sequence set forth in SEQ ID NO:206, and a CDR3 comprising the amino acid sequence set forth in SEQ ID NO: 197; or a CDR1 comprising the amino acid sequence set forth in SEQ ID NO:201, a CDR2 comprising the amino acid sequence set forth in SEQ ID NO:204, and a CDR3 comprising the amino acid sequence set forth in SEQ ID NO: 197.

3. The CD28-binding polypeptide of claim 2 comprising:

(a) a CDR1, a CDR2, and a CDR3 as comprised in the amino acid sequence set forth in SEQ ID NO:342; a CDR1, a CDR2, and a CDR3 as comprised in the amino acid sequence set forth in SEQ ID NO: 188; a CDR1, a CDR2, and a CDR3 as comprised in the amino acid sequence set forth in SEQ ID NO:213; a CDR1, a CDR2, and a CDR3 as comprised in the amino acid sequence set forth in SEQ ID NO:214; a CDR1, a CDR2, and a CDR3 as comprised in the amino acid sequence set forth in SEQ ID NO: 215; a CDR1, a CDR2, and a CDR3 as comprised in the amino acid sequence set forth in SEQ ID NO:216; a CDR1, a CDR2, and a CDR3 as comprised in the amino acid sequence set forth in SEQ ID NO:217; a CDR1, a CDR2, and a CDR3 as comprised in the amino acid sequence set forth in SEQ ID NO:218; a CDR1, a CDR2, and a CDR3 as comprised in the amino acid sequence set forth in SEQ ID NO:219; a CDR1, a CDR2, and a CDR3 as comprised in the amino acid sequence set forth in SEQ ID NO: 221; a CDR1, a CDR2, and a CDR3 as comprised in the amino acid sequence set forth in SEQ ID NO:222; a CDR1, a CDR2, and a CDR3 as comprised in the amino acid sequence set forth in SEQ ID NO:223; a CDR1, a CDR2, and a CDR3 as comprised in the amino acid sequence set forth in SEQ ID NO:224; a CDR1, a CDR2, and a CDR3 as comprised in the amino acid sequence set forth in SEQ ID NO:225; a CDR1, a CDR2, and a CDR3 as comprised in the amino acid sequence set forth in SEQ ID NO: 226; a CDR1, a CDR2, and a CDR3 as comprised in the amino acid sequence set forth in SEQ ID NO:227; a CDR1, a CDR2, and a CDR3 as comprised in the amino acid sequence set forth in SEQ ID NO:228; a CDR1, a CDR2, and a CDR3 as contained comprised in the amino acid sequence set forth in SEQ ID NO:229; a CDR1, a CDR2, and a CDR3 as comprised in the amino acid sequence set forth in SEQ ID NO:230; a CDR1, a CDR2, and a CDR3 as comprised in the amino acid sequence set forth in SEQ ID NO: 231; a CDR1, a CDR2, and a CDR3 as comprised in the amino acid sequence set forth in SEQ ID NO:232; a CDR1, a CDR2, and a CDR3 as comprised in the amino acid sequence set forth in SEQ ID NO:233; a CDR1, a CDR2, and a CDR3 as comprised in the amino acid sequence set forth in SEQ ID NO:234; a CDR1, a CDR2, and a CDR3 as comprised in the amino acid sequence set forth in SEQ ID NO:235; a CDR1, a CDR2, and a CDR3 as comprised in the amino acid sequence set forth in SEQ ID NO: 236; a CDR1, a CDR2, and a CDR3 as comprised in the amino acid sequence set forth in SEQ ID NO:237; a CDR1, a CDR2, and a CDR3 as comprised in the amino acid sequence set forth in SEQ ID NO:238; a CDR1, a CDR2, and a CDR3 as comprised in the amino acid sequence set forth in SEQ ID NO:239; a CDR1, a CDR2, and a CDR3 as comprised in the amino acid sequence set forth in SEQ ID NO:344; a CDR1, a CDR2, and a CDR3 as comprised in the amino acid sequence set forth in SEQ ID NO:345; a CDR1, a CDR2, and a CDR3 as comprised in the amino acid sequence set forth in SEQ ID NO:351; a CDR1, a CDR2, and a CDR3 as comprised in the amino acid sequence set forth in SEQ ID NO:353; a CDR1, a CDR2, and a CDR3 as comprised in the amino acid sequence set forth in SEQ ID NO:358; a CDR1, a CDR2, and a CDR3 as comprised in the amino acid sequence set forth in SEQ ID NO: 360 a CDR1, a CDR2, and a CDR3 as comprised in the amino acid sequence set forth in SEQ ID NO:365; a CDR1, a CDR2, and a CDR3 as comprised in the amino acid sequence set forth in SEQ ID NO:367; a CDR1, a CDR2, and a CDR3 as contained in the amino acid sequence set forth in SEQ ID NO: 379; or a CDR1, a CDR2, and a CDR3 as comprised in the amino acid sequence set forth in SEQ ID NO:381

(b) a CDR1, a CDR2, and a CDR3 as comprised in the amino acid sequence set forth in SEQ ID NO:186; or (c) a CDR1, a CDR2, and a CDR3 as comprised in the amino acid sequence set forth in SEQ ID NO:187.

4. The CD28-binding polypeptide of claim 3, wherein the at least VHH domain comprises the amino acid sequence set forth in any of SEQ ID NOS: 342, 186, 187, 188, 213, 214, 215, 216, 217, 218, 219, 221, 222, 223, 224, 225, 226, 227, 228, 229, 230, 231, 232, 233, 234, 235, 236, 237, 238, 239, 344, 345, 351, 353, 358, 360, 365, 367, 379, and 381, or a sequence of amino acids that exhibits at least 85% sequence identity to any of SEQ ID NOS: 342, 186, 187, 188, 213, 214, 215, 216, 217, 218, 219, 221, 222, 223, 224, 225, 226, 227, 228, 229, 230, 231, 232, 233, 234, 235, 236, 237, 238, 239, 344, 345, 351, 353, 358, 360, 365, 367, 379, and 381.

5. The CD28-binding polypeptide of claim 1, wherein the CD28-binding polypeptide is monovalent for CD28.

6. The CD28-binding polypeptide of claim 1, wherein the CD28-binding polypeptide is multivalent for CD28.

7. The CD28-binding polypeptide of claim 1, wherein the CD28-binding polypeptide is bivalent for CD28.

8. The CD28-binding polypeptide of claim 7, wherein the two-VHH domains are the same VHH domains, or wherein the VHH domains are different VHH domains, wherein each of the two VHH domains comprises a sequence of amino acids that exhibits at least 90% sequence identity to any of SEO ID NOS: 342, 213-219, 221-239, 344, 345, 351, 353, 358, 360, 365, 367, 379, and 381.

9. The CD28-binding polypeptide of claim 1, wherein the CD28-binding polypeptide comprises a moiety that binds protein A.

10. The CD28-binding polypeptide of claim 1, wherein the CD28-binding polypeptide comprises an amino acid modification that reduces binding to protein A, and wherein the amino acid modification is G65D by Kabat in framework region 3 (FR3).

11. An anti-CD28 sdAb-Fc fusion protein, comprising a CD28-binding polypeptide of claim 1 and an immunoglobulin Fc region.

12. A homodimeric Fe fusion protein, comprising two identical copies of the anti-CD28 sdAb-Fc fusion protein of claim 11.

13. A heterodimeric fusion protein, comprising two of the anti-CD28 sdAb-Fc fusion proteins of claim 11.

14. A multi-specific binding polypeptide comprising the CD28-binding polypeptide of claim 1 and one or more binding domain (BD) that binds to a target antigen other than CD28.

15. The multi-specific-binding polypeptide of claim 14, wherein the one or more BD binds a tumor associated antigen (TAA), or wherein the one or more BD binds a T cell surface marker that is a T cell activation marker or a T cell exhaustion marker, or wherein the one or more BD binds a cell surface marker that is a tumor microenvironment marker.

16. The multi-specific binding polypeptide of claim 14, wherein the one or more BD is a VHH domain.

17. The multi-specific binding polypeptide of claim 14, wherein the multi-specific binding polypeptide is an Fc fusion protein, wherein at least one of the one or more BD and/or the at least one CD28 VHH domain is linked to the immunoglobulin Fc region.

18. A homodimeric multi-specific Fc fusion protein, comprising two identical copies of the multi-specific binding polypeptide of claim 17.

19. A heterodimeric multi-specific Fc fusion protein, comprising two of the multi-specific binding polypeptides of claim 17.

20. An anti-CD28 VHH domain comprising:

(a) a complementarity determining region 1 (CDR1) comprising an amino acid sequence selected from the group consisting of SEQ ID NOS: 195, 198, 199, 200, and 201; a complementarity determining region 2 (CDR2) comprising an amino acid sequence selected from the group consisting of SEQ ID NOS: 196, 202, 204, 205, 206, 207, 208, 209, 210, 211, and 212; and a complementarity determining region 3 (CDR3) comprising an amino acid sequence set forth in SEQ ID NO: 197;

(b) a CDR1 comprising an amino acid sequence set forth in SEQ ID NO: 189; a CDR2 comprising an amino acid sequence set forth in SEQ ID NO: 190; and a CDR3 comprising an amino acid sequence set forth in SEQ ID NO: 191; or (c) a CDR1 comprising an amino acid sequence set forth in SEQ ID NO: 192; a CDR2 comprising an amino acid sequence set forth in SEQ ID NO: 193; and a CDR3 comprising an amino acid sequence set forth in SEQ ID NO: 194.

21. The anti-CD28 VHH domain of claim 20 comprising:

(a) a CDR1, a CDR2, and a CDR3 as contained in the amino acid sequence set forth in SEQ ID NO: 342; a CDR1, a CDR2, and a CDR3 as contained in the amino acid sequence set forth in SEQ ID NO:188; a CDR1, a CDR2, and a CDR3 as contained in the amino acid sequence set forth in SEQ ID NO:213; a CDR1, a CDR2, and a CDR3 as contained in the amino acid sequence set forth in SEQ ID NO:214; a CDR1, a CDR2, and a CDR3 as contained in the amino acid sequence set forth in SEQ ID NO:215; a CDR1, a CDR2, and a CDR3 as contained in the amino acid sequence set forth in SEQ ID NO:216; a CDR1, a CDR2, and a CDR3 as contained in the amino acid sequence set forth in SEQ ID NO:217; a CDR1, a CDR2, and a CDR3 as contained in the amino acid sequence set forth in SEQ ID NO:218; a CDR1, a CDR2, and a CDR3 as contained in the amino acid sequence set forth in SEQ ID NO:219; a CDR1, a CDR2, and a CDR3 as contained in the amino acid sequence set forth in SEQ ID NO: 221; a CDR1, a CDR2, and a CDR3 as contained in the amino acid sequence set forth in SEQ ID NO:222; a CDR1, a CDR2, and a CDR3 as contained in the amino acid sequence set forth in SEQ ID NO:223; a CDR1, a CDR2, and a CDR3 as contained in the amino acid sequence set forth in SEQ ID NO:224; a CDR1, a CDR2, and a CDR3 as contained in the amino acid sequence set forth in SEQ ID NO:225; a CDR1, a CDR2, and a CDR3 as contained in the amino acid sequence set forth in SEQ ID NO:226; a CDR1, a CDR2, and a CDR3 as contained in the amino acid sequence set forth in SEQ ID NO:227; a CDR1, a CDR2, and a CDR3 as contained in the amino acid sequence set forth in SEQ ID NO:228; a CDR1, a CDR2, and a CDR3 as contained in the amino acid sequence set forth in SEQ ID NO:229; a CDR1, a CDR2, and a CDR3 as contained in the amino acid sequence set forth in SEQ ID NO:230; a CDR1, a CDR2, and a CDR3 as contained in the amino acid sequence set forth in SEQ ID NO:231; a CDR1, a CDR2, and a CDR3 as contained in the amino acid sequence set forth in SEQ ID NO: 232; a CDR1, a CDR2, and a CDR3 as contained in the amino acid sequence set forth in SEQ ID NO:233; a CDR1, a CDR2, and a CDR3 as contained in the amino acid sequence set forth in SEQ ID NO:234; a CDR1, a CDR2, and a CDR3 as contained in the amino acid sequence set forth in SEQ ID NO:235; a CDR1, a CDR2, and a CDR3 as contained in the amino acid sequence set forth in SEQ ID NO:236; a CDR1, a CDR2, and a CDR3 as contained in the amino acid sequence set forth in SEQ ID NO:237; a CDR1, a CDR2, and a CDR3 as contained in the amino acid sequence set forth in SEQ ID NO:238; a CDR1, a CDR2, and a CDR3 as contained in the amino acid sequence set forth in SEQ ID NO:239; a CDR1, a CDR2, and a CDR3 as contained in the amino acid sequence set forth in SEQ ID NO: 344; a CDR1, a CDR2, and a CDR3 as contained in the amino acid sequence set forth in SEQ ID NO:345; a CDR1, a CDR2, and a CDR3 as contained in the amino acid sequence set forth in SEQ ID NO:351; a CDR1, a CDR2, and a CDR3 as contained in the amino acid sequence set forth in SEQ ID NO:353; a CDR1, a CDR2, and a CDR3 as contained in the amino acid sequence set forth in SEQ ID NO:358; a CDR1, a CDR2, and a CDR3 as contained in the amino acid sequence set forth in SEQ ID NO:360; a CDR1, a CDR2, and a CDR3 as contained in the amino acid sequence set forth in SEQ ID NO:365; a CDR1, a CDR2, and a CDR3 as contained in the amino acid sequence set forth in SEQ ID NO:367; a CDR1, a CDR2, and a CDR3 as contained in the amino acid sequence set forth in SEQ ID NO: 379; a CDR1, a CDR2, and a CDR3 as contained in the amino acid sequence set forth in SEQ ID NO:381;

(b) a CDR1, a CDR2, and a CDR3 as contained in the amino acid sequence set forth in SEQ ID NO:186; or (c) a CDR1, a CDR2, and a CDR3 as contained in the amino acid sequence set forth in SEQ ID NO: 187.

22. The CD28-binding polypeptide of claim 1, which comprises a CD3 binding region.

23. A multi-specific construct comprising at least one anti-CD28 VHH domain of claim 20, one or more binding domain (BD) that binds an antigen other than CD28, and a CD3 binding region.

24. The CD28-binding polypeptide of claim 22, wherein the CD28-binding polypeptide comprises an immunoglobulin Fc region.

25. A polynucleotide(s) encoding the CD28-binding polypeptide of claim 1, a fusion protein comprising the CD28-binding polypeptide of claim 1, or a multi-specific binding polypeptide comprising the CD28-binding polypeptide of claim 1.

26. A vector, comprising the polynucleotide of claim 25.

27. A cell comprising the polynucleotide or polynucleotides of claim 25.

28. A method of producing a polypeptide, the method comprising introducing into a cell a polynucleotide or polynucleotides of claim 25 and culturing the cell under conditions to produce the polypeptide.

29. A pharmaceutical composition comprising the CD28-binding polypeptide of claim 1, a fusion protein comprising the CD28-binding polypeptide of claim 1, or a multi-specific binding polypeptide comprising the CD28–binding polypeptide of claim 1.

30. A method of stimulating an immune response in a subject, the method comprising administering, to a subject in need thereof, the CD28-binding polypeptide of claim 1, a fusion protein comprising the CD28-binding polypeptide of claim 1, or a multi-specific binding polypeptide comprising the CD28-binding polypeptide of claim 1.

31. A method of treating cancer in a subject, the method comprising administering to a subject in need thereof a therapeutically effective amount of the CD28-binding polypeptide of claim 1, a fusion protein comprising the CD28-binding polypeptide of claim 1, or a multi-specific binding polypeptide comprising the CD28-binding polypeptide of claim 1.

32. A CD28-binding polypeptide comprising at least one VHH domain that binds CD28, wherein the at least one CD28 VHH domain comprises:

a complementarity determining region 1 (CDR1) comprising an amino acid sequence set forth in SEQ ID NO:189, a complementarity determining region 2 (CDR2) comprising an amino acid sequence set forth in SEQ ID NO: 190, and a complementarity determining region 3 (CDR3) comprising an amino acid sequence set forth in SEQ ID NO: 191; or a complementarity determining region 1 (CDR1) comprising an amino acid sequence set forth in SEQ ID NO:192, a complementarity determining region 2 (CDR2) comprising an amino acid sequence set forth in SEQ ID NO:193, and a complementarity determining region 3 (CDR3) comprising an amino acid sequence set forth in SEQ ID NO: 194.

* * * * *